US010407472B2

(12) United States Patent
Thompson et al.

(10) Patent No.: US 10,407,472 B2
(45) Date of Patent: *Sep. 10, 2019

(54) FUSION PROTEINS, RECOMBINANT BACTERIA, AND METHODS FOR USING RECOMBINANT BACTERIA

(71) Applicant: Spogen Biotech Inc., St. Louis, MO (US)

(72) Inventors: Brian Thompson, Creve Coeur, MO (US); Ashley Siegel, St. Louis, MO (US)

(73) Assignee: Spogen Biotech Inc., St. Louis, MO (US)

( * ) Notice: Subject to any disclaimer, the term of this patent is extended or adjusted under 35 U.S.C. 154(b) by 21 days.

This patent is subject to a terminal disclaimer.

(21) Appl. No.: 15/842,062

(22) Filed: Dec. 14, 2017

(65) Prior Publication Data

US 2018/0099999 A1 Apr. 12, 2018

Related U.S. Application Data

(63) Continuation of application No. 14/857,606, filed on Sep. 17, 2015, now Pat. No. 9,845,342.

(Continued)

(51) Int. Cl.
| | | |
|---|---|---|
| *C07K 14/32* | (2006.01) | |
| *A01N 37/44* | (2006.01) | |
| *A61L 2/18* | (2006.01) | |
| *C09K 8/62* | (2006.01) | |
| *E21B 43/16* | (2006.01) | |
| *A23K 20/147* | (2016.01) | |
| *C12P 21/02* | (2006.01) | |
| *C12N 1/20* | (2006.01) | |
| *C12N 3/00* | (2006.01) | |
| *C12N 15/62* | (2006.01) | |
| *C12N 15/75* | (2006.01) | |
| *A01N 63/02* | (2006.01) | |
| *C02F 3/34* | (2006.01) | |
| *A23K 10/18* | (2016.01) | |
| *A61K 39/00* | (2006.01) | |
| *C02F 103/00* | (2006.01) | |
| *C02F 103/06* | (2006.01) | |
| *C02F 103/10* | (2006.01) | |
| *C02F 103/14* | (2006.01) | |
| *C02F 103/16* | (2006.01) | |
| *C02F 103/26* | (2006.01) | |

(Continued)

(52) U.S. Cl.
CPC .............. *C07K 14/32* (2013.01); *A01N 37/44* (2013.01); *A01N 63/02* (2013.01); *A23K 20/147* (2016.05); *A61L 2/18* (2013.01); *C02F 3/342* (2013.01); *C02F 3/348* (2013.01); *C09K 8/62* (2013.01); *C12N 1/20* (2013.01); *C12N 3/00* (2013.01); *C12N 15/62* (2013.01); *C12N 15/75* (2013.01); *C12P 21/02* (2013.01); *E21B 43/16* (2013.01); *A23K 10/18* (2016.05); *A61K 39/00* (2013.01); *C02F 2101/10* (2013.01); *C02F 2101/30* (2013.01); *C02F 2103/002* (2013.01); *C02F 2103/003* (2013.01); *C02F 2103/007* (2013.01); *C02F 2103/06* (2013.01); *C02F 2103/10* (2013.01); *C02F 2103/14* (2013.01); *C02F 2103/16* (2013.01); *C02F 2103/26* (2013.01); *C02F 2103/28* (2013.01); *C07K 2319/01* (2013.01); *C07K 2319/035* (2013.01); *C07K 2319/40* (2013.01); *C09K 2208/24* (2013.01)

(58) Field of Classification Search
CPC ......... C07K 14/32; A61K 34/07; A01N 63/02
See application file for complete search history.

(56) References Cited

U.S. PATENT DOCUMENTS

| | | |
|---|---|---|
| 5,290,914 A | 3/1994 | Wilcox et al. |
| 5,348,743 A | 9/1994 | Ryals et al. |

(Continued)

FOREIGN PATENT DOCUMENTS

| | | |
|---|---|---|
| CA | 2146822 A1 | 10/1995 |
| CN | 102031231 A | 4/2011 |

(Continued)

OTHER PUBLICATIONS

Reetha, S., et al., "Screening of Cellulase and Pectinase by Using Pseudomonas Fluorescens and Bacillus subtilis," International Letters of Natural Sciences, 2014, pp. 75-80, vol. 8, No. 2.

(Continued)

*Primary Examiner* — Karen Cochrane Carlson
(74) *Attorney, Agent, or Firm* — Stinson LLP

(57) ABSTRACT

Fusion proteins containing a targeting sequence, an exosporium protein, or an exosporium protein fragment that targets the fusion protein to the exosporium of a *Bacillus cereus* family member are provided. Recombinant *Bacillus cereus* family members expressing such fusion proteins are also provided. Genetically inactivated *Bacillus cereus* family members and recombinant *Bacillus cereus* family members that overexpress exosporium proteins are also provided. Seeds coated with the recombinant *Bacillus cereus* family members and methods for using the recombinant *Bacillus cereus* family members (e.g., for stimulating plant growth) are also provided. Various modifications of the recombinant *Bacillus cereus* family members that express the fusion proteins are further provided. Fusion proteins comprising a spore coat protein and a protein or peptide of interest, recombinant bacteria that express such fusion proteins, seeds coated with such recombinant bacteria, and methods for using such recombinant bacteria (e.g., for stimulating plant growth) are also provided.

72 Claims, 16 Drawing Sheets

Specification includes a Sequence Listing.

Related U.S. Application Data

(60) Provisional application No. 62/051,885, filed on Sep. 17, 2014.

(51) Int. Cl.
*C02F 103/28* (2006.01)
*C02F 101/10* (2006.01)
*C02F 101/30* (2006.01)

(56) References Cited

U.S. PATENT DOCUMENTS

| | | | |
|---|---|---|---|
| 5,503,652 | A | 4/1996 | Kloepper et al. |
| 5,766,914 | A | 6/1998 | Deits |
| 5,776,448 | A | 7/1998 | Suslow et al. |
| 6,110,372 | A | 8/2000 | Perriello |
| 6,184,440 | B1 | 2/2001 | Shoseyov et al. |
| 6,232,270 | B1 | 5/2001 | Branly et al. |
| 6,309,440 | B1 | 10/2001 | Yamashita |
| 6,333,302 | B1 | 12/2001 | Beer et al. |
| 6,548,743 | B1 | 4/2003 | Sheen et al. |
| 6,630,340 | B2 | 10/2003 | Wilting et al. |
| 7,393,678 | B2 | 7/2008 | Triplett et al. |
| 7,417,181 | B2 | 8/2008 | Wang et al. |
| 7,432,097 | B2 | 10/2008 | Short et al. |
| 7,504,120 | B2 | 3/2009 | Steer et al. |
| 7,615,681 | B2 | 11/2009 | Georges et al. |
| 7,919,678 | B2 | 4/2011 | Mironov |
| 7,960,148 | B2 | 6/2011 | Steer et al. |
| 8,030,064 | B2 | 10/2011 | Lee et al. |
| 8,080,404 | B1 | 12/2011 | Turetsky et al. |
| 8,097,769 | B2 | 1/2012 | Sarria-Millan et al. |
| 8,105,613 | B2 | 1/2012 | Flick-Smith et al. |
| 8,114,659 | B2 | 2/2012 | Rawson et al. |
| 8,383,366 | B2 | 2/2013 | Ferrari et al. |
| 8,461,419 | B2 | 6/2013 | He et al. |
| 8,614,078 | B2 | 12/2013 | Lin et al. |
| 8,673,311 | B2 | 3/2014 | Cutting et al. |
| 9,068,194 | B2 | 6/2015 | Unkefer et al. |
| 9,125,419 | B2 | 9/2015 | Asolkar et al. |
| 9,132,175 | B2 | 9/2015 | Stewart et al. |
| 9,133,251 | B2 | 9/2015 | Stewart et al. |
| 9,392,796 | B2 | 7/2016 | Thompson et al. |
| 9,573,980 | B2 | 2/2017 | Thompson et al. |
| 9,826,743 | B2 | 11/2017 | Curtis et al. |
| 9,850,289 | B2 | 12/2017 | Thompson et al. |
| 2003/0228679 | A1 | 12/2003 | Smith et al. |
| 2004/0077090 | A1 | 4/2004 | Short |
| 2005/0232947 | A1 | 10/2005 | Cutting |
| 2007/0184018 | A1 | 8/2007 | Lahm et al. |
| 2008/0233175 | A1 | 9/2008 | Steer et al. |
| 2008/0248953 | A1 | 10/2008 | Smith et al. |
| 2009/0192040 | A1 | 7/2009 | Grobler |
| 2010/0071093 | A1 | 3/2010 | Sarria-Millan |
| 2010/0205690 | A1 | 8/2010 | Blasing et al. |
| 2010/0233124 | A1 | 9/2010 | Stewart et al. |
| 2010/0291100 | A1 | 11/2010 | Macinga |
| 2011/0281316 | A1 | 11/2011 | Stewart et al. |
| 2011/0321197 | A1 | 12/2011 | Schon et al. |
| 2012/0227134 | A1 | 9/2012 | Schon et al. |
| 2012/0259101 | A1 | 10/2012 | Tan et al. |
| 2012/0266327 | A1 | 10/2012 | Sanz Molinero et al. |
| 2013/0216653 | A1 | 8/2013 | Perkins et al. |
| 2013/0345056 | A1 | 12/2013 | Sada |
| 2014/0259225 | A1 | 9/2014 | Frank et al. |
| 2014/0274691 | A1 | 9/2014 | Thompson et al. |
| 2014/0274707 | A1 | 9/2014 | Thompson et al. |
| 2014/0342905 | A1 | 11/2014 | Bullis et al. |
| 2016/0031948 | A1 | 2/2016 | Thompson et al. |
| 2016/0051656 | A1 | 2/2016 | Stewart et al. |
| 2016/0053222 | A1 | 2/2016 | Stewart et al. |
| 2016/0236996 | A1 | 8/2016 | Chaudhry |
| 2016/0262402 | A1 | 9/2016 | Thompson et al. |
| 2016/0316761 | A1 | 11/2016 | Thompson et al. |
| 2016/0340658 | A1 | 11/2016 | Lessl et al. |
| 2017/0135353 | A1 | 5/2017 | Thompson et al. |

FOREIGN PATENT DOCUMENTS

| | | |
|---|---|---|
| EP | 0792363 B1 | 12/2003 |
| EP | 1465980 B1 | 8/2010 |
| EP | 1590466 B1 | 9/2010 |
| EP | 2069504 B1 | 6/2015 |
| IN | 801/CHE/2011 | 7/2014 |
| JP | H10-203917 A | 8/1998 |
| JP | 2005-298409 A | 10/2005 |
| JP | 2007-117066 A | 5/2007 |
| KR | 10-2011-0102787 A | 9/2011 |
| RU | 2 313 941 C2 | 1/2008 |
| RU | 2 458 132 C2 | 8/2012 |
| WO | 96/23063 A1 | 8/1999 |
| WO | 02/00232 A2 | 1/2002 |
| WO | 02/45513 A2 | 6/2002 |
| WO | 02/46388 A1 | 6/2002 |
| WO | 03/011487 A1 | 2/2003 |
| WO | 03/066846 A1 | 8/2003 |
| WO | 2005/028654 A1 | 3/2005 |
| WO | 2006/012366 A2 | 2/2006 |
| WO | 2007/078127 A1 | 7/2007 |
| WO | 2007/086898 A2 | 8/2007 |
| WO | 2008/017483 A2 | 2/2008 |
| WO | 2009/037329 A2 | 3/2009 |
| WO | 2009/056494 A2 | 5/2009 |
| WO | 2010/046221 A1 | 4/2010 |
| WO | 2011/106794 A1 | 9/2011 |
| WO | 2011/121408 A1 | 10/2011 |
| WO | 2013/090628 A1 | 6/2013 |
| WO | 2013/178649 A1 | 12/2013 |
| WO | 2013/178658 A1 | 12/2013 |
| WO | 2014/004487 A1 | 1/2014 |
| WO | 2014/079773 A1 | 5/2014 |
| WO | 2014/079814 A1 | 5/2014 |
| WO | 2015/118516 A1 | 8/2015 |

OTHER PUBLICATIONS

Ryu, C. M., et al., "Bacterial Volatiles Promote Growth in *Arabidopsis*," Proceedings of the National Academy of Sciences of the United States of America, Apr. 2003, pp. 4927-4932, vol. 100, No. 8.

Sachdev, D. P., et al., "Isolation and Characterization of Indole Acetic Acid (IAA) Producing Klebsiella pneumoniae Strains from Rhizosphere of Wheat (*Triticum aestivum*) and Their Effect on Plant Growth," Indian Journal of Experimental Biology, Dec. 2009, pp. 993-1000, vol. 47, No. 12.

Saleh, S., et al., "Involvement of gacS and rpoS in Enhancement of the Plant Growth-Promoting Capabilities of Enterobacter cloacae CAL2 and UW4," Canadian Journal of Microbiology, Aug. 2001, pp. 698-705, vol. 47, No. 8.

Sales, J., et al. "Coffee (*Coffea arabica* L.) Seeds Germination After Treatment with Different Concentrations and Embebding Times in Cellulase," Ciencia e Agrotecnologia [online], 2003, pp. 557-564, vol. 27, No. 3. ISSN 1413-7054. http://dx.doi.org/10.1590/S1413-70542003000300009, Abstract Only, 1 page.

Selvakumar, G., et al., "Isolation and Characterization of Nonrhizobial Plant Growth Promoting Bacteria from Nodules of Kudzu (*Pueraria thunbergiana*) and Their Effect on Wheat Seedling Growth," Current Microbiology, Feb. 2008, pp. 134-139, vol. 56, Issue 2.

Sequence Listing filed in WO 2007/078127 A1 published Jul. 12, 2007, downloaded from <http://patentscope.wipo.int/search/en/detail.jsf?docId=WO2007078127&recNum=1&tab=PCTDocuments&maxRec=&office=&prevFilter=&sortOption=&queryString=>, 5 pages.

Shahid, M., et al., "Root Colonization and Growth Promotion of Sunflower (*Helianthus annuus* L.) by Phosphate Solubilizing *Enterobacter* sp. Fs-11," World Journal of Microbiology & Biotechnology, 2012, pp. 2749-2758, vol. 28, No. 8.

Shani, Z., et al., "Expression of Endo-1,4-beta-glucanase (cel1) in *Arabidopsis thaliana* is Associated with Plant Growth, Xylem Development and Cell Wall Thickening," Plant Cell Reports, 2006, pp. 1067-1074, vol. 25, Issue 10.

Shankar, M., et al., "Root Colonization of a Rice Growth Promoting Strain of Enterobacter cloacae," Journal of Basic Microbiology, 2011, pp. 523-530, vol. 51, No. 5.

(56) References Cited

OTHER PUBLICATIONS

Shao, J., et al., "Contribution of Indole-3-Acetic Acid in the Plant Growth Promotion by the Rhizspheric Strain Bacillus amyloliquefaciens SQR9," Biology and Fertility of Soils, 2015, pp. 321-330, vol. 51, Issue 3.

Shen, M., et al., "Effect of Plant Growth-Promoting Rhizobacteria (PGPRs) on Plant Growth, Yield, and Quality of Tomato (*Lycopersicon esculentum* Mill.) under Simulated Seawater Irrigation," The Journal of General and Applied Microbiology, 2012, pp. 253-262, vol. 58, No. 4.

Siddikee, Md. A., et al., "Halotolerant Bacteria with ACC Deaminase Activity Alleviate Salt Stress Effect in Canola Seed Germination," Journal of the Korean Society for Applied Biological Chemistry, 2015, pp. 237-241, vol. 58, Issue 2.

Singh, B., et al., "Microbial Phytases in Phosphorous Acquisition and Plant Growth Promotion," Physiology and Molecular Biology of Plants, 2011, pp. 93-103, vol. 17, Issue 2.

Singh, B., et al., "Plant Growth Promotion by an Extracellular HAP-Phytase of a Thermophilic Mold Sporotrichum thermophile," Applied Biochemistry and Biotechnology, 2010, pp. 1267-1276, vol. 160, Issue 5.

Smirnova, I., et al., "The Effect of Inoculation by Cellulolytic Bacteria Bacillus cytaseus on Wheat Productivity," Institute of Microbiology and Virology Ministry of Education and Science, Kazakhstan, Almaty, pp. 185-191.

Stearns, J. C., et al., "Effects of Bacterial ACC Deaminase on *Brassica napus* Gene Expression," Molecular Plant-Microbe Interactions, May 2012, pp. 668-676, vol. 25, No. 5.

Steichen, C. T., et al., "Non-Uniform Assembly of the Bacillus anthracis Exosporium and a Bottle Cap Model for Spore Germination and Outgrowth," Molecular Microbiology, Apr. 2007, pp. 359-367, vol. 64, Issue 2.

Tan, L., et al., "An Unusual Mechanism of Isopeptide Bond Formation Attaches the Collagenlike Glycoprotein BclA to the Exosporium of Bacillus anthracis," mBio, May-Jun. 2011, 20 pages, vol. 2, No. 3.

Tan, L., et al., "An Unusual Mechanism of Isopeptide Bond Formation Attaches the Collagenlike Glycoprotein BclA to be Exosporium of Bacillus anthracis," mBio, May-Jun. 2011, 20 pages, vol. 2, No. 3 (Retraction).

Tan, L., et al., "Sequence Motifs and Proteolytic Cleavage of the Collagen-Like Glycoprotein BclA Required for Its Attachment to the Exosporium of Bacillus anthracis," Journal of Bacteriology, Mar. 2010, pp. 1259-1268, vol. 192, No. 5.

Thomas, P., et al., "Endophytic Bacteria Associated with Growing Shoot Tips of Banana (*Musa* sp.) cv. Grand Naine and the Affinity of Endophytes to the Host," Microbial Ecology, 2009, pp. 952-964, vol. 58, No. 4.

Thompson, B. M., "The Role of the Glycoprotein BclB in the Exosporium in the Exosporium of Bacillus Anthracis," Doctoral Dissertation presented to the Department of Diagnostic Medicine/Pathobiology, College of Veterinary Medicine, Kansas State University, 2002, 178 pages.

Thompson, B. M. et al., "A System of Efficient, Cost-Effective, and Customizable Vaccines for Use with Multiple Vaccine Candidates," Oct. 2010 poster presentation, 1 page.

Thompson, B. M., et al., "Assembly of the BclB Glycoprotein into the Exosporium and Evidence for its Role in the Formation of the Exosporium 'cap' Structure in Bacillus anthracis," Molecular Microbiology, Dec. 2012, pp. 1073-1084, vol. 86, No. 5.

Thompson, B. M., et al., "Localization and Assembly of the Novel Exosporium Protein BetA of Bacillus anthracis," Journal of Bacteriology, 2011, pp. 5098-5104, vol. 193, No. 19.

Thompson, B. M., et al., "Targeting of the BclA and BclB Proteins to the Bacillus anthracis Spore Surface," Molecular Microbiology, 2008, pp. 421-434, vol. 70, No. 2.

Thompson, B. M., et al., "The BclB Glycoprotein of Bacillus anthracis is Involved in Exosporium Integrity," Journal of Bacteriology, 2007, pp. 6704-6713, vol. 189, No. 18.

Thompson, B. M., et al., "The Co-Dependence of BxpB/ExsFA and BclA for Proper Incorporation into the Exosporium of Bacillus anthracis," Molecular Microbiology, 2011, pp. 799-813, vol. 79, No. 3.

Thompson, B. M., "Amino-Terminal Sequences of the Bacillus anthracis Exosporium Proteins BclA and BclB Important for Localization and Attachment to the Spore Surface," A Thesis presented to the Faculty of the Graduate School at the University of Missouri-Columbia, Aug. 2008, 165 pages.

Timmusk, S., et al., "The Plant-Growth-Promoting Rhizobacterium Paenibacillus polymyxa Induces Changes in *Arabidopsis thaliana* Gene Expression: A Possible Connection Between Biotic and Abiotic Stress Responses," Molecular Plant-Microbe Interactions, Nov. 1999, pp. 951-959, vol. 12, No. 11.

Timmusk, S., et al., "Paenibacillus polymyxa Invades Plant Roots and Forms Biofilms," Applied and Environmental Microbiology, Nov. 2005, pp. 7292-7300, vol. 71, No. 11.

Trivedi, P., et al., "Plant Growth Promotion Abilities and Formulation of Bacillus megaterium Strain B 388 (MTCC6521) Isolated from a Temperate Himalayan Location," Indian Journal of Microbiology, 2008, pp. 342-347, vol. 48, No. 3.

Vendan, R. T., et al., "Diversity of Endophytic Bacteria in Ginseng and Their Potential for Plant Growth Promotion," Journal of Microbiology, 2010, pp. 559-565, vol. 48, No. 5.

Von Der Weid, I., et al., "Diversity of Paenibacillus polymyxa Strains Isolated from the Rhizosphere of Maize Planted in Cerrado Soil," Research in Microbiology, Jun. 2000, pp. 369-381, vol. 151, No. 5.

Walker, R., et al., "Colonization of the Developing Rhizosphere of Sugar Beet Seedlings by Potential Biocontrol Agents Applied as Seed Treatments," Journal of Applied Microbiology, 2002, pp. 228-237, vol. 92, No. 2.

Waller, L. N., et al., "Identification of a Second Collagen-Like Glycoprotein Produced by Bacillus anthracis and Demonstration of Associated Spore-Specific Sugars," Journal of Bacteriology, Jul. 2005, pp. 4592-4597, vol. 187, No. 13.

Wang, X., et al., "PLD: Phospholipase Ds in Plant Signaling," Springer, Phospholipases in Plant Signaling, Signaling and Communication in Plants 20, Springer-Verlag Berlin Heidelberg 2014.

Yadav, S., et al., "Diversity and Phylogeny of Plant Growth-Promoting Bacilli from Moderately Acidic Soil," Journal of Basic Microbiology, Feb. 2011, pp. 98-106, vol. 51, No. 1.

Yegorenkova, I. V., et al., "Paenibacillus polymyxa Rhizobacteria and Their Synthesized Exoglycans in Interaction With Wheat Roots: Colonization and Root Hair Deformation," Current Microbiology, 2013, pp. 481-486, vol. 66, No. 5.

Zeigler, D. R., "Bacillus thuringiensis and Bacillus cereus," Bacillus Genetic Stock Center Catalog of Strains, 1999, Seventh Edition, vol. 2, 58 pages.

Zhou, Z., et al., "Immunogenicity of Recombinant Bacillus subtilis Spores Expressing Clonorchis sinensis Tegumental Protein," Parasitology Research, 2008, pp. 293-297, vol. 102, Issue 2.

Zhou, Z., et al., "Oral Administration of a Bacillus subtilis Spore-Based Vaccine Expressing Clonorchis sinensis Tegumental Protein 22.3 kDa Confers Protection Against Clonorchis sinensis," Vaccine, 2008, pp. 1817-1825, vol. 26, Issue 15.

Zou, C., et al., "Bacillus megaterium Strain XTBG34 Promotes Plant Growth by Producing 2-pentylfuran," Journal of Microbiology, Aug. 2010, pp. 460-466, vol. 48, No. 4.

Diaz, K., et al., "Root-Promoting Rhizobacteria in Eucalyptus globulus Cuttings," World Journal of Microbiology and Biotechnology, 2009, pp. 867-873, vol. 25.

Egorov, M. A., et al., "Growth Stimulating Effect of a Bacilus megaterium Strain in the Greenhouse Experiment," Vestnik of Altay State Agricultural University, 2012, pp. 46-49, vol. 89, No. 3.

Frankel, A. E., et al., "Characterization of Diphtheria Fusion Proteins Targeted to the Human Interleukin-3 Receptor," Protein Engineering, 2000, pp. 575-581, vol. 13, No. 8.

GenBank Accession No. JX047442.1, "*Bacillus* sp. SDT11 16S ribosomal RNA gene, Partial Sequence," accessed from NCBI website at <http://www.ncbi.nlm.nih.gov/nuccore/JX047442.1> on Jul. 10, 2012, 1 page.

(56) References Cited

OTHER PUBLICATIONS

Pakula, A. A., et al., "Genetic Analysis of Protein Stability and Function," Annual Review of Genetics, 1989, pp. 289-310, vol. 23 (Abstract Only).

Siddikee, Md. A., et al., "Regulation of Ethylene Biosynthesis Under Salt Stress in Red Pepper (*Capsicum annuum* L.) by 1-Aminocyclopropane-1-Carboxylic Acid (ACC) Deaminase-Producing Halotolerant Bacteria," Journal of Plant Growth Regulation, 2012, pp. 265-272, vol. 31, Issue 2.

Wang, W., et al., "Comparative Proteomic Analysis of Rice Seedlings in Response to Inoculation with Bacillus cereus," Letters in Applied Microbiology, 2012, pp. 208-215, vol. 56, Issue 3.

Fan, L., et al., "Antisense Suppression of Phospholipase D(alpha) Retards Abscisic Acid- and Ethylene-Promoted Senescence of Postharvest *Arabidopsis* Leaves," The Plant Cell, Dec. 1997, pp. 2183-2196, vol. 9.

Glass, M., et al., "Endo-(beta)-1,4-Glucanases Impact Plant Cell Wall Development by Influencing Cellulose Crystallization," Journal of Integrative Plant Biology, Apr. 2015, pp. 396-410, vol. 57, Issue 4.

Hong, Y., et al., "Phospholipase D(alpha)3 Is Involved in the Hyperormotic Response in *Arabidopsis*," The Plant Cell, Mar. 2008, pp. 803-816, vol. 20.

Li, M., et al., Overexpression of Patatin-Related Phospholipase AIII(delta) Altered Plant Growth and Increased Seed Oil content in Camelina, Plant Biotechnology Journal, 2015, pp. 766-778, vol. 13.

Shani, Z., et al., "Growth Enhancement of Transgenic Poplar Plants by Overexpression of *Arabidopsis thaliana* Endo-1,4-beta-Glucanase (cel1)," Molecular Breeding, 2004, pp. 321-330, vol. 14.

Zhuang, X., et al., "New Advances in Plant Growth-Promoting Rhizobacteria for Bioremediation," Environmental International, 2007, pp. 406-413, vol. 33.

Johnson M. J., et al., "ExsY and CotY are Required for the Correct Assembly of the Exosporium and Spore Coat of Bacillus cereus," Journal of Bacteriology, 2006, pp. 7905-7913, vol. 188, No. 22.

Karakurt, H., et al., "Effects of indol-3-butyric acid (IBA), Plant Growth Promoting Rhizobacteria (PGPR) and Carbohydrates on Rooting of Hardwood Cutting of MM106 Apple Rootstock," African Journal of Agricultural Research, Feb. 2009, pp. 060-064, vol. 4, No. 2.

Karigar, C., et al., "Role of Microbial Enzymes in the Bioremediation of Pollutants: A Review," SAGE-Hindawi Access to Research Enzyme Research, vol. 2011, Article ID 805187, 11 pages.

Khan, Z., et al., "A Plant Growth Promoting Rhizobacterium, Paenibacillus polymyxa Strain GBR-1, Suppresses Root-Knot Nematode," Bioresource Technology, May 2008, pp. 3016-3023, vol. 99, No. 8.

Kim, J. F., et al., "Genome Sequence of the Polymyxin-Producing Plant-Probiotic Rhizobacterium Paenibacillus polymyxa E681," Journal of Bacteriology, 2010, pp. 6103-6104, vol. 192, No. 22.

Kim, J. H., et al., "Bacterial Surface Display of GFP(uv) on Bacillus subtilis Spores," Journal of Microbiology and Biotechnology, Apr. 2007, pp. 677-680, vol. 17, No. 4.

Kim, J. H., et al., "Spore-Displayed Streptavidin: A Live Diagnostic Tool in Biotechnology," Biochemical and Biophysical Research Communications, May 2005, pp. 210-214, vol. 331, No. 1.

Kishore, G. K., et al., "Phylloplane Bacteria Increase Seedling Emergence, Growth and Yield of Field-Grown Groundnut (*Arachis hypogaea* L.)," Letters in Applied Microbiology, 2005, pp. 260-268, vol. 40, No. 4.

Kong, Z., et al., "Effects of 1-Aminocyclopropane-1-Carboxylate (ACC) Deaminase-Overproducing Sinorhizobium meliloti on Plant Growth and Copper Tolerance of Medicago lupulina," Plant and Soil, Jun. 2015, pp. 383-398, vol. 391, Issue 1.

Lamsal, K., et al., "Application of Rhizobacteria for Plant Growth Promotion Effect and Biocontrol of Anthracnose Caused by Colletotrichum acutatum on Pepper," Mycobiology, Dec. 2012, pp. 244-251, vol. 40, No. 4.

Lee, S., et al., "Growth Promotion of Xanthium italicum by Application of Rhizobacterial Isolates of Bacillus aryabhattai in Microcosm Soil," Journal of Microbiology, Feb. 2012, pp. 45-49, vol. 50, No. 1.

Leite, H. A., et al., "Bacillus subtilis and Enterobacter cloacae Endophytes from Healthy *Theobroma cacao* L. Trees can Systemically Colonize Seedlings and Promote Growth," Applied Microbiology and Biotechnology, Dec. 2012, pages 2639-2651, vol. 97, No. 6.

Leski, T. A., et al., "Identification and Classification of bcl Genes and Proteins of Bacillus cereus Group Organisms and Their Application in Bacillus anthracis Detection and Fingerprinting," Applied and Environmental Microbiology, Nov. 2009, pp. 7163-7172, vol. 75, No. 22.

Leveau, J. H. J., et al., "Utilization of the Plant Hormone Indole-3-Acetic Acid for Growth by Pseydomonas putida Strain 1290," Applied and Environmental Microbiology, May 2005, pp. 2365-2371, vol. 71, No. 5.

Li, J., et al., "An ACC Deaminase Minus Mutant of Enterobacter cloacae UW4 No Longer Promotes Root Elongation," Current Microbiology, Aug. 2000, pp. 101-105, vol. 41, No. 2.

Li, W., et al., "Cloning of the Thermostable Cellulose Gene from the Newly Isolated Bacillus subtillus and its Expression in *Excherichia coli*," Molecular Biotechnology, 2008, pp. 195-201, vol. 40, No. 2.

Liu, J. L., et al., "Effects of Two Plant Growth-Promoting Rhizobacteria Containing 1-Aminocyclopropane-1-Carboxylate Deaminase on Oat Growth in Petroleum Contaminated Soil," International Journal of Environmental Science and Technology, Dec. 2015, pp. 3887-3894, vol. 12, Issue 12.

Liu, X. et al., "Colonization of Maize and Rice Plants by Strain Bacillus megaterium C4," Current Microbiology, 2006, pp. 186-190, vol. 52, No. 3.

Liu, Y., et al., "Study on Mechanisms of Colonization of Nitrogen-Fixing PGPB, Klebsiella pneumoniae NG14 on the Root Surface of Rice and the Formation of Biofilm," Current Microbiology, 2011, pp. 1113-1122, vol. 62, No. 4.

Lopez-Bucio, J., et al., "Bacillus megaterium Rhizobacteria Promote Growth and Alter Root-System Architecture Through an Auxin- and Ethylene-Independent Signaling Mechanism in *Arabidopsis thaliana*," Molecular Plant-Microbe Interactions, Feb. 2007, pp. 207-217, vol. 20, No. 2.

Luiz, W. B., et al., "Boosting Systemic and Secreted Antibody Responses in Mice Orally Immunized with Recombinant Bacillus subtilis Strains Following Parenteral Priming with a DNA Vaccine Encoding the Enterotoxigenic *Escherichia coli* (ETEC) CFA/I fimbriae B Subunit," Vaccine, 2008, pp. 3998-4005, vol. 26, No. 32.

Madmony, A., et al., "Enterobacter cloacae, An Obligatory Endophyte of Pollen Grains of Mediterranean Pines," Folia Microbiologica (Praha), 2005, pp. 209-216, vol. 50, No. 3.

Maes, M., et al., "Experiences and Perspectives for the Use of A Paenibacillus Strain as a Plant Protectant," Communications in Agricultural and Applied Biological Sciences, 2003, pp. 457-462, vol. 68, No. 4, Part B.

Marulanda, A., et al., "Regulation of Plasma Membrane Aquaporins by Inoculation with a Bacillus megaterium Strain in Maize (*Zea mays* L.) Plants Under Unstressed and Salt-Stressed Conditions," Planta, 2010, pp. 533-543, vol. 232, No. 2.

Mauriello, E. M., et al., "Display of Heterologous Antigens on the Bacillus subtilis Spore Coat Using CotC as a Fusion Partner," Vaccine, Mar. 2004, pp. 1177-1187, vol. 22, Nos. 9-10.

Medie, F. M., "Genome Analyses Highlight the Different Biological Roles of Cellulases," Nature Reviews Microbiology, Mar. 2012, pp. 227-234, vol. 10.

Meldau, D. G., et al., "A Native Plant Growth Promoting Bacterium, Bacillus sp.B55, Rescues Growth Performance of an Ethylene-Insensitive Plant Genotype in Nature," Frontiers in Plant Science, Jun. 2012, pp. 1-13, vol. 3, Article 112.

Mercado, J. A., et al., "Expression of the beta-1,3-glucanase Gene bgn13.1 from Trichoderma harzianum in Strawberry Increases Tolerance to Crown Rot Diseases but Interferes with Plant Growth," Transgenic Research, Dec. 2015, pp. 979-989, vol. 24, Issue 6.

(56) References Cited

OTHER PUBLICATIONS

Negri, A., et al., "Expression and Display of Clostridium difficile Protein FliD on the Surface of Bacillus subtilis Spores," Journal of Medical Microbiology, 2013, pp. 1379-1385, vol. 62.

Ngamau, C., "Endophytic Bacteria Associated with Bananas (*Musi* spp.) in Kenya and Their Potential as Biological Fertilizers," A thesis submitted in fulfillment for the degree of Doctor of Philosophy in Plant Science in the Jomo Kenyatta University of Agriculture and Technology, 2013, 191 pages.

Oh, T., et al., "Expression of Aspergillus nidulans phy Gene in Nicotiana benthamiana Produces Active Phytase with Broad Specificities," International Journal of Molecular Sciences, 2014, pp. 15571-15591, vol. 15, No. 9.

Ortiz-Castro, R., et al., "Plant Growth Promotion by Bacillus megaterium Involves Cytokinin Signaling," Plant Signaling & Behavior, 2008, pp. 263-265, vol. 3, Issue 4.

Paccez, J. D., et al., "Evaluation of Different Promoter Sequences and Antigen Sorting Signals on the Immunogenicity of Bacillus subtilis Vaccine Vehicles," Vaccine, 2007, pp. 4671-4680, vol. 25, No. 24.

Paccez, J. D., et al., "Stable Episomal Expression System Under Control of a Stress Inducible Promoter Enhances the Immunogenicity of Bacillus subtilis as a Vector for Antigen Delivery," Vaccine, 2006, pp. 2935-2943, vol. 24, No. 15.

Park, T. J., et al., "Spore Display Using Bacillus thuringiensis Exosporium Protein InhA," Journal of Microbiology and Biotechnology, May 2009, pp. 495-501, vol. 19, No. 5.

Park, T. J., "Surface-Display of Recombinant Proteins on Bacterial Exosporium and its Biotechnological Applications," Doctoral Thesis presented to the Department of Chemical and Biomolecular Engineering, Korea Advanced Institute of Science and Technology, 2004, 104 pages.

Peixoto, R. S., et al., "Petroleum-Degrading Enzymes: Bioremediation and New Prospects," SAGE-Hindawi Access to Research Enzyme Research, vol. 2011, Article ID 475193, 7 pages.

Penrose, D. M., et al., "Levels of ACC and Related Compounds in Exudate and Extracts of Canola Seeds Treated with ACC Deaminase-Containing Plant Growth-Promoting Bacteria," Canadian Journal of Microbiology, Apr. 2001, pp. 368-372, vol. 47, No. 4.

Pereira, C. E., et al., "Compatibility Among Fungicide Treatments on Soybean Seeds Through Film Coating and Inoculation with Bradyrhizobium Strains," Acta Scientiarum. Agronomy, Maringá, 2010, pp. 585-589, vol. 32, No. 4.

Petrov, K., et al., "High Production of 2,3-Butanediol from Glycerol by Klebsiella pneumoniae G31," Applied Microbiology and Biotechnology, 2009, pp. 659-665, vol. 84, No. 4.

Phi, Q. T., et al., "Assessment of Root-Associated Paenibacillus polymyxa Groups on Growth Promotion and Induced Systemic Resistance in Pepper," Journal of Microbiology and Biotechnology, Dec. 2010, pp. 1605-1613, vol. 20, No. 12.

Phitsuwan, P., et al., "Present and Potential Applications of Cellulases in Agriculture, Biotechnology, and Bioenergy," Folia Microbiologica, 2013, pp. 163-176, vol. 58, No. 2.

Pilar-Izquierdo, M. C., et al., "Barley Seed Coating with Free and Immobilized Alkaline Phosphatase to Improve P Uptake and Plant Growth," Journal of Agricultural Science, 2012, pp. 691-701, vol. 150, Issue 6.

Ping, R., et al., Abstract, Journal of Northwest Forestry College, 2005, pp. 78-79, vol. 20, No. 1.

Prusty, R., et al., "The Plant Hormone Indoleacetic Acid Induces Invasive Growth in *Saccharomyces cerevisiae*," Proceedings of the National Academy of Sciences of the United States of America, Mar. 2004, pp. 4153-4157, vol. 101, No. 12.

Raddadi, N., et al., "Screening of Plant Growth Promoting Traits of Bacillus thuringiensis," Annals of Microbiology, 2008, pp. 47-52, vol. 58, No. 1.

Rasco, D. A., et al., UniProt KB database entry Q738B1-Q7381_BACC1, Jul. 5, 2004, 6 pages (referencing Rasco, D. A., et al., "The Genome Sequence of Bacillus cereus ATCC 10987 Reveals Metabolic Adaptations and a Large Plasmid Related to Bacillus anthracis pX01.," Nucleic Acids Research, 2004, pp. 977-988, vol. 32).

Rajendran, G., et al., "Enhanced Growth and Nodulation of Pigeon Pea by Co-Inoculation of Bacillus Strains with Rhizobium spp," Bioresource Technology, 2007, pp. 4544-4550, vol. 99, No. 11.

Rajkumar, M., et al., "Effects of Inoculation of Plant-Growth Promoting Bacteria on Ni Uptake by Indian Mustard," Bioresource Technology, 2008, pp. 3491-3498, vol. 99, No. 9.

Rao, M. A., et al., "Role of Enzymes in the Remediation of Polluted Environments," Journal of Soil Science and Plant Nutrition, 2010, 21 pages, vol. 10, No. 3.

Ahemad, M., et al., "Mechanisms and Applications of Plant Growth Promoting Rhizobacteria: Current Perspective," Journal of King Saud University—Science, 2014, pp. 1-20, vol. 26.

Anand, R., et al., "N2-Fixation and Seedling Growth Promotion of Lodgepole Pine by Endophytic Paenibacillus polymyxa," Microbial Ecology, 2013, pp. 369-374, vol. 66, No. 2.

Bae, C., et al., Multiple Classes of Immune Related Ptoteases Associated with the Cell Death Response in Pepper Plants, PLOS One, 2013, vol. 8, No. 5, e63533.

Bent, E., et al., "Alterations in Plant Growth and in Root Hormone Levels of Lodgepole Pines Inoculated with Rhizobacteria," Canadian Journal of Microbiology, Sep. 2001, pp. 793-800, vol. 47, No. 9.

Berlemont, R., et al., "Phylogenetic Distribution of Potential Cellulases in Bacteria," Applied and Environmental Microbiology, Mar. 2013, pp. 1545-1554, vol. 79, No. 5.

Boydston, J. A., et al., "The ExsY Protein is Required for Complete Formation of the Exosporium of Bacillus anthracis," Journal of Bacteriology, 2006, pp. 7440-7448, vol. 188, No. 21.

Chakraborty, U., et al., "Plant Growth Promotion and Induction of Resistance in Camellia sinensis by Bacillus megaterium," Journal of Basic Microbiology, 2006, pp. 186-195, vol. 46, No. 3.

Chapman, K. D., "Phospholipase Activity During Plant Growth and Development and in Response to Environmental Stress," Trends in Plant Science, Nov. 1998, pp. 419-426, vol. 3, Issue 11.

Choudhary, D. K., et al., "Interactions of Bacillus spp. and Plants—With Special Reference to Induced Systemic Resistance (ISR)," Microbiological Research, 2009, pp. 493-513, vol. 164.

Ciabattini, A., et al., "Oral Priming of Mice by Recombinant Spores of Bacillus subtilis," Vaccine, Oct. 2004, pp. 4139-4143, vol. 22, Nos. 31-32.

Corbineau, F. And Côme, D., "Improvement of Germination of Terminalia Ivorensis Seeds," Forest Genetic Resources Information No. 21, http://www.fao.org/docrep/006/v3030e/V3030E10.htm, 7 pages.

Da Mota, F. F., et al., "Auxin Production and Detection of the Gene Coding for the Auxin Efflux Carrier (AEC) Protein in Paenibacillus polymyxa," Journal of Microbiology, Jun. 2008, pp. 257-264, vol. 46, No. 3.

De Freitas, J. R., et al., "Phosphate-solubilizing Rhizobacteria Enhance the Growth and Yield but not Phosphorus Uptake of Canola (*Brassica napus* L.)," Biology and Fertility of Soils, May 1997, pp. 358-364, vol. 24, Issue 4.

Ding, Y., et al., "Isolation and Identification of Nitrogen-Fixing Bacilli from Plant Rhizospheres in Beijing Region," Journal of Applied Microbiology, 2005, pp. 1271-1281, vol. 99, No. 5.

Dong, Y.-H., et al., "Identification of Quorum-Quenching N-Acyl Homoserine Lactonases from *Bacillus* Species," Applied and Environmental Microbiology, 2002, pp. 1754-1759, vol. 68, No. 4.

Doronina, N. V., et al., "Emended Description of Paracoccus kondratievae," International Journal of Systematic and Evolutionary Microbiology, Mar. 2002, pp. 679-682, vol. 52, Part 2.

Dourado, M., et al., "Biotechnological and Agronomic Potential of Endophytic Pink-Pigmented Methylotrophic Methylobacterium spp.," BioMed Research International, vol. 2015, Article ID 909016, 19 pages.

Dowd, P. E., et al., "The Emerging Roles of Phospholipase C in Plant Growth and Development," Lipid Signaling in Plants, 2010, pp. 23-37, vol. 16.

Duc Le H., et al., "Bacterial Spores as Vaccine Vehicles," Infection and Immunity, May 2003, pp. 2810-2818, vol. 71, No. 5.

(56) References Cited

OTHER PUBLICATIONS

Duc, Le H., et al., "Immunization Against Anthrax Using Bacillus subtilis Spores Expressing the Anthrax Protective Antigen," Vaccine, Jan. 2007, pp. 346-355, vol. 25, No. 2.
English, M. M., et al., "Overexpression of hns in the Plant Growth-Promoting Bacterium Enterobacter cloacae UW5 Increases Root Colonization," Journal of Applied Microbiology, 2009, pp. 2180-2190, vol. 108, Issue 6.
Erturk, Y., et al., "Effects of Plant Growth Promoting Rhizobacteria (PGPR) on Rooting and Root Growth of Kiwifruit (*Actinidia deliciosa*) Stem Cuttings," Biological Research, 2010, pp. 91-98, vol. 43, No. 1.
Faria, D. C., et al., "Endophytic Bacteria Isolated from Orchid and Their Potential to Promote Plant Growth," World Journal of Microbiology & Biotechnology, 2013, pp. 217-221, vol. 29, No. 2.
Feng, F. et al., "Display of Human Proinsulin on the Bacillus subtilis Spore Surface for Oral Administration," Current Microbiology, Jul. 2013, pp. 1-8, vol. 67, Issue 1.
Forage, R. G., et al., "Glycerol Fermentation in Klebsiella pneumoniae: Functions of the Coenzyme B12-Dependent Glycerol and Diol Dehydratases," Journal of Bacteriology, Feb. 1982, pp. 413-419, vol. 149, No. 2.
Gamalero, E., et al., "Bacterial Modulation of Plant Ethylene Levels," Plant Physiology, Sep. 2015, pp. 13-22, vol. 169, Issue 1.
Glick, B. R., "Modulation of Plant Ethylene Levels by the Bacterial Enzyme ACC Deaminase," FEMS Microbiology Letters, Oct. 2005, pp. 1-7, vol. 251, Issue 1.
Gnanaraj, M., et al. "Isolation and Gene Expression Analysis of Phospholipase C in Response to Abiotic Stresses from *Vigna radiata* (L.) Wilczek," Indian Journal of Experimental Biology, Jun. 2015, pp. 335-341, vol. 53.
Goldberg, L. J., et al., "A Bacterial Spore Demonstrating Rapid Larvicidal Activity Against Anopheles Sergentii, Uranotaenia Unguiculata, Culex Univitattus, Aedes Aegypti and Culex Pipiens," Mosquito News, Sep. 1977, pp. 355-358, vol. 37, No. 3.
Guerchicoff, A., et al., "Identification and Characterization of a Previously Undescribed cyt Gene in *Bacillus thuringiensis* subsp. *israelensis*," Applied and Environmental Microbiology, Jul. 1997, pp. 2716-2721, vol. 63, No. 7.
Gujar, P. D., et al., "Effect of Phytase from Aspergillus niger on Plant Growth and Mineral Assimilation in Wheat (*Triticum aestivum* Linn.) and its Potential for Use as a Soil Amendment," Journal of the Science of Food and Agriculture, 2013, pp. 2242-2247, vol. 93, Issue 9.
Hafeez, F. Y., et al., "PGPR: Versatile Tool to Combat Soil Borne Pathogens and Improve Plant Health," Aspects of Applied Biology, 2011, pp. 241-245, vol. 106.
Haggag, W. M., et al., "Colonization of Peanut Roots by Biofilm-Forming Paenibacillus polymyxa Initiates Biocontrol Against Crown Rot Disease," Journal of Applied Microbiology, 2008, pp. 961-969, vol. 104, No. 4.
Han, W. et al., "The Application of Exogenous Cellulase to Improve Soil Fertility and Plant Growth Due to Acceleration of Straw Decomposition," Bioresource Technology, May 2010, pp. 3724-3731, vol. 101, Issue 10.
Hartati, S., et al., "Overexpression of Poplar Cellulase Accelerates Growth and Disturbs The Closing Movements of Leaves in Sengon," Plant Physiology, 2008, pp. 552-561, vol. 147, Issue 2.
Hinton, D. M., et al., "Enterobacter cloacae is an Endophytic Symbiont of Corn", Mycopathologia, 1995, pp. 117-125, vol. 129, No. 2.
Hoelscher, B., et al., "Removal of Toxic Contaminants from Polluted Soil and Water via Enzyme-Linked Bacillus Spores," Poster presented at Missouri Life Sciences Week Research Poster Session, Apr. 14, 2010.
Hong, Y. et al., "Phospholipases in Plant Response to Nitrogen and Phosphorus Availability," Springer, Phospholipases in Plant Signaling and Communication in Plants, 2013, pp. 159-180, vol. 20.
Hontzeas, N., et al., "Changes in Gene Expression in Canola Roots Induced by ACC-Deaminase-Containing Plant-Growth-Promoting Bacteria," Molecular Plant-Microbe Interactions, Aug. 2004, pp. 865-871, vol. 17, No. 8.
Howard, G., et al., "Effects of Cellulolytic Ruminol Bacteria and of Cell Extracts on Germination of *Euonymus americanus* L. Seeds," Applied and Environmental Microbiology, Jan. 1988, pp. 218-224, vol. 54, No. 1.
Idriss, E. E., et al., "Extraccellular Phytase Activity of Bacillus amyloliquefaciens FZB45 Contributes to its Plant-Growth-Promoting Effect," Microbiology, 2002, pp. 2097-2109, vol. 148.
Iniguez, A. L., et al., "Nitrogen Fixation in Wheat Provided by Klebsiella pneumoniae 342," Molecular Plant-Microbe Interactions, Oct. 2004, pp. 1078-1085, vol. 17, No. 10.
Invitation to Pay Additional Fees and, Where Applicable, Protest Fees, issued for PCT/US2015/050795, dated Jan. 14, 2016, 8 pages.
International Search Report and Written Opinion issued for PCT/US2015/050795, dated Mar. 31, 2016, 17 pages.
International Search Report and Written Opinion issued for PCT/US2015/050807, dated Dec. 10, 2015, 12 pages.
Islam, M. R., et al., "Characterization of Plant Growth-Promoting Traits of Free-Living Diazotrophic Bacteria and Their Inoculation Effects on Growth and Nitrogen Uptake of Crop Plants," Journal of Microbiology and Biotechnology, Oct. 2009, pp. 1213-1222, vol. 19, No. 10.
Isticato, R., et al., "Surface Display of Recombinant Proteins on Bacillus subtilis Spores," Journal of Bacteriology, Nov. 2001, pp. 6294-6301, vol. 183, No. 21.
Iwanicki, A., et al., "A System of Vectors for Bacillus subtilis Spore Surface Display," Microbial Cell Factories, 2014, pp. 1-9, vol. 13, No. 30.
Jackson, W. T., "Effect of Pectinase and Cellulase Preparations on the Growth and Development of Root Hairs," Physiologia Plantarum, 2006 (first published in 1959), pp. 502-510, vol. 12.
Jeong, H., et al., "Draft Genome Sequence of the Paenibacillus polymyxa Type Strain (ATCC 842T), A Plant Growth-Promoting Bacterium," Journal of Bacteriology, 2011, pp. 5026-5027, vol. 193, No. 18.
U.S. Appl. No. 14/849,123, filed Sep. 9, 2015.
U.S. Appl. No. 14/849,295, filed Sep. 9, 2015.
U.S. Appl. No. 15/211,044, filed Jul. 15, 2016.
U.S. Appl. No. 14/775,858, filed Sep. 14, 2015.
U.S. Appl. No. 15/414,050, filed Jan. 24, 2017.
U.S. Appl. No. 15/846,487, filed Dec. 19, 2017.
U.S. Appl. No. 15/511,839, filed Mar. 16, 2017.
U.S. Appl. No. 15/511,822, filed Mar. 16, 2017.
U.S. Appl. No. 15/511,854, filed Mar. 16, 2017.
U.S. Appl. No. 15/511,835, filed Mar. 16, 2017.
U.S. Appl. No. 15/511,864, filed Mar. 16, 2017.
U.S. Appl. No. 15/511,844, filed Mar. 16, 2017.
U.S. Appl. No. 15/460,468, filed Mar. 16, 2017.
U.S. Appl. No. 15/461,188, filed Mar. 16, 2017.
U.S. Appl. No. 62/460,250, filed Feb. 17, 2017.
U.S. Appl. No. 62/560,876, filed Sep. 20, 2017.

FIG. 1A

| | SEQ ID NO. | 20-35 %Identity | 25-35 %Identity |
|---|---|---|---|
| MSNNNYSNGLMFDESLSASAFTDPNLVGPTLPPITLPPFTLPFTG | 1 | 100% | 100% |
| MSEKYIILHGTALEPNLIGPTLPPITLPPFTFPNG | 3 | 81.3% | 90.9% |
| MVKVVEGNGGKSKIKSPLNSNFKILSDLVGPTFPPVPTGMTGIT | 5 | 50.0% | 72.7% |
| MKQNDKLWLDKGIIGPENIGPTFPVLPPIHIPPTG | 7 | 43.8% | 54.5% |
| MDEFLSSAALNPGSVGPTLPFMQPFQFRTG | 9 | 62.5% | 72.7% |
| MFDKNEIQKINGILQANALNPNLIGPTLPPITLPPTLPTG | 11 | 81.3% | 90.9% |
| MFDKNEMKKTNEVLQANALDPNIIGPTLPPITLPPTLPTG | 13 | 81.3% | 81.8% |
| MSRKDKFNRSRMSRKDRFNSPKIKSEISISPDLVGPTFPPIPSFTLPTG | 15 | 62.5% | 81.8% |
| MNEEYSILHGEALEPNLIGPTLPSIPPFTFPPTG | 17 | 75.0% | 81.8% |
| MKNRENNRKQNSLSSNFRIPPELIGPTFPVFTGFTGIG | 19 | 50.0% | 63.6% |
| MSDKHQMKKISEVLQANALDPNLIGPTLPFITPFTFPTG | 21 | 75.0% | 72.7% |
| MDEFLSFAALNPGSIGPTLPFVFPFQFPTG | 23 | 62.5% | 72.7% |
| MDEFLSSTALNPCSIGPTLPFMQPFQFPTG | 25 | 56.2% | 63.6% |
| MKERDRQNSLNSNFRISPNLIGPTFPVPTGIG | 27 | 56.2% | 63.6% |
| VFDKMEIQKINGILQANALNPNLIGPTLPPITLPPFLPTG | 29 | 81.3% | 90.9% |
| MDEFLYFAALNPGSIGPTLPPVQPFQPFQPTG | 31 | 56.2% | 63.6% |
| MDSKNIGPTFPLPSINFPG | 33 | 43.8% | 54.5% |
| MIGPENIGPTFFILPPIYIPFG | 35 | 43.8% | 54.5% |
| MSNNNIPSPFFNFNPELIGPTFPPITPLTLFTG | 43 | 68.8% | 81.8% |
| MFSEKKRKDLIFDNFLGAPALDPNLIGPTFPPIPSFTLFTG | 45 | 75.0% | 72.7% |
| MTRKOKFNRSRIGRPDRFNSPKIKSELISPDLVGPTFPPIPSFTLPTG | 47 | 62.5% | 81.8% |
| MSKKDRFNSPKIKSEISISPDLVGPTFPPIPSFTLPTG | 49 | 62.5% | 81.8% |
| MKERDNKGKQHSLNSNFRIPPELIGPTFPVPTGFTGIG | 51 | 50.0% | 63.6% |
| MRERDNKRQQHSLNPNNFRISPELIGPTFPPVPTGTGIG | 53 | 50.0% | 63.6% |
| MKNRDNKGKQQSNFRIPPELIGPTFPPVPTGFTGIG | 55 | 50.0% | 63.6% |
| MKFSKKSTVDSSIVGKRVVSKVNILRPYDAPSCQDKDVDGFVDVGELFTIFRKLNMEGSVQFKAHNSI GKTYYITINEVYVFVTVLLQYSTLIGGSYVFDNMEIQKINGILQANALNPNLIGPTLPPITLPPFTLPTG | 57 | 81.3% | 90.9% |

FIG. 1B

| | SEQ ID NO. | 20-35 %Identity | 25-35 %Identity |
|---|---|---|---|
| MSNNYSNGLNPDESLSASAFDPNLVGPTLPPIPPETLPTG | 1 | 100% | 100% |
| MKERDKQNSLNSNFRISPNLIGPTFPPVPTGFTGIG | 59 | 56.2% | 63.6% |
| MMENKKGSKHNEFLSAKAFNPNLVGPTLPPVPSFTLPTG | 61 | 81.3% | 81.8% |
| MSNNYSDGLNPDEFLSASAFDPNLVGPTLPPIPPETLPTG | 63 | 100% | 100% |
| MDEFLSSAAINPNLVGPTLPPVPPFTLPTG | 65 | 81.3% | 90.9% |
| MFDKNKILQANAFNSNLIGPTLPPIPPFTLPTG | 67 | 81.3% | 90.9% |
| MSDENEKKYSNELAQADFISAAAFDPSLVGPTLPPTPPFTLPTG | 69 | 87.5% | 90.9% |
| MSRKDRFNSPKIKSEISISPDLVGPTFPPIPSFTLPTG | 71 | 62.5% | 81.8% |
| MDEFLSSAALNPGSVGPTLPPMQPFQFSTG | 73 | 62.5% | 72.7% |
| MFLGGGYMERKNKWYGLNSNVNLSASSFDPNLVGPTLPPISPISVPTG | 75 | 87.5% | 90.9% |
| MDELLSSTLINPDLLGPTLPAIPPFTLPTG | 77 | 62.5% | 81.8% |
| MKNRDNNRKQNSLSSNFRIPPELIGPTFPPVPTGFTGIG | 79 | 50.0% | 63.6% |
| MVKVVEGNSGKSKIKSSLNSNFKLSSGLVGPTFPPVPTGMTGIT | 81 | 50.0% | 72.7% |
| MEGNGGKSKIKSPLNSNFKILSDIVGPTFPPVPTGMTGIT | 83 | 50.0% | 72.7% |
| MKQNDKLWLDKGIIGPENIGPTFPPVLPPIHIPPTG | 85 | 43.8% | 54.5% |
| MNSNEKLSLNKGMVRPENIGPTFPVLPPIYIPTG | 87 | 43.8% | 54.5% |
| MKRNDNLSLNKGMIGPENIGPTFPILPPIYIPPTG | 89 | 43.8% | 54.5% |
| MDSFVDVGEIFTIFRKLNMEGSLQFKVHNS | 91 | 81.3% | 90.9% |
| MGKTYYITINEVYYVFVTVLLQYSTLIGGSYVFDKNEIQKINGILQANALNPNLIGPTLPPIPPFTLPTG | | | |
| MKFSKKSTVDSSIVGKRVVSKVNILRFYDARSWQDKDVDGFVDVGELFTIFRKLNMEGSVQFKAHNSI | | | |
| GKTYYITINEVYYVFVTVLLQYSTLIGGSYVFDKNEIQKINGILQANALNPNLIGPTLPPIPPFTLPTG | 93 | 81.3% | 90.9% |

FUSION PROTEINS, RECOMBINANT BACTERIA, AND METHODS FOR USING RECOMBINANT BACTERIA

CROSS REFERENCE TO RELATED APPLICATIONS

This application is a continuation of U.S. Non-Provisional patent application Ser. No. 14/857,606, filed Sep. 17, 2015, which claims priority to U.S. Provisional Application No. 62/051,885, filed Sep. 17, 2014. Each of the above-cited applications is incorporated herein by reference in its entirety.

REFERENCE TO SEQUENCE LISTING SUBMITTED ELECTRONICALLY

The official copy of the sequence listing is submitted electronically via EFS-Web as an ASCII-formatted sequence listing with a file named "3005.US Gene Sequence Listing.txt" created on Sep. 10, 2015, and having a size of 488 kilobytes, and is filed concurrently with the specification. The sequence listing contained in this ASCII-formatted document is part of the specification and is herein incorporated by reference in its entirety.

FIELD OF THE INVENTION

The present invention generally relates to fusion proteins containing a targeting sequence, an exosporium protein, or an exosporium protein fragment that targets the fusion protein to the exosporium of a *Bacillus cereus* family member. The invention also relates to recombinant *Bacillus cereus* family members expressing such fusion proteins, formulations containing the recombinant *Bacillus cereus* family members, seeds coated with the recombinant *Bacillus cereus* family members, and methods for using the recombinant *Bacillus cereus* family members (e.g., for stimulating plant growth, protecting a plant from a pathogen, enhancing stress resistance in a plant, immobilizing a recombinant *Bacillus cereus* family member spore on a plant, stimulating germination of plant seeds, and delivering nucleic acids to plants). The invention additionally relates to recombinant *Bacillus cereus* family members that overexpress a protease or a nuclease, wherein overexpression of the protease or nuclease partially or completely inactivates spores of the *Bacillus cereus* family member or renders the spores more susceptible to physical or chemical inactivation. The present invention further relates to recombinant *Bacillus cereus* family members that overexpress exosporium proteins, seeds coated with such recombinant *Bacillus cereus* family members, and methods of using such recombinant *Bacillus cereus* family members (e.g., for stimulating plant growth, enhancing stress resistance in plants, and protecting plants from pathogens).

The invention further relates to various modifications of the recombinant *Bacillus cereus* family members that express the fusion proteins, including: (i) overexpression of modulator proteins that modulate the expression of the fusion protein in the recombinant *Bacillus cereus* members; (ii) genetic inactivation of the recombinant *Bacillus cereus* family members; and (iii) mutations or other genetic alterations of the recombinant *Bacillus cereus* family members that allow for the collection of exosporium fragments containing the fusion protein. The invention also relates to various methods for using the exosporium fragments.

The invention further relates to fusion proteins comprising a spore coat protein and a protein or peptide of interest, recombinant bacteria that express such fusion proteins, seeds coated with such recombinant bacteria, and methods for using such recombinant bacteria (e.g., for stimulating plant growth, protecting a plant from a pathogen, enhancing stress resistance in a plant, immobilizing a recombinant bacterial spore on a plant, stimulating germination of plant seeds, and delivering nucleic acids to plants).

The present invention further relates to biologically pure bacterial cultures of novel strains of bacteria.

The present invention additionally relates to plant seeds coated with an enzyme that catalyzes the production of nitric oxide or a superoxide dismutase, or with a recombinant spore-forming bacterium that overexpresses an enzyme that catalyzes the production of nitric oxide or a superoxide dismutase.

The invention also relates to methods for delivering beneficial bacteria and enzymes or vaccines to animals, and other methods of use.

BACKGROUND OF THE INVENTION

Within the zone surrounding a plant's roots is a region called the rhizosphere. In the rhizosphere, bacteria, fungi, and other organisms compete for nutrients and for binding to the root structures of the plant. Both detrimental and beneficial bacteria and fungi can occupy the rhizosphere. The bacteria, fungi, and the root system of the plant can all be influenced by the actions of peptides, enzymes, and other proteins in the rhizosphere. Augmentation of soil or treatment of plants with certain of these peptides, enzymes, or other proteins would have beneficial effects on the overall populations of beneficial soil bacteria and fungi, create a healthier overall soil environment for plant growth, improve plant growth, and provide for the protection of plants against certain bacterial and fungal pathogens. However, previous attempts to introduce peptides, enzymes, and other proteins into soil to induce such beneficial effects on plants have been hampered by the low survival of enzymes, proteins, and peptides in soil. Additionally, the prevalence of proteases naturally present in the soil leads to degradation of the proteins in the soil. The environment around the roots of a plant (the rhizosphere) is a unique mixture of bacteria, fungi, nutrients, and roots that has different qualities than that of native soil. The symbiotic relationship between these organisms is unique, and could be altered for the better with inclusion of exogenous proteins. The high concentration of fungi and bacteria in the rhizosphere causes even greater degradation of proteins due to abnormally high levels of proteases and other elements detrimental to proteins in the soil. In addition, enzymes and other proteins introduced into soil can dissipate away from plant roots quickly.

Thus, there exists a need in the art for a method for effectively delivering peptides, enzymes, and other proteins to plants (e.g., to plant root systems) and for extending the period of time during which such molecules remain active. Furthermore, there exists a need in the art for a method of selectively targeting such peptides, enzymes, and proteins to the rhizosphere and to plant leaves and plant roots in particular.

SUMMARY OF THE INVENTION

The features of the invention are defined in the appended claims. Other objects and features will be in part apparent and in part pointed out hereinafter.

BRIEF DESCRIPTION OF THE DRAWINGS

FIGS. 1A and 1B show alignments of the amino acid sequence of an amino-terminal portion of *Bacillus anthracis* Sterne strain BclA and with the corresponding region from various exosporium proteins from *Bacillus cereus* family members.

DEFINITIONS

Figure 2:
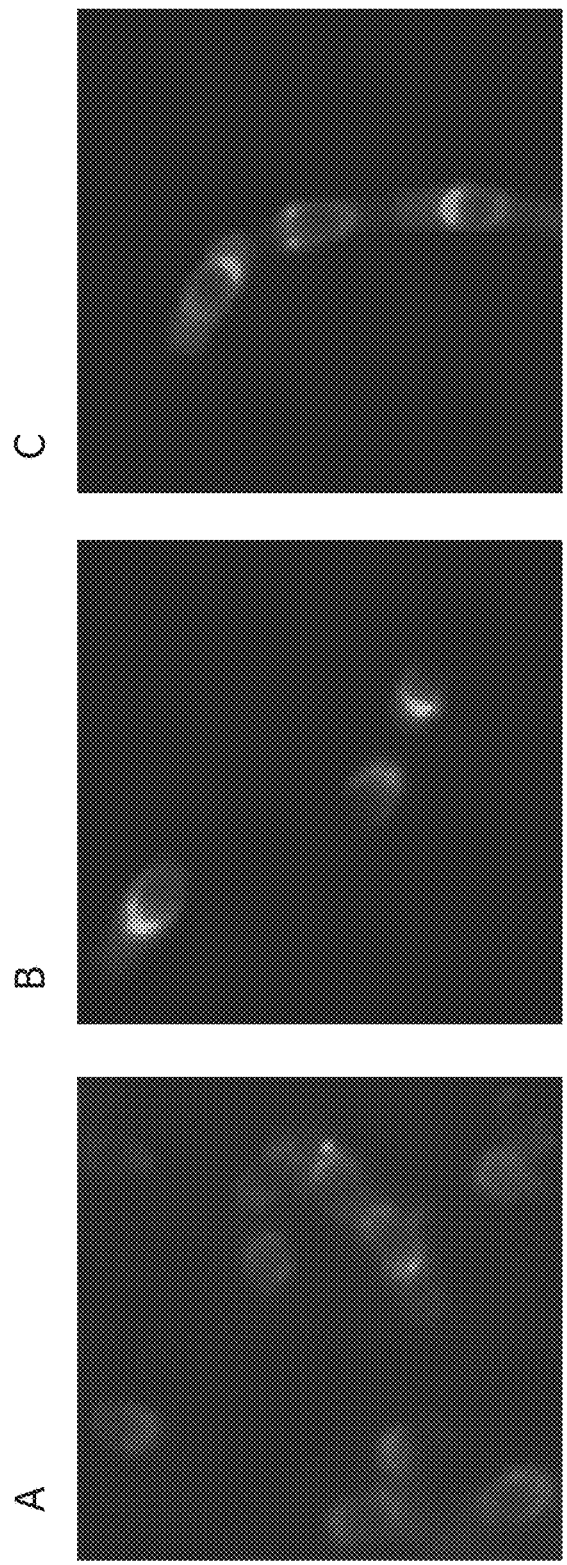
FIG. 2 shows exemplary fluorescent microscopy results for the expression of fusion proteins containing various exosporium proteins linked to an mCherry reporter on the exosporium of a recombinant *Bacillus cereus* family member.

When the articles "a," "an," "one," "the," and "said" are used herein, the mean "at least one" or "one or more" unless otherwise indicated.

The terms "agriculturally acceptable carrier" and "carrier" are used interchangeably herein.

The term "animal" encompasses any non-human animal as well as humans. For example, where the term "animal" is used herein, the animal can be a mammal (e.g., a human, a sheep, goat, cow, pig, deer, alpaca, bison, camel, donkey, horse, mule, llama, rabbit, dog, or cat), a bird (e.g., a chicken, turkey, duck, goose, quail, or pheasant), a fish (e.g., almon, trout, tilapia, tuna, catfish, or a carp), or a crustacean (e.g., a shrimp, prawn, lobster, crab, or crayfish).

A "biologically pure bacterial culture" refers to a culture of bacteria containing no other bacterial species in quantities sufficient to interfere with the replication of the culture or be detected by normal bacteriological techniques. Stated another way, it is a culture wherein virtually all of the bacterial cells present are of the selected strain.

The terms "comprising," "including," and "having" are intended to be inclusive and mean that there may be additional elements other than the listed elements.

The term "bioactive peptide" refers to any peptide that exerts a biological activity. "Bioactive peptides" can be generated, for example, via the cleavage of a protein, peptide, proprotein, or preproprotein by a protease or peptidase.

The term "effective amount" refers to a quantity which is sufficient to result in a statistically significant increase of growth and/or of protein yield and/or of grain yield of a plant as compared to the growth, protein yield and grain yield of the control-treated plant.

An "enzyme involved in the production or activation of a plant growth stimulating compound" includes any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure to an active or more active form of the compound. Such compounds include, for example, but are not limited to, small molecule plant hormones such as auxins and cytokinins, bioactive peptides, and small plant growth stimulating molecules synthesized by bacteria or fungi in the rhizosphere (e.g., 2,3-butanediol).

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "germination rate" as used herein refers to the number of seeds that germinate during a particular time period. For example, a germination rate of 85% indicates that 85 out of 100 seeds germinate during a given time period.

The term "inactivate" or "inactivation" as used herein in reference to the inactivation of spores of a recombinant *Bacillus cereus* family member or a recombinant spore-forming bacterium means that the spores are unable to germinate, or that the spores can germinate, but are damaged such that germination does not result in a living bacterium. The terms "partially inactivate" or "partial inactivation" mean that a percentage of the spores are inactivated, but that some spores retain the ability to germinate and return to a live, replicating state. The term "genetic inactivation" refers to inactivation of spores a recombinant *Bacillus cereus* family member or recombinant spore-forming bacterium by a mutation of the spore's DNA that results in complete or partial inactivation of the spore. The terms "physical inactivation" and "chemical inactivation refer to inactivation of spores using any physical or chemical means, e.g., by heat treatment, gamma irradiation, x-ray irradiation, UV-A irradiation, UV-B irradiation, or treatment with a solvent such as gluteraldehyde, formaldehyde, hydrogen peroxide, acetic acid, bleach, chloroform, or phenol, or any combination thereof.

The terms "immobilizing a recombinant *Bacillus cereus* family member spore on a plant" and "immobilizing a spore of a recombinant spore-forming bacterium on a plant" refers to the binding of a recombinant *Bacillus cereus* family member spore or a spore of a recombinant spore-forming bacterium to plant, e.g., to a root of a plant or to an aerial portion of a plant such as a leaf, stem, flower, or fruit, such that the spore is maintained at the plant's root structure or aerial portion instead of dissipating into the plant growth medium or into the environment surrounding the aerial portions of the plant.

The term "inoculant" as described in this invention is defined in several Federal, or State regulations as (1) "soil or plant inoculants shall include any carrier or culture of a specific micro-organism or mixture of micro-organisms represented to improve the soil or the growth, quality, or yield of plants, and shall also include any seed or fertilizer represented to be inoculated with such a culture" (New York State 10-A Consolidated Law); (2) "substances other than fertilizers, manufactured, sold or represented for use in the improvement of the physical condition of the soil or to aid plant growth or crop yields" (Canada Fertilizers Act); (3) "a formulation containing pure or predetermined mixtures of living bacteria, fungi or virus particles for the treatment of seed, seedlings or other plant propagation material for the purpose of enhancing the growth capabilities or disease resistance or otherwise altering the properties of the eventual plants or crop" (Ad hoc European Working Group, 1997) or (4) "meaning any chemical or biological substance of mixture of substances or device distributed in this state to be applied to soil, plants or seeds for soil corrective purposes; or which is intended to improve germination, growth, quality, yield, product quality, reproduction, flavor, or other desirable characteristics of plants or which is intended to produce any chemical, biochemical, biological or physical change in soil" (Section 14513 of the California Food and Agriculture Code).

A "modulator protein" includes any protein that, when overexpressed in a *Bacillus cereus* family member expressing any of the fusion proteins described herein, modulates expression of the fusion protein, such that the expression of the fusion protein is increased or decreased as compared to expression of the fusion protein in a *Bacillus cereus* family member that does not overexpress the modulator protein.

A "plant growth medium" includes any material that is capable of supporting the growth of a plant.

A "plant immune system enhancer protein or peptide" as used herein includes any protein or peptide that has a beneficial effect on the immune system of a plant.

The term "plant growth stimulating protein or peptide" as used herein includes any protein or peptide that increases plant growth in a plant exposed to the protein or peptide.

The term "probiotic" as used herein refers to microorganisms (e.g., bacteria) that provide health benefits when consumed by or administered to an animal.

The terms "promoting plant growth" and "stimulating plant growth" are used interchangeably herein, and refer to the ability to enhance or increase at least one of the plant's height, weight, leaf size, root size, or stem size, to increase protein yield from the plant or to increase grain yield of the plant.

A "protein or peptide that protects a plant from a pathogen" as used herein includes any protein or peptide that makes a plant exposed to the protein or peptide less susceptible to infection with a pathogen.

A "protein or peptide that enhances stress resistance in a plant" as used herein includes any protein or peptide that makes a plant exposed to the protein or peptide more resistant to stress.

The term "plant binding protein or peptide" refers to any peptide or protein capable of specifically or non-specifically binding to any part of a plant (e.g., roots or aerial portions of a plant such as leaves foliage, stems, flowers, or fruits) or to plant matter.

The term "pyrethrinase" refers to any enzyme that degrades a pyrethrin or a pyrethroid.

The term "rhizosphere" is used interchangeably with "root zone" to denote that segment of the soil that surrounds the roots of a plant and is influenced by them.

The term "targeting sequence" as used herein refers to a polypeptide sequence that, when present as part of a longer polypeptide or a protein, results in the localization of the longer polypeptide or the protein to a specific subcellular location. The targeting sequences described herein result in localization of proteins to the exosporium of a *Bacillus cereus* family member.

DESCRIPTION OF THE INVENTION

I. Fusion Proteins for Expression in *Bacillus Cereus* Family Members and Recombinant *Bacillus Cereus* Family Members Expressing Such Fusion Proteins The present invention relates to fusion proteins comprising a targeting sequence, an exosporium protein, or an exosporium protein fragment targets the fusion protein to the exosporium of a *Bacillus cereus* family member and at least one protein or peptide of interest. When expressed in *Bacillus cereus* family member bacteria, these fusion proteins are targeted to the exosporium layer of the spore and are physically oriented such that the protein or peptide of interest is displayed on the outside of the spore.

This *Bacillus* exosporium display (BEMD) system can be used to deliver peptides, enzymes, and other proteins to plants (e.g., to plant foliage, fruits, flowers, stems, or roots) or to a plant growth medium such as soil. Peptides, enzymes, and proteins delivered to the soil or another plant growth medium in this manner persist and exhibit activity in the soil for extended periods of time. Introduction of recombinant *Bacillus cereus* family member bacteria expressing the fusion proteins described herein into soil or the rhizosphere of a plant leads to a beneficial enhancement of plant growth in many different soil conditions. The use of the BEMD to create these enzymes allows them to continue to exert their beneficial results to the plant and the rhizosphere over the first months of a plants life.

A. Targeting Sequences, Exosporium Proteins, and Exosporium Protein Fragments for Targeting Proteins or Peptides of Interest to the Exosporium of a *Bacillus cereus* Family Member For ease of reference, descriptions of the amino acid sequences for the targeting sequences, exosporium proteins, and exosporium protein fragments that can be used for targeting of proteins or peptides of interest to the exosporium of a *Bacillus cereus* family members, are provided in Table 1 together with their SEQ ID NOs.

TABLE 1

Peptide and protein sequences used for targeting of proteins or peptides of interest to the exosporium of *Bacillus cereus* family members

| Protein, protein fragment, or targeting sequence | SEQ ID NO. |
| --- | --- |
| AA 1-41 of BclA (*B. anthracis* Sterne) | 1* |
| Full length BclA (*B. anthracis* Sterne) | 2* |
| AA 1-33 of BetA/BAS3290 (*B. anthracis* Sterne) | 3 |
| Full length BetA/BAS3290 (*B. anthracis* Sterne) | 4 |
| Met + AA 2-43 of BAS4623 (*B. anthracis* Sterne) | 5 |
| Full length BAS4623 (*B. anthracis* Sterne) | 6 |
| AA 1-34 of BclB (*B. anthracis* Sterne) | 7 |
| Full length BclB (*B. anthracis* Sterne) | 8 |
| AA 1-30 of BAS1882 (*B. anthracis* Sterne) | 9 |
| Full length BAS1882 (*B. anthracis* Sterne) | 10 |
| AA 1-39 of gene 2280 (*B. weihenstephensis* KBAB4) | 11 |
| Full length KBAB4 gene 2280 (*B. weihenstephensis* KBAB4) | 12 |
| AA 1-39 of gene 3572 (*B. weihenstephensis* KBAB4) | 13 |
| Full Length KBAB4 gene 3572 (*B. weihenstephensis* KBAB4) | 14 |
| AA 1-49 of Exosporium Leader Peptide (*B. cereus* VD200) | 15 |
| Full Length Exosporium Leader Peptide (*B. cereus* VD200) | 16 |
| AA 1-33 of Exosporium Leader Peptide (*B. cereus* VD166) | 17 |
| Full Length Exosporium Leader Peptide (*B. cereus* VD166) | 18 |
| AA 1-39 of hypothetical protein IKG_04663 (*B. cereus* VD200) | 19 |
| Hypothetical protein IKG_04663, partial (*B. cereus* VD200) | 20 |
| AA 1-39 of YVTN β-propeller protein (*B. weihenstephensis* KBAB4) | 21 |
| Full length YVTN β-propeller protein (*B. weihenstephensis* KBAB4) | 22 |
| AA 1-30 of hypothetical protein bcerkbab4_2363 (*B. weihenstephensis* KBAB4) | 23 |
| Full length hypothetical protein bcerkbab4_2363 (*B. weihenstephensis* KBAB4) | 24 |
| AA 1-30 of hypothetical protein bcerkbab4_2131 (*B. weihenstephensis* KBAB4) | 25 |
| Full length hypothetical protein bcerkbab4_2131 (*B. weihenstephensis* KBAB4) | 26 |
| AA 1-36 of triple helix repeat containing collagen (*B. weihenstephensis* KBAB4) | 27 |
| Full length triple helix repeat-containing collagen KBAB4 (*B. weihenstephensis* KBAB4) | 28 |
| AA 1-39 of hypothetical protein bmyco0001_21660 (*B. mycoides* 2048) | 29 |
| Full length hypothetical protein bmyco0001_21660 (*B. mycoides* 2048) | 30 |
| AA 1-30 of hypothetical protein bmyc0001_22540 (*B. mycoides* 2048) | 31 |
| Full length hypothetical protein bmyc0001_22540 (*B. mycoides* 2048) | 32 |
| AA 1-21 of hypothetical protein bmyc0001_21510 (*B. mycoides* 2048) | 33 |
| Full length hypothetical protein bmyc0001_21510 (*B. mycoides* 2048) | 34 |
| AA 1-22 of collagen triple helix repeat protein (*B. thuringiensis* 35646) | 35 |
| Full length collagen triple helix repeat protein (*B. thuringiensis* 35646) | 36 |
| AA 1-35 of hypothetical protein WP_69652 (*B. cereus*) | 43 |
| Full length hypothetical protein WP_69652 (*B. cereus*) | 44 |
| AA 1-41 of exosporium leader WP016117717 (*B. cereus*) | 45 |
| Full length exosporium leader WP016117717 (*B. cereus*) | 46 |
| AA 1-49 of exosporium peptide WP002105192 (*B. cereus*) | 47 |
| Full length exosporium peptide WP002105192 (*B. cereus*) | 48 |
| AA 1-38 of hypothetical protein WP87353 (*B. cereus*) | 49 |
| Full length hypothetical protein WP87353 (*B. cereus*) | 50 |
| AA 1-39 of exosporium peptide 02112369 (*B. cereus*) | 51 |
| Full length exosporium peptide 02112369 (*B. cereus*) | 52 |
| AA 1-39 of exosporium protein WP016099770 (*B. cereus*) | 53 |
| Full length exosporium protein WP016099770 (*B. cereus*) | 54 |
| AA 1-36 of hypothetical protein YP006612525 (*B. thuringiensis*) | 55 |
| Full length hypothetical protein YP006612525 (*B. thuringiensis*) | 56 |
| AA 1-136 of hypothetical protein TIGR03720 (*B. mycoides*) | 57** |
| Full length hypothetical protein TIGR03720 (*B. mycoides*) | 58** |
| AA 1-36 of collagen triple helix repeat domain protein (*B. cereus* ATCC 10987) | 59 |
| Full length collagen triple helix repeat domain protein (*B. cereus* ATCC 10987) | 60 |
| AA 1-39 of collagen-like protein (*B. cereus* E33L) | 61 |
| Full length collagen-like protein (*B. cereus* E33L) | 62 |
| AA 1-41 of triple helix repeat-containing collagen (*B. weihenstephanensis* KBAB4) | 63 |
| Full length triple helix repeat-containing collagen (*B. weihenstephanensis* KBAB4) | 64 |
| AA 1-30 of hypothetical protein BALH_2230 (*B. thuringiensis* str. Al Hakam) | 65 |
| Full length hypothetical protein BALH_2230 (*B. thuringiensis* str. Al Hakam) | 66 |
| AA 1-33 of triple helix repeat-containing collagen (*B. cereus* ATCC 14579) | 67 |
| Full length triple helix repeat-containing collagen (*B. cereus* ATCC 14579) | 68 |
| AA 1-44 of collagen triple helix repeat (*B. cereus*) | 69 |

TABLE 1-continued

Peptide and protein sequences used for targeting of proteins or peptides
of interest to the exosporium of *Bacillus cereus* family members

| Protein, protein fragment, or targeting sequence | SEQ ID NO. |
| --- | --- |
| Full length collagen triple helix repeat (*B. cereus*) | 70 |
| AA 1-38 of triple helix repeat-containing collagen (*B. cereus* ATCC 14579) | 71 |
| Full length triple helix repeat-containing collagen (*B. cereus* ATCC 14579) | 72 |
| AA 1-30 of hypothetical protein BCZK1835 (*B. cereus* E33L) | 73 |
| Full length hypothetical protein BCZK1835 (*B. cereus* E33L) | 74 |
| AA 1-48 of triple helix repeat-containing collagen (*B. weihenstephanensis* KBAB4) | 75 |
| Full length triple helix repeat-containing collagen (*B. weihenstephanensis* KBAB4) | 76 |
| AA 1-30 of triple helix repeat-containing collagen (*B. cereus* ATCC 14579) | 77 |
| Full length triple helix repeat-containing collagen (*B. cereus* ATCC 14579) | 78 |
| AA 1-39 of hypothetical protein BC4725 (*B. cereus* ATCC 14579) | 79 |
| Full length hypothetical protein BC4725 (*B. cereus* ATCC 14579) | 80 |
| AA 1-44 of hypothetical protein BCZK4476 (*B. cereus* E33L) | 81 |
| Full length hypothetical protein BCZK4476 (*B. cereus* E33L) | 82 |
| AA 1-40 of triple helix repeat-containing collagen (*B. anthracis* str. 'Ames Ancestor') | 83 |
| Full length triple helix repeat-containing collagen (*B. anthracis* str. 'Ames Ancestor') | 84 |
| AA 1-34 of BclA protein (*B. thuringiensis* serovar konkukian str. 97-27) | 85 |
| Full length BclA protein (*B. thuringiensis* serovar konkukian str. 97-27) | 86 |
| AA 1-34 of conserved hypothetical protein (*B. cereus* ATCC 10987) | 87 |
| Full length conserved hypothetical protein (*B. cereus* ATCC 10987) | 88 |
| AA 1-34 of triple helix repeat-containing collagen (*B. cereus* ATCC 14579) | 89 |
| Full length triple helix repeat-containing collagen (*B. cereus* ATCC 14579) | 90 |
| AA 1-99 of exosporium leader peptide partial sequence (*B. cereus*) | 91 |
| Exosporium leader peptide partial sequence (*B. cereus*) | 92 |
| AA 1-136 of hypothetical protein ER45_27600, partial sequence (*B. weihenstephanensis*) | 93 |
| Hypothetical protein ER45_27600, partial sequence (*B. weihenstephanensis*) | 94 |
| AA 1-196 of BclA (*B. anthracis* Sterne) | 95* |
| Met + AA 20-35 of BclA (*B. anthracis* Sterne) | 96 |
| Met + AA 12-27 of BetA/BAS3290 (*B. anthracis* Sterne) | 97 |
| Met + AA 18-33 of gene 2280 (*B. weihenstephensis* KBAB4) | 98 |
| Met + AA 18-33 of gene 3572 (*B. weihenstephensis* KBAB4) | 99 |
| Met + AA 12-27 of Exosporium Leader Peptide (*B. cereus* VD166) | 100 |
| Met + AA 18-33 of YVTN β-propeller protein (*B. weihenstephensis* KBAB4) | 101 |
| Met + AA 9-24 of hypothetical protein bcerkbab4_2363 (*B. weihenstephensis* KBAB4) | 102 |
| Met + AA 9-24 of hypothetical protein bcerkbab4_2131 (*B. weihenstephensis* KBAB4) | 103 |
| Met + AA 9-24 of hypothetical protein bmyc0001_22540 (*B. mycoides* 2048) | 104 |
| Met + AA 9-24 of BAS1882 (*B. anthracis* Sterne) | 105 |
| Met + AA 20-35 of exosporium leader WP016117717 (*B. cereus*) | 106 |
| Met + AA 9-24 of hypothetical protein BALH_2230 (*B. thuringiensis* str. Al Hakam) | 107 |
| Full length InhA (*B. mycoides*) | 108 |
| Full length BAS1141 (ExsY) (*B. anthracis* Sterne) | 109 |
| Full length BAS1144 (BxpB/ExsFA) (*B. anthracis* Sterne) | 110 |
| Full length BAS1145 (CotY) (*B. anthracis* Sterne) | 111 |
| Full length BAS1140 (*B. anthracis* Sterne) | 112 |
| Full length ExsFB (*B. anthracis* H9401) | 113 |
| Full length InhA1 (*B. thuringiensis* HD74) | 114 |
| Full length ExsJ (*B. cereus* ATCC 10876) | 115 |
| Full length ExsH (*B. cereus*) | 116 |
| Full length YjcA (*B. anthracis* Ames) | 117 |
| Full length YjcB (*B. anthracis*) | 118 |
| Full length BclC (*B. anthracis* Sterne) | 119 |
| Full length acid phosphatase (*Bacillus thuringiensis* serovar konkukian str. 97-27) | 120 |
| Full length InhA2 (*B. thuringiensis* HD74) | 121 |
| Full length InhA3 (*B. mycoides*) | 122 |

AA = amino acids

*B. anthracis* Sterne strain BclA has 100% sequence identity with *B. thuringiensis* BclA. Thus, SEQ ID NOs: 1, 2, and 95 also represent amino acids 1-41 of *B. thuringiensis* BclA, full length *B. thuringiensis* BclA, and amino acids 1-196 of *B. thuringiensis* BclA, respectively. Likewise, SEQ ID NO: 96 also represents a methionine residue plus amino acids 20-35 of *B. thuringiensis* BclA.

**B. mycoides* hypothetical protein TIGR03720 has 100% sequence identity with *B. mycoides* hypothetical protein WP003189234. Thus, SEQ ID NOs: 57 and 58 also represent amino acids 1-136 of *B. mycoides* hypothetical protein WP003189234 and full length *B. mycoides* hypothetical protein WP003189234, respectively.

*Bacillus* is a genus of rod-shaped bacteria. The *Bacillus cereus* family of bacteria includes any *Bacillus* species that is capable of producing an exosporium. Thus, the *Bacillus cereus* family of bacteria includes the species *Bacillus anthracis*, *Bacillus cereus*, *Bacillus thuringiensis*, *Bacillus mycoides*, *Bacillus pseudomycoides*, *Bacillus samanii*, *Bacillus gaemokensis*, *Bacillus weihenstephensis*, and *Bacillus toyoiensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein BclA, while the basal layer is comprised of a number of different proteins. Another collagen-related protein, BclB, is also present in the exosporium and exposed on endospores of *Bacillus cereus* family members. BclA, the major constituent of the surface nap, has been shown to be attached to the exosporium with its amino-terminus (N-terminus) positioned at the basal layer and its carboxy-terminus (C-terminus) extending outward from the spore.

It was previously discovered that certain sequences from the N-terminal regions of BclA and BclB could be used to target a peptide or protein to the exosporium of a *Bacillus cereus* endospore (see U.S. Patent Application Publication Nos. 2010/0233124 and 2011/0281316, and Thompson et al., *Targeting of the BclA and BclB proteins to the Bacillus anthracis spore surface*, Molecular Microbiology 70(2): 421-34 (2008)). It was also found that the BetA/BAS3290 protein of *Bacillus anthracis* localized to the exosporium.

In particular, amino acids 20-35 of BclA from *Bacillus anthracis* Sterne strain have been found to be sufficient for targeting to the exosporium. A sequence alignment of amino acids 1-41 of BclA (SEQ ID NO: 1) with the corresponding N-terminal regions of several other *Bacillus cereus* family exosporium proteins and *Bacillus cereus* family proteins having related sequences is shown in FIGS. 1A and 1B. As can be seen from FIGS. 1A and 1B, there is a region of high-homology among all of the proteins in the region corresponding to amino acids 20-41 of BclA. However, in these sequences, the amino acids corresponding to amino acids 36-41 of BclA contain secondary structure and are not necessary for fusion protein localization to the exosporium. The conserved targeting sequence region of BclA (amino acids 20-35 of SEQ ID NO: 1) is shown in bold in FIGS. 1A and 1B and corresponds to the minimal targeting sequence needed for localization to the exosporium. A more highly conserved region spanning amino acids 25-35 of BclA within the targeting sequence is underlined in the sequences in FIGS. 1A and 1B, and is the recognition sequence for ExsFA/BxpB/ExsFB and homologs, which direct and assemble the described proteins on the surface of the exosporium. The amino acid sequences of SEQ ID NOs. 3, 5, and 7 in FIG. 1A are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1A, each of these sequences contains a conserved region corresponding to amino acids 20-35 of BclA (SEQ ID NO: 1; shown in bold), and a more highly conserved region corresponding to amino acids 20-35 of BclA (underlined).

Additional proteins from *Bacillus cereus* family members also contain the conserved targeting region. In particular, in FIGS. 1A and 1B, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG_04663, SEQ ID NO: 21 is amino acids 1-39 of *Bacillus weihenstephensis* KBAB4 YVTN β-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, SEQ ID NO: 35 is amino acids 1-22 of *Bacillus thuringiensis* 35646 collagen triple helix repeat protein, SEQ ID NO: 43 is amino acids 1-35 of *Bacillus cereus* hypothetical protein WP_69652, SEQ ID NO: 45 is amino acids 1-41 of *Bacillus cereus* exosporium leader WP016117717, SEQ ID NO: 47 is amino acids 1-49 of *Bacillus cereus* exosporium peptide WP002105192, SEQ ID NO: 49 is amino acids 1-38 of *Bacillus cereus* hypothetical protein WP87353, SEQ ID NO: 51 is amino acids 1-39 of *Bacillus cereus* exosporium peptide 02112369, SEQ ID NO: 53 is amino acids 1-39 of *Bacillus cereus* exosporium protein WP016099770, SEQ ID NO: 55 is amino acids 1-36 of *Bacillus thuringiensis* hypothetical protein YP006612525, SEQ ID NO: 57 is amino acids 1-136 of *Bacillus mycoides* hypothetical protein TIGR03720, SEQ ID NO: 59 is amino acids 1-36 of *B. cereus* ATCC 10987 collagen triple helix repeat domain protein, SEQ ID NO: 61 is amino acids 1-39 of *B. cereus* E33L collagen-like protein, SEQ ID NO: 63 is amino acids 1-41 of *B. weihenstephanensis* KBAB4 triple helix repeat-containing collagen, SEQ ID NO: 65 is amino acids 1-30 of *B. thuringiensis* str. Al Hakam hypothetical protein BALH_2230, SEQ ID NO: 67 is amino acids 1-33 of *B. cereus* ATCC 14579 triple helix repeat-containing collagen, SEQ ID NO: 69 is amino acids 1-44 of *B. cereus* collagen triple helix repeat, SEQ ID NO: 71 is amino acids 1-38 of *B. cereus* ATCC 14579 triple helix repeat-containing collagen, SEQ ID NO: 73 is amino acids 1-30 of *B. cereus* E33L hypothetical protein BCZK1835, SEQ ID NO: 75 is amino acids 1-48 of *B. weihenstephanensis* KBAB4 triple helix repeat-containing collagen, SEQ ID NO: 77 is amino acids 1-30 of *B. cereus* ATCC 14579 triple helix repeat-containing collagen, SEQ ID NO: 79 is amino acids 1-39 of *B. cereus* ATCC 14579 hypothetical protein BC4725, SEQ ID NO: 81 is amino acids 1-44 of *B. cereus* E33L hypothetical protein BCZK4476, SEQ ID NO: 83 is amino acids 1-40 of *B. anthracis* str. 'Ames Ancestor' triple helix repeat-containing collagen, SEQ ID NO: 85 is amino acids 1-34 of *B. thuringiensis* serovar konkukian str. 97-27 BclA protein, SEQ ID NO: 87 is amino acids 1-34 of *B. cereus* ATCC 10987 conserved hypothetical protein, SEQ ID NO: 89 is amino acids 1-34 of *B. cereus* ATCC 14579 triple helix repeat-containing collagen, SEQ ID NO: 91 is amino acids 1-99 of *B. cereus* exosporium leader peptide partial sequence, and SEQ ID NO: 93 is amino acids 1-136 of *B. weihenstephanensis* hypothetical protein ER45_27600. As shown in FIGS. 1A and 1B, each of the N-terminal regions of these proteins contains a region that is conserved with amino acids 20-35 of BclA (SEQ ID NO: 1), and a more highly conserved region corresponding to amino acids 25-35 of BclA.

Any portion of BclA which includes amino acids 20-35 can be used as to target a fusion protein to the exosporium. In addition, full-length exosporium proteins or exosporium protein fragments can be used for targeting the fusion proteins to the exosporium. Thus, full-length BclA or a fragment of BclA that includes amino acids 20-35 can be used for targeting to the exosporium. For example, full length BclA (SEQ ID NO: 2) or a midsized fragment of BclA that lacks the carboxy-terminus such as SEQ ID NO: 95 (amino acids 1-196 of BclA) can be used to target the fusion proteins to the exosporium. Midsized fragments such as the fragment of SEQ ID NO: 95 have less secondary structure than full length BclA and has been found to be suitable for use as a targeting sequence. The targeting sequence can also comprise much shorter portions of BclA which include amino acids 20-35, such as SEQ ID NO: 1 (amino acids 1-41 of BclA), amino acids 1-35 of SEQ ID NO: 1, amino acids 20-35 of SEQ ID NO: 1, or SEQ ID NO: 96 (a methionine residue linked to amino acids 20-35 of BclA). Even shorter fragments of BclA which include only some of amino acids 20-35 also exhibit the ability to target fusion proteins to the exosporium. For example, the targeting sequence can comprise amino acids 22-31 of SEQ ID NO: 1, amino acids 22-33 of SEQ ID NO: 1, or amino acids 20-31 of SEQ ID NO: 1.

Alternatively, any portion of BetA/BAS3290, BAS4623, BclB, BAS1882, the KBAB4 2280 gene product, the KBAB4 3572 gene product, *B. cereus* VD200 exosporium leader peptide, *B. cereus* VD166 exosporium leader peptide, *B. cereus* VD200 hypothetical protein IKG_04663, *B. weihenstephensis* KBAB4 YVTN β-propeller protein, *B. weihenstephensis* KBAB4 hypothetical protein bcerkbab4_2363, *B. weihenstephensis* KBAB4 hypothetical protein bcerkbab4_2131, *B. weihenstephensis* KBAB4 triple helix repeat containing collagen, *B. mycoides* 2048 hypothetical protein bmyco0001_21660, *B. mycoides* 2048 hypothetical protein bmyc0001_22540, *B. mycoides* 2048 hypothetical protein bmyc0001_21510, *B. thuringiensis* 35646 collagen triple helix repeat protein, *B. cereus* hypothetical protein WP_69652, *B. cereus* exosporium leader WP016117717, *B. cereus* exosporium peptide WP002105192, *B. cereus* hypothetical protein WP87353, *B. cereus* exosporium peptide 02112369, *B. cereus* exosporium protein WP016099770, *B. thuringiensis* hypothetical protein YP006612525, *B. mycoides* hypothetical protein TIGR03720, *B. cereus* ATCC 10987 collagen triple helix repeat domain protein, *B. cereus* E33L collagen-like protein, *B. weihenstephanensis* KBAB4 triple helix repeat-containing collagen, *B. thuringiensis* str. Al Hakam hypothetical protein BALH_2230, *B. cereus* ATCC 14579 triple helix repeat-containing collagen, *B. cereus* collagen triple helix repeat, *B. cereus* ATCC 14579 triple helix repeat-containing collagen, *B. cereus* E33L hypothetical protein BCZK1835, *B. weihenstephanensis* KBAB4 triple helix repeat-containing collagen, *B. cereus* ATCC 14579 triple helix repeat-containing collagen, *B. cereus* ATCC 14579 hypothetical protein BC4725, *B. cereus* E33L hypothetical protein BCZK4476, *B. anthracis* str. 'Ames Ancestor' triple helix repeat-containing collagen, *B. thuringiensis* serovar konkukian str. 97-27 BclA protein, *B. cereus* ATCC 10987 conserved hypothetical protein, *B. cereus* ATCC 14579 triple helix repeat-containing collagen, *B. cereus* exosporium leader peptide partial sequence, or *B. weihenstephanensis* hypothetical protein ER45_27600 which includes the amino acids corresponding to amino acids 20-35 of BclA can serve as the targeting sequence.

As can be seen from FIG. 1A, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of *B. cereus* VD200 exosporium leader peptide, amino acids 12-27 of *B. cereus* VD166 exosporium leader peptide, amino acids 18-33 of *B. cereus* VD200 hypothetical protein IKG_04663, amino acids 18-33 *B. weihenstephensis* KBAB4 YVTN β-propeller protein, amino acids 9-24 of *B. weihenstephensis* KBAB4 hypothetical protein bcerkbab4_2363, amino acids 9-24 of *B. weihenstephensis* KBAB4 hypothetical protein bcerkbab4_2131, amino acids 15-30 of *B. weihenstephensis* KBAB4 triple helix repeat containing collagen, amino acids 18-33 of *B. mycoides* 2048 hypothetical protein bmyco0001_21660, amino acids 9-24 of *B. mycoides* 2048 hypothetical protein bmyc0001_22540, amino acids 1-15 of *B. mycoides* 2048 hypothetical protein bmyc0001_21510, amino acids 1-16 of *B. thuringiensis* 35646 collagen triple helix repeat protein, amino acids 14-29 of *B. cereus* hypothetical protein WP_69652, amino acids 20-35 of *B. cereus* exosporium leader WP016117717, amino acids 28-43 of *B. cereus* exosporium peptide WP002105192, amino acids 17-32 of *B. cereus* hypothetical protein WP87353, amino acids 18-33 of *B. cereus* exosporium peptide 02112369, amino acids 18-33 of *B. cereus* exosporium protein WP016099770, amino acids 15-30 of *B. thuringiensis* hypothetical protein YP006612525, and amino acids 115-130 of *B. mycoides* hypothetical protein TIGR03720 correspond to amino acids 20-35 of BclA. As can be seen from FIG. 1B, amino acids 15-30 of *B. cereus* ATCC 10987 collagen triple helix repeat domain protein, amino acids 18-33 of *B. cereus* E33L collagen-like protein, amino acids 20-35 of *B. weihenstephanensis* KBAB4 triple helix repeat-containing collagen, amino acids 9-24 of *B. thuringiensis* str. Al Hakam hypothetical protein BALH_2230, amino acids 12-27 of *B. cereus* ATCC 14579 triple helix repeat-containing collagen, amino acids 23-38 of *B. cereus* collagen triple helix repeat, amino acids 17-32 of *B. cereus* ATCC 14579 triple helix repeat-containing collagen, amino acids 9-24 of *B. cereus* E33L hypothetical protein BCZK1835, amino acids 27-42 of *B. weihenstephanensis* KBAB4 triple helix repeat-containing collagen, amino acids 9-24 of *B. cereus* ATCC 14579 triple helix repeat-containing collagen, amino acids 18-33 of *B. cereus* ATCC 14579 hypothetical protein BC4725, amino acids 23-38 of *B. cereus* E33L hypothetical protein BCZK4476, amino acids 19-34 *B. anthracis* str. 'Ames Ancestor' triple helix repeat-containing collagen, amino acids 13-28 of *B. thuringiensis* serovar konkukian str. 97-27 BclA protein, amino acids 13-28 of *B. cereus* ATCC 10987 conserved hypothetical protein, amino acids 13-28 of *B. cereus* ATCC 14579 triple helix repeat-containing collagen, amino acids 78-93 of *B. cereus* exosporium leader peptide partial sequence, and amino acids 115-130 of *B. weihenstephanensis* hypothetical protein ER45_27600 correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids can serve as the targeting sequence.

Thus, the targeting sequence can comprise amino acids 1-35 of SEQ ID NO: 1, amino acids 20-35 of SEQ ID NO: 1, SEQ ID NO: 1, SEQ ID NO: 96, amino acids 22-31 of SEQ ID NO: 1, amino acids 22-33 of SEQ ID NO: 1, or amino acids 20-31 of SEQ ID NO: 1. Alternatively, the targeting sequence consists of amino acids 1-35 of SEQ ID NO: 1, amino acids 20-35 of SEQ ID NO: 1, SEQ ID NO: 1, or SEQ ID NO: 96. Alternatively, the targeting sequence can consist of amino acids 22-31 of SEQ ID NO: 1, amino acids 22-33 of SEQ ID NO: 1, or amino acids 20-31 of SEQ ID NO: 1. Alternatively, the exosporium protein can comprise full length BclA (SEQ ID NO: 2), or the exosporium protein fragment can comprise a midsized fragment of BclA that lacks the carboxy-terminus, such as SEQ ID NO: 59 (amino acids 1-196 of BclA). Alternatively, the exosporium protein fragment can consist of SEQ ID NO: 59.

The targeting sequence can comprise amino acids 2-35 of SEQ ID NO: 1; amino acids 5-35 of SEQ ID NO: 1; amino acids 8-35 of SEQ ID NO: 1; amino acids 10-35 of SEQ ID NO: 1; or amino acids 15-35 of SEQ ID NO: 1.

The targeting sequence can also comprise amino acids 1-27 of SEQ ID NO: 3, amino acids 12-27 of SEQ ID NO: 3, or SEQ ID NO: 3, or the exosporium protein can comprise full length BetA/BAS3290 (SEQ ID NO: 4). It has also been found that a methionine residue linked to amino acids 12-27 of BetA/BAS3290 can be used as a targeting sequence. Thus, the targeting sequence can comprise SEQ ID NO: 97. The targeting sequence can also comprise amino acids 14-23 of SEQ ID NO: 3, amino acids 14-25 of SEQ ID NO: 3, or amino acids 12-23 of SEQ ID NO: 3.

The targeting sequence can comprise amino acids 2-27 of SEQ ID NO: 3; amino acids 5-27 of SEQ ID NO: 3; amino acids 8-27 of SEQ ID NO: 3; or amino acids 10-27 of SEQ ID NO: 3.

The targeting sequence can also comprise amino acids 1-38 of SEQ ID NO: 5, amino acids 23-38 of SEQ ID NO: 5, or SEQ ID NO: 5, or the exosporium protein can comprise full length BAS4623 (SEQ ID NO: 6).

The targeting sequence can comprise amino acids 2-38 of SEQ ID NO: 5; amino acids 5-38 of SEQ ID NO: 5; amino acids 8-38 of SEQ ID NO: 5; amino acids 10-38 of SEQ ID NO: 5; amino acids 15-38 of SEQ ID NO: 5; or amino acids 20-38 of SEQ ID NO: 5.

Alternatively, the targeting sequence can comprise amino acids 1-28 of SEQ ID NO: 7, amino acids 13-28 of SEQ ID NO: 7, or SEQ ID NO: 7, or the exosporium protein can comprise full length BclB (SEQ ID NO:8).

The targeting sequence can comprise amino acids 2-28 of SEQ ID NO: 7; amino acids 5-28 of SEQ ID NO: 7; amino acids 8-28 of SEQ ID NO: 7; or amino acids 10-28 of SEQ ID NO: 7.

The targeting sequence can also comprise amino acids 1-24 of SEQ ID NO: 9, amino acids 9-24 of SEQ ID NO: 9, or SEQ ID NO: 9, or the exosporium protein can comprise full length BAS1882 (SEQ ID NO: 10). A methionine residue linked to amino acids 9-24 of BAS1882 can also be used as a targeting sequence. Thus, the targeting sequence can comprise SEQ ID NO: 105.

The targeting sequence can comprise amino acids 2-24 of SEQ ID NO: 9; amino acids 5-24 of SEQ ID NO: 9; or amino acids 8-24 of SEQ ID NO: 9.

The targeting sequence can also comprise amino acids 1-33 of SEQ ID NO: 11, amino acids 18-33 of SEQ ID NO: 11, or SEQ ID NO: 11, or the exosporium protein can comprise the full length B. weihenstephensis KBAB4 2280 gene product (SEQ ID NO: 12). A methionine residue linked to amino acids 18-33 of the B. weihenstephensis KBAB4 2280 gene product can also be used as a targeting sequence. Thus, the targeting sequence can comprise SEQ ID NO: 98.

The targeting sequence can comprise amino acids 2-33 of SEQ ID NO: 11; amino acids 5-33 of SEQ ID NO: 11; amino acids 8-33 of SEQ ID NO: 11; amino acids 10-33 of SEQ ID NO: 11; or amino acids 15-33 of SEQ ID NO: 11.

The targeting sequence can also comprise amino acids 1-33 of SEQ ID NO: 13, amino acids 18-33 of SEQ ID NO: 13, or SEQ ID NO: 13, or the exosporium protein can comprise the full length B. weihenstephensis KBAB4 3572 gene product (SEQ ID NO: 14). A methionine residue linked to amino acids 18-33 of the B. weihenstephensis KBAB4 3572 gene product can also be used as a targeting sequence. Thus, the targeting sequence can comprise SEQ ID NO: 99.

The targeting sequence can comprise amino acids 2-33 of SEQ ID NO: 13; amino acids 5-33 of SEQ ID NO: 13; amino acids 8-33 of SEQ ID NO: 13; amino acids 10-33 of SEQ ID NO: 13; or amino acids 15-33 of SEQ ID NO: 13;

Alternatively, the targeting sequence can comprise amino acids 1-43 of SEQ ID NO: 15, amino acids 28-43 of SEQ ID NO: 15, or SEQ ID NO: 15, or the exosporium protein can comprise full length B. cereus VD200 exosporium leader peptide (SEQ ID NO: 16).

The targeting sequence can comprise amino acids 2-43 of SEQ ID NO: 15; amino acids 5-43 of SEQ ID NO: 15; amino acids 8-43 of SEQ ID NO: 15; amino acids 10-43 of SEQ ID NO: 15; amino acids 15-43 of SEQ ID NO: 15; amino acids 20-43 of SEQ ID NO: 15; or amino acids 25-43 of SEQ ID NO: 15.

The targeting sequence can also comprise amino acids 1-27 of SEQ ID NO: 17, amino acids 12-27 of SEQ ID NO: 17, or SEQ ID NO: 17, or the exosporium protein can comprise full-length B. cereus VD166 exosporium leader peptide (SEQ ID NO: 18). A methionine residue linked to amino acids 12-27 of the B. cereus VD166 exosporium leader peptide can also be used as a targeting sequence. Thus, the targeting sequence can comprise SEQ ID NO: 100.

The targeting sequence can comprise amino acids 2-27 of SEQ ID NO: 17; amino acids 5-27 of SEQ ID NO: 17; amino acids 8-27 of SEQ ID NO: 17; or amino acids 10-27 of SEQ ID NO: 17.

The targeting sequence can also comprise amino acids 1-33 of SEQ ID NO: 19, amino acids 18-33 of SEQ ID NO: 19, or SEQ ID NO: 19, or the exosporium protein can comprise full length B. cereus VD200 hypothetical protein IKG_04663 (SEQ ID NO:20).

The targeting sequence can comprise amino acids 2-33 of SEQ ID NO: 19; amino acids 5-33 of SEQ ID NO: 19; amino acids 8-33 of SEQ ID NO: 19; amino acids 10-33 of SEQ ID NO: 19; or amino acids 15-33 of SEQ ID NO: 19.

Alternatively, the targeting sequence comprises amino acids 1-33 of SEQ ID NO: 21, amino acids 18-33 of SEQ ID NO: 21, or SEQ ID NO:21, or the exosporium protein can comprise full length B. weihenstephensis KBAB4 YVTN 3-propeller protein (SEQ ID NO:22). A methionine residue linked to amino acids 18-33 of the B. weihenstephensis KBAB4 YVTN (3-propeller protein can also be used as a targeting sequence. Thus, the targeting sequence can comprise SEQ ID NO: 101.

The targeting sequence can comprise amino acids 2-33 of SEQ ID NO: 21; amino acids 5-33 of SEQ ID NO: 21; amino acids 8-33 of SEQ ID NO: 21; amino acids 10-33 of SEQ ID NO: 21; or amino acids 15-33 of SEQ ID NO: 21.

The targeting sequence can also comprise amino acids 1-24 of SEQ ID NO: 23, amino acids 9-24 of SEQ ID NO: 23, or SEQ ID NO:23, or the exosporium protein can comprise full length *B. weihenstephensis* KBAB4 hypothetical protein bcerkbab4_2363 (SEQ ID NO:24). A methionine residue linked to amino acids 9-24 of *B. weihenstephensis* KBAB4 hypothetical protein bcerkbab4_2363 can also be used as a targeting sequence. Thus, the targeting sequence can comprise SEQ ID NO: 102.

The targeting sequence can comprise amino acids 2-24 of SEQ ID NO:23; amino acids 5-24 of SEQ ID NO: 23; or amino acids 8-24 of SEQ ID NO: 23.

The targeting sequence comprise amino acids 1-24 of SEQ ID NO: 25, amino acids 9-24 of SEQ ID NO: 25, or SEQ ID NO: 25, or the exosporium protein can comprise full length *B. weihenstephensis* KBAB4 hypothetical protein bcerkbab4_2131 (SEQ ID NO:26). A methionine residue linked to amino acids 9-24 of *B. weihenstephensis* KBAB4 hypothetical protein bcerkbab4_2131 can also be used as a targeting sequence. Thus, the targeting sequence can comprise SEQ ID NO: 103.

The targeting sequence can comprise amino acids 2-24 of SEQ ID NO: 25; amino acids 5-24 of SEQ ID NO: 25; or amino acids 8-24 of SEQ ID NO: 25.

Alternatively, the targeting sequence comprises amino acids 1-30 of SEQ ID NO: 27, amino acids 15-30 of SEQ ID NO: 27, or SEQ ID NO:27, or the exosporium protein can comprise full length *B. weihenstephensis* KBAB4 triple helix repeat containing collagen (SEQ ID NO:28).

The targeting sequence can comprise amino acids 2-30 of SEQ ID NO: 27; amino acids 5-30 of SEQ ID NO: 27; amino acids 8-30 of SEQ ID NO: 27; or amino acids 10-30 of SEQ ID NO: 27.

The targeting sequence can also comprise amino acids 1-33 of SEQ ID NO: 29, amino acids 18-33 of SEQ ID NO: 29, or SEQ ID NO:29, or the exosporium protein can comprise full length *B. mycoides* 2048 hypothetical protein bmyco0001_21660 (SEQ ID NO:30).

The targeting sequence can comprise amino acids 2-33 of SEQ ID NO: 29; amino acids 5-33 of SEQ ID NO: 29; amino acids 8-33 of SEQ ID NO: 29; amino acids 10-33 of SEQ ID NO: 29; or amino acids 15-33 of SEQ ID NO: 29.

The targeting sequence can also comprise amino acids 1-24 of SEQ ID NO: 31, amino acids 9-24 of SEQ ID NO: 31, or SEQ ID NO:31, or the exosporium protein can comprise full length *B. mycoides* 2048 hypothetical protein bmyc0001_22540 (SEQ ID NO:32). A methionine residue linked to amino acids 9-24 of *B. mycoides* 2048 hypothetical protein bmyc0001_22540 can also be used as a targeting sequence. Thus, the targeting sequence can comprise SEQ ID NO: 104.

The targeting sequence can comprise amino acids 2-24 of SEQ ID NO: 31; amino acids 5-24 of SEQ ID NO: 31; or amino acids 8-24 of SEQ ID NO: 31.

Alternatively, the targeting sequence comprises amino acids 1-15 of SEQ ID NO: 33, SEQ ID NO:33, or the exosporium protein comprises full length *B. mycoides* 2048 hypothetical protein bmyc0001_21510 (SEQ ID NO:34).

The targeting sequence can also comprise amino acids 1-16 of SEQ ID NO: 35, SEQ ID NO:35, or the exosporium protein can comprise full length *B. thuringiensis* 35646 collagen triple helix repeat protein (SEQ ID NO:36).

The targeting sequence can comprise amino acids 1-29 of SEQ ID NO:43, amino acids 14-29 of SEQ ID NO: 43, or SEQ ID NO: 43, or the exosporium protein can comprise full length *B. cereus* hypothetical protein WP_69652 (SEQ ID NO: 44).

The targeting sequence can comprise amino acids 2-29 of SEQ ID NO: 43; amino acids 5-29 of SEQ ID NO: 43; amino acids 8-29 of SEQ ID NO: 43; or amino acids 10-29 of SEQ ID NO: 43.

Alternatively, the targeting sequence can comprise amino acids 1-35 of SEQ ID NO: 45, amino acids 20-35 of SEQ ID NO: 45, or SEQ ID NO: 45, or the exosporium protein can comprise full length *B. cereus* exosporium leader WP016117717 (SEQ ID NO: 46). A methionine residue linked to amino acids 20-35 of *B. cereus* exosporium leader WP016117717 can also be used as a targeting sequence. Thus, the targeting sequence can comprise SEQ ID NO: 106.

The targeting sequence can comprise amino acids 2-35 of SEQ ID NO: 45; amino acids 5-35 of SEQ ID NO: 45; amino acids 8-35 of SEQ ID NO: 45; amino acids 10-35 of SEQ ID NO: 45; or amino acids 15-35 of SEQ ID NO: 45.

The targeting sequence can comprise amino acids 1-43 of SEQ ID NO: 47, amino acids 28-43 of SEQ ID NO: 47, or SEQ ID NO: 47, or the exosporium protein can comprise full length *B. cereus* exosporium peptide WP002105192 (SEQ ID NO: 48).

The targeting sequence can comprise amino acids 2-43 of SEQ ID NO: 47; amino acids 5-43 of SEQ ID NO: 47; amino acids 8-43 of SEQ ID NO: 47; amino acids 10-43 of SEQ ID NO: 47; amino acids 15-43 of SEQ ID NO: 47; amino acids 20-43 of SEQ ID NO: 47; or amino acids 25-43 of SEQ ID NO: 47.

The targeting sequence can comprise amino acids 1-32 of SEQ ID NO: 49, amino acids 17-32 of SEQ ID NO: 49, or SEQ ID NO: 49, or the exosporium protein can comprise full length *B. cereus* hypothetical protein WP87353 (SEQ ID NO: 50).

The targeting sequence can comprise amino acids 2-32 of SEQ ID NO: 49; amino acids 5-32 of SEQ ID NO: 49; amino acids 8-32 of SEQ ID NO: 49; amino acids 10-32 of SEQ ID NO: 49; or amino acids 15-32 of SEQ ID NO: 49.

Alternatively, the targeting sequence can comprise amino acids 1-33 of SEQ ID NO: 51, amino acids 18-33 of SEQ ID NO: 51, or SEQ ID NO: 51, or the exosporium protein can comprise full length *B. cereus* exosporium peptide 02112369 (SEQ ID NO: 52).

The targeting sequence can comprise amino acids 2-33 of SEQ ID NO: 51; amino acids 5-33 of SEQ ID NO: 51; amino acids 8-33 of SEQ ID NO: 51; amino acids 10-33 of SEQ ID NO: 51; or amino acids 15-33 of SEQ ID NO: 51;

The targeting sequence can comprise amino acids 1-33 of SEQ ID NO: 53, amino acids 18-33 of SEQ ID NO: 53, or SEQ ID NO: 53, or the exosporium protein can comprise full length *B. cereus* exosporium protein WP016099770 (SEQ ID NO: 54).

The targeting sequence can comprise amino acids 2-33 of SEQ ID NO: 53; amino acids 5-33 of SEQ ID NO: 53; amino acids 8-33 of SEQ ID NO: 53; amino acids 10-33 of SEQ ID NO: 53; or amino acids 15-33 of SEQ ID NO: 53.

Alternatively, the targeting sequence can comprise acids 1-30 of SEQ ID NO: 55, amino acids 15-30 of SEQ ID NO: 55, or SEQ ID NO: 55, or the exosporium protein can comprise full length *B. thuringiensis* hypothetical protein YP006612525 (SEQ ID NO: 56).

The targeting sequence can comprise amino acids 2-30 of SEQ ID NO: 55; amino acids 5-30 of SEQ ID NO: 55; amino acids 8-30 of SEQ ID NO: 55; or amino acids 10-30 of SEQ ID NO: 55.

The targeting sequence can also comprise amino acids 1-130 of SEQ ID NO: 57, amino acids 115-130 of SEQ ID NO: 57, or SEQ ID NO: 57, or the exosporium protein can comprise full length *B. mycoides* hypothetical protein TIGR03720 (SEQ ID NO: 58).

The targeting sequence can comprise amino acids 2-130 of SEQ ID NO: 57; amino acids 5-130 of SEQ ID NO: 57; amino acids 10-130 of SEQ ID NO: 57; amino acids 20-130 of SEQ ID NO: 57; amino acids 30-130 of SEQ ID NO: 57; amino acids 40-130 of SEQ ID NO: 57; amino acids 50-130 of SEQ ID NO: 57; amino acids 60-130 of SEQ ID NO: 57; amino acids 70-130 of SEQ ID NO: 57; amino acids 80-130 of SEQ ID NO: 57; amino acids 90-130 of SEQ ID NO: 57; amino acids 100-130 of SEQ ID NO: 57; or amino acids 110-130 of SEQ ID NO: 57.

The targeting sequence can comprise amino acids 1-30 of SEQ ID NO: 59; or SEQ ID NO: 59; or the exosporium protein can comprise full length *B. cereus* ATCC 10987 collagen triple helix repeat domain protein (SEQ ID NO: 60).

The targeting sequence can comprise amino acids 2-30 of SEQ ID NO: 59; amino acids 4-30 of SEQ ID NO: 59; or amino acids 6-30 of SEQ ID NO: 59.

The targeting sequence can comprise amino acids 1-33 of SEQ ID NO: 61; amino acids 18-33 of SEQ ID NO: 61; or SEQ ID NO: 61; or the exosporium protein can comprise full length *B. cereus* E33L collagen-like protein (SEQ ID NO: 62).

The targeting sequence can comprise amino acids 2-33 of SEQ ID NO: 61; amino acids 5-33 of SEQ ID NO: 61; amino acids 10-33 of SEQ ID NO: 61; or amino acids 15-33 of SEQ ID NO: 61.

The targeting sequence can comprise amino acids 1-35 of SEQ ID NO: 63; or SEQ ID NO: 63; or the exosporium protein can comprise full length *B. weihenstephanensis* KBAB4 triple helix repeat-containing collagen (SEQ ID NO: 64).

The targeting sequence can comprise amino acids 2-35 of SEQ ID NO: 63; amino acids 5-35 of SEQ ID NO: 63; amino acids 8-35 of SEQ ID NO: 63; amino acids 10-35 of SEQ ID NO: 63; or amino acids 15-35 of SEQ ID NO: 63.

The targeting sequence can comprise amino acids 1-24 of SEQ ID NO: 65; acids 9-24 of SEQ ID NO: 65; SEQ ID NO: 65; or SEQ ID NO: 107; or the exosporium protein can comprise full length *B. thuringiensis* str. Al Hakam hypothetical protein BALH_2230 (SEQ ID NO: 66).

The targeting sequence can comprise amino acids 2-24 of SEQ ID NO: 65; or amino acids 5-24 of SEQ ID NO: 65.

The targeting sequence can comprise acids 1-27 of SEQ ID NO: 67; amino acids 12-27 of SEQ ID NO: 67; or SEQ ID NO: 67; or the exosporium protein can comprise full length *B. cereus* ATCC 14579 triple helix repeat-containing collagen (SEQ ID NO: 68).

The targeting sequence can comprise amino acids 2-27 of SEQ ID NO: 67; amino acids 5-27 of SEQ ID NO: 67; or amino acids 10-27 of SEQ ID NO: 67.

The targeting sequence can comprise amino acids 1-38 of SEQ ID NO: 69; amino acids 23-38 of SEQ ID NO: 69; or SEQ ID NO: 69; or the exosporium protein can comprise full length *B. cereus* collagen triple helix repeat (SEQ ID NO: 70).

The targeting sequence can comprise amino acids 2-38 of SEQ ID NO: 69; amino acids 5-38 of SEQ ID NO: 69; amino acids 10-38 of SEQ ID NO: 69; or amino acids 15-38 of SEQ ID NO: 69.

The exosporium protein can comprise full length *B. cereus* ATCC 14579 triple helix repeat-containing collagen (SEQ ID NO: 72).

The targeting sequence can comprise SEQ ID NO: 73, or the exosporium protein can comprise full length *B. cereus* E33L hypothetical protein BCZK1835 (SEQ ID NO: 74).

The targeting sequence can comprise amino acids 1-42 of SEQ ID NO: 75; amino acids 27-42 of SEQ ID NO: 75; or SEQ ID NO: 75; or the exosporium protein can comprise full length *B. weihenstephanensis* KBAB4 triple helix repeat-containing collagen (SEQ ID NO: 76).

The targeting sequence can comprise amino acids 2-42 of SEQ ID NO: 75; amino acids 5-42 of SEQ ID NO: 75; amino acids 10-42 of SEQ ID NO: 75; amino acids 15-42 of SEQ ID NO: 75; amino acids 20-42 of SEQ ID NO: 75; or amino acids 25-42 of SEQ ID NO: 75.

The targeting sequence can comprise amino acids 1-24 of SEQ ID NO: 77; amino acids 9-24 of SEQ ID NO: 77; or SEQ ID NO: 77; or the exosporium protein can comprise full length *B. cereus* ATCC 14579 triple helix repeat-containing collagen (SEQ ID NO: 78).

The targeting sequence can comprise amino acids 2-24 of SEQ ID NO: 77; or amino acids 5-24 of SEQ ID NO: 77;

The exosporium protein can comprise full length *B. cereus* ATCC 14579 hypothetical protein BC4725 (SEQ ID NO: 80).

The targeting sequence can comprise amino acids 1-38 of SEQ ID NO: 81; amino acids 23-38 of SEQ ID NO: 81; or SEQ ID NO: 81; or the exosporium protein can comprise full length *B. cereus* E33L hypothetical protein BCZK4476 (SEQ ID NO: 82).

The targeting sequence can comprise amino acids 2-38 of SEQ ID NO: 81; acids 5-38 of SEQ ID NO: 81; amino acids 10-38 of SEQ ID NO: 81; amino acids 15-38 of SEQ ID NO: 81; or amino acids 20-38 of SEQ ID NO: 81.

The targeting sequence can comprise amino acids 1-34 of SEQ ID NO: 83; or SEQ ID NO: 83; or the exosporium protein can comprise full length *B. anthracis* str. 'Ames Ancestor' triple helix repeat-containing collagen (SEQ ID NO: 84).

The exosporium protein can comprise full length *B. thuringiensis* serovar konkukian str. 97-27 BclA protein (SEQ ID NO: 86).

The targeting sequence can comprise amino acids 1-28 of SEQ ID NO: 87; amino acids 13-28 of SEQ ID NO: 87; or SEQ ID NO: 87; or the exosporium protein can comprise full length *B. cereus* ATCC 10987 conserved hypothetical protein (SEQ ID NO: 88).

The targeting sequence can comprise amino acids 2-28 of SEQ ID NO: 87; amino acids 5-28 of SEQ ID NO: 87; or amino acids 10-28 of SEQ ID NO: 87.

The targeting sequence can comprise amino acids 1-28 of SEQ ID NO: 89; or SEQ ID NO: 89; or the exosporium protein can comprise full length *B. cereus* ATCC 14579 triple helix repeat-containing collagen (SEQ ID NO: 90).

The targeting sequence can comprise amino acids 2-28 of SEQ ID NO: 89; amino acids 5-28 of SEQ ID NO: 89; or amino acids 10-28 of SEQ ID NO: 89

The targeting sequence can comprise amino acids 1-93 of SEQ ID NO: 91; or SEQ ID NO: 91; or the exosporium protein can comprise *B. cereus* exosporium leader peptide partial sequence (SEQ ID NO: 92).

The targeting sequence can comprise amino acids 2-93 of SEQ ID NO: 91; amino acids 10-93 of SEQ ID NO: 91; amino acids 20-93 of SEQ ID NO: 91; amino acids 30-93 of SEQ ID NO: 91; amino acids 40-93 of SEQ ID NO: 91; amino acids 50-93 of SEQ ID NO: 91; or amino acids 60-93 of SEQ ID NO: 91.

The targeting sequence can comprise amino acids 1-130 of SEQ ID NO: 93; or SEQ ID NO: 93; or the exosporium protein can comprise B. weihenstephanensis) hypothetical protein ER45_27600, partial sequence (SEQ ID NO: 94).

The targeting sequence can comprise amino acids 2-130 of SEQ ID NO: 93; amino acids 10-130 of SEQ ID NO: 93; amino acids 20-130 of SEQ ID NO: 93; or amino acids 30-130 of SEQ ID NO: 93.

Furthermore, as illustrated in the Examples provided hereinbelow, it has been found that sequences shorter than amino acids 20-35 of BclA can be used to target a fusion protein to the exosporium of a recombinant *Bacillus cereus* family member. In particular, amino acids 20-33 of BclA, amino acids 20-31 of BclA, amino acids 21-33 of BclA, or amino acids 23-31 of BclA can be used to target a fusion protein to the exosporium of a recombinant *Bacillus cereus* family member. Thus, the targeting sequence can consist of amino acids 20-33 of SEQ ID NO: 1, amino acids 20-31 of SEQ ID NO: 1, amino acids 21-33 of SEQ ID NO: 1, or amino acids 23-31 of SEQ ID NO: 1. The corresponding regions of any of the SEQ ID NOs. shown in FIGS. 1A and 1B can also be used to target a fusion protein to the exosporium of a recombinant *Bacillus cereus* family member. By "corresponding regions," it is meant that when the sequences are aligned with SEQ ID NO: 1, as shown in FIGS. 1A and 1B, the regions of the other amino acid sequences that align with the amino acids of SEQ ID NO: 1 are the "corresponding regions" of those sequences. Thus, for example, amino acids 12-25 of SEQ ID NO: 3, amino acids 23-36 of SEQ ID NO: 5, amino acids 13-26 of SEQ ID NO: 7, etc. can be used to target a fusion protein to the exosporium of a recombinant *Bacillus cereus* family member, since these regions align with amino acids 20-33 of SEQ ID NO: 1 as shown in FIG. 1A.

Even shorter regions within amino acids 20-35 of BclA can also be used for targeting a fusion protein to the exosporium of a recombinant *Bacillus cereus* family member. In particular, any amino acid sequence that includes amino acids 25-30 of SEQ ID NO: 1 or the corresponding amino acids from any of the sequences shown in FIGS. 1A and 1B can be used. A skilled person will recognize that starting with amino acids 25-30 of SEQ ID NO: 1 or the corresponding region of any of the sequences shown in FIGS. 1A and 1B, additional amino acids can be added to the amino-terminus, the carboxy terminus, or both the amino- and carboxy termini to create a targeting sequence that will be effective for targeting a fusion protein to the exosporium of a recombinant *Bacillus cereus* family member.

In addition, it can readily be seen from the sequence alignment in FIGS. 1A and 1B that while amino acids 20-35 of BclA are conserved, and amino acids 25-35 are more conserved, some degree of variation can occur in this region without affecting the ability of the targeting sequence to target a protein to the exosporium. FIGS. 1A and 1B list the percent identity of each of corresponding amino acids of each sequence to amino acids 20-35 of BclA ("20-35% Identity") and to amino acids 25-35 of BclA ("25-35% Identity"). Thus, for example, as compared to amino acids 20-35 of BclA, the corresponding amino acids of BetA/BAS3290 are about 81.3% identical, the corresponding amino acids of BAS4623 are about 50.0% identical, the corresponding amino acids of BclB are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIGS. 1A and 1B.

With respect to amino acids 25-35 of BclA, the corresponding amino acids of BetA/BAS3290 are about 90.9% identical, the corresponding amino acids of BAS4623 are about 72.7% identical, the corresponding amino acids of BclB are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIGS. 1A and 1B.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence consisting of 16 amino acids and having at least about 43% identity with amino acids 20-35 of SEQ ID NO: 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can also comprise an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

Alternatively, the targeting sequence can comprise an amino sequence having at least about 62% identity with amino acids 20-35 of SEQ ID NO: 1, wherein the identity with amino acids 25-35 is at least about 72%. The targeting sequence can also consist of an amino acid sequence consisting of 16 amino acids and having at least about 62% identity with amino acids 20-35 of SEQ ID NO: 1, wherein the identity with amino acids 25-35 of SEQ ID NO: 1 is at least about 72%.

The targeting sequence can comprise an amino acid sequence having at least 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least 68% identity with amino acids 20-35 of SEQ ID NO: 1, wherein the identity with amino acids 25-35 is at least about 81%.

The targeting sequence can also comprises an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 81%.

The targeting sequence can also comprise an amino acid sequence having at least about 81% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO:1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of BclA, the corresponding amino acids of BetA/BAS3290, BAS4263, BclB, BAS1882, the KBAB4 2280 gene product, or the KBAB 3572 gene product, or a sequence comprising any of the above noted sequence identities to amino acids 20-35 and 25-35 of BclA is present.

Certain *Bacillus cereus* family exosporium proteins which lack regions having homology to amino acids 25-35 of BclA can also be used to target a peptide or protein to the exosporium of a *Bacillus cereus* family member. In particular, the fusion proteins can comprise an exosporium protein comprising SEQ ID NO: 108 (*B. mycoides* InhA), an exosporium protein comprising SEQ ID NO: 109 (*B. anthracis* Sterne BAS1141 (ExsY)), an exosporium protein comprising SEQ ID NO: 110 (*B. anthracis* Sterne BAS1144 (BxpB/ExsFA)), an exosporium protein comprising SEQ ID NO: 111 (*B. anthracis* Sterne BAS1145 (CotY)), an exosporium protein comprising SEQ ID NO: 112 (*B. anthracis* Sterne BAS1140), an exosporium protein comprising SEQ ID NO: 113 (*B. anthracis* H9401 ExsFB), an exosporium protein comprising SEQ ID NO: 114 (*B. thuringiensis* HD74 InhA1), an exosporium protein comprising SEQ ID NO: 115 (*B. cereus* ATCC 10876 ExsJ), an exosporium protein comprising SEQ ID NO: 116 (*B. cereus* ExsH), an exosporium protein comprising SEQ ID NO: 117 (*B. anthracis* Ames YjcA), an exosporium protein comprising SEQ ID NO: 118 (*B. anthracis* YjcB), an exosporium protein comprising SEQ ID NO: 119 (*B. anthracis* Sterne BclC), an exosporium protein comprising SEQ ID NO: 120 (*Bacillus thuringiensis* serovar konkukian str. 97-27 acid phosphatase), an exosporium protein comprising SEQ ID NO: 121 (*B. thuringiensis* HD74 InhA2), or an exosporium protein comprising SEQ ID NO: 122 (*B. mycoides* InhA3). Inclusion of an exosporium protein comprising any of SEQ ID NOs: 108-122 in the fusion proteins described herein will result in targeting to the exosporium of a *B. cereus* family member.

Moreover, exosporium proteins having a high degree of sequence identity with any of the full-length exosporium proteins or the exosporium protein fragments described above can also be used to target a peptide or protein to the exosporium of a *Bacillus cereus* family member. Thus, the fusion protein can comprise an exosporium protein or exosporium protein fragment comprising an amino acid sequence having at least 85% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122. Alternatively, the fusion protein can comprise an exosporium protein having at least 90%, at least 95%, at least 98%, at least 99%, or 100% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

During sporulation of a recombinant *Bacillus cereus* family member expressing any of the fusion proteins described herein, the targeting motif, exosporium protein, or exosporium protein fragment is recognized by the spore exosporium assembly machinery and directed to the exosporium, resulting in display of the protein or peptide of interest portion of the fusion protein on the outside of the spore.

As illustrated further by the Examples provided hereinbelow, the use of different targeting sequences allows for control of the expression level of the fusion protein on the surface of the *Bacillus cereus* family member spore. Use of certain of the targeting sequences described herein will result in a higher level of expression of the fusion protein, whereas use of others of the targeting sequences will result in lower levels of expression of the fusion protein on the surface of the spore.

In any of the fusion proteins described herein, the targeting sequence, exosporium protein, or exosporium protein fragment can comprise the amino acid sequence GXT at its carboxy terminus, wherein X is any amino acid.

In any of the fusion proteins described herein, the targeting sequence, exosporium protein, or exosporium protein fragment, can comprise an alanine residue at the position of the targeting sequence that corresponds to amino acid 20 of SEQ ID NO: 1.

In any of the fusion proteins described herein, the targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

B. Fusion Proteins for Expression in Recombinant *Bacillus cereus* Family Members The present invention relates to fusion proteins comprising at least one protein or peptide of interest and a targeting sequence or exosporium protein. When the protein or peptide of interest is any protein or peptide of interest, the fusion protein can comprise: (1) a targeting sequence comprising amino acids 1-30 of SEQ ID NO: 59; (2) a targeting sequence comprising SEQ ID NO: 59; (3) an exosporium protein comprising an amino acid sequence having at least 85% identity with SEQ ID NO: 60; (4) a targeting sequence comprising amino acids 2-30 of SEQ ID NO: 59; (5) a targeting sequence comprising amino acids 4-30 of SEQ ID NO: 59; (6) a targeting sequence comprising amino acids 6-30 of SEQ ID NO: 59; (7) a targeting sequence comprising amino acids 1-33 of SEQ ID NO: 61; (8) a targeting sequence comprising amino acids 18-33 of SEQ ID NO: 61; (9) a targeting sequence comprising SEQ ID NO: 61; (10) an exosporium protein comprising an amino acid sequence having at least 85% sequence identity with SEQ ID NO: 62; (11) a targeting sequence comprising amino acids 2-33 of SEQ ID NO: 61; (12) a targeting sequence comprising amino acids 5-33 of SEQ ID NO: 61; (13) a targeting sequence comprising amino acids 10-33 of SEQ ID NO: 61; (14) a targeting sequence comprising amino acids 15-33 of SEQ ID NO: 61; (15) a targeting sequence comprising amino acids 1-35 of SEQ ID NO: 63; (16) a targeting sequence comprising SEQ ID NO: 63; (17) an exosporium protein comprising an amino acid sequence having at least 85% identity with SEQ ID NO: 64; (18) a targeting sequence comprising amino acids 2-35 of SEQ ID NO: 63; (19) a targeting sequence comprising amino acids 5-35 of SEQ ID NO: 63; (20) a targeting sequence comprising amino acids 8-35 of SEQ ID NO: 63; (21) a targeting sequence comprising amino acids 10-35 of SEQ ID NO: 63; (22) a targeting sequence comprising amino acids 15-35 of SEQ ID NO: 63; (23) a targeting sequence comprising amino acids 1-24 of SEQ ID NO: 65; (24) a targeting sequence comprising amino acids 9-24 of SEQ ID NO: 65; (25) a targeting sequence comprising SEQ ID NO: 65; (26) an exosporium protein comprising an amino acid sequence having at least 85% identity with SEQ ID NO: 66; (27) a targeting sequence comprising SEQ ID NO: 107; (28) a targeting sequence comprising amino acids 2-24 of SEQ ID NO: 65; (29) a targeting sequence comprising amino acids 5-24 of SEQ ID NO: 65; (30) a targeting sequence comprising amino acids 1-27 of SEQ ID NO: 67; (31) a targeting sequence comprising amino acids 12-27 of SEQ ID NO: 67; (32) a targeting sequence comprising SEQ ID NO: 67; (33) an exosporium protein comprising an amino acid sequence having at least 85% identity with SEQ ID NO: 68; (34) an targeting sequence comprising amino acids 2-27 of SEQ ID NO: 67; (35) a targeting sequence comprising amino acids 5-27 of SEQ ID NO: 67; (36) a targeting sequence comprising amino acids 10-27 of SEQ ID NO: 67; (37) a targeting sequence comprising amino acids 1-38 of SEQ ID NO: 69; (38) a targeting sequence comprising amino acids 23-38 of SEQ ID NO: 69; (39) a targeting sequence comprising SEQ ID NO: 69; (40) an exosporium protein comprising an amino acid sequence having at least 85% identity with SEQ ID NO: 70; (41) a targeting sequence comprising amino acids 2-38 of SEQ ID NO: 69; (42) a targeting sequence comprising amino acids 5-38 of SEQ ID NO: 69; (43) a targeting sequence comprising amino acids 10-38 of SEQ ID NO: 69; (44) a targeting sequence comprising amino acids 15-38 of SEQ ID NO: 69; (45) an exosporium protein comprising SEQ ID NO: 72; (46) a targeting sequence comprising SEQ ID NO: 73; (47) an exosporium protein comprising an amino acid sequence having at least 95% identity with SEQ ID NO: 74; (48) a targeting sequence comprising amino acids 1-42 of SEQ ID NO: 75; (49) a targeting sequence comprising amino acids 27-42 of SEQ ID NO: 75; (50) a targeting sequence comprising SEQ ID NO: 75; (51) an exosporium protein comprising an amino acid sequence having at least 85% identity with SEQ ID NO: 76; (52) a targeting sequence comprising amino acids 2-42 of SEQ ID NO: 75; (53) a targeting sequence comprising amino acids 5-42 of SEQ ID NO: 75; (54) a targeting sequence comprising amino acids 10-42 of SEQ ID NO: 75; (55) a targeting sequence comprising amino acids 15-42 of SEQ ID NO: 75; (56) a targeting sequence comprising amino acids 20-42 of SEQ ID NO: 75; (57) a targeting sequence comprising amino acids 25-42 of SEQ ID NO: 75; (58) a targeting sequence comprising amino acids 1-24 of SEQ ID NO: 77; (59) a targeting sequence comprising amino acids 9-24 of SEQ ID NO: 77; (60) a targeting sequence comprising SEQ ID NO: 77; (61) an exosporium protein comprising an amino acid sequence having at least 85% identity with SEQ ID NO: 78; (62) a targeting sequence comprising amino acids 2-24 of SEQ ID NO: 77; (63) a targeting sequence comprising amino acids 5-24 of SEQ ID NO: 77; (64) an exosporium protein comprising an amino acid sequence having at least 85% identity with SEQ ID NO: 80; (65) a targeting sequence comprising amino acids 1-38 of SEQ ID NO: 81; (66) a targeting sequence comprising amino acids 23-38 of SEQ ID NO: 81; (67) a targeting sequence comprising SEQ ID NO: 81; (68) an exosporium protein comprising an amino acid sequence having at least 85% identity with SEQ ID NO: 82; (69) a targeting sequence comprising amino acids 2-38 of SEQ ID NO: 81; (70) a targeting sequence comprising amino acids 5-38 of SEQ ID NO: 81; (71) a targeting sequence comprising amino acids 10-38 of SEQ ID NO: 81; (72) a targeting sequence comprising amino acids 15-38 of SEQ ID NO: 81; (73) a targeting sequence comprising amino acids 20-38 of SEQ ID NO: 81; (74) a targeting sequence comprising amino acids 1-34 of SEQ ID NO: 83; (75) a targeting sequence comprising SEQ ID NO: 83; (76) an exosporium protein comprising an amino acid sequence having at least 85% identity with SEQ ID NO: 84; (77) an exosporium protein comprising an amino acid sequence having at least 85% identity with SEQ ID NO: 86; (78) a targeting sequence comprising amino acids 1-28 of SEQ ID NO: 87; (79) a targeting sequence comprising amino acids 13-28 of SEQ ID NO: 87; (80) a targeting sequence comprising SEQ ID NO: 87; (81) an exosporium protein comprising an amino acid sequence having at least 85% identity with SEQ ID NO: 88; (82) a targeting sequence comprising amino acids 2-28 of SEQ ID NO: 87; (83) a targeting sequence comprising amino acids 5-28 of SEQ ID NO: 87; (84) a targeting sequence comprising amino acids 10-28 of SEQ ID NO: 87; (85) a targeting sequence comprising amino acids 1-28 of SEQ ID NO: 89; (86) a targeting sequence comprising SEQ ID NO: 89; (87) an exosporium protein comprising an amino acid sequence having at least 85% identity with SEQ ID NO: 90; (88) a targeting sequence comprising amino acids 2-28 of SEQ ID NO: 89; (89) a targeting sequence comprising amino acids 5-28 of SEQ ID NO: 89; (90) a targeting sequence comprising amino acids 10-28 of SEQ ID NO: 89; (91) a targeting sequence comprising amino acids 1-93 of SEQ ID NO: 91; (92) a targeting sequence comprising SEQ ID NO: 91; (93) an exosporium protein comprising an amino acid sequence having at least 85% identity with SEQ ID NO: 92; (94) a targeting sequence comprising amino acids 2-93 of SEQ ID NO: 91; (95) a targeting sequence comprising amino acids 10-93 of SEQ ID NO: 91; (96) a targeting sequence comprising amino acids 20-93 of SEQ ID NO: 91; (97) a targeting sequence comprising amino acids 30-93 of SEQ ID NO: 91; (98) a targeting sequence comprising amino acids 40-93 of SEQ ID NO: 91; (99) a targeting sequence comprising amino acids 50-93 of SEQ ID NO: 91; (100) a targeting sequence comprising amino acids 60-93 of SEQ ID NO: 91; (101) a targeting sequence comprising amino acids 1-130 of SEQ ID NO: 93; (102) a targeting sequence comprising SEQ ID NO: 93; (103) an exosporium protein comprising an amino acid sequence having at least 85% identity with SEQ ID NO: 94; (104) a targeting sequence comprising amino acids 2-130 of SEQ ID NO: 93;

(105) a targeting sequence comprising amino acids 10-130 of SEQ ID NO: 93; (106) a targeting sequence comprising amino acids 20-130 of SEQ ID NO: 93; (107) a targeting sequence comprising amino acids 30-130 of SEQ ID NO: 93; or (108) an exosporium protein comprising an amino acid sequence having at least 85% sequence identity with SEQ ID NO: 122.

For example, when the protein or peptide of interest is any protein or peptide of interest, the fusion protein can comprise: (1) a targeting sequence comprising amino acids 2-30 of SEQ ID NO: 59; (2) a targeting sequence comprising amino acids 4-30 of SEQ ID NO: 59; (3) a targeting sequence comprising amino acids 6-30 of SEQ ID NO: 59; (4) a targeting sequence comprising amino acids 2-33 of SEQ ID NO: 61; (5) a targeting sequence comprising amino acids 5-33 of SEQ ID NO: 61; (6) a targeting sequence comprising amino acids 10-33 of SEQ ID NO: 61; (7) a targeting sequence comprising amino acids 15-33 of SEQ ID NO: 61; (8) a targeting sequence comprising amino acids 2-35 of SEQ ID NO: 63; (9) a targeting sequence comprising amino acids 5-35 of SEQ ID NO: 63; (10) a targeting sequence comprising amino acids 8-35 of SEQ ID NO: 63; (11) a targeting sequence comprising amino acids 10-35 of SEQ ID NO: 63; (12) a targeting sequence comprising amino acids 15-35 of SEQ ID NO: 63; (13) a targeting sequence comprising amino acids 2-24 of SEQ ID NO: 65; (14) a targeting sequence comprising amino acids 5-24 of SEQ ID NO: 65; (15) a targeting sequence comprising amino acids 2-27 of SEQ ID NO: 67; (16) a targeting sequence comprising amino acids 5-27 of SEQ ID NO: 67; (17) a targeting sequence comprising amino acids 10-27 of SEQ ID NO: 67; (18) a targeting sequence comprising amino acids 2-38 of SEQ ID NO: 69; (19) a targeting sequence comprising amino acids 5-38 of SEQ ID NO: 69; (20) a targeting sequence comprising amino acids 10-38 of SEQ ID NO: 69; (21) a targeting sequence comprising amino acids 15-38 of SEQ ID NO: 69; (22) a targeting sequence comprising amino acids 2-42 of SEQ ID NO: 75; (23) a targeting sequence comprising amino acids 5-42 of SEQ ID NO: 75; (24) a targeting sequence comprising amino acids 10-42 of SEQ ID NO: 75; (25) a targeting sequence comprising amino acids 15-42 of SEQ ID NO: 75; (26) a targeting sequence comprising amino acids 20-42 of SEQ ID NO: 75; (27) a targeting sequence comprising amino acids 25-42 of SEQ ID NO: 75; (28) a targeting sequence comprising amino acids 2-24 of SEQ ID NO: 77; (29) a targeting sequence comprising amino acids 5-24 of SEQ ID NO: 77; (30) a targeting sequence comprising amino acids 2-38 of SEQ ID NO: 81; (31) a targeting sequence comprising amino acids 5-38 of SEQ ID NO: 81; (32) a targeting sequence comprising amino acids 10-38 of SEQ ID NO: 81; (33) a targeting sequence comprising amino acids 15-3 8 of SEQ ID NO: 81; (34) a targeting sequence comprising amino acids 20-38 of SEQ ID NO: 81; (35) a targeting sequence comprising amino acids 2-28 of SEQ ID NO: 87; (36) a targeting sequence comprising amino acids 5-28 of SEQ ID NO: 87; (37) a targeting sequence comprising amino acids 10-28 of SEQ ID NO: 87; (38) a targeting sequence comprising amino acids 2-28 of SEQ ID NO: 89; (39) a targeting sequence comprising amino acids 5-28 of SEQ ID NO: 89; (40) a targeting sequence comprising amino acids 10-28 of SEQ ID NO: 89; (41) a targeting sequence comprising amino acids 2-93 of SEQ ID NO: 91; (42) a targeting sequence comprising amino acids 10-93 of SEQ ID NO: 91; (43) a targeting sequence comprising amino acids 20-93 of SEQ ID NO: 91; (44) a targeting sequence comprising amino acids 30-93 of SEQ ID NO: 91; (45) a targeting sequence comprising amino acids 40-93 of SEQ ID NO: 91; (46) a targeting sequence comprising amino acids 50-93 of SEQ ID NO: 91; (47) a targeting sequence comprising amino acids 60-93 of SEQ ID NO: 91; (48) a targeting sequence comprising amino acids 2-130 of SEQ ID NO: 93; (49) a targeting sequence comprising amino acids 10-130 of SEQ ID NO: 93; (50) a targeting sequence comprising amino acids 20-130 of SEQ ID NO: 93; or (51) a targeting sequence comprising amino acids 30-130 of SEQ ID NO: 93.

Alternatively, when the protein or peptide of interest is any protein or peptide of interest, the fusion protein can comprise: (1) a targeting sequence consisting of amino acids 20-33 of SEQ ID NO: 1; (2) a targeting sequence consisting of amino acids 21-33 of SEQ ID NO: 1; (3) a targeting sequence consisting of amino acids 23-31 of SEQ ID NO: 1; (4) a targeting sequence consisting of amino acids 1-15 of SEQ ID NO: 96; (5) a targeting sequence consisting of amino acids 1-13 of SEQ ID NO: 96; (6) a targeting sequence consisting of amino acids 12-25 of SEQ ID NO: 3; (7) a targeting sequence consisting of amino acids 13-25 of SEQ ID NO: 3; (8) a targeting sequence consisting of amino acids 15-23 of SEQ ID NO: 3; (9) a targeting sequence consisting of amino acids 1-15 of SEQ ID NO: 97; (10) a targeting sequence consisting of amino acids 1-13 of SEQ ID NO: 98; (11) a targeting sequence consisting of amino acids 23-36 of SEQ ID NO: 5; (12) a targeting sequence consisting of amino acids 23-34 of SEQ ID NO: 5; (13) a targeting sequence consisting of amino acids 24-36 of SEQ ID NO: 5; (14) a targeting sequence consisting of amino acids 26-34 of SEQ ID NO: 5; (15) a targeting sequence consisting of amino acids 13-26 of SEQ ID NO: 7; (16) a targeting sequence consisting of amino acids 13-24 of SEQ ID NO: 7; (17) a targeting sequence consisting of amino acids 14-26 of SEQ ID NO: 7; (18) a targeting sequence consisting of amino acids 16-24 of SEQ ID NO: 7; (19) a targeting sequence consisting of amino acids 9-22 of SEQ ID NO: 9; (20) a targeting sequence consisting of amino acids 9-20 of SEQ ID NO: 9; (21) a targeting sequence consisting of amino acids 10-22 of SEQ ID NO: 9; (22) a targeting sequence consisting of amino acids 12-20 of SEQ ID NO: 9; (23) a targeting sequence consisting of amino acids 1-15 of SEQ ID NO: 105; (24) a targeting sequence consisting of amino acids 1-13 of SEQ ID NO: 105; (25) a targeting sequence consisting of amino acids 18-31 of SEQ ID NO: 11; (26) a targeting sequence consisting of amino acids 18-29 of SEQ ID NO: 11; (27) a targeting sequence consisting of amino acids 19-31 of SEQ ID NO: 11; (28) a targeting sequence consisting of amino acids 1-15 of SEQ ID NO: 98; (29) a targeting sequence consisting of amino acids 1-13 of SEQ ID NO: 98; (30) a targeting sequence consisting of amino acids 18-31 of SEQ ID NO: 13; (31) a targeting sequence consisting of amino acids 18-29 of SEQ ID NO: 13; (32) a targeting sequence consisting of amino acids 19-31 of SEQ ID NO: 13; (33) a targeting sequence consisting of amino acids 21-29 of SEQ ID NO: 13; (34) a targeting sequence consisting of amino acids 1-15 of SEQ ID NO: 99; (35) a targeting sequence consisting of amino acids 1-13 of SEQ ID NO: 99; (36) a targeting sequence consisting of amino acids 28-41 of SEQ ID NO: 15; (37) a targeting sequence consisting of amino acids 28-39 of SEQ ID NO: 15; (38) a targeting sequence consisting of amino acids 29-41 of SEQ ID NO: 15; (39) a targeting sequence consisting of amino acids 31-39 of SEQ ID NO: 15; (40) a targeting sequence consisting of amino acids 12-25 of SEQ ID NO: 17; (41) a targeting sequence consisting of amino acids 13-25 of SEQ ID NO: 17; (42) a targeting sequence consisting of amino acids 1-15 of SEQ ID NO: 100; (43) a targeting sequence consisting of amino acids 18-31 of SEQ ID NO: 19; (44) a targeting sequence consisting of amino acids 18-29 of SEQ ID NO: 19; (45) a targeting sequence consisting of amino acids 19-31 of SEQ ID NO: 19; (46) a targeting sequence consisting of amino acids 21-29 of SEQ ID NO: 19; (47) a targeting sequence consisting of amino acids 18-31 of SEQ ID NO: 21; (48) a targeting sequence consisting of amino acids 18-29 of SEQ ID NO: 21; (49) a targeting sequence consisting of amino acids 19-31 of SEQ ID NO: 21; (50) a targeting sequence consisting of amino acids 21-29 of SEQ ID NO: 21; (51) a targeting sequence consisting of amino acids 1-15 of SEQ ID NO: 101; (52) a targeting sequence consisting of amino acids 1-13 of SEQ ID NO: 101; (53) a targeting sequence consisting of amino acids 9-22 of SEQ ID NO: 23; (54) a targeting sequence consisting of amino acids 9-20 of SEQ ID NO: 23; (55) a targeting sequence consisting of amino acids 10-22 of SEQ ID NO: 23; (56) a targeting sequence consisting of amino acids 12-20 of SEQ ID NO: 23; (57) a targeting sequence consisting of amino acids 1-15 of SEQ ID NO: 102; (58) a targeting sequence consisting of amino acids 1-13 of SEQ ID NO: 102; (59) a targeting sequence consisting of amino acids 9-22 of SEQ ID NO: 25; (60) a targeting sequence consisting of amino acids 9-20 of SEQ ID NO: 25; (61) a targeting sequence consisting of amino acids 10-22 of SEQ ID NO: 25; (62) a targeting sequence consisting of amino acids 12-20 of SEQ ID NO: 25; (63) a targeting sequence consisting of amino acids 1-15 of SEQ ID NO: 103; (64) a targeting sequence consisting of amino acids 1-13 of SEQ ID NO: 103; (65) a targeting sequence consisting of amino acids 15-28 of SEQ ID NO: 27; (66) a targeting sequence consisting of amino acids 15-26 of SEQ ID NO: 27; (67) a targeting sequence consisting of amino acids 16-28 of SEQ ID NO: 27; (68) a targeting sequence consisting of amino acids 18-26 of SEQ ID NO: 27; (69) a targeting sequence consisting of amino acids 1-15 of SEQ ID NO: 104; (70) a targeting sequence consisting of amino acids 1-13 of SEQ ID NO: 104; (71) a targeting sequence consisting of amino acids 1-13 of SEQ ID NO: 33; (72) a targeting sequence consisting of amino acids 1-11 of SEQ ID NO: 33; (73) a targeting sequence consisting of amino acids 3-11 of SEQ ID NO: 33; (74) a targeting sequence consisting of amino acids 1-14 of SEQ ID NO: 35; (75) a targeting sequence consisting of amino acids 1-12 of SEQ ID NO: 35; (76) a targeting sequence consisting of amino acids 2-14 of SEQ ID NO: 35; (77) a targeting sequence consisting of amino acids 14-27 of SEQ ID NO: 43; (78) a targeting sequence consisting of amino acids 14-25 of SEQ ID NO: 43; (79) a targeting sequence consisting of amino acids 15-27 of SEQ ID NO: 43; (80) a targeting sequence consisting of amino acids 20-33 of SEQ ID NO: 45; (81) a targeting sequence consisting of amino acids 20-31 of SEQ ID NO: 45; (82) a targeting sequence consisting of amino acids 21-33 of SEQ ID NO: 45; (83) a targeting sequence consisting of amino acids 1-15 of SEQ ID NO: 106; (84) a targeting sequence consisting of amino acids 1-13 of SEQ ID NO: 106; (85) a targeting sequence consisting of amino acids 28-41 of SEQ ID NO: 47; (86) a targeting sequence consisting of amino acids 28-39 of SEQ ID NO: 47; (87) a targeting sequence consisting of amino acids 18-31 of SEQ ID NO: 53; (88) a targeting sequence consisting of amino acids 18-29 of SEQ ID NO: 53; (89) a targeting sequence consisting of amino acids 19-31 of SEQ ID NO: 53; (90) a targeting sequence comprising amino acids 18-31 of SEQ ID NO: 61; (91) a targeting sequence comprising amino acids 18-29 of SEQ ID NO: 61; (92) a targeting sequence comprising amino acids 19-31 of SEQ ID NO: 61; (93) a targeting sequence comprising amino acids 9-22 of SEQ ID NO: 65; (94) a targeting sequence comprising amino acids 9-20 of SEQ ID NO: 65; (95) a targeting sequence comprising amino acids 10-22 of SEQ ID NO: 65; (96) a targeting sequence comprising amino acids 1-15 of SEQ ID NO: 107; (97) a targeting sequence comprising amino acids 1-13 of SEQ ID NO: 107; (98) a targeting sequence comprising amino acids 12-25 of SEQ ID NO: 67; (99) a targeting sequence comprising amino acids 12-23 of SEQ ID NO: 67; (100) a targeting sequence comprising amino acids 13-25 of SEQ ID NO: 67; (101) a targeting sequence comprising amino acids 15-23 of SEQ ID NO: 67; (102) a targeting sequence comprising amino acids 23-36 of SEQ ID NO: 69; (103) a targeting sequence comprising amino acids 23-34 of SEQ ID NO: 69; (104) a targeting sequence comprising amino acids 24-36 of SEQ ID NO: 69; (105) a targeting sequence comprising amino acids 26-34 of SEQ ID NO: 69; (106) a targeting sequence comprising amino acids 27-40 of SEQ ID NO: 75; (107) a targeting sequence comprising amino acids 27-38 of SEQ ID NO: 75; (108) a targeting sequence comprising amino acids 9-22 of SEQ ID NO: 77; (109) a targeting sequence comprising amino acids 9-20 of SEQ ID NO: 77; (110) a targeting sequence comprising amino acids 10-22 of SEQ ID NO: 77; (111) a targeting sequence comprising amino acids 12-20 of SEQ ID NO: 77; (112) a targeting sequence comprising amino acids 23-36 of SEQ ID NO: 81; (113) a targeting sequence comprising amino acids 23-34 of SEQ ID NO: 81; (114) a targeting sequence comprising amino acids 24-36 of SEQ ID NO: 81; (115) a targeting sequence comprising amino acids 26-34 of SEQ ID NO: 81; (116) a targeting sequence comprising amino acids 13-26 of SEQ ID NO: 87; (117) a targeting sequence comprising amino acids 13-24 of SEQ ID NO: 87; or (118) a targeting sequence comprising amino acids 14-26 of SEQ ID NO: 87. The targeting sequence can also consist of any of these sequences.

The present invention relates to fusion proteins comprising at least one protein or peptide of interest and a targeting sequence, exosporium protein, or exosporium protein fragment. The protein or peptide of interest can be an enzyme that catalyzes the production of nitric oxide or a nucleic acid binding protein or peptide. When the protein or peptide of interest comprises an enzyme that catalyzes the production of nitric oxide or a nucleic acid binding protein or peptide, the targeting sequence, exosporium protein, or exosporium protein fragment can be any targeting sequence, exosporium protein, or exosporium protein fragment that targets the fusion protein to the exopsorium of a recombinant *Bacillus cereus* family member. For example, the targeting sequence exosporium protein or exosporium protein fragment can be any of the targeting sequences, exosporium proteins, or exosporium protein fragments listed above in paragraphs [00166]-[00168] for use with any protein or peptide of interest or: (1) a targeting sequence comprising an amino acid sequence having at least about 43% identity with amino acids 20-35 of SEQ ID NO: 1, wherein the identity with amino acids 25-35 is at least about 54%; (2) a targeting sequence comprising amino acids 1-35 of SEQ ID NO: 1; (3) a targeting sequence comprising amino acids 20-35 of SEQ ID NO: 1; (4) a targeting sequence comprising SEQ ID NO: 1; (5) an exosporium protein comprising an amino acid sequence having at least 85% identity with SEQ ID NO: 2; (6) a targeting sequence comprising amino acids 2-35 of SEQ ID NO: 1; (7) a targeting sequence comprising amino acids 5-35 of SEQ ID NO: 1; (8) a targeting sequence comprising amino acids 8-35 of SEQ ID NO: 1; (9) a targeting sequence comprising amino acids 10-35 of SEQ ID NO: 1; (10) a targeting sequence comprising amino acids 15-35 of SEQ ID NO: 1; (11) a targeting sequence comprising amino acids 1-27 of SEQ ID NO: 3; (12) a targeting sequence comprising amino acids 12-27 of SEQ ID NO: 3; (13) a targeting sequence comprising SEQ ID NO: 3; (14) an exosporium protein comprising an amino acid sequence having at least 85% identity with SEQ ID NO: 4; (15) a targeting sequence comprising amino acids 2-27 of SEQ ID NO: 3; (16) a targeting sequence comprising amino acids 5-27 of SEQ ID NO: 3; (17) a targeting sequence comprising amino acids 8-27 of SEQ ID NO: 3; (18) a targeting sequence comprising amino acids 10-27 of SEQ ID NO: 3; (19) a targeting sequence comprising amino acids 1-38 of SEQ ID NO: 5; (20) a targeting sequence comprising amino acids 23-38 of SEQ ID NO: 5; (21) a targeting sequence comprising SEQ ID NO: 5; (22) an exosporium protein comprising an amino acid sequence having at least 85% identity with SEQ ID NO: 6; (23) a targeting sequence comprising amino acids 2-38 of SEQ ID NO: 5; (24) a targeting sequence comprising amino acids 5-38 of SEQ ID NO: 5; (25) a targeting sequence comprising amino acids 8-38 of SEQ ID NO: 5; (26) a targeting sequence comprising amino acids 10-38 of SEQ ID NO: 5; (27) a targeting sequence comprising amino acids 15-38 of SEQ ID NO: 5; (28) a targeting sequence comprising amino acids 20-38 of SEQ ID NO: 5; (29) a targeting sequence comprising amino acids 1-28 of SEQ ID NO: 7; (30) a targeting sequence comprising amino acids 13-28 of SEQ ID NO: 7; (31) a targeting sequence comprising SEQ ID NO: 7; (32) an exosporium protein comprising an amino acid sequence having at least 85% identity with SEQ ID NO: 8; (33) a targeting sequence comprising amino acids 2-28 of SEQ ID NO: 7; (34) a targeting sequence comprising amino acids 5-28 of SEQ ID NO: 7; (35) a targeting sequence comprising amino acids 8-28 of SEQ ID NO: 7; (36) a targeting sequence comprising amino acids 10-28 of SEQ ID NO: 7; (37) a targeting sequence comprising amino acids 1-24 of SEQ ID NO: 9; (38) a targeting sequence comprising amino acids 9-24 of SEQ ID NO: 9; (39) a targeting sequence comprising SEQ ID NO: 9; (40) an exosporium protein comprising an amino acid sequence having at least 85% identity with SEQ ID NO: 10; (41) a targeting sequence comprising amino acids 2-24 of SEQ ID NO: 9; (42) a targeting sequence comprising amino acids 5-24 of SEQ ID NO: 9; (43) a targeting sequence comprising amino acids 8-24 of SEQ ID NO: 9; (44) a targeting sequence comprising amino acids 1-33 of SEQ ID NO: 11; (45) a targeting sequence comprising amino acids 18-33 of SEQ ID NO: 11; (46) a targeting sequence comprising SEQ ID NO: 11; (47) an exosporium protein comprising an amino acid sequence having at least 85% identity with SEQ ID NO: 12; (48) a targeting sequence comprising amino acids 2-33 of SEQ ID NO: 11; (49) a targeting sequence comprising amino acids 5-33 of SEQ ID NO: 11; (50) a targeting sequence comprising amino acids 8-33 of SEQ ID NO: 11; (51) a targeting sequence comprising amino acids 10-33 of SEQ ID NO: 11; (52) a targeting sequence comprising amino acids 15-33 of SEQ ID NO: 11; (53) a targeting sequence comprising amino acids 1-33 of SEQ ID NO: 13; (54) a targeting sequence comprising amino acids 18-33 of SEQ ID NO: 13; (55) a targeting sequence comprising SEQ ID NO:13; (56) an exosporium protein comprising an amino acid sequence having at least 85% identity with SEQ ID NO: 14; (57) a targeting sequence comprising amino acids 2-33 of SEQ ID NO: 13; (58) a targeting sequence comprising amino acids 5-33 of SEQ ID NO: 13; (59) a targeting sequence comprising amino acids 8-33 of SEQ ID NO: 13; (60) a targeting sequence comprising amino acids 10-33 of SEQ ID NO: 13; (61) a targeting sequence comprising amino acids 15-33 of SEQ ID NO: 13; (62) a targeting sequence comprising amino acids 1-43 of SEQ ID NO: 15; (63) a targeting sequence comprising amino acids 28-43 of SEQ ID NO: 15; (64) a targeting sequence comprising SEQ ID NO: 15; (65) an exosporium protein comprising an amino acid sequence having at least 85% identity with SEQ ID NO: 16; (66) a targeting sequence comprising amino acids 2-43 of SEQ ID NO: 15; (67) a targeting sequence comprising amino acids 5-43 of SEQ ID NO: 15; (68) a targeting sequence comprising amino acids 8-43 of SEQ ID NO: 15; (69) a targeting sequence comprising amino acids 10-43 of SEQ ID NO: 15; (70) a targeting sequence comprising amino acids 15-43 of SEQ ID NO: 15; (71) a targeting sequence comprising amino acids 20-43 of SEQ ID NO: 15; (72) a targeting sequence comprising amino acids 25-43 of SEQ ID NO: 15; (73) a targeting sequence comprising amino acids 1-27 of SEQ ID NO: 17; (74) a targeting sequence comprising amino acids 12-27 of SEQ ID NO: 17; (75) a targeting sequence comprising SEQ ID NO: 17; (76) an exosporium protein comprising an amino acid sequence having at least 85% identity with SEQ ID NO: 18; (77) a targeting sequence comprising amino acids 2-27 of SEQ ID NO: 17; (78) a targeting sequence comprising amino acids 5-27 of SEQ ID NO: 17; (79) a targeting sequence comprising amino acids 8-27 of SEQ ID NO: 17; (80) a targeting sequence comprising amino acids 10-27 of SEQ ID NO: 17; (81) a targeting sequence comprising amino acids 1-33 of SEQ ID NO: 19; (82) a targeting sequence comprising amino acids 18-33 of SEQ ID NO: 19; (83) a targeting sequence comprising SEQ ID NO:19; (84) an exosporium protein comprising an amino acid sequence having at least 85% identity with SEQ ID NO:20; (85) a targeting sequence comprising amino acids 2-33 of SEQ ID NO: 19; (86) a targeting sequence comprising amino acids 5-33 of SEQ ID NO: 19; (87) a targeting sequence comprising amino acids 8-33 of SEQ ID NO: 19; (88) a targeting sequence comprising amino acids 10-33 of SEQ ID NO: 19; (89) a targeting sequence comprising amino acids 15-33 of SEQ ID NO: 19; (90) a targeting sequence comprising amino acids 1-33 of SEQ ID NO: 21; (91) a targeting sequence comprising amino acids 18-33 of SEQ ID NO: 21; (92) a targeting sequence comprising SEQ ID NO:21; (93) an exosporium protein comprising an amino acid sequence having at least 85% identity with SEQ ID NO:22; (94) a targeting sequence comprising amino acids 2-33 of SEQ ID NO: 21; (95) a targeting sequence comprising amino acids 5-33 of SEQ ID NO: 21; (96) a targeting sequence comprising amino acids 8-33 of SEQ ID NO: 21; (97) a targeting sequence comprising amino acids 10-33 of SEQ ID NO: 21; (98) a targeting sequence comprising amino acids 15-33 of SEQ ID NO: 21; (99) a targeting sequence comprising amino acids 1-24 of SEQ ID NO: 23; (100) a targeting sequence comprising amino acids 9-24 of SEQ ID NO: 23; (101) a targeting sequence comprising SEQ ID NO:23; (102) an exosporium protein comprising an amino acid sequence having at least 85% identity with SEQ ID NO:24; (103) a targeting sequence comprising amino acids 2-24 of SEQ ID NO:23; (104) a targeting sequence comprising amino acids 5-24 of SEQ ID NO: 23; (105) a targeting sequence comprising amino acids 8-24 of SEQ ID NO: 23; (106) a targeting sequence comprising amino acids 1-24 of SEQ ID NO: 25; (107) a targeting sequence comprising amino acids 9-24 of SEQ ID NO: 25; (108) a targeting sequence comprising SEQ ID NO:25; (109) an exosporium protein comprising an amino acid sequence having at least 85% identity with SEQ ID NO:26; (110) a targeting sequence comprising amino acids 2-24 of SEQ ID NO: 25; (111) a targeting sequence comprising amino acids 5-24 of SEQ ID NO: 25; (112) a targeting sequence comprising amino acids 8-24 of SEQ ID NO: 25; (113) a targeting sequence comprising amino acids 1-30 of SEQ ID NO: 27; (114) a targeting sequence comprising amino acids 15-30 of SEQ ID NO: 27; (115) a targeting sequence comprising SEQ ID NO:27; (116) an exosporium protein comprising an amino acid sequence having at least 85% identity with SEQ ID NO:28; (117) a targeting sequence comprising amino acids 2-30 of SEQ ID NO: 27; (118) a targeting sequence comprising amino acids 5-30 of SEQ ID NO: 27; (119) a targeting sequence comprising amino acids 8-30 of SEQ ID NO: 27; (120) a targeting sequence comprising amino acids 10-30 of SEQ ID NO: 27; (121) a targeting sequence comprising amino acids 1-33 of SEQ ID NO: 29; (122) a targeting sequence comprising amino acids 18-33 of SEQ ID NO: 29; (123) a targeting sequence comprising SEQ ID NO:29; (124) an exosporium protein comprising an amino acid sequence having at least 85% identity with SEQ ID NO:30; (125) a targeting sequence comprising amino acids 2-33 of SEQ ID NO: 29; (126) a targeting sequence comprising amino acids 5-33 of SEQ ID NO: 29; (127) a targeting sequence comprising amino acids 8-33 of SEQ ID NO: 29; (128) a targeting sequence comprising amino acids 10-33 of SEQ ID NO: 29; (129) a targeting sequence comprising amino acids 15-33 of SEQ ID NO: 29; (130) a targeting sequence comprising amino acids 1-24 of SEQ ID NO: 31; (131) a targeting sequence comprising amino acids 9-24 of SEQ ID NO: 31; (132) a targeting sequence comprising SEQ ID NO:31; (133) an exosporium protein comprising an amino acid sequence having at least 85% identity with SEQ ID NO:32; (134) a targeting sequence comprising amino acids 2-24 of SEQ ID NO: 31; (135) a targeting sequence comprising amino acids 5-24 of SEQ ID NO: 31; (136) a targeting sequence comprising amino acids 8-24 of SEQ ID NO: 31; (137) a targeting sequence comprising amino acids 1-15 of SEQ ID NO: 33; (138) a targeting sequence comprising SEQ ID NO:33; (139) an exosporium protein comprising an amino acid sequence having at least 85% identity with SEQ ID NO:34; (140) a targeting sequence comprising amino acids 1-16 of SEQ ID NO: 35; (141) a targeting sequence comprising SEQ ID NO:35; (142) an exosporium protein comprising an amino acid sequence having at least 85% identity with SEQ ID NO:36; (143) a targeting sequence comprising amino acids 1-29 of SEQ ID NO:43; (144) a targeting sequence comprising amino acids 14-29 of SEQ ID NO: 43; (145) a targeting sequence comprising SEQ ID NO: 43; (146) an exosporium protein comprising an amino acid sequence having at least 85% identity with SEQ ID NO: 44; (147) a targeting sequence comprising amino acids 2-29 of SEQ ID NO: 43; (148) a targeting sequence comprising amino acids 5-29 of SEQ ID NO: 43; (149) a targeting sequence comprising amino acids 8-29 of SEQ ID NO: 43; (150) a targeting sequence comprising amino acids 10-29 of SEQ ID NO: 43; (151) a targeting sequence comprising amino acids 1-35 of SEQ ID NO: 45; (152) a targeting sequence comprising amino acids 20-3 5 of SEQ ID NO: 45; (153) a targeting sequence comprising SEQ ID NO: 45; (154) an exosporium protein comprising an amino acid sequence having at least 85% identity with SEQ ID NO: 46; (155) a targeting sequence comprising amino acids 2-35 of SEQ ID NO: 45; (156) a targeting sequence comprising amino acids 5-35 of SEQ ID NO: 45; (157) a targeting sequence comprising amino acids 8-35 of SEQ ID NO: 45; (158) a targeting sequence comprising amino acids 10-35 of SEQ ID NO: 45; (159) a targeting sequence comprising amino acids 15-35 of SEQ ID NO: 45; (160) a targeting sequence comprising amino acids 1-43 of SEQ ID NO: 47; (161) a targeting sequence comprising amino acids 28-43 of SEQ ID NO: 47; (162) a targeting sequence comprising SEQ ID NO: 47; (163) an exosporium protein comprising an amino acid sequence having at least 85% identity with SEQ ID NO: 48; (164) a targeting sequence comprising amino acids 2-43 of SEQ ID NO: 47; (165) a targeting sequence comprising amino acids 5-43 of SEQ ID NO: 47; (166) a targeting sequence comprising amino acids 8-43 of SEQ ID NO: 47; (167) a targeting sequence comprising amino acids 10-43 of SEQ ID NO: 47; (168) a targeting sequence comprising amino acids 15-43 of SEQ ID NO: 47; (169) a targeting sequence comprising amino acids 20-43 of SEQ ID NO: 47; (170) a targeting sequence comprising amino acids 25-43 of SEQ ID NO: 47; (171) a targeting sequence comprising amino acids 1-32 of SEQ ID NO: 49; (172) a targeting sequence comprising amino acids 17-32 of SEQ ID NO: 49; (173) a targeting sequence comprising SEQ ID NO: 49; (174) an exosporium protein comprising an amino acid sequence having at least 85% identity with SEQ ID NO: 50; (175) a targeting sequence comprising amino acids 2-32 of SEQ ID NO: 49; (176) a targeting sequence comprising amino acids 5-32 of SEQ ID NO: 49; (177) a targeting sequence comprising amino acids 8-32 of SEQ ID NO: 49; (178) a targeting sequence comprising amino acids 10-32 of SEQ ID NO: 49; (179) a targeting sequence comprising amino acids 15-32 of SEQ ID NO: 49; (180) a targeting sequence comprising amino acids 1-33 of SEQ ID NO: 51; (181) a targeting sequence comprising amino acids 18-33 of SEQ ID NO: 51; (182) a targeting sequence comprising SEQ ID NO: 51; (183) an exosporium protein comprising an amino acid sequence having at least 85% identity with SEQ ID NO: 52; (184) a targeting sequence comprising amino acids 2-33 of SEQ ID NO: 51; (185) a targeting sequence comprising amino acids 5-33 of SEQ ID NO: 51; (186) a targeting sequence comprising amino acids 8-33 of SEQ ID NO: 51; (187) a targeting sequence comprising amino acids 10-33 of SEQ ID NO: 51; (188) a targeting sequence comprising amino acids 15-33 of SEQ ID NO: 51; (189) a targeting sequence comprising amino acids 1-33 of SEQ ID NO: 53; (190) a targeting sequence comprising amino acids 18-33 of SEQ ID NO: 53; (191) a targeting sequence comprising SEQ ID NO: 53; (192) an exosporium protein comprising an amino acid sequence having at least 85% identity with SEQ ID NO: 54; (193) a targeting sequence comprising amino acids 2-33 of SEQ ID NO: 53; (194) a targeting sequence comprising amino acids 5-33 of SEQ ID NO: 53; (195) a targeting sequence comprising amino acids 8-33 of SEQ ID NO: 53; (196) a targeting sequence comprising amino acids 10-33 of SEQ ID NO: 53; (197) a targeting sequence comprising amino acids 15-33 of SEQ ID NO: 53; (198) a targeting sequence comprising amino acids 1-30 of SEQ ID NO: 55; (199) a targeting sequence comprising amino acids 15-30 of SEQ ID NO: 55; (200) a targeting sequence comprising SEQ ID NO: 55; (201) an exosporium protein comprising an amino acid sequence having at least 85% identity with SEQ ID NO: 56; (202) a targeting sequence comprising amino acids 2-30 of SEQ ID NO: 55; (203) a targeting sequence comprising amino acids 5-30 of SEQ ID NO: 55; (204) a targeting sequence comprising amino acids 8-30 of SEQ ID NO: 55; (205) a targeting sequence comprising amino acids 10-30 of SEQ ID NO: 55; (206) a targeting sequence comprising amino acids 1-130 of SEQ ID NO: 57; (207) a targeting sequence comprising amino acids 115-130 of SEQ ID NO: 57; (208) a targeting sequence comprising SEQ ID NO: 57; (209) an exosporium protein comprising an amino acid sequence having at least 85% identity with SEQ ID NO: 58; (210) a targeting sequence comprising amino acids 2-130 of SEQ ID NO: 57; (211) a targeting sequence comprising amino acids 5-130 of SEQ ID NO: 57; (212) a targeting sequence comprising amino acids 10-130 of SEQ ID NO: 57; (213) a targeting sequence comprising amino acids 20-130 of SEQ ID NO: 57; (214) a targeting sequence comprising amino acids 30-130 of SEQ ID NO: 57; (215) a targeting sequence comprising amino acids 40-130 of SEQ ID NO: 57; (216) a targeting sequence comprising amino acids 50-130 of SEQ ID NO: 57; (217) a targeting sequence comprising amino acids 60-130 of SEQ ID NO: 57; (218) a targeting sequence comprising amino acids 70-130 of SEQ ID NO: 57; (219) a targeting sequence comprising amino acids 80-130 of SEQ ID NO: 57; (220) a targeting sequence comprising amino acids 90-130 of SEQ ID NO: 57; (221) a targeting sequence comprising amino acids 100-130 of SEQ ID NO: 57; (222) a targeting sequence comprising amino acids 110-130 of SEQ ID NO: 57; (223) an exosporium protein fragment comprising an amino acid sequence having at least 85% identity with SEQ ID NO: 95; (224) a targeting sequence comprising SEQ ID NO: 96; (225) a targeting sequence comprising SEQ ID NO: 97; (226) a targeting sequence comprising SEQ ID NO: 98; (227) a targeting sequence comprising SEQ ID NO: 99; (228) a targeting sequence comprising SEQ ID NO: 100; (229) a targeting sequence comprising SEQ ID NO: 101; (230) a targeting sequence comprising SEQ ID NO: 102; (231) a targeting sequence comprising SEQ ID NO: 103; (232) a targeting sequence comprising SEQ ID NO: 104; (233) a targeting sequence comprising SEQ ID NO: 105; (234) a targeting sequence comprising SEQ ID NO: 106; (235) an exosporium protein comprising an amino acid sequence having at least 85% identity with SEQ ID NO: 108; (236) an exosporium protein comprising an amino acid sequence having at least 85% identity with SEQ ID NO: 109; (237) an exosporium protein comprising an amino acid sequence having at least 85% identity with SEQ ID NO: 110; (238) an exosporium protein comprising an amino acid sequence having at least 85% identity with SEQ ID NO: 111; (239) an exosporium protein comprising an amino acid sequence having at least 85% identity with SEQ ID NO: 112; (240) an exosporium protein comprising an amino acid sequence having at least 85% identity with SEQ ID NO: 113; (241) an exosporium protein comprising an amino acid sequence having at least 85% identity with SEQ ID NO: 114; (242) an exosporium protein comprising an amino acid sequence having at least 85% identity with SEQ ID NO: 115; (243) an exosporium protein comprising an amino acid sequence having at least 85% identity with SEQ ID NO: 116; (244) an exosporium protein comprising an amino acid sequence having at least 85% identity with SEQ ID NO: 117; (245) an exosporium protein comprising an amino acid sequence having at least 85% identity with SEQ ID NO: 118; (246) an exosporium protein comprising an amino acid sequence having at least 85% identity with SEQ ID NO: 119; (247) an exosporium protein comprising an amino acid sequence having at least 85% identity with SEQ ID NO: 120; (248) an exosporium protein comprising an amino acid sequence having at least 85% identity with SEQ ID NO: 121; (249) a targeting sequence comprising amino acids 22-31 of SEQ ID NO: 1; (250) a targeting sequence comprising amino acids 22-33 of SEQ ID NO: 1; (251) a targeting sequence comprising amino acids 20-31 of SEQ ID NO: 1; (252) a targeting sequence comprising amino acids 14-23 of SEQ ID NO: 3; (253) a targeting sequence comprising amino acids 14-25 of SEQ ID NO: 3; or (254) a targeting sequence comprising amino acids 12-23 of SEQ ID NO: 3.

For example, when the protein or peptide of interest comprises an enzyme that catalyzes the production of nitric oxide or a nucleic acid binding protein or peptide, the targeting sequence, exosporium protein, or exosporium protein fragment can be: (1) a targeting sequence comprising amino acids 2-35 of SEQ ID NO: 1; (2) a targeting sequence comprising amino acids 5-35 of SEQ ID NO: 1; (3) a targeting sequence comprising amino acids 8-35 of SEQ ID NO: 1; (4) a targeting sequence comprising amino acids 10-35 of SEQ ID NO: 1; (5) a targeting sequence comprising amino acids 15-35 of SEQ ID NO: 1; (6) a targeting sequence comprising amino acids 2-27 of SEQ ID NO: 3; (7) a targeting sequence comprising amino acids 5-27 of SEQ ID NO: 3; (8) a targeting sequence comprising amino acids 8-27 of SEQ ID NO: 3; (9) a targeting sequence comprising amino acids 10-27 of SEQ ID NO: 3; (10) a targeting sequence comprising amino acids 2-38 of SEQ ID NO: 5; (11) a targeting sequence comprising amino acids 5-38 of SEQ ID NO: 5; (12) a targeting sequence comprising amino acids 8-38 of SEQ ID NO: 5; (13) a targeting sequence comprising amino acids 10-38 of SEQ ID NO: 5; (14) a targeting sequence comprising amino acids 15-38 of SEQ ID NO: 5; (15) a targeting sequence comprising amino acids 20-38 of SEQ ID NO: 5; (16) a targeting sequence comprising amino acids 2-28 of SEQ ID NO: 7; (17) a targeting sequence comprising amino acids 5-28 of SEQ ID NO: 7; (18) a targeting sequence comprising amino acids 8-28 of SEQ ID NO: 7; (19) a targeting sequence comprising amino acids 10-28 of SEQ ID NO: 7; (20) a targeting sequence comprising amino acids 2-24 of SEQ ID NO: 9; (21) a targeting sequence comprising amino acids 5-24 of SEQ ID NO: 9; (22) a targeting sequence comprising amino acids 8-24 of SEQ ID NO: 9; (23) a targeting sequence comprising amino acids 2-33 of SEQ ID NO: 11; (24) a targeting sequence comprising amino acids 5-33 of SEQ ID NO: 11; (25) a targeting sequence comprising amino acids 8-33 of SEQ ID NO: 11; (26) a targeting sequence comprising amino acids 10-33 of SEQ ID NO: 11; (27) a targeting sequence comprising amino acids 15-33 of SEQ ID NO: 11; (28) a targeting sequence comprising amino acids 2-33 of SEQ ID NO: 13; (29) a targeting sequence comprising amino acids 5-33 of SEQ ID NO: 13; (30) a targeting sequence comprising amino acids 8-33 of SEQ ID NO: 13; (31) a targeting sequence comprising amino acids 10-33 of SEQ ID NO: 13; (32) a targeting sequence comprising amino acids 15-33 of SEQ ID NO: 13; (33) a targeting sequence comprising amino acids 2-43 of SEQ ID NO: 15; (34) a targeting sequence comprising amino acids 5-43 of SEQ ID NO: 15; (35) a targeting sequence comprising amino acids 8-43 of SEQ ID NO: 15; (36) a targeting sequence comprising amino acids 10-43 of SEQ ID NO: 15; (37) a targeting sequence comprising amino acids 15-43 of SEQ ID NO: 15; (38) a targeting sequence comprising amino acids 20-43 of SEQ ID NO: 15; (39) a targeting sequence comprising amino acids 25-43 of SEQ ID NO: 15; (40) a targeting sequence comprising amino acids 2-27 of SEQ ID NO: 17; (41) a targeting sequence comprising amino acids 5-27 of SEQ ID NO: 17; (42) a targeting sequence comprising amino acids 8-27 of SEQ ID NO: 17; (43) a targeting sequence comprising amino acids 10-27 of SEQ ID NO: 17; (44) a targeting sequence comprising amino acids 2-33 of SEQ ID NO: 19; (45) a targeting sequence comprising amino acids 5-33 of SEQ ID NO: 19;

(46) a targeting sequence comprising amino acids 8-33 of SEQ ID NO: 19; (47) a targeting sequence comprising amino acids 10-33 of SEQ ID NO: 19; (48) a targeting sequence comprising amino acids 15-33 of SEQ ID NO: 19; (49) a targeting sequence comprising amino acids 2-33 of SEQ ID NO: 21; (50) a targeting sequence comprising amino acids 5-33 of SEQ ID NO: 21; (51) a targeting sequence comprising amino acids 8-33 of SEQ ID NO: 21; (52) a targeting sequence comprising amino acids 10-33 of SEQ ID NO: 21; (53) a targeting sequence comprising amino acids 15-33 of SEQ ID NO: 21; (54) a targeting sequence comprising amino acids 2-24 of SEQ ID NO:23; (55) a targeting sequence comprising amino acids 5-24 of SEQ ID NO: 23; (56) a targeting sequence comprising amino acids 8-24 of SEQ ID NO: 23; (57) a targeting sequence comprising amino acids 2-24 of SEQ ID NO: 25; (58) a targeting sequence comprising amino acids 5-24 of SEQ ID NO: 25; (59) a targeting sequence comprising amino acids 8-24 of SEQ ID NO: 25; (60) a targeting sequence comprising amino acids 2-30 of SEQ ID NO: 27; (61) a targeting sequence comprising amino acids 5-30 of SEQ ID NO: 27; (62) a targeting sequence comprising amino acids 8-30 of SEQ ID NO: 27; (63) a targeting sequence comprising amino acids 10-30 of SEQ ID NO: 27; (64) a targeting sequence comprising amino acids 2-33 of SEQ ID NO: 29; (65) a targeting sequence comprising amino acids 5-33 of SEQ ID NO: 29; (66) a targeting sequence comprising amino acids 8-33 of SEQ ID NO: 29; (67) a targeting sequence comprising amino acids 10-33 of SEQ ID NO: 29; (68) a targeting sequence comprising amino acids 15-33 of SEQ ID NO: 29; (69) a targeting sequence comprising amino acids 2-24 of SEQ ID NO: 31; (70) a targeting sequence comprising amino acids 5-24 of SEQ ID NO: 31; (71) a targeting sequence comprising amino acids 8-24 of SEQ ID NO: 31; (72) a targeting sequence comprising amino acids 2-29 of SEQ ID NO: 43; (73) a targeting sequence comprising amino acids 5-29 of SEQ ID NO: 43; (74) a targeting sequence comprising amino acids 8-29 of SEQ ID NO: 43; (75) a targeting sequence comprising amino acids 10-29 of SEQ ID NO: 43; (76) a targeting sequence comprising amino acids 2-35 of SEQ ID NO: 45; (77) a targeting sequence comprising amino acids 5-35 of SEQ ID NO: 45; (78) a targeting sequence comprising amino acids 8-35 of SEQ ID NO: 45; (79) a targeting sequence comprising amino acids 10-35 of SEQ ID NO: 45; (80) a targeting sequence comprising amino acids 15-3 5 of SEQ ID NO: 45; (81) a targeting sequence comprising amino acids 2-43 of SEQ ID NO: 47; (82) a targeting sequence comprising amino acids 5-43 of SEQ ID NO: 47; (83) a targeting sequence comprising amino acids 8-43 of SEQ ID NO: 47; (84) a targeting sequence comprising amino acids 10-43 of SEQ ID NO: 47; (85) a targeting sequence comprising amino acids 15-43 of SEQ ID NO: 47; (86) a targeting sequence comprising amino acids 20-43 of SEQ ID NO: 47; (87) a targeting sequence comprising amino acids 25-43 of SEQ ID NO: 47; (88) a targeting sequence comprising amino acids 2-32 of SEQ ID NO: 49; (89) a targeting sequence comprising amino acids 5-32 of SEQ ID NO: 49; (90) a targeting sequence comprising amino acids 8-32 of SEQ ID NO: 49; (91) a targeting sequence comprising amino acids 10-32 of SEQ ID NO: 49; (92) a targeting sequence comprising amino acids 15-32 of SEQ ID NO: 49; (93) a targeting sequence comprising amino acids 2-33 of SEQ ID NO: 51; (94) a targeting sequence comprising amino acids 5-33 of SEQ ID NO: 51; (95) a targeting sequence comprising amino acids 8-33 of SEQ ID NO: 51; (96) a targeting sequence comprising amino acids 10-33 of SEQ ID NO: 51; (97) a targeting sequence comprising amino acids 15-33 of SEQ ID NO: 51; (98) a targeting sequence comprising amino acids 2-33 of SEQ ID NO: 53; (99) a targeting sequence comprising amino acids 5-33 of SEQ ID NO: 53; (100) a targeting sequence comprising amino acids 8-33 of SEQ ID NO: 53; (101) a targeting sequence comprising amino acids 10-33 of SEQ ID NO: 53; (102) a targeting sequence comprising amino acids 15-33 of SEQ ID NO: 53; (103) a targeting sequence comprising amino acids 2-30 of SEQ ID NO: 55; (104) a targeting sequence comprising amino acids 5-30 of SEQ ID NO: 55; (105) a targeting sequence comprising amino acids 8-30 of SEQ ID NO: 55; (106) a targeting sequence comprising amino acids 10-30 of SEQ ID NO: 55; (107) a targeting sequence comprising amino acids 2-130 of SEQ ID NO: 57; (108) a targeting sequence comprising amino acids 5-130 of SEQ ID NO: 57; (109) a targeting sequence comprising amino acids 10-130 of SEQ ID NO: 57; (110) a targeting sequence comprising amino acids 20-130 of SEQ ID NO: 57; (111) a targeting sequence comprising amino acids 30-130 of SEQ ID NO: 57; (112) a targeting sequence comprising amino acids 40-130 of SEQ ID NO: 57; (113) a targeting sequence comprising amino acids 50-130 of SEQ ID NO: 57; (114) a targeting sequence comprising amino acids 60-130 of SEQ ID NO: 57; (115) a targeting sequence comprising amino acids 70-130 of SEQ ID NO: 57; (116) a targeting sequence comprising amino acids 80-130 of SEQ ID NO: 57; (117) a targeting sequence comprising amino acids 90-130 of SEQ ID NO: 57; (118) a targeting sequence comprising amino acids 100-130 of SEQ ID NO: 57; or (119) a targeting sequence comprising amino acids 110-130 of SEQ ID NO: 57.

A fusion protein is provided which comprises an antigen or a remediation enzyme and a targeting sequence or exosporium protein. The targeting sequence or exosporium protein can comprise any of the targeting sequences or exosporium proteins listed above in paragraphs [00166]-[00168] for use with any protein or peptide of interest or: (1) a targeting sequence comprising amino acids 2-35 of SEQ ID NO: 1; (2) a targeting sequence comprising amino acids 5-35 of SEQ ID NO: 1; (3) a targeting sequence comprising amino acids 8-35 of SEQ ID NO: 1; (4) a targeting sequence comprising amino acids 10-35 of SEQ ID NO: 1; (5) a targeting sequence comprising amino acids 15-35 of SEQ ID NO: 1; (6) a targeting sequence comprising amino acids 22-31 of SEQ ID NO: 1; (7) a targeting sequence comprising amino acids 22-33 of SEQ ID NO: 1; (8) a targeting sequence comprising amino acids 20-31 of SEQ ID NO: 1; (9) a targeting sequence comprising amino acids 2-27 of SEQ ID NO: 3; (10) a targeting sequence comprising amino acids 5-27 of SEQ ID NO: 3; (11) a targeting sequence comprising amino acids 8-27 of SEQ ID NO: 3; (12) a targeting sequence comprising amino acids 10-27 of SEQ ID NO: 3; (13) a targeting sequence comprising amino acids 14-23 of SEQ ID NO: 3; (14) a targeting sequence comprising amino acids 14-25 of SEQ ID NO: 3; (15) a targeting sequence comprising amino acids 12-23 of SEQ ID NO: 3; (16) a targeting sequence comprising amino acids 2-38 of SEQ ID NO: 5; (17) a targeting sequence comprising amino acids 5-38 of SEQ ID NO: 5; (18) a targeting sequence comprising amino acids 8-38 of SEQ ID NO: 5; (19) a targeting sequence comprising amino acids 10-38 of SEQ ID NO: 5; (20) a targeting sequence comprising amino acids 15-38 of SEQ ID NO: 5; (21) a targeting sequence comprising amino acids 20-38 of SEQ ID NO: 5; (22) a targeting sequence comprising amino acids 2-28 of SEQ ID NO: 7;

(23) a targeting sequence comprising amino acids 5-28 of SEQ ID NO: 7; (24) a targeting sequence comprising amino acids 8-28 of SEQ ID NO: 7; (25) a targeting sequence comprising amino acids 10-28 of SEQ ID NO: 7; (26) a targeting sequence comprising amino acids 1-24 of SEQ ID NO: 9; (27) a targeting sequence comprising amino acids 9-24 of SEQ ID NO: 9; (28) a targeting sequence comprising SEQ ID NO: 9; (29) an exosporium protein comprising an amino acid sequence having at least 85% identity with SEQ ID NO: 10; (30) a targeting sequence comprising amino acids 2-24 of SEQ ID NO: 9; (31) a targeting sequence comprising amino acids 5-24 of SEQ ID NO: 9; (32) a targeting sequence comprising amino acids 8-24 of SEQ ID NO: 9; (33) a targeting sequence comprising amino acids 1-33 of SEQ ID NO: 11; (34) a targeting sequence comprising amino acids 18-33 of SEQ ID NO: 11; (35) a targeting sequence comprising SEQ ID NO: 11; (36) an exosporium protein comprising an amino acid sequence having at least 85% identity with SEQ ID NO: 12; (37) a targeting sequence comprising amino acids 2-33 of SEQ ID NO: 11; (38) a targeting sequence comprising amino acids 5-33 of SEQ ID NO: 11; (39) a targeting sequence comprising amino acids 8-33 of SEQ ID NO: 11; (40) a targeting sequence comprising amino acids 10-33 of SEQ ID NO: 11; (41) a targeting sequence comprising amino acids 15-33 of SEQ ID NO: 11; (42) a targeting sequence comprising amino acids 1-33 of SEQ ID NO: 13; (43) a targeting sequence comprising amino acids 18-33 of SEQ ID NO: 13; (44) a targeting sequence comprising SEQ ID NO:13; (45) an exosporium protein comprising an amino acid sequence having at least 85% identity with SEQ ID NO: 14; (46) a targeting sequence comprising amino acids 2-33 of SEQ ID NO: 13; (47) a targeting sequence comprising amino acids 5-33 of SEQ ID NO: 13; (48) a targeting sequence comprising amino acids 8-33 of SEQ ID NO: 13; (49) a targeting sequence comprising amino acids 10-33 of SEQ ID NO: 13; (50) a targeting sequence comprising amino acids 15-33 of SEQ ID NO: 13; (51) a targeting sequence comprising amino acids 1-43 of SEQ ID NO: 15; (52) a targeting sequence comprising amino acids 28-43 of SEQ ID NO: 15; (53) a targeting sequence comprising SEQ ID NO: 15; (54) an exosporium protein comprising an amino acid sequence having at least 85% identity with SEQ ID NO: 16; (55) a targeting sequence comprising amino acids 2-43 of SEQ ID NO: 15; (56) a targeting sequence comprising amino acids 5-43 of SEQ ID NO: 15; (57) a targeting sequence comprising amino acids 8-43 of SEQ ID NO: 15; (58) a targeting sequence comprising amino acids 10-43 of SEQ ID NO: 15; (59) a targeting sequence comprising amino acids 15-43 of SEQ ID NO: 15; (60) a targeting sequence comprising amino acids 20-43 of SEQ ID NO: 15; (61) a targeting sequence comprising amino acids 25-43 of SEQ ID NO: 15; (62) a targeting sequence comprising amino acids 1-27 of SEQ ID NO: 17; (63) a targeting sequence comprising amino acids 12-27 of SEQ ID NO: 17; (64) a targeting sequence comprising SEQ ID NO: 17; (65) an exosporium protein comprising an amino acid sequence having at least 85% identity with SEQ ID NO: 18; (66) a targeting sequence comprising amino acids 2-27 of SEQ ID NO: 17; (67) a targeting sequence comprising amino acids 5-27 of SEQ ID NO: 17; (68) a targeting sequence comprising amino acids 8-27 of SEQ ID NO: 17; (69) a targeting sequence comprising amino acids 10-27 of SEQ ID NO: 17; (70) a targeting sequence comprising amino acids 1-33 of SEQ ID NO: 19; (71) a targeting sequence comprising amino acids 18-33 of SEQ ID NO: 19; (72) a targeting sequence comprising SEQ ID NO:19; (73) an exosporium protein comprising an amino acid sequence having at least 85% identity with SEQ ID NO:20; (74) a targeting sequence comprising amino acids 2-33 of SEQ ID NO: 19; (75) a targeting sequence comprising amino acids 5-33 of SEQ ID NO: 19; (76) a targeting sequence comprising amino acids 8-33 of SEQ ID NO: 19; (77) a targeting sequence comprising amino acids 10-33 of SEQ ID NO: 19; (78) a targeting sequence comprising amino acids 15-33 of SEQ ID NO: 19; (79) a targeting sequence comprising amino acids 1-33 of SEQ ID NO: 21; (80) a targeting sequence comprising amino acids 18-33 of SEQ ID NO: 21; (81) a targeting sequence comprising SEQ ID NO:21; (82) an exosporium protein comprising an amino acid sequence having at least 85% identity with SEQ ID NO:22; (83) a targeting sequence comprising amino acids 2-33 of SEQ ID NO: 21; (84) a targeting sequence comprising amino acids 5-33 of SEQ ID NO: 21; (85) a targeting sequence comprising amino acids 8-33 of SEQ ID NO: 21; (86) a targeting sequence comprising amino acids 10-33 of SEQ ID NO: 21; (87) a targeting sequence comprising amino acids 15-33 of SEQ ID NO: 21; (88) a targeting sequence comprising amino acids 1-24 of SEQ ID NO: 23; (89) a targeting sequence comprising amino acids 9-24 of SEQ ID NO: 23; (90) a targeting sequence comprising SEQ ID NO:23; (91) an exosporium protein comprising an amino acid sequence having at least 85% identity with SEQ ID NO:24; (92) a targeting sequence comprising amino acids 2-24 of SEQ ID NO:23; (93) a targeting sequence comprising amino acids 5-24 of SEQ ID NO: 23; (94) a targeting sequence comprising amino acids 8-24 of SEQ ID NO: 23; (95) a targeting sequence comprising amino acids 1-24 of SEQ ID NO: 25; (96) a targeting sequence comprising amino acids 9-24 of SEQ ID NO: 25; (97) a targeting sequence comprising SEQ ID NO:25; (98) an exosporium protein comprising an amino acid sequence having at least 85% identity with SEQ ID NO:26; (99) a targeting sequence comprising amino acids 2-24 of SEQ ID NO: 25; (100) a targeting sequence comprising amino acids 5-24 of SEQ ID NO: 25; (101) a targeting sequence comprising amino acids 8-24 of SEQ ID NO: 25; (102) a targeting sequence comprising amino acids 1-30 of SEQ ID NO: 27; (103) a targeting sequence comprising amino acids 15-30 of SEQ ID NO: 27; (104) a targeting sequence comprising SEQ ID NO:27; (105) an exosporium protein comprising an amino acid sequence having at least 85% identity with SEQ ID NO:28; (106) a targeting sequence comprising amino acids 2-30 of SEQ ID NO: 27; (107) a targeting sequence comprising amino acids 5-30 of SEQ ID NO: 27; (108) a targeting sequence comprising amino acids 8-30 of SEQ ID NO: 27; (109) a targeting sequence comprising amino acids 10-30 of SEQ ID NO: 27; (110) a targeting sequence comprising amino acids 1-33 of SEQ ID NO: 29; (111) a targeting sequence comprising amino acids 18-33 of SEQ ID NO: 29; (112) a targeting sequence comprising SEQ ID NO:29; (113) an exosporium protein comprising an amino acid sequence having at least 85% identity with SEQ ID NO:30; (114) a targeting sequence comprising amino acids 2-33 of SEQ ID NO: 29; (115) a targeting sequence comprising amino acids 5-33 of SEQ ID NO: 29; (116) a targeting sequence comprising amino acids 8-33 of SEQ ID NO: 29; (117) a targeting sequence comprising amino acids 10-33 of SEQ ID NO: 29; (118) a targeting sequence comprising amino acids 15-33 of SEQ ID NO: 29; (119) a targeting sequence comprising amino acids 1-24 of SEQ ID NO: 31; (120) a targeting sequence comprising amino acids 9-24 of SEQ ID NO: 31; (121) a targeting sequence comprising SEQ ID NO:31; (122) an exosporium protein comprising an amino acid sequence having at least 85% identity with SEQ ID NO:32; (123) a targeting sequence comprising amino acids 2-24 of SEQ ID NO: 31; (124) a targeting sequence comprising amino acids 5-24 of SEQ ID NO: 31; (125) a targeting sequence comprising amino acids 8-24 of SEQ ID NO: 31; (126) a targeting sequence comprising amino acids 1-15 of SEQ ID NO: 33; (127) a targeting sequence comprising SEQ ID NO:33; (128) an exosporium protein comprising an amino acid sequence having at least 85% identity with SEQ ID NO:34; (129) a targeting sequence comprising amino acids 1-16 of SEQ ID NO: 35; (130) a targeting sequence comprising SEQ ID NO:35; (131) an exosporium protein comprising an amino acid sequence having at least 85% identity with SEQ ID NO:36; (132) a targeting sequence comprising amino acids 1-29 of SEQ ID NO:43; (133) a targeting sequence comprising amino acids 14-29 of SEQ ID NO: 43; (134) a targeting sequence comprising SEQ ID NO: 43; (135) an exosporium protein comprising an amino acid sequence having at least 85% identity with SEQ ID NO: 44; (136) a targeting sequence comprising amino acids 2-29 of SEQ ID NO: 43; (137) a targeting sequence comprising amino acids 5-29 of SEQ ID NO: 43; (138) a targeting sequence comprising amino acids 8-29 of SEQ ID NO: 43; (139) a targeting sequence comprising amino acids 10-29 of SEQ ID NO: 43; (140) a targeting sequence comprising amino acids 1-35 of SEQ ID NO: 45; (141) a targeting sequence comprising amino acids 20-35 of SEQ ID NO: 45; (142) a targeting sequence comprising SEQ ID NO: 45; (143) an exosporium protein comprising an amino acid sequence having at least 85% identity with SEQ ID NO: 46; (144) a targeting sequence comprising amino acids 2-35 of SEQ ID NO: 45; (145) a targeting sequence comprising amino acids 5-35 of SEQ ID NO: 45; (146) a targeting sequence comprising amino acids 8-35 of SEQ ID NO: 45; (147) a targeting sequence comprising amino acids 10-35 of SEQ ID NO: 45; (148) a targeting sequence comprising amino acids 15-35 of SEQ ID NO: 45; (149) a targeting sequence comprising amino acids 1-43 of SEQ ID NO: 47; (150) a targeting sequence comprising amino acids 28-43 of SEQ ID NO: 47; (151) a targeting sequence comprising SEQ ID NO: 47; (152) an exosporium protein comprising an amino acid sequence having at least 85% identity with SEQ ID NO: 48; (153) a targeting sequence comprising amino acids 2-43 of SEQ ID NO: 47; (154) a targeting sequence comprising amino acids 5-43 of SEQ ID NO: 47; (155) a targeting sequence comprising amino acids 8-43 of SEQ ID NO: 47; (156) a targeting sequence comprising amino acids 10-43 of SEQ ID NO: 47; (157) a targeting sequence comprising amino acids 15-43 of SEQ ID NO: 47; (158) a targeting sequence comprising amino acids 20-43 of SEQ ID NO: 47; (159) a targeting sequence comprising amino acids 25-43 of SEQ ID NO: 47; (160) a targeting sequence comprising amino acids 1-32 of SEQ ID NO: 49; (161) a targeting sequence comprising amino acids 17-32 of SEQ ID NO: 49; (162) a targeting sequence comprising SEQ ID NO: 49; (163) an exosporium protein comprising an amino acid sequence having at least 85% identity with SEQ ID NO: 50; (164) a targeting sequence comprising amino acids 2-32 of SEQ ID NO: 49; (165) a targeting sequence comprising amino acids 5-32 of SEQ ID NO: 49; (166) a targeting sequence comprising amino acids 8-32 of SEQ ID NO: 49; (167) a targeting sequence comprising amino acids 10-32 of SEQ ID NO: 49; (168) a targeting sequence comprising amino acids 15-32 of SEQ ID NO: 49; (169) a targeting sequence comprising amino acids 1-33 of SEQ ID NO: 51; (170) a targeting sequence comprising amino acids 18-33 of SEQ ID NO: 51; (171) a targeting sequence comprising SEQ ID NO: 51; (172) an exosporium protein comprising an amino acid sequence having at least 85% identity with SEQ ID NO: 52; (173) a targeting sequence comprising amino acids 2-33 of SEQ ID NO: 51; (174) a targeting sequence comprising amino acids 5-33 of SEQ ID NO: 51; (175) a targeting sequence comprising amino acids 8-33 of SEQ ID NO: 51; (176) a targeting sequence comprising amino acids 10-33 of SEQ ID NO: 51; (177) a targeting sequence comprising amino acids 15-33 of SEQ ID NO: 51; (178) a targeting sequence comprising amino acids 1-33 of SEQ ID NO: 53; (179) a targeting sequence comprising amino acids 18-33 of SEQ ID NO: 53; (180) a targeting sequence comprising SEQ ID NO: 53; (181) an exosporium protein comprising an amino acid sequence having at least 85% identity with SEQ ID NO: 54; (182) a targeting sequence comprising amino acids 2-33 of SEQ ID NO: 53; (183) a targeting sequence comprising amino acids 5-33 of SEQ ID NO: 53; (184) a targeting sequence comprising amino acids 8-33 of SEQ ID NO: 53; (185) a targeting sequence comprising amino acids 10-33 of SEQ ID NO: 53; (186) a targeting sequence comprising amino acids 15-33 of SEQ ID NO: 53; (187) a targeting sequence comprising amino acids 1-30 of SEQ ID NO: 55; (188) a targeting sequence comprising amino acids 15-30 of SEQ ID NO: 55; (189) a targeting sequence comprising SEQ ID NO: 55; (190) an exosporium protein comprising an amino acid sequence having at least 85% identity with SEQ ID NO: 56; (191) a targeting sequence comprising amino acids 2-30 of SEQ ID NO: 55; (192) a targeting sequence comprising amino acids 5-30 of SEQ ID NO: 55; (193) a targeting sequence comprising amino acids 8-30 of SEQ ID NO: 55; (194) a targeting sequence comprising amino acids 10-30 of SEQ ID NO: 55; (195) a targeting sequence comprising amino acids 1-130 of SEQ ID NO: 57; (196) a targeting sequence comprising amino acids 115-130 of SEQ ID NO: 57; (197) a targeting sequence comprising SEQ ID NO: 57; (198) an exosporium protein comprising an amino acid sequence having at least 85% identity with SEQ ID NO: 58; (199) a targeting sequence comprising amino acids 2-130 of SEQ ID NO: 57; (200) a targeting sequence comprising amino acids 5-130 of SEQ ID NO: 57; (201) a targeting sequence comprising amino acids 10-130 of SEQ ID NO: 57; (202) a targeting sequence comprising amino acids 20-130 of SEQ ID NO: 57; (203) a targeting sequence comprising amino acids 30-130 of SEQ ID NO: 57; (204) a targeting sequence comprising amino acids 40-130 of SEQ ID NO: 57; (205) a targeting sequence comprising amino acids 50-130 of SEQ ID NO: 57; (206) a targeting sequence comprising amino acids 60-130 of SEQ ID NO: 57; (207) a targeting sequence comprising amino acids 70-130 of SEQ ID NO: 57; (208) a targeting sequence comprising amino acids 80-130 of SEQ ID NO: 57; (209) a targeting sequence comprising amino acids 90-130 of SEQ ID NO: 57; (210) a targeting sequence comprising amino acids 100-130 of SEQ ID NO: 57; (211) a targeting sequence comprising amino acids 110-130 of SEQ ID NO: 57; (212) a targeting sequence comprising SEQ ID NO: 97; (213) a targeting sequence comprising SEQ ID NO: 98; (214) a targeting sequence comprising SEQ ID NO: 99; (215) a targeting sequence comprising SEQ ID NO: 100; (216) a targeting sequence comprising SEQ ID NO: 101; (217) a targeting sequence comprising SEQ ID NO: 102; (218) a targeting sequence comprising SEQ ID NO: 103; (219) a targeting sequence comprising SEQ ID NO: 104; (220) a targeting sequence comprising SEQ ID NO: 105; (221) a targeting sequence comprising SEQ ID NO: 106; (222) an exosporium protein comprising an amino acid sequence having at least 85% identity with SEQ ID NO:

108; (223) an exosporium protein comprising an amino acid sequence having at least 85% identity with SEQ ID NO: 109; (224) an exosporium protein comprising an amino acid sequence having at least 85% identity with SEQ ID NO: 110; (225) an exosporium protein comprising an amino acid sequence having at least 85% identity with SEQ ID NO: 111; (226) an exosporium protein comprising an amino acid sequence having at least 85% identity with SEQ ID NO: 112; (227) an exosporium protein comprising an amino acid sequence having at least 85% identity with SEQ ID NO: 113; (228) an exosporium protein comprising an amino acid sequence having at least 85% identity with SEQ ID NO: 114; (229) an exosporium protein comprising an amino acid sequence having at least 85% identity with SEQ ID NO: 115; (230) an exosporium protein comprising an amino acid sequence having at least 85% identity with SEQ ID NO: 116; (231) an exosporium protein comprising an amino acid sequence having at least 85% identity with SEQ ID NO: 117; (232) an exosporium protein comprising an amino acid sequence having at least 85% identity with SEQ ID NO: 118; (233) an exosporium protein comprising an amino acid sequence having at least 85% identity with SEQ ID NO: 119; (234) an exosporium protein comprising an amino acid sequence having at least 85% identity with SEQ ID NO: 120; or (235) an exosporium protein comprising an amino acid sequence having at least 85% identity with SEQ ID NO: 121.

A fusion protein is provided which comprises an enzyme suitable for breaking an emulsion or gel in a hydraulic fracturing fluid or an antibacterial protein or peptide and a targeting sequence, exosporium protein, or exosporium protein fragment. The targeting sequence, exosporium protein, or exosporium protein fragment can comprise any of the targeting sequences or exosporium proteins listed above in paragraphs [00166]-[00168] for use with any protein or peptide of interest or: (1) a targeting sequence comprising an amino acid sequence having at least about 43% identity with amino acids 20-35 of SEQ ID NO: 1, wherein the identity with amino acids 25-35 is at least about 54%; (2) a targeting sequence comprising amino acids 1-35 of SEQ ID NO: 1; (3) a targeting sequence comprising amino acids 20-35 of SEQ ID NO: 1; (4) a targeting sequence comprising SEQ ID NO: 1; (5) an exosporium protein comprising an amino acid sequence having at least 85% identity with SEQ ID NO: 2; (6) a targeting sequence comprising amino acids 2-35 of SEQ ID NO: 1; (7) a targeting sequence comprising amino acids 5-35 of SEQ ID NO: 1; (8) a targeting sequence comprising amino acids 8-35 of SEQ ID NO: 1; (9) a targeting sequence comprising amino acids 10-35 of SEQ ID NO: 1; (10) a targeting sequence comprising amino acids 15-3 5 of SEQ ID NO: 1; (11) a targeting sequence comprising amino acids 1-27 of SEQ ID NO: 3; (12) a targeting sequence comprising amino acids 12-27 of SEQ ID NO: 3; (13) a targeting sequence comprising SEQ ID NO: 3; (14) an exosporium protein comprising an amino acid sequence having at least 85% identity with SEQ ID NO: 4; (15) a targeting sequence comprising amino acids 2-27 of SEQ ID NO: 3; (16) a targeting sequence comprising amino acids 5-27 of SEQ ID NO: 3; (17) a targeting sequence comprising amino acids 8-27 of SEQ ID NO: 3; (18) a targeting sequence comprising amino acids 10-27 of SEQ ID NO: 3; (19) a targeting sequence comprising amino acids 1-38 of SEQ ID NO: 5; (20) a targeting sequence comprising amino acids 23-38 of SEQ ID NO: 5; (21) a targeting sequence comprising SEQ ID NO: 5; (22) an exosporium protein comprising an amino acid sequence having at least 85% identity with SEQ ID NO: 6; (23) a targeting sequence comprising amino acids 2-38 of SEQ ID NO: 5; (24) a targeting sequence comprising amino acids 5-38 of SEQ ID NO: 5; (25) a targeting sequence comprising amino acids 8-38 of SEQ ID NO: 5; (26) a targeting sequence comprising amino acids 10-38 of SEQ ID NO: 5; (27) a targeting sequence comprising amino acids 15-38 of SEQ ID NO: 5; (28) a targeting sequence comprising amino acids 20-38 of SEQ ID NO: 5; (29) a targeting sequence comprising amino acids 1-28 of SEQ ID NO: 7; (30) a targeting sequence comprising amino acids 13-28 of SEQ ID NO: 7; (31) a targeting sequence comprising SEQ ID NO: 7; (32) an exosporium protein comprising an amino acid sequence having at least 85% identity with SEQ ID NO: 8; (33) a targeting sequence comprising amino acids 2-28 of SEQ ID NO: 7; (34) a targeting sequence comprising amino acids 5-28 of SEQ ID NO: 7; (35) a targeting sequence comprising amino acids 8-28 of SEQ ID NO: 7; (36) a targeting sequence comprising amino acids 10-28 of SEQ ID NO: 7; (37) a targeting sequence comprising amino acids 1-24 of SEQ ID NO: 9; (38) a targeting sequence comprising amino acids 9-24 of SEQ ID NO: 9; (39) a targeting sequence comprising SEQ ID NO: 9; (40) an exosporium protein comprising an amino acid sequence having at least 85% identity with SEQ ID NO: 10; (41) a targeting sequence comprising amino acids 2-24 of SEQ ID NO: 9; (42) a targeting sequence comprising amino acids 5-24 of SEQ ID NO: 9; (43) a targeting sequence comprising amino acids 8-24 of SEQ ID NO: 9; (44) a targeting sequence comprising amino acids 1-33 of SEQ ID NO: 11; (45) a targeting sequence comprising amino acids 18-33 of SEQ ID NO: 11; (46) a targeting sequence comprising SEQ ID NO: 11; (47) an exosporium protein comprising an amino acid sequence having at least 85% identity with SEQ ID NO: 12; (48) a targeting sequence comprising amino acids 2-33 of SEQ ID NO: 11; (49) a targeting sequence comprising amino acids 5-33 of SEQ ID NO: 11; (50) a targeting sequence comprising amino acids 8-33 of SEQ ID NO: 11; (51) a targeting sequence comprising amino acids 10-33 of SEQ ID NO: 11; (52) a targeting sequence comprising amino acids 15-33 of SEQ ID NO: 11; (53) a targeting sequence comprising amino acids 1-33 of SEQ ID NO: 13; (54) a targeting sequence comprising amino acids 18-33 of SEQ ID NO: 13; (55) a targeting sequence comprising SEQ ID NO: 13; (56) an exosporium protein comprising an amino acid sequence having at least 85% identity with SEQ ID NO: 14; (57) a targeting sequence comprising amino acids 2-33 of SEQ ID NO: 13; (58) a targeting sequence comprising amino acids 5-33 of SEQ ID NO: 13; (59) a targeting sequence comprising amino acids 8-33 of SEQ ID NO: 13; (60) a targeting sequence comprising amino acids 10-33 of SEQ ID NO: 13; (61) a targeting sequence comprising amino acids 15-33 of SEQ ID NO: 13; (62) a targeting sequence comprising amino acids 1-43 of SEQ ID NO: 15; (63) a targeting sequence comprising amino acids 28-43 of SEQ ID NO: 15; (64) a targeting sequence comprising SEQ ID NO: 15; (65) an exosporium protein comprising an amino acid sequence having at least 85% identity with SEQ ID NO: 16; (66) a targeting sequence comprising amino acids 2-43 of SEQ ID NO: 15; (67) a targeting sequence comprising amino acids 5-43 of SEQ ID NO: 15; (68) a targeting sequence comprising amino acids 8-43 of SEQ ID NO: 15; (69) a targeting sequence comprising amino acids 10-43 of SEQ ID NO: 15; (70) a targeting sequence comprising amino acids 15-43 of SEQ ID NO: 15; (71) a targeting sequence comprising amino acids 20-43 of SEQ ID NO: 15; (72) a targeting sequence comprising amino acids 25-43 of SEQ ID NO: 15; (73) a targeting sequence comprising amino acids 1-27 of SEQ ID NO: 17; (74) a targeting sequence comprising amino acids 12-27 of SEQ ID NO: 17; (75) a targeting sequence comprising SEQ ID NO: 17; (76) an exosporium protein comprising an amino acid sequence having at least 85% identity with SEQ ID NO: 18; (77) a targeting sequence comprising amino acids 2-27 of SEQ ID NO: 17; (78) a targeting sequence comprising amino acids 5-27 of SEQ ID NO: 17; (79) a targeting sequence comprising amino acids 8-27 of SEQ ID NO: 17; (80) a targeting sequence comprising amino acids 10-27 of SEQ ID NO: 17; (81) a targeting sequence comprising amino acids 1-33 of SEQ ID NO: 19; (82) a targeting sequence comprising amino acids 18-33 of SEQ ID NO: 19; (83) a targeting sequence comprising SEQ ID NO: 19; (84) an exosporium protein comprising an amino acid sequence having at least 85% identity with SEQ ID NO: 20; (85) a targeting sequence comprising amino acids 2-33 of SEQ ID NO: 19; (86) a targeting sequence comprising amino acids 5-33 of SEQ ID NO: 19; (87) a targeting sequence comprising amino acids 8-33 of SEQ ID NO: 19; (88) a targeting sequence comprising amino acids 10-33 of SEQ ID NO: 19; (89) a targeting sequence comprising amino acids 15-33 of SEQ ID NO: 19; (90) a targeting sequence comprising amino acids 1-33 of SEQ ID NO: 21; (91) a targeting sequence comprising amino acids 18-33 of SEQ ID NO: 21; (92) a targeting sequence comprising SEQ ID NO:21; (93) an exosporium protein comprising an amino acid sequence having at least 85% identity with SEQ ID NO:22; (94) a targeting sequence comprising amino acids 2-33 of SEQ ID NO: 21; (95) a targeting sequence comprising amino acids 5-33 of SEQ ID NO: 21; (96) a targeting sequence comprising amino acids 8-33 of SEQ ID NO: 21; (97) a targeting sequence comprising amino acids 10-33 of SEQ ID NO: 21; (98) a targeting sequence comprising amino acids 15-33 of SEQ ID NO: 21; (99) a targeting sequence comprising amino acids 1-24 of SEQ ID NO: 23; (100) a targeting sequence comprising amino acids 9-24 of SEQ ID NO: 23; (101) a targeting sequence comprising SEQ ID NO:23; (102) an exosporium protein comprising an amino acid sequence having at least 85% identity with SEQ ID NO: 24; (103) a targeting sequence comprising amino acids 2-24 of SEQ ID NO: 23; (104) a targeting sequence comprising amino acids 5-24 of SEQ ID NO: 23; (105) a targeting sequence comprising amino acids 8-24 of SEQ ID NO: 23; (106) a targeting sequence comprising amino acids 1-24 of SEQ ID NO: 25; (107) a targeting sequence comprising amino acids 9-24 of SEQ ID NO: 25; (108) a targeting sequence comprising SEQ ID NO:25; (109) an exosporium protein comprising an amino acid sequence having at least 85% identity with SEQ ID NO:26; (110) a targeting sequence comprising amino acids 2-24 of SEQ ID NO: 25; (111) a targeting sequence comprising amino acids 5-24 of SEQ ID NO: 25; (112) a targeting sequence comprising amino acids 8-24 of SEQ ID NO: 25; (113) a targeting sequence comprising amino acids 1-30 of SEQ ID NO: 27; (114) a targeting sequence comprising amino acids 15-30 of SEQ ID NO: 27; (115) a targeting sequence comprising SEQ ID NO:27; (116) an exosporium protein comprising an amino acid sequence having at least 85% identity with SEQ ID NO:28; (117) a targeting sequence comprising amino acids 2-30 of SEQ ID NO: 27; (118) a targeting sequence comprising amino acids 5-30 of SEQ ID NO: 27; (119) a targeting sequence comprising amino acids 8-30 of SEQ ID NO: 27; (120) a targeting sequence comprising amino acids 10-30 of SEQ ID NO: 27; (121) a targeting sequence comprising amino acids 1-33 of SEQ ID NO: 29; (122) a targeting sequence comprising amino acids 18-33 of SEQ ID NO: 29; (123) a targeting sequence comprising SEQ ID NO:29; (124) an exosporium protein comprising an amino acid sequence having at least 85% identity with SEQ ID NO:30; (125) a targeting sequence comprising amino acids 2-33 of SEQ ID NO: 29; (126) a targeting sequence comprising amino acids 5-33 of SEQ ID NO: 29; (127) a targeting sequence comprising amino acids 8-33 of SEQ ID NO: 29; (128) a targeting sequence comprising amino acids 10-33 of SEQ ID NO: 29; (129) a targeting sequence comprising amino acids 15-33 of SEQ ID NO: 29; (130) a targeting sequence comprising amino acids 1-24 of SEQ ID NO: 31; (131) a targeting sequence comprising amino acids 9-24 of SEQ ID NO: 31; (132) a targeting sequence comprising SEQ ID NO:31; (133) an exosporium protein comprising an amino acid sequence having at least 85% identity with SEQ ID NO:32; (134) a targeting sequence comprising amino acids 2-24 of SEQ ID NO: 31; (135) a targeting sequence comprising amino acids 5-24 of SEQ ID NO: 31; (136) a targeting sequence comprising amino acids 8-24 of SEQ ID NO: 31; (137) a targeting sequence comprising amino acids 1-15 of SEQ ID NO: 33; (138) a targeting sequence comprising SEQ ID NO:33; (139) an exosporium protein comprising an amino acid sequence having at least 85% identity with SEQ ID NO:34; (140) a targeting sequence comprising amino acids 1-16 of SEQ ID NO: 35; (141) a targeting sequence comprising SEQ ID NO:35; (142) an exosporium protein comprising an amino acid sequence having at least 85% identity with SEQ ID NO:36; (143) a targeting sequence comprising amino acids 1-29 of SEQ ID NO:43; (144) a targeting sequence comprising amino acids 14-29 of SEQ ID NO: 43; (145) a targeting sequence comprising SEQ ID NO: 43; (146) an exosporium protein comprising an amino acid sequence having at least 85% identity with SEQ ID NO: 44; (147) a targeting sequence comprising amino acids 2-29 of SEQ ID NO: 43; (148) a targeting sequence comprising amino acids 5-29 of SEQ ID NO: 43; (149) a targeting sequence comprising amino acids 8-29 of SEQ ID NO: 43; (150) a targeting sequence comprising amino acids 10-29 of SEQ ID NO: 43; (151) a targeting sequence comprising amino acids 1-35 of SEQ ID NO: 45; (152) a targeting sequence comprising amino acids 20-35 of SEQ ID NO: 45; (153) a targeting sequence comprising SEQ ID NO: 45; (154) an exosporium protein comprising an amino acid sequence having at least 85% identity with SEQ ID NO: 46; (155) a targeting sequence comprising amino acids 2-35 of SEQ ID NO: 45; (156) a targeting sequence comprising amino acids 5-35 of SEQ ID NO: 45; (157) a targeting sequence comprising amino acids 8-35 of SEQ ID NO: 45; (158) a targeting sequence comprising amino acids 10-35 of SEQ ID NO: 45; (159) a targeting sequence comprising amino acids 15-35 of SEQ ID NO: 45; (160) a targeting sequence comprising amino acids 1-43 of SEQ ID NO: 47; (161) a targeting sequence comprising amino acids 28-43 of SEQ ID NO: 47; (162) a targeting sequence comprising SEQ ID NO: 47; (163) an exosporium protein comprising an amino acid sequence having at least 85% identity with SEQ ID NO: 48; (164) a targeting sequence comprising amino acids 2-43 of SEQ ID NO: 47; (165) a targeting sequence comprising amino acids 5-43 of SEQ ID NO: 47; (166) a targeting sequence comprising amino acids 8-43 of SEQ ID NO: 47; (167) a targeting sequence comprising amino acids 10-43 of SEQ ID NO: 47; (168) a targeting sequence comprising amino acids 15-43 of SEQ ID NO: 47; (169) a targeting sequence comprising amino acids 20-43 of SEQ ID NO: 47; (170) a targeting sequence comprising amino acids 25-43 of SEQ ID NO: 47; (171) a targeting sequence comprising amino acids 1-32 of SEQ ID NO: 49; (172) a targeting sequence comprising amino acids 17-32 of SEQ ID NO: 49; (173) a targeting sequence comprising SEQ ID NO: 49; (174) an exosporium protein comprising an amino acid sequence having at least 85% identity with SEQ ID NO: 50; (175) a targeting sequence comprising amino acids 2-32 of SEQ ID NO: 49; (176) a targeting sequence comprising amino acids 5-32 of SEQ ID NO: 49; (177) a targeting sequence comprising amino acids 8-32 of SEQ ID NO: 49; (178) a targeting sequence comprising amino acids 10-32 of SEQ ID NO: 49; (179) a targeting sequence comprising amino acids 15-32 of SEQ ID NO: 49; (180) a targeting sequence comprising amino acids 1-33 of SEQ ID NO: 51; (181) a targeting sequence comprising amino acids 18-33 of SEQ ID NO: 51; (182) a targeting sequence comprising SEQ ID NO: 51; (183) an exosporium protein comprising an amino acid sequence having at least 85% identity with SEQ ID NO: 52; (184) a targeting sequence comprising amino acids 2-33 of SEQ ID NO: 51; (185) a targeting sequence comprising amino acids 5-33 of SEQ ID NO: 51; (186) a targeting sequence comprising amino acids 8-33 of SEQ ID NO: 51; (187) a targeting sequence comprising amino acids 10-33 of SEQ ID NO: 51; (188) a targeting sequence comprising amino acids 15-33 of SEQ ID NO: 51; (189) a targeting sequence comprising amino acids 1-33 of SEQ ID NO: 53; (190) a targeting sequence comprising amino acids 18-33 of SEQ ID NO: 53; (191) a targeting sequence comprising SEQ ID NO: 53; (192) an exosporium protein comprising an amino acid sequence having at least 85% identity with SEQ ID NO: 54; (193) a targeting sequence comprising amino acids 2-33 of SEQ ID NO: 53; (194) a targeting sequence comprising amino acids 5-33 of SEQ ID NO: 53; (195) a targeting sequence comprising amino acids 8-33 of SEQ ID NO: 53; (196) a targeting sequence comprising amino acids 10-33 of SEQ ID NO: 53; (197) a targeting sequence comprising amino acids 15-33 of SEQ ID NO: 53; (198) a targeting sequence comprising amino acids 1-30 of SEQ ID NO: 55; (199) a targeting sequence comprising amino acids 15-30 of SEQ ID NO: 55; (200) a targeting sequence comprising SEQ ID NO: 55; (201) an exosporium protein comprising an amino acid sequence having at least 85% identity with SEQ ID NO: 56; (202) a targeting sequence comprising amino acids 2-30 of SEQ ID NO: 55; (203) a targeting sequence comprising amino acids 5-30 of SEQ ID NO: 55; (204) a targeting sequence comprising amino acids 8-30 of SEQ ID NO: 55; (205) a targeting sequence comprising amino acids 10-30 of SEQ ID NO: 55; (206) a targeting sequence comprising amino acids 1-130 of SEQ ID NO: 57; (207) a targeting sequence comprising amino acids 115-130 of SEQ ID NO: 57; (208) a targeting sequence comprising SEQ ID NO: 57; (209) an exosporium protein comprising an amino acid sequence having at least 85% identity with SEQ ID NO: 58; (210) a targeting sequence comprising amino acids 2-130 of SEQ ID NO: 57; (211) a targeting sequence comprising amino acids 5-130 of SEQ ID NO: 57; (212) a targeting sequence comprising amino acids 10-130 of SEQ ID NO: 57; (213) a targeting sequence comprising amino acids 20-130 of SEQ ID NO: 57; (214) a targeting sequence comprising amino acids 30-130 of SEQ ID NO: 57; (215) a targeting sequence comprising amino acids 40-130 of SEQ ID NO: 57; (216) a targeting sequence comprising amino acids 50-130 of SEQ ID NO: 57; (217) a targeting sequence comprising amino acids 60-130 of SEQ ID NO: 57; (218) a targeting sequence comprising amino acids 70-130 of SEQ ID NO: 57; (219) a targeting sequence comprising amino acids 80-130 of SEQ ID NO: 57; (220) a targeting sequence comprising amino acids 90-130 of SEQ ID NO: 57; (221) a targeting sequence comprising amino acids 100-130 of SEQ ID NO: 57; (222) a targeting sequence comprising amino acids 110-130 of SEQ ID NO: 57; (223) an exosporium protein fragment comprising an amino acid sequence having at least 85% identity with SEQ ID NO: 95; (224) a targeting sequence comprising SEQ ID NO: 96; (225) a targeting sequence comprising SEQ ID NO: 97; (226) a targeting sequence comprising SEQ ID NO: 98; (227) a targeting sequence comprising SEQ ID NO: 99; (228) a targeting sequence comprising SEQ ID NO: 100; (229) a targeting sequence comprising SEQ ID NO: 101; (230) a targeting sequence comprising SEQ ID NO: 102; (231) a targeting sequence comprising SEQ ID NO: 103; (232) a targeting sequence comprising SEQ ID NO: 104; (233) a targeting sequence comprising SEQ ID NO: 105; (234) a targeting sequence comprising SEQ ID NO: 106; (235) an exosporium protein comprising an amino acid sequence having at least 85% identity with SEQ ID NO: 108; (236) an exosporium protein comprising an amino acid sequence having at least 85% identity with SEQ ID NO: 109; (237) an exosporium protein comprising an amino acid sequence having at least 85% identity with SEQ ID NO: 110; (238) an exosporium protein comprising an amino acid sequence having at least 85% identity with SEQ ID NO: 111; (239) an exosporium protein comprising an amino acid sequence having at least 85% identity with SEQ ID NO: 112; (240) an exosporium protein comprising an amino acid sequence having at least 85% identity with SEQ ID NO: 113; (241) an exosporium protein comprising an amino acid sequence having at least 85% identity with SEQ ID NO: 114; (242) an exosporium protein comprising an amino acid sequence having at least 85% identity with SEQ ID NO: 115; (243) an exosporium protein comprising an amino acid sequence having at least 85% identity with SEQ ID NO: 116; (244) an exosporium protein comprising an amino acid sequence having at least 85% identity with SEQ ID NO: 117; (245) an exosporium protein comprising an amino acid sequence having at least 85% identity with SEQ ID NO: 118; (246) an exosporium protein comprising an amino acid sequence having at least 85% identity with SEQ ID NO: 119; (247) an exosporium protein comprising an amino acid sequence having at least 85% identity with SEQ ID NO: 120; (248) an exosporium protein comprising an amino acid sequence having at least 85% identity with SEQ ID NO: 121; (249) a targeting sequence comprising amino acids 22-31 of SEQ ID NO: 1; (250) a targeting sequence comprising amino acids 22-33 of SEQ ID NO: 1; (251) a targeting sequence comprising amino acids 20-31 of SEQ ID NO: 1; (252) a targeting sequence comprising amino acids 14-23 of SEQ ID NO: 3; (253) a targeting sequence comprising amino acids 14-25 of SEQ ID NO: 3; or (254) a targeting sequence comprising amino acids 12-23 of SEQ ID NO: 3.

When the protein or peptide of interest comprises an antigen, a remediation enzyme, an enzyme suitable for breaking an emulsion or gel in a hydraulic fracturing fluid or an antibacterial protein or peptide, preferably, the targeting sequence or exosporium protein comprises any of the targeting sequences or exosporium proteins listed above in paragraph [00167] for use with any protein or peptide of interest or: (1) a targeting sequence comprising amino acids 2-35 of SEQ ID NO: 1; (2) a targeting sequence comprising amino acids 5-35 of SEQ ID NO: 1; (3) a targeting sequence comprising amino acids 8-35 of SEQ ID NO: 1; (4) a targeting sequence comprising amino acids 10-35 of SEQ ID NO: 1; (5) a targeting sequence comprising amino acids 15-35 of SEQ ID NO: 1; (6) a targeting sequence comprising amino acids 2-27 of SEQ ID NO: 3; (7) a targeting sequence comprising amino acids 5-27 of SEQ ID NO: 3; (8) a targeting sequence comprising amino acids 8-27 of SEQ ID NO: 3; (9) a targeting sequence comprising amino acids 10-27 of SEQ ID NO: 3; (10) a targeting sequence comprising amino acids 2-38 of SEQ ID NO: 5; (11) a targeting sequence comprising amino acids 5-38 of SEQ ID NO: 5; (12) a targeting sequence comprising amino acids 8-38 of SEQ ID NO: 5; (13) a targeting sequence comprising amino acids 10-38 of SEQ ID NO: 5; (14) a targeting sequence comprising amino acids 15-3 8 of SEQ ID NO: 5; (15) a targeting sequence comprising amino acids 20-38 of SEQ ID NO: 5; (16) a targeting sequence comprising amino acids 2-28 of SEQ ID NO: 7; (17) a targeting sequence comprising amino acids 5-28 of SEQ ID NO: 7; (18) a targeting sequence comprising amino acids 8-28 of SEQ ID NO: 7; (19) a targeting sequence comprising amino acids 10-28 of SEQ ID NO: 7; (20) a targeting sequence comprising amino acids 2-24 of SEQ ID NO: 9; (21) a targeting sequence comprising amino acids 5-24 of SEQ ID NO: 9; (22) a targeting sequence comprising amino acids 8-24 of SEQ ID NO: 9; (23) a targeting sequence comprising amino acids 2-33 of SEQ ID NO: 11; (24) a targeting sequence comprising amino acids 5-33 of SEQ ID NO: 11; (25) a targeting sequence comprising amino acids 8-33 of SEQ ID NO: 11; (26) a targeting sequence comprising amino acids 10-33 of SEQ ID NO: 11; (27) a targeting sequence comprising amino acids 15-33 of SEQ ID NO: 11; (28) a targeting sequence comprising amino acids 2-33 of SEQ ID NO: 13; (29) a targeting sequence comprising amino acids 5-33 of SEQ ID NO: 13; (30) a targeting sequence comprising amino acids 8-33 of SEQ ID NO: 13; (31) a targeting sequence comprising amino acids 10-33 of SEQ ID NO: 13; (32) a targeting sequence comprising amino acids 15-33 of SEQ ID NO: 13; (33) a targeting sequence comprising amino acids 2-43 of SEQ ID NO: 15; (34) a targeting sequence comprising amino acids 5-43 of SEQ ID NO: 15; (35) a targeting sequence comprising amino acids 8-43 of SEQ ID NO: 15; (36) a targeting sequence comprising amino acids 10-43 of SEQ ID NO: 15; (37) a targeting sequence comprising amino acids 15-43 of SEQ ID NO: 15; (38) a targeting sequence comprising amino acids 20-43 of SEQ ID NO: 15; (39) a targeting sequence comprising amino acids 25-43 of SEQ ID NO: 15; (40) a targeting sequence comprising amino acids 2-27 of SEQ ID NO: 17; (41) a targeting sequence comprising amino acids 5-27 of SEQ ID NO: 17; (42) a targeting sequence comprising amino acids 8-27 of SEQ ID NO: 17; (43) a targeting sequence comprising amino acids 10-27 of SEQ ID NO: 17; (44) a targeting sequence comprising amino acids 2-33 of SEQ ID NO: 19; (45) a targeting sequence comprising amino acids 5-33 of SEQ ID NO: 19; (46) a targeting sequence comprising amino acids 8-33 of SEQ ID NO: 19; (47) a targeting sequence comprising amino acids 10-33 of SEQ ID NO: 19; (48) a targeting sequence comprising amino acids 15-33 of SEQ ID NO: 19; (49) a targeting sequence comprising amino acids 2-33 of SEQ ID NO: 21; (50) a targeting sequence comprising amino acids 5-33 of SEQ ID NO: 21; (51) a targeting sequence comprising amino acids 8-33 of SEQ ID NO: 21; (52) a targeting sequence comprising amino acids 10-33 of SEQ ID NO: 21; (53) a targeting sequence comprising amino acids 15-33 of SEQ ID NO: 21; (54) a targeting sequence comprising amino acids 2-24 of SEQ ID NO:23; (55) a targeting sequence comprising amino acids 5-24 of SEQ ID NO: 23; (56) a targeting sequence comprising amino acids 8-24 of SEQ ID NO: 23; (57) a targeting sequence comprising amino acids 2-24 of SEQ ID NO: 25; (58) a targeting sequence comprising amino acids 5-24 of SEQ ID NO: 25; (59) a targeting sequence comprising amino acids 8-24 of SEQ ID NO: 25; (60) a targeting sequence comprising amino acids 2-30 of SEQ ID NO: 27; (61) a targeting sequence comprising amino acids 5-30 of SEQ ID NO: 27; (62) a targeting sequence comprising amino acids 8-30 of SEQ ID NO: 27; (63) a targeting sequence comprising amino acids 10-30 of SEQ ID NO: 27; (64) a targeting sequence comprising amino acids 2-33 of SEQ ID NO: 29; (65) a targeting sequence comprising amino acids 5-33 of SEQ ID NO: 29; (66) a targeting sequence comprising amino acids 8-33 of SEQ ID NO: 29; (67) a targeting sequence comprising amino acids 10-33 of SEQ ID NO: 29; (68) a targeting sequence comprising amino acids 15-33 of SEQ ID NO: 29; (69) a targeting sequence comprising amino acids 2-24 of SEQ ID NO: 31; (70) a targeting sequence comprising amino acids 5-24 of SEQ ID NO: 31; (71) a targeting sequence comprising amino acids 8-24 of SEQ ID NO: 31; (72) a targeting sequence comprising amino acids 2-29 of SEQ ID NO: 43; (73) a targeting sequence comprising amino acids 5-29 of SEQ ID NO: 43; (74) a targeting sequence comprising amino acids 8-29 of SEQ ID NO: 43; (75) a targeting sequence comprising amino acids 10-29 of SEQ ID NO: 43; (76) a targeting sequence comprising amino acids 2-35 of SEQ ID NO: 45; (77) a targeting sequence comprising amino acids 5-35 of SEQ ID NO: 45; (78) a targeting sequence comprising amino acids 8-35 of SEQ ID NO: 45; (79) a targeting sequence comprising amino acids 10-35 of SEQ ID NO: 45; (80) a targeting sequence comprising amino acids 15-35 of SEQ ID NO: 45; (81) a targeting sequence comprising amino acids 2-43 of SEQ ID NO: 47; (82) a targeting sequence comprising amino acids 5-43 of SEQ ID NO: 47; (83) a targeting sequence comprising amino acids 8-43 of SEQ ID NO: 47; (84) a targeting sequence comprising amino acids 10-43 of SEQ ID NO: 47; (85) a targeting sequence comprising amino acids 15-43 of SEQ ID NO: 47; (86) a targeting sequence comprising amino acids 20-43 of SEQ ID NO: 47; (87) a targeting sequence comprising amino acids 25-43 of SEQ ID NO: 47; (88) a targeting sequence comprising amino acids 2-32 of SEQ ID NO: 49; (89) a targeting sequence comprising amino acids 5-32 of SEQ ID NO: 49; (90) a targeting sequence comprising amino acids 8-32 of SEQ ID NO: 49; (91) a targeting sequence comprising amino acids 10-32 of SEQ ID NO: 49; (92) a targeting sequence comprising amino acids 15-32 of SEQ ID NO: 49; (93) a targeting sequence comprising amino acids 2-33 of SEQ ID NO: 51; (94) a targeting sequence comprising amino acids 5-33 of SEQ ID NO: 51; (95) a targeting sequence comprising amino acids 8-33 of SEQ ID NO: 51; (96) a targeting sequence comprising amino acids 10-33 of SEQ ID NO: 51; (97) a targeting sequence comprising amino acids 15-33 of SEQ ID NO: 51; (98) a targeting sequence comprising amino acids 2-33 of SEQ ID NO: 53; (99) a targeting sequence comprising amino acids 5-33 of SEQ ID NO: 53; (100) a targeting sequence comprising amino acids 8-33 of SEQ ID NO: 53; (101) a targeting sequence comprising amino acids 10-33 of SEQ ID NO: 53; (102) a targeting sequence comprising amino acids 15-33 of SEQ ID NO: 53; (103) a targeting sequence comprising amino acids 2-30 of SEQ ID NO: 55; (104) a targeting sequence comprising amino acids 5-30 of SEQ ID NO: 55; (105) a targeting sequence comprising amino acids 8-30 of SEQ ID NO: 55; (106) a targeting sequence comprising amino acids 10-30 of SEQ ID NO: 55; (107) a targeting sequence comprising amino acids 2-130 of SEQ ID NO: 57; (108) a targeting sequence comprising amino acids 5-130 of SEQ ID NO: 57; (109) a targeting sequence comprising amino acids 10-130 of SEQ ID NO: 57; (110) a targeting sequence comprising amino acids 20-130 of SEQ ID NO: 57; (111) a targeting sequence comprising amino acids 30-130 of SEQ ID NO: 57; (112) a targeting sequence comprising amino acids 40-130 of SEQ ID NO: 57; (113) a targeting sequence comprising amino acids 50-130 of SEQ ID NO: 57; (114) a targeting sequence comprising amino acids 60-130 of SEQ ID NO: 57; (115) a targeting sequence comprising amino acids 70-130 of SEQ ID NO: 57; (116) a targeting sequence comprising amino acids 80-130 of SEQ ID NO: 57; (117) a targeting sequence comprising amino acids 90-130 of SEQ ID NO: 57; (118) a targeting sequence comprising amino acids 100-130 of SEQ ID NO: 57; (119) a targeting sequence comprising amino acids 110-130 of SEQ ID NO: 57.

When the protein or peptide of interest comprises an antigen, a remediation enzyme, an enzyme suitable for breaking an emulsion or gel in a hydraulic fracturing fluid or an antibacterial protein or peptide, more preferably, the targeting sequence or exosporium protein comprises any of the targeting sequences or exosporium proteins listed above in paragraph [00167] for use with any protein or peptide of interest or: (1) a targeting sequence comprising amino acids 2-24 of SEQ ID NO: 9; (2) a targeting sequence comprising amino acids 5-24 of SEQ ID NO: 9; (3) a targeting sequence comprising amino acids 8-24 of SEQ ID NO: 9; (4) a targeting sequence comprising amino acids 2-33 of SEQ ID NO: 11; (5) a targeting sequence comprising amino acids 5-33 of SEQ ID NO: 11; (6) a targeting sequence comprising amino acids 8-33 of SEQ ID NO: 11; (7) a targeting sequence comprising amino acids 10-33 of SEQ ID NO: 11; (8) a targeting sequence comprising amino acids 15-33 of SEQ ID NO: 11; (9) a targeting sequence comprising amino acids 2-33 of SEQ ID NO: 13; (10) a targeting sequence comprising amino acids 5-33 of SEQ ID NO: 13; (11) a targeting sequence comprising amino acids 8-33 of SEQ ID NO: 13; (12) a targeting sequence comprising amino acids 10-33 of SEQ ID NO: 13; (13) a targeting sequence comprising amino acids 15-33 of SEQ ID NO: 13; (14) a targeting sequence comprising amino acids 2-43 of SEQ ID NO: 15; (15) a targeting sequence comprising amino acids 5-43 of SEQ ID NO: 15; (16) a targeting sequence comprising amino acids 8-43 of SEQ ID NO: 15; (17) a targeting sequence comprising amino acids 10-43 of SEQ ID NO: 15; (18) a targeting sequence comprising amino acids 15-43 of SEQ ID NO: 15; (19) a targeting sequence comprising amino acids 20-43 of SEQ ID NO: 15; (20) a targeting sequence comprising amino acids 25-43 of SEQ ID NO: 15; (21) a targeting sequence comprising amino acids 2-27 of SEQ ID NO: 17; (22) a targeting sequence comprising amino acids 5-27 of SEQ ID NO: 17; (23) a targeting sequence comprising amino acids 8-27 of SEQ ID NO: 17; (24) a targeting sequence comprising amino acids 10-27 of SEQ ID NO: 17; (25) a targeting sequence comprising amino acids 2-33 of SEQ ID NO: 19; (26) a targeting sequence comprising amino acids 5-33 of SEQ ID NO: 19; (27) a targeting sequence comprising amino acids 8-33 of SEQ ID NO: 19; (28) a targeting sequence comprising amino acids 10-33 of SEQ ID NO: 19; (29) a targeting sequence comprising amino acids 15-33 of SEQ ID NO: 19; (30) a targeting sequence comprising amino acids 2-33 of SEQ ID NO: 21; (31) a targeting sequence comprising amino acids 5-33 of SEQ ID NO: 21; (32) a targeting sequence comprising amino acids 8-33 of SEQ ID NO: 21; (33) a targeting sequence comprising amino acids 10-33 of SEQ ID NO: 21; (34) a targeting sequence comprising amino acids 15-33 of SEQ ID NO: 21; (35) a targeting sequence comprising amino acids 2-24 of SEQ ID NO:23; (36) a targeting sequence comprising amino acids 5-24 of SEQ ID NO: 23; (37) a targeting sequence comprising amino acids 8-24 of SEQ ID NO: 23; (38) a targeting sequence comprising amino acids 2-24 of SEQ ID NO: 25; (39) a targeting sequence comprising amino acids 5-24 of SEQ ID NO: 25; (40) a targeting sequence comprising amino acids 8-24 of SEQ ID NO: 25; (41) a targeting sequence comprising amino acids 2-30 of SEQ ID NO: 27; (42) a targeting sequence comprising amino acids 5-30 of SEQ ID NO: 27; (43) a targeting sequence comprising amino acids 8-30 of SEQ ID NO: 27; (44) a targeting sequence comprising amino acids 10-30 of SEQ ID NO: 27; (45) a targeting sequence comprising amino acids 2-33 of SEQ ID NO: 29; (46) a targeting sequence comprising amino acids 5-33 of SEQ ID NO: 29; (47) a targeting sequence comprising amino acids 8-33 of SEQ ID NO: 29; (48) a targeting sequence comprising amino acids 10-33 of SEQ ID NO: 29; (49) a targeting sequence comprising amino acids 15-33 of SEQ ID NO: 29; (50) a targeting sequence comprising amino acids 2-24 of SEQ ID NO: 31; (51) a targeting sequence comprising amino acids 5-24 of SEQ ID NO: 31; (52) a targeting sequence comprising amino acids 8-24 of SEQ ID NO: 31; (53) a targeting sequence comprising amino acids 2-29 of SEQ ID NO: 43; (54) a targeting sequence comprising amino acids 5-29 of SEQ ID NO: 43; (55) a targeting sequence comprising amino acids 8-29 of SEQ ID NO: 43; (56) a targeting sequence comprising amino acids 10-29 of SEQ ID NO: 43; (57) a targeting sequence comprising amino acids 2-35 of SEQ ID NO: 45; (58) a targeting sequence comprising amino acids 5-35 of SEQ ID NO: 45; (59) a targeting sequence comprising amino acids 8-35 of SEQ ID NO: 45; (60) a targeting sequence comprising amino acids 10-35 of SEQ ID NO: 45; (61) a targeting sequence comprising amino acids 15-3 5 of SEQ ID NO: 45; (62) a targeting sequence comprising amino acids 2-43 of SEQ ID NO: 47; (63) a targeting sequence comprising amino acids 5-43 of SEQ ID NO: 47; (64) a targeting sequence comprising amino acids 8-43 of SEQ ID NO: 47; (65) a targeting sequence comprising amino acids 10-43 of SEQ ID NO: 47; (66) a targeting sequence comprising amino acids 15-43 of SEQ ID NO: 47; (67) a targeting sequence comprising amino acids 20-43 of SEQ ID NO: 47; (68) a targeting sequence comprising amino acids 25-43 of SEQ ID NO: 47; (69) a targeting sequence comprising amino acids 2-32 of SEQ ID NO: 49; (70) a targeting sequence comprising amino acids 5-32 of SEQ ID NO: 49; (71) a targeting sequence comprising amino acids 8-32 of SEQ ID NO: 49; (72) a targeting sequence comprising amino acids 10-32 of SEQ ID NO: 49; (73) a targeting sequence comprising amino acids 15-32 of SEQ ID NO: 49; (74) a targeting sequence comprising amino acids 2-33 of SEQ ID NO: 51; (75) a targeting sequence comprising amino acids 5-33 of SEQ ID NO: 51; (76) a targeting sequence comprising amino acids 8-33 of SEQ ID NO: 51; (77) a targeting sequence comprising amino acids 10-33 of SEQ ID NO: 51; (78) a targeting sequence comprising amino acids 15-33 of SEQ ID NO: 51; (79) a targeting sequence comprising amino acids 2-33 of SEQ ID NO: 53; (80) a targeting sequence comprising amino acids 5-33 of SEQ ID NO: 53; (81) a targeting sequence comprising amino acids 8-33 of SEQ ID NO: 53; (82) a targeting sequence comprising amino acids 10-33 of SEQ ID NO: 53; (83) a targeting sequence comprising amino acids 15-33 of SEQ ID NO: 53; (84) a targeting sequence comprising amino acids 2-30 of SEQ ID NO: 55; (85) a targeting sequence comprising amino acids 5-30 of SEQ ID NO: 55; (86) a targeting sequence comprising amino acids 8-30 of SEQ ID NO: 55; (87) a targeting sequence comprising amino acids 10-30 of SEQ ID NO: 55; (88) a targeting sequence comprising amino acids 2-130 of SEQ ID NO: 57; (89) a targeting sequence comprising amino acids 5-130 of SEQ ID NO: 57; (90) a targeting sequence comprising amino acids 10-130 of SEQ ID NO: 57; (91) a targeting sequence comprising amino acids 20-130 of SEQ ID NO: 57; (92) a targeting sequence comprising amino acids 30-130 of SEQ ID NO: 57; (93) a targeting sequence comprising amino acids 40-130 of SEQ ID NO: 57; (94) a targeting sequence comprising amino acids 50-130 of SEQ ID NO: 57; (95) a targeting sequence comprising amino acids 60-130 of SEQ ID NO: 57; (96) a targeting sequence comprising amino acids 70-130 of SEQ ID NO: 57; (97) a targeting sequence comprising amino acids 80-130 of SEQ ID NO: 57; (98) a targeting sequence comprising amino acids 90-130 of SEQ ID NO: 57; (99) a targeting sequence comprising amino acids 100-130 of SEQ ID NO: 57; (100) a targeting sequence comprising amino acids 110-130 of SEQ ID NO: 57.

When the protein or peptide of interest comprises an antigen, a remediation enzyme, an enzyme suitable for breaking an emulsion or gel in a hydraulic fracturing fluid or an antibacterial protein or peptide, even more preferably, the targeting sequence or exosporium protein comprises: (1) a targeting sequence comprising amino acids 5-24 of SEQ ID NO: 9; (2) a targeting sequence comprising amino acids 8-24 of SEQ ID NO: 9; (3) a targeting sequence comprising amino acids 5-33 of SEQ ID NO: 11; (4) a targeting sequence comprising amino acids 8-33 of SEQ ID NO: 11; (5) a targeting sequence comprising amino acids 10-33 of SEQ ID NO: 11; (6) a targeting sequence comprising amino acids 15-33 of SEQ ID NO: 11; (7) a targeting sequence comprising amino acids 5-33 of SEQ ID NO: 13; (8) a targeting sequence comprising amino acids 8-33 of SEQ ID NO: 13; (9) a targeting sequence comprising amino acids 10-33 of SEQ ID NO: 13; (10) a targeting sequence comprising amino acids 15-33 of SEQ ID NO: 13; (11) a targeting sequence comprising amino acids 5-43 of SEQ ID NO: 15; (12) a targeting sequence comprising amino acids 8-43 of SEQ ID NO: 15; (13) a targeting sequence comprising amino acids 10-43 of SEQ ID NO: 15; (14) a targeting sequence comprising amino acids 15-43 of SEQ ID NO: 15; (15) a targeting sequence comprising amino acids 20-43 of SEQ ID NO: 15; (16) a targeting sequence comprising amino acids 25-43 of SEQ ID NO: 15; (17) a targeting sequence comprising amino acids 5-27 of SEQ ID NO: 17; (18) a targeting sequence comprising amino acids 8-27 of SEQ ID NO: 17; (19) a targeting sequence comprising amino acids 10-27 of SEQ ID NO: 17; (20) a targeting sequence comprising amino acids 5-33 of SEQ ID NO: 19; (21) a targeting sequence comprising amino acids 8-33 of SEQ ID NO: 19; (22) a targeting sequence comprising amino acids 10-33 of SEQ ID NO: 19; (23) a targeting sequence comprising amino acids 15-33 of SEQ ID NO: 19; (24) a targeting sequence comprising amino acids 5-33 of SEQ ID NO: 21; (25) a targeting sequence comprising amino acids 8-33 of SEQ ID NO: 21; (26) a targeting sequence comprising amino acids 10-33 of SEQ ID NO: 21; (27) a targeting sequence comprising amino acids 15-33 of SEQ ID NO: 21; (28) a targeting sequence comprising amino acids 5-24 of SEQ ID NO: 23; (29) a targeting sequence comprising amino acids 8-24 of SEQ ID NO: 23; (30) a targeting sequence comprising amino acids 5-24 of SEQ ID NO: 25; (31) a targeting sequence comprising amino acids 8-24 of SEQ ID NO: 25; (32) a targeting sequence comprising amino acids 5-30 of SEQ ID NO: 27; (33) a targeting sequence comprising amino acids 8-30 of SEQ ID NO: 27; (34) a targeting sequence comprising amino acids 10-30 of SEQ ID NO: 27; (35) a targeting sequence comprising amino acids 5-33 of SEQ ID NO: 29; (36) a targeting sequence comprising amino acids 8-33 of SEQ ID NO: 29; (37) a targeting sequence comprising amino acids 10-33 of SEQ ID NO: 29; (38) a targeting sequence comprising amino acids 15-33 of SEQ ID NO: 29; (39) a targeting sequence comprising amino acids 5-24 of SEQ ID NO: 31; (40) a targeting sequence comprising amino acids 8-24 of SEQ ID NO: 31; (41) a targeting sequence comprising amino acids 5-29 of SEQ ID NO: 43; (42) a targeting sequence comprising amino acids 8-29 of SEQ ID NO: 43; (43) a targeting sequence comprising amino acids 10-29 of SEQ ID NO: 43; (44) a targeting sequence comprising amino acids 5-35 of SEQ ID NO: 45; (45) a targeting sequence comprising amino acids 8-35 of SEQ ID NO: 45; (46) a targeting sequence comprising amino acids 10-35 of SEQ ID NO: 45; (47) a targeting sequence comprising amino acids 15-35 of SEQ ID NO: 45; (48) a targeting sequence comprising amino acids 5-43 of SEQ ID NO: 47; (49) a targeting sequence comprising amino acids 8-43 of SEQ ID NO: 47; (50) a targeting sequence comprising amino acids 10-43 of SEQ ID NO: 47; (51) a targeting sequence comprising amino acids 15-43 of SEQ ID NO: 47; (52) a targeting sequence comprising amino acids 20-43 of SEQ ID NO: 47; (53) a targeting sequence comprising amino acids 25-43 of SEQ ID NO: 47; (54) a targeting sequence comprising amino acids 5-32 of SEQ ID NO: 49; (55) a targeting sequence comprising amino acids 8-32 of SEQ ID NO: 49; (56) a targeting sequence comprising amino acids 10-32 of SEQ ID NO: 49; (57) a targeting sequence comprising amino acids 15-32 of SEQ ID NO: 49; (58) a targeting sequence comprising amino acids 5-33 of SEQ ID NO: 51; (59) a targeting sequence comprising amino acids 8-33 of SEQ ID NO: 51; (60) a targeting sequence comprising amino acids 10-33 of SEQ ID NO: 51; (61) a targeting sequence comprising amino acids 15-33 of SEQ ID NO: 51; (62) a targeting sequence comprising amino acids 5-33 of SEQ ID NO: 53; (63) a targeting sequence comprising amino acids 8-33 of SEQ ID NO: 53; (64) a targeting sequence comprising amino acids 10-33 of SEQ ID NO: 53; (65) a targeting sequence comprising amino acids 15-33 of SEQ ID NO: 53; (66) a targeting sequence comprising amino acids 5-30 of SEQ ID NO: 55; (67) a targeting sequence comprising amino acids 8-30 of SEQ ID NO: 55; (68) a targeting sequence comprising amino acids 10-30 of SEQ ID NO: 55; (69) a targeting sequence comprising amino acids 5-130 of SEQ ID NO: 57; (70) a targeting sequence comprising amino acids 10-130 of SEQ ID NO: 57; (71) a targeting sequence comprising amino acids 20-130 of SEQ ID NO: 57; (72) a targeting sequence comprising amino acids 30-130 of SEQ ID NO: 57; (73) a targeting sequence comprising amino acids 40-130 of SEQ ID NO: 57; (74) a targeting sequence comprising amino acids 50-130 of SEQ ID NO: 57; (75) a targeting sequence comprising amino acids 60-130 of SEQ ID NO: 57; (76) a targeting sequence comprising amino acids 70-130 of SEQ ID NO: 57; (77) a targeting sequence comprising amino acids 80-130 of SEQ ID NO: 57; (78) a targeting sequence comprising amino acids 90-130 of SEQ ID NO: 57; (79) a targeting sequence comprising amino acids 100-130 of SEQ ID NO: 57; (80) a targeting sequence comprising amino acids 110-130 of SEQ ID NO: 57; (81) a targeting sequence comprising amino acids 4-30 of SEQ ID NO: 59; (82) a targeting sequence comprising amino acids 6-30 of SEQ ID NO: 59; (83) a targeting sequence comprising amino acids 5-33 of SEQ ID NO: 61; (84) a targeting sequence comprising amino acids 10-33 of SEQ ID NO: 61; (85) a targeting sequence comprising amino acids 15-33 of SEQ ID NO: 61; (86) a targeting sequence comprising amino acids 5-35 of SEQ ID NO: 63; (87) a targeting sequence comprising amino acids 8-35 of SEQ ID NO: 63; (88) a targeting sequence comprising amino acids 10-35 of SEQ ID NO: 63; (89) a targeting sequence comprising amino acids 15-35 of SEQ ID NO: 63; (90) a targeting sequence comprising amino acids 5-24 of SEQ ID NO: 65; (91) a targeting sequence comprising amino acids 5-27 of SEQ ID NO: 67; (92) a targeting sequence comprising amino acids 10-27 of SEQ ID NO: 67; (93) a targeting sequence comprising amino acids 5-38 of SEQ ID NO: 69; (94) a targeting sequence comprising amino acids 10-38 of SEQ ID NO: 69; (95) a targeting sequence comprising amino acids 15-38 of SEQ ID NO: 69; (96) a targeting sequence comprising amino acids 5-42 of SEQ ID NO: 75; (97) a targeting sequence comprising amino acids 10-42 of SEQ ID NO: 75; (98) a targeting sequence comprising amino acids 15-42 of SEQ ID NO: 75; (99) a targeting sequence comprising amino acids 20-42 of SEQ ID NO: 75; (100) a targeting sequence comprising amino acids 25-42 of SEQ ID NO: 75; (101) a targeting sequence comprising amino acids 5-24 of SEQ ID NO: 77; (102) a targeting sequence comprising amino acids 5-38 of SEQ ID NO: 81; (103) a targeting sequence comprising amino acids 10-38 of SEQ ID NO: 81; (104) a targeting sequence comprising amino acids 15-38 of SEQ ID NO: 81; (105) a targeting sequence comprising amino acids 20-38 of SEQ ID NO: 81; (106) a targeting sequence comprising amino acids 5-28 of SEQ ID NO: 87; (107) a targeting sequence comprising amino acids 10-28 of SEQ ID NO: 87; (108) a targeting sequence comprising amino acids 5-28 of SEQ ID NO: 89; (109) a targeting sequence comprising amino acids 10-28 of SEQ ID NO: 89; (110) a targeting sequence comprising amino acids 10-93 of SEQ ID NO: 91; (111) a targeting sequence comprising amino acids 20-93 of SEQ ID NO: 91; (112) a targeting sequence comprising amino acids 30-93 of SEQ ID NO: 91; (113) a targeting sequence comprising amino acids 40-93 of SEQ ID NO: 91; (114) a targeting sequence comprising amino acids 50-93 of SEQ ID NO: 91; (115) a targeting sequence comprising amino acids 60-93 of SEQ ID NO: 91; (116) a targeting sequence comprising amino acids 10-130 of SEQ ID NO: 93; (117) a targeting sequence comprising amino acids 20-130 of SEQ ID NO: 93; or (118) a targeting sequence comprising amino acids 30-130 of SEQ ID NO: 93.

The protein or peptide of interest of the fusion protein described above can comprise an antigen.

The protein or peptide of interest of the fusion protein described above can comprise a remediation enzyme.

The protein or peptide of interest of the fusion protein described above can comprise an enzyme suitable for breaking an emulsion or gel in a hydraulic fracturing fluid.

The protein or peptide of interest of the fusion protein described above can comprise an antibacterial protein or peptide.

C. Recombinant *Bacillus cereus* Family Members that Express Fusion Proteins

The present invention further relates to recombinant *Bacillus cereus* family members that express a fusion protein. The fusion protein can be any of the fusion proteins described above in Section I.B.

II. Modulation of Fusion Protein Expression in Recombinant *Bacillus cereus* Family Members that Express a Fusion Protein by Co-Overexpression of Modulator Proteins Recombinant *Bacillus cereus* family members that express the fusion proteins described herein display the protein or peptide of interest portion of the fusion protein on the outside of their spores. It has been found that overexpression of certain exosporium proteins (referred to herein as "modulator proteins") in a recombinant *Bacillus cereus* family member that also expresses a fusion protein allows for modulation (i.e., increasing or decreasing) the expression level of the fusion protein, thereby increasing or decreasing the amount of the protein or peptide of interest that is displayed on the outside of the spore. The ability to the control the amount of the protein or peptide of interest that is displayed on the outside of the spore is beneficial, since in some cases, it will be desirable to increase the amount of the protein or peptide of interest that is displayed. For example, where the protein of interest is an enzyme that degrades a plant nutrient source, it may be desirable to increase the amount of the enzyme displayed on the spore, such that greater enzymatic activity and greater stimulation of plant growth can be achieved upon introducing the spores into a plant growth medium or application of the spores to a plant or plant seed or an area surrounding a plant or a plant seed. In other instances, it will be desirable to decrease the amount of the protein or peptide of interest that is displayed. For example, where the protein or peptide of interest comprises a plant immune system enhancer protein or peptide, it may be desirable to decrease the amount of the protein or peptide displayed on the spore, since excess stimulation of a plant's immune system can lead to undesirable effects.

As is described further hereinbelow, the recombinant *Bacillus cereus* family members that express a modulator protein can be used in any of the various fields and methods described herein, and for any of the uses described herein. For example, the recombinant *Bacillus cereus* family members that express a modulator protein can be used in methods for stimulating plant growth; methods for protecting a plant from a pathogen; methods for enhancing stress resistance in plants; methods for immobilizing recombinant *Bacillus cereus* family member spores on plants; methods for stimulating germination of a plant seed; methods for delivering nucleic acids to a plant; methods for delivering nucleic acids to animals, insects, worms (e.g., nematodes), fungi, or protozoans; methods for delivering enzymes to a plant; methods for altering a property of a plant; methods for delivering proteins or peptides to an animal; vaccines and methods of producing an immunogenic response in a subject; methods for reducing contaminants in an environment; methods for phytoremediation of contaminated soil; methods of treating a hydraulic fracturing fluid to break an emulsion or gel within the fluid; methods of disinfecting a surface; and for uses such as grease, oil, or fat treatment or degumming; leather hide processing; biofuel, biodiesel, or bioethanol formation; sugar processing or conversion; starch treatment; paper or linen processing; animal or fungal byproduct treatment or amino acid recovery; targeted digestion of facility wastes; feed or food additives; dietary supplements; animal nutrition; industrial cleaning; grain processing; cosmetic manufacturing; odor control; food or beverage processing; brewing enhancement or additives; detergent additives; or textile or yarn processing.

For many applications of proteins (e.g., enzymes), there is a biological response curve wherein an optimal concentration of a protein or enzyme leads to the desired effect, and an excess of the protein or too small of an amount of the protein leads to undesirable or diminished effects. One example of this biological curve is the demonstration that a biological drug, such as the protein drug insulin for diabetes treatment, requires an optimum dose in order to reduce blood sugar levels in diabetic patients. Too little insulin leads to an insufficient response and maintenance of undesired elevated blood sugar levels and potential hyperkalemia. Too great of a dose of insulin leads to low blood sugar levels and potential hypokalemia and related morbidity.

Similar biological response curves exist for many of the proteins and peptides of interest comprised within the fusion proteins described herein. Thus, for the various fields of use and methods for the recombinant *Bacillus cereus* family members described herein, it may be desirable to modulate the expression level of the protein or peptide of interest on the exosporium. By increasing or decreasing the expression levels of the protein or peptide of interest on the exosporium of the recombinant *Bacillus cereus* family member, expression levels can be optimized to maintain the overall expression level of the protein or peptide of interest at the most effective concentration.

For example, it would be desirable to modulate expression levels of the fusion protein in cases where the protein or peptide of interest comprises a protein or peptide involved in direct signaling in plants, such as the flagellin peptide flg22, and the recombinant *Bacillus cereus* family member expressing the fusion protein is to be applied to a plant to provide a beneficial effect to the plant. Such modulation would be beneficial to avoid a signaling response that is great enough that it would lead to detrimental responses to the plant (e.g., too great of a response to flg22 can result in necrosis), or a signaling response that is low enough that it would yield a poor or insufficient response to the peptide.

A biological response curve would also be relevant for recombinant *Bacillus cereus* family members expressing a fusion protein wherein the protein or peptide of interest comprises an antigen. In such cases, it would be desirable to modulate the expression level of the fusion protein comprising the antigen to achieve an optimal range for generating a proper immune response in an animal. Too large of a dose could lead to injection site edema and unwanted inflammation, whereas too small of a dose could lead to insufficient vaccination or immune response.

Modulation of the expression level of a fusion protein on the exosporium of a recombinant *Bacillus cereus* family member also provides benefits, for example, when the recombinant *Bacillus cereus* family member is used for breaking an emulsion or gel in a hydraulic fracturing fluid. Polysaccharide gels are frequently used in the hydraulic fracturing processing gels. These gels require breaking. When the gel solution is ready to break, the operator will desire that the break, which is an enzymatic reaction, happen at a particular optimized rate. Breaking the gel too quickly can lead to undesired side effects such as pooling of undigested gel fragments. On the other hand, breaking the gel too slowly leads to long wait times and increased expense. Using the techniques described hereinbelow, the enzyme levels on the exosporium of a recombinant *Bacillus cereus* family member expressing a fusion protein comprising an enzyme suitable for breaking an emulsion or gel in a hydraulic fracturing fluid can be modulated to ensure that an optimized level of enzyme is present for breaking gels, leading to preferred results when used in the field.

A recombinant *Bacillus cereus* family member is provided that expresses: (i) a fusion protein comprising at least one protein or peptide of interest and a targeting sequence, exosporium protein, or exosporium protein fragment that targets the fusion protein to the exosporium of the recombinant *Bacillus cereus* family member; and (ii) a modulator protein, wherein the expression of the modulator protein is increased as compared to expression of the modulator protein in a wild-type *Bacillus cereus* family member under the same conditions. The modulator protein, when co-expressed with the fusion protein in the recombinant *Bacillus cereus* family member, results in increased or decreased expression of the fusion protein as compared to the expression level of the fusion protein in a recombinant *Bacillus cereus* family member that does not express the modulator protein at an increased level under the same conditions as compared to the expression of the modulator protein in a wild-type *Bacillus cereus* family member.

The modulator protein can comprise an ExsY protein, an ExsFA/BxpB protein, a CotY protein, a CotO protein, an ExsFB protein, an InhA1 protein, an InhA2 protein, an ExsJ protein, an ExsH protein, a YjcA protein, a YjcB protein, a BclC protein, an AcpC protein, an InhA3 protein, an alanine racemase 1, an alanine racemase 2, a BclA protein, a BclB protein, a BxpA protein, a BclE protein, a BetA/BAS3290 protein, a CotE protein, an ExsA protein, an ExsK protein, an ExsB protein, a YabG protein, a Tgl protein, a SODA1 protein, a SODA2 protein, a variant of any thereof, or a combination of any thereof.

For example, the modulator protein, when co-expressed in the recombinant *Bacillus cereus* family member with the fusion protein, results in increased expression of the fusion protein as compared to the expression level of the fusion protein in a recombinant *Bacillus cereus* family member that does not express the modulator protein at an increased level under the same conditions as compared to the expression of the modulator protein in a wild-type *Bacillus cereus* family member. Where the modulator protein, when co-expressed in the recombinant *Bacillus cereus* family member with the fusion protein, results in such increased expression of the fusion protein, the modulator protein can comprise a BclB protein, a CotE protein, a BxpB protein, a CotO protein, a BclA protein, a variant of any thereof, or a combination of any thereof Alternatively, the modulator protein, when co-expressed in the recombinant *Bacillus cereus* family member with the fusion protein, results in decreased expression of the fusion protein as compared to the expression level of the fusion protein in a recombinant *Bacillus cereus* family member that does not express the modulator protein at an increased level under the same conditions as compared to the expression of the modulator protein in a wild-type *Bacillus cereus* family member. Where the modulator protein, when co-expressed in the recombinant *Bacillus cereus* family member with the fusion protein, results in such decreased expression of the fusion protein, the modulator protein can comprise a BclC protein, an ApcC protein, a YjcB protein, a variant of any thereof, or a combination of any thereof.

For example, the modulator protein can comprise a CotO protein, a BclB protein, an ExsFA/BxpB protein, a YjcB protein, a variant of any thereof, or a combination of any thereof.

For ease of reference, descriptions of the modulator proteins and their SEQ ID NOs. are listed in Table 2 below.

TABLE 2

Amino Acid Sequences for Modulator Proteins

| Modulator Protein | SEQ ID NO. |
|---|---|
| ExsY, *Bacillus thuringiensis* | 123 |
| ExsFA/BxpB, *Bacillus thuringiensis* | 124 |
| CotY, *Bacillus cereus* | 125 |
| CotO, *Bacillus anthracis* | 126 |
| ExsFB, Variant 1, *Bacillus cereus* | 127 |
| ExsFB, Variant 2, *Bacillus cereus* | 128 |
| InhA1, *Bacillus cereus* | 129 |
| InhA3, *Bacillus mycoides* | 130 |
| ExsJ, *Bacillus cereus* ATCC 10876 | 131 |
| ExsH, *Bacillus cereus* | 132 |
| YjcA, *Bacillus cereus* | 133 |
| YjcB, Variant 1, *Bacillus cereus* | 134 |
| YjcB, Variant 2, *Bacillus cereus* | 135 |
| BclC, *Bacillus anthracis* | 136 |
| AcpC, *Bacillus cereus* | 137 |
| InhA2, *Bacillus cereus* | 138 |
| Alanine racemase 1, *Bacillus cereus* | 139 |
| Alanine racemase 2, *Bacillus cereus* | 140 |
| BclA, variant 1, *Bacillus anthracis* Sterne | 141 |
| BclA, variant 2, *Bacillus anthracis* | 142 |
| BclB, variant 1, *Bacillus anthracis* Sterne | 143 |
| BclB, variant 2, *Bacillus anthracis* Sterne | 144 |
| BxpA, *Bacillus anthracis* | 145 |
| BAS4623/BclE, variant 1, *Bacillus anthracis* Sterne | 146 |
| BAS4623/BclE, variant 2, *Bacillus anthracis* Sterne | 147 |
| BetA/BAS3290, *Bacillus anthracis* | 148 |
| CotE, *Bacillus cereus* group | 149 |
| ExsA, *Bacillus cereus* | 150 |
| ExsK, *Bacillus cereus* AH187 | 151 |
| ExsB, *Bacillus cereus* | 152 |
| YabG, *Bacillus cereus* | 153 |
| Tgl, *Bacillus cereus* group | 154 |
| SODA1, *Bacillus cereus* | 155 |
| SODA2, *Bacillus thuringiensis* | 156 |

Many of the modulator proteins have homologs, paralogs, or genetic rearrangements. Thus, many proteins that have at least 70% homology to any of the modulator sequences listed above in Table 2 will retain the ability to act as modulator proteins when overexpressed in a recombinant *Bacillus cereus* family member that also expresses any of the fusion proteins described herein. In addition, many of the modulator proteins (e.g., BclA, BclB, and BclE) have internal repeat regions that can differ significantly between strains. Additions or reductions in the number of repeats in the internal repeat region would affect overall sequence homology, but so long as the homology of amino- and carboxy-terminal regions of the protein retain at least 75% sequence identity to any of the amino acid sequences of the modulator proteins listed in the table above, such homologs would be expected to retain the ability to act as modulator proteins.

Thus, for example, the modulator protein can comprise an amino acid sequence having at least 70% sequence identity with any of SEQ ID NOs: 123-156.

The modulator protein can comprise an amino acid sequence having at least 75% sequence identity with any of SEQ ID NOs: 123-156.

The modulator protein can comprise an amino acid sequence having at least 85% sequence identity with any of SEQ ID NOs: 123-156.

The modulator protein can comprise an amino acid sequence having at least 90% sequence identity with any of SEQ ID NOs: 123-156.

The modulator protein can comprise an amino acid sequence having at least 95% sequence identity with any of SEQ ID NOs: 123-156.

The modulator protein can comprise an amino acid sequence having at least 98% sequence identity with any of SEQ ID NOs: 123-156.

The modulator protein can comprise an amino acid sequence having at least 99% sequence identity with any of SEQ ID NOs: 123-156.

The modulator protein can comprise an amino acid sequence having 100% sequence identity with any of SEQ ID NOs: 123-156.

For example, the modulator protein can comprise SEQ ID NO: 124, 126, 134, 135, 143, or 144.

The recombinant *Bacillus cereus* family members that express a modulator protein can comprise a vector encoding the modulator protein. For example, the vector can comprise a multicopy plasmid. Multicopy plasmids allow for high expression levels of the modulator protein.

III. Promoters for Expression of Fusion Proteins and/or Modulator Proteins in Recombinant *Bacillus cereus* Family Members When the fusion protein comprises a targeting sequence, exosporium protein, or exosporium protein fragment that targets the fusion protein to the exosporium of a *Bacillus cereus* family member, the DNA encoding the fusion protein is suitably under the control of a sporulation promoter which will cause expression of the fusion protein on the exosporium of a *B. cereus* family member endospore (e.g., a native bclA promoter from a *B. cereus* family member).

Thus, any of the fusion proteins described above in Section 1.B can be expressed in the recombinant *Bacillus cereus* family member under the control of a sporulation promoter that is native to the targeting sequence, exosporium protein, or exosporium protein fragment of the fusion protein, or a portion of such a promoter.

Similarly, any of the modulator proteins described above in Section II can be expressed under the control of its native promoter or a portion thereof.

Any of the fusion proteins or modulator proteins can be expressed under the control of a high-expression sporulation promoter.

The high-expression sporulation promoter comprises a sigma-K sporulation-specific polymerase promoter sequence.

For ease of reference, exemplary nucleotide sequences for promoters that can be used to express any of the fusion proteins or any of the modulator proteins in a recombinant *Bacillus cereus* family member are provided in Table 3 below, together with their SEQ ID NOs. Table 3 also provides exemplary minimal promoter sequences for many of the promoters. In Table 3, sigma-K sporulation-specific polymerase promoter sequences in the promoters are indicated by bold and underlined text. Several of the sequences have multiple sigma K sequences that overlap with one another. The overlaps are indicated by double underlining in the table. The promoter sequences are immediately upstream of the start codon for each of the indicated genes. In other words, in the sequences shown in Table 3 below, the last nucleotide of the promoter sequence immediately precedes the first nucleotide of the start codon for the coding region of the gene encoding the indicated protein.

TABLE 3

Promoter Sequences for Expression of Fusion Proteins and Modulator Proteins in Recombinant *Bacillus cereus* family members

| Promoter (SEQ ID NO) | Promoter Sequence |
|---|---|
| ExsY promoter (*B. cereus* F837/76) (SEQ ID NO: 157) | TTTCTTAATCCTTTACCCTTTACTTTTGTAAAAGTTGATACACTT CCATCCGGCTCTGTAATTTCTAATTCATCAATAAATGGTCTTCG CAAAAAGCCTGTAATTTTATCATAAACAATTAAACGAGTGAGC CTAAAAGCAGCTAACGCGAAAATAAAAAATAAAAGCCAGCTT GTAAACAGCATAATTCCACCTTCCCTTATCCTCTTTCGCCTATT TAAAAAAAGGTCTTGAGATTGTGACCAAATCTCCTCAACTCCA ATATCTTATTAATGTAAATACAAACAAGAAGATAAGGA |
| ExsY minimal promoter (*B. cereus* F837/76) (SEQ ID NO: 158) | ACCAAATCTCCTCAACTCCAATATCTTATTAATGTAAATACAA ACAAGAAGATAAGGA |
| ExsFA/BxpB promoter (*B. anthracis* Sterne) (SEQ ID NO: 159) | ACCACCTACCGACGATCCAATCTGTACATTCCTAGCTGTACCA AATGCAAGATTAATATCGACTAACACTTGTCTTACTGTTGATTT AAGTTGCTTCTGTGCGATTCAATGCTTGCGTGATGTTACGATTT AAAACTAAATAATGAGCTAAGCATGGATTGGGTGGCAGAATT ATCTGCCACCCAATCCATGCTTAACGAGTATTATTATGTAAATT TCTTAAAATTGGGAACTTGTCTAGAACATAGAACCTGTCCTTTT CATTAACTGAAAGTAGAAACAGATAAAGGAGTGAAAAAC |
| ExsFA/BxpB minimal promoter (*B. anthracis* Sterne) (SEQ ID NO: 160) | ACATAGAACCTGTCCTTTTCATTAACTGAAAGTAGAAACAGAT AAAGGAGTGAAAAAC |
| CotY/CotZ promoter (*B. anthracis* Sterne) (SEQ ID NO: 161) | TAGAAGAAGAACGCCGACTACTTTATGTCGCAATTACACGGGC GAAAGAAGAACTTTACATTTCCTCTCCGCAATTTTTTAGAGGA AAAAAATTAGATATATCTCGTTTTTTATACACTGTGCGAAAAG ATTTACCTGAAAAGACATCCACTAAATAAGGATGTCTTTTTTTA TATTGTATTATGTACATCCCTACTATATAAATTCCCTGCTTTTAT CGTAAGAATTAACGTAATATCAACCATATCCCGTTCATATTGT AGTAGTGTATGTCAGAACTCACGAGAAGGAGTGAACATA |
| CotY/CotZ minimal promoter (*B. anthracis* Sterne) (SEQ ID NO: 162) | TCAACCATATCCCGTTCATATTGTAGTAGTGTATGTCAGAACT CACGAGAAGGAGTGAACATA |
| CotO promoter (*B. cereus*) (SEQ ID NO: 163) | TAACTCAATCTTAAGAGAAATTGAGGAGCGCGCACCCACTTCGT CGTACAACAACGCAAGAAGAAGTTGGGGATACAGCAGTATTCT TATTCAGTGATTTAGCACGCGGCGTAACAGGAGAAAACATTCA CGTTGATTCAGGGTATCATATCTTAGGATAAATATAATATTAA TTTTAAAGGACAATCTCTACATGTTGAGATTGTCCTTTTTATTT GTTCTTAGAAAGAACGATTTTTAACGAAAGTTCTTACCACGTTA TGAATATAAGTATAATAGTACACGATTTATTCAGCTACGT |
| CotO minimal promoter (*B. cereus*) (SEQ ID NO: 164) | ACGTTGATTCAGGGTATCATATCTTAGGATAAATATAATATTA ATTTTAAAGGACAATCTCTACATGTTGAGATTGTCCTTTTTATT TGTTCTTAGAAAGAACGATTTTTAACGAAAGTTCTTACCACGTT ATGAATATAAGTATAATAGTACACGATTTATTCAGCTACGT |
| ExsFB promoter (*B. cereus* F837/76) (SEQ ID NO: 165) | CATAAAAATCTACTTTTCTTGTCAAAGAGTATGCTTATATGCGT GCTCTTTTTATTTGGTTTTCTTTCATTTCTAAATAACATTTTCAA CTCTATTCATACTATTCTTTCAACTTTAGGTTACAAACTATTTCT GTAAGCGTAGTGTTTCTTTTGTACTATAGGCAGTTAGTTTTATC CATAACAGTACACCTCTGCACTATTCACTATAAATTTTCATATA TTATATTGTGCTTGTCCAAAACATGTGGTTATTACTCACGCGAT CTAAATGAAAGAAAGGAGTGAAAAT |
| ExsFB minimal promoter (*B. cereus* F837/76) (SEQ ID NO: 166) | ACTATTCACTATAAATTTTCATATATTATATTGTGCTTGTCCAA AACATGTGGTTATTACTCACGCGATCTAAATGAAAGAAAGGAG TGAAAAT |
| InhA1 promoter (*B. thuringiensis* serovar *kurstaki* str. HD-1) (SEQ ID NO: 167) | AATACATGATAATGAAATCCGATTTTGTGTTTTATATAGTGAAT TATCAAATATTGTGTAGATGAAACAAAGATAAAATCCCCATTA AACTCCCTCTATGGAAATTATAAATTGTTCGATAAAAACTTTCA ATATTTTCAGAAAACATTGTTGAATTGTGATATATTCGTATGCT AACTATGAAATTTTTACAAATATATTAAAAACATTACATAATA TGACTAAATATTGAAAAATATTGAATTTTTAATAAAATTTAA TTTGTAATACATATTATTTATTAGGGGAGGAAATAAGGG |

TABLE 3-continued

Promoter Sequences for Expression of Fusion Proteins and Modulator Proteins in Recombinant *Bacillus cereus* family members

| Promoter (SEQ ID NO) | Promoter Sequence |
|---|---|
| InhA1 minimal promoter (*B. thuringiensis* serovar kurstaki str. HD-1) (SEQ ID NO: 168) | AAAATTTAATTTGTAATACATATTATTTATTAGGGGAGGAAAT<br>AAGGG |
| InhA2 promoter (*B. mycoides* strain 219298) (SEQ ID NO: 169) | AATTGTGCATATTGTCTTTTAAATTTTCTATCTAAGTTATTTAAT<br>ATATAATAAATAACTCTTTTTTGTGAGTTTTTTTGATACGAGGT<br>AAATAATCAGTACAGGGTCTGACCAGAGGACTGGAGGGCATG<br>ATTCTATAAGGGAATATTTACTATTCCATGATTATAGAACTATG<br>TCTTTTTTATTGTATATAGAAGGGGGGATAGGTCTATATTATA<br>GAACTTATATATATTGTGCATTCCATATTATCAATTATCTAAAT<br>TTTAAGTCTTGTTACAATTAATAAGGGAGGAAATAGTA |
| InhA2 minimal promoter (*B. mycoides* strain 219298) (SEQ ID NO: 170) | ACTTATATATATTGTGCATTCCATATTATCAATTATCTAAATTT<br>TAAGTCTTGTTACAATTAATAAGGGAGGAAATAGTA |
| ExsJ promoter (*B. thuringiensis* serovar kurstaki) (SEQ ID NO: 171) | AATGACGTTTTCAAGTTTGATTATCATTCATGTTTCCTATTTTAA<br>GAGAAACATATAACTCAACTACTTTTTTCAATGGCATCTTTTA<br>TAGTACTTAGAATAGGAAAACACTCAACTATAAGAAAAGTAA<br>GGAGGAAATAA |
| ExsJ minimal promoter (*B. thuringiensis* serovar kurstaki) (SEQ ID NO: 172) | ACTACTTTTTTCAATGGCATCTTTTATAGTACTTAGAATAGGA<br>AAACACTCAACTATAAGAAAAGTAAGGAGGAAATAA |
| ExsH promoter (*B. cereus* F837/76) (SEQ ID NO: 173) | ATATGCTAATGCTTAGTTTTTATACTCAAGTTAAAATGTGCTTT<br>TGGACCTAAGAGATAAACGTGGAAAAATAAAATAAACTCTTA<br>AGTTTAGGTGTTTAATCTAAGCAGTCAATTATTAAAAACATAT<br>AATTAATATGTGAGTCATGAACATAATTAAATAATGTTTTCAA<br>GTTTAATTATCGTTCATGTTTCCTATTTTAAGCAGAACAAATAA<br>CTCAATTACTTTTTTCGATTGGATCTTTTTTAACTCTTATAATAG<br>GAAAACACTCAACTATAAAAATAAGTAAGGAGGAAATAA |
| ExsH minimal promoter (*B. cereus* F837/76) (SEQ ID NO: 174) | AATATGTGAGTCATGAACATAATTAAATAATGTTTTCAAGTTT<br>AATTATCGTTCATGTTTCCTATTTTAAGCAGAACAAATAACTCA<br>ATTACTTTTTTCGATTGGATCTTTTTTAACTCTTATAATAGGAA<br>AACACTCAACTATAAAAATAAGTAAGGAGGAAATAA |
| YjcA promoter (*B. thuringiensis* serovar kurstaki str. 141)73) (SEQ ID NO: 175) | TATAAAATAAAAGGGCGTGTATTTGCTACTGATGCAGTATTGT<br>GTGCGCCTAAAAATGGAATTTCACAACCAGATCCACATGTTGT<br>TGTAGAACAATCTTGTAATTCATTGATGAATTTTACAACGTCAA<br>CTACACAATGAGAAGAGCCATGGTGTTTATTTTCGTTACAACTC<br>ATTAATGTCACTCCTTATCTTCTTGTTTGTATTTACATTAATAA<br>GATATTGGAGTTGAGGAGATTTGGTCACAATCTCAAGACCTTT<br>TTTTTAAATAGGCGAAAGAGGATAAGGGAAGGTGGAATT |
| YjcA minimal promoter (*B. thuringiensis* serovar kurstaki str. HD73) (SEQ ID NO: 176) | TCTTGTTTGTATTTACATTAATAAGATATTGGAGTTGAGGAGAT<br>TTGGTCACAATCTCAAGACCTTTTTTTAAATAGGCGAAAGAG<br>GATAAGGGAAGGTGGAATT |
| YjcB promoter (*B. thuringiensis* serovar kurstaki str. HD73) (SEQ ID NO: 177) | ATCAACTTTTACAAAAGTAAAGGGTAAAGGATTAAGAAAGTG<br>GATTGGCGAATTATTAAGCTGTTATTGGTGTACAGGTGTATGG<br>GTTAGTGCTTTTTTATTAGTTTTATATAATTGGATTCCGATCGTT<br>GCAGAGCCGTTACTTGCATTATTAGCTATTGCAGGAGCAGCAG<br>CAATCATTGAAACGATTACAGGATATTTTATGGGAGAATAAT<br>ATATTTTCATAATACGAGAAAAAGCGGAGTTTAAAAGAATGAG<br>GGAACGGAAATAAAGAGTTGTTCATATAGTAAATAGACAGAA |
| YjcB minimal promoter (*B. thuringiensis* serovar kurstaki str. HD73) (SEQ ID NO: 178) | ACGGAAATAAAGAGTTGTTCATATAGTAAATAGACAGAA |
| BclC promoter (*B. anthracis* Sterne) (SEQ ID NO: 179) | TGAAGTATCTAGAGCTAATTTACGCAAAGGAATCTCAGGACAA<br>CACTTTCGCAACACCTATATTTTAAATTTAATAAAAAAAGAGA<br>CTCCGGAGTCAGAAATTATAAAGCTAGCTGGGTTCAAATCAAA<br>AATTTCACTAAAACGATATTATCAATACGCAGAAAATGGAAAA<br>AACGCCTTATCATAAGGCGTTTTTTCCATTTTTTCTTCAAACAA<br>ACGATTTTACTATGACCATTTAACTAATTTTTGCATCTACTATG<br>ATGAGTTTCATTCACATTCTCATTAGAAAGGAGAGATTTA |

TABLE 3-continued

Promoter Sequences for Expression of Fusion Proteins and Modulator Proteins in Recombinant *Bacillus cereus* family members

| Promoter (SEQ ID NO) | Promoter Sequence |
|---|---|
| BclC minimal promoter (*B. anthracis* Sterne) (SEQ ID NO: 180) | ACCATTTAACTAATTTTTGCATCTACTATGATGAGTTTCATTCA CATTCTCATTAGAAAGGAGAGATTTA |
| AcpC promoter (*B. cereus* F837/76) (SEQ ID NO: 181) | GACTATGTTTATTCAGGATAAAATATAGCACTACACTCTCTCCT CTTATTATGTAGCATCTCTCTAATCCATCATTTGTTTCATTTAGT TAAAATTGTAAATAAAATCACATGATTTGTCAATTATAATTGTC ATTTCGACAATTAAACTTGTCAAAATAATTCTCATCATTTTTTC TCATCTTTCTAATATAGGACATACTACTATATATACAAAAGAC AATATGCAAATGTTCATACAAAAAATATTATTTTTCGATATAT AATATTAACTGATTTTCTAACATCAAGGAGGGTACAT |
| AcpC minimal promoter (*B. cereus* F837/76) (SEQ ID NO: 182) | AGACAATATGCAAATGTTCATACAAAAAATATTATTTTTCGATATATAATATTAACTGATTTTCTAACATCAAGGAGGGTACAT |
| InhA3 promoter (*B. thuringiensis* serovar kurstaki str. 141)73) (SEQ ID NO: 183) | ATAGTGAGTAATATGGTAATCCATAGATTAAATAGTATAGAA AATATTTAATTCTTATTTTTATTAAAAAAGCATGAATCCCAGAT TTACTGGGTTTTGATTGTAACTAAGAACATATAAAAGTTCACT GTTATTTATAGGAGAGTCTGTTTGTTTTTATATCTTATGTATTT CACCCTGCATAAAAAAATATTTCTCAACATTTTATTTGTTGAAA AATATTGAATATTCGTATTATAACGAATATTATGTTGTTATCGG CAAAAAACGATAATTTGCAGACACTGGGGAGGAAATACA |
| InhA3 minimal promoter (*B. thuringiensis* serovar kurstaki str. HD73) (SEQ ID NO: 184) | TCTTATGTATTTCACCCTGCATAAAAAAATATTTCTCAACATTT TATTTGTTGAAAATATTGAATATTCGTATTATAACGAATATTA TGTTGTTATCGGCAAAAAACGATAATTTGCAGACACTGGGGAG GAAATACA |
| Alanine racemase 1 promoter (*B. cereus* F837/76) (SEQ ID NO: 185) | CTTCGTCAGCAATAAGTGTGAGCGGAGAATTGGTTGATCTTGG CTTTACAATTGGAGCATTGACGAAAGACTCTTTAACGTGGTCG CATAACGGAGTAGAATATATGCTCGTGTCTAAAGGTTTAGAGC CGAAGGAGCTATTAATGGTTGCTCGTTCAGTTACAGAGAAGCA AGTGAAGTAAACTTCTTAGACGTGGTGATATATGTGCACCACG TCTTTTCTTAGTTTGAAGGGTGGATTTCATAAAAGAAGCATAT AAAAGAATAAGCTTCGCATATCGTGTATAAGGAAGTGTATTT |
| Alanine racemase 1 minimal promoter (*B. cereus* F837/76) (SEQ ID NO: 186) | ATAAAAGAATAAGCTTCGCATATCGTGTATAAGGAAGTGTAT TT |
| Alanine racemase 2 promoter (*B. thuringiensis* serovar kurstaki str. HD73) (SEQ ID NO: 187) | CATTTCAAATAATGAACGCTTCGATTGAATCGGAGCTATTTTCA AATCAATTTCAGTATATTGATCCAGCATTTGAATAGAAGTATC AACAGCAACTTTAAGTTGATGCAATGCAGATTGTACAAACATT GTAATTCTCCTCTTCTCCGTATATAATAGTTTCTTGAGGGTATT ATATCATGCTCAAAATTCCGAAAATTCTAGTAGTTTGACTAGC ATATTGAAAAGTATTATATTGTAAAAGGTCATATGAAACGTG AAATAGAATGGAATGCAATTATTGAGTTAGGAGTTAGACCA |
| Alanine racemase 2 minimal promoter (*B. thuringiensis* serovar kurstaki str. HD73) (SEQ ID NO: 188) | TTATATTGTAAAAGGTCATATGAAACGTGAAATAGAATGGAA TGCAATTATTGAGTTAGGAGTTAGACCA |
| BclA promoter (*B. cereus* F837/76) (SEQ ID NO: 189) | ATCGATGGAACCTGTATCAACCACTATAATTTCATCCACAATTT TTTCAACTGAGTCTAAACAACGGGCTATTGTCTTCTCCTCATCT CGAACAATCATACATAAACTAATTGTAATTCCTTGCTTGTTCA ACATAATCACCCTCTTCCAAATCAATCATATGTTATACATATA CTAAACTTTCCATTTTTTTAAATTGTTCAAGTAGTTTAAGATTT CTTTTCAATAATTCAAATGTCCGTGTCATTTTCTTTCGGTTTTGC ATCTACTATATAATGAACGCTTTATGGAGGTGAATTT |
| BclA minimal promoter (*B. cereus* F837/76) (SEQ ID NO: 190) | AATCAATCATATGTTATACATATACTAAACTTTCCATTTTTTT AAATTGTTCAAGTAGTTTAAGATTTCTTTTCAATAATTCAAATG TCCGTGTCATTTTCTTTCGGTTTTGCATCTACTATATAATGAAC GCTTTATGGAGGTGAATTT |
| BclB promoter (*B. thuringiensis* serovar lconkulcian str. 97-27) (SEQ ID NO: 191) | GACCTGTAAGTCTGTAGGGAAGAATAATTTCAAGAGCCAGTGA TAATAGATTTTTTGTTTTTCATTCTTATCTTGAATATAAATCA CCTCATCTTTTAATTAGAACGTAACCAATTTAGTATTTTGAAA TAGAGCTATCATTTTATAAATGAATACTACTAGTTATAGAAA CGGCAAAAAGTTTAATATATGTAAAAATCATTTGGATATGAAA |

TABLE 3-continued

Promoter Sequences for Expression of Fusion Proteins and Modulator Proteins in Recombinant *Bacillus cereus* family members

| Promoter (SEQ ID NO) | Promoter Sequence |
|---|---|
| | AAAGTAGCCATAGATTTTTTCGAAATGATAAATGTTTTATTTT<br>GTTAATTAGGAAACAAAAATGTGGAATGAGGGGGATTTAA |
| BclB minimal promoter (*B. thuringiensis* serovar konkukian str. 97-27) (SEQ ID NO: 192) | ATATGAAAAAAGTAGCCATAGATTTTTTCGAAATGATAAATGT<br>TTTATTTTGTTAATTAGGAAACAAAAATGTGGAATGAGGGGGA<br>TTTAA |
| BxpA promoter (*B. I* str. Sterne) (SEQ ID NO: 193) | TTTTCATCTGCTACATCGTGAAGTAATGCTGCCATTTCAATTAT<br>AAAACGATTTCCTCCTTCTTGCTCGGATAAAGAAATCGCCAGTT<br>TATGTACACGCTCAATATGATACCAATCATGCCCACTGGCATC<br>TTTTTCTAAAATATGTTTTACAAAAGTAATTGTTTTTTCTATCTT<br>TTCTTGTTTTGTCATTTTATCTTCACCCAGTTACTTATTGTAACA<br>CGCCCGCATTTTTTCATCACATATTTTCTTGTCCGCCCATACA<br>CTAGGTGGTAGGCATCATCATGAAGGAGGAATAGAT |
| BxpA minimal promoter (*B. anthracis* str. Sterne) (SEQ ID NO: 194) | ACATATTTTCTTGTCCGCCCATACACTAGGTGGTAGGCATCAT<br>CATGAAGGAGGAATAGAT |
| BelE promoter (*B. anthracis* ΔSterne) (SEQ ID NO: 195) | GGTGACGACAACATATACAAGAGGCACTCCTGCTGGTACTGTA<br>ACAGGAACAAATATGGGCAAAGTGTAAATACATCGGGTATA<br>GCACAAGCTGTCCCGAATACAGATAATATGGATTCAACGGCG<br>GGACTCCCTTAAGAAATTAGGGGAGTCTTTATTTGGAAAAAGA<br>GCTTATGTTACATAAAAACAGGAGTAATTGTTTTAAAAGTAGT<br>ATTGGTGACGTTGTTAGAAAATACAATTTAAGTAGAAGGTGCG<br>TTTTTATATGAAATATATTTTATAGCTGTACTTTACCTTTCAAG |
| BelE minimal promoter (*B. anthracis* ΔSterne) (SEQ ID NO: 196) | ACAAGCTGTCCCGAATACAGATAATATGGATTCAACGGCGGG<br>ACTCCCTTAAGAAATTAGGGGAGTCTTTATTTGGAAAAAGAGC<br>TTATGTTACATAAAAACAGGAGTAATTGTTTTAAAAGTAGTAT<br>TGGTGACGTTGTTAGAAAATACAATTTAAGTAGAAGGTGCGTT<br>TTTATATGAAATATATTTTATAGCTGTACTTTACCTTTCAAG |
| BetA promoter (*B. anthracis* Sterne) (SEQ ID NO: 197) | ATTTATTTCATTCAATTTTTCCTATTTAGTACCTACCGCACTCAC<br>AAAAAGCACCTCTCATTAATTTATATTATAGTCATTGAAATCTA<br>ATTTAATGAAATCATCATACTATATGTTTTATAAGAAGTAAAG<br>GTACCATACTTAATTAATACATATCTATACACTTCAATATCAC<br>AGCATGCAGTTGAATTATATCCAACTTTCATTTCAAATTAAATA<br>AGTGCCTCCGCTATTGTGAATGTCATTTACTCTCCCTACTACAT<br>TTAATAATTATGACAAGCAATCATAGGAGGTTACTAC |
| BetA minimal promoter (*B. anthracis* Sterne) (SEQ ID NO: 198) | TAAGAAGTAAAGGTACCATACTTAATTAATACATATCTATACA<br>CTTCAATATCACAGCATGCAGTTGAATTATATCCAACTTTCATT<br>TCAAATTAAATAAGTGCCTCCGCTATTGTGAATGTCATTTACTC<br>TCCCTACTACATTTAATAATTATGACAAGCAATCATAGGAGGT<br>TACTAC |
| CotE promoter (*B. cereus* AH820) (SEQ ID NO: 199) | AGTTGTACAAGAATTTAAATCTTCACAAACATATGTAAATGAC<br>TTACTACAGCTAGTTGCAAGTACGATTTCTAACAACGTAACAG<br>ATGAAATATTAATTTCAACTAATGGCGATGTATTGAAGGGTGA<br>AACGGGCGCAGCGGTAGAAAGTAAAAAAGGAAATTGTGGTTG<br>TTAAAGAGATGTCGAAATGACATCTCTTTTTTTAGTGGATTAAA<br>CGTAAGTTCTTCTCAAAAAAAGAATGACACATTCCGCTATTGT<br>CACGCATATGATTAAGTGAATAGTGATTGAGGAGGGTTACGA |
| CotE minimal promoter (*B. cereus* AH820) (SEQ ID NO: 200) | ACATTCCGCTATTGTCACGCATATGATTAAGTGAATAGTGATT<br>GAGGAGGGTTACGA |
| ExsA promoter (*B. cereus* strain ATCC 10876) (SEQ ID NO: 201) | AACGTTATTAGCGTAGACAAACAAGTAACGGCAGAAGCAGTTC<br>TTGCATTAAATCGTATGTTAGAGCGTGTGTAAAGCAACGGTAT<br>TCCCGTTGCTTTTTTTCATACATATAATCATAACGAGAACGAA<br>ATGGGCATACATTGTTTTGAAGAAATCATTGTGGTTCTTTATG<br>CTTATTCCACTTCGAATGATATTGAAAATCGAAGAAGTGATAA<br>AAGTAAAAAGAAGTTAATGTTATTTAGAAAGAGTTACTTCATG<br>AGATTTGTTACTTATAGATAAGTTATACAGGAGGGGAAAAT |
| ExsA minimal promoter (*B. cereus* strain ATCC 10876) (SEQ ID NO: 202) | TCATGAGATTTGTTACTTATAGATAAGTTATACAGGAGGGGA<br>AAAT |
| ExsK promoter (*B. thuringiensis* serovar | AAGCCGCGGTCAATGCTGTATATGCAAATAAGATTGCAGCTTT<br>ACCTGAAGAAGAGCGTGATAGCTTCATTGCTGAAAAACGAGA |

TABLE 3-continued

Promoter Sequences for Expression of Fusion Proteins and Modulator Proteins in Recombinant *Bacillus cereus* family members

| Promoter (SEQ ID NO) | Promoter Sequence |
|---|---|
| konkukian str. 97-27)<br>(SEQ ID NO: 203) | AGAGTATAAGAAAGATATTGATATTTACCATTTAGCATCAGAG<br>ATGGTCATTGATGGTATTGTTCATCCAAACAATTTAAGAGAAG<br>AGTTAAAAGGACGATTCGAAATGTATATGAGTAAATATCAAGT<br>ATTTACGGATCGTAAACATCCTGTTTATCCAGTTTAAAAGCCC<br>TATTTAGGGCTTTCTTGCTCAAAAAGTTAAGGAGGGGAAAACA |
| ExsK minimal promoter (*B. thuringiensis* serovar konkukian str. 97-27)<br>(SEQ ID NO: 204) | TCAAGTATTTACGGATCGTAAACATCCTGTTTATCCAGTTTAA<br>AAGCCCTATTTAGGGCTTTCTTGCTCAAAAAGTTAAGGAGGGG<br>AAAACA |
| ExsB promoter (*B. cereus* F837/76)<br>(SEQ ID NO: 205) | AGGATTTCAGTGGGACGCCTCCTCTCTTCTTACATTAAATTAAT<br>CATACTATAAAATGAAAGAAATGAAATGAAAAATAGCGGAAA<br>AATCAGAAATTTTTTCTGGTAGTATACAATATGTTACAATAAG<br>CTTTGTCAATGAAAGAAGGAATTCCGTGCAATGCACGGGAGAG<br>GTTCGCGAACTCCCTCTATAAAAAACTATGGAAACAACAATAT<br>CTTTAGGTATTGTTTTGTTTTTTTATTGTGACAGTTCAAGAACG<br>TTCTTTCTTCTTATTCGTAGTAGAGAAGGAGAATGAGTGAA |
| ExsB minimal promoter (*B. cereus* F837/76)<br>(SEQ ID NO: 206) | ACTATGGAAACAACAATATCTTTAGGTATTGTTTTGTTTTTTTA<br>TTGTGACAGTTCAAGAACGTTCTTTCTTCTTATTCGTAGTAGAG<br>AAGGAGAATGAGTGAA |
| YabG promoter (*B. cereus* AH820)<br>(SEQ ID NO: 207) | TTTTGCACAACGCCGTAAAACTTTAATGAATAATTTATCAAAT<br>AATTTAAATGGTTTCCCGAAAGATAAAGAGCTGTTGGATCGAA<br>TTTTAACAGAAGTAGGAATTGATCCAAAACGAAGAGGCGAAA<br>CGCTATCTATCGAAGAGTTTGCGACATTAAGTAATGCATTAGTT<br>CTTCATAAGTTATCATAAGAATACAAAAGGGACAGTTCAATTT<br>GAACTGTCCCTTTTGTCACCTTTCTCCTCCTAAATTCATACTTT<br>AAAAACAGGTAAGATGGCCTAACGAGTTTGGAGGTAGGAGA |
| YabG minimal promoter (*B. cereus* AH820)<br>(SEQ ID NO: 208) | TCTCCTCCTAAATTCATACTTTAAAAACAGGTAAGATGGCCTA<br>ACGAGTTTGGAGGTAGGAGA |
| Tgl promoter (*B. thuringiensis* serovar konkukian str. 97-27)<br>(SEQ ID NO: 209) | GGAAACAGAAGTCATCCCATTTGAAAATGCAGCAGGTCGTATT<br>ATAGCTGATTTCGTTATGGTTTATCCGCCAGGGATTCCAATCTT<br>TACTCCGGGGGAAATTATTACACAAGACAACTTAGAGTATATT<br>CGTAAAAACTTAGAAGCAGGTTTACCTGTACAAGGTCCTGAAG<br>ATATGACATTACAAACATTACGCGTGATCAAAGAGTACAAGCC<br>TATCAGTTGATAGGCTTTTTTTCACCCTTTTTCCCTTTTCTCATA<br>CGATATTATGTAATGTAACGTATAGGTGGGGATACTACT |
| Tgl minimal promoter (*B. thuringiensis* serovar konkukian str. 97-27)<br>(SEQ ID NO: 210) | ACCCTTTTTCCCTTTTCTCATACGATATTATGTAATGTAACGTA<br>TAGGTGGGGATACTACT |
| Superoxide dismutase (SODA1) promoter (*B. cereus* F837/76)<br>(SEQ ID NO: 211) | ATTGTGGACCCTTAGCTCAGCTGGTTAGAGCAGACGGCTCATA<br>ACCGTCCGGTCGTAGGTTCGAGTCCTACAGGGTCCATATCCATT<br>TCACATGTTTATTATGTCGGCAGGAAGCTTCCTTGTAGAAGGG<br>AGCTTTTTTTATGAAATATATGAGCATTTTAATTGAAATGAAGT<br>GGGAATTTTGCTACTTTAATGATAGCAAGACAATGTGATTTATT<br>TGTTTGCACCCTATGGCAATTAGGGTAGAATGAAGTTGTATGT<br>CACTTAAGTGGCAATACATAAACTGGGAGGAATATAACA |
| Superoxide dismutase (SODA1) minimal promoter (*B. cereus* F837/76)<br>(SEQ ID NO: 212) | ACTTAAGTGGCAATACATAAACTGGGAGGAATATAACA |
| Superoxide dismutase (SODA2) promoter (*B. cereus* AH820)<br>(SEQ ID NO: 213) | AATATAACAGAAAATTCTGATGTTTTTTCAAATCCTATAATAAG<br>GAGTGTTCCGTATGATGCCTTTATATTTTCCGGAAGATAAAAC<br>AGAATATATTATTCCAGGGATTGTTTGTGTTCTATTTATCATCG<br>GTGCGATTGCTACGTGGCGTATGTTCATTCGTGTATCAAAACG<br>AGAAGCAGAGCGATTACAGAAAGTTGAAGAAAAGCTGTTAGC<br>TGAAAAGAAACAGTAACTCATTTTTGTATGTTTCCCTCTATGCT<br>CGGACAATCTAAGGGCAGAATGTATTTTGGAGGGAATGAA |
| Superoxide dismutase (SODA2) minimal promoter (*B. cereus* AH820) | TCCGGAAGATAAAACAGAATATATTATTCCAGGGATTGTTTGT<br>GTTCTATTTATCATCGGTGCGATTGCTACGTGGCGTATGTTCAT<br>TCGTGTATCAAAACGAGAAGCAGAGCGATTACAGAAAGTTGA |

TABLE 3-continued

Promoter Sequences for Expression of Fusion Proteins and Modulator Proteins in Recombinant *Bacillus cereus* family members

| Promoter (SEQ ID NO) | Promoter Sequence |
|---|---|
| (SEQ ID NO: 214) | AGAAAAGCTGTTAGCTGAAAAGAAACAGTAACTCATTTTTGTA TGTTTCCCTCTATGCTCGGACAATCTAAGGGCAGAATGTATTTT GGAGGGAATGAA |
| BclA promoter (*B. anthracis* Sterne) (SEQ ID NO: 215) | TAATCACCCTCTTCCAAATCAATCATATGTTATACATATACTA AACTTTCCATTTTTTAAATTGTTCAAGTAGTTTAAGATTTCTT TTCAATAATTCAAATGTCCGTGTCATTTTCTTTCGGTTTTGCAT CTACTATATAATGAACGCTTTATGGAGGTGAATTT |
| BAS1882 promoter (*B. anthracis* Sterne) (SEQ ID NO: 216) | AATTACATAACAAGAACTACATTAGGGAGCAAGCAGTCTAGCG AAAGCTAACTGCTTTTTTATTAAATAACTATTTTATTAAATTTC ATATATACAATCGCTTGTCCATTTCATTTGGCTCTACCCACGCA TTTACTATTAGTAATATGAATTTTTCAGAGGTGGATTTTATT |
| Gene 3572 promoter (*B. weihenstephensis* KBAB 4) (SEQ ID NO: 217) | CTATGATTTAAGATACACAATAGCAAAAGAGAAACATATTAT ATAACGATAAATGAAACTTATGTATATGTATGGTAACTGTATA TATTACTACAATACAGTATACTCATAGGAGGTAGGT |
| YVTN (β-propeller protein promoter (*B. weihenstephensis* KBAB 4) (SEQ ID NO: 218) | GGTAGGTAGATTTGAAATATGATGAAGAAAAGGAATAACTAA AAGGAGTCGATATCCGACTCCTTTTAGTTATAAATAATGTGGA ATTAGAGTATAATTTTATATAGGTATATTGTATTAGATGAACGC TTTATCCTTTAATTGTGATTAATGATGGATTGTAAGAGAAGGG GCTTACAGTCCTTTTTTTATGGTGTTCTATAAGCCTTTTTAAAA GGGGTACCACCCCACACCCAAAAACAGGGGGGGTTATAACTA CATATTGGATGTTTTGTAACGTACAAGAATCGGTATTAATTACC CTGTAAATAAGTTATGTGTATATAAGGTAACTTTATATATTCT CCTACAATAAAATAAAGGAGGTAATAAA |
| Cry1A promoter (*B. thuringiensis* HD-73) (SEQ ID NO: 219) | AACCCTTAATGCATTGGTTAAACATTGTAAAGTCTAAAGCATG GATAATGGGCGAGAAGTAAGTAGATTGTTAACACCCTGGGTCA AAAATTGATATTTAGTAAAATTAGTTGCACTTTGTGCATTTTTT CATAAGATGAAGTCATATGTTTTAAATTGTAGTAATGAAAAAC AGTATTATATCATAATGAATTGGTATCTTAATAAAAGAGATGG AGGTAACTTA |
| ExsY promoter (*B. thuringiensis* serovar konkukian str. 97-27) (SEQ ID NO: 220) | TAATTCCACCTTCCCTTATCCTCTTTCGCCTATTTAAAAAAGG TCTTGAGATTGTGACCAAATCTCCTCAACTCCAATATCTTATTA ATGTAAATACAAACAAGAAGATAAGGA |
| CotY promoter (*B. thuringiensis* Al Hakam) (SEQ ID NO: 221) | AGGATGTCTTTTTTTATATTGTATTATGTACATCCCTACTATATA AATTCCCTGCTTTTATCGTAAGAATTAACGTAATATCAACCATA TCCCGTTCATATTGTAGTAGTGTATGTCAGAACTCACGAGAAG GAGTGAACATAA |
| YjcA promoter (*B. thuringiensis* serovar kurstaki str. HD73) (SEQ ID NO: 222) | TTAATGTCACTCCTTATCTTCTTGTTTGTATTTACATTAATAAG ATATTGGAGTTGAGGAGATTTGGTCACAATCTCAAGACCTTTTT TTTAAATAGGCGAAAGAGGATAAGGGAAGGTGGAATT |
| YjcB promoter (*B. thuringiensis* serovar kurstaki str. HD73) (SEQ ID NO: 223) | ATATATTTTCATAATACGAGAAAAAGCGGAGTTTAAAAGAATG AGGGAACGGAAATAAAGAGTTGTTCATATAGTAAATAGACAG AA |
| ExsFA/BxpB promoter (*B. thuringiensis* Al Hakam) (SEQ ID NO: 224) | AAACTAAATAATGAGCTAAGCATGGATTGGGTGGCAGAATTAT CTGCCACCCAATCCATGCTTAACGAGTATTATTATGTAAATTT CTTAAAATTGGGAACTTGTCTAGAACATAGAACCTGTCCTTTTC ATTAACTGAAAGTAGAAACAGATAAAGGAGTGAAAAAC |
| Rhamnose promoter (*B. thuringiensis* Al Hakam) (SEQ ID NO: 225) | ATTCACTACAACGGGGATGAGTTTGATGCGGATACATATGAG AAGTACCGGAAAGTGTTTGTAGAACATTACAAAGATATATTAT CTCCATCATAAAGGAGAGATGCAAAG |
| CotO promoter (*B. anthracis* Sterne) (SEQ ID NO: 226) | CGCGCACCACTTCGTCGTACAACAACGCAAGAAGAAGTTGGGG ATACAGCAGTATTCTTATTCAGTGATTTAGCACGCGGCGTAAC AGGAGAAAACATTCACGTTGATTCAGGGTATCATATCTTAGGA TAAATATAATATTAATTTTAAAGGACAATCTCTACATGTTGAG ATTGTCCTTTTTATTTGTTCTTAGAAAGAACGATTTTTAACGAA AGTTCTTACCACGTTATGAATATAAGTATAATAGTACACGATTT ATTCAGCTACGTA |

TABLE 3-continued

Promoter Sequences for Expression of Fusion Proteins and Modulator Proteins in Recombinant *Bacillus cereus* family members

| Promoter (SEQ ID NO) | Promoter Sequence |
|---|---|
| Sigma K promoter (*B. anthracis* Sterne) (SEQ ID NO: 227) | TATATCATATGTAAAATTAGTTCTTATTCCCACATATCATATAG AATCGCCATATTATACATGCAGAAAACTAAGTATGGTATTATT CTTAAATTGTTTAGCACCTTCTAATATTACAGATAGAATCCGTC ATTTTCAACAGTGAACATGGATTTCTTCTGAACACAACTCTTTT TCTTTCCTTATTTCCAAAAAGAAAAGCAGCCCATTTTAAAATAC GGCTGCTTGTAATGTACATTA |
| InhA1 promoter (*B. thuringiensis* Al Hakam) (SEQ ID NO: 228) | TATCACATAACTCTTTATTTTTAATATTTCGACATAAAGTGAAA CTTTAATCAGTGGGGGCTTTGTTCATCCCCCCACTGATTATTAA TTGAACCAAGGGATAAAAAGATAGAGGGTCTGACCAGAAAAC TGGAGGGCATGATTCTATAACAAAAAGCTTAATGTTTATAGAA TTATGTCTTTTTATATAGGGAGGGTAGTAAACAGAGATTTGGA CAAAAATGCACCGATTTATCTGAATTTTAAGTTTTATAAAGGG GAGAAATG |
| BclA cluster glycosyl transferase operon 1 (*B. thuringiensis* serovar konkukian str. 97-27) (SEQ ID NO: 229) | ATTTTTTACTTAGCAGTAAAACTGATATCAGTTTTACTGCTTTTT CATTTTTAAATTCAATCATTAAATCTTCCTTTTCTACATAGTCA TAATGTTGTATGACATTCCGTAGGAGGCACTTATA |
| BclA cluster glycosyl transferase operon 2 (*B. thuringiensis* serovar kurstaki str. HD73) (SEQ ID NO: 230) | ACATAAATTCACCTCCATAAAGCGTTCATTATATAGTAGATGC AAAACCGAAAGAAAATGACACGGACATTTGAATTATTGAAAA GAAATCTTAAACTACTTGAACAATTTAAAAAAATGGAAAGTTT AGTATATGTATAACATATGATTGATTTGGAAGAGGGTGATTA |
| Glycosyl transferase promoter (*B. thuringiensis* Al Hakam) (SEQ ID NO: 231) | TTCTATTTTCCAACATAACATGCTACGATTAAATGGTTTTTGC AAATGCCTTCTTGGGAAGAAGGATTAGAGCGTTTTTTTATAGA AACCAAAAGTCATTAACAATTTTAAGTTAATGACTTTTTTGTTT GCCTTTAAGAGGTTTTATGTTACTATAATTATAGTATCAGGTAC TAATAACAAGTATAAGTATTTCTGGGAGGATATATCA |

The sigma-K sporulation-specific polymerase promoter sequences in the promoter sequences shown in Table 3 result in high expression levels of the fusion protein or modulator protein during late sporulation. The consensus sequence for the sigma-K sporulation-specific polymerase promoter sequence is CATANNNTN; however, this sequence can comprise up to two mutations and still be functional. The sigma-K sporulation-specific polymerase promoter sequence is generally found upstream of the ribosome binding site (RBS).

Promoters having a high degree of sequence identity to any of the sequences shown above in Table 3 can also be used to express the fusion proteins or the modulator proteins.

For example, the fusion protein or modulator protein can be expressed under the control of a promoter comprising a nucleic acid sequence having at least 80% identity with a nucleic acid sequence of any one of SEQ ID NOs: 157-231.

The fusion protein or modulator protein can be expressed under the control of a promoter comprising a nucleic acid sequence having at least 90% identity with a nucleic acid sequence of any one of SEQ ID NOs: 157-231.

The fusion protein or modulator protein can be expressed under the control of a promoter comprising a nucleic acid sequence having at least 95% identity with a nucleic acid sequence of any one of SEQ ID NOs: 157-231.

The fusion protein or modulator protein can be expressed under the control of a promoter comprising a nucleic acid sequence having at least 98% identity with a nucleic acid sequence of any one of SEQ ID NOs: 157-231.

The fusion protein or modulator protein can be expressed under the control of a promoter comprising a nucleic acid sequence having at least 99% identity with a nucleic acid sequence of any one of SEQ ID NOs: 157-231.

The fusion protein or modulator protein can be expressed under the control of a promoter comprising a nucleic acid sequence having 100% identity with a nucleic acid sequence of any one of SEQ ID NOs: 157-231.

For example, the modulator protein or fusion protein can be expressed under the control of a BclA promoter (e.g., SEQ ID NO: 189, 190, 215, 229 or 230), a CotY promoter (e.g., SEQ ID NO: 161, 162 or 221), an ExsY promoter (e.g., SEQ ID NO: 157, 158 or 220), or a rhamnose promoter (e.g., SEQ ID NO: 225). For example, the fusion protein can be expressed under the control of a promoter comprising a nucleic acid sequence having at least 80% identity with a nucleic acid sequence of any one of SEQ ID NOs: 157, 158, 161, 162, 189, 190, 215, 220, 221, 225, 229, or 230.

The fusion protein can be expressed under the control of a promoter comprising a nucleic acid sequence having at least 85% identity with a nucleic acid sequence of any one of SEQ ID NOs: 157, 158, 161, 162, 189, 190, 215, 220, 221, 225, 229, or 230.

The fusion protein can be expressed under the control of a promoter comprising a nucleic acid sequence having at least 90% identity with a nucleic acid sequence of any one of SEQ ID NOs: 157, 158, 161, 162, 189, 190, 215, 220, 221, 225, 229, or 230.

The fusion protein can be expressed under the control of a promoter comprising a nucleic acid sequence having at least 95% identity with a nucleic acid sequence of any one of SEQ ID NOs: 157, 158, 161, 162, 189, 190, 215, 220, 221, 225, 229, or 230.

The fusion protein can be expressed under the control of a promoter comprising a nucleic acid sequence having at least 98% identity with a nucleic acid sequence of any one of SEQ ID NOs: 157, 158, 161, 162, 189, 190, 215, 220, 221, 225, 229, or 230.

The fusion protein can be expressed under the control of a promoter comprising a nucleic acid sequence having at least 99% identity with a nucleic acid sequence of any one of SEQ ID NOs: 157, 158, 161, 162, 189, 190, 215, 220, 221, 225, 229, or 230.

The fusion protein can be expressed under the control of a promoter comprising a nucleic acid sequence having 100% identity with a nucleic acid sequence of any one of SEQ ID NOs: 157, 158, 161, 162, 189, 190, 215, 220, 221, 225, 229, or 230.

The fusion protein or modulator protein can be expressed under the control of a promoter comprising a sigma-K sporulation specific polymerase promoter sequence, wherein the sigma-K sporulation-specific polymerase promoter sequence or sequences have 100% identity with the corresponding nucleotides of any of SEQ ID NOs: 157-231.

The fusion proteins can be expressed under the control of a promoter that is native to the targeting sequence, exosporium protein, or exosporium protein fragment of the fusion protein. Thus, for example, where the targeting sequence is derived from BclA, the fusion protein can be expressed under the control of a native BclA promoter (e.g., SEQ ID NO: 189, 190, 215, 229 or 230).

The modulator proteins can be expressed under the control of their native promoters. Thus, for example, where the modulator protein comprises CotO, the CotO can be expressed under the control of a native CotO promoter (e.g., SEQ ID NO: 163 or 226). Native promoter sequences for each of the modulator proteins are provided above in Table 3.

Table 3 also provides exemplary minimal promoter sequences for each modulator protein. The modulator proteins and fusion proteins can be expressed under any of these minimal promoter sequences. For example, the modulator protein can be expressed under a minimal promoter that comprises a portion of the native promoter sequence. For instance, where the modulator protein comprises CotO, the CotO can be expressed under the minimal CotO promoter (SEQ ID NO: 164).

Alternatively, the modulator proteins can be expressed under the control of any promoter comprising a sigma-K sporulation-specific polymerase promoter sequence, regardless of whether the promoter is the native promoter for the modulator protein. As can be seen from Table 3, each of the native promoters and the minimal promoters for the modulator proteins contains at least one sigma-K sporulation-specific polymerase promoter sequence. Thus, for example, where the modulator protein is BxpB, the BxpB can be expressed under the control of a BclA promoter (e.g., SEQ ID NO: 189, 190, 215, 229 or 230) or any of the other promoters listed in Table 3.

Furthermore, the modulator protein or the fusion protein can be expressed under a portion of any of the promoters listed above in Table 3, so long as the portion of the promoter includes a sigma-K sporulation-specific polymerase promoter sequence. For example, the modulator protein can be expressed under a promoter region that comprises the first 25, 50, 100, 150, 200, 250, or 300 nucleotides upstream of the start codon, so long as that region comprises a sigma-K sporulation-specific polymerase promoter sequence.

IV. Mutations and Other Genetic Alterations to Recombinant *Bacillus cereus* Family Members that Allow for Collection of Free Exosporium As is described further hereinbelow, the recombinant *Bacillus cereus* family members that express fusion proteins comprising a protein or peptide of interest and a targeting sequence, an exosporium protein, or an exosporium protein fragment that targets the fusion protein to the exosporium of the recombinant *Bacillus cereus* family member can be used to deliver proteins or peptides of interest to plants, seeds, a plant growth medium, or an area surrounding a seed or a plant (e.g., via soil drench, foliar application, or as a seed treatment). In addition, the recombinant *Bacillus cereus* family members can be used to deliver nucleic acid molecules to animals, insects, worms (e.g., nematodes), fungi, and protozoans; to deliver proteins or peptides to an animal; in vaccines and for producing an immunogenic response; for remediation; for treating a hydraulic fracturing fluid to break an emulsion or gel within the fluid; for disinfection; and for various other uses described hereinbelow. However, in some cases, the presence of the living microorganisms may not be desirable, and instead, it would be desirable to separate the living spore from the fusion proteins in the exosporium on the outside surface of the spore. For example, in some applications it will be desirable to increase enzyme activity without concern for spore integrity. In such situations, the exosporium fragments may be preferred over living microorganisms having the enzyme on their exosporium.

In addition, for some uses, it may be desirable to reduce the density of the product. In such instances, it would be desirable to separate the dense spore from the exosporium (containing the fusion proteins). In the field of vaccines, it may be desirable to separate the spore from the exosporium (containing fusion proteins that comprise an antigen) in order to remove potential antigens present on the spore itself from the vaccine preparation. Furthermore, under some circumstances the presence of live spores would lead to potential for bacterial growth in a product, which would be undesirable for some applications (e.g., animal feed supplementation and leather hide processing).

Mutations or other genetic alterations (e.g., overexpression of a protein) can be introduced into the recombinant *Bacillus cereus* family members that allow free exosporium to be separated from spores of the recombinant *Bacillus cereus* family member. This separation process yields exosporium fragments that contain the fusion proteins but that are substantially free of the spores themselves. By "substantially free of spores" it is meant that once the free exosporium is separated from the spores, a preparation is obtained that contains less than 5% by volume of spores, preferably less than 3% by volume of spores, even more preferably less than 1% by volume of spores, and most preferably contains no spores or if spores are present, they are undetectable. These exosporium fragments can be used in place of the recombinant *Bacillus cereus* family members themselves and can be used to deliver proteins or peptides of interest to plants, seeds, a plant growth medium, or an area surrounding a seed or a plant, or for any of the other purposes described herein.

Thus, a recombinant *Bacillus cereus* family member is provided that expresses a fusion protein comprising at least one protein or peptide of interest and a targeting sequence, exosporium protein, or exosporium protein fragment that targets the fusion protein to the exosporium of the recombinant *Bacillus cereus* family member. The recombinant *Bacillus cereus* family member comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* spores having an exosporium that is easier to remove from the spore as compared to the exosporium of a wild-type spore.

A further recombinant *Bacillus cereus* family member is provided that expresses a fusion protein comprising at least one protein or peptide of interest and a targeting sequence, exosporium protein, or exosporium protein fragment that targets the fusion protein to the exosporium of the recombinant *Bacillus cereus* family member. The recombinant *Bacillus cereus* family member: (i) comprises a mutation in a CotE gene; (ii) expresses an ExsY protein, wherein the expression of the ExsY protein is increased as compared to the expression of the ExsY protein in a wild-type *Bacillus cereus* family member under the same conditions, and wherein the ExsY protein comprises a carboxy-terminal tag comprising a globular protein; (iii) expresses a BclB protein, wherein the expression of the BclB protein is increased as compared to the expression of the BclB protein in a wild-type *Bacillus cereus* family member under the same conditions; (iv) expresses a YjcB protein, wherein the expression of the YjcB protein is increased as compared to the expression of the YjcB protein in a wild-type *Bacillus cereus* family member under the same conditions; (v) comprises a mutation in an ExsY gene; (vi) comprises a mutation in a CotY gene; (vii) comprises a mutation in an ExsA gene; or (viii) comprises a mutation in a CotO gene.

The recombinant *Bacillus cereus* family member can comprise a mutation in the CotE gene, such as a knock-out of the CotE gene or a dominant negative form of the CotE gene. The mutation in the CotE gene can partially or completely inhibit the ability of CotE to attach the exosporium to the spore.

The recombinant *Bacillus cereus* family member can express an ExsY protein. The ExsY protein comprises a carboxy-terminal tag comprising a globular protein (e.g., a green fluorescent protein (GFP) or a variant thereof), and the expression of the ExsY protein is increased as compared to the expression of the ExsY protein in a wild-type *Bacillus cereus* family member under the same conditions. The globular protein can have a molecular weight of between 25 kDa and 100 kDa. Expression of the ExsY protein comprising the carboxy-terminal tag comprising a globular protein can also inhibit binding of the ExsY protein to its targets in the exosporium.

The recombinant *Bacillus cereus* family member can express a BclB protein, which may result in the formation of a fragile exosporium. The expression of the BclB protein can be increased as compared to the expression of the BclB protein in a wild-type *Bacillus cereus* family member under the same conditions.

The recombinant *Bacillus cereus* family member can express a YjcB protein, which may cause the exosporium to form in pieces rather than in a complete structure. The expression of the YjcB protein can be increased as compared to the expression of the YjcB protein in a wild-type *Bacillus cereus* family member under the same conditions.

The recombinant *Bacillus cereus* family member can comprise a mutation an ExsY gene, such as a knock-out of the ExsY gene. The mutation in the ExsY gene can partially or completely inhibit the ability of ExsY to complete the formation of the exosporium or attach the exosporium to the spore.

The recombinant *Bacillus cereus* family member can comprise a mutation a CotY gene, such as a knock-out of the CotY gene. The mutation in the CotY gene can result in the formation of a fragile exosporium.

The recombinant *Bacillus cereus* family member can comprise a mutation an ExsA gene, such as a knock-out of the ExsA gene. The mutation in the ExsA gene can result in the formation of a fragile exosporium.

The recombinant *Bacillus cereus* family member can comprise a mutation a CotO gene, such as a knock-out of the CotO gene or a dominant negative form of the CotO gene. The mutation in the CotO gene can cause the exosporium to form in strips.

Exosporium fragments can be prepared from any of these recombinant *Bacillus cereus* family members and used for various purposes as described further hereinbelow. The exosporium fragments comprise the fusion proteins. Upon purification of the exosporium fragments that contain the fusion proteins from the spores, a cell-free protein preparation is obtained in which the fusion proteins are stabilized and supported through covalent bonds to the exosporium fragments.

Due to the strong covalent bonds between the fusion proteins and the exosporium fragments, the fusion proteins become resistant to heat. The heat resistance of the fusion proteins bound to the exosporium fragments allows them to be used for applications that require heat-resistant proteins or enzymes (e.g., in feed additives).

V. Inactivation of Spores of *Bacillus* Genus Bacteria, Including Spores of Recombinant *Bacillus cereus* Family Members Spores of bacteria of the genus *Bacillus* can be genetically inactivated. Genetic inactivation of the spores can be advantageous, for example because it allows for delivery of spores to a plant or a plant growth medium while eliminating any detrimental effects that the live bacteria might have on a plant. In addition, use of inactivated spores can provide many of the same benefits (e.g., prevention of bacterial growth in a product) as discussed above in Section IV with respect to the use of exosporium fragments.

A. Genetic Inactivation by Overexpression of a Protease or a Nuclease

A recombinant bacterium of the genus *Bacillus* that expresses a protease or a nuclease is provided. The expression of the protease or nuclease is increased as compared to the expression of the protease or the nuclease in a wild-type bacterium of the genus *Bacillus* under the same conditions. The increased expression of the protease or the nuclease partially or completely inactivates spores of the recombinant bacterium of the genus *Bacillus* or renders spores of the recombinant bacterium of the genus *Bacillus* more susceptible to physical or chemical inactivation.

The recombinant bacterium of the genus *Bacillus* is preferably a recombinant *Bacillus cereus* family member.

The recombinant *Bacillus cereus* family member can also express a fusion protein comprising at least one protein or peptide of interest and a targeting sequence, exosporium protein, or exosporium protein fragment that targets the fusion protein to the exosporium of the recombinant *Bacillus cereus* family member.

The recombinant bacterium of the genus *Bacillus* can express both a protease and a nuclease, wherein the expression of the protease is increased as compared to the expression of the protease in a wild-type bacterium of the genus *Bacillus* under the same conditions and the expression of the nuclease is increased as compared to the expression of the nuclease in a wild-type bacterium of the genus *Bacillus* under the same conditions.

The protease of the recombinant bacterium can comprise a non-specific protease.

The protease of the recombinant bacterium can comprise a serine protease, a threonine protease, a cysteine protease, an aspartate protease, a glutamic acid protease, an alkaline protease, a subtilisin, a histidine protease, or a metalloprotease.

The protease of the recombinant bacterium can comprise a germination spore protease, such as a *Bacillus subtilis* germination spore protease, a *Bacillus mycoides* germination spore protease, or a *Bacillus thuringiensis* germination spore protease.

The germination spore protease can comprise an active form of the germination spore protease. This protease is naturally inactive in the spore. Upon germination, the protease becomes active due to cleavage of the protease into a proprotein active form. Thus, the recombinant bacterium can comprise an active protease rather than the naturally inactive form. The active protease can digest the protective SASP proteins in the spore prior to germination.

The nuclease of the recombinant bacterium can comprise an endonuclease or an exonuclease. The nuclease can comprise a non-specific endonuclease, such as *Bacillus subtilis* endonuclease 1. For example, the germination spore protease and endonuclease 1 can have the amino acid sequences listed below in Table 4.

TABLE 4

Amino acid sequences of a germination spore protease and endonuclease 1

| Protein | SEQ ID NO. |
|---|---|
| Endonuclease 1, *B. subtilis* 168 | 232 |
| GPR Protease, *B. subtilis* 168 | 233 |
| GPR Protease, *B. cereus* | 234 |

A protease or a nuclease having a high degree of amino acid identity to the sequences listed above in Table 4 can also be used.

Thus, for example, the germination spore protease can comprise an amino acid sequence having at least 85% identity with SEQ ID NO: 233 or 234.

The germination spore protease can comprise an amino acid sequence having at least 90% identity with SEQ ID NO: 233 or 234.

The germination spore protease can comprise an amino acid sequence having at least 95% identity with SEQ ID NO: 233 or 234.

The germination spore protease can comprise an amino acid sequence having at least 98% identity with SEQ ID NO: 233 or 234.

The germination spore protease can comprise an amino acid sequence having at least 99% identity with SEQ ID NO: 233 or 234.

The germination spore protease can comprise an amino acid sequence having 100% identity with SEQ ID NO: 233 or 234.

Similarly, the non-specific endonuclease can comprise an amino acid having at least 85% identity with SEQ ID NO: 232.

The non-specific endonuclease can comprise an amino acid having at least 90% identity with SEQ ID NO: 232.

The non-specific endonuclease can comprise an amino acid having at least 95% identity with SEQ ID NO: 232.

The non-specific endonuclease can comprise an amino acid having at least 98% identity with SEQ ID NO: 232.

The non-specific endonuclease can comprise an amino acid having at least 99% identity with SEQ ID NO: 232.

The non-specific endonuclease can comprise an amino acid having 100% identity with SEQ ID NO: 232.

The protease or nuclease can be expressed under the control of a promoter comprising a sigma G promoter sequence. For example, the promoter can have one of the sequences shown in Table 5 below. The consensus sequence for binding of the sigma G transcription factor is CATNNTA, where N is any nucleotide. The sigma G promoter sequences in the promoters in Table 5 are indicated by bold and underlined text.

TABLE 5

Promoter Sequences having sigma G sequences

| Promoter | Nucleic Acid Sequence |
|---|---|
| GPR Protease, *B. subtilis* 168 (SEQ ID NO: 235) | GTAACTAAAGCTTCTACAGTTTTAACAGCTGAACGCATGTCAGACTT GATAGAAGCGTTATGTGCACGACGCTCTTCGCTAAGTTTAGCGCGTT TGATAGCAGATTTAATGTTTGCCATACTTTTCACCTCCCTGGTGCGA TCGAGTGACTCGATACTTACATAGAACAAGTGATATTCTATCAAACG GAGAAGAGAATTGCAATAGCGAGATCAATGAAATTTCATGTAAAGG AAAGAATGACCTTATATATTTTTGGGGAATCTAACTATATTTACTAT GAATTGCGGAGGAGATACG |
| GPR Protease minimal promoter, *B. subtilis* 168 (SEQ ID NO: 236) | GCAATAGCGAGATCAATGAAATTTCATGTAAAGGAAAGAATGACCT TATATATTTTTGGGGAATCTAACTATATTTACTATGAATTGCGGAGG AGATACG |
| GPR Protease, *B. subtilis* 168 (SEQ ID NO: 237) | TTTCACCTCCTAAGATACAACCTGTAGCACAGTGTCTTAAGGTTAAA TCTTCTTCACAATAGAACAAATTGTATTCTATCAAACACACCTTTAG ATTGCAATATAAATGTAAAGTATTTTTCATTGAAGGTTCTCTTTTTAG CATGATTTATTCAGCAAATGGCAACAATATAGGTACTTAATGTGAA GGAGGCCCCTGT |
| GPR Protease minimal promoter, *B. subtilis* 168 (SEQ ID NO: 238) | GAAGGTTCTCTTTTTAGCATGATTTATTCAGCAAATGGCAACAATAT AGGTACTTAATGTGAAGGAGGCCCCTGT |
| SASPα, *B. subtilis* 168 | GCTTTGTTGATTTCGAGCCGTATATTCAAGAAGCGGTAGATAACATT GAGACAATGACCCTTTATAGCGAACAAGAAGCTAACGATAAATTCG |

TABLE 5-continued

Promoter Sequences having sigma G sequences

| Promoter | Nucleic Acid Sequence |
|---|---|
| (SEQ ID NO: 239) | CTGAACTCTTTTAAATCAATTTTCAGCTCCTGTATACAATTACCAAAG<br>TTTTTCTGAATGAAGCCATGTGTTTTGACACATTCTATACTCACAAG<br>GAGGTGAGACAC |
| SASPα minimal promoter, *B. subtilis* 168 (SEQ ID NO: 240) | GAATGAAGCCATGTGTTTTGACACATTCTATACTCACAAGGAGGTG<br>AGACAC |
| SASPβ, *B. subtilis* 168 (SEQ ID NO: 241) | AAACGGCTAAGCTTTTTTTATTTCTCAAGATTTACCACACAATTCTCC<br>GCATGATTTTCCGGCCATTTTAACATAATACGTAGTAACAAGCCGGC<br>AAAGCATTGGGTTACGCCGAGGCGGCAGTGACACCCGAGAAGGGTT<br>CACAGATTGGTGCAACTCCAGTTAACCCAACCATACTAAATAAAAA<br>GGAGATTTTACAC |
| SASPβ minimal promoter, *B. subtilis* 168 (SEQ ID NO: 242) | GATTGGTGCAACTCCAGTTAACCCAACCATACTAAATAAAAAGGAG<br>ATTTTACAC |
| SASPγ, *B. subtilis* 168 (SEQ ID NO: 243) | TTCGCTTCTCCCACTTAATCTGATTTACATTCCAAGGAATCCAATGAT<br>TTATATGGAGATCTGAAACATAATCAATTTTCATTTTGTCTCCACCTT<br>TCTTAATGAAAAATTTATTTCTTTGGCGTGTATAAATTAAAATAATCT<br>CTCCATAATATGATTCAAACAAGCTTGTTTTCATTACACTTTAGGAG<br>ATGAATAAG |
| SASPγ minimal promoter, *B. subtilis* 168 (SEQ ID NO: 244) | GTATAAATTAAAATAATCTCTCCATAATATGATTCAAACAAGCTTGT<br>TTTCATTACACTTTAGGAGATGAATAAG |
| SASPδ, *B. subtilis* 168 (SEQ ID NO: 245) | TACAGTCCTCTCCATTTTGACATTCCATATTCAGGCAACCGCACATA<br>AAATGACAGCAGACATTCTATAGTCTGCGCCACCCCGGCTCAGAGG<br>CCGGGGTTTTATTTTTCTCCACAACAATTGCCAGCATAAATAAACCC<br>CGTATATTTCAAACTAAATACGCGTTAAGAATTTCTTTATCGAAAAA<br>GGAGATGAAAAAG |
| SASPδ minimal promoter, *B. subtilis* 168 (SEQ ID NO: 246) | GCAACCGCACATAAAATGACAGCAGACATTCTATAGTCTGCGCCAC<br>CCCGGCTCAGAGGCCGGGGTTTTATTTTTCTCCACAACAATTGCCAG<br>CATAAATAAACCCCGTATATTTCAAACTAAATACGCGTTAAGAATTT<br>CTTTATCGAAAAAGGAGATGAAAAAG |

Expression of a nuclease or protease under a sigma G promoter allows for site-specific expression of the nuclease or protease in the forespore, where the enzyme's activity is directed towards the forespore and, the region where the bacterial target DNA is located. Extensive cleavage of the forespore DNA is lethal to the bacterial spore when it begins to germinate.

For example, as illustrated further in the Examples provided hereinbelow, overexpression of germination spore protease (GPR) in its active form in the forespore of a *Bacillus cereus* family member during sporulation results in proteolytic cleavage of proteins in the forespore and inactivation of the spore and/or renders the spore more sensitive to inactivation by ultraviolet or gamma irradiation. Similarly, overexpression of a non-specific endonuclease in the forespore during sporulation destroys the DNA in the spore, leading to a high number of inactivated spore particle. These methods for inactivating *Bacillus cereus* family member spores can be used separately or in conjunction with each other and/or with other spore inactivation methods.

Expression of genes in *Bacillus* spores is tightly regulated by expression of specific sporulation sigma factors that direct the RNA polymerase to the genes that need to be expressed during each stage of sporulation. Late expression of genes in the forespore, where bacterial DNA and essential proteins are packaged, is regulated by the sigma factor sigma G. During late sporulation, the bacterial DNA is packaged with protective proteins called small acid soluble proteins (SASPs). These SASP proteins include SASPα, SASPβ, and SASPγ, among others. The SASP proteins protect the bacterial DNA from UV irradiation and other assaults. Upon germination, the proprotein germination spore protease is activated and digests these SASP proteins.

By expressing a GPR under the control of a sigma G promoter, the GPR is expressed in the forespore and the protective SASP proteins are degraded as sporulation commences, leaving the bacterial DNA more susceptible to degradation. Similarly, expression of a non-specific nuclease under the control of a sigma G promoter leads to digestion of the host DNA. Since the spore is unable to repair the large scale damage to its DNA, this ultimately leads to killing of the spore. Overexpression of a GPR and a non-specific endonuclease can be used together to both degrade the protective SASP proteins and the host DNA.

The protease or the nuclease can be expressed under the control of any promoter comprising a sigma G promoter sequence.

Thus, the protease or nuclease can be expressed under the control of any of the promoters listed in Table 5 above. In addition, the protease or nuclease can be expressed under the control of a promoter having a high degree of sequence identity with any of the promoter sequences listed above in Table 5.

For example, the promoter can comprise a nucleic acid sequence having at least 95% identity with a nucleic acid sequence of any of SEQ ID NOs: 235-246.

The promoter can comprise a nucleic acid sequence having at least 98% identity with a nucleic acid sequence of any of SEQ ID NOs: 235-246.

The promoter can comprise a nucleic acid sequence having at least 99% identity with a nucleic acid sequence of any of SEQ ID NOs: 235-246.

The promoter can comprise a nucleic acid sequence having 100% identity with a nucleic acid sequence of any of SEQ ID NOs: 235-246.

In any of the recombinant bacteria of the genus *Bacillus* that express a protease or a nuclease, spores of the recombinant bacterium of the genus *Bacillus* can be more susceptible to inactivation, for example, by ultraviolet irradiation, gamma irradiation, or by treatment with bleach, hydrogen peroxide, chloroform, phenol, or acetic acid, as compared to the same spores that do not expresses the protease or the nuclease at an increased level as compared to expression of the protease or the nuclease in a wild-type bacterium of the genus *Bacillus*, treated under the same conditions.

B. Genetic Inactivation by Mutation of a Gene Encoding a Germination Receptor, a Spore Core Lytic Enzyme, a Small Acid-Soluble Spore Protein (SASP), or a Spore Coat Protein Spores of any of the recombinant *Bacillus cereus* family member spores that express a fusion protein comprising a targeting sequence, an exosporium protein, or an exosporium protein fragment that targets the fusion protein to the exosporium of the recombinant *Bacillus cereus* family member can also be genetically inactivated or rendered more susceptible to physical or chemical inactivation by modification of the *Bacillus cereus* family member to comprise a mutation.

Such mutations include knock-out or other inactivating mutations in one or more genes encoding a germination receptor. The germination receptor genes include, for example, GerA, GerB, GerK, GerH, GerI, GerG, GerL, GerQ, GerR, GerS, GerN, GerU, or GerX.

Such mutations also include knock-out or other inactivating mutations in spore cortex lytic enzymes. For example, the spore cortex lytic enzymes SleB and CwJ can be mutated to inactivate spores. Such mutations prevent outgrowth of the spore upon germination and effectively inactivate the spores.

Such mutations further include knock-out or other inactivating mutations of SASP genes (e.g., SASPα, SASPβ, or SASPγ). Such mutations eliminate the UV protection of the spores and render them more susceptible to inactivation by ultraviolet irradiation and other methods.

Such methods also include making knock-out or other inactivating mutations in genes encoding spore coat or cortex proteins (e.g., CotA, CotB, or CotC). Such mutations render the spores more susceptible to inactivation by physical or chemical methods such as exposure to ultraviolet irradiation, gamma irradiation, or treatment with solvents such as bleach, hydrogen peroxide, chloroform, phenol, or acetic acid.

Thus, the present invention relates to a recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member. The recombinant *Bacillus cereus* family member comprises a mutation that partially or completely inactivates spores of the recombinant *Bacillus cereus* family member or renders spores of the recombinant *Bacillus cereus* family more susceptible to physical or chemical inactivation as compared to the same spores that do not comprise the mutation. The mutation comprises a mutation in a gene encoding a germination receptor, a mutation in a gene encoding a spore cortex lytic enzyme, a mutation in a gene encoding a small acid-soluble spore protein (SASP), or a mutation in a gene encoding a spore coat or cortex protein.

The present invention further relates to a recombinant *Bacillus cereus* family member that expresses a fusion protein as described in Section I above. The recombinant *Bacillus cereus* family member comprises a mutation that partially or completely inactivates spores of the recombinant *Bacillus cereus* family member or renders spores of the recombinant *Bacillus cereus* family more susceptible to physical or chemical inactivation as compared to the same spores that do not comprise the mutation.

Any of the recombinant *Bacillus cereus* family members described above in Section V.A that express a protease or a nuclease can also comprise a mutation that partially or completely inactivates spores of the recombinant *Bacillus cereus* family member or renders spores of the recombinant *Bacillus cereus* family more susceptible to physical or chemical inactivation as compared to the same spores that do not comprise the mutation. For example, the mutation can comprise a mutation in a gene encoding a germination receptor, a mutation in a gene encoding a spore cortex lytic enzyme, a mutation in a gene encoding a small acid-soluble spore protein (SASP), or a mutation in a gene encoding a spore coat or cortex protein.

For example, the mutation can comprise a mutation in a gene encoding a germination receptor, such as a knock-out mutation of the gene encoding the germination receptor. The germination receptor can comprise GerA, GerB, GerK, GerH, GerI, GerG, GerL, GerQ, GerR, GerS, GerN, GerU, or GerX.

For example, the mutation can comprise a mutation in a gene encoding a spore cortex lytic enzyme, such as a knock-out mutation of the gene encoding the spore cortex lytic enzyme. The spore cortex lytic enzyme can comprise SleB or CwlJ.

For example, the mutation can comprise a mutation in a gene encoding a SASP, such as a mutation in a SspA gene, a mutation in a SspB gene, a mutation in a SspC gene, a mutation in a SspD gene, a mutation in a SspE gene, a mutation in a SspF gene, a mutation in a SspG gene, a mutation in a SspH gene, a mutation in a SspI gene, a mutation in a SspJ gene, a mutation in a SspK gene, a mutation in a SspL gene, a mutation in a SspM gene, a mutation in a SspN gene, a mutation in a SspO gene, a mutation in a SspP gene, or a combination thereof. The SASP can comprise SASPα, SASPβ, or SASPγ. The spores of the recombinant *Bacillus cereus* family member may be more susceptible to inactivation by ultraviolet irradiation or gamma irradiation as compared to the same spores that do not comprise the mutation in the gene encoding the SASP.

For example, the mutation can comprise a mutation in a gene encoding a spore coat or cortex protein, such as a knock-out mutation of the gene encoding the spore coat or cortex protein. The spore coat or cortex protein can comprise CotA, CotB, or CotC. The spores of the recombinant *Bacillus cereus* family member may be more susceptible to inactivation by ultraviolet irradiation, gamma irradiation or by treatment with bleach, hydrogen peroxide, chloroform, phenol, or acetic acid, as compared to the same spores that do not comprise the mutation in the spore coat or cortex protein, treated under the same conditions.

VI. Recombinant *Bacillus cereus* Family Members that Overexpress Exosporium Enzymes that have Beneficial Effects on Plants or Delay Germination of *Bacillus cereus* Family Member Spores Recombinant *Bacillus cereus* family members that overexpress various exosporium proteins to provide beneficial effects on plants or delay spore germination are also provided.

A recombinant *Bacillus cereus* family member that expresses an exosporium protein is provided, wherein the expression of the exosporium protein is increased as compared to the expression of the exosporium protein in a wild-type *Bacillus cereus* family member under the same conditions. The exosporium protein can comprise an exosporium enzyme, wherein the exosporium enzyme comprises an enzyme involved in nutrient solubilization, an inosine-uridine hydrolase, a protease, an enzyme that catalyzes the degradation of a free radical, an arginase, or an alanine racemase. Alternatively, the exosporium protein can comprise a BclA protein, a BclB protein, a CotE protein a CotO protein, an ExsY protein, an ExsFA/BxpB protein, a CotY protein, an ExsFB protein, an ExsJ protein, an ExsH protein, a YjcA protein, a YjcB protein, a BclC protein, a BxpA protein, a BclE protein, a BetA/BAS3290 protein, an ExsA protein, an ExsK protein, an ExsB protein, a YabG protein, or a Tgl protein.

The exosporium protein is preferably not part of a fusion protein.

Exemplary amino acid sequences for AcpC, InhA1, InhA2, InhA3, SODA1, and SODA2 are provided above in Tables 1 and 2. Exemplary sequences for alanine racemase 1, alanine racemase 2, arginase, IunH1, and IunH2 are provided by the SEQ ID NOs. referenced in Table 6 below.

TABLE 6

Exemplary amino acid sequences for exosporium enzymes

| Protein and Strain | SEQ ID NO. |
|---|---|
| Alanine Racemase 1, *B. anthracis* ΔSterne | 247 |
| Alanine Racemase 2, *Bacillus cereus* F837/78 | 248 |
| Arginase, *Bacillus thuringiensis* pondicheriensis 4BA1 | 249 |
| IunH1, *B. cereus* Str. CI | 250 |
| IunH2, *Bacillus thuringiensis* | 251 |

Overexpression of inosine-uridine hydrolases and alanine racemases hinders the ability of spores to germinate and thereby maintains the spores in a dormant stage and increases the stability of the spores.

The SODA enzymes and arginase degrade free radicals. Spores that overexpress these enzymes have increased resistance to stress caused by free radicals.

Where the exosporium protein comprises an exosporium enzyme, and the exosporium enzyme comprises an enzyme involved in nutrient solubilization, the enzyme involved in nutrient solubilization can comprise an enzyme involved in phosphate solubilization, such as an acid phosphatase (e.g., AcpC). The acid phosphatase can comprise an amino acid sequence having at least 90% identity with SEQ ID NO: 137.

The acid phosphatase can comprise an amino acid sequence having at least 95% identity with SEQ ID NO: 137.

The acid phosphatase can comprise an amino acid sequence having at least 98% identity with SEQ ID NO: 137.

The acid phosphatase can comprise an amino acid sequence having at least 99% identity with SEQ ID NO: 137.

The acid phosphatase can comprise an amino acid sequence having 100% identity with SEQ ID NO: 137.

Where the exosporium protein comprises an exosporium enzyme, and the exosporium enzyme comprises an inosine-uridine hydrolase, the inosine-uridine hydrolase can comprise IunH1 or IunH2. The inosine-uridine hydrolase can comprise an amino acid sequence having at least 85% identity with SEQ ID NO: 250 or 251.

The inosine-uridine hydrolase can comprise an amino acid sequence having at least 90% identity with SEQ ID NO: 250 or 251.

The inosine-uridine hydrolase can comprise an amino acid sequence having at least 95% identity with SEQ ID NO: 250 or 251.

The inosine-uridine hydrolase can comprise an amino acid sequence having at least 98% identity with SEQ ID NO: 250 or 251.

The inosine-uridine hydrolase can comprise an amino acid sequence having at least 99% identity with SEQ ID NO: 250 or 251.

The inosine-uridine hydrolase can comprise an amino acid sequence having 100% identity with SEQ ID NO: 250 or 251.

Where the exosporium protein comprises an exosporium enzyme, and the exosporium enzyme comprises a protease, the protease can be a metalloprotease (e.g., InhA1, InhA2, or InhA3). The metalloprotease can comprise an amino acid sequence having at least 85% identity with SEQ ID NO: 114, 121, 122, 129, 130, or 138.

The metalloprotease can comprise an amino acid sequence having at least 85% identity with SEQ ID NO: 114, 121, 122, 129, 130, or 138.

The metalloprotease can comprise an amino acid sequence having at least 90% identity with SEQ ID NO: 114, 121, 122, 129, 130, or 138.

The metalloprotease can comprise an amino acid sequence having at least 95% identity with SEQ ID NO: 114, 121, 122, 129, 130, or 138.

The metalloprotease can comprise an amino acid sequence having at least 98% identity with SEQ ID NO: 114, 121, 122, 129, 130, or 138.

The metalloprotease can comprise an amino acid sequence having at least 99% identity with SEQ ID NO: 114, 121, 122, 129, 130, or 138.

The metalloprotease can comprise an amino acid sequence having 100% identity with SEQ ID NO: 114, 121, 122, 129, 130, or 138.

Where the exosporium protein comprises an exosporium enzyme, and the exosporium enzyme comprises an enzyme that catalyzes the degradation of a free radical, the enzyme that catalyzes the degradation of a free radical can comprise a superoxide dismutase (e.g., superoxide dismutase 1 (SODA1) or superoxide dismutase 2 (SODA2)). The superoxide dismutase can comprise an amino acid sequence having at least 85% identity with SEQ ID NO: 155 or 156.

The superoxide dismutase can comprise an amino acid sequence having at least 90% identity with SEQ ID NO: 155 or 156.

The superoxide dismutase can comprise an amino acid sequence having at least 95% identity with SEQ ID NO: 155 or 156.

The superoxide dismutase can comprise an amino acid sequence having at least 98% identity with SEQ ID NO: 155 or 156.

The superoxide dismutase can comprise an amino acid sequence having at least 99% identity with SEQ ID NO: 155 or 156.

The superoxide dismutase can comprise an amino acid sequence having 100% identity with SEQ ID NO: 155 or 156.

Where the exosporium protein comprises an exosporium enzyme, and the exosporium enzyme comprises an arginase, the arginase can comprise a *Bacillus thuringiensis* arginase. The arginase can comprise an amino acid sequence having at least 85% identity with SEQ ID NO: 249.

The arginase can comprise an amino acid sequence having at least 90% identity with SEQ ID NO: 249.

The arginase can comprise an amino acid sequence having at least 95% identity with SEQ ID NO: 249.

The arginase can comprise an amino acid sequence having at least 98% identity with SEQ ID NO: 249.

The arginase can comprise an amino acid sequence having at least 99% identity with SEQ ID NO: 249.

The arginase can comprise an amino acid sequence having 100% identity with SEQ ID NO: 249.

Where the exosporium protein comprises an exosporium enzyme, and the exosporium enzyme comprises an alanine racemase, the alanine racemase can comprise alanine racemase 1 (ALR1) or alanine racemase 2 (ALR2). The alanine racemase can comprise an amino acid sequence having at least 85% identity with SEQ ID NO: 247 or 248.

The alanine racemase can comprise an amino acid sequence having at least 90% identity with SEQ ID NO: 247 or 248.

The alanine racemase can comprise an amino acid sequence having at least 95% identity with SEQ ID NO: 247 or 248.

The alanine racemase can comprise an amino acid sequence having at least 98% identity with SEQ ID NO: 247 or 248.

The alanine racemase can comprise an amino acid sequence having at least 99% identity with SEQ ID NO: 247 or 248.

The alanine racemase can comprise an amino acid sequence having 100% identity with SEQ ID NO: 247 or 248.

The exosporium protein can comprise a BclA protein, a BclB protein, a CotE protein a CotO protein, an ExsY protein, an ExsFA/BxpB protein, a CotY protein, an ExsFB protein, an ExsJ protein, an ExsH protein, a YjcA protein, a YjcB protein, a BclC protein, a BxpA protein, a BclE protein, a BetA/BAS3290 protein, an ExsA protein, an ExsK protein, an ExsB protein, a YabG protein, or a Tgl protein. The exosporium protein preferably comprises a BclA protein, a BclB protein, a CotE protein, or a CotO protein. Exemplary amino acid sequences for these exosporium proteins can be found in Table 2 above.

The exosporium protein can comprise a BclA protein. The BclA protein can comprise an amino acid sequence having at least 85% identity with SEQ ID NO: 141 or 142.

The BclA protein can comprise an amino acid sequence having at least 90% identity with SEQ ID NO: 141 or 142.

The BclA protein can comprise an amino acid sequence having at least 95% identity with SEQ ID NO: 141 or 142.

The BclA protein can comprise an amino acid sequence having at least 98% identity with SEQ ID NO: 141 or 142.

The BclA protein can comprise an amino acid sequence having at least 99% identity with SEQ ID NO: 141 or 142.

The BclA protein can comprise an amino acid sequence having 100% identity with SEQ ID NO: 141 or 142.

The exosporium protein can comprise a BclB protein. The BclB protein can comprise an amino acid sequence having at least 85% identity with SEQ ID NO: 143 or 144.

The BclB protein can comprise an amino acid sequence having at least 90% identity with SEQ ID NO: 143 or 144.

The BclB protein can comprise an amino acid sequence having at least 95% identity with SEQ ID NO: 143 or 144.

The BclB protein can comprise an amino acid sequence having at least 98% identity with SEQ ID NO: 143 or 144.

The BclB protein can comprise an amino acid sequence having at least 99% identity with SEQ ID NO: 143 or 144.

The BclB protein can comprise an amino acid sequence having 100% identity with SEQ ID NO: 143 or 144.

The exosporium protein can comprise a CotE protein. The CotE protein can comprise an amino acid sequence having at least 85% identity with SEQ ID NO: 149.

The CotE protein can comprise an amino acid sequence having at least 90% identity with SEQ ID NO: 149.

The CotE protein can comprise an amino acid sequence having at least 95% identity with SEQ ID NO: 149.

The CotE protein can comprise an amino acid sequence having at least 98% identity with SEQ ID NO: 149.

The CotE protein can comprise an amino acid sequence having at least 99% identity with SEQ ID NO: 149.

The CotE protein can comprise an amino acid sequence having 100% identity with SEQ ID NO: 149.

The exosporium protein can comprise a CotO protein. The CotO protein can comprise an amino acid sequence having at least 85% identity with SEQ ID NO: 126.

The CotO protein can comprise an amino acid sequence having at least 90% identity with SEQ ID NO: 126.

The CotO protein can comprise an amino acid sequence having at least 95% identity with SEQ ID NO: 126.

The CotO protein can comprise an amino acid sequence having at least 98% identity with SEQ ID NO: 126.

The CotO protein can comprise an amino acid sequence having at least 99% identity with SEQ ID NO: 126.

The CotO protein can comprise an amino acid sequence having at least 100% identity with SEQ ID NO: 126.

The exosporium protein can comprise an ExsY protein. The ExsY protein can comprise an amino acid sequence having at least 85%, at least 90%, at least 95%, at least 98%, at least 99%, or 100% identity with SEQ ID NO: 123.

The exosporium protein can comprise an ExsFA/BxpB protein. The ExsFA/BxpB protein can comprise an amino acid sequence having at least 85%, at least 90%, at least 95%, at least 98%, at least 99%, or 100% identity with SEQ ID NO: 124.

The exosporium protein can comprise a CotY protein. The CotY protein can comprise an amino acid sequence having at least 85%, at least 90%, at least 95%, at least 98%, at least 99%, or 100% identity with SEQ ID NO: 125.

The exosporium protein can comprise an ExsFB protein. The ExsFB protein can comprise an amino acid sequence having at least 85%, at least 90%, at least 95%, at least 98%, at least 99%, or 100% identity with SEQ ID NO: 127 or 128.

The exosporium protein can comprise an ExsJ protein. The ExJ protein can comprise an amino acid sequence having at least 85%, at least 90%, at least 95%, at least 98%, at least 99%, or 100% identity with SEQ ID NO: 131.

The exosporium protein can comprise an ExsH protein. The ExsH protein can comprise an amino acid sequence having at least 85%, at least 90%, at least 95%, at least 98%, at least 99%, or 100% identity with SEQ ID NO: 132.

The exosporium protein can comprise a YjcA protein. The YjcA protein can comprise an amino acid sequence having at least 85%, at least 90%, at least 95%, at least 98%, at least 99%, or 100% identity with SEQ ID NO: 133.

The exosporium protein can comprise a YjcB protein. The YjcB protein can comprise an amino acid sequence having at least 85%, at least 90%, at least 95%, at least 98%, at least 99%, or 100% identity with SEQ ID NO: 134 or 135.

The exosporium protein can comprise a BclC protein. The BclC protein can comprise an amino acid sequence having at least 85%, at least 90%, at least 95%, at least 98%, at least 99%, or 100% with SEQ ID NO: 136.

The exosporium protein can comprise a BxpA protein. The BxpA protein can comprise an amino acid sequence having at least 85%, at least 90%, at least 95%, at least 98%, at least 99%, or 100% with SEQ ID NO: 145.

The exosporium protein can comprise a BclE protein. The BclE protein can comprise an amino acid sequence having at least 85%, at least 90%, at least 95%, at least 98%, at least 99%, or 100% identity with SEQ ID NO: 146 or 147.

The exosporium protein can comprise a BetA/BAS3290 protein. The BetA/BAS3290 protein can comprise an amino acid sequence having at least 85%, at least 90%, at least 95%, at least 98%, at least 99%, or 100% identity with SEQ ID NO: 148.

The exosporium protein can comprise an ExsA protein. The ExsA protein can comprise an amino acid sequence having at least 85%, at least 90%, at least 95%, at least 98%, at least 99%, or 100% identity with SEQ ID NO: 150.

The exosporium protein can comprise an ExsK protein. The ExsK protein can comprise an amino acid sequence having at least 85%, at least 90%, at least 95%, at least 98%, at least 99%, or 100% identity with SEQ ID NO: 151.

The exosporium protein can comprise an ExsB protein. The ExsB protein can comprise an amino acid sequence having at least 85%, at least 90%, at least 95%, at least 98%, at least 99%, or 100% identity with SEQ ID NO: 152.

The exosporium protein can comprise a YabG protein. The YabG protein can comprise an amino acid sequence having at least 85%, at least 90%, at least 95%, at least 98%, at least 99%, or 100% identity with SEQ ID NO: 153.

The exosporium protein can comprise a Tgl protein. The Tjl protein can comprise an amino acid sequence having at least 85%, at least 90%, at least 95%, at least 98%, at least 99%, or 100% identity with SEQ ID NO: 156.

The recombinant *Bacillus cereus* family member can also express a fusion protein comprising at least one protein or peptide of interest and a targeting sequence, exosporium protein, or exosporium protein fragment that targets the fusion protein to the exosporium of the recombinant *Bacillus cereus* family member.

VII. Expression of Fusion Proteins in Endophytic *Bacillus cereus* Family Members, in *Bacillus cereus* Family Members Capable of Degrading Herbicides or Pesticides, or in Probiotic *Bacillus cereus* Family Members Any of the fusion proteins comprising a protein or peptide of interest and a targeting sequence, an exosporium protein, or an exosporium protein fragment that targets the fusion protein to the exosporium of a recombinant *Bacillus cereus* family member, can be expressed an endophytic *Bacillus cereus* family member, a strain of bacteria that is capable of degrading an herbicide or a pesticide, or a probiotic strain of bacteria.

The expression of the fusion proteins in an endophytic strain of bacteria provides the ability to deliver the protein or peptide of interest into the plant itself. The endophytic strains can be delivered to plants using various methods, e.g., the endophytic strains can be delivered via seed treatment, treatment of the plant growth medium (e.g., soil), irrigation, application to the plant itself (e.g., foliar application to the aerial portions of a plant). Once inside the plant, the bacteria multiply and colonize the internal tissues of the plant.

As is explained further hereinbelow, probiotic strains of bacteria that express of the fusion proteins, and in particular strains that are both probiotic and endophytic that express the fusion proteins, are useful in methods for delivering the proteins or peptides of interest (e.g., enzymes) to animals.

While any of the fusion proteins comprising a protein or peptide of interest and a targeting sequence, an exosporium protein, or an exosporium protein fragment that targets the fusion protein to the exosporium of a recombinant *Bacillus cereus* family member can be expressed in *Bacillus cereus* family member strain that is capable of degrading an herbicide or a pesticide, as explained further hereinbelow, these strains are particularly useful in methods for decontamination of an environment contaminated with an herbicide and/or a pesticide.

The present invention therefore relates to a recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member, wherein the recombinant *Bacillus cereus* family member comprises an endophytic strain of bacteria, a strain of bacteria that is capable of degrading an herbicide or a pesticide, or a probiotic strain of bacteria.

The endophytic strain of bacteria can comprise *Bacillus cereus* family member EE349, *Bacillus cereus* family member EE439, *Bacillus thuringiensis* EE417, *Bacillus cereus* EE444, or *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363.

For example, the endophytic strain of bacteria can comprise *Bacillus cereus* family member EE439, *Bacillus thuringiensis* EE417, *Bacillus cereus* EE444, or *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363.

The strain of bacteria that is capable of degrading an herbicide or a pesticide can comprise *Bacillus cereus* family member EE349, *Bacillus cereus* family member EE-B00377, *Bacillus pseudomycoides* EE-B00366, or *Bacillus mycoides* EE-B00363.

The probiotic strain of bacteria can comprise *Bacillus cereus* family member EE349, *Bacillus cereus* family member EE439, *Bacillus thuringiensis* EE417, or *Bacillus cereus* EE444.

The present invention further relates to a recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member, wherein the recombinant *Bacillus cereus* family member comprises an endophytic strain of bacteria, and the fusion protein comprises any of the fusion proteins described in Section I above.

VIII. Targeting Sequences, Exosporium Proteins, and Exosporium Protein Fragments for Use in: (a) Recombinant *Bacillus cereus* Family Members that Express a Fusion Protein and Co-Overexpress a Modulator Protein; (b) Recombinant *Bacillus cereus* Family Members that Comprise a Mutation or Other Genetic Alteration that Allows for Collection of Free Exosporium; (c) Recombinant *Bacillus cereus* Family Members that Overexpress a Protease or a Nuclease; (d) Recombinant *Bacillus cereus* Family Members that Express a Fusion Protein and Overexpress an Exosporium Protein that has Beneficial Effects on Plants; or (e) or Endophytic Recombinant *Bacillus cereus* Family Members that Express Fusion Proteins Any of the targeting sequences, exosporium proteins, or exosporium proteins described in this section can be in any of the fusion proteins in:

(a) any of the recombinant *Bacillus cereus* family members that express a fusion protein and overexpress a modulator protein, described in Section II above;

(b) any of the recombinant *Bacillus cereus* family members that express a fusion protein and comprise a mutation or other genetic alteration that allows for collection of free exosporium, described in Section IV above;

(c) any of the recombinant *Bacillus cereus* family members that expresses a fusion protein and overexpress a protease or a nuclease, described above in Section V.A;

(d) any of the recombinant *Bacillus cereus* family members that express a fusion protein and overexpress an exosporium protein that has beneficial effects on plants, described in Section VI above; and (e) any of the endophytic recombinant *Bacillus cereus* family members that express a fusion protein, described in Section VII above.

In any of the recombinant *Bacillus cereus* members (a) through (e), the targeting sequence, exosporium protein, or exosporium protein fragment can comprise: (1) a targeting sequence comprising an amino acid sequence having at least about 43% identity with amino acids 20-35 of SEQ ID NO: 1, wherein the identity with amino acids 25-35 is at least about 54%; (2) a targeting sequence comprising amino acids 1-35 of SEQ ID NO: 1; (3) a targeting sequence comprising amino acids 20-35 of SEQ ID NO: 1; (4) a targeting sequence comprising SEQ ID NO: 1; (5) an exosporium protein comprising an amino acid sequence having at least 85% identity with SEQ ID NO: 2; (6) a targeting sequence comprising amino acids 2-35 of SEQ ID NO: 1; (7) a targeting sequence comprising amino acids 5-35 of SEQ ID NO: 1; (8) a targeting sequence comprising amino acids 8-35 of SEQ ID NO: 1; (9) a targeting sequence comprising amino acids 10-35 of SEQ ID NO: 1; (10) a targeting sequence comprising amino acids 15-3 5 of SEQ ID NO: 1; (11) a targeting sequence comprising amino acids 1-27 of SEQ ID NO: 3; (12) a targeting sequence comprising amino acids 12-27 of SEQ ID NO: 3; (13) a targeting sequence comprising SEQ ID NO: 3; (14) an exosporium protein comprising an amino acid sequence having at least 85% identity with SEQ ID NO: 4; (15) a targeting sequence comprising amino acids 2-27 of SEQ ID NO: 3; (16) a targeting sequence comprising amino acids 5-27 of SEQ ID NO: 3; (17) a targeting sequence comprising amino acids 8-27 of SEQ ID NO: 3; (18) a targeting sequence comprising amino acids 10-27 of SEQ ID NO: 3; (19) a targeting sequence comprising amino acids 1-38 of SEQ ID NO: 5; (20) a targeting sequence comprising amino acids 23-38 of SEQ ID NO: 5; (21) a targeting sequence comprising SEQ ID NO: 5; (22) an exosporium protein comprising an amino acid sequence having at least 85% identity with SEQ ID NO: 6; (23) a targeting sequence comprising amino acids 2-38 of SEQ ID NO: 5; (24) a targeting sequence comprising amino acids 5-38 of SEQ ID NO: 5; (25) a targeting sequence comprising amino acids 8-38 of SEQ ID NO: 5; (26) a targeting sequence comprising amino acids 10-38 of SEQ ID NO: 5; (27) a targeting sequence comprising amino acids 15-38 of SEQ ID NO: 5; (28) a targeting sequence comprising amino acids 20-38 of SEQ ID NO: 5; (29) a targeting sequence comprising amino acids 1-28 of SEQ ID NO: 7; (30) a targeting sequence comprising amino acids 13-28 of SEQ ID NO: 7; (31) a targeting sequence comprising SEQ ID NO: 7; (32) an exosporium protein comprising an amino acid sequence having at least 85% identity with SEQ ID NO: 8; (33) a targeting sequence comprising amino acids 2-28 of SEQ ID NO: 7; (34) a targeting sequence comprising amino acids 5-28 of SEQ ID NO: 7; (35) a targeting sequence comprising amino acids 8-28 of SEQ ID NO: 7; (36) a targeting sequence comprising amino acids 10-28 of SEQ ID NO: 7; (37) a targeting sequence comprising amino acids 1-24 of SEQ ID NO: 9; (38) a targeting sequence comprising amino acids 9-24 of SEQ ID NO: 9; (39) a targeting sequence comprising SEQ ID NO: 9; (40) an exosporium protein comprising an amino acid sequence having at least 85% identity with SEQ ID NO: 10; (41) a targeting sequence comprising amino acids 2-24 of SEQ ID NO: 9; (42) a targeting sequence comprising amino acids 5-24 of SEQ ID NO: 9; (43) a targeting sequence comprising amino acids 8-24 of SEQ ID NO: 9; (44) a targeting sequence comprising amino acids 1-33 of SEQ ID NO: 11; (45) a targeting sequence comprising amino acids 18-33 of SEQ ID NO: 11; (46) a targeting sequence comprising SEQ ID NO: 11; (47) an exosporium protein comprising an amino acid sequence having at least 85% identity with SEQ ID NO: 12; (48) a targeting sequence comprising amino acids 2-33 of SEQ ID NO: 11; (49) a targeting sequence comprising amino acids 5-33 of SEQ ID NO: 11; (50) a targeting sequence comprising amino acids 8-33 of SEQ ID NO: 11; (51) a targeting sequence comprising amino acids 10-33 of SEQ ID NO: 11; (52) a targeting sequence comprising amino acids 15-33 of SEQ ID NO: 11; (53) a targeting sequence comprising amino acids 1-33 of SEQ ID NO: 13; (54) a targeting sequence comprising amino acids 18-33 of SEQ ID NO: 13; (55) a targeting sequence comprising SEQ ID NO:13; (56) an exosporium protein comprising an amino acid sequence having at least 85% identity with SEQ ID NO: 14; (57) a targeting sequence comprising amino acids 2-33 of SEQ ID NO: 13; (58) a targeting sequence comprising amino acids 5-33 of SEQ ID NO: 13; (59) a targeting sequence comprising amino acids 8-33 of SEQ ID NO: 13; (60) a targeting sequence comprising amino acids 10-33 of SEQ ID NO: 13; (61) a targeting sequence comprising amino acids 15-33 of SEQ ID NO: 13; (62) a targeting sequence comprising amino acids 1-43 of SEQ ID NO: 15; (63) a targeting sequence comprising amino acids 28-43 of SEQ ID NO: 15; (64) a targeting sequence comprising SEQ ID NO: 15; (65) an exosporium protein comprising an amino acid sequence having at least 85% identity with SEQ ID NO: 16; (66) a targeting sequence comprising amino acids 2-43 of SEQ ID NO: 15; (67) a targeting sequence comprising amino acids 5-43 of SEQ ID NO: 15; (68) a targeting sequence comprising amino acids 8-43 of SEQ ID NO: 15; (69) a targeting sequence comprising amino acids 10-43 of SEQ ID NO: 15; (70) a targeting sequence comprising amino acids 15-43 of SEQ ID NO: 15; (71) a targeting sequence comprising amino acids 20-43 of SEQ ID NO: 15; (72) a targeting sequence comprising amino acids 25-43 of SEQ ID NO: 15; (73) a targeting sequence comprising amino acids 1-27 of SEQ ID NO: 17; (74) a targeting sequence comprising amino acids 12-27 of SEQ ID NO: 17; (75) a targeting sequence comprising SEQ ID NO: 17; (76) an exosporium protein comprising an amino acid sequence having at least 85% identity with SEQ ID NO: 18; (77) a targeting sequence comprising amino acids 2-27 of SEQ ID NO: 17; (78) a targeting sequence comprising amino acids 5-27 of SEQ ID NO: 17; (79) a targeting sequence comprising amino acids 8-27 of SEQ ID NO: 17; (80) a targeting sequence comprising amino acids 10-27 of SEQ ID NO: 17; (81) a targeting sequence comprising amino acids 1-33 of SEQ ID NO: 19; (82) a targeting sequence comprising amino acids 18-33 of SEQ ID NO: 19; (83) a targeting sequence comprising SEQ ID NO:19; (84) an exosporium protein comprising an amino acid sequence having at least 85% identity with SEQ ID NO:20; (85) a targeting sequence comprising amino acids 2-33 of SEQ ID NO: 19; (86) a targeting sequence comprising amino acids 5-33 of SEQ ID NO: 19; (87) a targeting sequence comprising amino acids 8-33 of SEQ ID NO: 19; (88) a targeting sequence comprising amino acids 10-33 of SEQ ID NO: 19; (89) a targeting sequence comprising amino acids 15-33 of SEQ ID NO: 19; (90) a targeting sequence comprising amino acids 1-33 of SEQ ID NO: 21; (91) a targeting sequence comprising amino acids 18-33 of SEQ ID NO: 21; (92) a targeting sequence comprising SEQ ID NO:21; (93) an exosporium protein comprising an amino acid sequence having at least 85% identity with SEQ ID NO:22; (94) a targeting sequence comprising amino acids 2-33 of SEQ ID NO: 21; (95) a targeting sequence comprising amino acids 5-33 of SEQ ID NO: 21; (96) a targeting sequence comprising amino acids 8-33 of SEQ ID NO: 21; (97) a targeting sequence comprising amino acids 10-33 of SEQ ID NO: 21; (98) a targeting sequence comprising amino acids 15-33 of SEQ ID NO: 21; (99) a targeting sequence comprising amino acids 1-24 of SEQ ID NO: 23; (100) a targeting sequence comprising amino acids 9-24 of SEQ ID NO: 23; (101) a targeting sequence comprising SEQ ID NO:23; (102) an exosporium protein comprising an amino acid sequence having at least 85% identity with SEQ ID NO:24; (103) a targeting sequence comprising amino acids 2-24 of SEQ ID NO:23; (104) a targeting sequence comprising amino acids 5-24 of SEQ ID NO: 23; (105) a targeting sequence comprising amino acids 8-24 of SEQ ID NO: 23; (106) a targeting sequence comprising amino acids 1-24 of SEQ ID NO: 25; (107) a targeting sequence comprising amino acids 9-24 of SEQ ID NO: 25; (108) a targeting sequence comprising SEQ ID NO:25; (109) an exosporium protein comprising an amino acid sequence having at least 85% identity with SEQ ID NO:26; (110) a targeting sequence comprising amino acids 2-24 of SEQ ID NO: 25; (111) a targeting sequence comprising amino acids 5-24 of SEQ ID NO: 25; (112) a targeting sequence comprising amino acids 8-24 of SEQ ID NO: 25; (113) a targeting sequence comprising amino acids 1-30 of SEQ ID NO: 27; (114) a targeting sequence comprising amino acids 15-30 of SEQ ID NO: 27; (115) a targeting sequence comprising SEQ ID NO:27; (116) an exosporium protein comprising an amino acid sequence having at least 85% identity with SEQ ID NO:28; (117) a targeting sequence comprising amino acids 2-30 of SEQ ID NO: 27; (118) a targeting sequence comprising amino acids 5-30 of SEQ ID NO: 27; (119) a targeting sequence comprising amino acids 8-30 of SEQ ID NO: 27; (120) a targeting sequence comprising amino acids 10-30 of SEQ ID NO: 27; (121) a targeting sequence comprising amino acids 1-33 of SEQ ID NO: 29; (122) a targeting sequence comprising amino acids 18-33 of SEQ ID NO: 29; (123) a targeting sequence comprising SEQ ID NO:29; (124) an exosporium protein comprising an amino acid sequence having at least 85% identity with SEQ ID NO:30; (125) a targeting sequence comprising amino acids 2-33 of SEQ ID NO: 29; (126) a targeting sequence comprising amino acids 5-33 of SEQ ID NO: 29; (127) a targeting sequence comprising amino acids 8-33 of SEQ ID NO: 29; (128) a targeting sequence comprising amino acids 10-33 of SEQ ID NO: 29; (129) a targeting sequence comprising amino acids 15-33 of SEQ ID NO: 29; (130) a targeting sequence comprising amino acids 1-24 of SEQ ID NO: 31; (131) a targeting sequence comprising amino acids 9-24 of SEQ ID NO: 31; (132) a targeting sequence comprising SEQ ID NO:31; (133) an exosporium protein comprising an amino acid sequence having at least 85% identity with SEQ ID NO:32; (134) a targeting sequence comprising amino acids 2-24 of SEQ ID NO: 31; (135) a targeting sequence comprising amino acids 5-24 of SEQ ID NO: 31; (136) a targeting sequence comprising amino acids 8-24 of SEQ ID NO: 31; (137) a targeting sequence comprising amino acids 1-15 of SEQ ID NO: 33; (138) a targeting sequence comprising SEQ ID NO:33; (139) an exosporium protein comprising an amino acid sequence having at least 85% identity with SEQ ID NO:34; (140) a targeting sequence comprising amino acids 1-16 of SEQ ID NO: 35; (141) a targeting sequence comprising SEQ ID NO:35; (142) an exosporium protein comprising an amino acid sequence having at least 85% identity with SEQ ID NO:36; (143) a targeting sequence comprising amino acids 1-29 of SEQ ID NO:43; (144) a targeting sequence comprising amino acids 14-29 of SEQ ID NO: 43; (145) a targeting sequence comprising SEQ ID NO: 43; (146) an exosporium protein comprising an amino acid sequence having at least 85% identity with SEQ ID NO: 44; (147) a targeting sequence comprising amino acids 2-29 of SEQ ID NO: 43; (148) a targeting sequence comprising amino acids 5-29 of SEQ ID NO: 43; (149) a targeting sequence comprising amino acids 8-29 of SEQ ID NO: 43; (150) a targeting sequence comprising amino acids 10-29 of SEQ ID NO: 43; (151) a targeting sequence comprising amino acids 1-35 of SEQ ID NO: 45; (152) a targeting sequence comprising amino acids 20-35 of SEQ ID NO: 45; (153) a targeting sequence comprising SEQ ID NO: 45; (154) an exosporium protein comprising an amino acid sequence having at least 85% identity with SEQ ID NO: 46; (155) a targeting sequence comprising amino acids 2-35 of SEQ ID NO: 45; (156) a targeting sequence comprising amino acids 5-35 of SEQ ID NO: 45; (157) a targeting sequence comprising amino acids 8-35 of SEQ ID NO: 45; (158) a targeting sequence comprising amino acids 10-35 of SEQ ID NO: 45; (159) a targeting sequence comprising amino acids 15-35 of SEQ ID NO: 45; (160) a targeting sequence comprising amino acids 1-43 of SEQ ID NO: 47; (161) a targeting sequence comprising amino acids 28-43 of SEQ ID NO: 47; (162) a targeting sequence comprising SEQ ID NO: 47; (163) an exosporium protein comprising an amino acid sequence having at least 85% identity with SEQ ID NO: 48; (164) a targeting sequence comprising amino acids 2-43 of SEQ ID NO: 47; (165) a targeting sequence comprising amino acids 5-43 of SEQ ID NO: 47; (166) a targeting sequence comprising amino acids 8-43 of SEQ ID NO: 47; (167) a targeting sequence comprising amino acids 10-43 of SEQ ID NO: 47; (168) a targeting sequence comprising amino acids 15-43 of SEQ ID NO: 47; (169) a targeting sequence comprising amino acids 20-43 of SEQ ID NO: 47; (170) a targeting sequence comprising amino acids 25-43 of SEQ ID NO: 47; (171) a targeting sequence comprising amino acids 1-32 of SEQ ID NO: 49; (172) a targeting sequence comprising amino acids 17-32 of SEQ ID NO: 49; (173) a targeting sequence comprising SEQ ID NO:

49; (174) an exosporium protein comprising an amino acid sequence having at least 85% identity with SEQ ID NO: 50; (175) a targeting sequence comprising amino acids 2-32 of SEQ ID NO: 49; (176) a targeting sequence comprising amino acids 5-32 of SEQ ID NO: 49; (177) a targeting sequence comprising amino acids 8-32 of SEQ ID NO: 49; (178) a targeting sequence comprising amino acids 10-32 of SEQ ID NO: 49; (179) a targeting sequence comprising amino acids 15-32 of SEQ ID NO: 49; (180) a targeting sequence comprising amino acids 1-33 of SEQ ID NO: 51; (181) a targeting sequence comprising amino acids 18-33 of SEQ ID NO: 51; (182) a targeting sequence comprising SEQ ID NO: 51; (183) an exosporium protein comprising an amino acid sequence having at least 85% identity with SEQ ID NO: 52; (184) a targeting sequence comprising amino acids 2-33 of SEQ ID NO: 51; (185) a targeting sequence comprising amino acids 5-33 of SEQ ID NO: 51; (186) a targeting sequence comprising amino acids 8-33 of SEQ ID NO: 51; (187) a targeting sequence comprising amino acids 10-33 of SEQ ID NO: 51; (188) a targeting sequence comprising amino acids 15-33 of SEQ ID NO: 51; (189) a targeting sequence comprising amino acids 1-33 of SEQ ID NO: 53; (190) a targeting sequence comprising amino acids 18-33 of SEQ ID NO: 53; (191) a targeting sequence comprising SEQ ID NO: 53; (192) an exosporium protein comprising an amino acid sequence having at least 85% identity with SEQ ID NO: 54; (193) a targeting sequence comprising amino acids 2-33 of SEQ ID NO: 53; (194) a targeting sequence comprising amino acids 5-33 of SEQ ID NO: 53; (195) a targeting sequence comprising amino acids 8-33 of SEQ ID NO: 53; (196) a targeting sequence comprising amino acids 10-33 of SEQ ID NO: 53; (197) a targeting sequence comprising amino acids 15-33 of SEQ ID NO: 53; (198) a targeting sequence comprising amino acids 1-30 of SEQ ID NO: 55; (199) a targeting sequence comprising amino acids 15-30 of SEQ ID NO: 55; (200) a targeting sequence comprising SEQ ID NO: 55; (201) an exosporium protein comprising an amino acid sequence having at least 85% identity with SEQ ID NO: 56; (202) a targeting sequence comprising amino acids 2-30 of SEQ ID NO: 55; (203) a targeting sequence comprising amino acids 5-30 of SEQ ID NO: 55; (204) a targeting sequence comprising amino acids 8-30 of SEQ ID NO: 55; (205) a targeting sequence comprising amino acids 10-30 of SEQ ID NO: 55; (206) a targeting sequence comprising amino acids 1-130 of SEQ ID NO: 57; (207) a targeting sequence comprising amino acids 115-130 of SEQ ID NO: 57; (208) a targeting sequence comprising SEQ ID NO: 57; (209) an exosporium protein comprising an amino acid sequence having at least 85% identity with SEQ ID NO: 58; (210) a targeting sequence comprising amino acids 2-130 of SEQ ID NO: 57; (211) a targeting sequence comprising amino acids 5-130 of SEQ ID NO: 57; (212) a targeting sequence comprising amino acids 10-130 of SEQ ID NO: 57; (213) a targeting sequence comprising amino acids 20-130 of SEQ ID NO: 57; (214) a targeting sequence comprising amino acids 30-130 of SEQ ID NO: 57; (215) a targeting sequence comprising amino acids 40-130 of SEQ ID NO: 57; (216) a targeting sequence comprising amino acids 50-130 of SEQ ID NO: 57; (217) a targeting sequence comprising amino acids 60-130 of SEQ ID NO: 57; (218) a targeting sequence comprising amino acids 70-130 of SEQ ID NO: 57; (219) a targeting sequence comprising amino acids 80-130 of SEQ ID NO: 57; (220) a targeting sequence comprising amino acids 90-130 of SEQ ID NO: 57; (221) a targeting sequence comprising amino acids 100-130 of SEQ ID NO: 57; (222) a targeting sequence comprising amino acids 110-130 of SEQ ID NO: 57; (223) an exosporium protein fragment comprising an amino acid sequence having at least 85% identity with SEQ ID NO: 95; (224) a targeting sequence comprising SEQ ID NO: 96; (225) a targeting sequence comprising SEQ ID NO: 97; (226) a targeting sequence comprising SEQ ID NO: 98; (227) a targeting sequence comprising SEQ ID NO: 99; (228) a targeting sequence comprising SEQ ID NO: 100; (229) a targeting sequence comprising SEQ ID NO: 101; (230) a targeting sequence comprising SEQ ID NO: 102; (231) a targeting sequence comprising SEQ ID NO: 103; (232) a targeting sequence comprising SEQ ID NO: 104; (233) a targeting sequence comprising SEQ ID NO: 105; (234) a targeting sequence comprising SEQ ID NO: 106; (235) an exosporium protein comprising an amino acid sequence having at least 85% identity with SEQ ID NO: 108; (236) an exosporium protein comprising an amino acid sequence having at least 85% identity with SEQ ID NO: 109; (237) an exosporium protein comprising an amino acid sequence having at least 85% identity with SEQ ID NO: 110; (238) an exosporium protein comprising an amino acid sequence having at least 85% identity with SEQ ID NO: 111; (239) an exosporium protein comprising an amino acid sequence having at least 85% identity with SEQ ID NO: 112; (240) an exosporium protein comprising an amino acid sequence having at least 85% identity with SEQ ID NO: 113; (241) an exosporium protein comprising an amino acid sequence having at least 85% identity with SEQ ID NO: 114; (242) an exosporium protein comprising an amino acid sequence having at least 85% identity with SEQ ID NO: 115; (243) an exosporium protein comprising an amino acid sequence having at least 85% identity with SEQ ID NO: 116; (244) an exosporium protein comprising an amino acid sequence having at least 85% identity with SEQ ID NO: 117; (245) an exosporium protein comprising an amino acid sequence having at least 85% identity with SEQ ID NO: 118; (246) an exosporium protein comprising an amino acid sequence having at least 85% identity with SEQ ID NO: 119; (247) an exosporium protein comprising an amino acid sequence having at least 85% identity with SEQ ID NO: 120; (248) an exosporium protein comprising an amino acid sequence having at least 85% identity with SEQ ID NO: 121; (249) a targeting sequence comprising amino acids 22-31 of SEQ ID NO: 1; (250) a targeting sequence comprising amino acids 22-33 of SEQ ID NO: 1; (251) a targeting sequence comprising amino acids 20-31 of SEQ ID NO: 1; (252) a targeting sequence comprising amino acids 14-23 of SEQ ID NO: 3; (253) a targeting sequence comprising amino acids 14-25 of SEQ ID NO: 3; (254) a targeting sequence comprising amino acids 12-23 of SEQ ID NO: 3; (255) a targeting sequence comprising amino acids 1-30 of SEQ ID NO: 59; (256) a targeting sequence comprising SEQ ID NO: 59; (257) an exosporium protein comprising an amino acid sequence having at least 85% identity with SEQ ID NO: 60; (258) a targeting sequence comprising amino acids 2-30 of SEQ ID NO: 59; (259) a targeting sequence comprising amino acids 4-30 of SEQ ID NO: 59; (260) a targeting sequence comprising amino acids 6-30 of SEQ ID NO: 59; (261) a targeting sequence comprising amino acids 1-33 of SEQ ID NO: 61; (262) a targeting sequence comprising amino acids 18-33 of SEQ ID NO: 61; (263) a targeting sequence comprising SEQ ID NO: 61; (264) an exosporium protein comprising an amino acid sequence having at least 85% sequence identity with SEQ ID NO: 62; (265) a targeting sequence comprising amino acids 2-33 of SEQ ID NO: 61; (266) a targeting sequence comprising amino acids 5-33 of SEQ ID NO: 61; (267) a targeting sequence comprising amino acids 10-33 of SEQ ID NO: 61; (268) a targeting sequence comprising amino acids 15-33 of SEQ ID NO: 61; (269) a targeting sequence comprising amino acids 1-35 of SEQ ID NO: 63; (270) a targeting sequence comprising SEQ ID NO: 63; (271) an exosporium protein comprising an amino acid sequence having at least 85% identity with SEQ ID NO: 64; (272) a targeting sequence comprising amino acids 2-35 of SEQ ID NO: 63; (273) a targeting sequence comprising amino acids 5-35 of SEQ ID NO: 63; (274) a targeting sequence comprising amino acids 8-35 of SEQ ID NO: 63; (275) a targeting sequence comprising amino acids 10-35 of SEQ ID NO: 63; (276) a targeting sequence comprising amino acids 15-35 of SEQ ID NO: 63; (277) a targeting sequence comprising amino acids 1-24 of SEQ ID NO: 65; (278) a targeting sequence comprising amino acids 9-24 of SEQ ID NO: 65; (279) a targeting sequence comprising SEQ ID NO: 65; (280) an exosporium protein comprising an amino acid sequence having at least 85% identity with SEQ ID NO: 66; (281) a targeting sequence comprising SEQ ID NO: 107; (282) a targeting sequence comprising amino acids 2-24 of SEQ ID NO: 65; (283) a targeting sequence comprising amino acids 5-24 of SEQ ID NO: 65; (284) a targeting sequence comprising amino acids 1-27 of SEQ ID NO: 67; (285) a targeting sequence comprising amino acids 12-27 of SEQ ID NO: 67; (286) a targeting sequence comprising SEQ ID NO: 67; (287) an exosporium protein comprising an amino acid sequence having at least 85% identity with SEQ ID NO: 68; (288) an targeting sequence comprising amino acids 2-27 of SEQ ID NO: 67; (289) a targeting sequence comprising amino acids 5-27 of SEQ ID NO: 67; (290) a targeting sequence comprising amino acids 10-27 of SEQ ID NO: 67; (291) a targeting sequence comprising amino acids 1-38 of SEQ ID NO: 69; (292) a targeting sequence comprising amino acids 23-38 of SEQ ID NO: 69; (293) a targeting sequence comprising SEQ ID NO: 69; (294) an exosporium protein comprising an amino acid sequence having at least 85% identity with SEQ ID NO: 70; (295) a targeting sequence comprising amino acids 2-38 of SEQ ID NO: 69; (296) a targeting sequence comprising amino acids 5-38 of SEQ ID NO: 69; (297) a targeting sequence comprising amino acids 10-38 of SEQ ID NO: 69; (298) a targeting sequence comprising amino acids 15-38 of SEQ ID NO: 69; (299) an exosporium protein comprising SEQ ID NO: 72; (300) a targeting sequence comprising SEQ ID NO: 73; (301) an exosporium protein comprising an amino acid sequence having at least 95% identity with SEQ ID NO: 74; (302) a targeting sequence comprising amino acids 1-42 of SEQ ID NO: 75; (303) a targeting sequence comprising amino acids 27-42 of SEQ ID NO: 75; (304) a targeting sequence comprising SEQ ID NO: 75; (305) an exosporium protein comprising an amino acid sequence having at least 85% identity with SEQ ID NO: 76; (306) a targeting sequence comprising amino acids 2-42 of SEQ ID NO: 75; (307) a targeting sequence comprising amino acids 5-42 of SEQ ID NO: 75; (308) a targeting sequence comprising amino acids 10-42 of SEQ ID NO: 75; (309) a targeting sequence comprising amino acids 15-42 of SEQ ID NO: 75; (310) a targeting sequence comprising amino acids 20-42 of SEQ ID NO: 75; (311) a targeting sequence comprising amino acids 25-42 of SEQ ID NO: 75; (312) a targeting sequence comprising amino acids 1-24 of SEQ ID NO: 77; (313) a targeting sequence comprising amino acids 9-24 of SEQ ID NO: 77; (314) a targeting sequence comprising SEQ ID NO: 77; (315) an exosporium protein comprising an amino acid sequence having at least 85% identity with SEQ ID NO: 78; (316) a targeting sequence comprising amino acids 2-24 of SEQ ID NO: 77; (317) a targeting sequence comprising amino acids 5-24 of SEQ ID NO: 77; (318) an exosporium protein comprising an amino acid sequence having at least 85% identity with SEQ ID NO: 80; (319) a targeting sequence comprising amino acids 1-38 of SEQ ID NO: 81; (320) a targeting sequence comprising amino acids 23-38 of SEQ ID NO: 81; (321) a targeting sequence comprising SEQ ID NO: 81; (322) an exosporium protein comprising an amino acid sequence having at least 85% identity with SEQ ID NO: 82; (323) a targeting sequence comprising amino acids 2-38 of SEQ ID NO: 81; (324) a targeting sequence comprising amino acids 5-38 of SEQ ID NO: 81; (325) a targeting sequence comprising amino acids 10-38 of SEQ ID NO: 81; (326) a targeting sequence comprising amino acids 15-38 of SEQ ID NO: 81; (327) a targeting sequence comprising amino acids 20-38 of SEQ ID NO: 81; (328) a targeting sequence comprising amino acids 1-34 of SEQ ID NO: 83; (329) a targeting sequence comprising SEQ ID NO: 83; (330) an exosporium protein comprising an amino acid sequence having at least 85% identity with SEQ ID NO: 84; (331) an exosporium protein comprising an amino acid sequence having at least 85% identity with SEQ ID NO: 86; (332) a targeting sequence comprising amino acids 1-28 of SEQ ID NO: 87; (333) a targeting sequence comprising amino acids 13-28 of SEQ ID NO: 87; (334) a targeting sequence comprising SEQ ID NO: 87; (335) an exosporium protein comprising an amino acid sequence having at least 85% identity with SEQ ID NO: 88; (336) a targeting sequence comprising amino acids 2-28 of SEQ ID NO: 87; (337) a targeting sequence comprising amino acids 5-28 of SEQ ID NO: 87; (338) a targeting sequence comprising amino acids 10-28 of SEQ ID NO: 87; (339) a targeting sequence comprising amino acids 1-28 of SEQ ID NO: 89; (340) a targeting sequence comprising SEQ ID NO: 89; (341) an exosporium protein comprising an amino acid sequence having at least 85% identity with SEQ ID NO: 90; (342) a targeting sequence comprising amino acids 2-28 of SEQ ID NO: 89; (343) a targeting sequence comprising amino acids 5-28 of SEQ ID NO: 89; (344) a targeting sequence comprising amino acids 10-28 of SEQ ID NO: 89; (345) a targeting sequence comprising amino acids 1-93 of SEQ ID NO: 91; (346) a targeting sequence comprising SEQ ID NO: 91; (347) an exosporium protein comprising an amino acid sequence having at least 85% identity with SEQ ID NO: 92; (348) a targeting sequence comprising amino acids 2-93 of SEQ ID NO: 91; (349) a targeting sequence comprising amino acids 10-93 of SEQ ID NO: 91; (350) a targeting sequence comprising amino acids 20-93 of SEQ ID NO: 91; (351) a targeting sequence comprising amino acids 30-93 of SEQ ID NO: 91; (352) a targeting sequence comprising amino acids 40-93 of SEQ ID NO: 91; (353) a targeting sequence comprising amino acids 50-93 of SEQ ID NO: 91; (354) a targeting sequence comprising amino acids 60-93 of SEQ ID NO: 91; (355) a targeting sequence comprising amino acids 1-130 of SEQ ID NO: 93; (356) a targeting sequence comprising SEQ ID NO: 93; (357) an exosporium protein comprising an amino acid sequence having at least 85% identity with SEQ ID NO: 94; (358) a targeting sequence comprising amino acids 2-130 of SEQ ID NO: 93; (359) a targeting sequence comprising amino acids 10-130 of SEQ ID NO: 93; (360) a targeting sequence comprising amino acids 20-130 of SEQ ID NO: 93; (361) a targeting sequence comprising amino acids 30-130 of SEQ ID NO: 93; (362) an exosporium protein comprising an amino acid sequence having at least 85% identity with SEQ ID NO: 122; (363) a targeting sequence consisting of amino acids 20-33 of SEQ ID NO: 1; (364) a targeting sequence consisting of amino acids 21-33 of SEQ ID NO: 1; (365) a targeting sequence consisting of amino acids 23-31 of SEQ ID NO: 1; (366) a targeting sequence consisting of amino acids 1-15 of SEQ ID NO: 96; (367) a targeting sequence consisting of amino acids 1-13 of SEQ ID NO: 96; (368) a targeting sequence consisting of amino acids 12-25 of SEQ ID NO: 3; (369) a targeting sequence consisting of amino acids 13-25 of SEQ ID NO: 3; (370) a targeting sequence consisting of amino acids 15-23 of SEQ ID NO: 3; (371) a targeting sequence consisting of amino acids 1-15 of SEQ ID NO: 97; (372) a targeting sequence consisting of amino acids 1-13 of SEQ ID NO: 98; (373) a targeting sequence consisting of amino acids 23-36 of SEQ ID NO: 5; (374) a targeting sequence consisting of amino acids 23-34 of SEQ ID NO: 5; (375) a targeting sequence consisting of amino acids 24-36 of SEQ ID NO: 5; (376) a targeting sequence consisting of amino acids 26-34 of SEQ ID NO: 5; (377) a targeting sequence consisting of amino acids 13-26 of SEQ ID NO: 7; (378) a targeting sequence consisting of amino acids 13-24 of SEQ ID NO: 7; (379) a targeting sequence consisting of amino acids 14-26 of SEQ ID NO: 7; (380) a targeting sequence consisting of amino acids 16-24 of SEQ ID NO: 7; (381) a targeting sequence consisting of amino acids 9-22 of SEQ ID NO: 9; (382) a targeting sequence consisting of amino acids 9-20 of SEQ ID NO: 9; (383) a targeting sequence consisting of amino acids 10-22 of SEQ ID NO: 9; (384) a targeting sequence consisting of amino acids 12-20 of SEQ ID NO: 9; (385) a targeting sequence consisting of amino acids 1-15 of SEQ ID NO: 105; (386) a targeting sequence consisting of amino acids 1-13 of SEQ ID NO: 105; (387) a targeting sequence consisting of amino acids 18-31 of SEQ ID NO: 11; (388) a targeting sequence consisting of amino acids 18-29 of SEQ ID NO: 11; (389) a targeting sequence consisting of amino acids 19-31 of SEQ ID NO: 11; (390) a targeting sequence consisting of amino acids 1-15 of SEQ ID NO: 98; (391) a targeting sequence consisting of amino acids 1-13 of SEQ ID NO: 98; (392) a targeting sequence consisting of amino acids 18-31 of SEQ ID NO: 13; (393) a targeting sequence consisting of amino acids 18-29 of SEQ ID NO: 13; (394) a targeting sequence consisting of amino acids 19-31 of SEQ ID NO: 13; (395) a targeting sequence consisting of amino acids 21-29 of SEQ ID NO: 13; (396) a targeting sequence consisting of amino acids 1-15 of SEQ ID NO: 99; (397) a targeting sequence consisting of amino acids 1-13 of SEQ ID NO: 99; (398) a targeting sequence consisting of amino acids 28-41 of SEQ ID NO: 15; (399) a targeting sequence consisting of amino acids 28-39 of SEQ ID NO: 15; (400) a targeting sequence consisting of amino acids 29-41 of SEQ ID NO: 15; (401) a targeting sequence consisting of amino acids 31-39 of SEQ ID NO: 15; (402) a targeting sequence consisting of amino acids 12-25 of SEQ ID NO: 17; (403) a targeting sequence consisting of amino acids 13-25 of SEQ ID NO: 17; (404) a targeting sequence consisting of amino acids 1-15 of SEQ ID NO: 100; (405) a targeting sequence consisting of amino acids 18-31 of SEQ ID NO: 19; (406) a targeting sequence consisting of amino acids 18-29 of SEQ ID NO: 19; (407) a targeting sequence consisting of amino acids 19-31 of SEQ ID NO: 19; (408) a targeting sequence consisting of amino acids 21-29 of SEQ ID NO: 19; (409) a targeting sequence consisting of amino acids 18-31 of SEQ ID NO: 21; (410) a targeting sequence consisting of amino acids 18-29 of SEQ ID NO: 21; (411) a targeting sequence consisting of amino acids 19-31 of SEQ ID NO: 21; (412) a targeting sequence consisting of amino acids 21-29 of SEQ ID NO: 21; (413) a targeting sequence consisting of amino acids 1-15 of SEQ ID NO: 101; (414) a targeting sequence consisting of amino acids 1-13 of SEQ ID NO: 101; (415) a targeting sequence consisting of amino acids 9-22 of SEQ ID NO: 23; (416) a targeting sequence consisting of amino acids 9-20 of SEQ ID NO: 23; (417) a targeting sequence consisting of amino acids 10-22 of SEQ ID NO: 23; (418) a targeting sequence consisting of amino acids 12-20 of SEQ ID NO: 23; (419) a targeting sequence consisting of amino acids 1-15 of SEQ ID NO: 102; (420) a targeting sequence consisting of amino acids 1-13 of SEQ ID NO: 102; (421) a targeting sequence consisting of amino acids 9-22 of SEQ ID NO: 25; (422) a targeting sequence consisting of amino acids 9-20 of SEQ ID NO: 25; (423) a targeting sequence consisting of amino acids 10-22 of SEQ ID NO: 25; (424) a targeting sequence consisting of amino acids 12-20 of SEQ ID NO: 25; (425) a targeting sequence consisting of amino acids 1-15 of SEQ ID NO: 103; (426) a targeting sequence consisting of amino acids 1-13 of SEQ ID NO: 103; (427) a targeting sequence consisting of amino acids 15-28 of SEQ ID NO: 27; (428) a targeting sequence consisting of amino acids 15-26 of SEQ ID NO: 27; (429) a targeting sequence consisting of amino acids 16-28 of SEQ ID NO: 27; (430) a targeting sequence consisting of amino acids 18-26 of SEQ ID NO: 27; (431) a targeting sequence consisting of amino acids 1-15 of SEQ ID NO: 104; (432) a targeting sequence consisting of amino acids 1-13 of SEQ ID NO: 104; (433) a targeting sequence consisting of amino acids 1-13 of SEQ ID NO: 33; (434) a targeting sequence consisting of amino acids 1-11 of SEQ ID NO: 33; (435) a targeting sequence consisting of amino acids 3-11 of SEQ ID NO: 33; (436) a targeting sequence consisting of amino acids 1-14 of SEQ ID NO: 35; (437) a targeting sequence consisting of amino acids 1-12 of SEQ ID NO: 35; (438) a targeting sequence consisting of amino acids 2-14 of SEQ ID NO: 35; (439) a targeting sequence consisting of amino acids 14-27 of SEQ ID NO: 43; (440) a targeting sequence consisting of amino acids 14-25 of SEQ ID NO: 43; (441) a targeting sequence consisting of amino acids 15-27 of SEQ ID NO: 43; (442) a targeting sequence consisting of amino acids 20-33 of SEQ ID NO: 45; (443) a targeting sequence consisting of amino acids 20-31 of SEQ ID NO: 45; (444) a targeting sequence consisting of amino acids 21-33 of SEQ ID NO: 45; (445) a targeting sequence consisting of amino acids 1-15 of SEQ ID NO: 106; (446) a targeting sequence consisting of amino acids 1-13 of SEQ ID NO: 106; (447) a targeting sequence consisting of amino acids 28-41 of SEQ ID NO: 47; (448) a targeting sequence consisting of amino acids 28-39 of SEQ ID NO: 47; (449) a targeting sequence consisting of amino acids 18-31 of SEQ ID NO: 53; (450) a targeting sequence consisting of amino acids 18-29 of SEQ ID NO: 53; (451) a targeting sequence consisting of amino acids 19-31 of SEQ ID NO: 53; (452) a targeting sequence comprising amino acids 18-31 of SEQ ID NO: 61; (453) a targeting sequence comprising amino acids 18-29 of SEQ ID NO: 61; (454) a targeting sequence comprising amino acids 19-31 of SEQ ID NO: 61; (455) a targeting sequence comprising amino acids 9-22 of SEQ ID NO: 65; (456) a targeting sequence comprising amino acids 9-20 of SEQ ID NO: 65; (457) a targeting sequence comprising amino acids 10-22 of SEQ ID NO: 65; (458) a targeting sequence comprising amino acids 1-15 of SEQ ID NO: 107; (459) a targeting sequence comprising amino acids 1-13 of SEQ ID NO: 107; (460) a targeting sequence comprising amino acids 12-25 of SEQ ID NO: 67; (461) a targeting sequence comprising amino acids 12-23 of SEQ ID NO: 67; (462) a targeting sequence comprising amino acids 13-25 of SEQ ID NO: 67; (463) a targeting sequence comprising amino acids 15-23 of SEQ ID NO: 67; (464) a targeting sequence comprising amino acids 23-36 of SEQ ID NO: 69; (465) a targeting sequence comprising amino acids 23-34 of SEQ ID NO: 69; (466) a targeting sequence comprising amino acids 24-36 of SEQ ID NO: 69; (467) a targeting sequence comprising amino acids 26-34 of SEQ ID NO: 69; (468) a targeting sequence comprising amino acids 27-40 of SEQ ID NO: 75; (469) a targeting sequence comprising amino acids 27-38 of SEQ ID NO: 75; (470) a targeting sequence comprising amino acids 9-22 of SEQ ID NO: 77; (471) a targeting sequence comprising amino acids 9-20 of SEQ ID NO: 77; (472) a targeting sequence comprising amino acids 10-22 of SEQ ID NO: 77; (473) a targeting sequence comprising amino acids 12-20 of SEQ ID NO: 77; (474) a targeting sequence comprising amino acids 23-36 of SEQ ID NO: 81; (475) a targeting sequence comprising amino acids 23-34 of SEQ ID NO: 81; (476) a targeting sequence comprising amino acids 24-36 of SEQ ID NO: 81; (477) a targeting sequence comprising amino acids 26-34 of SEQ ID NO: 81; (478) a targeting sequence comprising amino acids 13-26 of SEQ ID NO: 87; (479) a targeting sequence comprising amino acids 13-24 of SEQ ID NO: 87; or (480) a targeting sequence comprising amino acids 14-26 of SEQ ID NO: 87.

For example, the targeting sequence can comprise an amino acid sequence having at least about 50% identity with amino acids 20-35 of SEQ ID NO: 1, wherein the identity with amino acids 25-35 is at least about 63%.

For example, the targeting sequence can comprise an amino acid sequence having at least about 56% identity with amino acids 20-35 of SEQ ID NO: 1, wherein the identity with amino acids 25-35 is at least about 63%.

For example, the targeting sequence can comprise an amino acid sequence having at least about 50% identity with amino acids 20-35 of SEQ ID NO: 1, wherein the identity with amino acids 25-35 is at least about 72%.

For example, the targeting sequence can comprise an amino acid sequence having at least about 62% identity with amino acids 20-35 of SEQ ID NO: 1, wherein the identity with amino acids 25-35 is at least about 72%.

For example, the targeting sequence can comprise an amino acid sequence having at least about 75% identity with amino acids 20-35 of SEQ ID NO: 1, wherein the identity with amino acids 25-35 is at least about 72%.

For example, the targeting sequence can comprise an amino acid sequence having at least about 68% identity with amino acids 20-35 of SEQ ID NO: 1, wherein the identity with amino acids 25-35 is at least about 81%.

For example, the targeting sequence can comprise an amino acid sequence having at least about 75% identity with amino acids 20-35 of SEQ ID NO: 1, wherein the identity with amino acids 25-35 is at least about 81%.

For example, the targeting sequence can comprise an amino acid sequence having at least about 81% identity with amino acids 20-35 of SEQ ID NO: 1, wherein the identity with amino acids 25-35 is at least about 81%.

For example, the targeting sequence can comprise an amino acid sequence having at least about 81% identity with amino acids 20-35 of SEQ ID NO: 1, wherein the identity with amino acids 25-35 is at least about 90%.

For example, the targeting sequence can consist of: (a) an amino acid sequence consisting of 16 amino acids and having at least about 43% identity with amino acids 20-35 of SEQ ID NO: 1, wherein the identity with amino acids 25-35 is at least about 54%; (b) amino acids 1-35 of SEQ ID NO: 1; (c) amino acids 20-35 of SEQ ID NO: 1; (d) SEQ ID NO: 1; (e) SEQ ID NO: 96; or (f) SEQ ID NO: 120.

The targeting sequence can consist of the amino acid sequence as described in these examples.

The fusion protein can comprise an exosporium protein or an exosporium protein fragment comprising an amino acid sequence having at least 90% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having at least 95% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having at least 98% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having at least 99% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having 100% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein comprising an amino acid sequence having at least 90% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having at least 95% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having at least 98% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having at least 99% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having 100% identity with SEQ ID NO: 60, 62, 64, 66, 68, 70, 76, 78, 80, 82, 84, 86, 88, 90, 92, 94 or 122.

The targeting sequence, exosporium protein, or exosporium protein fragment of the fusion protein can comprise the amino acid sequence GXT at its carboxy terminus, wherein X is any amino acid.

The targeting sequence, exosporium protein, or exosporium protein fragment can comprise an alanine residue at the position of the targeting sequence that corresponds to amino acid 20 of SEQ ID NO: 1.

The targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

IX. Fusion Proteins Comprising a Protein or Peptide of Interest and a Spore Coat Protein, Recombinant Spore-Coat Forming Bacteria, and Seeds Coated with Recombinant Spore-Coat Forming Bacteria A. Spore Coat Proteins that can be Used to Target a Fusion Protein Comprising the Spore Coat Protein to a Surface of a Spore of a Recombinant Spore-Forming Bacterium A number of spore coat proteins can be used to display proteins or peptides of interest on a surface of a spore of a recombinant spore-forming bacterium. Such bacteria include any spore-forming bacteria, and in particular include spore-forming bacteria of the genuses *Bacillus, Lysinibacillus, Virginibacillus, Clostridia*, and *Paenibacillus*. Spore-forming bacteria of the genus *Bacillus* include *Bacillus cereus* family members as well as other *Bacillus* species that are not *Bacillus cereus* family members (e.g., *Bacillus* species bacteria that lack an exosporium). These spore coat proteins include CotB, CotC, CgeA, CotB/H, CotG, spore coat protein X, and CotY. For ease of reference, the descriptions of the amino acid sequences for exemplary spore coat proteins that can be used for targeting of proteins or peptides of interest to a spore surface of a recombinant spore-forming bacterium are provided in Table 7 below, together with their SEQ ID NOs.

TABLE 7

Spore coat protein sequences used for targeting of proteins and peptides of interest to a spore surface of a recombinant spore-forming bacterium

| Spore coat protein | SEQ ID NO. |
|---|---|
| CotB (*Bacillus subtilis*) | 252 |
| CotC (*Bacillus subtilis*) | 253 |
| CgeA (*Bacillus amyloliquefaciens*) | 254 |
| CotB/H (*Bacillus amyloliquefaciens*) | 255 |
| CotG (*Bacillus subtilis*) | 256 |
| Spore Coat Protein X (*Bacillus megaterium*) | 257 |
| CotY (*Bacillus amyloliquefaciens*) | 258 |
| CotY (*Bacillus licheniformis*) | 259 |

B. Fusion Proteins Comprising a Protein or Peptide of Interest and a Spore Coat Protein The present invention also relates to fusion proteins comprising at least one protein or peptide of interest and a spore coat protein, wherein the spore coat protein comprises a CotB/H protein, a spore protein X protein, or a CotY protein, wherein the CotY protein comprises an amino acid sequence having at least 80% identity with SEQ ID NO: 258 or 259.

For example, the spore coat protein can comprise a CotB/H protein.

For example, the spore coat protein can comprise a spore protein X protein.

For example, the spore coat protein can comprise a CotY protein, wherein the CotY protein comprises an amino acid sequence having at least 80% identity with SEQ ID NO: 258 or 259.

The spore coat protein can comprises an amino acid sequence having at least 85% identity with SEQ ID NO: 255, 257, 258, or 259.

The spore coat protein can comprises an amino acid sequence having at least 90% identity with SEQ ID NO: 255, 257, 258, or 259.

The spore coat protein can comprises an amino acid sequence having at least 95% identity with SEQ ID NO: 255, 257, 258, or 259.

The spore coat protein can comprises an amino acid sequence having at least 98% identity with SEQ ID NO: 255, 257, 258, or 259.

The spore coat protein can comprises an amino acid sequence having at least 99% identity with SEQ ID NO: 255, 257, 258, or 259.

The spore coat protein can comprises an amino acid sequence having at least 100% identity with SEQ ID NO: 255, 257, 258, or 259.

C. Recombinant Spore-Coat Forming Bacteria that Express Fusion Proteins and Plant Seeds Coated with Recombinant Spore-Coat Forming Bacteria Recombinant spore-forming bacteria that expresses any of the fusion proteins described in Section IX.B are provided. The recombinant spore-forming bacteria can comprise an endophytic strain of bacteria, a plant growth-promoting strain of bacteria, or a strain of bacteria that is both endophytic and plant growth-promoting.

The present invention further relates to a recombinant spore-forming bacterium that expresses a fusion protein comprising at least one protein or peptide of interest and a spore coat protein that targets the fusion protein to the surface of a spore of the bacterium, wherein the spore coat protein comprises a CotB protein, a CotC protein, a CgeA protein, a CotB/H protein, a CotG protein, a spore coat protein X protein, or a CotY protein; and wherein the recombinant spore-forming bacterium comprises an endophytic strain of bacteria, a plant growth-promoting strain of bacteria, or a strain of bacteria that is both endophytic and plant growth-promoting.

Expression of the fusion protein in an endophytic strain of bacteria allows for delivery of the protein or peptide of interest internally to a plant. The endophytic strains can be delivered to plants using various methods, e.g., the endophytic strains can be delivered via seed treatment, treatment of the plant growth medium (e.g., soil), irrigation, application to the plant itself (e.g., foliar application to the aerial portions of a plant). Once inside the plant, the bacteria multiply and colonize the internal tissues of the plant.

The present invention also relates to plant seeds coated with a recombinant spore-forming bacterium, wherein the recombinant spore-forming bacterium expresses a fusion protein comprising at least one protein or peptide of interest and a spore coat protein that targets the fusion protein to the surface of a spore of the bacterium, wherein the spore coat protein comprises a cotB protein, a CotC protein, a CgeA protein, a CotB/H protein, a Cot G protein, a spore protein X protein, or a cotY protein.

The recombinant spore-coat forming bacterium can comprise a bacterium of the genus *Bacillus* or *Lysinibacillus.*

The present invention further relates to a recombinant bacterium of the genus *Bacillus*, wherein the recombinant bacterium comprises a recombinant spore-forming bacterium and wherein the recombinant spore-forming bacterium expresses a fusion protein comprising at least one protein or peptide of interest and a spore coat protein that targets the fusion protein to the surface of a spore of the bacterium, wherein the spore coat protein comprises a CotB protein, a CotC protein, a CgeA protein, a CotB/H protein, a Cot G protein, a spore coat protein X protein, or a CotY protein. The recombinant spore-coat forming bacterium expresses a protease or a nuclease, wherein the expression of the protease or nuclease is increased as compared to the expression of the protease or the nuclease in a wild-type bacterium of the genus *Bacillus* under the same conditions, and wherein the increased expression of the protease or the nuclease partially or completely inactivates spores of the recombinant bacterium of the genus *Bacillus* or renders spores of the recombinant bacterium of the genus *Bacillus* more susceptible to physical or chemical inactivation. The protease or nuclease can be any of the proteases or nucleases described above in Section V.A, and can be expressed under the control of any of the promoters described above in Section V.A. The invention further relates to plant seeds coated with such spore-forming bacteria. The recombinant bacterium can comprise an endophytic strain of bacteria, a plant growth-promoting strain of bacteria, or a strain of bacteria that is both endophytic and plant growth-promoting.

In any of the plant seeds described in this Section, the recombinant spore-forming bacterium can comprise an endophytic strain of bacteria, a plant growth-promoting strain of bacteria, or a strain of bacteria that is both endophytic and plant growth-promoting.

In any of the recombinant spore-forming bacteria or seeds, the endophytic strain of bacteria, the plant growth-promoting strain of bacteria, or the strain of bacteria that is both endophytic and plant growth-promoting can comprise *Bacillus megaterium* EE385, *Bacillus* sp. EE387, *Bacillus circulans* EE388, *Bacillus subtilis* EE405, *Lysinibacillus fusiformis* EE442, or *Lysinibacillus sphaericus* EE443, *Bacillus pumilus* EE-B00143, *Bacillus subtilis* EE148, *Bacillus subtilis* EE218, or *Bacillus megaterium* EE281. For example, the endophytic strain of bacteria can comprise *Bacillus subtilis* EE405 or *Bacillus megaterium* EE385.

Alternatively, the endophytic strain, the plant growth-promoting strain of bacteria, or the strain of bacteria that is both endophytic and plant growth-promoting of bacteria can comprise *Bacillus cereus* family member EE349, *Bacillus cereus* family member EE439, *Bacillus thuringiensis* EE417, *Bacillus cereus* EE444, or *Bacillus thuringiensis* EE319, *Bacillus thuringiensis* EE-B00184, *Bacillus cereus* family member EE-B00377, *Bacillus pseudomycoides* EE-B00366, *Bacillus mycoides* EE-B00363, *Bacillus mycoides* BT155, *Bacillus mycoides* EE118, *Bacillus mycoides* EE141, *Bacillus mycoides* BT46-3, *Bacillus cereus* family member EE128, *Bacillus thuringiensis* BT013A, or *Bacillus cereus* family member EE349.

In any of the recombinant spore-forming bacteria or seeds, the spore coat protein can comprise an amino acid sequence having at least 85% identity with any of SEQ ID NOs: 252-259.

The spore coat protein can comprise an amino acid sequence having at least 90% identity with any of SEQ ID NOs: 252-259.

The spore coat protein can comprise an amino acid sequence having at least 95% identity with any of SEQ ID NOs: 252-259.

The spore coat protein can comprise an amino acid sequence having at least 98% identity with any of SEQ ID NOs: 252-259.

The spore coat protein can comprise an amino acid sequence having at least 99% identity with any of SEQ ID NOs: 252-259.

The spore coat protein can comprise an amino acid sequence having 100% identity with any of SEQ ID NOs: 252-259.

A recombinant spore-forming bacterium that expresses a fusion protein comprising at least one protein or peptide of interest and a protein that targets the fusion protein to the surface of a spore of the bacterium is also provided. The recombinant spore-forming bacterium is not a recombinant *Bacillus cereus* family member. The protein that targets the fusion protein to the surface of a spore of the bacterium comprises amino acids 20-35 of SEQ ID NO: 1, SEQ ID NO: 96, or an amino acid sequence having at least 85% identity with SEQ ID NO: 108, SEQ ID NO: 111, SEQ ID NO: 114, SEQ ID NO: 120, or SEQ ID NO: 121.

The protein that targets the fusion protein of the surface of a spore of the bacterium can comprise an amino acid sequence having at least 90% identity with SEQ ID NO: 108, SEQ ID NO: 111, SEQ ID NO: 114, SEQ ID NO: 120, or SEQ ID NO: 121.

The protein that targets the fusion protein of the surface of a spore of the bacterium can comprise an amino acid sequence having at least 95% identity with SEQ ID NO: 108, SEQ ID NO: 111, SEQ ID NO: 114, SEQ ID NO: 120, or SEQ ID NO: 121.

The protein that targets the fusion protein of the surface of a spore of the bacterium can comprise an amino acid sequence having at least 98% identity with SEQ ID NO: 108, SEQ ID NO: 111, SEQ ID NO: 114, SEQ ID NO: 120, or SEQ ID NO: 121.

The protein that targets the fusion protein of the surface of a spore of the bacterium can comprise an amino acid sequence having at least 99% identity with SEQ ID NO: 108, SEQ ID NO: 111, SEQ ID NO: 114, SEQ ID NO: 120, or SEQ ID NO: 121.

The protein that targets the fusion protein of the surface of a spore of the bacterium can comprise an amino acid sequence having at least 100% identity with SEQ ID NO: 108, SEQ ID NO: 111, SEQ ID NO: 114, SEQ ID NO: 120, or SEQ ID NO: 121.

For example, the protein that targets the fusion protein to a surface of a spore of the bacterium can comprise amino acids 20-35 of SEQ ID NO: 1, SEQ ID NO: 96, SEQ ID NO: 108, SEQ ID NO: 120, or SEQ ID NO: 121.

The recombinant-spore forming bacterium comprises an endophytic strain of bacteria, a plant growth-promoting strain of bacteria, or a strain of bacteria that is both endophytic and plant growth-promoting. For example, the endophytic strain of bacteria, the plant growth-promoting strain of bacteria, or the strain of bacteria that is both endophytic and plant growth-promoting comprises *Bacillus megaterium* EE385, *Bacillus* sp. EE387, *Bacillus circulans* EE388, *Bacillus subtilis* EE405, *Lysinibacillus fusiformis* EE442, *Lysinibacillus sphaericus* EE443, *Bacillus pumilus* EE-B00143, *Bacillus subtilis* EE148, *Bacillus subtilis* EE218, or *Bacillus megaterium* EE281. The endophytic strain of bacteria preferably comprises *Bacillus* sp. EE387.

X. Methods for Making the Fusion Proteins

Any of the fusion proteins described herein can be made using standard cloning and molecular biology methods known in the art. For example, a gene encoding a protein or peptide of interest (e.g., a gene encoding a plant growth stimulating protein or peptide) can be amplified by polymerase chain reaction (PCR) and ligated to DNA coding for any of the above-described targeting sequences, exosporium proteins, exosporium protein fragments, or spore coat proteins, to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the fusion protein can be integrated into the chromosomal DNA of the *B. cereus* family member or spore-forming bacterium host.

XI. Tags, Markers, and Linkers that can be Included in the Fusion Proteins

Any of the fusion proteins described herein can also comprise additional polypeptide sequences that are not part of the targeting sequence, exosporium protein, exosporium protein fragment, or the plant growth stimulating protein or peptide, the protein or peptide that protects a plant from a pathogen, the protein or peptide that enhances stress resistance in a plant, or the plant binding protein or peptide. For example, the fusion protein can include tags or markers to facilitate purification or visualization of the fusion protein (e.g., a polyhistidine tag or a fluorescent protein such as GFP or YFP) or visualization of recombinant *Bacillus cereus* family member spores expressing the fusion protein.

Expression of fusion proteins on the exosporium of a *Bacillus cereus* family member or on a surface of a spore of a spore-forming bacterium using the targeting sequences, exosporium proteins, exosporium protein fragments, and spore coat proteins described herein is enhanced due to a lack of secondary structure in the amino-termini of these sequences, which allows for native folding of the fused proteins and retention of activity. Proper folding can be further enhanced by the inclusion of a short amino acid linker between the targeting sequence, exosporium protein, exosporium protein fragment, spore coat protein, and the protein or peptide of interest.

Thus, any of the fusion proteins described herein can comprise an amino acid linker between the targeting sequence, the exosporium protein, the exosporium protein fragment, or the spore coat protein and the protein or peptide of interest.

The linker can comprise a polyalanine linker or a polyglycine linker. A linker comprising a mixture of both alanine and glycine residues can also be used.

For example, in a fusion protein where the targeting sequence comprises SEQ ID NO: 1, a fusion protein can have one of the following structures:

No linker: SEQ ID NO: 1-POI
Alanine Linker: SEQ ID NO: 1-$A_n$-POI
*Glycine* Linker: SEQ ID NO: 1-$G_n$-POI
Mixed Alanine and *Glycine* Linker: SEQ ID NO: 1-$(A/G)_n$-POI where $A_n$, $G_n$, and $(A/G)_n$ are any number of alanines, any number of glycines, or any number of a mixture of alanines and glycines, respectively. For example, n can be 1 to 25, and is preferably 6 to 10. Where the linker comprises a mixture of alanine and glycine residues, any combination of glycine and alanine residues can be used. In the above structures, "POI" represents the protein or peptide of interest.

Alternatively or in addition, the linker can comprise a protease recognition site. Inclusion of a protease recognition site allows for targeted removal, upon exposure to a protease that recognizes the protease recognition site, of the protein or peptide of interest.

XII. Proteins and Peptides of Interest

The protein or peptide of interest can comprise any protein or peptide.

The protein or peptide of interest in the fusion proteins described herein can comprise, for example: (a) a plant growth stimulating protein or peptide; (b) a protein or peptide that protects a plant from a pathogen; (c) a protein or peptide that enhances stress resistance of a plant; (d) a plant binding protein or peptide; (e) an enzyme that catalyzes the production of nitric oxide; (f) a nucleic acid binding protein or peptide; or (g) a plant signaling molecule or a protein or peptide that alters the composition of a plant; (h) an antigen; (i) a remediation enzyme; (j) an enzyme suitable for breaking an emulsion or gel in a hydraulic fracturing fluid; or (k) an antibacterial protein or peptide.

A. Plant Growth Stimulating Proteins or Peptides

The protein or peptide of interest can comprise a plant growth stimulating protein or peptide.

The plant growth stimulating protein or peptide can comprise a peptide hormone, a non-hormone peptide, an enzyme involved in the production or activation of a plant growth stimulating compound, or an enzyme that degrades or modifies a bacterial, fungal, or plant nutrient source.

For example, the plant growth stimulating protein or peptide can comprise a peptide hormone.

The peptide hormone can comprise a phytosulfokine (e.g., phytosulfokine-α), *clavata* 3 (CLV3), systemin, ZmIGF, or a SCR/SP11.

The plant growth stimulating protein or peptide can comprise a non-hormone peptide.

The non-hormone peptide can comprise a RKN 16D10, Hg-Syv46, an eNOD40 peptide, melittin, mastoparan, Mas7, RHPP, POLARIS, or kunitz trypsin inhibitor (KTI).

The plant growth stimulating protein or peptide can comprise an enzyme involved in the production or activation of a plant growth stimulating compound. The enzyme involved in the production or activation of a plant growth stimulating compound can be any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure into an active or more active form of the compound.

The plant growth stimulating compound can comprise a compound produced by bacteria or fungi in the rhizosphere, e.g., 2,3-butanediol.

Alternatively, the plant growth stimulating compound can comprise a plant growth hormone.

The plant growth hormone can comprise a cytokinin or a cytokinin derivative, ethylene, an auxin or an auxin derivative, a gibberellic acid or a gibberellic acid derivative, abscisic acid or an abscisic acid derivative, or ajasmonic acid or ajasmonic acid derivative.

Where the plant growth stimulating compound comprises a cytokinin or a cytokinin derivative, the cytokinin or the cytokinin derivative can comprise kinetin, cis-zeatin, trans-zeatin, 6-benzylaminopurine, dihydroxyzeatin, N6-(D2-isopentenyl) adenine, ribosylzeatin, N6-(D2-isopentenyl) adenosine, 2-methylthio-cis-ribosylzeatin, cis-ribosylzeatin, trans-ribosylzeatin, 2-methylthio-trans-ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, meta-methyltopolin, or a combination thereof.

Where the plant growth stimulating compound comprises an auxin or an auxin derivative, the auxin or the auxin derivative can comprise an active auxin, an inactive auxin, a conjugated auxin, a naturally occurring auxin, or a synthetic auxin, or a combination thereof. For example, the auxin or auxin derivative can comprise indole-3-acetic acid, indole-3-pyruvic acid, indole-3-acetaldoxime, indole-3-acetamide, indole-3-acetonitrile, indole-3-ethanol, indole-3-pyruvate, indole-3-acetaldoxime, indole-3-butyric acid, a phenylacetic acid, 4-chloroindole-3-acetic acid, a glucose-conjugated auxin, or a combination thereof.

The enzyme involved in the production or activation of a plant growth stimulating compound can comprise an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase (e.g., tryptophan aminotransferase), a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyl-transferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, or an enzyme involved in producing a nod factor (e.g., nodA, nodB, or nodI).

Where the enzyme comprises a protease or peptidase, the protease or peptidase can be a protease or peptidase that cleaves proteins, peptides, proproteins, or preproproteins to create a bioactive peptide. The bioactive peptide can be any peptide that exerts a biological activity.

Examples of bioactive peptides include RKN 16D10 and RHPP.

The protease or peptidase that cleaves proteins, peptides, proproteins, or preproproteins to create a bioactive peptide can comprise subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

The protease or peptidase can cleave proteins in a protein-rich meal (e.g., soybean meal or yeast extract).

Where the enzyme comprises a chitosanase, the chitosanase can comprise an amino acid sequence having at least 85% identity with SEQ ID NO: 313.

The chitosanase can comprise an amino acid sequence having at least 90% identity with SEQ ID NO: 313.

The chitosanase can comprise an amino acid sequence having at least 95% identity with SEQ ID NO: 313.

The chitosanase can comprise an amino acid sequence having at least 98% identity with SEQ ID NO: 313.

The chitosanase can comprise an amino acid sequence having at least 99% identity with SEQ ID NO: 313.

The chitosanase can comprise an amino acid sequence having at least 100% identity with SEQ ID NO: 313.

For example, the fusion protein can comprise amino acids 20-35 of BclA (amino acids 20-35 of SEQ ID NO: 1) as the targeting sequence and an amino acid sequence comprising SEQ ID NO: 313 as the enzyme that is specific for a cellular component of a bacterium or fungus. The fusion protein can further comprise a linker (e.g., a polyalanine linker) between the targeting sequence and the enzyme.

The plant growth stimulating protein or peptide can comprise an enzyme that degrades or modifies a bacterial, fungal, or plant nutrient source.

The enzyme that degrades or modifies a bacterial, fungal, or plant nutrient source can comprise a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, or a siderophore.

When introduced into a plant growth medium or applied to a plant, seed, or an area surrounding a plant or a plant seed, fusion proteins comprising enzymes that degrade or modify a bacterial, fungal, or plant nutrient source can aid in the processing of nutrients in the vicinity of the plant and result in enhanced uptake of nutrients by the plant or by beneficial bacteria or fungi in the vicinity of the plant.

The enzyme that degrades or modifies a bacterial, fungal, or plant nutrient source can comprise a cellulase.

The cellulase can comprise an endocellulase (e.g., an endoglucanase such as a Bacillus subtilis endoglucanase, a Bacillus thuringiensis endoglucanase, a Bacillus cereus endoglucanase, or a Bacillus clausii endoglucanase), an exocellulase (e.g., a Trichoderma reesei exocellulase), or a β-glucosidase (e.g., a Bacillus subtilis β-glucosidase, a Bacillus thuringiensis β-glucosidase, a Bacillus cereus β-glucosidase, or a Bacillus clausii β-glucosidase). The cellulase preferably comprises a Bacillus subtilis endoglucanase.

The endoglucanase can comprise an amino acid sequence having at least 85% identity with SEQ ID NO: 311.

The endoglucanase can comprise an amino acid sequence having at least 90% identity with SEQ ID NO: 311.

The endoglucanase can comprise an amino acid sequence having at least 95% identity with SEQ ID NO: 311.

The endoglucanase can comprise an amino acid sequence having at least 98% identity with SEQ ID NO: 311.

The endoglucanase can comprise an amino acid sequence having at least 99% identity with SEQ ID NO: 311.

The endoglucanase can comprise an amino acid sequence having 100% identity with SEQ ID NO: 311.

For example, the fusion protein can comprise amino acids 20-35 of BclA (amino acids 20-35 of SEQ ID NO: 1) as the targeting sequence and an amino acid sequence comprising SEQ ID NO: 311 as the enzyme that degrades or modifies a bacterial, fungal, or plant nutrient source. The fusion protein can further comprise a linker (e.g., a polyalanine linker) between the targeting sequence and the enzyme.

The enzyme that degrades or modifies a bacterial, fungal, or plant nutrient source can comprise a lipase (e.g., a Bacillus subtilis lipase, a Bacillus thuringiensis lipase, a Bacillus cereus lipase, or a Bacillus clausii lipase).

The enzyme that degrades or modifies a bacterial, fungal, or plant nutrient source can comprise a lignin oxidase. For example, the lignin oxidase can comprise a lignin peroxidase, a laccase, a glyoxal oxidase, a ligninase, or a manganese peroxidase.

The enzyme that degrades or modifies a bacterial, fungal, or plant nutrient source can comprise a protease. For example, the protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

The enzyme that degrades or modifies a bacterial, fungal, or plant nutrient source can comprise a phosphatase. For example, the phosphatase can comprise a phosphoric monoester hydrolase, a phosphomonoesterase (e.g., PhoA4), a phosphoric diester hydrolase, a phosphodiesterase, a triphosphoric monoester hydrolase, a phosphoryl anhydride hydrolase, a pyrophosphatase, a phytase (e.g., a *Bacillus subtilis* EE148 phytase or a *Bacillus thuringiensis* BT013A phytase), a trimetaphosphatase, or a triphosphatase.

The enzyme that degrades or modifies a bacterial, fungal, or plant nutrient source can comprise a nitrogenase. For example the nitrogenase can comprise a Nif family nitrogenase (e.g., *Paenibacillus massiliensis* NifBDEHKNXV).

The enzyme that degrades or modifies a bacterial, fungal, or plant nutrient source can comprise a phospholipase. For example, the phospholipase can comprise a phospholipase A1, a phospholipase A2, a phospholipase C, a phospholipase D, or a lysophospholipase. The phospholipase preferably comprises a phospholipsae C.

The phospholipase C can comprise an amino acid sequence having at least 85% identity with SEQ ID NO: 312.

The phospholipase C can comprise an amino acid sequence having at least 90% identity with SEQ ID NO: 312.

The phospholipase C can comprise an amino acid sequence having at least 95% identity with SEQ ID NO: 312.

The phospholipase C can comprise an amino acid sequence having at least 98% identity with SEQ ID NO: 312.

The phospholipase C can comprise an amino acid sequence having at least 99% identity with SEQ ID NO: 312.

The phospholipase C can comprise an amino acid sequence having 100% identity with SEQ ID NO: 312.

For example, the fusion protein can comprise amino acids 20-35 of BclA (amino acids 20-35 of SEQ ID NO: 1) as the targeting sequence and an amino acid sequence comprising SEQ ID NO: 312 as the enzyme that degrades or modifies a bacterial, fungal, or plant nutrient source. The fusion protein can further comprise a linker (e.g., a polyalanine linker) between the targeting sequence and the enzyme.

B. Proteins or Peptides that Protect Plants from Pathogens

The protein or peptide of interest can comprise a protein or peptide that protects a plant from a pathogen.

The protein or peptide that protects a plant from a pathogen can comprise a plant immune system enhancer protein or peptide.

For example, the plant immune system enhancer protein or peptide can comprise a harpin, a harpin-like protein, an α-elastin, a β-elastin, a systemin, a phenylalanine ammonia-lyase, an elicitin, a defensin, a cryptogein, a flagellin protein, or a flagellin peptide (e.g., flg22).

The protein or peptide that protects a plant from a pathogen can be a protein or peptide that has antibacterial activity, antifungal activity, or both antibacterial and antifungal activity. Examples of such proteins and peptides include bacteriocins, lysozymes, lysozyme peptides (e.g., LysM), siderophores, avidins, streptavidins, non-ribosomal active peptides, conalbumins, albumins, lactoferrins, lactoferrin peptides (e.g., LfcinB), and TasA.

The protein or peptide that protects a plant from a pathogen can be a protein or a peptide that has insecticidal activity, helminthicidal activity, suppresses insect or worm predation, or a combination thereof. For example, the protein or peptide that protects a plant from a pathogen can comprise an insecticidal bacterial toxin (e.g., a VIP insecticidal protein), an endotoxin, a Cry toxin (e.g., a Cry toxin from *Bacillus thuringiensis*), a protease inhibitor protein or peptide (e.g., a trypsin inhibitor or an arrowhead protease inhibitor), a cysteine protease, or a chitinase. Where the Cry toxin comprises a Cry toxin from *Bacillus thuringiensis*, the Cry toxin can be a Cry5B protein or a Cry21A protein. Cry5B and Cry21A have both insecticidal and nematocidal activity.

The protein that protects a plant from a pathogen can comprise an enzyme. For example, the enzyme can comprise a protease or a lactonase. The proteases and lactonases can be specific for a bacterial signaling molecule (e.g., a bacterial lactone homoserine signaling molecule).

Where the enzyme comprises a lactonase, the lactonase can comprise 1,4-lactonase, 2-pyrone-4,6-dicarboxylate lactonase, 3-oxoadipate enol-lactonase, actinomycin lactonase, deoxylimonate A-ring-lactonase, gluconolactonase L-rhamnono-1,4-lactonase, limonin-D-ring-lactonase, steroid-lactonase, triacetate-lactonase, or xylono-1,4-lactonase.

The enzyme can comprise an enzyme that is specific for a cellular component of a bacterium or fungus. For example, the enzyme can comprise a β-1,3-glucanase, a β-1,4-glucanase, a β-1,6-glucanase, a chitosanase, a chitinase, a chitosanase-like enzyme, a lyticase, a peptidase, a proteinase, a protease (e.g., an alkaline protease, an acid protease, or a neutral protease), a mutanolysin, a stapholysin, or a lysozyme.

Where the enzyme comprises a chitosanase, the chitosanase can comprise an amino acid sequence having at least 85% identity with SEQ ID NO: 313.

The chitosanase can comprise an amino acid sequence having at least 90% identity with SEQ ID NO: 313.

The chitosanase can comprise an amino acid sequence having at least 95% identity with SEQ ID NO: 313.

The chitosanase can comprise an amino acid sequence having at least 98% identity with SEQ ID NO: 313.

The chitosanase can comprise an amino acid sequence having at least 99% identity with SEQ ID NO: 313.

The chitosanase can comprise an amino acid sequence having at least 100% identity with SEQ ID NO: 313.

For example, the fusion protein can comprise amino acids 20-35 of BclA (amino acids 20-35 of SEQ ID NO: 1) as the targeting sequence and an amino acid sequence comprising SEQ ID NO: 313 as the enzyme that is specific for a cellular component of a bacterium or fungus. The fusion protein can further comprise a linker (e.g., a polyalanine linker) between the targeting sequence and the enzyme.

For any of the above proteins or peptides that protect a plant from a pathogen, the pathogen can comprise a protein or a peptide of interest that protects a plant from a bacterial pathogen, a fungal pathogen, a worm pathogen, or an insect pathogen.

For example, the bacterial pathogen can comprise an α-class Proteobacterium, a β-class Proteobacterium, a γ-class Proteobacterium, or a combination thereof; or wherein the bacterial pathogen comprises *Agrobacterium tumefaciens, Pantoea stewartii, Erwinia carotovora, Ralstonia solanacearum, Pseudomonas syringae, Pseudomonas aeruginosa, Xanthomonas campestris*, or a combination thereof.

The protein or peptide that protects a plant from a pathogen can comprise a protein or peptide protects the plant from predation by a worm or an insect pathogen.

The worm or insect pathogen can comprise an army worm, a black cutworm, a European corn borer, a fall armyworm, a cutworm, a Japanese beetle, a lesser cornstalk borer, a maize billbug, a seed corn maggot, a webworm, a southern cornstalk borer, a southern corn rootworm, a southern potato wireworm, a stalk borer, a sugarcane beetle, a white grub, a cabbage looper, a boll weevil, a yellow striped armyworm, a cereal leaf beetle, a chinch bug, an aphid, a beet armyworm, a Mexican bean beetle, a soybean looper, soybean stem borer, or a combination thereof.

C. Proteins or Peptides that Enhance Stress-Resistance in Plants

The protein or peptide of interest can comprise a protein or peptide that enhances stress resistance in a plant.

For example, the protein or peptide that enhances stress resistance in a plant can comprise an enzyme that degrades a stress-related compound. Stress-related compounds include, but are not limited to, aminocyclopropane-1-carboxylic acid (ACC), reactive oxygen species, nitric oxide, oxylipins, and phenolics. Specific reactive oxygen species include hydroxyl, hydrogen peroxide, oxygen, and superoxide.

The enzyme that degrades a stress-related compound can comprise a superoxide dismutase, an oxidase, a catalase, an aminocyclopropane-1-carboxylic acid deaminase, a peroxidase, an antioxidant enzyme, or an antioxidant peptide.

When the enzyme that degrades a stress-related compound comprises a superoxide dismutase, the superoxide dismutase can comprise superoxide dismutase 1 (SODA1) or superoxide dismutase 2 (SODA2).

The superoxide dismutase can comprise an amino acid sequence having at least 85% identity with SEQ ID NO: 155 or 156.

The superoxide dismutase can comprise an amino acid sequence having at least 90% identity with SEQ ID NO: 155 or 156.

The superoxide dismutase can comprise an amino acid sequence having at least 95% identity with SEQ ID NO: 155 or 156.

The superoxide dismutase can comprise an amino acid sequence having at least 98% identity with SEQ ID NO: 155 or 156.

The superoxide dismutase can comprise an amino acid sequence having at least 99% identity with SEQ ID NO: 155 or 156.

The superoxide dismutase can comprise an amino acid sequence having 100% identity with SEQ ID NO: 155 or 156.

The protein or peptide that enhances stress resistance in a plant can comprise a protein or peptide that protects a plant from an environmental stress. The environmental stress can comprise, for example, drought, flood, heat, freezing, salt, heavy metals, low pH, high pH, or a combination thereof. For instance, the protein or peptide that protects a plant from an environmental stress can comprises an ice nucleation protein, a prolinase, a phenylalanine ammonia lyase, an isochorismate synthase, an isochorismate pyruvate lyase, or a choline dehydrogenase.

D. Plant Binding Proteins or Peptides

The protein or peptide of interest can comprise a plant binding protein or peptide. The plant binding protein or peptide can be any protein or peptide that is capable of specifically or non-specifically binding to any part of a plant (e.g., a plant root or an aerial portion of a plant such as a leaf, stem, flower, or fruit) or to plant matter. Thus, for example, the plant binding protein or peptide can be a root binding protein or peptide, or a leaf binding protein or peptide.

Suitable plant binding proteins and peptides include adhesins (e.g., rhicadhesin), flagellins, omptins, lectins, expansins, biofilm structural proteins (e.g., TasA or YuaB) pilus proteins, curlus proteins, intimins, invasins, agglutinins, and afimbrial proteins.

E. Enzymes that Catalyze the Production of Nitric Oxide

Many plant species do not inherently have a high germination rate. For such plants, it would be desirable to increase the germination rate. Nitric oxide is a powerful germinant that when present in proximity to a plant seed, increases germination.

The present invention relates to fusion proteins comprising any of the targeting sequences, exosporium proteins, exosporium protein fragments, or spore coat proteins described herein and an enzyme that catalyzes the production of nitric oxide synthase. Thus, the protein or peptide of interest can comprise an enzyme that catalyzes the production of nitric oxide. Fusion proteins comprising an enzyme that catalyzes the production of nitric oxide can be expressed in recombinant *Bacillus cereus* family members or recombinant spore-forming bacteria for the purpose of delivering the enzyme that catalyzes the production of nitric oxide to a plant seed, a plant, a plant growth medium, or an area surrounding a plant or a plant seed, and thereby stimulating germination.

For example, the enzyme that catalyzes the production of nitric oxide can comprise a nitric oxide synthase (e.g., a *Bacillus thuringiensis* nitric oxide synthase or a *Bacillus subtilis* nitric oxide synthase, for example a nitric oxide synthase from *Bacillus thuringiensis* BT013A or *Bacillus subtilis* 168) or an arginase.

For example, the nitric oxide synthase can comprise one of the amino acid sequences described below in Table 8.

TABLE 8

Exemplary nitric oxide synthase sequences

| Nitric oxide synthase | SEQ ID NO. |
|---|---|
| *Bacillus subtilis* Nitric Oxide Synthatase | 260 |
| *Bacillus thuringiensis* Nitric Oxide Synthatase | 261 |

The nitric oxide synthase can also comprise a sequence having a high degree of sequence identity with the nitric oxide synthase sequences shown in Table 8 above. For example, the nitric oxide synthase can comprise an amino acid sequence having at least 85% sequence identity with SEQ ID NO: 260 or 261.

The nitric oxide synthase can comprise an amino acid sequence having at least 90% sequence identity with SEQ ID NO: 260 or 261.

the nitric oxide synthase can comprise an amino acid sequence having at least 95% sequence identity with SEQ ID NO: 260 or 261.

the nitric oxide synthase can comprise an amino acid sequence having at least 98% sequence identity with SEQ ID NO: 260 or 261.

the nitric oxide synthase can comprise an amino acid sequence having at least 99% sequence identity with SEQ ID NO: 260 or 261.

the nitric oxide synthase can comprise an amino acid sequence having at least 100% sequence identity with SEQ ID NO: 260 or 261.

When the protein or peptide of interest comprises a nitric oxide synthase, the fusion protein can comprise one of the amino acid sequences shown in Table 9 below. In the sequences shown in Table 9 below, the targeting sequence is shown in boldface text, a six amino acid alanine linker is indicated by underlining, and the sequence of the nitric oxide synthase is shown in plain text. Thus, the fusion protein can comprise SEQ ID NO: 262 or 263.

TABLE 9

Exemplary fusion proteins comprising a nitric oxide synthase

| Fusion protein (SEQ ID NO) | Amino Acid Sequence |
|---|---|
| Met + Amino acids 20-35 of BclA, alanine linker, and *Bacillus subtilis* Nitric Oxide Synthatase (SEQ ID NO: 262) | MAFDPNLVGPTLPPIPPAAAAAAMEEKEILWNEAKAFIAACYQE LGKEEEVKDRLADIKSEIDLTGSYVHTKEELEHGAKMAWRNSNRC IGRLFWNSLNVIDRRDVRTKEEVRDALFHHIETATNNGKIRPTITIF PPEEKGEKQVEIWNHQLIRYAGYESDGERIGDPASCSLTAACEELG WRGERTDFDLLPLIFRMKGDEQPVWYELPRSLVIEVPITHPDIEAFS DLELKWYGVPIISDMKLEVGGIHYNAAPFNGWYMGTEIGARNLA DEKRYDKLKKVASVIGIAADYNTDLWKDQALVELNKAVLHSYKK QGVSIVDHHTAASQFKRFEEQEEEAGRKLTGDWTWLIPPISPAATH IFHRSYDNSIVKPNYFYQDKPYE |
| Met + Amino acids 20-35 of BclA, alanine linker, and *Bacillus thuringiensis* Nitric Oxide Synthatase (SEQ ID NO: 263) | MAFDPNLVGPTLPPIPPAAAAAAMSKTKQLIEEASHFITICYKELS KEHFIEERMKEIQAEIEKTGTYEHTFEELVHGSRMAWRNSNRCIGR LFWSKMHILDAREVNDEEGVYHALIHHIKYATNDGKVKPTITIFKQ YQGEENNIRIYNHQLIRYAGYKTEMGVTGDSHSTAFTDFCQELGW QGEGTNFDVLPLVFSIDGKAPIYKEIPKEEVKEVPIEHPEYPISSLGA KWYGVPMISDMRLEIGGISYTAAPFNGWYMGTEIGARNLADHDR YNLLPAVAEMMDLDTSRNGTLWKDKALIELNVAVLHSFKKQGVS IVDHHTAAQQFQQFEKQEAACGRVVTGNWVWLIPPLSPATTHIYH KPYPNEILKPNFFH |

Nitric oxide synthases from a number species, including *Bacillus thuringiensis, Bacillus cereus, Bacillus subtilis* and *Bacillus mycoides* can be used as the protein or peptide of interest in the fusion proteins.

F. Nucleic Acid Binding Proteins and Peptides

The delivery of nucleic acids to plants in the field would be desirable, but has been hampered by the instability of nucleic acids, which degrade rapidly when introduced the environment (e.g., into a plant growth medium such as soil).

The present invention relates to fusion proteins comprising any of the targeting sequences, exosporium proteins, exosporium protein fragments, or spore coat proteins described herein and a nucleic acid binding protein or peptide. Such fusion proteins stabilize nucleic acids and can be used to deliver nucleic acids to soil and/or to plants.

Thus, the protein or peptide of interest can comprise a nucleic acid binding protein or peptide. For example, the nucleic acid binding protein or peptide can comprise an RNA binding protein or peptide or a DNA binding protein or peptide.

The RNA binding protein or peptide can comprise a non-specific RNA binding protein or peptide or a specific RNA binding protein or peptide.

For example, the RNA binding peptide can comprise an Hfq protein (e.g., a *Bacillus thuringiensis* Hqf protein).

The DNA binding protein or peptide can comprise a small acid-soluble spore protein (SASP). For example, the SASP can comprise a SASP encoded by an SspA gene, an SspB gene, an SspC gene, an SspD gene, an SspE gene, an SspF gene, an SspG gene, an SspH gene, an SspI gene, an SspJ gene, an SspK gene, an SspL gene, an SspM gene, an SspN gene, an SspO gene, or an SspP gene. For example, the SASP can comprise a SASPα, a SASPβ, or a SASPγ. The SASP can comprise a *Bacillus thuringiensis* SASP.

The nucleic acid binding protein can comprise one of the amino acid sequences described below in Table 10.

TABLE 10

Exemplary SASP and Hfq sequences

| Fusion protein | SEQ ID NO. |
|---|---|
| SASPα | 264 |
| SASPγ | 265 |
| Hfq | 266 |

The nucleic acid binding protein can also comprise a sequence having a high degree of sequence identity with any of the sequences shown above in Table 10. For example, the nucleic acid binding protein can comprise a nucleic acid sequence having at least 85% identity with any of SEQ ID NOs: 264-266.

The nucleic acid binding protein can comprise a nucleic acid sequence having at least 90% identity with any of SEQ ID NOs: 264-266.

The nucleic acid binding protein can comprise a nucleic acid sequence having at least 95% identity with any of SEQ ID NOs: 264-266.

The nucleic acid binding protein can comprise a nucleic acid sequence having at least 98% identity with any of SEQ ID NOs: 264-266.

The nucleic acid binding protein can comprise a nucleic acid sequence having at least 99% identity with any of SEQ ID NOs: 264-266.

The nucleic acid binding protein can comprise a nucleic acid sequence having at least 100% identity with any of SEQ ID NOs: 264-266.

For example, when the protein or peptide of interest comprises a nucleic acid binding protein or peptide, the fusion protein can comprise one of the amino acid sequences shown in Table 11 below. In the sequences shown in Table 11 below, the targeting sequence is shown in boldface text, a six amino acid alanine linker is indicated by underlining, and the sequence of the nucleic acid binding protein or peptide (SASPα, SASPβ, or Hfq) is shown in plain text. Thus, for example, the fusion protein can comprise SEQ ID NO: 267, 268, or 269.

TABLE 11

Exemplary fusion proteins comprising a nucleic acid binding protein

| Fusion protein (SEQ ID NO) | Amino Acid Sequence |
|---|---|
| Met + Amino acids 20-35 of BclA, alanine linker, and SASPα (SEQ ID NO: 267) | MAFDPNLVGPTLPPIPPAAAAAAAAMAQQSRSRSNNNN DLLIPQAASAIEQMKLEIASEFGVQLGAETTSRANGSVGGE ITKRLVRLAQQNMGGQFH |
| Met + Amino acids 20-35 of BclA, alanine linker, and SASPγ (SEQ ID NO: 268) | MAFDPNLVGPTLPPIPPAAAAAAAAMANNNSGNSNNLL VPGAAQAIDQMKLEIASEFGVNLGADTTSRANGSVGGEIT KRLVSFAQQNMGGGQF |
| Met + Amino acids 20-35 of BclA, alanine linker, and Hfq (SEQ ID NO: 269) | MAFDPNLVGPTLPPIPPAAAAAAAAMKPINIQDQFLNQIR KENTYVTVFLLNGFQLRGQVKGFDNFTVLLESEGKQQLIY KHAISTFAPQKNVQLELE |

Nucleases can also be used to both bind to and cleave nucleic acid molecules. Nucleases have high affinity for RNA and DNA molecules, and exert their enzymatic activity by cleaving RNA and/or DNA molecules into smaller RNA and/or DNA fragments. Nucleases can be specific, recognizing and cleaving specific DNA or RNA sequences, or non-specific, cleaving any DNA and/or RNA that they come in contact with. Nucleases can be categorized into exonucleases (nucleases that cleave nucleotides off of the ends of RNA and/or DNA molecules), or endonucleases (nucleases that cleave a phosphodiester bond within a polynucleotide chain). Each nuclease enzyme has an active site that comprises particular amino acids that act to catalyze the cleavage of the nucleic acid molecule. Mutation of these active sites can inactivate the active site and allow for high affinity binding of the nuclease to its nucleic acid substrate, without cleavage of the substrate. Thus, such mutants can bind to and stabilize the nucleic acid molecule without cleaving the nucleic acid molecule.

Thus, the nucleic acid binding protein can comprise a nuclease (e.g., a nuclease having an inactivated active site).

When the protein or peptide of interest comprises a nucleic acid binding protein or peptide, a nucleic acid molecule can be bound to the nucleic acid binding protein or peptide. The nucleic acid can comprise, for example, a modulating RNA molecule; an RNAi molecule; a microRNA; an aptamer; or a DNA molecule that encodes a modulating RNA molecule, an RNAi molecule, a microRNA, or an aptamer.

XIII. Recombinant *Bacillus cereus* Family Member Hosts

As described above, a *Bacillus cereus* family member can serve as a host for expression of fusion proteins comprising a targeting sequence, an exosporium protein, or an exosporium protein fragment that targets the fusion protein to the exosporium of the *Bacillus cereus* family member; serve as a host for expression of modulator proteins that modulate the expression of a fusion protein; can serve as a host for overexpression of an exosporium enzyme; can be genetically inactivated; or can comprise a mutation or other genetic alteration that allows for collection of free exosporium.

The recombinant *Bacillus cereus* family member can coexpress two or more of any of the fusion proteins discussed above. For example, the recombinant *Bacillus cereus* family member can coexpress at least one fusion protein that comprises a plant binding protein or peptide, together with a fusion protein comprising a plant growth stimulating protein or peptide, a fusion protein comprising a protein or peptide that protects a plant from a pathogen, a fusion protein comprising protein or peptide that enhances stress resistance in a plant, a fusion protein comprising an enzyme that catalyzes the production of nitric oxide, or a fusion protein comprising a nucleic acid binding protein or peptide.

The recombinant *Bacillus cereus* family member can comprise any *Bacillus* species that is capable of producing an exosporium. For example, the recombinant *Bacillus cereus* family member can comprise *Bacillus anthracis*, *Bacillus cereus*, *Bacillus thuringiensis*, *Bacillus mycoides*, *Bacillus pseudomycoides*, *Bacillus samanii*, *Bacillus gaemokensis*, *Bacillus weihenstephensis*, *Bacillus toyoiensis*, or a combination thereof. In particular, the recombinant *Bacillus cereus* family member can comprise *Bacillus thuringiensis* or *Bacillus mycoides*.

To generate a recombinant *Bacillus cereus* family member expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *B. cereus* family member host. The recombinant *Bacillus cereus* family member can then exposed to conditions which will induce sporulation. Suitable conditions for inducing sporulation are known in the art. For example, the recombinant *Bacillus cereus* family member can be plated onto agar plates, and incubated at a temperature of about 30° C. for several days (e.g., 3 days).

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family member spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with gluteraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Many *Bacillus cereus* family member strains have inherent beneficial attributes. For example, some strains have plant-growth promoting effects. Any of the recombinant Bacillus cereus family members described herein can comprise a plant-growth promoting strain of bacteria.

The plant-growth promoting strain of bacteria can comprise a strain of bacteria that produces an insecticidal toxin (e.g., a Cry toxin), produces a fungicidal compound (e.g., a β-1,3-glucanase, a chitosanase, a lyticase, or a combination thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

For example, where the recombinant Bacillus cereus family member comprises a plant-growth promoting strain of bacteria, the plant growth-promoting strain of bacteria can comprise (a) Bacillus mycoides BT155 (NRRL No. B-50921), (b) Bacillus mycoides EE118 (NRRL No. B-50918), (c) Bacillus mycoides EE141 (NRRL No. B-50916), (d) Bacillus mycoides BT46-3 (NRRL No. B-50922), (e) Bacillus cereus family member EE128 (NRRL No. B-50917), (f) Bacillus thuringiensis BT013A (NRRL No. B-50924), (g) Bacillus cereus family member EE349 (NRRL No. B-50928), (h) Bacillus cereus family member EE-B00377 (NRRL B-67119), (i) Bacillus pseudomycoides EE-B00366 (NRRL B-67120), or (j) Bacillus mycoides EE-B00363 (NRRL B-67121). Each of the strains (a) through (g) was deposited with the United States Department of Agriculture (USDA) Agricultural Research Service (ARS), having the address 1815 North University Street, Peoria, Ill. 61604 U.S.A., on Mar. 10, 2014, and is identified by the NRRL deposit number provided in parentheses. Bacillus thuringiensis BT013A is also known as Bacillus thuringiensis 4Q7. Each of the strains (h) through (j) were deposited with the USDA ARS on Aug. 19, 2015, and is identified by the NRRL deposit number provided in parentheses. It is hereby certified that the deposits were made in compliance with the terms of the Budapest Treaty and that: (a) during the pendency of this application, access to the deposited organisms will be afforded to the Commissioner upon request; (b) all restrictions upon availability to the public of the deposited materials will be irrevocably removed upon granting of the patent, subject to 37 C.F.R. § 1.808(b); (c) the deposit will be maintained for a period of 30 years or 5 years after the last request or for the effective life of the patent, whichever is longer; and (d) the deposit will be replaced if it should ever become non-viable.

These plant-growth promoting strains were isolated from the rhizospheres of various vigorous plants and were identified by their 16S rRNA sequences (listed below in Table 12), and through biochemical assays. The strains were identified at least to their genus designation by means of conventional biochemistry and morphological indicators. Biochemical assays for confirmed Gram-positive strains such as Bacillus included growth on PEA medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility. Identification of these strains and demonstration of their plant-growth promoting effects are described further in the Examples hereinbelow.

TABLE 12

Partial 16S rRNA sequences for plant-growth promoting Bacillus cereus family members

| Strain | SEQ ID NO. for partial 16S ribosomal RNA sequence |
|---|---|
| Bacillus mycoides EE118 | 270 |
| Bacillus mycoides EE141 | 271 |
| Bacillus mycoides BT46-3 | 272 |
| Bacillus cereus family member EE128 | 273 |
| Bacillus thuringiensis BT013A | 274 |
| Bacillus cereus family member EE349 | 275 |
| Bacillus mycoides BT155 | 276 |

For example, the recombinant Bacillus cereus family member comprising a plant-growth promoting strain of bacteria can comprise Bacillus mycoides BT155, Bacillus mycoides EE141, or Bacillus thuringiensis BT013A.

The recombinant Bacillus cereus family member can comprises an endophytic strain of bacteria. For example, the endophytic strain of bacteria can comprise Bacillus cereus family member EE349, Bacillus cereus family member EE439, Bacillus thuringiensis EE417, Bacillus cereus EE444, or Bacillus thuringiensis EE319, Bacillus thuringiensis EE-B00184, Bacillus cereus family member EE-B00377; Bacillus pseudomycoides EE-B00366; or Bacillus mycoides EE-B00363.

Bacillus cereus family member EE349 is also a plant growth promoting strain of bacteria and is described above. As discussed further in the Examples below, Bacillus cereus family member EE349 has also been found to be endophytic.

Bacillus cereus family member EE439, Bacillus thuringiensis EE417, Bacillus cereus EE444, Bacillus thuringiensis EE319, Bacillus thuringiensis EE-B00184, Bacillus cereus family member EE-B00377; Bacillus pseudomycoides EE-B00366; or Bacillus mycoides EE-B00363 are described further below in Section XIV.

The endophytic strain of bacteria can comprise Bacillus cereus family member EE439, Bacillus thuringiensis EE417, Bacillus cereus EE444, Bacillus thuringiensis EE319, Bacillus thuringiensis EE-B00184, Bacillus cereus family member EE-B00377; Bacillus pseudomycoides EE-B00366; or Bacillus mycoides EE-B00363.

The recombinant Bacillus cereus family member can comprise a strain of bacteria that is capable of degrading an herbicide or a pesticide. As discussed further below in the Examples, Bacillus cereus family member EE349, Bacillus cereus family member EE-B00377, Bacillus pseudomycoides EE-B00366, and Bacillus mycoides EE-B00363 have been found to be capable of degrading herbicides and/or pesticides. Thus, when the recombinant Bacillus cereus family member comprises a strain of bacteria that is capable of degrading an herbicide, the strain of bacteria that is capable of degrading an herbicide can comprise Bacillus cereus family member EE349, Bacillus cereus family member EE-B00377, Bacillus pseudomycoides EE-B00366, or Bacillus mycoides EE-B00363.

The strain of bacteria that is capable of degrading an herbicide or a pesticide can degrade a sulfonylurea herbicide (e.g., sulfentrazone), an aryl triazine herbicide, dicamba, 2,4-D, a phenoxy herbicide, a pyrethrin, a pyrethroid, or a combination thereof.

The strain of bacteria that is capable of degrading a pesticide can be a strain of bacteria that is capable of degrading a pyrethrin.

The recombinant Bacillus cereus family member can comprise a probiotic strain of bacteria. For example, the probiotic strain of bacteria can comprise *Bacillus cereus* family member EE349, *Bacillus cereus* family member EE439, *Bacillus thuringiensis* EE417, or *Bacillus cereus* EE444.

The recombinant *Bacillus cereus* family member can comprise an inactivating mutation in its BclA gene, its CotE gene, or its CotO gene (e.g., a knock-out of the BclA gene, CotE gene, or CotO gene). For example, the recombinant *Bacillus cereus* family member can comprise an inactivating mutation in its BclA gene (e.g., a knock-out of the BclA gene). It has been found that expression of fusion proteins in a recombinant *Bacillus cereus* family member having such a mutation results in increased expression levels of the fusion protein.

XIV. Endophytic Bacterial Strains

The present invention further relates to endophytic bacterial strains. While many bacteria of the rhizosphere have a symbiotic relationship with the plant, only a small subset of these bacteria are capable of being internalized into the plant and growing endophytically. As described further in the Examples hereinbelow, several *Bacillus cereus* family member strains and several non-*Bacillus cereus* family member bacterial strains were isolated from corn seedlings and found to have the ability to grow endophytically in plants.

A. Endophytic *Bacillus cereus* Family Members

The present invention relates to biologically pure bacterial cultures of bacteria that have the ability to grow endophytically. The bacterial strain in each of these bacterial cultures can be: (a) *Bacillus cereus* family member EE439 (NRRL B-50979); (b) *Bacillus thuringiensis* EE417 (NRRL B-50974); (c) *Bacillus cereus* EE444 (NRRL B-50977); (d) *Bacillus thuringiensis* EE319 (NRRL B-50983), (e) *Bacillus thuringiensis* EE-B00184 (NRRL B-67122); (f) *Bacillus cereus* family member EE-B00377 (NRRL B-67119); (g) *Bacillus pseudomycoides* EE-B00366 (NRRL B-67120); or (h) *Bacillus mycoides* EE-B00363 (NRRL B-67121). Each of strains (a) through (c) was deposited with the United States Department of Agriculture (USDA) Agricultural Research Service (ARS), having the address 1815 North University Street, Peoria, Ill. 61604 U.S.A., on Sep. 10, 2014, and are identified by the NRRL numbers provided in parentheses following the names of each strain. Strain (d) was deposited with the USDA ARS on Sep. 17, 2014 and is identified by the NRRL number provided in parentheses following the name of the strain. Each of strains (e) through (h) was deposited with the USDA ARS on Aug. 19, 2015 and are identified by the NRRL numbers provided in parentheses following the names of each strain. It is hereby certified that the deposits were made in compliance with the terms of the Budapest Treaty and that: (a) during the pendency of this application, access to the deposited organisms will be afforded to the Commissioner upon request; (b) all restrictions upon availability to the public of the deposited materials will be irrevocably removed upon granting of the patent, subject to 37 C.F.R. § 1.808(b); (c) the deposit will be maintained for a period of 30 years or 5 years after the last request or for the effective life of the patent, whichever is longer; and (d) the deposit will be replaced if it should ever become non-viable.

The novel strains disclosed herein were identified by 16S ribosomal RNA (rRNA) sequencing. Thus, *Bacillus cereus* family member EE439 has a 16S ribosomal RNA sequence having at least 98%, at least 99%, or 100% sequence identity with the sequence of SEQ ID NO: 277. *Bacillus thuringiensis* EE417 has a 16S ribosomal RNA sequence having at least 98%, at least 99%, or 100% sequence identity with the sequence of SEQ ID NO: 278. *Bacillus cereus* EE444 has a 16S ribosomal RNA sequence having at least 98%, at least 99%, or 100% sequence identity with the sequence of SEQ ID NO: 279. *Bacillus thuringiensis* EE319 has a 16S ribosomal RNA sequence having at least 98%, at least 99%, or 100% sequence identity with the sequence of SEQ ID NO: 280. *Bacillus thuringiensis* EE-B00184 has a 16S ribosomal RNA sequence having at least 98%, at least 99%, or 100% sequence identity with the sequence of SEQ ID NO: 301. *Bacillus cereus* family member EE-B00377 has a 16S ribosomal RNA sequence having at least 98%, at least 99%, or 100% sequence identity with the sequence of SEQ ID NO: 304. *Bacillus pseudomycoides* EE-B00366 has a 16S ribosomal RNA sequence having at least 98%, at least 99%, or 100% sequence identity with the sequence of SEQ ID NO: 303. *Bacillus mycoides* EE-B00363 (NRRL B-67121) and the bacteria has a 16S ribosomal RNA sequence having at least 98%, at least 99%, or 100% sequence identity with the sequence of SEQ ID NO: 302. The 16S rRNA sequences are listed below in Table 13.

TABLE 13

Partial 16S rRNA sequences for *Bacillus cereus* family member endophytic strains

| Strain | SEQ ID NO. for partial 16S rRNA sequence |
|---|---|
| *Bacillus cereus* family member EE439 | 277 |
| *Bacillus thuringiensis* EE417 | 278 |
| *Bacillus cereus* EE444 | 279 |
| *Bacillus thuringiensis* EE319 | 280 |
| *Bacillus thuringiensis* EE-B00184 | 301 |
| *Bacillus mycoides* EE-B00363 | 302 |
| *Bacillus pseudomycoides* EE-B00366 | 303 |
| *Bacillus cereus* family member EE-B00377 | 304 |

The present invention further relates to a biologically pure bacterial culture wherein the bacteria in the bacterial culture are mutants of *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363 comprising one or more mutations, wherein the bacteria are endophytic.

B. Other Endophytic Bacterial Strains

The present invention also relates to other biologically pure bacterial cultures of bacteria (non-*Bacillus cereus* family members) that have the ability to grow endophytically. These strains were isolated from corn seedlings, as described in detail below in the Examples.

The bacterial strain in each of these bacterial cultures can be (a) *Bacillus megaterium* EE385 (NRRL B-50980), (b) *Bacillus* sp. EE387 (NRRL B-50981), (c) *Bacillus circulans* EE388 (NRRL B-50982), (d) *Bacillus subtilis* EE405 (NRRL B-50978), (e) *Lysinibacillus fusiformis* EE442 (NRRL B-50975), (f) *Lysinibcaillus sphaericus* EE443 (NRRL B-50976), or (g) *Bacillus pumilus* EE-B00143 (NRRL B-67123). Each of the strains (a) through (f) was deposited with the United States Department of Agriculture (USDA) Agricultural Research Service (ARS), having the address 1815 North University Street, Peoria, Ill. 61604 U.S.A., on Sep. 10, 2014, and are identified by the NRRL numbers provided in parentheses following the names of each strain. Following deposit, *Bacillus* sp. EE387 was determined to be a *Bacillus pumilus*-like strain. Strain (g) was deposited with the USDA ARS on Aug. 19, 2015 and is identified by the NRRL number provided in parentheses following its name.

The novel strains disclosed herein were identified by 16S ribosomal RNA (rRNA) sequencing. Thus, *Bacillus megaterium* EE385 has a 16S ribosomal RNA sequence having at least 98%, at least 99%, or 100% sequence identity with the sequence of SEQ ID NO: 281. *Bacillus* sp. EE387 has a 16S ribosomal RNA sequence having at least 98%, at least 99%, or 100% sequence identity with the sequence of SEQ ID NO: 282. *Bacillus circulans* EE388 has a 16S ribosomal RNA sequence having at least 98%, at least 99%, or 100% sequence identity with the sequence of SEQ ID NO: 283. *Bacillus subtilis* EE405 has a 16S ribosomal RNA sequence having at least 98%, at least 99%, or 100% sequence identity with the sequence of SEQ ID NO: 284. *Lysinibacillus fusiformis* EE442 has a 16S ribosomal RNA sequence having at least 98%, at least 99%, or 100% sequence identity with the sequence of SEQ ID NO: 285. *Lysinibcaillus sphaericus* EE443 has a 16S ribosomal RNA sequence having at least 98%, at least 99%, or 100% sequence identity with the sequence of SEQ ID NO: 286. *Bacillus pumilus* EE-B00143 has a 16S ribosomal RNA sequence having at least 98%, at least 99%, or 100% sequence identity with the sequence of SEQ ID NO: 305. The 16s rRNA sequences are listed below in Table 14.

TABLE 14

Partial 16S rRNA sequences for non-*Bacillus cereus* family member endophytic strains

| Strain (SEQ ID NO) | SEQ ID NO. for partial 16S rRNA sequence |
|---|---|
| *Bacillus megaterium* EE385 | 281 |
| *Bacillus* sp. EE387 | 282 |
| *Bacillus circulans* EE388 | 283 |
| *Bacillus subtilis* EE405 | 284 |
| *Lysinibacillus fusiformis* EE442 | 285 |
| *Lysinibcaillus sphaericus* EE443 | 286 |
| *Bacillus pumilus* EE-B00143 | 305 |

The present invention further relates to a biologically pure bacterial culture wherein the bacteria in the bacterial culture are mutants of *Bacillus megaterium* EE385, *Bacillus* sp. EE387, *Bacillus circulans* EE388, *Bacillus subtilis* EE405, *Lysinibacillus fusiformis* EE442, or *Lysinibcaillus sphaericus* EE443, comprising one or more mutations, wherein the bacteria are endophytic.

The present invention also relates to a biologically pure bacterial culture wherein the bacteria in the bacterial culture are mutants of *Bacillus megaterium* EE385, *Bacillus* sp. EE387, *Bacillus circulans* EE388, *Bacillus subtilis* EE405, *Lysinibacillus fusiformis* EE442, or *Lysinibcaillus sphaericus* EE443, comprising one or more mutations, wherein the bacteria are probiotic.

XV. Inoculums

The invention further relates to inoculums of any of the biologically pure bacterial strains described above in the preceding section. The inoculums are for application to plants, plant seeds, a plant growth medium, or an area surrounding a plant or a plant seed, wherein the inoculum comprises an effective amount of any one of the biologically pure bacterial cultures and an agriculturally acceptable carrier.

The inoculum can comprise an effective amount of a mixture comprising at least two of the biologically pure bacterial cultures described above in the immediately preceding section.

The inoculum can further comprise an effective amount of a rhizobacteria. The rhizobacteria can be a biologically pure bacterial culture of a rhizobacteria strain. The rhizobacteria can comprise *Bradyrhizobium* genus bacteria (e.g., *Bradyrhizobium japonicum*), *Rhizobium* genus bacteria (e.g., *Rhizobium phaseoli*, *Rhizobium leguminosarum*, or a combination thereof), or a combination thereof.

XVI. Plant Seeds Coated with an Enzyme that Catalyzes the Production of Nitric Oxide or with Recombinant Bacteria that Overexpress an Enzyme that Catalyzes the Production of Nitric Oxide A plant seed is also provided which is coated with: (i) an enzyme that catalyzes the production of nitric oxide; (ii) a superoxide dismutase or (iii) a recombinant microorganism that expresses an enzyme that catalyzes the production of nitric oxide or a superoxide dismutase, wherein the expression of the enzyme that catalyzes the production of nitric oxide or the superoxide dismutase is increased as compared to the expression of the enzyme that catalyzes the production of nitric oxide or the superoxide dismutase in a wild-type microorganism under the same conditions.

The enzyme that catalyzes the production of nitric oxide can comprise a nitric oxide synthase or an arginase.

The enzyme that catalyzes the production of nitric oxide can comprise a nitric oxide synthase, such as a nitric oxide synthase from *Bacillus thuringiensis* BT013A or *Bacillus subtilis* 168.

For example, the nitric oxide synthase can comprise an amino acid sequence having at least 85% sequence identity with SEQ ID NO: 260 or 261.

The nitric oxide synthase can comprise an amino acid sequence having at least 90% sequence identity with SEQ ID NO: 260 or 261.

The nitric oxide synthase can comprise an amino acid sequence having at least 95% sequence identity with SEQ ID NO: 260 or 261.

The nitric oxide synthase can comprise an amino acid sequence having at least 98% sequence identity with SEQ ID NO: 260 or 261.

The nitric oxide synthase can comprise an amino acid sequence having at least 99% sequence identity with SEQ ID NO: 260 or 261.

The nitric oxide synthase can comprise an amino acid sequence having 100% sequence identity with SEQ ID NO: 260 or 261.

The superoxide dismutase can comprise superoxide dismutase 1 (SODA1) or superoxide dismutase 2 (SODA2).

The superoxide dismutase comprises an amino acid sequence having at least 85% identity with SEQ ID NO: 155 or 156.

The superoxide dismutase comprises an amino acid sequence having at least 90% identity with SEQ ID NO: 155 or 156.

The superoxide dismutase comprises an amino acid sequence having at least 95% identity with SEQ ID NO: 155 or 156.

The superoxide dismutase comprises an amino acid sequence having at least 98% identity with SEQ ID NO: 155 or 156.

The superoxide dismutase comprises an amino acid sequence having at least 99% identity with SEQ ID NO: 155 or 156.

The superoxide dismutase comprises an amino acid sequence having at least 100% identity with SEQ ID NO: 155 or 156.

When the plant seed is coated with the recombinant microorganism, the recombinant microorganism can comprise a *Bacillus* species, *Escherechia coli*, an *Aspergillus* species such as *Aspergillus niger*, or a *Saccharomyces* species such as *Saccharomyces cerevisiae*.

For example, the recombinant microorganism can comprise a *Bacillus cereus* family member, *Bacillus subtilis*, *Bacillus licheniformis*, or *Bacillus megaterium*.

Amino acid sequences for exemplary nitric oxide synthetase enzymes are provided above in Table 8. Amino acid sequences for exemplary superoxide dismutases are provided above in Table 2.

XVII. Formulations

Formulations are provided which comprise a recombinant *Bacillus cereus* family member as described herein, exosporium fragments derived from spores of a recombinant *Bacillus cereus* family member as described herein or a recombinant spore-forming bacterium as described herein, and an agriculturally acceptable carrier.

The agriculturally acceptable carrier can comprise an additive, such as an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material, or a combination thereof.

The agriculturally acceptable carrier can comprise a thickener, such as a long chain alkylsulfonate of polyethylene glycol, a polyoxyethylene oleate, or a combination thereof; a surfactant such as a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof; or an anti-caking agent such as a sodium salt (e.g., a sodium salt of monomethyl naphthalene sulfonate, a sodium salt of dimethyl naphthalene sulfonate, a sodium sulfite, a sodium sulfate, or a combination thereof), a calcium carbonate, diatomaceous earth, or a combination thereof.

The additive can comprise a proteinaceous material such as a milk product, wheat flour, soybean meal, blood, albumin, gelatin, alfalfa meal, yeast extract, or a combination thereof;

The agriculturally acceptable carrier can comprise vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

The formulation can comprise a seed coating formulation, a liquid formulation for application to plants or to a plant growth medium, or a solid formulation for application to plants or to a plant growth medium. The seed coating formulation can comprise an aqueous or oil-based solution for application to seeds or a powder or granular formulation for application to seeds. The liquid formulation for application to plants or to a plant growth medium can comprise a concentrated formulation or a ready-to-use formulation. The solid formulation for application to plants or to a plant growth medium can comprise a granular formulation or a powder agent.

The formulation further can comprise a fertilizer, a micronutrient fertilizer material, an insecticide, an herbicide, a plant growth amendment, a fungicide, an insecticide, a molluscicide, an algicide, a bacterial inoculant, a fungal inoculant, or a combination thereof.

The bacterial inoculant can comprise a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillum*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

The bacterial inoculant can comprise a plant-growth promoting strain of bacteria. The plant-growth promoting strain of bacteria can produce an insecticidal toxin, produce a fungicidal compound, produce a nematocidal compound, produce a bacteriocidal compound, can be resistant to one or more antibiotics, can comprise one or more freely replicating plasmids, bind to plant roots, colonize plant roots, form biofilms, solubilize nutrients, secrete organic acids, or combinations thereof.

For example, the bacterial inoculant can comprise *Bacillus aryabhattai* CAP53 (NRRL No. B-50819), *Bacillus* aryabhattai CAP56 (NRRL No. B-50817), *Bacillus flexus* BT054 (NRRL No. B-50816), *Paracoccus kondratievae* NC35 (NRRL No. B-50820), *Bacillus mycoides* BT155 (NRRL No. B-50921), *Enterobacter cloacae* CAP12 (NRRL No. B-50822), *Bacillus nealsonii* BOBA57 (NRRL No. NRRL B-50821), *Bacillus mycoides* EE118 (NRRL No. B-50918), *Bacillus subtilis* EE148 (NRRL No. B-50927), *Alcaligenes faecalis* EE107 (NRRL No. B-50920), *Bacillus mycoides* EE141 (NRRL NO. B-50916), *Bacillus mycoides* BT46-3 (NRRL No. B-50922), *Bacillus cereus* family member EE128 (NRRL No. B-50917), *Bacillus thuringiensis* BT013A (NRRL No. B-50924), *Paenibacillus massiliensis* BT23 (NRRL No. B-50923), *Bacillus cereus* family member EE349 (NRRL No. B-50928), *Bacillus subtilis* EE218 (NRRL No. B-50926), *Bacillus megaterium* EE281 (NRRL No. B-50925), *Bacillus cereus* family member EE-B00377 (NRRL B-67119); *Bacillus pseudomycoides* EE-B00366 (NRRL B-67120), *Bacillus mycoides* EE-B00363 (NRRL B-67121), *Bacillus pumilus* EE-B00143 (NRRL B-67123), or *Bacillus thuringiensis* EE-B00184 (NRRL B-67122) or a combination thereof. Each of these strains was deposited with the United States Department of Agriculture (USDA) Agricultural Research Service (ARS), having the address 1815 North University Street, Peoria, Ill. 61604 U.S.A., on Mar. 7, 2013 (*Bacillus* aryabhattai CAP53, *Bacillus* aryabhattai CAP56, *Bacillus flexus* BT054, *Paracoccus kondratievae* NC35, *Enterobacter cloacae* CAP12, and *Bacillus nealsonii* BOBA57), on Mar. 10, 2014 (*Bacillus mycoides* BT155, *Bacillus mycoides* EE118, *Bacillus subtilis* EE148, *Alcaligenes faecalis* EE107, *Bacillus mycoides* EE141, *Bacillus mycoides* BT46-3, *Bacillus cereus* family member EE128, *Bacillus thuringiensis* BT013A, *Paenibacillus massiliensis* BT23, *Bacillus cereus* family member EE349, *Bacillus subtilis* EE218, and *Bacillus megaterium* EE281), or on Aug. 19, 2015 (*Bacillus cereus* family member EE-B00377; *Bacillus pseudomycoides* EE-B00366, *Bacillus mycoides* EE-B00363, *Bacillus pumilus* EE-B00143, or *Bacillus thuringiensis* EE-B00184) and is identified by the NRRL numbers provided in parentheses.

These plant-growth promoting strains were isolated from the rhizospheres of various vigorous plants and were identified by their 16S rRNA sequences, and through biochemical assays. The strains were identified at least to their genus designation by means of conventional biochemistry and morphological indicators. Biochemical assays for confirmed Gram-negative strains such as *Paracoccus kondratievae, Alcaligenes faecalis*, and *Enterobacter cloacae* included growth on MacConkey medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; starch hydrolysis; oxidase reaction, catalase production, urease production and motility. Similarly, the biochemical assays for confirmed Gram-positive strains such as *Bacillus* and *Paenibacillus* included growth on PEA medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility. Identification of these strains and demonstration of their plant-growth promoting effects are described further in the Examples hereinbelow. Partial 16S rRNA sequences for the strains *Bacillus mycoides* BT155, *Bacillus mycoides* EE118, *Bacillus mycoides* EE141, *Bacillus mycoides* BT46-3, *Bacillus cereus* family member EE128, *Bacillus thuringiensis* BT013A, and *Bacillus cereus* family member EE349 are provided in Table 12 above. Partial 16S rRNA sequences for the strains *Bacillus aryabhattai* CAP53, *Bacillus aryabhattai* CAP56, *Bacillus flexus* BT054, *Paracoccus kondratievae* NC35, *Enterobacter cloacae* CAP12, *Bacillus nealsonii* BOBA57, *Bacillus subtilis* EE148, *Alcaligenes faecalis* EE107, *Paenibacillus massiliensis* BT23, *Bacillus subtilis* EE218, and *Bacillus megaterium* EE281 are listed in Table 15 below.

TABLE 15

Partial 16S rRNA sequences for additional plant-growth promoting strains of bacteria

| Strain | SEQ ID NO. for partial 16S ribosomal RNA sequence |
|---|---|
| *Bacillus aryabhattai* CAP53 | 287 |
| *Bacillus aryabhattai* CAP56 | 288 |
| *Bacillus flexus* BT054 | 289 |
| *Paracoccus kondratievae* NC35 | 290 |
| *Enterobacter cloacae* CAP12 | 291 |
| *Bacillus nealsonii* BOBA57 | 292 |
| *Bacillus subtilis* EE148 | 293 |
| *Alcaligenes faecalis* EE107 | 294 |
| *Paenibacillus massiliensis* BT23 | 295 |
| *Bacillus subtilis* EE218 | 296 |
| *Bacillus megaterium* EE281 | 297 |

For example, the formulation can comprise a plant-growth promoting strain of bacteria comprising *Paracoccus kondratievae* NC35, *Bacillus aryabhattai* CAP53, or *Bacillus megaterium* EE281, wherein the formulation further comprises any of the recombinant *Bacillus cereus* family members described herein, including any of the recombinant plant-growth promoting *Bacillus cereus* family member strains herein (e.g., recombinant *Bacillus mycoides* BT155, *Bacillus mycoides* EE141, or *Bacillus thuringiensis* BT013A).

The fungal inoculant can comprise a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof.

The spore-forming bacterium, alone or in combination with the insecticide, can further comprise an effective amount of at least one fungicide.

Typical fungicidal ingredients also include Captan (N-trichloromethyl)thio-4-cyclohexane-1,2-dicarboximide), Fludioxoni 1 (4-(2,2-difluoro-1,3-benzodioxol-4-yl)-1-H-pyrrol-3-carbonitril; carbendazim iprodione (commercially available under the tradename Rovral®), tebuconazole, thiabendazole, azoxystrobin, prochloraz, and Oxadixyl (N-(2, 6-dimethylphenyl)-2-methoxy-N-(2-oxo-3-oxazolidinyl) acetamide).

If a formulation, plant seed, or inoculum comprises a fungicide, the fungicide can comprise aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, boscalid, bromuconazole, bupirimate, buthiobate, calcium polysulphide, capsimycin, captafol, captan, carbendazim, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, dimethirimol, dimethomorph, dimoxystrobin, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, prothiocinazole, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, tioxymid, tolclofos-methyl, tolylfluanid, triadimefon, triadimenol, triazbutil, triazoxide, trichlamide, tricyclazole, tridemorph, trifloxystrobin, triflumizole, triforine, uniconazole, validamycin A, vinclozolin, viniconazole, zarilamide, zineb, ziram and also Dagger G, OK-8705, OK-8801, a-(1,1-dimethylethyl)-(3-(2-phenoxyethyl)-1H-1,2,4-triazole-1-ethanol, a-(2,4-dichlorophenyl)-[3-fluoro-3-propyl-1H-1,2,4-triazole-1-ethanol, a-(2,4-dichlorophenyl)-[3-methoxy-a-methyl-1H-1,2,4-triazol e-1-ethanol, a-(5-methyl-1,3-dioxan-5-yl)-[3-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenyl methyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1, 3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-(3-D-glycopyranosyl)-a-D-glucopyranos yl]-amino]-4-methoxy-1H-pyrrolo [2,3-d] pyrimidine-5-carbonitrile, 2-aminobutane, 2-bromo-2-(bromomethyl)-pentanedinitrile, 2-chloro-N-(2,3-dihydro-1, 3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4, 5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2, 5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethyl phenyl)-2-methoxy-N-(tetra hydro-2-oxo-3-furanyl)-acetamide, N-(2,6-dimethyl phenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5, 6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, 0,0-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, and spiro [2H]-1-benzopyrane-2,1'(3'H)-isobenzofuran]-3'-one, N-trichloromethyl)thio-4-cyclohexane-1,2-dicarboximide, tetramethylthioperoxydicarbonic diamide, methyl N-(2,6-dimethylphenyl)-N-(methoxyacetyl)-DL-alaninate, 4-(2,2-difluoro-1,3-benzodioxol-4-yl)-1-H-pyrrol-3-carbonitril or a combination thereof.

Additionally, suitable fungicides include the following: (1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid; (2) a compound capable to inhibit the mitosis and cell division like benomyl, carbendazim, diethofencarb, ethaboxam, fuberidazole, pencycuron, thiabendazole thiophanate-methyl, zoxamide; (3) a compound capable to inhibit the respiration for example as CI-respiration inhibitor like diflumetorim; as CII-respiration inhibitor like boscalid, fenfuram, flutolanil, furametpyr, furmecyclox, mepronil, oxycarboxine, penthiopyrad, thifluzamide; as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, trifloxystrobin; (4) a compound capable of to act as an uncoupler like dinocap, fluazinam, meptyldinocap; (5) a compound capable to inhibit ATP production like fentin acetate, fentin chloride, fentin hydroxide; (6) a compound capable to inhibit AA and protein biosynthesis like andoprim, blasticidin-S, cyprodinil, kasugamycin, kasugamycin hydrochloride hydrate, mepanipyrim, pyrimethanil; (7) a compound capable to inhibit the signal transduction like fenpiclonil, quinoxyfen; (8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin; (9) a compound capable to inhibit ergosterol biosynthesis like aldimorph, azaconazole, bitertanol, bromuconazole, cyproconazole, diclobutrazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, uniconazole, viniconazole, voriconazole; (10) a compound capable to inhibit cell wall synthesis like benthiavalicarb, bialaphos, dimethomorph, flumorph, iprovalicarb, mandipropamid, polyoxins, polyoxorim, validamycin A; (11) a compound capable to inhibit melanine biosynthesis like carpropamid, diclocymet, fenoxanil, phthalide, pyroquilon, tricyclazole; (12) a compound capable to induce a host defense like acibenzolar-S-methyl, probenazole, tiadinil; (13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, tolylfluanid, zineb, ziram; (14) a compound selected in the following list: (2E)-2-(2-{[6-(3-chloro-2-methylphenoxy)-5-fluoropyrimidin-4-yl]oxy}pheny-1)-2-(methoxyimino)-N-methylacetamide, (2E)-2-{2-[({[(1E)-1-(3-{[(E)-1-fluoro-2-phenylvinyl]oxy}phenyl)ethyliden-e]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylat-e, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]t-riazolo[1,5-a]pyrimidin-7-amine, 5-chloro-7-(4-methylpiperidin-1-yl)-6-(2,4,6-trifluorophenyl) [1,2,4]triazolo[1,5-a]pyrimidine, 5-chloro-N-[(1R)-1,2-dimethylpropyl]-6-(2,4,6-trifluorophenyl) [1,2,4]triazolo[1,5-a]pyrimidin-7-amine, 8-hydroxyquino line sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl-}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-[2-(1,3-dimethylbutyl)phenyl]-5-fluoro-1,3-dimethyl-1H-pyrazole-4-carbo-xamide, N-(3',4'-dichloro-5-fluorobiphenyl-2-yl)-3-(difluoromethyl)-1-meth-yl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)pheny-1]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N&-It;-(methylsulfonyl)valinamide, N-{(Z)-[(cyclopropylmethoxy)imino][6-(difluoromethoxy)-2,3-difluorophenyl-]methyl}-2-phenylacetamide, N-{2-[1,1'-bi(cyclopropyl)-2-yl]phenyl}-3-(difluoromethyl)-, 1-methyl-1H-pyrazole-4-carboxamide, N-{2-[3-chloro-5-(trifluoromethyl)pyridin-2-yl]ethyl}-2-(trifluoromethyl)-benzamide, natamycin, N-ethyl-N-methyl-N'-{2-methyl-5-(trifluoromethyl)-4-[3-(trimethylsilyl)pr-poxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, tecloftalam, tecnazene, triazoxide, trichlamide, valiphenal, zarilamid.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

If a formulation, plant seed, or inoculum comprises a fungicide, the fungicide can be a foliar fungicide. Foliar fungicides include copper, mancozeb, penthiopyrad, triazoles, cyproconazole, metconazole, propiconazole, prothioconazole, tebuconazole, azoxystrobin, pyraclastobin, fluoxastrobin, picoxystrobin, trifloxystrobin, sulfur, boscalid, thiophanate methyl, chlorothanonil, penthiopyrad, difenconazole, flutriafol, cyprodinil, fluzinam, iprodione, penflufen, cyazofamid, flutolanil, cymoxanil, dimethomorph, pyrimethanil, zoxamide, mandipropamid, metrinam, propamocarb, fenamidone, tetraconazole, chloronab, hymexazol, tolclofos, and fenbuconazole.

If a formulation, plant seed, or inoculum comprises a bacterial inoculant of the genus *Bacillus*, the bacterial inoculant can comprise *Bacillus argri, Bacillus aizawai, Bacillus albolactis, Bacillus amyloliquefaciens, Bacillus cereus, Bacillus coagulans, Bacillus endoparasiticus, Bacillus endorhythmos, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus* spp., *Bacillus subtilis, Bacillus thuringiensis, Bacillus unifagellatu*, or a combination thereof plus those listed in the category of *Bacillus* Genus in Bergey's Manual of Systematic Bacteriology, First Ed. (1986), hereby incorporated in full by reference.

If a formulation, plant seed, or inoculum comprises an insecticide, the insecticide can be a nematicide. Suitable nematicides include antibiotic nematicides such as abamectin; carbaate nematicides such as acetoprole, *Bacillus chitonosporus*, chloropicrin, benclothiaz, benomyl, *Burholderia cepacia*, carbofuran, carbosulfan, and cleothocard; dazomet, DBCP, DCIP, alanycarb, aldicarb, aldoxycarb, oxamyl, diamidafos, fenamiphos, fosthietan, phosphamidon, cadusafos, chlorpyrifos, diclofenthion, dimethoate, ethoprophos, fensulfothion, fostiazate, harpins, heterophos, imicyafos, isamidofos, isazofos, methomyl, mecarphon, *Myrothecium verrucaria, Paecilomyces lilacinus*, phorate, phosphocarb, terbufos, thionazin, triazophos, dazomet, 1,2-dicloropropane, 1,3-dichloropropene, furfural, iodomethane, metam, methyl bromide, methyl isothiocyanate, and xylenols.

For example and without limitation, the nematicide and insecticide can be provided in the form of the commercial product Avicta Duo, which is a mixture of abamectin and thiamethoxam commercially available from Syngenta.

If a formulation, plant seed, or inoculum comprises a bactericide, it may include streptomycin, penicillins, tetracyclines, ampicillin, and oxolinic acid.

The fertilizer can comprise a liquid fertilizer. The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The fertilizer can comprise ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesium limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination thereof.

A formulation, plant seed, or inoculum can also include at least one biological control agent selected from (1) bacteria, in particular spore-forming bacteria, (2) fungi or yeasts, and (3) isoflavones. Preference is given to combinations comprising as biological control agent a bacterium, in particular a spore-forming, root-colonizing bacterium, or a bacterium useful as biofungicide, selected from the group consisting of [Group (1)]: (1.1) *Bacillus agri*, (1.2) *Bacillus aizawai*, (1.3) *Bacillus albolactis*, (1.4) *Bacillus amyloliquefaciens*, (1.5) *Bacillus cereus*, (1.6) *Bacillus coagulans*, (1.7) *Bacillus endoparasiticus*, (1.8) *Bacillus endorhythmos*, (1.9), (1.10) *Bacillus kurstaki*, (1.11) *Bacillus lacticola*, (1.12) *Bacillus lactimorbus*, (1.13) *Bacillus lactis*, (1.14) *Bacillus laterosporus*, (1.15) *Bacillus lentimorbus*, (1.16) *Bacillus licheniformis*, (1.17) *Bacillus medusa*, (1.18) *Bacillus megaterium*, (1.19) *Bacillus metiens*, (1.20) *Bacillus natto*, (1.21) *Bacillus nigrificans*, (1.22) *Bacillus popillae*, (1.23) *Bacillus pumilus*, (1.24) *Bacillus siamensis*, (1.25) *Bacillus sphaericus* (products known as VectoLex.sup.S), (1.26) *Bacillus subtilis*, or *B. subtilis* var. *amyloliquefaciens*, (1.27) *Bacillus thuringiensis*, in particular *B. thuringiensis* var. *israelensis* (products known as VectoBac®) or *B. thuringiensis* subsp. *aizawai* strain ABTS-1857 (products known as XenTari), or *B. thuringiensis* subsp. *kurstaki* strain HD-1 (products known as Dipel ES), (1.28) *Bacillus uniflagellatus*, (1.29) *Delftia acidovorans*, in particular strain RAY209 (products known as BioBoost), (1.30) *Lysobacter antibioticus*, in particular strain 13-1 (Biological Control 2008, 45, 288-296), (1.31) *Lysobacter enzymogenes*, in particular strain 3.1T8, (1.32) *Pseudomonas chlororaphis*, in particular strain MA 342 (products known as Cedomon), (1.33) *Pseudomonas proradix* (products known as Proradix®), (1.34) *Streptomyces galbus*, in particular strain K61 (products known as Mycostop®, cf. Crop Protection 2006, 25, 468-475), (1.35) *Streptomyces griseoviridis* (products known as Mycostop®).

Preference is further given to combinations comprising as biological control agent a fungus or a yeast selected from the group consisting of [Group (2)]: (2.1) *Ampelomyces quisqualis*, in particular strain AQ 10 (product known as AQ 10®), (2.2) *Aureobasidium pullulans*, in particular blastospores of strain DSM14940 or blastospores of strain DSM 14941 or mixtures thereof (product known as Blossom Protect®), (2.3) *Beauveria bassiana*, in particular strain ATCC 74040 (products known as Naturalis®), (2.4) *Candida oleophila*, in particular strain O (products known as Nexy), (2.5) *Cladosporium cladosporioides* H39 (cf. Eur. J. Plant Pathol. 2009, 123, 401-414), (2.6), (2.7) *Dilophosphora alopecuri* (products known as Twist Fungus), (2.8) *Gliocladium catenulatum*, in particular strain J1446 (products known as Prestop), (2.9) *Lecanicillium lecanii* (formerly known as *Verticillium lecanii*), in particular conidia of strain KV01 (products known as Mycotal®, Vertalec®), (2.10) Metarhizium anisopliea (products known as BIO 1020), (2.11) *Metschnikovia fructicola*, in particular the strain NRRL Y-30752 (products known as Shemer™), (2.12) *Microsphaeropsis ochracea* (products known as Microx), (2.13), (2.14) *Nomuraea rileyi*, (2.15), (2.16) *Penicillium bilaii*, in particular strain ATCC22348 (products known as JumpStart®, PB-50, Provide), (2.17) *Pichia anomala*, in particular strain WRL-076, (2.18) *Pseudozyma flocculosa*, in particular strain PF-A22 UL (products known as Sporodex L), (2.19) *Pythium oligandrum* DV74 (products known as Polyversum), (2.20) *Trichoderma asperellum*, in particular strain ICC 012 (products known as Bioten), (2.21) *Trichoderma harzianum*, in particular *T. harzianum* T39 (products known e.g. as Trichodex).

Preference is further given to combinations comprising as biological control agent an isoflavone selected from the group consisting of [Group (3)]: (3.1) genistein, (3.2) biochanin A10, (3.3) formononetin, (3.4) daidzein. (3.5) glycitein, (3.6) hesperetin, (3.7) naringenin, (3.8) chalcone, (3.9) coumarin, (3.10) Ambiol (2-methyl-4-dimethylaminomethyl-5-hydroxybenzimidazol dihydrochloride) (3.11) ascorbate and (3.12) pratensein and the salts and esters thereof.

If a formulation, plant seed, or inoculum comprises an insecticide, the insecticide can include pyrethroids, organophosphates, caramoyloximes, pyrazoles, amidines, halogenated hydrocarbons, neonicotinoids, and carbamates and derivatives thereof. Particularly suitable classes of insecticides include organophosphates, phenylpyrazoles and pyrethoids. Preferred insecticides are those known as terbufos, chlorpyrifos, chlorethoxyfos, tefluthrin, carbofuran, and tebupirimfos. Commercially available insecticides include thiomethoxam (commercially available from Syngenta under the tradename Cruiser.

The insecticide can comprise an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

Suitable insecticides for use herein also include the following: (1) acetylcholine receptor agonists/antagonists such as chloronicotinyls/nconicotinoids, nicotine, bensultap or cartap. Suitable examples of chloronicotinyls/neonicotinoids include acetamiprid, dinotefuran, nitenpyram, nithiazine, thiacloprid, thiamethoxam, imidaclothiz and (2E)-1-[(2-chloro-1,3-thiazol-5-yl)methyl]-3,5-dimethyl-N-nitro-1, 3,5-tri-azinan-2-imine; (2) acetylcholinesterase (ACNE)

inhibitors such as carbamates and organophosphates. Suitable examples of carbamates include alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methomyl, metolcarb, oxamyl, phosphocarb, pirimicarb, promecarb, propoxur, thiofanox, triazamate, trimethacarb, XMC and xylylcarb. Suitable examples of organophosphates include acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon and vamidothion; (3) sodium channel modulators/voltage-gated sodium channel blockers such as pyrethroids and oxadiazines. Suitable examples of pyrethroids include acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralletrin, tetramethrin (1R-isomer), tralocythrin, tralomethrin, transfluthrin, ZXI 8901 and pyrethrins (pyrethrum). Suitable example of oxadiazines includes indoxacarb; (4) acetylcholine receptor modulators such as spinosyns. Suitable example of spinosyns includes spinosad; (5) GABA-gated chloride channel antagonists such as cyclodiene organochlorines and fiproles. Suitable examples of cyclodiene organochlorines include camphechlor, chlordane, endosulfan, gamma-HCH, HCH, heptachlor, lindane and methoxychlor. Suitable examples of fiproles include acetoprole, and vaniliprole; (6) chloride channel activators such as mectins. Suitable examples of mectins include abamectin, avermectin, emamectin, emamectin-benzoate, ivermectin, lepimectin, milbemectin and milbemycin; (7) juvenile hormone mimetics such as diofenolan, epofenonane, fenoxycarb, hydroprene, kinoprene, methoprene, pyriproxifen, triprene; (8) ecdysone agonists/disruptors such as diacylhydrazines. Suitable examples of diacylhydrazines include chromafenozide, halofenozide, methoxyfenozide and tebufenozide; (9) inhibitors of chitin-biosynthesis such as benzoylureas, buprofezin and cyromazine. Suitable examples of benzoylureas include bistrifluron, chlofluazuron, diflubenzuron, fluazuron, flucycloxuron, flufenoxuron, hexaflumuron, lufenuron, novaluron, noviflumuron, penfluron, teflubenzuron and triflumuron; (10) inhibitors of oxidative phosphorylation, ATP disruptors such as organotins and diafenthiuron. Suitable examples of organotins include azocyclotin, cyhexatin and fenbutatin oxide; (11) decouplers of oxidative phosphorylation by disruption of the H proton gradient such as pyrroles and dinitrophenols. Suitable example of pyrroles includes chlorfenapyr. Suitable examples of dinitrophenols include binapacyrl, dinobuton, dinocap and DNOC; (12) site I electron transport inhibitors such as METIs, hydramethylnone and dicofol. Suitable examples of METIs include fenazaquin, fenpyroximate, pyrimidifen, pyridaben, tebufenpyrad, tolfenpyrad; (13) site II electron transport inhibitors such as rotenone; (14) site III electron transport inhibitors such as acequinocyl and fluacrypyrim; (15) microbial disrupters of the intestinal membrane of insects such as *Bacillus thuringiensis* strains; (16) inhibitors of lipid synthesis such as tetronic acids and tetramic acids. Suitable examples of tetronic acids include spirodiclofen, spiromesifen and spirotetramat. Suitable example of tetramic acids includes cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester (CAS Reg. No.: 382608-10-8); (17) carboxamides such as flonicamid; (18) octopaminergic agonists such as amitraz; (19) inhibitors of the magnesium-stimulated ATPase such as propargite; (20) ryanodin receptor agonists such as phthalamides or rynaxapyr. Suitable example of phthalamides includes N.sup.2-[1,1-dimethyl-2-(methylsulphonyl)ethyl]-3-iodo-N.sup. 1-[2-methyl—4-[1,2,2,2-tetrafluoro-1-(trifluoromethyl)ethyl]phenyl]-1,2-benzenedicarbo-xamide (i.e. flubendiamide, CAS reg. No.: 272451-65-7); (21) nereistoxin analogues such as thiocyclam hydrogen oxalate andthiosultap-sodium; (22) biologics, hormones or pheromones such as azadirachtin, *Bacillus* spec., *Beauveria* spec., codlemone, *Metarrhizium* spec., *Paecilomyces* spec., *thuringiensis* and *Verticillium* spec; (23) active compounds having unknown or non-specified mechanisms of action such as fumigants, selective feeding inhibitors, mite growth inhibitors, amidoflumet; benclothiaz, benzoximate, bifenazate, bromopropylate, buprofezin, chinomethioat, chlordimeform, chlorobenzilate, chloropicrin, clothiazoben, cyclopren, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyraflu-prole, pyridalyl, pyriprole, sulfluramid, tetradifon, tetrasul, triarathene, verbutin, furthermore the compound 3-methyl-phenyl propylcarbamate (Tsumacide Z), the compound 3-(5-chloro-3-pyridinyl)-8-(2,2,2-trifluoroethyl)-8-azabicyclo [3.2.1]octa-ne-3-carbonitrile (CAS reg. No. 185982-80-3) and the corresponding 3-endo isomer (CAS reg. No. 185984-60-5) (cf. WO 96/37494, WO 98/25923), and also preparations comprising insecticidal effective plant extracts, nematodes, fungi or viruses. Suitable examples of fumigants include aluminium phosphide, methyl bromide and sulphuryl fluoride. Suitable examples of selective feeding inhibitors include cryolite, flonicamid and pymetrozine. Suitable examples of mite growth inhibitors include clofentezine, etoxazole and hexythiazox.

Commercially available nematicidal ingredients include abamectin (commercially available from Syngenta under the tradename Avicta).

If a formulation, plant seed, or inoculum comprises an herbicide, the herbicide can comprise 2,4-D, 2,4-DB, acetochlor, acifluorfen, alachlor, ametryn, atrazine, aminopyralid, benefin, bensulfuron, bensulide, bentazon, bromacil, bromoxynil, butylate, carfentrazone, chlorimuron, chlorsulfuron, clethodim, clomazone, clopyralid, cloransulam, cycloate, DCPA, desmedipham, dicamba, dichlobenil, diclofop, diclosulam, diflufenzopyr, dimethenamid, diquat, diuron, DSMA, endothall, EPTC, ethalfluralin, ethofumesate, fenoxaprop, fluazifop-P, flucarbazone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaben, isoxaflutole, lactofen, linuron, MCPA, MCPB, mesotrione, metolachlors, metribuzin, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, a sulfonylurea, an aryl triazine, or a combination thereof.

The formulation can comprise an herbicide and a strain of bacteria that is capable of degrading the herbicide.

The strain of bacteria that is capable of degrading an herbicide can comprise *Bacillus cereus* family member EE349 (NRRL No. B-50928), *Bacillus cereus* family member EE-B00377 (NRRL B-67119), *Bacillus pseudomycoides* EE-B00366 (NRRL B-67120), or *Bacillus mycoides* EE-B00363 (NRRL B-67121), or a combination thereof.

The herbicide to be degraded can comprise a sulfonylurea such as sulfentrazone, an aryl triazine, dicamba, a phenoxy herbicide, 2,4-D, a pyrethrin, a pyrethroid, or a combination thereof Binders can be included in the formulations, such as carboxymethylcellulose and natural and synthetic polymers in the form of powders, granules, or latexes, such as gum Arabic, chitin, polyvinyl alcohol and polyvinyl acetate, as well as natural phospholipids, such as cephalins and lecithins, and synthetic phospholipids. Binders include those composed preferably of an adhesive polymer that can be natural or synthetic without phytotoxic effect on the seed to be coated. Additional binders that can be included, either alone or in combination, include, for example, polyesters, polyether esters, polyanhydrides, polyester urethanes, polyester amides; polyvinyl acetates; polyvinyl acetate copolymers; polyvinyl alcohols and tylose; polyvinyl alcohol copolymers; polyvinylpyrolidones; polysaccharides, including starches, modified starches and starch derivatives, dextrins, maltodextrins, alginates, chitosanes and celluloses, cellulose esters, cellulose ethers and cellulose ether esters including ethylcelluloses, methylcelluloses, hydroxymethylcelluloses, hydroxypropylcelluloses and carboxymethylcellulose; fats; oils; proteins, including casein, gelatin and zeins; gum arabics; shellacs; vinylidene chloride and vinylidene chloride copolymers; lignosulfonates, in particular calcium lignosulfonates; polyacrylates, polymethacrylates and acrylic copolymers; polyvinylacrylates; polyethylene oxide; polybutenes, polyisobutenes, polystyrene, polybutadiene, polyethyleneamines, polyethylenamides; acrylamide polymers and copolymers; polyhydroxyethyl acrylate, methylacrylamide monomers; and polychloroprene.

A variety of colorants may be employed, including organic chromophores classified as nitroso, nitro, azo, including monoazo, bisazo, and polyazo, diphenylmethane, triarylmethane, xanthene, methane, acridine, thiazole, thiazine, indamine, indophenol, azine, oxazine, anthraquinone, and phthalocyanine.

Other additives that can be added include trace nutrients such as salts of iron, manganese, boron, copper, cobalt, molybdenum, and zinc.

One or more preservatives (e.g., antimicrobial agents or other biocidal agents) may also be included for preservation and stabilization of the formulation. Examples of suitable bactericides include those based on dichlorophene and benzylalcohol hemi formal (Proxel® from ICI or Acticide® RS from Thor Chemie and Kathon® MK from Dow Chemical) and isothiazolinone derivatives such as alkylisothiazolinones and benzisothiazolinones (Acticide® MBS from Thor Chemie). As further examples, suitable preservatives include MIT (2-methyl-4-isothiazolin-3-one), BIT (1,2-benzisothiazolin-3-one, which can be obtained from Avecia, Inc. as Proxel GXL as a solution in sodium hydroxide and dipropylene glycol), 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one-hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one-calcium chloride complex, 2-octyl-2H-isothiazol-3-one and benzyl alcohol hemiformal.

Examples of suitable thickeners for the formulations include polysaccharides, organic clays, or a water-soluble polymer that exhibits pseudoplastic properties in an aqueous medium, such as, for example, gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxy ethyl cellulose, methyl cellulose, carboxymethyl cellulose salt, cellulose sulfate salt, polyacrylamide, alkali metal salts of the maleic anhydride copolymers, alkali metal salts of poly(meth)acrylate.

Suitable antifreeze ingredients for the formulation include, for example and without limitation, ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and combinations thereof.

XVIII. Plant Seeds The present invention further relates to plant seeds coated with any of the recombinant *Bacillus cereus* family members described herein, with any of the recombinant spore-forming bacteria described herein, with any of the biologically pure bacterial cultures described herein, with any of the inoculums described herein, with any enzyme that catalyzes the production of nitric oxide, with any recombinant microorganism that expresses an enzyme that catalyzes the production of nitric oxide, or with any of the formulations other than vaccines as described herein.

XIX. Methods Relating to Plants and Plant Seeds, Methods for Delaying Germination of a Spore of a Recombinant *Bacillus cereus* Family Member, and Methods for Making and Using Exosporium Fragments The present invention further relates to methods for stimulating plant growth, methods for protecting a plant from a pathogen or enhancing stress resistance in a plant, methods for immobilizing recombinant *Bacillus cereus* family member spores or recombinant spore forming bacteria on a plant, methods for stimulating germination of a plant seed, methods for delivering nucleic acids to plants, methods for delaying germination of a spore of a recombinant *Bacillus cereus* family member, methods for making and using exosporium fragments, and methods for delivering beneficial bacteria to animals.

A. Methods for Stimulating Plant Growth

The present invention relates to methods for stimulating plant growth.

One method for stimulating plant growth of the present invention comprises introducing into a plant growth medium any of the recombinant *Bacillus cereus* family members described above or any of the formulations comprising a recombinant *Bacillus cereus* family member described above. Alternatively, any of the recombinant *Bacillus cereus* family members described above or any of the formulations comprising a recombinant *Bacillus cereus* family member described above can be applied to a plant, a plant seed, or to an area surrounding a plant or a plant seed. In such methods, the recombinant *Bacillus cereus* family member expresses a fusion protein comprising a plant growth stimulating protein or peptide. The plant growth stimulating protein or peptide can be physically attached to the exosporium of the recombinant *Bacillus cereus* family member.

Another method for stimulating plant growth comprises introducing into a plant growth medium any of the recombinant spore-forming bacteria described above or any of the formulations comprising a recombinant spore-forming bacterium described above. Alternatively, any of the recombinant spore-forming bacteria described above or any of the formulations comprising a recombinant spore-forming bacterium described above can be applied to a plant, a plant seed, or to an area surrounding a plant or a plant seed. In such methods, the recombinant spore-forming bacterium expresses a fusion protein comprising a plant growth stimulating protein or peptide. The plant growth stimulating protein or peptide can be physically attached to the spore coat of the recombinant spore-forming bacterium.

Yet another method for stimulating plant growth comprises introducing into a plant growth medium a recombinant *Bacillus cereus* family member or a formulation comprising a recombinant *Bacillus cereus* family member. Alternatively, the recombinant *Bacillus cereus* family member or the formulation can be applied to a plant, a plant seed, or to an area surrounding a plant or a plant seed. The recombinant *Bacillus cereus* family member expresses an enzyme involved in nutrient solubilization, a protease, a BclA protein, a BclB protein, a CotE protein a CotO protein, an ExsY protein, an ExsFA/BxpB protein, a CotY protein, an ExsFB protein, an ExsJ protein, an ExsH protein, a YjcA protein, a YjcB protein, a BclC protein, a BxpA protein, a BclE protein, a BetA/BAS3290 protein, an ExsA protein, an ExsK protein, an ExsB protein, a YabG protein, or a Tgl protein, wherein the expression of the enzyme involved in nutrient solubilization, the protease, a BclA protein, a BclB protein, a CotE protein a CotO protein, an ExsY protein, an ExsFA/BxpB protein, a CotY protein, an ExsFB protein, an ExsJ protein, an ExsH protein, a YjcA protein, a YjcB protein, a BclC protein, a BxpA protein, a BclE protein, a BetA/BAS3290 protein, an ExsA protein, an ExsK protein, an ExsB protein, a YabG protein, or a Tgl protein is increased as compared to the expression of the enzyme involved in nutrient solubilization, the protease, a BclA protein, a BclB protein, a CotE protein a CotO protein, an ExsY protein, an ExsFA/BxpB protein, a CotY protein, an ExsFB protein, an ExsJ protein, an ExsH protein, a YjcA protein, a YjcB protein, a BclC protein, a BxpA protein, a BclE protein, a BetA/BAS3290 protein, an ExsA protein, an ExsK protein, an ExsB protein, a YabG protein, or a Tgl protein in a wild-type *Bacillus cereus* family member under the same conditions.

Additional methods for stimulating plant growth, involving the use of exosporium fragments derived from a recombinant *Bacillus cereus* family member, are described below.

B. Methods for Protecting a Plant from a Pathogen or Enhancing Stress Resistance in a Plant The present invention also relates to methods for protecting a plant from a pathogen or enhancing stress resistance in a plant.

One method for protecting a plant from a pathogen or enhancing stress resistance in a plant comprises introducing into a plant growth medium any of the recombinant *Bacillus cereus* family members described above or any of the formulations comprising a recombinant *Bacillus cereus* family member described above. Alternatively, any of the recombinant *Bacillus cereus* family members described above or any of the formulations comprising a recombinant *Bacillus cereus* family member described above can be applied to a plant, a plant seed, or to an area surrounding a plant or a plant seed. In such methods, the recombinant *Bacillus cereus* family member expresses a fusion protein comprising a protein or peptide that protects a plant from a pathogen or a protein or peptide that enhances stress resistance in a plant. The protein or peptide that protects a plant from a pathogen or the protein or peptide that enhances stress resistance in a plant can be physically attached to the exosporium of the recombinant *Bacillus cereus* family member.

Another method for protecting a plant from a pathogen or enhancing stress resistance in a plant comprises introducing into a plant growth medium any of the recombinant spore-forming bacteria described above or any of the formulations comprising a recombinant spore-forming bacterium described above. Alternatively, any of the recombinant spore-forming bacteria described above or any of the formulations comprising a recombinant spore-forming bacterium described above can be applied to a plant, a plant seed, or to an area surrounding a plant or a plant seed. In such methods, the recombinant spore-forming bacterium expresses a fusion protein comprising a protein or peptide that protects a plant from a pathogen or a protein or peptide that enhances stress resistance in a plant. The protein or peptide that protects a plant from a pathogen or the protein or peptide that enhances stress resistance in a plant can be physically attached to the spore coat of the recombinant spore-forming bacterium.

In any of the methods for protecting a plant from a pathogen, plants grown in the plant growth medium comprising the recombinant *Bacillus cereus* family member or the recombinant spore-forming bacterium are preferably less susceptible to infection with the pathogen as compared to plants grown under the same conditions in the identical plant growth medium that does not contain the recombinant *Bacillus cereus* family member or the recombinant spore-forming bacterium.

In any of the methods for enhancing stress resistance in a plant plants grown in the plant growth medium comprising the recombinant *Bacillus cereus* family member or the recombinant spore-forming bacterium are preferably less susceptible to stress as compared to plants grown under the same conditions in the identical plant growth medium that does not contain the recombinant *Bacillus cereus* family member or the recombinant spore-forming bacterium.

Another method for enhancing stress resistance in a plant comprises introducing into a plant growth medium a recombinant *Bacillus cereus* family member or a formulation comprising the recombinant *Bacillus cereus* family member. Alternatively, the recombinant *Bacillus cereus* or the formulation can be applied to a plant, a plant seed, or to an area surrounding a plant or a plant seed. The recombinant *Bacillus cereus* family member expresses a superoxide dismutase or an arginase, wherein the expression of the superoxide dismutase or the arginase is increased as compared to the expression of the superoxide dismutase or the arginase in a wild-type *Bacillus cereus* family member under the same conditions.

Another method for protecting a plant from a pathogen comprises introducing into a plant growth medium a recombinant *Bacillus cereus* family member or a formulation comprising the recombinant *Bacillus cereus* family member. Alternatively, the recombinant *Bacillus cereus* or the formulation can be applied to a plant, a plant seed, or to an area surrounding a plant or a plant seed. The recombinant *Bacillus cereus* family member expresses a protease, wherein the expression of the protease is increased as compared to the expression of the protease in a wild-type *Bacillus cereus* family member under the same conditions.

Additional methods for protecting a plant from a pathogen or enhancing stress resistance in a plant, involving the use of exosporium fragments derived from a recombinant *Bacillus cereus* family member, are described below.

C. Methods for Immobilizing Recombinant *Bacillus cereus* Family Member Spores or Recombinant Spore Forming Bacteria on a Plant The present invention further relates to methods for immobilizing recombinant *Bacillus cereus* family member spores or recombinant spore forming bacteria on a plant.

One method for immobilizing a recombinant *Bacillus cereus* family member spore on a plant comprises introducing into a plant growth medium any of the recombinant *Bacillus cereus* family members described above or any of the formulations comprising a recombinant *Bacillus cereus* family member described above. Alternatively, any of the recombinant *Bacillus cereus* family members described above or any of the formulations comprising a recombinant *Bacillus cereus* family member described above can be applied to a plant, a plant seed, or to an area surrounding a plant or a plant seed. In such methods, the recombinant *Bacillus cereus* family member expresses a fusion protein comprising a plant binding protein or peptide. The plant binding protein or peptide can be physically attached to the exosporium of the recombinant *Bacillus cereus* family member.

Another method for immobilizing a spore of a recombinant spore-forming bacterium on a plant comprises introducing into a plant growth medium any of the recombinant spore-forming bacteria described above or any of the formulations comprising a recombinant spore-forming bacterium described above. Alternatively, any of the recombinant spore-forming bacteria described above or any of the formulations comprising a recombinant spore-forming bacterium described above can be applied to a plant, a plant seed, or to an area surrounding a plant or a plant seed. In such methods, the recombinant spore-forming bacterium expresses a fusion protein comprising a plant binding peptide and the plant binding protein or peptide can be physically attached to the spore coat of the recombinant spore-forming bacterium.

The plant binding protein or peptide preferably selectively targets and maintains the recombinant *Bacillus cereus* family member or the recombinant spore-forming bacterium on a plant. For example, the plant binding protein or peptide can selectively target and maintain the recombinant *Bacillus cereus* family member on at plant roots, substructures of roots, an aerial portion of a plant, or a substructure of an aerial portion of a plant.

D. Methods for Stimulating Germination of a Plant Seed

1. Methods for Stimulating Germination Involving the Use of a Recombinant *Bacillus cereus* Family Member of a Recombinant Spore-Forming Bacterium The present invention also provides methods for stimulating germination of a plant seed.

One method for stimulating germination of a plant seed comprises introducing into a plant growth medium any of the recombinant *Bacillus cereus* family members described above or any of the formulations comprising a recombinant *Bacillus cereus* family member described above. Alternatively, any of the recombinant *Bacillus cereus* family members described above or any of the formulations comprising a recombinant *Bacillus cereus* family member described above can be applied to a plant, a plant seed, or to an area surrounding a plant or a plant seed. In such methods, the recombinant *Bacillus cereus* family member expresses a fusion protein comprising an enzyme that catalyzes the production of nitric oxide. The enzyme that catalyzes the production of nitric oxide can be physically attached to the exosporium of the recombinant *Bacillus cereus* family member.

Another method for stimulating germination of a plant seed comprises introducing into a plant growth medium any of the recombinant spore-forming bacteria described above or any of the formulations comprising a recombinant spore-forming bacterium described above. Alternatively, any of the recombinant spore-forming bacteria described above or any of the formulations comprising a recombinant spore-forming bacterium described above can be applied to a plant, a plant seed, or to an area surrounding a plant or a plant seed. In such methods, the recombinant spore-forming bacterium expresses a fusion protein comprising an enzyme that catalyzes the production of nitric oxide, and the enzyme that catalyzes the production of nitric oxide can be physically attached to the spore coat of the recombinant spore-forming bacterium.

The above methods for stimulating germination of a plant seed preferably comprise applying the recombinant *Bacillus cereus* family member, the recombinant spore-forming bacterium, or the formulation to a plant seed.

Any of the above methods for stimulating germination of a plant seed can further comprise applying a substrate for the enzyme that catalyzes production of nitric oxide to the plant growth medium, the plant seed, the plant, or the area surrounding the plant or the plant seed. For example, the method suitably further comprises adding L-arginine to the plant growth medium, the plant seed, the plant, or the area surrounding the plant or the plant seed. For example, the L-arginine can be applied to an aerial portion of the plant. The L-arginine is preferably applied to the plant seed.

The presence of L-arginine enhances the reaction and leads to a more pronounced output of NO by the nitric oxide synthase. Furthermore, L-arginine on a plant seed, a plant growth medium, or an area surrounding a plant can serve as a substrate for the production of nitric oxide by native bacterial enzymes.

In any of the above methods for stimulating germination of a plant seed, seeds in the plant growth medium comprising the recombinant *Bacillus cereus* family member or the recombinant spore-forming bacterium or seeds to which the recombinant *Bacillus cereus* family member or the recombinant spore-forming bacterium has been applied preferably have an increased germination rate as compared to seeds grown under the same conditions in the identical plant growth medium that does not contain the recombinant *Bacillus cereus* family member or the recombinant spore-forming bacterium or seeds to which the recombinant *Bacillus cereus* family member or the recombinant spore-forming bacterium has not been applied, grown under the same conditions.

In any of the above methods for stimulating germination of a plant seed, seeds in the plant growth medium comprising the recombinant *Bacillus cereus* family member or the recombinant spore-forming bacterium or seeds to which the recombinant *Bacillus cereus* family member or the recombinant spore-forming bacterium has been applied preferably have a longer taproot after germination as compared to seeds grown under the same conditions in the identical plant growth medium that does not contain the recombinant *Bacillus cereus* family member or the recombinant spore-forming bacterium or seeds to which the recombinant *Bacillus cereus* family member or the recombinant spore-forming bacterium has not been applied under the same conditions.

Additional methods for stimulating germination of a plant seed, involving the use of exosporium fragments derived from a recombinant *Bacillus cereus* family member, are described below.

2. Methods for Stimulating Germination by Delivering to Plants Enzymes that Catalyze the Production of Nitric Oxide or Recombinant Microorganisms that Overexpress Such Enzymes Yet another method for stimulating germination of a plant seed comprises introducing into a plant growth medium, or applying to a plant, a plant seed, or an area surrounding a plant or a plant seed: (i) an enzyme that catalyzes the production of nitric oxide; (ii) a superoxide dismutase; or (iii) a recombinant microorganism that expresses an enzyme that catalyzes the production of nitric oxide or a superoxide dismutase, wherein the expression of the enzyme that catalyzes the production of nitric oxide or the superoxide dismutase is increased as compared to the expression of the enzyme that catalyzes the production of nitric oxide or the superoxide dismutase in a wild type microorganism under the same conditions.

The method preferably comprises applying the enzyme or the microorganism to a plant seed.

The method can further comprise applying a substrate for the enzyme that catalyzes production of nitric oxide to the plant growth medium, the plant seed, the plant, or the area surrounding the plant or the plant seed. For example, the method suitably further comprises adding L-arginine to the plant growth medium, the plant seed, the plant, or the area surrounding the plant or the plant seed. For example, the L-arginine can be applied to an aerial portion of the plant. The L-arginine is preferably applied to the plant seed.

Seeds in the plant growth medium comprising the enzyme or the microorganism or seeds to which the enzyme or the microorganism has been applied preferably have an increased germination rate as compared to seeds grown under the same conditions in the identical plant growth medium that does not contain enzyme or the microorganism or seeds to which the enzyme or the microorganism has not been applied, grown under the same conditions.

Seeds in the plant growth medium comprising the enzyme or the microorganism or seeds to which the enzyme or the microorganism has been applied preferably have a longer taproot after germination as compared to seeds grown under the same conditions in the identical plant growth medium that does not contain the enzyme or the microorganism or seeds to which the enzyme or the microorganism has not been applied under the same conditions.

The enzyme that catalyzes the production of nitric oxide synthase can comprise a nitric oxide synthase or an arginase. Where the enzyme that catalyzes the production of nitric oxide comprises a nitric oxide synthase, the nitric oxide synthase can comprise, for example, a nitric oxide synthase from *Bacillus thuringiensis* BT013A or *Bacillus subtilis* 168. For example, the nitric oxide synthase can have at least 85% sequence identity with SEQ ID NO: 260 or 261.

The nitric oxide synthase can have at least 90% sequence identity with SEQ ID NO: 260 or 261.

The nitric oxide synthase can have at least 95% sequence identity with SEQ ID NO: 260 or 261.

The nitric oxide synthase can have at least 98% sequence identity with SEQ ID NO: 260 or 261.

The nitric oxide synthase can have at least 99% sequence identity with SEQ ID NO: 260 or 261.

The nitric oxide synthase can have 100% sequence identity with SEQ ID NO: 260 or 261.

The superoxide dismutase can comprise a superoxide dismutase 1 (SODA1) or a superoxide dismutase 2 (SODA2). The superoxide dismutase can comprise an amino acid sequence having at least 85% identity with SEQ ID NO: 155 or 156.

The superoxide dismutase can comprise an amino acid sequence having at least 90% identity with SEQ ID NO: 155 or 156.

The superoxide dismutase can comprise an amino acid sequence having at least 95% identity with SEQ ID NO: 155 or 156.

The superoxide dismutase can comprise an amino acid sequence having at least 98% identity with SEQ ID NO: 155 or 156.

The superoxide dismutase can comprise an amino acid sequence having at least 99% identity with SEQ ID NO: 155 or 156.

The superoxide dismutase can comprise an amino acid sequence having at least 100% identity with SEQ ID NO: 155 or 156.

The recombinant microorganism that expresses an enzyme that catalyzes the production of nitric oxide can comprise a *Bacillus* species (e.g., a *Bacillus cereus* family member, *Bacillus subtilis, Bacillus licheniformis*, or *Bacil-*

*lus megaterium*), *Escherechia coli*, an *Aspergillus* species (e.g., *Aspergillus niger*), or a *Saccharomyces* species (e.g., *Saccharomyces cerevisiae*).

In any of the above methods, the enzyme or the recombinant microorganism can be introduced into the plant growth medium, or applied to a plant, a plant seed, or an area surrounding a plant or a plant seed in a formulation comprising the enzyme or the recombinant microorganism and an agriculturally acceptable carrier. The formulation can comprise any of the agriculturally acceptable carriers and other components discussed herein.

The enzyme that catalyzes the production of nitric oxide can be delivered purified or unpurified, and can be delivered alone or in combination with other beneficial proteins, inoculants, or chemicals to the plant seed, the plant growth medium, or an area surrounding the plant or the plant seed.

E. Methods for Delivering Nucleic Acids to Plants

Methods for delivering nucleic acids to plants are also provided by the present invention.

One method for delivering nucleic acids to a plant comprises introducing into a plant growth medium any of the recombinant *Bacillus cereus* family members described above or any of the formulations comprising a recombinant *Bacillus cereus* family member described above. Alternatively, any of the recombinant *Bacillus cereus* family members described above or any of the formulations comprising a recombinant *Bacillus cereus* family member described above can be applied to a plant, a plant seed, or to an area surrounding a plant or a plant seed. In such methods, the recombinant *Bacillus cereus* family member expresses a fusion protein comprising a nucleic acid binding protein. The nucleic acid binding protein or peptide is bound to a nucleic acid molecule. The nucleic acid binding protein or peptide can be physically attached to the exosporium of the recombinant *Bacillus cereus* family member.

In such methods, the recombinant *Bacillus cereus* family member can comprise an endophytic strain of bacteria. The endophytic strain of bacteria can comprise *Bacillus cereus* family member EE349, *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363. For example, the endophytic strain of bacteria can comprise *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363.

Another method for delivering nucleic acids to a plant comprises introducing into a plant growth medium any of the recombinant spore-forming bacteria described above or any of the formulations comprising a recombinant spore-forming bacterium described above. Alternatively, any of the recombinant spore-forming bacteria described above or any of the formulations comprising a recombinant spore-forming bacterium described above can be applied to a plant, a plant seed, or to an area surrounding a plant or a plant seed. In such methods, the recombinant spore-forming bacterium expresses a fusion protein comprising a nucleic acid binding protein. The nucleic acid binding protein or peptide is bound to a nucleic acid molecule. The nucleic acid binding protein or peptide can be physically attached to the spore coat of the recombinant spore-forming bacterium.

The recombinant spore-forming bacterium can comprise an endophytic strain of bacteria. For example, the endophytic strain of bacteria can comprise *Bacillus megaterium* EE385, *Bacillus* sp. EE387, *Bacillus circulans* EE388, *Bacillus subtilis* EE405, *Lysinibacillus fusiformis* EE442, *Lysinibacillus sphericus* EE443, or *Bacillus pumilus* EE-B00143.

In any of the above methods for delivering nucleic acids to a plant, the nucleic acid molecule can comprise a modulating RNA molecule; an RNAi molecule; a microRNA; an aptamer; or a DNA molecule that encodes a modulating RNA molecule, an RNAi molecule, a microRNA, or an aptamer.

The nucleic acid molecules to be delivered to the plant can be produced by any means known the art (e.g., chemical synthesis, recombinant production by a microorganism, etc.). The nucleic acid molecules can then be bound to the nucleic acid binding protein or peptide portion of the fusion proteins described herein in preparation for delivery of such nucleic acids to a plant or plants. The nucleic acid binding proteins and peptides immobilize and stabilize the nucleic acids and allow them to be delivered to the plant intact. The nucleic acid molecules to be delivered to the plant can be in an active form, or in an inactive form that can be processed into an active form by the plant.

To accomplish the binding of the nucleic acid molecules to the nucleic acid binding protein or peptide, the nucleic acids molecules can be incubated with the any of the recombinant *Bacillus cereus* members or recombinant spore-forming bacteria described herein that express a fusion protein comprising a nucleic acid binding protein or peptide.

Additional methods for delivering nucleic acids to a plant, involving the use of exosporium fragments derived from a recombinant *Bacillus cereus* family member, are described below.

F. Methods for Delaying Germination of a Spore of a Recombinant *Bacillus cereus* Family Member The present invention further relates to a method for delaying germination of a spore of a *Bacillus cereus* family member. The method comprises modifying the *Bacillus cereus* family member to express an inosine-uridine hydrolase or an alanine racemase, wherein the expression of the inosine-uridine hydrolase or the alanine racemase is increased as compared to the expression of the inosine-uridine hydrolase or the alanine racemase in a wild-type *Bacillus cereus* family member under the same conditions.

G. Inactivation of the *Bacillus cereus* Family Member or Recombinant Spore-Forming Bacterium Prior to Use In any of the above methods that use a recombinant *Bacillus cereus* family member or a recombinant spore forming bacterium, the method can further comprise inactivating the recombinant *Bacillus cereus* family member or the recombinant spore-forming bacterium prior to introduction into the plant growth medium or application to a plant, a plant seed, or an area surrounding a plant or a plant seed.

For example, the inactivating can comprise subjecting the recombinant *Bacillus cereus* family member or the recombinant spore-forming bacterium to heat treatment; gamma irradiation; x-ray irradiation; UV-A irradiation; UV-B irradiation; treatment with gluteraldehyde, formaldehyde, hydrogen peroxide, acetic acid, bleach, chloroform, or phenol, or a combination thereof.

Alternatively or in addition, the inactivating can comprise modifying the recombinant *Bacillus cereus* family member recombinant or spore-forming bacterium to express a germination spore protease or a non-specific endonuclease, wherein the expression of the germination spore protease or the non-specific endonuclease is increased as compared to the expression of the germination spore protease or the non-specific endonuclease in a wild-type *Bacillus cereus* family member under the same conditions, and wherein the recombinant spore-forming bacterium comprises a recombinant bacterium of the genus *Bacillus*.

H. Methods for Making and Using Exosporium Fragments

The present invention further relates to methods for making and using exosporium fragments. These methods relate to the recombinant *Bacillus cereus* family members described in Section IV hereinabove, i.e., recombinant *Bacillus cereus* family members that comprise a mutation or another genetic alteration that allows for the collection of free exosporium.

Thus, the present invention relates to a method for removing exosporium from spores of a recombinant *Bacillus cereus* family member. The method comprises subjecting a suspension comprising any of the recombinant *Bacillus cereus* family members described in Section IV hereinabove to centrifugation or filtration to produce fragments of exosporium that are separated from the spores. The exosporium fragments comprise the fusion protein.

The method for removing exosporium from spores of a recombinant *Bacillus cereus* family member can comprise subjecting the suspension comprising the spores to centrifugation and collecting the supernatant, wherein the supernatant comprises the fragments of the exosporium and is substantially free of spores.

Alternatively, the method for removing exosporium from spores of a recombinant *Bacillus cereus* family member can comprise subjecting the suspension comprising the spores to filtration and collecting the filtrate, wherein the filtrate comprises the fragments of the exosporium and is substantially free of spores.

The suspension of spores can be agitated or mechanically disrupted prior to centrifugation or filtration.

The exosporium fragments can also be separated from the spores by gradient centrifugation, affinity purification, or by allowing the spores to settle out of the suspension.

The present invention further relates to methods for using the exosporium fragments.

A method for stimulating plant growth is provided. The method comprises introducing exosporium fragments or a formulation of comprising the exosporium fragments and an agriculturally acceptable carrier into a plant growth medium. Alternatively, the exosporium fragments or the formulation can be applied to a plant, a plant seed, or an area surrounding a plant or a plant seed. The exosporium fragments are derived from spores of a recombinant *Bacillus cereus* family member described in Section IV hereinabove and comprise the fusion protein. The fusion protein comprises a plant growth stimulating protein or peptide.

A method for protecting a plant from a pathogen or enhancing stress resistance in a plant is also provided. The method comprises introducing exosporium fragments or a formulation of comprising the exosporium fragments and an agriculturally acceptable carrier into a plant growth medium. Alternatively, the exosporium fragments or the formulation can be applied to a plant, a plant seed, or an area surrounding a plant or a plant seed. The exosporium fragments are derived from spores of a recombinant *Bacillus cereus* family member described in Section IV hereinabove and comprise the fusion protein. The fusion protein comprises a protein or peptide that protects a plant from a pathogen or a protein or peptide that enhances stress resistance in a plant.

When the method is a method for protecting a plant from a pathogen, the fusion protein comprises protein or peptide that protects a plant from a pathogen.

In the methods for protecting a plant from a pathogen, plants grown in the plant growth medium comprising the exosporium fragments are preferably less susceptible to infection with the pathogen as compared to plants grown under the same conditions in the identical plant growth medium that does not contain the exosporium fragments.

When the method is a method for enhancing stress resistance in a plant, the fusion protein comprises a protein or peptide that enhances stress resistance in a plant.

In the methods for enhancing stress resistance in a plant of, plants grown in the plant growth medium comprising the exosporium fragments are preferably less susceptible to stress as compared to plants grown under the same conditions in the identical plant growth medium that does not contain the exosporium fragments.

A method for immobilizing exosporium fragments on a plant is also provided. The method comprises introducing exosporium fragments or a formulation of comprising the exosporium fragments and an agriculturally acceptable carrier into a plant growth medium. Alternatively, the exosporium fragments or the formulation can be applied to a plant, a plant seed, or an area surrounding a plant or a plant seed. The exosporium fragments are derived from spores of a recombinant *Bacillus cereus* family member described in Section IV hereinabove and comprise the fusion protein. The fusion protein comprises a plant binding protein or peptide.

The plant binding protein or peptide preferably selectively targets and maintains the exosporium fragments on a plant. For example, the plant binding protein or peptide can selectively target and maintain the exosporium fragments on at plant roots, substructures of roots, an aerial portion of a plant, or a substructure of an aerial portion of a plant.

A method for stimulating germination of a plant seed is also provided. The method comprises introducing exosporium fragments or a formulation of comprising the exosporium fragments and an agriculturally acceptable carrier into a plant growth medium. Alternatively, the exosporium fragments or the formulation can be applied to a plant, a plant seed, or an area surrounding a plant or a plant seed. The exosporium fragments are derived from spores of a recombinant *Bacillus cereus* family member described in Section IV hereinabove and comprise the fusion protein. The fusion protein comprises a superoxide dismutase or an enzyme that catalyzes the production of nitric oxide.

In the methods for stimulating germination, the method preferably comprises applying the exosporium fragments to a plant seed.

The methods for stimulating germination can further comprise applying a substrate for the enzyme that catalyzes production of nitric oxide to the plant growth medium, the plant seed, the plant, or the area surrounding the plant or the plant seed. For example, the method suitably further comprises adding L-arginine to the plant growth medium, the plant seed, the plant, or the area surrounding the plant or the plant seed. For example, the L-arginine can be applied to an aerial portion of the plant. The L-arginine is preferably applied to the plant seed.

The presence of L-arginine enhances the reaction and leads to a more pronounced output of NO by the nitric oxide synthase. Furthermore, L-arginine on a plant seed, a plant growth medium, or an area surrounding a plant can serve as a substrate for the production of nitric oxide by native bacterial enzymes.

In the methods for stimulating germination of a plant seed, seeds in the plant growth medium comprising the exosporium fragments or seeds to which the exosporium fragments have been applied preferably have an increased germination rate as compared to the same seeds grown under the same conditions in the identical plant growth medium that does not contain the exosporium fragments or the same seeds grown under the same conditions to which the exosporium fragments have not been applied.

In the methods for stimulating germination of a plant seed, seeds in the plant growth medium comprising the exosporium fragments or seeds to which the exosporium fragments have been applied preferably have a longer taproot after germination as compared to the same seeds grown under the same conditions in the identical plant growth medium that does not contain the exosporium fragments or the same seeds grown under the same conditions to which the exosporium fragments have not been applied.

A method for delivering nucleic acids to a plant is also provided. The method comprises introducing exosporium fragments or a formulation of comprising the exosporium fragments and an agriculturally acceptable carrier into a plant growth medium. Alternatively, the exosporium fragments or the formulation can be applied to a plant, a plant seed, or an area surrounding a plant or a plant seed. The exosporium fragments are derived from spores of a recombinant *Bacillus cereus* family member described in Section IV hereinabove and comprise the fusion protein. The fusion protein comprises a nucleic acid binding protein or peptide. The nucleic acid binding protein or peptide is bound to a nucleic acid molecule.

In the method for delivering nucleic acids to a plant, the nucleic acid molecule can comprise a modulating RNA molecule; an RNAi molecule; a microRNA; an aptamer; or a DNA molecule that encodes a modulating RNA molecule, an RNAi molecule, a microRNA, or an aptamer.

The nucleic acid molecules to be delivered to the plant can be produced by any means known the art (e.g., chemical synthesis, recombinant production by a microorganism, etc.). The nucleic acid molecules can then be bound to the nucleic acid binding protein or peptide portion of the fusion proteins described herein in preparation for delivery of such nucleic acids to a plant or plants. The nucleic acid binding proteins and peptides immobilize and stabilize the nucleic acids and allow them to be delivered to the plant intact. The nucleic acid molecules to be delivered to the plant can be in an active form, or in an inactive form that can be processed into an active form by the plant.

To accomplish the binding of the nucleic acid molecules to the nucleic acid binding protein or peptide, the nucleic acids molecules can be incubated with the exosporium fragments containing a fusion protein comprising a nucleic acid binding protein or peptide.

I. Plant Growth Medium

In any of the methods described herein involving the use of a plant growth medium, the plant growth medium can comprise soil, water, an aqueous solution, sand, gravel, a polysaccharide, mulch, compost, peat moss, straw, logs, clay, soybean meal, yeast extract, or a combination thereof.

Furthermore, the plant growth medium can be supplemented with a substrate or a cofactor for an enzyme. For example, the substrate or the cofactor can comprise tryptophan, an adenosine monophosphate, an adenosine diphosphate, an adenosine triphosphate (e.g., adenosine-3-triphosphate), indole, a trimetaphosphate, ferrodoxin, acetoin, diacetyl, pyruvate, acetolactate, pectin, cellulose, methylcellulose, starch, chitin, pectin, a protein meal, a cellulose derivative, a phosphate, acetoin, chitosan, an inactive derivative of indole-3-acetic acid, an inactive derivative of gibberellic acid, a xylan, an arabinoxylan, a fat, a wax, an oil, a phytic acid, a lignin, a humic acid, choline, a choline derivative, proline, a polyproline, a proline-rich protein, a proline-rich meal, phenylalanine, chorismate, L-arginine, NADH, NADPH, ATP, GTP, cytochrome C, cytochrome p450, or a combination thereof.

J. Methods of Application

The methods described herein can comprise coating seeds with the recombinant *Bacillus cereus* family member, the recombinant spore-forming bacterium, or the exosporium fragments or a formulation containing the recombinant *Bacillus cereus* family member, the recombinant spore-forming bacterium, or the or exosporium fragments prior to planting.

The methods described herein can comprise applying the recombinant *Bacillus cereus* family member, the recombinant spore-forming bacterium, or the exosporium fragments, or a formulation containing the recombinant *Bacillus cereus* family member, the recombinant spore-forming bacterium, or the exosporium fragments to an aerial portion of a plant.

In the methods described herein, introducing the recombinant *Bacillus cereus* family member, the recombinant spore-forming bacterium, or the exosporium fragments into the plant growth medium can comprise applying a liquid or solid formulation containing the recombinant *Bacillus cereus* family member, the recombinant spore-forming bacterium, or the exosporium fragments to the medium. The plant growth medium can comprise soil (e.g., potting soil), compost, peat moss, sand, seed starter mix, or a combination thereof. The method can comprise applying the formulation to the plant growth medium prior to, concurrently with, or after planting of seeds, seedlings, cuttings, bulbs, or plants in the plant growth medium.

K. Agrochemicals

In the methods described herein, the method can further comprise introducing at least one agrochemical into the plant growth medium or applying at least one agrochemical to plants or seeds.

The agrochemical can comprise a fertilizer (e.g., a liquid fertilizer), a micronutrient fertilizer material (e.g., boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof), an insecticide (e.g., an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof), an herbicide (e.g., a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivatives, oxadiazolinone, a phosphate, a phthalate, a picolinic acid compound, a triazine, a triazole, a uracil, a urea derivative, endothall, sodium chlorate, or a combination thereof), a fungicide (e.g., a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof), a molluscicide, an algicide, a plant growth amendment, a bacterial inoculant (e.g., a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof), a fungal inoculant (e.g., a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof), or a combination thereof.

The fertilizer can comprise ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination thereof.

The agrochemical can comprise any of the fungicides, bacterial inoculants, or herbicides, described above in section XVII.

L. Plants and Seeds

In any of the above methods relating to plants, the plant can be a dicotyledon, a monocotyledon, or a gymnosperm.

For example, where the plant is a dicotyledon, the dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, chrysanthemum, cinnamon, citron, clementine, clove, clover, coffee, cola nut, colza, corn, cotton, cottonseed, cowpea, crambe, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, lespedeza, lettuce, lime, liquorice, litchi, loquat, lupine, macadamia nut, mace, mandarin, mangel, mango, medlar, melon, mint, mulberry, mustard, nectarine, niger seed, nutmeg, okra, olive, opium, orange, papaya, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus Cinchona, quinoa, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, cassia, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, sassafras, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild betel, West African pepper, yerba santa, tarragon, parsley, chervil, land cress, burnet saxifrage, honeyherb, butterbur, shiso, water pepper, perilla, bitter bean, oca, kampong, Chinese celery, lemon basil, Thai basil, water mimosa, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

Where the plant is a monocotyledon, the monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, areca, bajra, betel nut, broom millet, broom sorghum, citronella, coconut, cocoyam, maize, dasheen, durra, durum wheat, edo, fique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Where the plant is a gymnosperm, the gymnosperm can be from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

The plants and plant seeds described herein may include transgenic plants or plant seeds, such as transgenic cereals (wheat, rice), maize, soybean, potato, cotton, tobacco, oilseed rape and fruit plants (fruit of apples, pears, citrus fruits and grapes. Preferred transgenic plants include corn, soybeans, potatoes, cotton, tobacco and oilseed rape.

Suitable transgenic plants and seeds can be characterized by the plant's formation of toxins, especially from the *Bacillus thuringiensis* genetic material (e.g., by gene CryIA (a), CryIA(b), CryIA (c), CryIIA, CryIIIA, CryIIIB2, Cry9c, Cry2Ab, Cry3Bb, CryIF or a combination thereof). The formation of toxins in plants increases the plants resistance to insects, arachnids, nematodes and slugs and snails (hereinafter referred to as "Bt plants"). Bt plants, for example, are commercially available under the tradename YIELD GARD® (for example maize, cotton, soybeans), KnockOut® (for example maize), StarLink® (for example maize), Bollgard® (cotton), Nucotn® (cotton) and NewLeaf® (potato) maize varieties, cotton varieties, soybean varieties and potato varieties. Herbicide tolerance plants include plants under the trade names Roundup Ready® (a glyphosate tolerance, such as corn, cotton, soybeans), Clearfield® (for example maize), Liberty Link® (tolerance with glufosinate, for example oilseed rape), IMI® (with imidazolinone tolerance) and STS® (tolerance to a sulfonylurea, such as maize).

Plant seeds as described herein can be genetically modified (e.g., any seed that results in a genetically modified plant or plant part that expresses herbicide tolerance, tolerance to environmental factors such as water stress, drought, viruses, and nitrogen production, or resistance to bacterial, fungi or insect toxins). Suitable genetically modified seeds include those of cole crops, vegetables, fruits, trees, fiber crops, oil crops, tuber crops, coffee, flowers, legume, cereals, as well as other plants of the monocotyledonous and dicotyledonous species. Preferably, the genetically modified seeds include peanut, tobacco, grasses, wheat, barley, rye, sorghum, rice, rapeseed, sugarbeet, sunflower, tomato, pepper, bean, lettuce, potato, and carrot. Most preferably, the genetically modified seeds include cotton, soybean, and corn (sweet, field, seed, or popcorn).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

XX. Methods for Delivering Beneficial Bacteria and Proteins or Peptides to Animals The present invention further relates to methods for delivering beneficial bacteria and/or proteins or peptides to animals.

The administration of bacterial strains that are both probiotic and are also endophytic to a plant allows for entry of the bacteria into the plant where they divide and multiply. The endophytic and probiotic strains can be delivered to plants using various methods, e.g., the endophytic and probiotic strains can be delivered via seed treatment, treatment of the plant growth medium (e.g., soil), irrigation, application to the plant itself (e.g., foliar application to the aerial portions of a plant). Once inside the plant, the bacteria multiply and colonize the internal tissues of the plant. The plant can then be fed to an animal, which allows for delivery of the probiotic bacteria to the animal. Costs are decreased as to traditional methods for delivering probiotic bacteria to animals, since the endophytic nature of the bacteria allows them to divide and multiply within the plant. By initially delivering a small amount of a probiotic and endophytic strain of bacteria to a plant and allowing the bacteria to increase in number inside the plant, the dose increases. In addition, the probiotic and endophytic strain can spread across a target crop prior to harvest and digestion.

Bacterial strains that are capable of colonizing the phylloplane of a plant and are also probiotic can also be used for these purposes. Strains that are capable of colonizing the phylloplane of a plant can be initially delivered to plants in small doses, and will then divide and colonize the external surfaces of the plants.

Suitable bacterial strains that are both endophytic or phylloplane-colonizing and probiotic include those strains that can both replicate in the field in or on a plant and that provide benefits to animals upon ingestion. Benefits of probiotic bacteria in animals include but are not limited to regulation of the microbiome of the digestive tract of the animal, secretion of enzymes that aid in digestion of plant material, and stimulation of the animals immune system. Examples of digestion-enhancing enzymes that would provide benefit include, but are not limited to cellulases, endoglucanases, exoglucanases, β-glucosidases, amylases, proteases, pectinases, xylanases, xylosidases, lipases, phospholipases, and lignases.

The *Bacillus* and *Lysinibacillus* genera are unique in that they contain a large number of species that are both endophytic and thus colonize plants, but that can also act as probiotics in vertebrates. Thus, *Bacillus* and *Lysinibacillus* species are highly suitable for delivery of probiotics to animals through passaging and growth in plants. Common

*Bacillus* species that can be both endophytic and probiotic include *Bacillus subtilis, Bacillus firmus, Bacillus amyloliquefaciens, Bacillus cereus, Bacillus toyocerin, Bacillus megaterium, Bacillus pumilus,* and *Bacillus licheniformis. Lysinibacillus* species that are both endophytic and probiotic can also be used.

A method for delivering beneficial bacteria to an animal is provided. The method comprises feeding to an animal a plant modified to comprise a level of an endophytic and probiotic strain of bacteria that is greater than the level of the endophytic and probiotic strain of bacteria in the same plant that has not been modified grown under the same conditions.

The plant fed to the animal can comprise a plant grown in a plant growth medium containing the endophytic and probiotic strain of bacteria or a formulation comprising the endophytic and probiotic strain of bacteria, a plant to which the endophytic and probiotic strain of bacteria was applied, a plant grown from a plant seed to which the endophytic and probiotic strain of bacteria was applied, a plant grown in an area to which the endophytic and probiotic strain of bacteria was applied, or a seed grown in the area to which the endophytic and probiotic strain of bacteria was applied.

The endophytic and probiotic strain of bacteria can comprise a *Bacillus* or *Lysinibacillus* species. For example, the *Bacillus* species can comprise *Bacillus subtilis, Bacillus firmus, Bacillus amyloliquefaciens, Bacillus cereus, Bacillus toyocerin, Bacillus megaterium, Bacillus pumilus, Bacillus licheniformis,* or a combination thereof.

The endophytic and probiotic strain of bacteria can comprise *Bacillus cereus* family member EE349, *Bacillus cereus* family member EE439, *Bacillus thuringiensis* EE417, *Bacillus cereus* EE444, *Bacillus megaterium* EE385, *Bacillus* sp. EE387, *Bacillus circulans* EE388, *Bacillus subtilis* EE405, *Lysinibacillus fusiformis* EE442, *Lysinibacillus sphericus* EE443, *Bacillus pumilus* EE-B00143, or a combination thereof.

In addition, proteins or peptides (e.g., enzymes) can be delivered to animals by feeding recombinant *Bacillus cereus* family members expressing a fusion protein containing the protein or peptide, exosporium fragments comprising such fusion proteins, or recombinant spore-forming bacteria expressing such fusion proteins to the animals. The recombinant *Bacillus cereus* family member or the recombinant spore-forming bacteria can be an endophytic strain of bacteria or a strain of bacteria that is capable of colonizing the phylloplane of a plant, which allows for delivery of the protein or peptide to the animal via ingestion of a plant that has been colonized by the bacteria. Probiotic recombinant *Bacillus cereus* family member strains or strains of recombinant spore-forming bacteria can also be used so that the animal that ingests the recombinant *Bacillus cereus* family member or the recombinant spore-forming bacteria obtains both the benefits of the probiotic bacteria and the benefits of the protein or peptide. Recombinant *Bacillus cereus* family member strains and strains of recombinant spore-forming bacteria that are both endophytic or phylloplane colonizing and probiotic can also be used to deliver proteins or peptides to animals.

Accordingly, a method for delivering proteins or peptides to an animal is also provided. The method comprises feeding to an animal a recombinant *Bacillus cereus* family member expressing a fusion protein comprising a protein or peptide of interest and a targeting sequence, exosporium protein, or exosporium protein fragment that targets the fusion protein to the exosporium of the recombinant *Bacillus cereus* family member. Alternatively, the method comprises feeding to an animal exosporium fragments derived from a recombinant *Bacillus cereus* family member expressing a fusion protein comprising a protein or peptide of interest and a targeting sequence, exosporium protein, or exosporium protein fragment that targets the fusion protein to the exosporium of the recombinant *Bacillus cereus* family member.

The recombinant *Bacillus cereus* family member can comprise any of the recombinant *Bacillus cereus* family members described herein that express a fusion protein.

The exosporium fragments can comprise exosporium fragments derived from any of the *Bacillus cereus* family members described above in Section IV.

The recombinant *Bacillus cereus* family member can comprise an endophytic strain of bacteria. The endophytic strain of bacteria can comprise *Bacillus cereus* family member EE349, *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363. For example, the endophytic strain of bacteria comprises *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363.

The recombinant *Bacillus cereus* family member can comprise a probiotic strain of bacteria. The probiotic strain of bacteria can comprise *Bacillus cereus* family member EE349 (NRRL No. B-50928), *Bacillus cereus* family member EE439 (NRRL B-50979), *Bacillus thuringiensis* EE417 (NRRL B-50979), *Bacillus cereus* EE444 (NRRL B-50977), *Bacillus thuringiensis* BT013A (NRRL No. B-50924), or a combination thereof.

The recombinant *Bacillus cereus* family member can be comprised within a plant that is fed to the animal.

Alternatively, the recombinant *Bacillus cereus* family can comprise a strain of bacteria that is capable of colonizing the phylloplane of a plant. For example, the strain of bacteria that is capable of colonizing the phylloplane of a plant can comprise *Bacillus mycoides* BT155, *Bacillus mycoides* EE118, *Bacillus mycoides* EE141, *Bacillus mycoides* BT46-3, *Bacillus cereus* family member EE218, *Bacillus thuringiensis* BT013A, *Bacillus cereus* family member EE-B00377, *Bacillus pseudomycoides* EE-B00366, or *Bacillus mycoides* EE-B00363.

The recombinant *Bacillus cereus* family member can be present on the phylloplane of a plant that is fed to the animal.

The targeting sequence, exosporium protein, or exosporium protein fragment can comprise: (1) a targeting sequence comprising an amino acid sequence having at least about 43% identity with amino acids 20-35 of SEQ ID NO: 1, wherein the identity with amino acids 25-35 is at least about 54%; (2) a targeting sequence comprising amino acids 1-35 of SEQ ID NO: 1; (3) a targeting sequence comprising amino acids 20-3 5 of SEQ ID NO: 1; (4) a targeting sequence comprising SEQ ID NO: 1; (5) an exosporium protein comprising an amino acid sequence having at least 85% identity with SEQ ID NO: 2; (6) a targeting sequence comprising amino acids 2-35 of SEQ ID NO: 1; (7) a targeting sequence comprising amino acids 5-35 of SEQ ID NO: 1; (8) a targeting sequence comprising amino acids 8-35 of SEQ ID NO: 1; (9) a targeting sequence comprising amino acids 10-35 of SEQ ID NO: 1; (10) a targeting sequence comprising amino acids 15-35 of SEQ ID NO: 1; (11) a targeting sequence comprising amino acids 1-27 of SEQ ID NO: 3; (12) a targeting sequence comprising amino acids 12-27 of SEQ ID NO: 3; (13) a targeting sequence comprising SEQ ID NO: 3; (14) an exosporium protein comprising an amino acid sequence having at least 85% identity with SEQ ID NO: 4; (15) a targeting sequence comprising amino acids 2-27 of SEQ ID NO: 3; (16) a targeting sequence comprising amino acids 5-27 of SEQ ID NO: 3; (17) a targeting sequence comprising amino acids 8-27 of SEQ ID NO: 3; (18) a targeting sequence comprising amino acids 10-27 of SEQ ID NO: 3; (19) a targeting sequence comprising amino acids 1-38 of SEQ ID NO: 5; (20) a targeting sequence comprising amino acids 23-38 of SEQ ID NO: 5; (21) a targeting sequence comprising SEQ ID NO: 5; (22) an exosporium protein comprising an amino acid sequence having at least 85% identity with SEQ ID NO: 6; (23) a targeting sequence comprising amino acids 2-38 of SEQ ID NO: 5; (24) a targeting sequence comprising amino acids 5-38 of SEQ ID NO: 5; (25) a targeting sequence comprising amino acids 8-38 of SEQ ID NO: 5; (26) a targeting sequence comprising amino acids 10-38 of SEQ ID NO: 5; (27) a targeting sequence comprising amino acids 15-38 of SEQ ID NO: 5; (28) a targeting sequence comprising amino acids 20-38 of SEQ ID NO: 5; (29) a targeting sequence comprising amino acids 1-28 of SEQ ID NO: 7; (30) a targeting sequence comprising amino acids 13-28 of SEQ ID NO: 7; (31) a targeting sequence comprising SEQ ID NO: 7; (32) an exosporium protein comprising an amino acid sequence having at least 85% identity with SEQ ID NO: 8; (33) a targeting sequence comprising amino acids 2-28 of SEQ ID NO: 7; (34) a targeting sequence comprising amino acids 5-28 of SEQ ID NO: 7; (35) a targeting sequence comprising amino acids 8-28 of SEQ ID NO: 7; (36) a targeting sequence comprising amino acids 10-28 of SEQ ID NO: 7; (37) a targeting sequence comprising amino acids 1-24 of SEQ ID NO: 9; (38) a targeting sequence comprising amino acids 9-24 of SEQ ID NO: 9; (39) a targeting sequence comprising SEQ ID NO: 9; (40) an exosporium protein comprising an amino acid sequence having at least 85% identity with SEQ ID NO: 10; (41) a targeting sequence comprising amino acids 2-24 of SEQ ID NO: 9; (42) a targeting sequence comprising amino acids 5-24 of SEQ ID NO: 9; (43) a targeting sequence comprising amino acids 8-24 of SEQ ID NO: 9; (44) a targeting sequence comprising amino acids 1-33 of SEQ ID NO: 11; (45) a targeting sequence comprising amino acids 18-33 of SEQ ID NO: 11; (46) a targeting sequence comprising SEQ ID NO: 11; (47) an exosporium protein comprising an amino acid sequence having at least 85% identity with SEQ ID NO: 12; (48) a targeting sequence comprising amino acids 2-33 of SEQ ID NO: 11; (49) a targeting sequence comprising amino acids 5-33 of SEQ ID NO: 11; (50) a targeting sequence comprising amino acids 8-33 of SEQ ID NO: 11; (51) a targeting sequence comprising amino acids 10-33 of SEQ ID NO: 11; (52) a targeting sequence comprising amino acids 15-33 of SEQ ID NO: 11; (53) a targeting sequence comprising amino acids 1-33 of SEQ ID NO: 13; (54) a targeting sequence comprising amino acids 18-33 of SEQ ID NO: 13; (55) a targeting sequence comprising SEQ ID NO:13; (56) an exosporium protein comprising an amino acid sequence having at least 85% identity with SEQ ID NO: 14; (57) a targeting sequence comprising amino acids 2-33 of SEQ ID NO: 13; (58) a targeting sequence comprising amino acids 5-33 of SEQ ID NO: 13; (59) a targeting sequence comprising amino acids 8-33 of SEQ ID NO: 13; (60) a targeting sequence comprising amino acids 10-33 of SEQ ID NO: 13; (61) a targeting sequence comprising amino acids 15-33 of SEQ ID NO: 13; (62) a targeting sequence comprising amino acids 1-43 of SEQ ID NO: 15; (63) a targeting sequence comprising amino acids 28-43 of SEQ ID NO: 15; (64) a targeting sequence comprising SEQ ID NO: 15; (65) an exosporium protein comprising an amino acid sequence having at least 85% identity with SEQ ID NO: 16; (66) a targeting sequence comprising amino acids 2-43 of SEQ ID NO: 15; (67) a targeting sequence comprising amino acids 5-43 of SEQ ID NO: 15; (68) a targeting sequence comprising amino acids 8-43 of SEQ ID NO: 15; (69) a targeting sequence comprising amino acids 10-43 of SEQ ID NO: 15; (70) a targeting sequence comprising amino acids 15-43 of SEQ ID NO: 15; (71) a targeting sequence comprising amino acids 20-43 of SEQ ID NO: 15; (72) a targeting sequence comprising amino acids 25-43 of SEQ ID NO: 15; (73) a targeting sequence comprising amino acids 1-27 of SEQ ID NO: 17; (74) a targeting sequence comprising amino acids 12-27 of SEQ ID NO: 17; (75) a targeting sequence comprising SEQ ID NO: 17; (76) an exosporium protein comprising an amino acid sequence having at least 85% identity with SEQ ID NO: 18; (77) a targeting sequence comprising amino acids 2-27 of SEQ ID NO: 17; (78) a targeting sequence comprising amino acids 5-27 of SEQ ID NO: 17; (79) a targeting sequence comprising amino acids 8-27 of SEQ ID NO: 17; (80) a targeting sequence comprising amino acids 10-27 of SEQ ID NO: 17; (81) a targeting sequence comprising amino acids 1-33 of SEQ ID NO: 19; (82) a targeting sequence comprising amino acids 18-33 of SEQ ID NO: 19; (83) a targeting sequence comprising SEQ ID NO:19; (84) an exosporium protein comprising an amino acid sequence having at least 85% identity with SEQ ID NO:20; (85) a targeting sequence comprising amino acids 2-33 of SEQ ID NO: 19; (86) a targeting sequence comprising amino acids 5-33 of SEQ ID NO: 19; (87) a targeting sequence comprising amino acids 8-33 of SEQ ID NO: 19; (88) a targeting sequence comprising amino acids 10-33 of SEQ ID NO: 19; (89) a targeting sequence comprising amino acids 15-33 of SEQ ID NO: 19; (90) a targeting sequence comprising amino acids 1-33 of SEQ ID NO: 21; (91) a targeting sequence comprising amino acids 18-33 of SEQ ID NO: 21; (92) a targeting sequence comprising SEQ ID NO:21; (93) an exosporium protein comprising an amino acid sequence having at least 85% identity with SEQ ID NO:22; (94) a targeting sequence comprising amino acids 2-33 of SEQ ID NO: 21; (95) a targeting sequence comprising amino acids 5-33 of SEQ ID NO: 21; (96) a targeting sequence comprising amino acids 8-33 of SEQ ID NO: 21; (97) a targeting sequence comprising amino acids 10-33 of SEQ ID NO: 21; (98) a targeting sequence comprising amino acids 15-33 of SEQ ID NO: 21; (99) a targeting sequence comprising amino acids 1-24 of SEQ ID NO: 23; (100) a targeting sequence comprising amino acids 9-24 of SEQ ID NO: 23; (101) a targeting sequence comprising SEQ ID NO:23; (102) an exosporium protein comprising an amino acid sequence having at least 85% identity with SEQ ID NO:24; (103) a targeting sequence comprising amino acids 2-24 of SEQ ID NO:23; (104) a targeting sequence comprising amino acids 5-24 of SEQ ID NO: 23; (105) a targeting sequence comprising amino acids 8-24 of SEQ ID NO: 23; (106) a targeting sequence comprising amino acids 1-24 of SEQ ID NO: 25; (107) a targeting sequence comprising amino acids 9-24 of SEQ ID NO: 25; (108) a targeting sequence comprising SEQ ID NO:25; (109) an exosporium protein comprising an amino acid sequence having at least 85% identity with SEQ ID NO:26; (110) a targeting sequence comprising amino acids 2-24 of SEQ ID NO: 25; (111) a targeting sequence comprising amino acids 5-24 of SEQ ID NO: 25; (112) a targeting sequence comprising amino acids 8-24 of SEQ ID NO: 25; (113) a targeting sequence comprising amino acids 1-30 of SEQ ID NO: 27; (114) a targeting sequence comprising amino acids 15-30 of SEQ ID NO: 27; (115) a targeting sequence comprising SEQ ID NO:27; (116) an exosporium protein comprising an amino acid sequence having at least 85% identity with SEQ ID NO:28; (117) a targeting sequence comprising amino acids 2-30 of SEQ ID NO: 27; (118) a targeting sequence comprising amino acids 5-30 of SEQ ID NO: 27; (119) a targeting sequence comprising amino acids 8-30 of SEQ ID NO: 27; (120) a targeting sequence comprising amino acids 10-30 of SEQ ID NO: 27; (121) a targeting sequence comprising amino acids 1-33 of SEQ ID NO: 29; (122) a targeting sequence comprising amino acids 18-33 of SEQ ID NO: 29; (123) a targeting sequence comprising SEQ ID NO:29; (124) an exosporium protein comprising an amino acid sequence having at least 85% identity with SEQ ID NO:30; (125) a targeting sequence comprising amino acids 2-33 of SEQ ID NO: 29; (126) a targeting sequence comprising amino acids 5-33 of SEQ ID NO: 29; (127) a targeting sequence comprising amino acids 8-33 of SEQ ID NO: 29; (128) a targeting sequence comprising amino acids 10-33 of SEQ ID NO: 29; (129) a targeting sequence comprising amino acids 15-33 of SEQ ID NO: 29; (130) a targeting sequence comprising amino acids 1-24 of SEQ ID NO: 31; (131) a targeting sequence comprising amino acids 9-24 of SEQ ID NO: 31; (132) a targeting sequence comprising SEQ ID NO:31; (133) an exosporium protein comprising an amino acid sequence having at least 85% identity with SEQ ID NO:32; (134) a targeting sequence comprising amino acids 2-24 of SEQ ID NO: 31; (135) a targeting sequence comprising amino acids 5-24 of SEQ ID NO: 31; (136) a targeting sequence comprising amino acids 8-24 of SEQ ID NO: 31; (137) a targeting sequence comprising amino acids 1-15 of SEQ ID NO: 33; (138) a targeting sequence comprising SEQ ID NO:33; (139) an exosporium protein comprising an amino acid sequence having at least 85% identity with SEQ ID NO:34; (140) a targeting sequence comprising amino acids 1-16 of SEQ ID NO: 35; (141) a targeting sequence comprising SEQ ID NO:35; (142) an exosporium protein comprising an amino acid sequence having at least 85% identity with SEQ ID NO:36; (143) a targeting sequence comprising amino acids 1-29 of SEQ ID NO:43; (144) a targeting sequence comprising amino acids 14-29 of SEQ ID NO: 43; (145) a targeting sequence comprising SEQ ID NO: 43; (146) an exosporium protein comprising an amino acid sequence having at least 85% identity with SEQ ID NO: 44; (147) a targeting sequence comprising amino acids 2-29 of SEQ ID NO: 43; (148) a targeting sequence comprising amino acids 5-29 of SEQ ID NO: 43; (149) a targeting sequence comprising amino acids 8-29 of SEQ ID NO: 43; (150) a targeting sequence comprising amino acids 10-29 of SEQ ID NO: 43; (151) a targeting sequence comprising amino acids 1-35 of SEQ ID NO: 45; (152) a targeting sequence comprising amino acids 20-3 5 of SEQ ID NO: 45; (153) a targeting sequence comprising SEQ ID NO: 45; (154) an exosporium protein comprising an amino acid sequence having at least 85% identity with SEQ ID NO: 46; (155) a targeting sequence comprising amino acids 2-35 of SEQ ID NO: 45; (156) a targeting sequence comprising amino acids 5-35 of SEQ ID NO: 45; (157) a targeting sequence comprising amino acids 8-35 of SEQ ID NO: 45; (158) a targeting sequence comprising amino acids 10-35 of SEQ ID NO: 45; (159) a targeting sequence comprising amino acids 15-35 of SEQ ID NO: 45; (160) a targeting sequence comprising amino acids 1-43 of SEQ ID NO: 47; (161) a targeting sequence comprising amino acids 28-43 of SEQ ID NO: 47; (162) a targeting sequence comprising SEQ ID NO: 47; (163) an exosporium protein comprising an amino acid sequence having at least 85% identity with SEQ ID NO: 48; (164) a targeting sequence comprising amino acids 2-43 of SEQ ID NO: 47; (165) a targeting sequence comprising amino acids 5-43 of SEQ ID NO: 47; (166) a targeting sequence comprising amino acids 8-43 of SEQ ID NO: 47; (167) a targeting sequence comprising amino acids 10-43 of SEQ ID NO: 47; (168) a targeting sequence comprising amino acids 15-43 of SEQ ID NO: 47; (169) a targeting sequence comprising amino acids 20-43 of SEQ ID NO: 47; (170) a targeting sequence comprising amino acids 25-43 of SEQ ID NO: 47; (171) a targeting sequence comprising amino acids 1-32 of SEQ ID NO: 49; (172) a targeting sequence comprising amino acids 17-32 of SEQ ID NO: 49; (173) a targeting sequence comprising SEQ ID NO: 49; (174) an exosporium protein comprising an amino acid sequence having at least 85% identity with SEQ ID NO: 50; (175) a targeting sequence comprising amino acids 2-32 of SEQ ID NO: 49; (176) a targeting sequence comprising amino acids 5-32 of SEQ ID NO: 49; (177) a targeting sequence comprising amino acids 8-32 of SEQ ID NO: 49; (178) a targeting sequence comprising amino acids 10-32 of SEQ ID NO: 49; (179) a targeting sequence comprising amino acids 15-32 of SEQ ID NO: 49; (180) a targeting sequence comprising amino acids 1-33 of SEQ ID NO: 51; (181) a targeting sequence comprising amino acids 18-33 of SEQ ID NO: 51; (182) a targeting sequence comprising SEQ ID NO: 51; (183) an exosporium protein comprising an amino acid sequence having at least 85% identity with SEQ ID NO: 52; (184) a targeting sequence comprising amino acids 2-33 of SEQ ID NO: 51; (185) a targeting sequence comprising amino acids 5-33 of SEQ ID NO: 51; (186) a targeting sequence comprising amino acids 8-33 of SEQ ID NO: 51; (187) a targeting sequence comprising amino acids 10-33 of SEQ ID NO: 51; (188) a targeting sequence comprising amino acids 15-33 of SEQ ID NO: 51; (189) a targeting sequence comprising amino acids 1-33 of SEQ ID NO: 53; (190) a targeting sequence comprising amino acids 18-33 of SEQ ID NO: 53; (191) a targeting sequence comprising SEQ ID NO: 53; (192) an exosporium protein comprising an amino acid sequence having at least 85% identity with SEQ ID NO: 54; (193) a targeting sequence comprising amino acids 2-33 of SEQ ID NO: 53; (194) a targeting sequence comprising amino acids 5-33 of SEQ ID NO: 53; (195) a targeting sequence comprising amino acids 8-33 of SEQ ID NO: 53; (196) a targeting sequence comprising amino acids 10-33 of SEQ ID NO: 53; (197) a targeting sequence comprising amino acids 15-33 of SEQ ID NO: 53; (198) a targeting sequence comprising amino acids 1-30 of SEQ ID NO: 55; (199) a targeting sequence comprising amino acids 15-30 of SEQ ID NO: 55; (200) a targeting sequence comprising SEQ ID NO: 55; (201) an exosporium protein comprising an amino acid sequence having at least 85% identity with SEQ ID NO: 56; (202) a targeting sequence comprising amino acids 2-30 of SEQ ID NO: 55; (203) a targeting sequence comprising amino acids 5-30 of SEQ ID NO: 55; (204) a targeting sequence comprising amino acids 8-30 of SEQ ID NO: 55; (205) a targeting sequence comprising amino acids 10-30 of SEQ ID NO: 55; (206) a targeting sequence comprising amino acids 1-130 of SEQ ID NO: 57; (207) a targeting sequence comprising amino acids 115-130 of SEQ ID NO: 57; (208) a targeting sequence comprising SEQ ID NO: 57; (209) an exosporium protein comprising an amino acid sequence having at least 85% identity with SEQ ID NO: 58; (210) a targeting sequence comprising amino acids 2-130 of SEQ ID NO: 57; (211) a targeting sequence comprising amino acids 5-130 of SEQ ID NO: 57; (212) a targeting sequence comprising amino acids 10-130 of SEQ ID NO: 57; (213) a targeting sequence comprising amino acids 20-130 of SEQ ID NO: 57; (214) a targeting sequence comprising amino acids 30-130 of SEQ ID NO: 57; (215) a targeting sequence comprising amino acids 40-130 of SEQ ID NO: 57; (216) a targeting sequence comprising amino acids 50-130 of SEQ ID NO: 57; (217) a targeting sequence comprising amino acids 60-130 of SEQ ID NO: 57; (218) a targeting sequence comprising amino acids 70-130 of SEQ ID NO: 57; (219) a targeting sequence comprising amino acids 80-130 of SEQ ID NO: 57; (220) a targeting sequence comprising amino acids 90-130 of SEQ ID NO: 57; (221) a targeting sequence comprising amino acids 100-130 of SEQ ID NO: 57; (222) a targeting sequence comprising amino acids 110-130 of SEQ ID NO: 57; (223) an exosporium protein fragment comprising an amino acid sequence having at least 85% identity with SEQ ID NO: 95; (224) a targeting sequence comprising SEQ ID NO: 96; (225) a targeting sequence comprising SEQ ID NO: 97; (226) a targeting sequence comprising SEQ ID NO: 98; (227) a targeting sequence comprising SEQ ID NO: 99; (228) a targeting sequence comprising SEQ ID NO: 100; (229) a targeting sequence comprising SEQ ID NO: 101; (230) a targeting sequence comprising SEQ ID NO: 102; (231) a targeting sequence comprising SEQ ID NO: 103; (232) a targeting sequence comprising SEQ ID NO: 104; (233) a targeting sequence comprising SEQ ID NO: 105; (234) a targeting sequence comprising SEQ ID NO: 106; (235) an exosporium protein comprising an amino acid sequence having at least 85% identity with SEQ ID NO: 108; (236) an exosporium protein comprising an amino acid sequence having at least 85% identity with SEQ ID NO: 109; (237) an exosporium protein comprising an amino acid sequence having at least 85% identity with SEQ ID NO: 110; (238) an exosporium protein comprising an amino acid sequence having at least 85% identity with SEQ ID NO: 111; (239) an exosporium protein comprising an amino acid sequence having at least 85% identity with SEQ ID NO: 112; (240) an exosporium protein comprising an amino acid sequence having at least 85% identity with SEQ ID NO: 113; (241) an exosporium protein comprising an amino acid sequence having at least 85% identity with SEQ ID NO: 114; (242) an exosporium protein comprising an amino acid sequence having at least 85% identity with SEQ ID NO: 115; (243) an exosporium protein comprising an amino acid sequence having at least 85% identity with SEQ ID NO: 116; (244) an exosporium protein comprising an amino acid sequence having at least 85% identity with SEQ ID NO: 117; (245) an exosporium protein comprising an amino acid sequence having at least 85% identity with SEQ ID NO: 118; (246) an exosporium protein comprising an amino acid sequence having at least 85% identity with SEQ ID NO: 119; (247) an exosporium protein comprising an amino acid sequence having at least 85% identity with SEQ ID NO: 120; (248) an exosporium protein comprising an amino acid sequence having at least 85% identity with SEQ ID NO: 121; (249) a targeting sequence comprising amino acids 22-31 of SEQ ID NO: 1; (250) a targeting sequence comprising amino acids 22-33 of SEQ ID NO: 1; (251) a targeting sequence comprising amino acids 20-31 of SEQ ID NO: 1; (252) a targeting sequence comprising amino acids 14-23 of SEQ ID NO: 3; (253) a targeting sequence comprising amino acids 14-25 of SEQ ID NO: 3; (254) a targeting sequence comprising amino acids 12-23 of SEQ ID NO: 3; (255) a targeting sequence comprising amino acids 1-30 of SEQ ID NO: 59; (256) a targeting sequence comprising SEQ ID NO: 59; (257) an exosporium protein comprising an amino acid sequence having at least 85% identity with SEQ ID NO: 60; (258) a targeting sequence comprising amino acids 2-30 of SEQ ID NO: 59; (259) a targeting sequence comprising amino acids 4-30 of SEQ ID NO: 59; (260) a targeting sequence comprising amino acids 6-30 of SEQ ID NO: 59; (261) a targeting sequence comprising amino acids 1-33 of SEQ ID NO: 61; (262) a targeting sequence comprising amino acids 18-33 of SEQ ID NO: 61; (263) a targeting sequence comprising SEQ ID NO: 61; (264) an exosporium protein comprising an amino acid sequence having at least 85% sequence identity with SEQ ID NO: 62; (265) a targeting sequence comprising amino acids 2-33 of SEQ ID NO: 61; (266) a targeting sequence comprising amino acids 5-33 of SEQ ID NO: 61; (267) a targeting sequence comprising amino acids 10-33 of SEQ ID NO: 61; (268) a targeting sequence comprising amino acids 15-33 of SEQ ID NO: 61; (269) a targeting sequence comprising amino acids 1-35 of SEQ ID NO: 63; (270) a targeting sequence comprising SEQ ID NO: 63; (271) an exosporium protein comprising an amino acid sequence having at least 85% identity with SEQ ID NO: 64; (272) a targeting sequence comprising amino acids 2-35 of SEQ ID NO: 63; (273) a targeting sequence comprising amino acids 5-35 of SEQ ID NO: 63; (274) a targeting sequence comprising amino acids 8-35 of SEQ ID NO: 63; (275) a targeting sequence comprising amino acids 10-35 of SEQ ID NO: 63; (276) a targeting sequence comprising amino acids 15-35 of SEQ ID NO: 63; (277) a targeting sequence comprising amino acids 1-24 of SEQ ID NO: 65; (278) a targeting sequence comprising amino acids 9-24 of SEQ ID NO: 65; (279) a targeting sequence comprising SEQ ID NO: 65; (280) an exosporium protein comprising an amino acid sequence having at least 85% identity with SEQ ID NO: 66; (281) a targeting sequence comprising SEQ ID NO: 107; (282) a targeting sequence comprising amino acids 2-24 of SEQ ID NO: 65; (283) a targeting sequence comprising amino acids 5-24 of SEQ ID NO: 65; (284) a targeting sequence comprising amino acids 1-27 of SEQ ID NO: 67; (285) a targeting sequence comprising amino acids 12-27 of SEQ ID NO: 67; (286) a targeting sequence comprising SEQ ID NO: 67; (287) an exosporium protein comprising an amino acid sequence having at least 85% identity with SEQ ID NO: 68; (288) an targeting sequence comprising amino acids 2-27 of SEQ ID NO: 67; (289) a targeting sequence comprising amino acids 5-27 of SEQ ID NO: 67; (290) a targeting sequence comprising amino acids 10-27 of SEQ ID NO: 67; (291) a targeting sequence comprising amino acids 1-38 of SEQ ID NO: 69; (292) a targeting sequence comprising amino acids 23-38 of SEQ ID NO: 69; (293) a targeting sequence comprising SEQ ID NO: 69; (294) an exosporium protein comprising an amino acid sequence having at least 85% identity with SEQ ID NO: 70; (295) a targeting sequence comprising amino acids 2-38 of SEQ ID NO: 69; (296) a targeting sequence comprising amino acids 5-38 of SEQ ID NO: 69; (297) a targeting sequence comprising amino acids 10-38 of SEQ ID NO: 69; (298) a targeting sequence comprising amino acids 15-38 of SEQ ID NO: 69; (299) an exosporium protein comprising SEQ ID NO: 72; (300) a targeting sequence comprising SEQ ID NO: 73; (301) an exosporium protein comprising an amino acid sequence having at least 95% identity with SEQ ID NO: 74; (302) a targeting sequence comprising amino acids 1-42 of SEQ ID NO: 75; (303) a targeting sequence comprising amino acids 27-42 of SEQ ID NO: 75; (304) a targeting sequence comprising SEQ ID NO: 75; (305) an exosporium protein comprising an amino acid sequence having at least 85% identity with SEQ ID NO: 76; (306) a targeting sequence comprising amino acids 2-42 of SEQ ID NO: 75; (307) a targeting sequence comprising amino acids 5-42 of SEQ ID NO: 75; (308) a targeting sequence comprising amino acids 10-42 of SEQ ID NO: 75; (309) a targeting sequence comprising amino acids 15-42 of SEQ ID NO: 75; (310) a targeting sequence comprising amino acids 20-42 of SEQ ID NO: 75; (311) a targeting sequence comprising amino acids 25-42 of SEQ ID NO: 75; (312) a targeting sequence comprising amino acids 1-24 of SEQ ID NO: 77; (313) a targeting sequence comprising amino acids 9-24 of SEQ ID NO: 77; (314) a targeting sequence comprising SEQ ID NO: 77; (315) an exosporium protein comprising an amino acid sequence having at least 85% identity with SEQ ID NO: 78; (316) a targeting sequence comprising amino acids 2-24 of SEQ ID NO: 77; (317) a targeting sequence comprising amino acids 5-24 of SEQ ID NO: 77; (318) an exosporium protein comprising an amino acid sequence having at least 85% identity with SEQ ID NO: 80; (319) a targeting sequence comprising amino acids 1-38 of SEQ ID NO: 81; (320) a targeting sequence comprising amino acids 23-38 of SEQ ID NO: 81; (321) a targeting sequence comprising SEQ ID NO: 81; (322) an exosporium protein comprising an amino acid sequence having at least 85% identity with SEQ ID NO: 82; (323) a targeting sequence comprising amino acids 2-38 of SEQ ID NO: 81; (324) a targeting sequence comprising amino acids 5-38 of SEQ ID NO: 81; (325) a targeting sequence comprising amino acids 10-38 of SEQ ID NO: 81; (326) a targeting sequence comprising amino acids 15-38 of SEQ ID NO: 81; (327) a targeting sequence comprising amino acids 20-38 of SEQ ID NO: 81; (328) a targeting sequence comprising amino acids 1-34 of SEQ ID NO: 83; (329) a targeting sequence comprising SEQ ID NO: 83; (330) an exosporium protein comprising an amino acid sequence having at least 85% identity with SEQ ID NO: 84; (331) an exosporium protein comprising an amino acid sequence having at least 85% identity with SEQ ID NO: 86; (332) a targeting sequence comprising amino acids 1-28 of SEQ ID NO: 87; (333) a targeting sequence comprising amino acids 13-28 of SEQ ID NO: 87; (334) a targeting sequence comprising SEQ ID NO: 87; (335) an exosporium protein comprising an amino acid sequence having at least 85% identity with SEQ ID NO: 88; (336) a targeting sequence comprising amino acids 2-28 of SEQ ID NO: 87; (337) a targeting sequence comprising amino acids 5-28 of SEQ ID NO: 87; (338) a targeting sequence comprising amino acids 10-28 of SEQ ID NO: 87; (339) a targeting sequence comprising amino acids 1-28 of SEQ ID NO: 89; (340) a targeting sequence comprising SEQ ID NO: 89; (341) an exosporium protein comprising an amino acid sequence having at least 85% identity with SEQ ID NO: 90; (342) a targeting sequence comprising amino acids 2-28 of SEQ ID NO: 89; (343) a targeting sequence comprising amino acids 5-28 of SEQ ID NO: 89; (344) a targeting sequence comprising amino acids 10-28 of SEQ ID NO: 89; (345) a targeting sequence comprising amino acids 1-93 of SEQ ID NO: 91; (346) a targeting sequence comprising SEQ ID NO: 91; (347) an exosporium protein comprising an amino acid sequence having at least 85% identity with SEQ ID NO: 92; (348) a targeting sequence comprising amino acids 2-93 of SEQ ID NO: 91; (349) a targeting sequence comprising amino acids 10-93 of SEQ ID NO: 91; (350) a targeting sequence comprising amino acids 20-93 of SEQ ID NO: 91; (351) a targeting sequence comprising amino acids 30-93 of SEQ ID NO: 91; (352) a targeting sequence comprising amino acids 40-93 of SEQ ID NO: 91; (353) a targeting sequence comprising amino acids 50-93 of SEQ ID NO: 91; (354) a targeting sequence comprising amino acids 60-93 of SEQ ID NO: 91; (355) a targeting sequence comprising amino acids 1-130 of SEQ ID NO: 93; (356) a targeting sequence comprising SEQ ID NO: 93; (357) an exosporium protein comprising an amino acid sequence having at least 85% identity with SEQ ID NO: 94; (358) a targeting sequence comprising amino acids 2-130 of SEQ ID NO: 93; (359) a targeting sequence comprising amino acids 10-130 of SEQ ID NO: 93; (360) a targeting sequence comprising amino acids 20-130 of SEQ ID NO: 93; (361) a targeting sequence comprising amino acids 30-130 of SEQ ID NO: 93; (362) an exosporium protein comprising an amino acid sequence having at least 85% identity with SEQ ID NO: 122; (363) a targeting sequence consisting of amino acids 20-33 of SEQ ID NO: 1; (364) a targeting sequence consisting of amino acids 21-33 of SEQ ID NO: 1; (365) a targeting sequence consisting of amino acids 23-31 of SEQ ID NO: 1; (366) a targeting sequence consisting of amino acids 1-15 of SEQ ID NO: 96; (367) a targeting sequence consisting of amino acids 1-13 of SEQ ID NO: 96; (368) a targeting sequence consisting of amino acids 12-25 of SEQ ID NO: 3; (369) a targeting sequence consisting of amino acids 13-25 of SEQ ID NO: 3; (370) a targeting sequence consisting of amino acids 15-23 of SEQ ID NO: 3; (371) a targeting sequence consisting of amino acids 1-15 of SEQ ID NO: 97; (372) a targeting sequence consisting of amino acids 1-13 of SEQ ID NO: 98; (373) a targeting sequence consisting of amino acids 23-36 of SEQ ID NO: 5; (374) a targeting sequence consisting of amino acids 23-34 of SEQ ID NO: 5; (375) a targeting sequence consisting of amino acids 24-36 of SEQ ID NO: 5; (376) a targeting sequence consisting of amino acids 26-34 of SEQ ID NO: 5; (377) a targeting sequence consisting of amino acids 13-26 of SEQ ID NO: 7; (378) a targeting sequence consisting of amino acids 13-24 of SEQ ID NO: 7; (379) a targeting sequence consisting of amino acids 14-26 of SEQ ID NO: 7; (380) a targeting sequence consisting of amino acids 16-24 of SEQ ID NO: 7; (381) a targeting sequence consisting of amino acids 9-22 of SEQ ID NO: 9; (382) a targeting sequence consisting of amino acids 9-20 of SEQ ID NO: 9; (383) a targeting sequence consisting of amino acids 10-22 of SEQ ID NO: 9; (384) a targeting sequence consisting of amino acids 12-20 of SEQ ID NO: 9; (385) a targeting sequence consisting of amino acids 1-15 of SEQ ID NO: 105; (386) a targeting sequence consisting of amino acids 1-13 of SEQ ID NO: 105; (387) a targeting sequence consisting of amino acids 18-31 of SEQ ID NO: 11; (388) a targeting sequence consisting of amino acids 18-29 of SEQ ID NO: 11; (389) a targeting sequence consisting of amino acids 19-31 of SEQ ID NO: 11; (390) a targeting sequence consisting of amino acids 1-15 of SEQ ID NO: 98; (391) a targeting sequence consisting of amino acids 1-13 of SEQ ID NO: 98; (392) a targeting sequence consisting of amino acids 18-31 of SEQ ID NO: 13; (393) a targeting sequence consisting of amino acids 18-29 of SEQ ID NO: 13; (394) a targeting sequence consisting of amino acids 19-31 of SEQ ID NO: 13; (395) a targeting sequence consisting of amino acids 21-29 of SEQ ID NO: 13; (396) a targeting sequence consisting of amino acids 1-15 of SEQ ID NO: 99; (397) a targeting sequence consisting of amino acids 1-13 of SEQ ID NO: 99; (398) a targeting sequence consisting of amino acids 28-41 of SEQ ID NO: 15; (399) a targeting sequence consisting of amino acids 28-39 of SEQ ID NO: 15; (400) a targeting sequence consisting of amino acids 29-41 of SEQ ID NO: 15; (401) a targeting sequence consisting of amino acids 31-39 of SEQ ID NO: 15; (402) a targeting sequence consisting of amino acids 12-25 of SEQ ID NO: 17; (403) a targeting sequence consisting of amino acids 13-25 of SEQ ID NO: 17; (404) a targeting sequence consisting of amino acids 1-15 of SEQ ID NO: 100; (405) a targeting sequence consisting of amino acids 18-31 of SEQ ID NO: 19; (406) a targeting sequence consisting of amino acids 18-29 of SEQ ID NO: 19; (407) a targeting sequence consisting of amino acids 19-31 of SEQ ID NO: 19; (408) a targeting sequence consisting of amino acids 21-29 of SEQ ID NO: 19; (409) a targeting sequence consisting of amino acids 18-31 of SEQ ID NO: 21; (410) a targeting sequence consisting of amino acids 18-29 of SEQ ID NO: 21; (411) a targeting sequence consisting of amino acids 19-31 of SEQ ID NO: 21; (412) a targeting sequence consisting of amino acids 21-29 of SEQ ID NO: 21; (413) a targeting sequence consisting of amino acids 1-15 of SEQ ID NO: 101; (414) a targeting sequence consisting of amino acids 1-13 of SEQ ID NO: 101; (415) a targeting sequence consisting of amino acids 9-22 of SEQ ID NO: 23; (416) a targeting sequence consisting of amino acids 9-20 of SEQ ID NO: 23; (417) a targeting sequence consisting of amino acids 10-22 of SEQ ID NO: 23; (418) a targeting sequence consisting of amino acids 12-20 of SEQ ID NO: 23; (419) a targeting sequence consisting of amino acids 1-15 of SEQ ID NO: 102; (420) a targeting sequence consisting of amino acids 1-13 of SEQ ID NO: 102; (421) a targeting sequence consisting of amino acids 9-22 of SEQ ID NO: 25; (422) a targeting sequence consisting of amino acids 9-20 of SEQ ID NO: 25; (423) a targeting sequence consisting of amino acids 10-22 of SEQ ID NO: 25; (424) a targeting sequence consisting of amino acids 12-20 of SEQ ID NO: 25; (425) a targeting sequence consisting of amino acids 1-15 of SEQ ID NO: 103; (426) a targeting sequence consisting of amino acids 1-13 of SEQ ID NO: 103; (427) a targeting sequence consisting of amino acids 15-28 of SEQ ID NO: 27; (428) a targeting sequence consisting of amino acids 15-26 of SEQ ID NO: 27; (429) a targeting sequence consisting of amino acids 16-28 of SEQ ID NO: 27; (430) a targeting sequence consisting of amino acids 18-26 of SEQ ID NO: 27; (431) a targeting sequence consisting of amino acids 1-15 of SEQ ID NO: 104; (432) a targeting sequence consisting of amino acids 1-13 of SEQ ID NO: 104; (433) a targeting sequence consisting of amino acids 1-13 of SEQ ID NO: 33; (434) a targeting sequence consisting of amino acids 1-11 of SEQ ID NO: 33; (435) a targeting sequence consisting of amino acids 3-11 of SEQ ID NO: 33; (436) a targeting sequence consisting of amino acids 1-14 of SEQ ID NO: 35; (437) a targeting sequence consisting of amino acids 1-12 of SEQ ID NO: 35; (438) a targeting sequence consisting of amino acids 2-14 of SEQ ID NO: 35; (439) a targeting sequence consisting of amino acids 14-27 of SEQ ID NO: 43; (440) a targeting sequence consisting of amino acids 14-25 of SEQ ID NO: 43; (441) a targeting sequence consisting of amino acids 15-27 of SEQ ID NO: 43; (442) a targeting sequence consisting of amino acids 20-33 of SEQ ID NO: 45; (443) a targeting sequence consisting of amino acids 20-31 of SEQ ID NO: 45; (444) a targeting sequence consisting of amino acids 21-33 of SEQ ID NO: 45; (445) a targeting sequence consisting of amino acids 1-15 of SEQ ID NO: 106; (446) a targeting sequence consisting of amino acids 1-13 of SEQ ID NO: 106; (447) a targeting sequence consisting of amino acids 28-41 of SEQ ID NO: 47; (448) a targeting sequence consisting of amino acids 28-39 of SEQ ID NO: 47; (449) a targeting sequence consisting of amino acids 18-31 of SEQ ID NO: 53; (450) a targeting sequence consisting of amino acids 18-29 of SEQ ID NO: 53; (451) a targeting sequence consisting of amino acids 19-31 of SEQ ID NO: 53; (452) a targeting sequence comprising amino acids 18-31 of SEQ ID NO: 61; (453) a targeting sequence comprising amino acids 18-29 of SEQ ID NO: 61; (454) a targeting sequence comprising amino acids 19-31 of SEQ ID NO: 61; (455) a targeting sequence comprising amino acids 9-22 of SEQ ID NO: 65; (456) a targeting sequence comprising amino acids 9-20 of SEQ ID NO: 65; (457) a targeting sequence comprising amino acids 10-22 of SEQ ID NO: 65; (458) a targeting sequence comprising amino acids 1-15 of SEQ ID NO: 107; (459) a targeting sequence comprising amino acids 1-13 of SEQ ID NO: 107; (460) a targeting sequence comprising amino acids 12-25 of SEQ ID NO: 67; (461) a targeting sequence comprising amino acids 12-23 of SEQ ID NO: 67; (462) a targeting sequence comprising amino acids 13-25 of SEQ ID NO: 67; (463) a targeting sequence comprising amino acids 15-23 of SEQ ID NO: 67; (464) a targeting sequence comprising amino acids 23-36 of SEQ ID NO: 69; (465) a targeting sequence comprising amino acids 23-34 of SEQ ID NO: 69; (466) a targeting sequence comprising amino acids 24-36 of SEQ ID NO: 69; (467) a targeting sequence comprising amino acids 26-34 of SEQ ID NO: 69; (468) a targeting sequence comprising amino acids 27-40 of SEQ ID NO: 75; (469) a targeting sequence comprising amino acids 27-38 of SEQ ID NO: 75; (470) a targeting sequence comprising amino acids 9-22 of SEQ ID NO: 77; (471) a targeting sequence comprising amino acids 9-20 of SEQ ID NO: 77; (472) a targeting sequence comprising amino acids 10-22 of SEQ ID NO: 77; (473) a targeting sequence comprising amino acids 12-20 of SEQ ID NO: 77; (474) a targeting sequence comprising amino acids 23-36 of SEQ ID NO: 81; (475) a targeting sequence comprising amino acids 23-34 of SEQ ID NO: 81; (476) a targeting sequence comprising amino acids 24-36 of SEQ ID NO: 81; (477) a targeting sequence comprising amino acids 26-34 of SEQ ID NO: 81; (478) a targeting sequence comprising amino acids 13-26 of SEQ ID NO: 87; (479) a targeting sequence comprising amino acids 13-24 of SEQ ID NO: 87; or (480) a targeting sequence comprising amino acids 14-26 of SEQ ID NO: 87.

For example, the targeting sequence can comprise or consist of an amino acid sequence having at least about 50% identity with amino acids 20-35 of SEQ ID NO: 1, wherein the identity with amino acids 25-35 is at least about 63%.

The targeting sequence can comprise or consist of an amino acid sequence having at least about 50% identity with amino acids 20-35 of SEQ ID NO: 1, wherein the identity with amino acids 25-35 is at least about 72%.

The targeting sequence can comprise or consist of an amino acid sequence having at least about 56% identity with amino acids 20-35 of SEQ ID NO: 1, wherein the identity with amino acids 25-35 is at least about 63%.

The targeting sequence can comprise or consist of an amino sequence having at least about 62% identity with amino acids 20-35 of SEQ ID NO: 1, wherein the identity with amino acids 25-35 is at least about 72%.

The targeting sequence can comprise or consist of an amino acid sequence having at least about 68% identity with amino acids 20-35 of SEQ ID NO: 1, wherein the identity with amino acids 25-35 is at least about 81%.

The targeting sequence can comprise or consist of an amino sequence having at least about 75% identity with amino acids 20-35 of SEQ ID NO: 1, wherein the identity with amino acids 25-35 is at least about 72%.

The targeting sequence can comprise or consist of an amino sequence having at least about 75% identity with amino acids 20-35 of SEQ ID NO: 1, wherein the identity with amino acids 25-35 is at least about 81%.

The targeting sequence can comprise or consist of an amino acid sequence having at least about 81% identity with amino acids 20-35 of SEQ ID NO: 1, wherein the identity with amino acids 25-35 is at least about 81%.

The targeting sequence can comprise or consist of an amino acid sequence having at least about 81% identity with amino acids 20-35 of SEQ ID NO: 1, wherein the identity with amino acids 25-35 is at least about 90%.

The targeting sequence can consist of: (a) an amino acid sequence consisting of 16 amino acids and having at least about 43% identity with amino acids 20-35 of SEQ ID NO: 1, wherein the identity with amino acids 25-35 is at least about 54%; (b) amino acids 1-35 of SEQ ID NO: 1; (c) amino acids 20-35 of SEQ ID NO: 1; (d) SEQ ID NO: 1; (e) SEQ ID NO: 96; or (f) SEQ ID NO: 120.

The exosporium protein or exosporium protein fragment can comprise an amino acid sequence having at least 90% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 76, 78, 80, 82, 84, 86, 88, 90, 92, 94, 95, 108, 109, 110, 111, 112, 113, 114, 115, 116, 117, 118, 119, 120, 121, and 122.

The exosporium protein or exosporium protein fragment can comprise an amino acid sequence having at least 95% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 76, 78, 80, 82, 84, 86, 88, 90, 92, 94, 95, 108, 109, 110, 111, 112, 113, 114, 115, 116, 117, 118, 119, 120, 121, and 122.

The exosporium protein or exosporium protein fragment can comprise an amino acid sequence having at least 98% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 76, 78, 80, 82, 84, 86, 88, 90, 92, 94, 95, 108, 109, 110, 111, 112, 113, 114, 115, 116, 117, 118, 119, 120, 121, and 122.

The exosporium protein or exosporium protein fragment can comprise an amino acid sequence having at least 99% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 76, 78, 80, 82, 84, 86, 88, 90, 92, 94, 95, 108, 109, 110, 111, 112, 113, 114, 115, 116, 117, 118, 119, 120, 121, and 122.

The exosporium protein or exosporium protein fragment can comprise an amino acid sequence having at least 100% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 76, 78, 80, 82, 84, 86, 88, 90, 92, 94, 95, 108, 109, 110, 111, 112, 113, 114, 115, 116, 117, 118, 119, 120, 121, and 122.

The targeting sequence, exosporium protein, or exosporium protein fragment can comprise the amino acid sequence GXT at its carboxy terminus, wherein X is any amino acid.

The targeting sequence, exosporium protein, or exosporium protein fragment can comprise an alanine residue at the position of the targeting sequence that corresponds to amino acid 20 of SEQ ID NO: 1.

The targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

The fusion protein can further comprise an amino acid linker between the targeting sequence, the exosporium protein, or the exosporium protein fragment and the protein or peptide of interest. The linker can be any of the linkers described above in Section XI.

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

A further method for delivering proteins or peptides to an animal is also provided. The method comprises feeding to an animal a recombinant spore-forming bacterium. The recombinant spore-forming bacterium can be any of the recombinant spore-forming bacteria described above in Section IX.

The recombinant spore-forming bacterium can be comprised within a plant that is fed to the animal.

The recombinant spore-forming bacterium can comprise an endophytic and probiotic strain of bacteria. For example, the endophytic and probiotic strain of bacteria can comprise *Bacillus megaterium* EE385 (NRRL B-50980), *Bacillus* sp. EE387 (NRRL B-50981), *Bacillus circulans* EE388 (NRRL B-50982), *Bacillus subtilis* EE405 (NRRL B-50978), *Lysinibacillus fusiformis* EE442 (NRRL B-50975), or *Lysinibacillus sphaericus* EE443 (NRRL B-50976), *Bacillus pumilus* EE-B00143 (NRRL B-67123), or a combination thereof.

In any of the above methods, the plant can be processed prior to feeding to the animal.

In any of the above methods involving feeding a plant to an animal, the method can further comprise introducing the endophytic strain of bacteria or a formulation comprising the endophytic strain of bacteria into a plant growth medium. Alternatively, the method can comprise applying the endophytic strain of bacteria or a formulation comprising the endophytic strain of bacteria to a plant, a plant seed, or an area surrounding a plant or a plant seed. The plant fed to the animal comprises a plant grown in a plant growth medium containing the endophytic and probiotic strain of bacteria or a formulation comprising the endophytic and probiotic strain of bacteria, a plant to which the endophytic and probiotic strain of bacteria was applied, a plant grown from a plant seed to which the endophytic and probiotic strain of bacteria was applied, a plant grown in an area to which the endophytic and probiotic strain of bacteria was applied, or a seed grown in the area to which the endophytic and probiotic strain of bacteria was applied.

In any of the above methods for delivering proteins or peptides to an animal, the protein or peptide of interest comprises an enzyme. For example, the enzyme can comprise a xylanase, a xylosidase, a phytase, a phosphatase, a protease, a cellulase, an endoglucanase, an exogluconase, a glucanase, an amylase (e.g., α-amylase or a β-amylase), a lipase, a phospholipase, a glycosylase, a galactanase, an α-galactosidase, a β-glucosidase, an amylase, a pectinase, a biotinase, a polygalacturonase, a ligninase, or a combination thereof. The lipase can comprise a phospholipase A1, a phospholipase A2, a phospholipase C, a phospholipase D, a lysophospholipase, or a combination thereof. The enzyme preferably comprises a xylanase or a phytase.

In any of the methods comprising feeding a plant to an animal, the plant can be processed prior to feeding to the animal.

In any of the above methods comprising delivery of bacteria, proteins, or peptides to an animal, the animal can be a mammal (e.g., a sheep, goat, cow, pig, deer, alpaca, bison, camel, donkey, horse, mule, llama, rabbit, dog, or cat), a bird (e.g., a chicken, turkey, duck, goose, quail, or pheasant), a fish (e.g., salmon, trout, tilapia, tuna, catfish, or a carp), or a crustacean (e.g., a shrimp, prawn, lobster, crab, or crayfish).

XXI. Methods for Delivering Beneficial Nucleic Acids to Animals, Insects, Worms, Fungi, and Protozoans The invention further relates to methods for delivering a nucleic acid molecule to an animal, insect, worm, fungus, or protozoan.

The method can comprise feeding to an animal, an insect, or worm a plant modified to comprise a level of the nucleic acid molecule that is greater than the level of the nucleic acid molecule in the same plant that has not been modified, grown under the same conditions.

A further method for delivering a nucleic acid molecule to an animal, insect, or worm is provided. The method can comprise feeding to an animal, insect, or worm a recombinant *Bacillus cereus* family member expressing a fusion protein comprising a protein or peptide of interest and a targeting sequence, exosporium protein, or exosporium protein fragment that targets the fusion protein to the exosporium of the recombinant *Bacillus cereus* family member. Alternatively, the method can comprise feeding to an animal, insect, or worm a recombinant spore-forming bacterium that expresses a fusion protein comprising at least one protein or peptide of interest and a spore coat protein that targets the fusion protein to the surface of a spore of the bacterium. The protein or peptide of interest comprises a nucleic acid binding protein or peptide and the nucleic acid molecule is bound to the DNA or RNA binding protein or peptide. The nucleic acid binding protein or peptide can be physically attached to the exosporium of the recombinant *Bacillus cereus* family member or to the spore coat of the recombinant spore-forming bacterium.

Another method for delivering a nucleic acid molecule to an animal, insect, or worm is provided. The method comprises feeding to an animal, insect, or worm exosporium fragments derived from a recombinant *Bacillus cereus* family member. The exosporium fragments are derived from spores of a recombinant *Bacillus cereus* family member described in Section IV hereinabove and comprise the fusion protein. The fusion protein comprises a nucleic acid binding protein or peptide, and wherein the nucleic acid binding protein or peptide is bound to a nucleic acid molecule.

The worm is preferably a nematode.

A method for delivering a nucleic acid molecule to a fungus or a protozoan is provided. The method comprises contacting a fungus or a protozoan with a recombinant *Bacillus cereus* family member expressing a fusion protein comprising a protein or peptide of interest and a targeting sequence, exosporium protein, or exosporium protein fragment that targets the fusion protein to the exosporium of the recombinant *Bacillus cereus* family member. Alternatively, the method comprises contacting a fungus or a protozoan with a recombinant spore-forming bacterium that expresses a fusion protein comprising at least one protein or peptide of interest and a spore coat protein that targets the fusion protein to the surface of a spore of the bacterium. The protein or peptide of interest comprises a nucleic acid binding protein or peptide and the nucleic acid molecule is bound to the nucleic acid binding protein or peptide.

A further method for delivering a nucleic acid molecule to a fungus or a protozoan is provided. The method comprises contacting a fungus or a protozoan with exosporium fragments. The exosporium fragments are derived from spores of a recombinant *Bacillus cereus* family member described in Section IV hereinabove and comprise the fusion protein. The fusion protein comprises a nucleic acid binding protein or peptide, and wherein the nucleic acid binding protein or peptide is bound to a nucleic acid molecule.

The nucleic acid molecule can comprise a modulating RNA molecule; an RNAi molecule; a microRNA; an aptamer; or a DNA molecule that encodes a modulating RNA molecule, an RNAi molecule, a microRNA, or an aptamer.

The recombinant *Bacillus cereus* family member can comprise any of the recombinant *Bacillus cereus* family members that express a fusion protein.

The fusion protein can comprise any of the fusion proteins described herein that include a nucleic acid binding protein.

The spore coat protein comprises a CotB protein, a CotC protein, a CgeA protein, a CotB/H protein, a CotG protein, a spore coat protein X protein, or a CotY protein.

The spore coat protein can comprise an amino acid sequence having at least 85% identity with any of SEQ ID NOs: 252-259.

The spore coat protein can comprise an amino acid sequence having at least 90% identity with any of SEQ ID NOs: 252-259.

The spore coat protein can comprise an amino acid sequence having at least 95% identity with any of SEQ ID NOs: 252-259.

The spore coat protein can comprise an amino acid sequence having at least 98% identity with any of SEQ ID NOs: 252-259.

The spore coat protein can comprise an amino acid sequence having at least 99% identity with any of SEQ ID NOs: 252-259.

The spore coat protein can comprise an amino acid sequence having 100% identity with any of SEQ ID NOs: 252-259.

The above-described methods can be used for numerous purposes. For example, these methods can be used to deliver RNA or DNA to animals for the purpose of decreasing susceptibility of the animal to a disease or treating a disease in the animal (e.g., organic disease such as stroke, diabetes, heart disease, and degenerative diseases). RNAs and DNAs have also been demonstrated to be effective for eliminating or treating disease caused by animal pathogens, such as bacteria, viruses, worms (e.g., nematodes), and fungi. The RNAs and DNAs can act directly on the pathogen, or can work with the animal's immune system to activate or increase the immune response.

In addition, the above methods can be used for eliminating pests, including insects, worms (e.g., nematodes), fungi, and protozoans. Delivery of specific RNAs or DNAs to the pest can lead to decreased ability to of the pest to infect a host (e.g., a plant host), decreased feeding on target hosts or plants, direct killing through blocking of key genes, or various other effects.

XXII. Vaccines and a Method of Producing an Immunogenic Response

A vaccine is provided which comprises a pharmaceutically acceptable carrier and recombinant *Bacillus cereus* family member spores that express a fusion protein as described above in paragraphs [00171], [00173]-[00176] of Section I wherein the protein or peptide of interest is an antigen or an immunogen.

A further vaccine is provided which comprises a pharmaceutically acceptable carrier and exosporium fragments. The exosporium fragments are derived from spores of a recombinant *Bacillus cereus* family member described in Section IV hereinabove and comprise the fusion protein. The fusion protein comprises an antigen.

Yet another vaccine is provided which comprises a pharmaceutically acceptable carrier and a recombinant *Bacillus cereus* family member. The recombinant *Bacillus cereus* family member is a recombinant *Bacillus cereus* family member as described above in Section II.

In the vaccines that comprise exosporium fragments or a recombinant *Bacillus cereus* family member as described above in Section II, the targeting sequence, exosporium protein, or exosporium protein fragment can comprise any of the targeting sequences, exosporium proteins, or exosporium protein fragments described herein. In particular, the targeting sequence, exosporium protein, or exosporium protein fragment can comprise any of the targeting sequences, exosporium proteins, or exosporium protein fragments described above in paragraphs [00782]-[00801].

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

When the protein or peptide of interest is an antigen, display of the antigen on the outside of the spore or on an exosporium fragment provides an immune system response to achieve vaccination against various pathogens or diseases. Suitable antigens or small molecules are those that are known or expected to illicit a desired immune response that is sufficient to yield a therapeutic or protective effect when expressed on the exterior of a *Bacillus* spore or displayed on an exosporium fragment. Suitability in large part will be determined by the folding in the three-dimensional structure once the recombinant antigen is incorporated into the exosporium, i.e. the antigenic portion(s) of the recombinant molecule must be available for detection by the immune system.

The pathogens or diseases from which the antigen can be derived include, but are not limited to, *Acintobacter* infections, caused by *Acinetobacter baumannii*; Actinomycosis, caused by *Actinomyces israelii, Actinomyces gerencseriae*, and *Propionibacterium propionicus*; African sleeping sickness, caused by *Trypanosoma brucei*; Acquired immune deficiency syndrome (AIDS), caused by Human immunodeficiency virus; Amebiasis, caused by *Entamoeba histolytica*; Anaplasmosis, caused by *Anaplasma* genus; Anthrax, caused by *Bacillus anthracis; Arcanobacterium haemolyticum* infection, caused by *Arcanobacterium haemolyticum*; Argentine hemorrhagic fever, caused by Junin virus; Ascariasis, caused by *Ascaris lumbricoides*, Astrovirus infection, caused by Astroviradae family; Babesiosis, *Babesia* genus; *Bacillus cereus* infection, caused by *Bacillus cereus*; Bacterial pneumonia; Bacterial vaginosis; *Bacteroides* infection, caused by *Bacteroides* genus; Balantidiasis, caused by *Balantidium coli; Baylisascaris* infection, caused by *Baylisascaris* genus; BK virus infection, caused by BK virus; Black piedra, caused by Piedraia hortae; *Blastocystis hominis* infection, caused by *Blastocystis hominis*; Blastomycosis, caused by *Blastomyces dermatitidis*; Bolivian hemorrhagic fever, caused by Machupo virus; *Borrelia* infection, caused by *Borrelia* genus; Botulism (and Infant botulism), caused by the intake of *Clostridium botulinum* toxin; Brazilian hemorrhagic fever, caused by Sabia; Brucellosis, caused by *Brucella* genus; *Burkholderia* infection, caused by usually *Burkholderia cepacia* and other *Burkholderia* species; Buruli ulcer, caused by *Mycobacterium ulcerans*; Calicivirus infection (Norovirus and Sapovirus), caused by Caliciviridae family; Campylobacteriosis, caused by *Campylobacter* genus; Candidiasis (Moniliasis; Thrush) usually caused by *Candida albicans* and other *Candida* species; Cat-scratch disease, caused by *Bartonella henselae*; Cellulitis, caused by usually Group A *Streptococcus* and *Staphylococcus*; Chagas Disease (American trypanosomiasis), caused by *Trypanosoma cruzi*; Chancroid, caused by *Haemophilus ducreyi*; Chickenpox, caused by Varicella zoster virus (VZV); Chlamydia, caused by *Chlamydia trachomatis; Chlamydophila pneumoniae* infection, caused by *Chlamydophila pneumoniae*; Cholera, caused by *Vibrio cholerae*; Chromoblastomycosis, caused by usually Fonsecaeapedrosoi; Clonorchiasis, caused by *Clonorchis sinensis; Clostridium difficile* infection, caused by *Clostridium difficile*; Coccidioidomycosis, caused by *Coccidioides immitis* and *Coccidioides posadasii*; Colorado tick fever (CTF), caused by Colorado tick fever virus (CTFV); Common cold (Acute viral rhinopharyngitis; Acute coryza), caused by usually rhinoviruses and coronaviruses; Creutzfeldt-Jakob disease (CJD), caused by CJD prion; Crimean-Congo hemorrhagic fever (CCHF), caused by Crimean-Congo hemorrhagic fever virus; Cryptococcosis, caused by *Cryptococcus neoformans*; Cryptosporidiosis, caused by *Cryptosporidium* genus; Cutaneous larva migrans (CLM), caused by usually *Ancylostoma braziliense* and multiple other parasites; Cyclosporiasis, caused by *Cyclospora cayetanensis*; Cysticercosis, caused by *Taenia solium*; Cytomegalovirus infection, caused by Cytomegalovirus; Dengue fever, caused by Dengue viruses (DEN-1, DEN-2, DEN-3 and DEN-4)-Flaviviruses; Dientamoebiasis, caused by *Dientamoeba fragilis*; Diphtheria, caused by *Corynebacterium diphtheriae*; Diphyllobothriasis, caused by *Diphyllobothrium*; Dracunculiasis, caused by *Dracunculus medinensis*; Ebola hemorrhagic fever, caused by Ebolavirus (EBOV); Echinococcosis, caused by *Echinococcus* genus; Ehrlichiosis, caused by *Ehrlichia* genus; Enterobiasis (Pinworm infection), caused by *Enterobius vermicularis; Enterococcus* infection, caused by *Enterococcus* genus; Enterovirus infection, caused by Enterovirus genus; Epidemic typhus, caused by *Rickettsia prowazekii*; Erythema infectiosum (Fifth disease), caused by Parvovirus B19; Exanthem subitum, caused by Human herpesvirus 6 (HHV-6) and Human herpesvirus 7 (HHV-7); Fasciolopsiasis, caused by *Fasciolopsis buski*; Fasciolosis, caused by *Fasciola hepatica* and *Fasciola gigantica*; Fatal familial insomnia (FFI), caused by FFI prion; Filariasis, caused by Filarioidea superfamily; Food poisoning caused by *Clostridium perfringens*; Free-living amebic infection; *Fusobacterium* infection, caused by *Fusobacterium* genus; Gas gangrene (*Clostridial myonecrosis*), caused by usually *Clostridium perfringens* or other *Clostridium* species; Geotrichosis, caused by *Geotrichum candidum*; Gerstmann-Straussler-Scheinker syndrome (GSS), caused by GSS prion; Giardiasis, caused by Giardia intestinalis; Glanders, caused by *Burkholderia mallei*; Gnathostomiasis, caused by *Gnathostoma spinigerum* and *Gnathostoma hispidum*; Gonorrhea, caused by *Neisseria gonorrhoeae*; Granuloma inguinale (Donovanosis), caused by *Klebsiella granulomatis*; Group A streptococcal infection, caused by *Streptococcus pyogenes*; Group B streptococcal infection, caused by *Streptococcus agalactiae; Haemophilus influenzae* infection, caused by *Haemophilus influenzae*; Hand, foot and mouth disease (HFMD), caused by Enteroviruses, mainly Coxsackie A virus and Enterovirus 71 (EV71); Hantavirus Pulmonary Syndrome (HPS), caused by Sin Nombre virus; *Helicobacter pylori* infection, caused by *Helicobacter pylori*; Hemolytic-uremic syndrome (HUS), caused by *Escherichia coli* O157:H7; Hemorrhagic fever with renal syndrome (HFRS), caused by Bunyaviridae family; Hepatitis A, caused by Hepatitis A Virus; Hepatitis B, caused by Hepatitis B Virus; Hepatitis C, caused by Hepatitis C Virus; Hepatitis D caused by Hepatitis D Virus; Hepatitis E, caused by Hepatitis E Virus; Herpes simplex, caused by Herpes simplex virus 1 and 2 (HSV-1 and HSV-2); Histoplasmosis, caused by *Histoplasma capsulatum*; Hookworm infection, caused by *Ancylostoma duodenale* and *Necator americanus*; Human bocavirus infection, caused by Human bocavirus (HBoV); Human *ewingii* ehrlichiosis, caused by *Ehrlichia ewingii*; Human granulocytic anaplasmosis (HGA), caused by *Anaplasma phagocytophilum*; Human metapneumovirus infection, caused by Human metapneumovirus (hMPV); Human monocytic ehrlichiosis, caused by *Ehrlichia chaffeensis*; Human papillomavirus (HPV) infection, caused by Human papillomavirus (HPV); Human parainfluenza virus infection, caused by Human parainfluenza viruses (HPIV); Hymenolepiasis, caused by *Hymenolepis nana* and *Hymenolepis diminuta*; Epstein-Barr Virus Infectious Mononucleosis (Mono), caused by Epstein-Ban Virus (EBV); Influenza (flu), caused by Orthomyxoviridae family; Isosporiasis, caused by *Isospora Belli*; Kawasaki disease (cause unknown but evidence supports that it is infectious); Keratitis; Kingella kingae infection, caused by Kingella kingae; Kuru, caused by Kuru prion; Lassa fever, caused by Lassa virus; Legionellosis (Legionnaires' disease), caused by *Legionella pneumophila*; Legionellosis (Pontiac fever), caused by *Legionella pneumophila*; Leishmaniasis, caused by *Leishmania* genus; Leprosy, caused by *Mycobacterium leprae* and *Mycobacterium* lepromatosis; Leptospirosis, caused by Leptospira genus; Listeriosis, caused by *Listeria monocytogenes*; Lyme disease (Lyme borreliosis), caused by usually *Borrelia burgdorferi* and other *Borrelia* species; Lymphatic filariasis (Elephantiasis), caused by *Wuchereria bancrofti* and *Brugia malayi*; Lymphocytic choriomeningitis, caused by Lymphocytic choriomeningitis virus (LCMV); Malaria, caused by *Plasmodium* genus; Marburg hemorrhagic fever (MHF), caused by Marburg virus; Measles, caused by Measles virus; Melioidosis (Whitmore's disease), caused by Burkholderiapseudomallei; Meningitis; Meningococcal disease, caused by *Neisseria meningitidis*; Metagonimiasis, caused by usually *Metagonimus* yokagawai; Microsporidiosis, caused by Microsporidia phylum; Molluscum contagiosum (MC), caused by Molluscum contagiosum virus (MCV); Mumps, caused by Mumps virus; Murine typhus (Endemic typhus), caused by *Rickettsia typhi; Mycoplasma* pneumonia, caused by *Mycoplasma pneumoniae*; Mycetoma, caused by numerous species of bacteria (Actinomycetoma) and fungi (Eumycetoma); Myiasis, caused by parasitic dipterous fly larvae; Neonatal conjunctivitis (Ophthalmia neonatorum), caused by most commonly *Chlamydia trachomatis* and *Neisseria gonorrhoeae*; (New) Variant Creutzfeldt-Jakob disease (vCJD, nvCJD), caused by vCJD prion; Nocardiosis, caused by usually *Nocardia asteroides* and other *Nocardia* species; Onchocerciasis (River blindness), caused by *Onchocerca volvulus*; Paracoccidioidomycosis (South American blastomycosis), caused by *Paracoccidioides brasiliensis*; Paragonimiasis, caused by usually *Paragonimus westermani* and other *Paragonimus* species; Pasteurellosis, caused by *Pasteurella* genus; Pediculosis capitis (Head lice), caused by *Pediculus humanus* capitis; Pediculosis corporis (Body lice), caused by *Pediculus humanus* corporis; Pediculosis pubis (Pubic lice, Crab lice), caused by Phthirus pubis; Pelvic inflammatory disease (PID); Pertussis (Whooping cough), caused by *Bordetella pertussis*; Plague, caused by Yersiniapestis; Pneumococcal infection, caused by *Streptococcus pneumoniae; Pneumocystis* pneumonia (PCP), caused by Pneumocystisjirovecii; Pneumonia; Poliomyelitis, caused by Poliovirus; *Prevotella* infection, caused by *Prevotella* genus; Primary amoebic meningoencephalitis (PAM), caused by usually *Naegleria fowleri*; Progressive multifocal leukoencephalopathy, caused by JC virus; Psittacosis, caused by *Chlamydophila psittaci*; Q fever, caused by *Coxiella burnetii*; Rabies, caused by Rabies virus; Rat-bite fever, caused by *Streptobacillus moniliformis* and Spirillum minus; Respiratory syncytial virus infection, caused by Respiratory syncytial virus (RSV); Rhinosporidiosis, caused by *Rhinosporidium seeberi*; Rhinovirus infection, caused by Rhinovirus; Rickettsial infection, caused by *Rickettsia* genus; Rickettsialpox, caused by *Rickettsia akari*; Rift Valley fever (RVF), caused by Rift Valley fever virus; Rocky mountain spotted fever (RMSF), caused by *Rickettsia rickettsii*; Rotavirus infection, caused by Rotavirus; Rubella, caused by Rubella virus; Salmonellosis, caused by *Salmonella* genus; SARS (Severe Acute Respiratory Syndrome), caused by SARS coronavirus; Scabies, caused by *Sarcoptes scabiei*; Schistosomiasis, caused by *Schistosoma* genus; Sepsis; Shigellosis (Bacillary dysentery), caused by *Shigella* genus; Shingles (Herpes zoster), caused by Varicella zoster virus (VZV); Smallpox (Variola), caused by Variola major or Variola minor; Sporotrichosis, caused by *Sporothrix schenckii*; Staphylococcal food poisoning, caused by *Staphylococcus* genus; Staphylococcal infection, caused by *Staphylococcus* genus; Strongyloidiasis, caused by *Strongyloides stercoralis*; Syphilis, caused by *Treponema pallidum*; Taeniasis, caused by *Taenia* genus; Tetanus (Lockjaw), caused by *Clostridium tetani*; Tinea barbae (Barber's itch), caused by usually *Trichophyton* genus; Tinea capitis (Ringworm of the Scalp), caused by usually *Trichophyton tonsurans*; Tinea corporis (Ringworm of the Body), caused by usually *Trichophyton* genus; Tinea cruris (Jock itch), caused by usually *Epidermophyton floccosum, Trichophyton rubrum,* and *Trichophyton mentagrophytes*; Tinea manuum (Ringworm of the Hand), caused by *Trichophyton rubrum*; Tinea nigra, caused by usually *Hortaea werneckii*; Tinea pedis (Athlete's foot), caused by usually *Trichophyton* genus; Tinea unguium (Onychomycosis), caused by usually *Trichophyton* genus; Tinea *versicolor* (Pityriasis versicolor), caused by *Malassezia* genus; Toxocariasis (Ocular Larva Migrans (OLM)), caused by *Toxocara canis* or *Toxocara cati*; Toxocariasis (Visceral Larva Migrans (VLM)), caused by *Toxocara canis* or *Toxocara cati*; Toxoplasmosis, caused by *Toxoplasma gondii*; Trichinellosis, caused by *Trichinella spiralis*; Trichomoniasis, caused by *Trichomonas vaginalis*; Trichuriasis (Whipworm infection), caused by *Trichuris trichiura*; Tuberculosis, caused by usually *Mycobacterium tuberculosis*; Tularemia, caused by *Francisella tularensis; Ureaplasma urealyticum* infection, caused by *Ureaplasma urealyticum*; Venezuelan equine encephalitis, caused by Venezuelan equine encephalitis virus; Venezuelan hemorrhagic fever, caused by Guanarito virus; Viral pneumonia; West Nile Fever, caused by West Nile virus; White *piedra* (Tinea blanca), caused by *Trichosporon beigelii; Yersinia pseudotuberculosis* infection, caused by *Yersinia pseudotuberculosis*; Yersiniosis, caused by *Yersinia enterocolitica*; Yellow fever, caused by Yellow fever virus; Zygomycosis, caused by Mucorales order (Mucormycosis) and *Entomophthorales* order (Entomophthoramycosis).

When the protein or peptide of interest is an antigen, any *Bacillus cereus* family member can be used to express the fusion protein. *Bacillus thuringiensis* or *Bacillus mycoides* are preferred.

To prepare a vaccine, the antigen of interest is incorporated into the fusion protein by known methods such as PCR splicing by overlapping extension, restriction endonuclease digestion and ligation, or de novo gene synthesis. The fusion protein gene is then introduced into a recombinant *Bacillus cereus* family member by transfection, transformation, conjugation, electroporation or other known methods. The recombinant *Bacillus cereus* family member is then grown in culture media (e.g., minimal liquid media) and allowed to sporulate. Preferably, sporulation continues to completion before the spores are collected and stored. Spores can be collected by either centrifugation or swabbing of spores off of growth plates and introduction into liquid media (e.g., PBS or water) followed by centrifugation and washing of the resulting spore pellet in liquid media. Prior to use, the spore pellet can be resuspended in liquid media to a desired concentration for use or injection. Where the vaccine is to comprise exosporium fragments, the exosporium fragments can be prepared using any of the methods described in section XIX.H above.

The desired concentration of recombinant *Bacillus cereus* family member spores or exosporium fragments in a vaccine is based on the size of the subject, the amount of active antigen on the surface of the spores, and the presence and concentration of adjuvants in the vaccine formulation. A vaccine of the invention can contain conventional adjuvants including pharmaceutically acceptable carriers.

A method of producing an immunogenic response in a subject is provided. The method comprises administering a vaccine containing recombinant *Bacillus cereus* family member spores expressing fusion proteins or exosporium fragments comprising fusion proteins as described herein to the subject.

The vaccine as described herein is suitable for intravenous, intrarterial, intraperitoneal, intramuscular, subcutaneous, intrapleural, topical, oral, intranasal, intradermal, transepithelial administration or by inhalation.

The vaccine can be administered to a subject which is human, murine, avian, porcine, bovine, ovine, feline, canine, equine, caprine, reptilian or a non-human primate. The subject is preferably mammalian and most preferably human.

XXIII. Remediation

When the protein or peptide of interest is a remediation protein or peptide, a toxic substance is catalytically converted by the remediation protein or peptide to a non-toxic or less toxic substance.

When the remediation protein or peptide comprises an enzyme, the enzyme is displayed and stabilized on the outside of the spore and can be delivered into contaminated soil or contaminated water in a form which is active against a target pollutant or target chemical.

Suitable enzymes depend upon the pollutant or chemical being targeted for remediation.

To prepare a remediation composition, the enzyme of interest is incorporated into the fusion protein by known methods such as PCR splicing by overlapping extension, restriction endonuclease digestion and ligation, or de novo gene synthesis. The fusion protein gene is then introduced into a recombinant *Bacillus cereus* family member by transfection, transformation, conjugation, electroporation or other known methods. The recombinant *Bacillus cereus* family member is then grown in culture media (e.g., minimal liquid media) and allowed to sporulate. Preferably, sporulation continues to completion before the spores are collected and stored. Spores can be collected by either centrifugation or swabbing of spores off of growth plates and introduction into liquid media (e.g., PBS or water) followed by centrifugation and washing of the resulting spore pellet in liquid media. Prior to use, the spore pellet can be resuspended in liquid media to a desired concentration for use. Alternatively, the spore pellet can be formulated into granules at a desired concentration for use and application to the contaminated environment. Where exosporium fragments are to be used for remediation, the exosporium fragments can be prepared using any of the methods described in section XIX.H above.

A method of reducing contaminants in an environment is provided. The method comprises exposing a contaminated environment to a recombinant *Bacillus cereus* family member spore that express the fusion protein as described above in paragraphs [00171], [00173]-[00175] and [00177] of Section I wherein the protein or peptide of interest comprises a remediation enzyme.

A further method for reducing contaminants in an environment is provided. The method comprises exposing a contaminated environment to exosporium fragments. The exosporium fragments are derived from a recombinant *Bacillus cereus* family member described in Section IV hereinabove and comprise the fusion protein. The fusion protein comprises a remediation enzyme.

Yet another method for reducing contaminants in an environment is provided. The method comprises exposing a contaminated environment to spores of a recombinant *Bacillus cereus* family member. The recombinant *Bacillus cereus* family member is a recombinant *Bacillus cereus* family member as described above in Section II.

In the methods for reducing contaminants that comprise exposing a contaminated environment to exosporium fragments or to a recombinant *Bacillus cereus* family member as described above in Section II, the targeting sequence, exosporium protein, or exosporium protein fragment can be any of the targeting sequences, exosporium proteins, or exosporium protein fragments described herein. In particular, the targeting sequence, exosporium protein, or exosporium protein fragment can comprise any of the targeting sequences, exosporium protein, or exosporium protein fragments described above in paragraphs [00782]-[00801].

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

When the protein or peptide of interest is a remediation enzyme, any *Bacillus cereus* family member can be used to express the fusion protein. *Bacillus thuringiensis, Bacillus cereus,* or *Bacillus mycoides* are preferred.

The recombinant *Bacillus cereus* family member spores can comprise an endophytic strain of bacteria for phytoremediation, such as *Bacillus cereus* family member EE349, *Bacillus cereus* family member EE439, *Bacillus thuringiensis* EE417, *Bacillus cereus* EE444, or *Bacillus thuringiensis* EE319.

The contaminated environment to be treated can be gas, liquid, semi-liquid, gel, film, semi-solid, or solid. The solid environment can be soil such as surface soil and subsurface soil, compost, crop residue, leaves, mulch, cut trees, a biofilm, a slime layer, mold, sludge, sand, slag, sediment, sewage, waste rock, nuclear waste, munitions and ordnance, hospital waste, junked auto parts, metal cuttings, insulation waste, food waste, asbestos, batteries, industrial scrap, landfill waste, wood waste, textile waste, glass waste, leather waste, rubber waste, plastic waste, electronic component waste, agricultural waste, photographic waste, ceramic waste, pharmaceutical waste, wax, spent catalysts, or a combination thereof. The liquid environment can be drinking water, groundwater, surface water, brine, storage tanks, lagoons, an aquatic system, industrial wastewater, acid mine drainage, spent autofluid, spent plating baths, degreasing solutions, dry cleaning solutions, machine coolants, drilling fluid waste, cutting fluid waste, hydraulic fracturing fluid waste, lubricant waste, paint, greywater, oily wastewater, pulp mill effluent, a water treatment system, a septic system, a sewer system, a precipitation lagoon, a holding pond, a lake, a river, or combinations thereof. The gaseous environment can be air, a flue gas such as emissions from power plants, waste incinerators, crematoria or refineries, a process exhaust stream, landfill gas, natural gas, propane gas, or a combination thereof.

The contaminated environment can be contaminated by various contaminants including, but not limited to, a chemical warfare agent comprising sarin (GB; o-isopropyl methylphosphonofluoridate); soman (GD; o-pinacolyl methylphosphonofluoridate); cyclosarin (GF; o-cyclohexyl methylphosphonofluoridate); VX (O-ethyl S-[2-(diisopropylamino)ethyl]methylphosphonothioate); tabun (GA; N,N-dimethylethyl phosphoroamidocyanidate), DFP (diisopropyl phophorofluoridate), or a mustard agent; an inorganic compound comprising arsenic, antimony, barium, beryllium, cadmium, chromium, copper, iron, lead, manganese, mercury, nickel, selenium, silver, tin, thallium, uranium, zinc or a combination thereof; an organic compound comprising a polycyclic aromatic hydrocarbon (PAH), a chlorinated aromatic compound, a chlorinated aliphatic compound, a nitroaromatic compound (NAC), a phenolic compound, a cyano compound, dioxin, or a combination thereof; a crude oil, a refined oil, a fuel oil, a diesel oil, a gasoline, a hydraulic oil, and kerosene, or a volatile constituent thereof such as benzene, toluene, ethylbenzene, xylene, or naphthalene; an explosive, a fertilizer, a pesticide, an insecticide, or an herbicide The concentration of recombinant spores or exosporium fragments needed to treat a contaminated environment is based on factors including the volume or area to be treated, the extent of the target chemical, pollutant or organic matter present, the amount of time available for treatment, and amount of active enzyme on the surface of the spores.

The recombinant *Bacillus cereus* family member spores or exosporium fragments can contact the contaminated environment by incorporating the spores or exosporium fragments into a stream containing the contaminant, contacting a stream containing the contaminant with an immobilization material containing the spores or exosporium fragments (e.g., a filter, membrane, sponge or cassette), incorporating the spores or exosporium fragments into granules to be mixed with the contaminated environment, spraying the spores or exosporium fragments onto or into the contaminated environment, injecting the spores or exosporium fragments into the contaminated environment, or drenching the contaminated environment with the spores or exosporium fragments.

The spores can be combined with bacterial inoculants, chemicals, solvents, and other products that can expedite the decomposition process.

The remediation enzyme includes, but is not limited to, a phosphate binding protein, a protease, a carbohydrate hydrolyase, a lipase, a phospholipase, a nuclease, a nutrient binding protein, a cellulase, an oxidoreductase, a monooxygenase, a dioxygenase, a laccase, a lignin peroxidase, a manganese peroxidase, a peroxidase, a dehalogenase, a catalase, an amylase, a reductase, an oxidase, an amidase, a ligninase, a xylanase, a pectinase, a xylosidase, an endoglucanase, an exoglucanase, a glucosidase, a biofilm inhibitory peptide, an herbicide-degrading enzyme, a pesticide-degrading enzyme (e.g., a pyrethrinase), or a combination thereof.

Where the enzyme comprises an herbicide-degrading enzyme or a pesticide-degrading enzyme, the recombinant *Bacillus cereus* family member suitably comprises a strain of bacteria that is capable of degrading an herbicide or a pesticide. For example, the strain of bacteria that is capable of degrading an herbicide or a pesticide can comprise *Bacillus cereus* family member EE349 (NRRL No. B-50928), *Bacillus cereus* family member EE-B00377 (NRRL B-67119); *Bacillus pseudomycoides* EE-B00366 (NRRL B-67120); or *Bacillus mycoides* EE-B00363 (NRRL B-67121).

A method for phytoremediation of contaminated soil is also provided. The method comprises introducing recombinant *Bacillus cereus* family member spores into contaminated soil; or applying the recombinant *Bacillus cereus* family member spores to a plant planted in contaminated soil, or a plant seed for planting in contaminated soil, or an area of contaminated soil surrounding a plant or a plant seed; wherein the recombinant *Bacillus cereus* family member spores express a fusion protein comprising at least one protein or peptide of interest and a targeting sequence, exosporium protein, or exosporium protein fragment that targets the fusion protein to the exosporium of the recombinant *Bacillus cereus* family member spore, wherein the fusion protein is the fusion protein as described above wherein the protein or peptide of interest comprises a remediation enzyme, and wherein the recombinant *Bacillus cereus* family member comprises an endophytic strain of bacteria or a root colonizing strain of bacteria. For example, the recombinant spore-forming bacterium can comprise an endophytic strain of bacteria.

A further method for phytoremediation of contaminated soil is provided. The method comprises expressing a remediation enzyme in a *Bacillus cereus* family member spore, wherein the expression of the remediation enzyme in the recombinant *Bacillus cereus* family member spore is increased as compared to the expression of the remediation enzyme in a wild-type *Bacillus cereus* family member spore.

Another method for phytoremediation of contaminated soil is also provided. The method comprises introducing a recombinant spore-forming bacterium into contaminated soil; or applying the recombinant spore-forming bacterium to a plant planted in contaminated soil, or a plant seed to be planted in contaminated soil, or an area of contaminated soil surrounding a plant or a plant seed. The recombinant spore-forming bacterium expresses a fusion protein comprising at least one protein or peptide of interest and a spore coat protein that targets the fusion protein to the surface of a spore of the bacterium. The spore coat protein comprises a CotB protein, a CotC protein, a CgeA protein, a CotB/H protein, a Cot G protein, a spore coat protein X protein, or a CotY protein. The recombinant spore-forming bacterium comprises an endophytic strain of bacteria or a root colonizing strain of bacteria. The protein or peptide of interest comprises a remediation enzyme.

Another method for phytoremediation of contaminated soil is also provided. The method comprises introducing exosporium fragments into contaminated soil or applying exosporium fragments to a plant planted in contaminated soil, or a plant seed to be planted in contaminated soil, or an area of contaminated soil surrounding a plant or a plant seed. The exosporium fragments are derived from spores of a recombinant *Bacillus cereus* family member described in Section IV herein above and comprise the fusion protein. The fusion protein comprises a remediation enzyme.

Yet another method for phytoremediation of contaminated soil is provided. The method comprises introducing spores of a recombinant *Bacillus cereus* family member into contaminated soil. Alternatively, the method comprises applying spores of a recombinant *Bacillus cereus* family member to a plant planted in contaminated soil, or a plant seed to be planted in contaminated soil, or an area of contaminated soil surrounding a plant or a plant seed. The recombinant *Bacillus cereus* family member is a recombinant *Bacillus cereus* family member as described above in Section II, and the fusion protein comprises a remediation enzyme.

In the methods for phytoremediation of contaminated soil that involve the use of exosporium fragments or a recombinant *Bacillus cereus* family member as described above in Section II, the targeting sequence, exosporium protein, or exosporium protein fragment can comprise any of the targeting sequences, exosporium proteins, or exosporium protein fragments described herein. In particular, the targeting sequence, exosporium protein, or exosporium protein fragment can comprise any of the targeting sequences, exosporium proteins, or exosporium protein fragments described above in paragraphs [00782]-[00801].

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

The remediation enzyme is displayed on the outside of the spores and within the plant so that both the plant and spores can convert the target contaminant. The plant can take up the target contaminant while the spores convert the contaminant into a non-toxic or less toxic form within the plant or its root system.

The recombinant *Bacillus cereus* family member spores can comprise an endophytic strain of bacteria, such as *Bacillus cereus* family member EE349, *Bacillus cereus* family member EE439, *Bacillus thuringiensis* EE417, *Bacillus cereus* EE444, or *Bacillus thuringiensis* EE319, *Bacillus thuringiensis* EE-B00184, *Bacillus cereus* family member EE-B00377, *Bacillus pseudomycoides* EE-B00366, or *Bacillus mycoides* EE-B00363.

The spores or the exosporium fragments can be applied to the plant or the plant seed, and the plant or plant grown from the plant seed is tolerant to a target contaminant to be remediated from the contaminated soil In the method for phytoremediation, recombinant *Bacillus cereus* family members undergo sporulation within the plant.

The recombinant *Bacillus cereus* family member spores can be introduced into the plant growth medium by various methods such as soil drench at the time of planting. The spores can also be coated onto the plant seed as a seed treatment.

Preferably, the plant to be treated with the remediation enzyme is tolerant to the target contaminant so that the plant is not injured by the target contaminant.

The concentration of recombinant spores needed for the phytoremediation method is based on factors including volume or area to be treated, the ability of the endophytic strains to colonize the plant roots, the extent that the target contaminant is present, and the amount of active enzyme on the surface of the spores.

A further method for reducing contaminants in an environment is provided. The method comprises exposing a contaminated environment to spores of a *Bacillus cereus* family member strain that is capable of degrading an herbicide or a pesticide. The contaminants in the environment comprise an herbicide, a pesticide, or a combination thereof. The *Bacillus cereus* family member strain that is capable of degrading an herbicide or a pesticide comprises *Bacillus cereus* family member EE349 (NRRL No. B-50928), *Bacillus cereus* family member EE-B00377 (NRRL B-67119); *Bacillus pseudomycoides* EE-B00366 (NRRL B-67120); *Bacillus mycoides* EE-B00363 (NRRL B-67121), or a combination thereof.

The *Bacillus cereus* family member strain that is capable of degrading an herbicide or a pesticide can comprise a recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member. The protein or peptide of interest preferably comprises an herbicide-degrading enzyme, a pesticide-degrading enzyme, or a combination thereof.

In this way, dual pesticide or herbicide degrading activity can be obtained since both the *Bacillus cereus* family member strains and the herbicide-degrading or pesticide-degrading enzymes in the fusion protein will exert pesticide- and/or herbicide-degrading activity. The herbicides and/or pesticides that are degraded by the *Bacillus cereus* family strain that is capable of degrading an herbicide or a pesticide can be the same as or different from the herbicides and/or pesticides that are degraded by the herbicide-degrading enzyme or the pesticide-degrading enzyme. Thus, where an environment is contaminated with a single type of herbicide or pesticide, dual degrading action against that single herbicide or pesticide can be obtained. Alternatively, where an environment is contaminated with more than one type of herbicide or pesticide, dual degrading action against two or more different herbicides or pesticides can be obtained.

In the methods of reducing contaminants involving the use of one of the *Bacillus cereus* family member strains described herein that is capable of degrading an herbicide or a pesticide, the targeting sequence, exosporium protein, or exosporium protein fragment can comprise any of the targeting sequences, exosporium proteins, or exosporium protein fragments described herein. In particular, the targeting sequence, exosporium protein, or exosporium protein fragment can comprise any of the targeting sequences, exosporium proteins, or exosporium protein fragments described above in paragraphs [00782]-[00801].

XXIV. Breaking Emulsions or Gels in a Hydraulic Fracturing Fluid

A method of treating a hydraulic fracturing fluid to break an emulsion or gel within the fluid is provided. The method comprises adding spores of a recombinant *Bacillus cereus* family member spores to a hydraulic fracturing fluid. The recombinant *Bacillus cereus* family member expresses a fusion protein comprising at least one protein or peptide of interest and a targeting sequence, exosporium protein, or exosporium protein fragment that targets the fusion protein to the exosporium of the recombinant *Bacillus cereus* family member spore. Such a fusion protein is described above wherein the protein or peptide of interest comprises an enzyme suitable for breaking the emulsion or gel.

The recombinant *Bacillus cereus* family member can comprise any of the recombinant *Bacillus cereus* family members described herein that express a fusion protein.

A further method of treating a hydraulic fracturing fluid to break an emulsion or gel within the fluid is provided. The method comprises adding exosporium fragments to a hydraulic fracturing fluid. The exosporium fragments are derived from a recombinant *Bacillus cereus* family member described in Section IV hereinabove and comprise the fusion protein. The fusion protein comprises an enzyme suitable for breaking the emulsion or gel.

The enzyme is selected based upon the target emulsion or gel to be treated and the pH of the hydraulic fracturing fluid. Enzymes include, but are not limited to, a hemicellulase, an amylase, a pectinase, a carbohydrate hydrolyase, a cellulase, an agarase, a polygalacturonase, an endoglucanase, or a combination thereof.

The emulsion or gel contains a polymer or other component which the enzyme can digest. The emulsion or gel can comprise a polymer, *Arabica* gum, agar, xanthan gum, cellulose, carboxymethylcellulose, carboxymethylhydroxyethyl cellulose, hydroxyethyl methylcellulose, guar, a guar derivative, or a combination thereof.

When the protein or peptide of interest is an enzyme for breaking an emulsion or gel, any *Bacillus cereus* family member can be used to express the fusion protein. *Bacillus thuringiensis* or *Bacillus mycoides* are preferred.

The spores or exosporium fragments can be injected into a well that is in contact with a subterranean hydrocarbon-containing formation such as a sandstone reservoir or a carbonate reservoir.

The concentration of spores or exosporium fragments needed is based on factors including the size of the well to be treated, the type of emulsion or gel, the amount of active enzyme on the surface of the spores or exosporium fragments, and the presence and concentration of adjuvants delivered with the enzymes.

The enzymes can digest polymers or other components within the emulsion or gel, or can dissolve such components so that the hydraulic fracturing fluid can be pumped out of the well.

In the methods of treating a hydraulic fracturing fluid to break an emulsion or gel within the fluid, any of the targeting sequences, exosporium proteins, or exosporium protein fragments described herein can be used. In particular, the targeting sequence, exosporium protein, or exosporium protein fragment can comprise any of the targeting sequences, exosporium protein, or exosporium protein fragments described above in paragraphs [00782]-[00801].

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

XXV. Feedstock Processing

Feedstock is generated from plants that are harvested for their biomass, and processed into feed (bailing, silage, extrusion, pelleting, etc). The plant biomass that constitutes the feedstock is often difficult to digest due to the fibrous nature of the material. The presence of enzymes can greatly assist in the degradation of this fibrous material, leading to a more digestible and easier to process material. Enzymes are traditionally added after the feedstock has been processed and upon delivery to the organism that is ingesting the feedstock. Enzymes delivered in feedstock can improve health and weight gain of target animals, as well as reduce the environmental impact of the waste products of animals fed such enzyme-supplemented feed.

These same systems can be utilized to pretreat feedstock that is destined for biofuel production, including processing into bioethanol, biodiesel, or other biofuels.

Many species of spores have the ability to persist on foliar surfaces, such as leaves, stems, and fruit, for long periods of time. By using spore display technologies as described herein to display the enzymes on these spores, active enzyme is provided to the feedstock that will be present as the feedstock is harvested. These target enzymes can also be delivered to the feedstock plant at planting, either through delivery of recombinant spores on the plant seeds, or delivery of the recombinant spores to the plant growth medium or area around the plant.

A method for delivering enzymes to a plant is provided. The method comprises introducing into a plant growth medium a recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member or a formulation comprising a recombinant *Bacillus cereus* family member as described herein; or applying to a plant, a plant seed, or an area surrounding a plant or a plant seed the recombinant *Bacillus cereus* family member or the formulation comprising a recombinant *Bacillus cereus* family member. The protein or peptide of interest comprises an enzyme. The enzyme can be physically attached to the exosporium of the recombinant *Bacillus cereus* family member.

Another method for delivering enzymes to a plant is provided. The method comprises introducing into a plant growth medium a recombinant spore-forming bacterium or a formulation comprising the recombinant spore-forming bacterium; or applying to a plant, a plant seed, or an area surrounding a plant or a plant seed the recombinant spore-forming bacterium or a formulation comprising the recombinant spore-forming bacterium. The recombinant spore-forming bacterium expresses a fusion protein comprising at least one protein or peptide of interest and a spore coat protein that targets the fusion protein to the surface of a spore of the bacterium. The spore coat protein comprises a CotB protein, a CotC protein, a CgeA protein, a CotB/H protein, a Cot G protein, a spore coat protein X protein, or a CotY protein. The recombinant spore-forming bacterium comprises an endophytic strain of bacteria. The protein or peptide of interest comprises an enzyme, and the enzyme is physically attached to the spore coat of the recombinant spore-forming bacterium Yet another method for delivering enzymes to a plant is provided. The method comprises introducing exosporium fragments or a formulation containing the exosporium fragments into a plant growth medium; or applying exosporium fragments or a formulation containing the exosporium fragments to a plant, a plant seed, or an area surrounding a plant or a plant seed. The exosporium fragments are derived from spores of a recombinant *Bacillus cereus* family member described in Section IV hereinabove and comprise the fusion protein. The protein or peptide of interest comprises an enzyme.

Where the method for delivering enzymes to a plant comprises the use of exosporium fragments, the method can further comprise treating the plant with a penetrating agent, a surfactant, a detergent, an oil, or a combination thereof.

Optimal bacteria strains for these methods include, but are not limited to, *Bacillus cereus* family members, including *Bacillus cereus, Bacillus mycoides, Bacillus thuringiensis*, and *Bacillus pseudomycoides*, as well as other *Bacillus* spore formers, including *Bacillus megaterium, Bacillus firmus, Bacillus flexus, Bacillus subtilis* clade members, *Bacillus pumilus, Bacillus licheniformis*, and *Bacillus subtilis*.

Application can be directly onto the plant material, optionally in conjunction with adjuvants, such as nonionic or other surfactants. The recombinant *Bacillus cereus* family member can be applied to foliage of the plant prior to harvest such as by spraying onto the foliage.

Application to the plant seed is generally performed as a seed dip, a slurry, or a polymer-based seed coating. Optionally, the application can be done in conjunction with seed applied inoculants, fungicides, insecticides, or nematocides.

Application to the plant growth medium or area around the plant can be performed prior to planting, at planting, or post planting of seeds, optionally in conjunction with fertilizers, fungicides, herbicides, or insecticides.

The enzyme is suitable for degrading biomass, digesting cellulosic material, aiding digestion in a digestive system of a target animal to which the plant can be fed, or for biofuel production (e.g., for production of bioethanol or biodiesel).

The enzyme includes, but is not limited to, a nonspecific protease, a metalloprotease, a cellulase, a xylanase, a phosphatase, an endoglucanase, an exoglucanase, a 3-glucosidase, an amylase, a pectinase, a xylosidase, a lipase, a phospholipase, or a combination thereof.

The selection of enzymes may depend on the feedstock and the intended use of the feedstock. The enzymes are preferably degradative enzymes.

Enzymes of interest in the protease family include nonspecific proteases, such as serine proteases, histidine proteases, aspartate proteases, as well as metalloproteases.

Enzymes of interest in the cellulase family would include exoglucanases, endoglucanases, β-1,3 glucosidases, cellulases, hemicellulases, a-glucosidases.

Enzymes of interest in the xylanases family include xylosidases, endoxylanases, exoxylanases, pectinases, methyl pectinases, polygalacturonase.

Enzymes of interest in the phosphatases include acid phosphatases, alkaline phosphatases, polyphosphatases, phytases, monophosphatases, and diphosphatases.

Many of these enzymes are also beneficial to plant growth.

These enzymes can not only "predigest" some of the feedstock to increase absorption of key nutrients by a target animal to which the feedstock is fed, but can also aid digestion in the digestive system of the target animal.

The "predigestion" of cellulosic material at harvest can liberate free cellulose during processing for bioethanol and biofuel production, as well as preprocessing of oils destined for biofuel production.

The bacterium can be an endophytic bacterium. Selection of endophytic recombinant bacteria will allow for the bacteria to enter into the plant, but also colonize and grow inside the plant tissues. This will establish a growing number of recombinant spore forming organisms inside the plant as it grows from use of a relatively minor amount of recombinant spores on the seed or with the seed at planting. Upon harvest of the plant biomass material, the bacterial will undergo sporulation, creating new enzymes in planta, which are active on the feedstock as it is harvested, transported, and utilized, for example, either as animal feed or for biofuel production. This can significantly reduce the input cost of degradative enzymes as compared to existing techniques. This is a unique method of delivering digestive enzymes to the biomass prior to industrial processing.

While the optimal bacterial strains are as described above, selection of endophytic strains will increase efficacy. Preferably, the endophytic bacteria comprises *Bacillus cereus* family member EE349, *Bacillus cereus* family member 439, *Bacillus thuringiensis* EE417, *Bacillus cereus* EE444, *Bacillus megaterium* EE385, *Bacillus* sp. EE387, *Bacillus circulans* EE388, *Bacillus subtilis* EE405, *Lysinibacillus fusiformis* EE442, *Lysinibacillus sphaericus* EE443, or a combination thereof.

The plant can be a crop selected from corn, alfalfa, wheat, a pasture crop, a forage crop, soybean, switchgrass, jicama, sweet sorghum, sugarcane, or a combination thereof, and other biofuel and bioethanol feedstocks.

For the methods for delivering enzymes to a plant, any of the targeting sequences, exosporium proteins, or exosporium protein fragments described herein can be used.

XXVI. Use of Spores in Altering Properties of Target Plants

The recombinant *Bacillus cereus* family members and recombinant spore-forming bacterium as described herein allow for the interaction of surface displayed signaling molecules impacting biochemical pathways, and a number of other proteins that benefit plant health. The presence of the spore displayed proteins or peptides can lead to alteration in the metabolism of the target plant, leading to changes in the composition of the plant, its fruit, or other properties or characteristics.

The expression of fusion proteins can be directly used to alter the composition of the target plant. Selection of different enzymes leads to varying effects on the target plant.

A method for altering a property of a plant is provided. The method comprises introducing into a plant growth medium a recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member or a formulation comprising a recombinant *Bacillus cereus* family member as described herein; or applying to a plant, a plant seed, or an area surrounding a plant or a plant seed the recombinant *Bacillus cereus* family member or the formulation comprising a recombinant *Bacillus cereus* family member. The protein or peptide of interest comprises a plant signaling molecule or an enzyme that affects plant composition, and the protein or peptide of interest can be physically attached to the exosporium of the recombinant *Bacillus cereus* family member.

Another method for altering a property of a plant is provided. The method comprises introducing into a plant growth medium a recombinant spore-forming bacterium or a formulation comprising the recombinant spore-forming bacterium; or applying to a plant, a plant seed, or an area surrounding a plant or a plant seed the recombinant spore-forming bacterium or a formulation comprising the recombinant spore-forming bacterium. The recombinant spore-forming bacterium expresses a fusion protein comprising at least one protein or peptide of interest and a spore coat protein that targets the fusion protein to the surface of a spore of the bacterium. The spore coat protein comprises a CotB protein, a CotC protein, a CgeA protein, a CotB/H protein, a Cot G protein, a spore coat protein X protein, or a CotY protein. The recombinant spore-forming bacterium comprises an endophytic strain of bacteria. The protein or peptide of interest comprises a plant signaling molecule or an enzyme that affects plant composition, and the protein or peptide of interest can be physically attached to the spore coat of the recombinant spore-forming bacterium Yet another method for altering a property of a plant is provided. The method comprises introducing exosporium fragments or a formulation containing the exosporium fragments into a plant growth medium; or applying exosporium fragments or a formulation containing the exosporium fragments to a plant, a plant seed, or an area surrounding a plant or a plant seed. The exosporium fragments are derived from spores of a recombinant *Bacillus cereus* family member described in Section IV hereinabove and comprise the fusion protein. The protein or peptide of interest comprises a plant signaling molecule or an enzyme that affects plant composition.

Where the method for altering a property of a plant comprises the use of exosporium fragments, the method can further comprise treating the plant with a penetrating agent, a surfactant, a detergent, an oil, or a combination thereof.

The target bacterium preferably survives or thrives in the environment and on the roots of the target plant. Optimal bacteria strains for these methods include, but are not limited to, *Bacillus cereus* family member EE349, *Bacillus cereus* family member 439, *Bacillus thuringiensis* EE417, *Bacillus cereus* EE444, *Bacillus megaterium* EE385, *Bacillus* sp. EE387, *Bacillus circulans* EE388, *Bacillus subtilis* EE405, *Lysinibacillus fusiformis* EE442, or *Lysinibacillus sphaericus* EE443.

The plant signaling molecules or enzymes can also be delivered to the plant at planting, either through delivery of recombinant spores on the plant seeds, or delivery of the recombinant spores to the plant growth medium or area around the plant.

Application can be directly onto the plant material, optionally in conjunction with adjuvants, such as nonionic or other surfactants. The recombinant *Bacillus cereus* family member, the recombinant spore-forming bacterium, or the exosporium fragments can be applied to foliage of the plant prior to harvest such as by spraying onto the foliage.

Application to the plant seed is generally performed as a seed dip, a slurry, or a polymer-based seed coating. Optionally, the application can be done in conjunction with seed applied inoculants, fungicides, insecticides, or nematocides.

Application to the plant growth medium or area around the plant can be performed prior to planting, at planting, or post planting of seeds, optionally in conjunction with fertilizers, fungicides, herbicides, or insecticides.

The enzyme includes, but is not limited to, comprises endoglucanases, proteases, phospholipases, aminocarboxy-1-propanedeaminase, aminocyclopropane-1-carboxylic acid deaminases, lipases, or a combination thereof.

The plant signaling molecules include, but are not limited to, flg22 and flagellin peptides, cryptogein, harpins, harpin-like proteins, enzymes that degrade or modify a bacterial, fungal, or plant nutrient source, or a combination thereof.

The enzymes or plant signaling molecules can cause desired metabolic changes to the host plant, including increasing the macronutrient and micronutrient uptake or content of the plant tissues through enlargement of the root systems, increasing the protein content of plants such as grains, cereals, and fruit through modifications to metabolism and increased nitrogen uptakes, and modifications to oil content in rapeseed, canola, soybeans and sunflower, sugar content (sucrose) in grapes, sugar cane, switchgrass, sweet sorghum and other biofuel feedstock, medicinal compound content, and cannabinoid content in marijuana. These alterations not only increase the value of the plants of interest, but also increase the utility of these plants in various industries such as biofuel formation, sugar production, and feedstock production.

For the methods for altering a property of a plant, any of the targeting sequences, exosporium proteins, or exosporium protein fragments described herein can be used.

XXVII. Disinfection

A method of disinfecting a surface is provided. The method comprises exposing a surface to a recombinant *Bacillus cereus* family member that expresses a fusion protein as described above in paragraphs [00172]-[00175] and [00179] of Section I, wherein the protein or peptide of interest comprises an antibacterial protein or peptide.

A further method of disinfecting a surface is provided. The method comprises exposing a surface to exosporium fragments. The exosporium fragments are derived from a recombinant *Bacillus cereus* family member described in Section IV hereinabove and comprise the fusion protein. The fusion protein comprises an antibacterial protein or peptide.

Yet another method of disinfecting a surface is provided. The method comprises exposing a surface to a recombinant *Bacillus cereus* family member. The recombinant *Bacillus cereus* family member is a recombinant *Bacillus cereus* family member as described above in Section II.

In the methods for disinfecting a surface that comprise exposing a surface to exosporium fragments or to a recombinant *Bacillus cereus* family member as described above in Section II, the targeting sequence, exosporium protein, or exosporium protein fragment can be any of the targeting sequences, exosporium proteins, or exosporium protein fragments described herein. In particular, the targeting sequence, exosporium protein, or exosporium protein fragment can comprise any of the targeting sequences, exosporium protein, or exosporium protein fragments described above in paragraphs [00782]-[00801].

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

The antibacterial protein or peptide minimizes or prevents viral agents, bacteria, amoebas, pests, or molds from forming on or binding to the surface.

The antibacterial protein or peptide includes, but is not limited to, proteases, nucleases, antimicrobial peptides, LysM, LfcinB, lysostaphin, albumin, defensins, bacteriocins, lipopeptides, innate immune system peptides, lysozyme, lyticase, or a combination thereof.

The recombinant *Bacillus cereus* family member spores can be used in conjunction with other antimicrobial agents, including disinfectants, cleaners, antibiotics, antifungals, and antivirals.

Although any of the *Bacillus cereus* family can be utilized to express the fusion proteins, either *Bacillus thuringiensis* or *Bacillus mycoides* is preferred.

For these methods, any of the targeting sequences, exosporium proteins, or exosporium protein fragments described herein can be used.

XXVIII. Other Uses

The fusion proteins wherein the protein or peptide of interest is an enzyme or recombinant *Bacillus cereus* members wherein the protein or peptide of interest is an enzyme that can be used for grease, oil, or fat treatment or degumming; leather hide processing; biofuel, biodiesel, or bioethanol formation; sugar processing or conversion; starch treatment; paper or linen processing; animal or fungal byproduct treatment or amino acid recovery; targeted digestion of facility wastes; feed or food additives; dietary supplements; animal nutrition; industrial cleaning; grain processing; cosmetic manufacturing; odor control; food or beverage processing; brewing enhancement or additives; detergent additives; or textile or yarn processing.

By displaying an enzyme on the outside of the spore or on exosporium fragments, the enzyme can be stabilized, immobilized, and able to be reused.

Industrial processes generally involve harsh conditions, including high temperatures, presence of solvents, and large amounts of organic matter. These conditions hinder traditional enzymes. Expression of the target enzyme on the surface of the spore or on exosporium fragments allows for resistance to high temperatures and harsh conditions, and allows for the enzymes to be reisolated and reused.

Key enzymes of interest for such uses include: β-lactamases, proteases, lipases, phospholipases, cellulases, endoglucanases, exogluconases, pectinases, ligninases, amylases (e.g., α-amylases, β-amylases, or glucoamylases), polygalacturonases, glucosidases, galactosidases, carbohydrate hydrolyases, cell wall hydrolases, nucleases, hemicellulases, xylanases, mannases, laccases, lactases, esterases (e.g., pectin methyl esterases), phytases, phosphatases, invertases, glucose oxidases, catalases, lyticases, acetolactate decarboxylass, and ureases.

Preferred enzymes for grease, oil, or fat treatment or degumming, or for cosmetic manufacturing include lipases, phospholipases, esterases, and proteases.

Preferred enzymes for leather hide processing include lipases, proteases, peptidases, collagenases, and phospholipases.

Preferred enzymes for biofuel, biodiesel, or bioethanol formation can include, but are not limited to, lipases and esterases.

Preferred enzymes for sugar processing or conversion, for grain processing, and for textile or yarn processing include carbohydrate hydrolases, amylases, mannases, glucoamylases, invertases, cellulases, hemicellulases, pectinases, pectin methyl esterases, xylanases, endoglucanases, exoglucanases, glucosidases, galactosidases, laccases, lactases, catalases, and glucose oxidases.

Preferred enzymes for starch treatment include amylases and glucoamylases.

Preferred enzymes for paper or linen processing include cellulases, hemicellulases, xylanases, endoglucanases, laccases, ligninases, exoglucanases, phytases, catalases, and glucosidases.

Preferred enzymes for animal or fungal byproduct treatment or amino acid recovery include proteases, peptidases, lipases, lyticases, cell wall hydrolases, phospholipases, endoglucanases, cellulases, glucanases and carbohydrate hydrolases.

Preferred enzymes for targeted digestion of facility wastes, industrial cleaning, detergent additives, and odor control include lipases, phospholipases, proteases, peptidases, amylases, lyticases, cell wall hydrolases, glucoamylases, cellulases, hemicellulases, xylanases, esterases, glucosidases, galactosidases, laccases, lactases, ureases, phytases, phosphatases, and carbohydrate hydrolases.

Preferred enzymes for feed or food additives, dietary supplements, animal nutrition, brewing additives, beverage additives, or wine processing include mannases, laccases, lyticases, proteases, peptidases, carbohydrate hydrolases, pectinases, pectin methyl esterases, esterases, lipases, cellulases, hemicellulases, xylanases, phytases, phosphatases, invertases, glucosidases, galactosidases, lactases, catalases, glucanases, endoglucanases, acetolactate decarboxylase, and glucose oxidases.

Although any of the *Bacillus cereus* family can be utilized to express the fusion proteins for these uses, either *Bacillus thuringiensis* or *Bacillus mycoides* is preferred.

A use of fusion proteins comprising an enzyme as the protein or peptide of interest or a recombinant *Bacillus cereus* family member expressing a fusion protein comprising an enzyme as the protein or peptide of interest is provided. The fusion protein can be any of the fusion proteins described above in paragraphs [00171]-[00175], [00177], and [00179] of Section I. The use can be a use for grease, oil, or fat treatment or degumming; leather hide processing; biofuel, biodiesel, or bioethanol formation; sugar processing or conversion; starch treatment; paper or linen processing; animal or fungal byproduct treatment or amino acid recovery; targeted digestion of facility wastes; feed or food additives; dietary supplements; animal nutrition; industrial cleaning; grain processing; cosmetic manufacturing; odor control; food or beverage processing; brewing enhancement or additives; detergent additives; or textile or yarn processing.

A use of exosporium fragments is also provided. The use can be for grease, oil, or fat treatment or degumming; leather hide processing; biofuel, biodiesel, or bioethanol formation; sugar processing or conversion; starch treatment; paper or linen processing; animal or fungal byproduct treatment or amino acid recovery; targeted digestion of facility wastes; feed or food additives; dietary supplements; animal nutrition; industrial cleaning; grain processing; cosmetic manufacturing; odor control; food or beverage processing; brewing enhancement or additives; detergent additives; or textile or yarn processing. The exosporium fragments are derived from a recombinant *Bacillus cereus* family member described in Section IV hereinabove and comprise the fusion protein. The fusion protein comprises an enzyme.

A further use of a recombinant *Bacillus cereus* family member is provided. The recombinant *Bacillus cereus* family member is a recombinant *Bacillus cereus* family member as described above in Section II. The use can be for grease, oil, or fat treatment or degumming; leather hide processing; biofuel, biodiesel, or bioethanol formation; sugar processing or conversion; starch treatment; paper or linen processing; animal or fungal byproduct treatment or amino acid recovery; targeted digestion of facility wastes; feed or food additives; dietary supplements; animal nutrition; industrial cleaning; grain processing; cosmetic manufacturing; odor control; food or beverage processing; brewing enhancement or additives; detergent additives; or textile or yarn processing. The fusion protein comprises an enzyme.

In the uses of exosporium fragments or the recombinant *Bacillus cereus* family members as described above in Section II, the targeting sequence, exosporium protein, or exosporium protein fragment can be any of the targeting sequences, exosporium proteins, or exosporium protein fragments described herein. In particular, the targeting sequence, exosporium protein, or exosporium protein fragment can comprise any of the targeting sequences, exosporium protein, or exosporium protein fragments described above in paragraphs [00782]-[00801].

The fusion protein can be expressed under the control of a sporulation promoter native to the targeting sequence, exosporium protein, or exosporium protein fragment of the fusion protein or a portion thereof and/or under the control of a high-expression sporulation promoter. The promoter can be any of the promoters described above in Section III.

Having described the invention in detail, it will be apparent that modifications and variations are possible without departing from the scope of the invention defined in the appended claims.

EXAMPLES

The following non-limiting examples are provided to further illustrate the present invention.

Example 1. Use of a Recombinant *Bacillus cereus* Family Member Displaying a Lipase or an Endoglucanase to Stimulate Plant Growth in Soybeans The *Bacillus subtilis* lipase and endoglucanase genes were amplified via polymerase chain reaction (PCR) using the following primers shown below in Table 16:

TABLE 16

| | lipase | endoglucanase |
|---|---|---|
| forward | ggatccatggctgaacacaatcc (SEQ ID NO: 37) | ggatccatgaaacggtcaatc (SEQ ID NO: 39) |
| reverse | ggatccttaattcgtattctggcc (SEQ ID NO: 38) | ggatccttactaatttggttctgt (SEQ ID NO: 40) |

To create fusion constructs, genes were fused to the native bclA promoter of *Bacillus thuringiensis* DNA encoding the first 35 amino acids of BclA (amino acids 1-35 of SEQ ID NO: 1) using the splicing by overlapping extension (SOE) technique. Correct amplicons were cloned into the *E. coli Bacillus* shuttle vector pHP13, and correct clones screened by DNA sequencing. Correct clones were electroporated into *Bacillus thuringiensis* (Cry-, plasmid-) and screened for chloramphenicol resistance. Correct transformants were grown in brain heart infusion broth overnight at 30° C., plated onto nutrient agar plates, and incubated at 30° C. for 3 days. Spores expressing the fusion construct (BEMD spores) were collected off of the plates by washing in phosphate buffered saline (PBS) and purified by centrifugation and additional washes in PBS. Non-transformed control *Bacillus thuringiensis* (B.t.) spores were created identically.

Soybeans (strain Jake 011-28-04) were planted 2.54 cm deep in 10 cm deep pots filled with standard loam topsoil. Spores were diluted to a concentration of $1\times10^4$/ml in 50 ml of water and applied to each seed at planting. Plants were grown under ideal light using T5 lamps, 54 watts, and exposed to 11 hours of light a day under controlled temperature conditions between 15.5-25.5° C. Plants were watered to saturation every three days over a two week trial. At the end of two weeks, the height of each plant was measured and measurements were normalized to control *Bacillus thuringiensis* spores. Two independent trials were performed.

Results are shown in Table 17, together with the standard error of the mean. In both trials, soybeans grown in the presence of BEMD spores displaying either lipase or endoglucanase grew significantly taller than control B.t. spore treated soybeans (statistical analysis assayed via a t-test).

TABLE 17

| | Treatment | Soybeans Avg. Height, cm | Comparison to Control | SEM |
|---|---|---|---|---|
| Trial #1 | Control Bt | 14.034 | 100.0% | .521 |
| | Lipase, BEMD | 17.93 | 127.8% | .395 |
| | Endocellulase, BEMD | 16.31 | 116.2% | .411 |
| Trial #2 | Control Bt | 15.39 | 100.0% | .749 |
| | Lipase, BEMD | 19.15 | 124.4% | .428 |
| | Endocellulase, BEMD | 17.65 | 114.7% | .313 |

Example 2. Use of a Recombinant *Bacillus cereus* Family Member Displaying an Endoglucanase to Stimulate Plant Growth in Corn BEMD spores expressing endoglucanase were created in an identical fashion as described above in Example 1. Field corn was planted 3.8 cm deep in 10 cm deep pots filled with standard loam topsoil. Spores, control and BEMD expressing endoglucanase, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 15.5-25.5° C. Plants were watered to saturation every three days over the one week trial. At the end of one week, the height of each plant was measured, and measurements were normalized to control *Bacillus thuringiensis* spores.

Results are shown in Table 18, together with the standard error of the mean. Corn grown in the presence of BEMD spores displaying endoglucanase grew significantly taller than both control B.t. spore treated soybeans and water-only control plants (statistical analysis assayed via a t-test).

TABLE 18

| | Height, cm | Comparison | SEM |
|---|---|---|---|
| $H_2O$ | 15.44 | 100% | 0.318 |
| Bt | 18.92 | 122.50% | 0.645 |
| BEMD Endo | 22.71 | 143.40% | 0.616 |

Example 3. Use of a Recombinant *Bacillus cereus* Family Member Displaying an Endoglucanase or a Protease to Stimulate Plant Growth in Wheat BEMD spores expressing endoglucanase were created in an identical fashion as described above in Example 1. BEMD spores expressing *E. coli* protease PtrB were created using similar methods to those described above in Example 1 and the following primers: ggatccatgctaccaaaagcc (forward, SEQ ID NO: 41) and ggatccttagtccgcaggcgtagc (reverse, SEQ ID NO: 42).

Winter hard wheat was planted 2.54 cm deep in 10 cm deep pots filled with standard loam topsoil. Spores, control and BEMD expressing endoglucanase or protease, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 15.5-25.5° C. Plants were watered to saturation every three days over the one week trial. At the end of one week, the height of each plant was measured, and measurements were normalized to control water only plants.

Results are shown in Table 19, together with the standard error of the mean. Wheat grown in the presence of BEMD spores displaying endoglucanase or protease grew significantly taller than control B.t. spore treated or water control soybeans (statistical analysis assayed via a t-test).

TABLE 19

|  | Height, cm | Comparison | SEM |
|---|---|---|---|
| H₂O | 18.11 | 100% | 0.721 |
| Bt Control | 19.96 | 110.33% | 0.752 |
| BEMD Endo | 24.76 | 136.80% | 0.21 |
| BEMD Protease | 22.35 | 123.40% | 0.354 |

Example 4. Use of Recombinant *Bacillus cereus* Family Members Displaying an Endoglucanase to Stimulate Plant Growth in Ryegrass BEMD spores expressing endoglucanase were created in an identical fashion as described above in Example 1. Perennial ryegrass was planted 6.4 mm deep in 10 cm deep pots filled with standard loam topsoil. Spores, both control and BEMD expressing endoglucanase, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 15.5-25.5° C. Plants were watered to saturation every three days over the two week trial. At the end of two weeks, the height of each plant was measured, and measurements were normalized to control water only plants.

Results are shown in Table 20, together with the standard error of the mean. Ryegrass grown in the presence of BEMD spores displaying endocellulase grew significantly taller than control B.t. spore treated or water control ryegrass (statistical analysis assayed via a t-test).

TABLE 20

| | Height, cm | Comparison | SEM |
|---|---|---|---|
| $H_2O$ | 11.43 | 100.0% | 0.137 |
| Bt Control | 12.29 | 107.7% | 0.128 |
| BEMD Endo | 12.78 | 111.9% | 0.137 |

Example 5. Use of Recombinant *Bacillus cereus* Family Members Displaying Enzymes Involved in the Synthesis or Activation of Plant Hormones to Stimulate Plant Growth The BEMD system can also be used to display enzymes involved in the synthesis of plant hormones. For example, the plant hormone indole-3-acetic acid is a potent growth stimulator in plants. Indole-3-acetic acid is synthesized in vivo from tryptophan by the enzymes tryptophan monooxygenase and indole-3-acetamide hydrolase. Indole-3-acetic acid and other auxin hormones can also be synthesized in vivo from tryptophan and/or indole by the enzymes nitrilase, tryptophan aminotransferase, indole-3-acetaldehyde dehydrogenase, indole-3-pyruvate decarboxylase, amine oxidase, tryptophan decarboxylase, and tryptophan side chain oxidases.

The BEMD system can also be used to display enzymes involved in the modification of plant growth hormones into bioactive or inactive forms. For example, nitrilase can be expressed on the BEMD system to catalyze the conversion of indole-3-acetonitrile into the bioactive indole-3-acetic acid. Additionally, inactive forms of plant hormones, such as indole-3-acetonitrile can be added into the plant growth media with the BEMD-expressed nitrilase to provide a gradual release of active hormone into the plant growth media. Many other inactive or less active forms of plant hormones can be modified using their corresponding enzymes.

Related plant growth hormones (auxins) include indole-3-pyruvic acid, indole-3-acetaldoxime, indole-3-acetamide, indole-3-acetonitrile, indole-3-ethanol, indole-3-pyruvate, indole-3-butyric acid, phenylacetic acids, 4-chloroindole-3-acetic acid, and indole-3-acetaldoxime. These hormones are synthesized from tryptophan and/or indole in vivo via the enzymes tryptophan monooxygenase, indole-3-acetamide hydrolase, nitrilase, nitrile hydrolase, acetolactate synthetase, alpha acetolactate decarboxylase, tryptophan aminotransferase, indole-3-acetaldehyde dehydrogenase, indole-3-pyruvate decarboxylase, amine oxidase, tryptophan decarboxylase, and tryptophan side chain oxidases.

Growth hormones of the cytokinin family can also be synthesized by enzymes expressed in the BEMD system. Examples of cytokinins include kinetin, zeatin (cis and trans), 6-benzylaminopurine, dihydroxyzeatin, N6-(D2-isopentenyl) adenine, ribosylzeatin, N6-(D2-isopentenyl) adenosine, 2 methylthio-cis-ribosylzeatin, cis ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, and meta-methyltopolin. These plant growth stimulating compounds are synthesized in vivo from mevalonate or adenosine mono/di/triphosphate by enzymes including adenosine phosphate isopentenyltransferases, phosphatases, adenosine kinases, adenine phosphoribosyltransferase, CYP735A, 5'ribonucleotide phosphohydrolase, adenosine nucleosidases, zeatin cis-trans isomerase, zeatin O-glucosyltransferases, β-glucosidases, cis-hydroxylases, CK cis-hydroxylases, CK N-glucosyltransferases, 2,5-ribonucleotide phosphohydrolases, adenosine nucleosidases, purine nucleoside phosphorylases, and zeatin reductases.

Using methods similar to those described above in Example 1, any of these enzymes can be incorporated into the BEMD system for display on BEMD spores by creating a fusion construct comprising the enzyme and a targeting sequence that targets the expressed enzyme to the exosporium when the fusion construct is expressed in a *Bacillus cereus* family member. A recombinant *Bacillus cereus* family member expressing such a construct can then be added to the soil or other plant growth medium or applied directly to plant foliage using methods similar to those described above in Example 1 for stimulation of plant growth.

The plant growth medium can be supplemented with precursors or substrates for the enzymes. For example, the plant growth medium can be supplemented with tryptophan, adenosine monophosphates, adenosine diphosphates, adenosine triphosphates, or indole. Suitable concentrations of these substrates are between 100 nM and 100 μM.

Example 6. Use of Recombinant *Bacillus cereus* Family Members Displaying Proteases or Peptidases that Cleave Proteins, Peptides, Proproteins, or Preproproteins into Bioactive Peptides for Stimulation of Plant Growth Proteases and peptidases can be expressed in the BEMD system that can enzymatically cleave available proteins in the plant growth media to bioactive peptides that can act on the plant directly or indirectly. Examples include the enzymatic cleavage of soybean meal, yeast extract, or other protein rich meals added to the plant growth medium into active peptides that can directly stimulate plant growth. Bioactive peptides generated by enzymatic cleavage of protein meals include RHPP and RKN 16D10, potent stimulators of plant root development. Additionally, proproteins or preproproteins can be cleaved into active forms by BEMD-expressed proteases and peptidases to their bioactive forms. Inactive proproteins or preproproteins can be added in the plant growth medium to facilitate their gradual cleavage by BEMD proteases and slow release of bioactive proteins.

Using methods similar to those described above in Example 1, any of these proteases and peptidases can be incorporated into the BEMD system for display on BEMD spores by creating a fusion construct comprising the protease or peptidase and a targeting sequence that targets the expressed enzyme to the exosporium when the fusion construct is expressed in a *Bacillus cereus* family member. A recombinant *Bacillus cereus* family member expressing such a construct can then be added to soil or other plant growth medium supplemented with soybean meal, yeast extract, or another-protein-rich meal for stimulation of plant growth. The soybean meal, yeast extract, or other protein-rich meal is suitably added to the plant growth medium in the form of a liquid composition comprising about 10 μg/L to about 100 mg/L of the protein meal, yeast extract, or other protein-rich meal.

Example 7. Use of BEMD Spores Expressing the Protease PtrB for Stimulation of Plant Growth BEMD spores expressing *E. coli* protease PtrB were created as described above in Example 3. Soybean seeds were planted 2.54 cm deep in 10 cm deep pots filled with standard loam topsoil. Spores, both control and BEMD expressing protease, were diluted to a concentration of $1 \times 10^4$/ml in 50 ml of water and applied to each plant at planting. A water-only control was also included. Soybean meal at 25 mg/pot was added in water at planting. Plants were grown under ideal light using T5 lamps, 54 watts, and exposed to 13 hours of light a day under controlled temperature conditions between 15.5-25.5° C. Plants were watered to saturation every three days over the one week trial. At the end of two weeks, the height of each plant was measured, and measurements were normalized to control water only plants.

Results are shown in Table 21, together with the standard error of the mean as a percentage of water control. Soy grown in the presence of BEMD spores displaying protease grew significantly taller than control B.t. spore treated or water control soybeans (statistical analysis assayed via a t-test). The addition of soybean meal to water control or *B. thuringiensis* control plants had little effect. By contrast, in the presence of the soybean meal and the BEMD protease system, the soybean plants responded significantly over all other treatments.

TABLE 21

| Treatment | Soybean Meal | Height (cm) | Normalized to water | SEM, as percentage of water |
|---|---|---|---|---|
| Water only | No | 12.10 | 100% | 3.1% |
| Water only | 25 mg/pot | 12.43 | 102.7% | 7.4% |
| B. thuringiensis | No | 12.52 | 103.5% | 5.2% |
| B. thuringiensis | 25 mg/pot | 11.99 | 99.1% | 5.0% |

TABLE 21-continued

| Treatment | Soybean Meal | Height (cm) | Normalized to water | SEM, as percentage of water |
|---|---|---|---|---|
| BEMD Protease | No | 12.97 | 107.2% | 6.1% |
| BEMD Protease | 25 mg/pot | 14.44 | 119.3% | 4.8% |

Example 8. Use of Recombinant *Bacillus cereus* Family Members Displaying Proteins or Peptides Involved in the Stimulation of Plant Growth The BEMD system can also be used to display proteins or peptides that are directly involved in the promotion of plant growth. For example, plant peptide hormones or non-hormone peptides that stimulate plant growth can be expressed in the BEMD system. For example, non-hormone peptides that directly bind to and active plant receptors can be expressed in the BEMD system to directly act on receptors in the plant and roots of target plants. Such peptide hormones and non-hormone peptides include phytosulfokine, calcalva 3 (CLV3), systemin, RKN 16D10, Hg-Syv46, eNOD40, NOD family proteins, ZmIGF, SCR/SP11 family proteins and peptides, RHPP, POLARIS, and KTI. These peptides and related peptides can be expressed in the BEMD system and delivered to plant growth medium or directly applied to foliage to stimulate plant growth.

Using methods similar to those described above in Example 1, any of these proteins or peptides can be incorporated into the BEMD system for display on BEMD spores by creating a fusion construct comprising the enzyme and a targeting sequence that targets the expressed enzyme to the exosporium when the fusion construct is expressed in a *Bacillus cereus* family member. A recombinant *Bacillus cereus* family member expressing such a construct can then be added to the soil or other plant growth medium or applied directly to plant foliage using methods similar to those described above in Example 1 for stimulation of plant growth.

Example 9. Use of BEMD Spores Expressing POLARIS or KTI for Stimulation of Plant Growth BEMD spores expressing the plant peptide POLARIS and soy peptide KTI were created by synthesizing genes coding for the POLARIS or KIT peptides linked to the targeting sequence of SEQ ID NO: 96. The genes were then introduced genes into *Bacillus thuringiensis* and spores were made as described in Example 1. Soybean seeds were planted 2.54 cm deep in 10 cm deep pots filled with standard loam topsoil. BEMD spores expressing POLARIS or KTI were diluted to a concentration of $1 \times 10^4$/ml in 50 ml of water and applied to each plant at planting. A water-only control was also included. Pure POLARIS and KTI peptides were also tested for their effects on soybeans at 0.05 mg/pot. Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, the roots measured, and measurements were normalized to control water only plants.

Results are shown in Table 22, together with the standard error of the mean as a percentage of water control. Soy grown in the presence of BEMD spores displaying POLARIS grew taller and had a slight increase in root development than water control soybeans. The presence of free KTI peptide led to a significant stunting of the plants, losing between 6-8% of their heights, but adding 15% to the length of the roots. Expression of KTI on the BEMD system led to the root growth benefit, but without the stunting effect on the plant height. Importantly, the presence of the *Bacillus thuringiensis* control spores with the free KTI peptide did not prevent the stunting effect of KTI, while the BEMD with KTI displayed no such stunting.

TABLE 22

| Treatment | Peptide | Roots Normalized to Water | SEM | Height, Normalized to Water | SEM |
|---|---|---|---|---|---|
| Water | No | 100% | 6.8% | 100% | 4.3% |
| Water | KTI, 0.05 mg/Pot | 115% | 8.4% | 91.8% | 3.1% |
| BEMD POLARIS | No | 106.3% | 7.9% | 107.3% | 1.7% |
| BEMD KTI | No | 113.3% | 5.8% | 99.4% | 3.4% |
| *B. thuringiensis* | KTI, 0.05 mg/pot | 115% | 7.7% | 93.4% | 4.2% |

Example 10. Use of Recombinant *Bacillus cereus* Family Members Displaying Enzymes that Degrade or Modify a Bacterial, Fungal, or Plant Nutrient Source to Stimulate Plant Growth and/or Process Nutrients The BEMD system can also be used to display enzymes that degrade or modify beneficially a bacterial, fungal, or plant nutrient source present in soil or another plant growth medium. Such enzymes degrade products present in the soil or other plant growth medium into forms that can easily be taken up by plants and/or the beneficial bacteria and/or fungi of the rhizosphere. Such enzymes include, for example, glucoside hydrolases to degrade complex carbohydrates, cellulases to degrade cellulose; lipases to degrade lipids, including oil, fats, and waxes; lignin oxidases to degrade lignin and humic acids; proteases to degrade polypeptides; phospholipases to degrade membranes; amidases and nitrogenases to recover nitrogen; amylases to process starches; nucleases to recover nucleotides, pectinases to break down pectin, sulfatases to recover sulfur, and xylanases to break down xylans and arabinoxylans. The resultant products, including simple sugars, amino acids, fatty acids, and other nutrients will be readily available for direct uptake by plants and/or for stimulating beneficial bacteria and/or fungi to grow and thrive in the rhizospheres of the plants.

In addition, enzymes and other biological molecules can be utilized to release or sequester phosphate, nitrogen, and other key elemental nutrients for plant uptake from their various organic and inorganic forms in soil. For example, phosphatases can be used to degrade phosphates in the environment into usable inorganic phosphates for plant use. The phosphates can be naturally occurring phosphates present in a plant growth medium. Alternatively or in addition, the plant growth medium can be supplemented with phosphates such as trimetaphosphate, a common agricultural amendment. Examples of useful phosphatases include phosphoric monoester hydrolases, phosphomonoesterases, phosphoric diester hydrolases, phosphodiesterases, triphosphoric monoester hydrolases, phosphoryl anhydride hydrolases, pyrophosphatases, phytase, trimetaphosphatases, and triphosphatases. For example, the enzymes trimetaphosphatase, triphosphatase, and pyrophosphatase sequentially break down trimetaphosphate into usable inorganic phosphate.

The nitrogenase family of enzymes converts atmospheric nitrogen ($N_2$) into ammonia, thereby converting nitrogen that would otherwise be inaccessible to plants into a usable form. Suitable enzymes belong to the Nif family of nitrogenases.

Chemical energy can also be directly added into the plant growth medium as adenosine-3-triphosphate, ferrodoxin, or additional enzymes that create such energy into the BEMD system. These are cofactors for the nitrogenases and are limited in soil. Thus, such cofactors can be added to soil to enhance the reactions described above.

Other supplements that can be added to the plant growth medium include starches, cellulose and cellulose derivatives, pectins, xylans and arabinoxylans, fats, waxes, oils, phytic acids, lignins, humic acids, and other nutrient sources that the above enzyme classes exert activity upon.

Using methods similar to those described above in Example 1, any of these enzymes can be incorporated into the BEMD system for display on BEMD spores by creating a fusion construct comprising the enzyme and a targeting sequence for targeting the fusion construct to the exosporium of a *Bacillus cereus* family member. The fusion construct can then be expressed in a *Bacillus cereus* family member, and this recombinant *Bacillus cereus* family member can be added to soil or another plant growth medium using methods similar to those described above in Example 1 for stimulation of plant growth.

Example 11. Use of BEMD Spores Expressing a Phosphatase for Stimulation of Plant Growth BEMD spores expressing *Bacillus subtilis* Phosphatase A4 (PhoA4) were created by synthesizing a gene coding for PhoA4 linked to the targeting sequence of SEQ ID NO: 96. This gene was then introduced into *Bacillus thuringiensis* and spores were made as in Example 1. Corn was planted 2.54 cm deep in 10 cm deep pots filled with standard loam topsoil. BEMD spores expressing PhoA4, were diluted to a concentration of $1\times10^4$/ml in 50 ml of water and applied to each plant at planting. A water-only control was also included. Polyphosphate was added to pots in liquid at a rate of 0.5 mg/pot. Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, and measurements were normalized to control water only plants.

Results are shown in Table 23. Corn grown in the presence of BEMD spores displaying PhoA4 exhibit enhanced growth, especially in the presence of added polyphosphate. This effect was greater than the effect of the polyphosphate alone.

TABLE 23

| Treatment | Additive | Growth, Comparison to Water |
|---|---|---|
| Water | None | 100% |
| Water | Polyphosphate | 110.8% |

TABLE 23-continued

| Treatment | Additive | Growth, Comparison to Water |
|---|---|---|
| BEMD PhoA4 | None | 108.3% |
| BEMD PhoA4 | Polyphosphate | 114.8% |

Example 12. Use of Recombinant *Bacillus cereus* Family Members Displaying Enzymes Involved in the Synthesis of 2,3-Butanediol or the Synthesis or Activation of Gibberellic Acid for Stimulation of Plant Growth The BEMD system can also be used display enzymes involved in the synthesis of the plant-growth promoting compound 2,3-butanediol. In vivo, 2,3-butanediol is synthesized by beneficial bacteria and fungi in the rhizosphere from acetoin, diacetyl, acetolactate, or pyruvate by the enzymes acetolactate synthetase, α-acetolactate decarboxylase, pyruvate decarboxylase, diacetyl reductase, butanediol dehydrogenases, and acetoin reductase.

The BEMD system can also be used to display enzymes involved in the synthesis or activation of the plant-growth promoting compound gibberellic acid. Gibberellic acid can be produced from inactive or less active forms via the action of enzymes, including but not limited to hydroxylamine reductases, 2-oxogluturate dioxygenases, gibberellin 2B/3B hydrolases, gibberellin 3-oxidases, and gibberellin 20-oxidases.

Any of these enzymes can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for stimulation of plant growth.

To increase the effect of the enzymes displayed on BEMD, the soil can be supplemented with substrates for the enzymes. For example, the soil or other plant growth medium can be supplemented with acetoin, which is a substrate for acetoin reductase; pyruvate, which is a substrate for pyruvate decarboxylase; diacetyl, which is a substrate for diacetyl reductase; and/or acetolactate, which is a substrate for acetolactate decarboxylase. Alternatively or in addition, the soil or other plant growth medium can be supplemented with less potent or inactive forms of gibberellic acid, which will converted into more active forms by the enzymes described above in the soil or other plant growth medium.

Example 13. Use of Recombinant *Bacillus cereus* Family Members Displaying Proteases for Protecting Plants from Pathogens The BEMD system can also be used display proteases that protect plants from one or more pathogens. For example, certain bacterial pathogens can communicate between individual members via secretion of bacterial lactone homoserines or related signaling molecules. Thus, proteases specific for bacterial lactone homoserine signaling molecules can protect plants from such bacterial pathogens by disrupting communication between bacteria, a step essential for the bacteria to secrete toxins and upregulate virulence factors. Suitable proteases specific for bacterial lactone homoserine signaling molecules include endopeptidases and exopeptidases.

Proteases specific for bacterial lactone homoserine signaling molecules can be incorporated into the BEMD system using methods similar to those described above in Example 1. A fusion construct can be prepared that comprises the protease and a targeting sequence that targets the protease to the exosporium when the fusion construct is expressed in a *Bacillus cereus* family member. The fusion construct is then expressed in a *Bacillus cereus* family member, and the *Bacillus cereus* family member is added to soil or another plant growth medium. The protease can then degrade the bacterial lactone homoserine signaling molecules, blocking a key step in the virulence of these organisms and thereby helping to protect the plant from these pathogens. Other proteases and peptidases work effectively in this capacity on the BEMD system as demonstrated above in Example 6 and 7.

Example 14. Use of Recombinant *Bacillus cereus* Family Members Displaying Antimicrobial Proteins and Peptides for Protecting Plants from Pathogens The BEMD system can also be used display enzymes that exhibit antibacterial and/or antifungal activities that can help protect plants from one or more pathogens. For example, antimicrobial proteins and peptides such as bacteriocins, lysozymes (e.g., LysM), siderophores, avidins, streptavidins, conalbumin, albumin, lactoferrins (e.g., LfcinB), or TasA can all be expressed in the BEMD system to exert their effect on bacterial and fungal pathogens of plants. Bacteriocins, albumin, conalbumin, lysozymes, and lactoferrin exert direct antimicrobial action on their targets, whereas siderophores, avidins, and streptavidins bind essential nutrients that pathogens require for virulence. For example, the peptide LfcinB of lactoferrin, when expressed on the surface of the BEMD system would lyse bacteria cells that are susceptible to the lactoferrin peptides in the plant growth medium. These proteins and peptides have specific action on select microbes, and can selectively target a group of pathogens without obstructing all microbes in the plant growth medium.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from one or more pathogens.

Example 15. Use of BEMD Spores Expressing Antimicrobial Peptides for Protecting Plants from Bacteria Genes were synthesized that coded for either of two antimicrobial peptides, LfcinB (derived from bovine lactoferrin) and LysM (derived from chicken lysozyme), linked to a BclA targeting sequence (SEQ ID NO: 96), under the control of the BclA promoter (SEQ ID NO: 215). The genes were introduced into *Bacillus thuringiensis* BT013A and spores were made by growing an overnight culture of the transformed *Bacillus* in brain heart infusion broth, plating onto nutrient agar plates at 30° C. and allowing to grow for 3 days. Spores were washed off the plates and rinsed 3× in PBS. *Staphylococcus epidermidis* cultures were grown overnight in TSB broth at 37° C. The overnight culture was then pelleted, washed in PBS, and resuspended in PBS at an Abs595=0.2. 1×10$^4$ BEMD expressing the LysM or LfcinB peptides was incubated in the PBS with the *S. epidermidis* for 3 hours at 37° C., with shaking. A control sample of *S. epidermidis* was left untreated (no BEMD spores). After the 3 hour incubation, dilution plates of the *S. epidermidis* were made and incubated at 37° C. overnight. *S. epidermidis* cultures were counted the next day, and percent killing quantified. In Table 24 below, a record of the killing activity was recorded. The BEMD expressed peptides killed a significant number of *S. epidermidis* cells. This would directly translate into killing of bacteria on the rhizosphere, seed, or other plant material. The selection of peptides specific to certain classes of bacteria can also skew the population of the microorganisms near the plant in a beneficial way, or can selectively target key pathogens.

TABLE 24

| Treatment | Survival | % Killed |
|---|---|---|
| None | 100% | 0% |
| BEMD LysM | 71% | 29% |
| BEMD LfcinB | 23% | 77% |

Example 16. Use of Recombinant *Bacillus cereus* Family Members Displaying Enzymes for Protecting Plants from Pathogens The BEMD system can also be used display enzymes that protect plants from one or more pathogens. For example, yeast and mold cell walls are degraded by enzymes such as β-1,3-glucanases, β-1,4-glucanases, β-1,6-glucanases, chitosanases, chitinases, chitosanase-like proteins, and lyticases. Bacteria cell walls are degraded by enzymes selected from proteinases, proteases, mutanolysin, stapholysin, and lysozymes. Each of these cell wall degrading enzymes can be expressed on the BEMD system and added to plant growth medium for selective inhibition of pathogenic microbes in the rhizosphere.

The BEMD system can also be used to display enzymes or proteins that protect plants from insect or worm pathogens, for example by suppressing insect and/or worm predation of desired plants. Examples of such proteins and enzymes of interest include endotoxins, Cry toxins, other insecticidal protein toxins, protease inhibitors, cysteine proteases, the Cry5B protein, the Cry 21A protein, chitinase, protease inhibitor proteins, protease inhibitor peptides, trypsin inhibitors, and arrowhead protease inhibitors.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from pathogens.

Example 17. Use of BEMD Spores Expressing an Antifungal Enzyme for Protecting Plants, and Demonstration of Efficacy Against *Saccharomyces*

A gene was synthesized that encoded an antifungal enzyme, β-1,3-glucanase from *Bacillus subtilis*, linked to a BclA targeting sequence (SEQ ID NO: 96) under the control of the BclA promoter (SEQ ID NO: 215). The gene was and introduced into *Bacillus thuringiensis* BT013A and pores were made by growing an overnight culture of the transformed *Bacillus* in brain heart infusion broth, plating onto nutrient agar plates at 30° C., and allowing to grow for 3 days. Spores were washed off the plates and rinsed 3× in PBS. *Saccharomyces cerevisiae* cultures were grown overnight in YZ broth at 37° C. The overnight culture was then pelleted, washed in PBS, and resuspended in PBS at an Abs595=0.2. 1×10$^4$ BEMD expressing β-1,3-glucanase was incubated in the PBS with the *Saccharomyces* for 1 hour at 37° C., with shaking. A control sample of *Saccharomyces* was left untreated (no BEMD spores). After the 3 hour incubation, dilution plates of the *Saccharomyces* were made and incubated at 37° C. overnight. *Saccharomyces* cultures were counted the next day, and percent killing quantified. In Table 25 below shows the killing activity of the BEMD spores expressing β-1,3-glucanase. The BEMD-expressed enzyme killed a significant number of *Saccharomyces* cells. This would directly translate into killing of fungal microorganisms on the rhizosphere, seed, or other plant material. The selection of proteins specific to certain classes of fungi can also skew the population of the microorganisms near the plant in a beneficial way, or can selectively target key fungal pathogens.

TABLE 25

| Treatment | Survival | % Killed |
|---|---|---|
| None | 100% | 0% |
| BEMD β-1,3-glucanase | 83% | 17% |

Example 18. Use of Recombinant *Bacillus cereus* Family Members Displaying Plant Immune System Stimulatory Peptides or Proteins for Protecting Plants from Pathogens The BEMD system can also be used display plant immune system enhancer peptides and proteins. These proteins can be expressed on the outside of the BEMD spore and delivered into the plant growth medium to stimulate the plant immune system to allow the plant to protect itself from plant pathogens. Example proteins and peptides include harpin, α-elastins, β-elastins, systemins, phenylalanine ammonia-lyase, elicitins, defensins, cryptogein, and flagellin proteins and peptides. Exposure of plants to these proteins and peptides will stimulate resistance to many plant pathogens in plants.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the Bacillus cereus family member is added to soil or another plant growth medium for protection of plants from pathogens.

Example 19. Use of Recombinant *Bacillus cereus* Family Members Displaying a Root or Leaf Binding Protein or Peptide to Immobilize the Recombinant *Bacillus cereus* Family Member on a Root System of a Plant or on Plant Leaves Root and leaf binding proteins and peptides can also be incorporated into the BEMD system to allow the BEMD spores to be immobilized on a root system or on leaves of a plant. Display of such root or leaf binding ligands on the BEMD spores allows for targeting of the spores to the root system of a plant or to substructures of the root system or to the leaves or to substructures of leaves to maintain the BEMD spores at an optimal location for other displayed biological molecules and enzymes to be effective.

For example, rhicadhesin is a root binding ligand that binds to root hairs. Thus, display of rhicadhesin on the BEMD spores thus targets the spores to root hairs. Additional proteins that could be utilized for selective binding to plant roots or leaves include adhesins, flagellin, omptins, lectins, pili proteins, curlus proteins, intimins, invasins, agglutinin, afimbrial proteins, TasA, or YuaB.

Such root or leaf binding proteins and peptides can be incorporated into the BEMD system using methods similar to those described above in Example 1. A fusion construct can be prepared that comprises the root or leaf binding protein or peptide and a targeting sequence that targets the protein or peptide to the exosporium when the construct is expressed in a *Bacillus cereus* family member. The fusion construct containing the root or leaf binding ligand is then expressed in a *Bacillus cereus* family member. Such fusion constructs can be coexpressed with one or more additional fusion constructs comprising any of the beneficial enzymes discussed herein (e.g., an enzyme involved in the synthesis of a plant hormone, an enzyme that degrades a nutrient source, or a proteases that protects a plant from a pathogen). The recombinant *Bacillus cereus* family member is added to soil or another plant growth medium, or applied to the leaves of a plant. The root or leaf binding ligand targets the *Bacillus cereus* family member to the root system of the plant or to the leaves of the plant and immobilizes it there, thus allowing the coexpressed fusion construct to exert its effects in close proximity to the root or leaf system.

Example 20. Use of Recombinant *Bacillus cereus* Family Members Displaying Proteins or Enzymes to Enhance Stress Resistance of Plants Proteins, peptides, and enzymes that enhance stress resistance in a plant can be incorporated into the BEMD system and delivered to target plants via addition to roots, leaves, or the plant growth medium. During periods of stress, plants release stress-related compounds, including aminocyclopropane-1-carboxlic acid (ACC), reactive oxygen species, and others, resulting in a negative impact on plant growth. The BEMD system can be used to display enzymes that degrade such stress-related compounds, such as aminocyclopropane-1-carboxylic acid deaminase, superoxide dismutases, oxidases, catalases, and other enzymes that act on reactive oxygen species. Such enzymes reduce the amount of these stress-related compounds and allow plants to continue to grow and even thrive under stressed conditions.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or to another plant growth medium or applied to the leaves of a plant for enhancing the stress resistance of a target plant.

Example 21. Preparation of BEMD Spores Expressing the Protective Enzyme Catalase A gene was synthesized that encoded the protective enzyme catalase from *Bacillus cereus* linked to a BetA targeting sequence (SEQ ID NO: 97) under the control of the BetA promoter (SEQ ID NO: 197). This gene was and introduced into *Bacillus thuringiensis* BT013A. Spores were made by growing an overnight culture of the transformed *Bacillus* and wildtype strain in brain heart infusion broth, plating onto nutrient agar plates at 30° C., and allowing to grow for 3 days. Spores were washed off the plates and rinsed 3× in PBS. 3 drops of hydrogen peroxide was added to each spore pellet. The enzyme catalase converts the hydrogen peroxide into water and $O_2$ gas. The control spores did not bubble, while the BEMD-catalase spores readily did, demonstrating enzyme activity on the surface of the spores. Other protective enzymes can be displayed in a similar fashion and delivered to the plant to act upon free radicals produced during stress by the plants.

Example 22. Use of Recombinant *Bacillus cereus* Family Members Displaying Proteins or Enzymes that Protect Seeds or Plants from an Environmental Stress Proteins, peptides, and enzymes that protect a plant from an environmental stress can be incorporated into the BEMD system and delivered to target plants via addition to roots, leaves, fruit, or the plant growth medium. During periods of freezing, plants can be damaged by the effect of ice. The BEMD system can be used to display peptides, proteins, or enzymes that protect plants from such effects. For example, the BEMD system can be used to display choline dehydrogenases, which act by producing protective products that protect the plant or seed from frost. Substrates for these enzymes (e.g., choline and/or choline derivatives) can also be added to the plant growth medium. Addition of such substrates can enhance the amount of protectant (betaine and related chemistries) produced in the plant environment by the BEMD expressed enzymes. Betaine derivatives are known to protect seeds from cold stress.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or to another plant growth medium or applied to the leaves of a plant for protecting the plant from environmental stresses and factors.

Example 23. Enhanced Expression of Fusion Constructs on the BEMD System by Use of Enhanced or Alternative Promoter Elements The BEMD system can display a wide range of proteins, peptides, and enzymes using one or more of the targeting sequences described herein. Some of these targeting sequences have a high affinity for the exosporium which would be beneficial for fusion protein expression, but their low fusion protein expression level limits their use on the BEMD system. For such fusion proteins and sequences, alternative high-expression sporulation promoters can be used instead of the native promoters.

For example, SEQ ID NO: 13 (amino acids 1-39 of *B. weihenstephensis* KBAB4 gene 3572) provides a very effective N-terminal sequence for the delivery of proteins to the exosporium of *Bacillus cereus* family members, as shown in Table 26 below. All genes were synthesized in their complete form (including promoter regions and regions coding for fusion proteins) as described herein. When the native promoter elements for *B. weihenstephensis* KBAB4 gene 3572 (SEQ ID NO: 217) were used to express a fusion protein comprising the targeting sequence of SEQ ID NO: 13 fused to a 3-galactosidase enzyme (from *E. coli*), a low level of fusion protein was expressed, leading to a reduction in enzyme activity on the surface of the spore. Enzyme activity was measure by the conversion of 0.5M o-nitrophenylgalactoside in solution over 10 minutes. Enzyme conversion was measured with a spectrophotometer at $ABS_{540}$. Replacement of the native promoter elements of the *B. weihenstephensis* KBAB4 gene 3572 with the high-expression promoters of SEQ ID NO: 197 (*B. anthracis* BetA/BAS3290) or SEQ ID NO: 218 (*B. weihenstephensis* KBAB4 YVTN β-propeller protein) led to a dramatic increase in the enzymatic activity of the spores. On the other hand, replacement of the native promoter elements for *B. weihenstephensis* KBAB4 gene 3572 with the promoter native to *B. anthracis* Sterne BAS1882 (SEQ ID NO: 216) led to a decrease in the enzymatic activity of the spores. The expression level of the targeting sequence of SEQ ID NO: 13 fused to 3-galactosidase was much lower (0.38×) when driven by the promoter of BAS1882 (SEQ ID NO: 216), and was greatly improved when driven from the BetA promoter (SEQ ID NO: 197) or YVTN protein promoter (SEQ ID NO: 218).

TABLE 26

| Promoter | Fusion Protein | β-galactosidase activity on BEMD system, normalized | Fold Change |
|---|---|---|---|
| SEQ ID NO: 217 | SEQ ID NO: 13 - β-galactosidase | 100% | |
| SEQ ID NO: 197 | SEQ ID NO: 13 - β-galactosidase | 213.4% | 2.13X |
| SEQ ID NO: 218 | SEQ ID NO: 13 - β-galactosidase | 220.7% | 2.21X |
| SEQ NO: ID 216 | SEQ ID NO: 13 - β-galactosidase | 38.1% | 0.38X |

Example 24. Isolation and Identification of Plant-Growth Promoting Bacterial Strains Soil samples from rhizospheres of the healthiest and most resistant potato (*Solanum tuberosum*), yellow summer squash (*Cucurbita pepo*), tomato (*Solanum lycopersicum*), and pole bean (*Phaseolus coccineus*) plants were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten lettuce seeds per treatment were planted at a depth of 1 cm in loam top soil (Columbia, Mo.) that was sieved to remove large debris. Seeds were inoculated at planting in 4 cm pots with 0.5 μl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. After one week, plant heights and leaf diameters, as well as overall health of the plants were collected. Initial screening of rhizosphere isolates resulted in obtaining greater than 200 distinct species of bacteria and fungi from the rhizosphere of the four plants. Some of the bacterial species are described in Table 27. Identified strains are indicated by their proper bacterial identifications. Other strains are indicated by their unknown identification number. Inoculants giving results near control (+/−2%) were not included in the table.

TABLE 27

| Bacterial Inoculant | Butterhead Lettuce Avg. Height (cm) | Comparison | SEM |
|---|---|---|---|
| Uninoculated | 1.8 | Control | .07 |
| *Paracoccus kondratiavae* NC35 | 2 | 111.1% | .05 |
| *B. aryabhattai* CAP53 | 3.65 | 202.8% | .45 |
| *B. flexus* BT054 | 2.45 | 136.1% | .11 |
| *Bacillus mycoides* strain BT155 | 2.17 | 120.4% | .21 |
| *B. aryabhattai* CAP56 | 2.1 | 116.7% | .20 |
| *B. nealsonii* BOBA57 | 2.8 | 155.6% | .03 |
| *E. cloacae* CAP12 | 2.4 | 133.3% | .41 |
| Unknown 8 | 1.77 | 77.8% | .65 |
| Unknown 122 | 1.9 | 105.6% | .11 |
| Unknown 15 | 1.4 | 77.8% | .41 |
| Unknown 39 | 1.8 | 100.0% | .20 |
| Unknown 401 | 2 | 111.1% | .21 |
| Unknown 402 | 1.53 | 85.2% | .27 |
| Unknown 41 | 1.45 | 80.6% | .31 |
| Unknown 42 | 1.4 | 77.8% | .15 |
| Unknown 44 | 2.2 | 133.3% | .08 |
| Unknown 51 | 1.83 | 102.9% | .21 |

Bacterial strains that produced the greatest effect on the overall plant health and plant height in the initial lettuce trial were subjected to further identification. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 298), E1099R A 5'-GGG TTG CGC TCG TTG C-3' (SEQ ID NO: 299), and E1099R B5'-GGG TTG CGC TCG TTA C-3' (SEQ ID NO: 300). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 27. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and are listed in Table 28.

TABLE 28

| Test | E. cloacae CAP12 | P. kondratiavae NC35 | B. aryabhattai CAP53 | B. flexus BT054 | B. mycoides BT155 | B. aryabhattai CAP56 | B. nealsoni BOBA57 |
|---|---|---|---|---|---|---|---|
| Urease | − | − | − | − | − | − | + |
| Catalase | + | + | + | + | + | + | + |
| Oxidase | − | + | + | + | − | − | − |
| Nitrate | + | + | − | + | + | − | + |
| Growth, 5% NaCl | + | − | + | + | − | + | + |
| Growth, 7.5% NaCl | − | − | + | + | − | + | − |
| Growth, 42° C. | + | + | + | + | + | + | + |
| Growth, 50° C. | − | − | + | + | − | + | − |
| Growth, pH 5 | + | − | + | + | − | + | − |
| Growth, pH 9 | + | + | + | + | + | + | + |
| Acid, Cellobiose | + | − | + | + | + | + | − |
| Acid, Lactose | + | − | + | + | + | − | + |
| Acid, Starch | − | − | − | + | − | + | − |

Example 25. Isolation and Identification of Additional Plant-Growth Promoting Bacterial Strains Soil samples from agricultural fields near Gas, Kans. were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Corn seeds were coated with commercial seed polymer mixed with water alone (1.6 µl per seed total) or commercial seed polymer containing selected bacterial strains (1.6 µl per seed total). Coated seeds were planted in (3 inch) 7.62 cm diameter pots at a depth of 1 inch (2.54 cm) in loam top soil (Columbia, Mo.) that was sieved to remove large debris. Plants were grown at temperatures between 18-24° C. (65-75° F.) with 11 hours of light/day, and 50 ml of watering at planting and every 3 days. After two weeks, plant heights and leaf diameters, as well as overall health of the plants were collected. For germination assays and determining 3 day root length, seeds were coated as indicated above and evenly dispersed at 10 seeds per paper towel. The paper towels were wetted with 10 mls of water, rolled up, placed in a small plastic bag and incubated at 30° C. or placed on a germination heat mat at 27-30° C. (80-85° F.). Root measurements were recorded after 3 days. Initial screening of rhizosphere isolates resulted in obtaining greater than 100 distinct species of bacteria and fungi from the rhizosphere. Some of the bacterial species are described in Table 29. Identified strains are indicated by their proper bacterial identifications.

TABLE 29

| Bacterial Inoculant | Corn Seed Treatments Avg. Height (2 weeks) normalized to polymer control (%) | Avg. Root Length (3 days) normalized to polymer control (%) |
|---|---|---|
| Polymer control | 100 | 100 |
| B. mycoides EE118 | 111.1 | 189.1 |

TABLE 29-continued

| Bacterial Inoculant | Corn Seed Treatments Avg. Height (2 weeks) normalized to polymer control (%) | Avg. Root Length (3 days) normalized to polymer control (%) |
|---|---|---|
| B. subtilis EE148 | 99.4 | 172.8 |
| Alcaligenes faecalis EE107 | 111.5 | 129.2 |
| B. mycoides EE141 | 109.2 | 143.5 |
| B. mycoides BT46-3 | 105.6 | 141.3 |
| B. cereus family member EE128 | 105.6 | — |
| B. thuringiensis BT013A | 101.8 | 103.8 |
| Paenibacillus massiliensis BT23 | 104.2 | 139.4 |
| B. cereus family member EE349 | 105.2 | — |
| B. subtilis EE218 | 106.6 | — |
| B. megaterium EE281 | 107.8 | — |

Bacterial strains that produced the greatest effect on plant health are described in Table 29. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 298), E1099R A 5'-GGG TTG CGC TCG TTG C-3' (SEQ ID NO: 299), and E1099R B 5'-GGG TTG CGC TCG TTA C-3' (SEQ ID NO: 300). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 16. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and the differentiated strains are listed in Table 30.

11 hours of light/day, and 5 ml of watering every 3 days. Alfalfa was allowed to grow for 1 week to analyze emergence and initial outgrowth of plants under described conditions. Identified strains indicated by their proper bacterial identifications and final height data are listed in Table 31.

TABLE 30

| Test | B. thuringiensis BT013A | B. cereus family member EE349 | B. subtilis EE148 | B. subtilis EE218 | B. megaterium EE281 | Paenibacillus massiliensis BT23 |
|---|---|---|---|---|---|---|
| Motility | + | + | + | + | + | + |
| Rhizoid Colony | − | − | − | − | − | + |
| Catalase | + | + | + | + | + | + |
| Oxidase | + | − | − | − | − | − |
| Nitrate | + | + | wk | − | − | − |
| Growth, 5% NaCl | + | wk | − | + | + | − |
| Growth, 7.5% NaCl | Wk | − | − | + | + | − |
| Growth, 42° C. | − | + | + | + | + | + |
| Growth, 50° C. | − | − | − | − | − | − |
| Growth, pH 5 | Wk | − | + | + | + | − |
| Growth, pH 9 | + | + | − | + | + | − |
| Acid, Cellobiose | − | − | wk | + | − | + |
| Acid, Lactose | − | + | + | + | + | − |
| Acid, Starch | − | + | − | + | + | − |

| Test | B. mycoides BT46-3 | Alcaligenes faecalis EE107 | B. mycoides EE118 | B. cereus family member EE128 | B. mycoides EE141 |
|---|---|---|---|---|---|
| Motility | − | + | − | − | − |
| Rhizoid Colony | + | − | + | − | + |
| Catalase | + | + | + | + | + |
| Oxidase | − | + | − | − | − |
| Nitrate | + | + | + | + | + |
| Growth, 5% NaCl | + | + | − | + | − |
| Growth, 7.5% NaCl | − | − | − | − | − |
| Growth, 42° C. | + | + | − | + | − |
| Growth, 50° C. | − | − | − | − | − |
| Growth, pH 5 | wk | + | − | + | − |
| Growth, pH 9 | wk | + | + | + | − |
| Acid, Cellobiose | + | wk | + | − | wk |
| Acid, Lactose | + | + | − | + | wk |
| Acid, Starch | + | wk | + | + | − | wk = weak growth or low growth

Example 26. Testing of Plant-Growth Promoting Bacterial Strains on Alfalfa

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and bacteria resuspended in an equal amount of distilled water. Ten Zeba-coated alfalfa seeds were planted for each treatment at a depth of 0.6 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with

TABLE 31

| Bacterial Inoculant | Alfalfa Avg. Height (cm) | Comparison | SEM |
|---|---|---|---|
| Uninoculated | 4.82 | — | .008 |
| B. aryabhattai CAP56 | 4.85 | 101.20% | .016 |
| B. nealsonii BOBA57 | 4.86 | 101.70% | .021 |
| E. cloacae CAP12 | 5.6 | 116.23% | .020 |

Example 27. Testing of Plant-Growth Promoting Bacterial Strains on Cucumbers

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in equal amount of distilled water. Ten cucumber seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Cucumbers were allowed to grow for 2 weeks to analyze emergence and initial outgrowth of plants under described conditions. Identified strains indicated by their proper bacterial identifications and final height data are listed in Table 32.

TABLE 32

| Bacterial Inoculant | Cucumbers Avg. Height (cm) | Comparison | SEM |
|---|---|---|---|
| Uninoculated | 11.23 | — | .067 |
| B. aryabhattai CAP53 | 11.5 | 102.00% | .023 |
| B. aryabhattai CAP56 | 11.35 | 101.20% | .035 |
| B. nealsonii BOBA57 | 11.33 | 101.10% | .014 |

Example 28. Testing of Plant-Growth Promoting Bacterial Strains on Yellow Squash The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten yellow squash seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Squash was allowed to grow for 2 weeks to analyze emergence and initial outgrowth of plants under described conditions. Identified strains indicated by their proper bacterial identifications, final height data, and final leaf diameter (by span of the two leaves) data are listed in Table 33.

TABLE 33

| Bacterial Inoculant | Avg. Height (cm) | Yellow Squash Comparison | SEM | Leaf Diameter (cm) | Comparison |
|---|---|---|---|---|---|
| Uninoculated | 10.16 | — | .028 | 5.08 | — |
| B. aryabhattai CAP53 | 11.75 | 115.60% | .055 | 7.25 | 142.60% |
| B. flexus BT054 | 11.88 | 116.90% | .017 | 6.36 | 125.20% |
| Bacillus mycoides BT155 | 11.92 | 117.20% | .051 | 6.33 | 124.60% |
| B. aryabhattai CAP56 | 11.95 | 117.60% | .027 | 6.33 | 124.60% |
| B. nealsonii BOBA57 | 11.89 | 117.00% | .118 | 6.42 | 126.40% |
| E. cloacae CAP12 | 11.42 | 112.30% | .039 | 6.83 | 134.40% |

Example 29. Testing of Plant-Growth Promoting Bacterial Strains on Ryegrass

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Thirty ryegrass seeds were planted for each treatment at a depth of 0.3 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Ryegrass was allowed to grow for 1.5 weeks to analyze emergence and initial outgrowth of plants under described conditions. Identified strains indicated by their proper bacterial identifications and height data are listed in Table 34.

TABLE 34

| Bacterial Inoculant | Ryegrass Avg. Height (cm) | Comparison | SEM |
|---|---|---|---|
| Uninoculated | 1.61 | — | .023 |
| B. aryabhattai CAP53 | 2.01 | 124.70% | .012 |
| B. flexus ET054 | 2.21 | 137.30% | .034 |
| Bacillus mycoides BT155 | 2.29 | 142.20% | .049 |
| B. aryabhattai CAP56 | 2.19 | 136.00% | .009 |
| B. nealsonii BOBA57 | 2.29 | 142.40% | .045 |
| E. cloacae CAP12 | 1.98 | 122.50% | .015 |

Example 30. Testing of Plant-Growth Promoting Bacterial Strains on Corn

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 35.

TABLE 35

| Bacterial Inoculant | Corn Avg. Height (cm) | Comparison | SEM |
|---|---|---|---|
| Uninoculated | 8.9 | — | .039 |
| B. aryabhattai CAP53 | 11.01 | 123.60% | .081 |
| B. flexus BT054 | 9.96 | 112.00% | .095 |
| Bacillus mycoides strain BT155 | 9.6 | 107.90% | .041 |
| B. aryabhattai CAP56 | 9.54 | 107.10% | .088 |
| B. nealsonii BOBA57 | 9.23 | 103.70% | .077 |

Example 31. Testing of Plant-Growth Promoting Bacterial Strains on Soybeans

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight, or for *Bradyrhizobium* or *Rhizobium* on yeast mannitol media). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$. When testing two bacterial strains, 0.5 µl of each resuspended bacteria was mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 36. Co-inoculation of bacteria strains in the present invention with members of the *Bradyrhizobium* sp. or *Rhizobium* sp. lead to an increase in plant growth compared to either inoculant alone.

TABLE 36

| Bacterial Inoculant | Soybeans Avg. Height (cm) | Comparison | SEM |
|---|---|---|---|
| Uninoculated | 13.94 | — | .089 |
| B. aryabhattai CAP53 | 16.32 | 117.1% | .146 |
| B. flexus BT054 | 17.85 | 128.0% | .177 |
| Bacillus mycoides strain BT155 | 18.93 | 135.8% | .117 |
| B. aryabhattai CAP56 | 17.23 | 123.6% | .133 |
| B. aryabhattai CAP53 | 16.32 | 117.1% | .077 |
| B. aryabhattai CAP53 and Bradyrhizobium sp. | 16.72 | 119.9% | .182 |
| B. aryabhattai CAP53 and Rhizobium sp. | 17.32 | 124.2% | .086 |
| Bradyrhizobium sp. | 14.25 | 102.2% | |
| Rhizobium sp. | 14.75 | 105.8% | |

Example 32. *Bacillus cereus* Family Members with Plant Growth Promoting Attributes

*Bacillus mycoides* strain BT155, *Bacillus mycoides* strain EE118, *Bacillus mycoides* strain EE141, *Bacillus mycoides* strain BT46-3, *Bacillus cereus* family member strain EE349, *Bacillus thuringiensis* strain BT013A, and *Bacillus megaterium* strain EE281 were grown in Luria Bertani broth at 37° C. and overnight cultures were spun down, media decanted off, and resuspended in equal amount of distilled water. 20 corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 50 ml of $H_2O$. Fifty ml of $H_2O$ was sufficient to deliver the bacteria into the 29 $in^3$ (442.5 $cm^3$) of soil as well as saturate the soil for proper germination of seeds. Plants were grown at temperatures between 65-72° F. with 13 hours of light/day, and 5 ml of watering every 3 days. Seedlings were allowed to grow for 2 weeks to analyze emergence and initial outgrowth of plants under described conditions. Identified strains indicated by their proper bacterial identifications and final height data are listed in Table 37.

TABLE 37

| Bacterial Inoculant | Avg. Height, cm, Corn | Percentage | SEM, |
|---|---|---|---|
| $H_2O$ Control | 11.41 | 100% | .123 |
| B. mycoides EE118 | 12.43 | 108.9% | .207 |
| B. mycoides EE141 | 12.84 | 112.5% | .231 |
| B. mycoides BT46-3 | 11.81 | 103.5% | .089 |
| Bacillus thuringiensis BT013A | 12.05 | 105.6% | .148 |
| Bacillus cereus family member EE128 | 13.12 | 114.9% | .159 |
| Bacillus mycoides BT155 | 12.85 | 112.6% | .163 |
| Bacillus megaterium EE281 | 11.99 | 105.1% | .098 |

All plant growth promoting bacteria tested had a beneficial effect on corn height at two weeks under the described conditions. The *Bacillus cereus* family member EE128 strain had the greatest effect in this trial, giving a greater than at 14% boost in corn height.

Example 33. Enhanced Selection of *Bacillus cereus* Family Members to Screen for Plant Growth-Promoting and Other Beneficial Activities as BEMD Expression Host The BEMD system can be used to display a wide range of proteins, peptides, and enzymes using any of the targeting sequences described herein to provide beneficial agricultural effects. Additional beneficial effects can be obtained by selecting an expression host (a *Bacillus cereus* family member) having inherent beneficial attributes. Many strains of members of the *Bacillus cereus* family have plant-growth promoting benefits. Additionally, many *Bacillus cereus* family member strains provide have protective effects, through direct fungicidal, insecticidal, nematocidal, or other protective activities. By using such strains these as the expression host for the BEMD system, the end spore product would have a combination of positive benefits in agriculture.

Table 38 provides results for an experiment wherein a fusion protein was expressed in various *Bacillus cereus* family member strains. All strains are expressed a fusion protein comprising amino acids 1-35 of SEQ ID NO: 1 and the phosphatase PhoA4 from *Bacillus subtilis*, a beneficial enzyme for enhanced phosphate uptake in corn. The gene was synthesized, cloned into the pMK4 vector, and introduced into each of the *Bacillus* spp. indicated in Table 38 below. Strains were taken into sporulation by incubation at 30° C. on nutrient agar plates containing chloramphenicol 10 μg/ml for three days. Spores were collected, washed, and applied to corn at planting at a rate of $1\times10^5$ CFU/ml in 50 ml of water per 7.62 cm diameter pot with 5 mg polyphosphate per pot. Corn was grown in silt loam soil for two weeks. Plants were grown under ideal light using T5 lamps, 54 watts, and exposed to 13 hours of light a day under controlled temperature conditions between 15.5-25.5° C. Plants were watered to saturation every three days over a two week trial. At the end of two weeks, the height of each plant was measured and measurements were normalized to control *Bacillus thuringiensis* spores. Expression of the SEQ ID NO: 1—Phosphatase fusion protein led to an increase in corn height at 2 weeks regardless of the expression host strain selected. As shown in Table 38, use of a plant-growth promoting *Bacillus cereus* family member further increased corn height.

TABLE 38

| Bacillus Species | Strain | Fusion Protein | Height at 2 weeks, Normalized |
|---|---|---|---|
| B. thuringiensis | Strain BT013A | None | 100% |
| B. thuringiensis | Strain BT013A | SEQ ID NO: 1-Phosphatase | 117.4% |
| B. mycoides | Strain EE141 | None | 107.3% |
| B. mycoides | Strain EE141 | SEQ ID NO: 1-Phosphatase | 123.3% |
| B. cereus family member | Strain EE128 | None | 124.1% |
| B. cereus family member | Strain EE128 | SEQ ID NO: 1-Phosphatase | 131.7% |
| B. mycoides | Strain BT155 | None | 104.8% |
| B. mycoides | Strain BT155 | SEQ ID NO: 1-Phosphatase | 121.9% |

Example 34. Use of Various Targeting Sequences to Express β-Galactosidase on the Surface of *Bacillus thuringiensis*

A wide variety of targeting sequences that that have a high degree homology with amino acids 20-35 of BclA (amino acids 20-35 of SEQ ID NO: 1) can be used to display enzymes, proteins, and peptides on the surface of *Bacillus cereus* family members. Several targeting sequences were compared by making fusion proteins containing the targeting sequences linked to *Bacillus subtilis* lipase. Fusion constructs were synthesized using the promoters native to the targeting sequence, cloned into the replicating plasmid pMK4, and introduced into *Bacillus thuringiensis* BT013A. Strains were taken into sporulation by incubation at 30° C. on nutrient agar plates containing chloramphenicol 10 µg/ml for 3 days. Spores were collected, washed, and resuspended in PBS at a rate of $1\times10^8$/ml. $1\times10^5$ spores for each fusion construct spores were suspended in 400 µl dH$_2$O. The reactions were warmed with the reaction components to the desired reaction temperature (40° C.). 200 µl working buffer was added (9:1 Solution A: Solution B). Solution A was 50 mM Tris pH 10 and 13.6 mM deoxycholic acid and Solution B was 3 mg/ml p-nitrophenyl palmitate in isopropanol. The reaction was incubated at 40° C. for 10 minutes and placed on ice, centrifuged to remove spores, and absorbance at 420 nm was recorded. The results are shown in Table 39 below. Activity was normalized to a control fusion protein comprising amino acids 1-35 of SEQ ID NO: 1 fused to *Bacillus subtilis* lipase.

TABLE 39

| Strain | Targeting sequence | Enzyme | Relative activity |
|---|---|---|---|
| B. thuringiensis BT013A | Amino acids 1-35 of SEQ ID NO: 1 | Lipase | 100% |
| B. thuringiensis BT013A | Amino acids 1-27 of SEQ ID NO: 3 | Lipase | 92.5% |
| B. thuringiensis BT013A | Amino acids 1-28 of SEQ ID NO: 7 | Lipase | 13.5% |
| B. thuringiensis BT013A | Amino acid 1-24 of SEQ ID NO: 9 | Lipase | 24.8% |
| B. thuringiensis BT013A | Amino acid 1-33 of SEQ ID NO: 13 | Lipase | 98.5% |
| B. thuringiensis BT013A | Amino acid 1-33 of SEQ ID NO: 21 | Lipase | 107.8% |

TABLE 39-continued

| Strain | Targeting sequence | Enzyme | Relative activity |
|---|---|---|---|
| B. thuringiensis BT013A | SEQ ID NO: 96 | Lipase | 137.1% |
| B. thuringiensis BT013A | SEQ ID NO: 98 | Lipase | 146.3% |
| B. thuringiensis BT013A | SEQ ID NO: 100 | Lipase | 115.7% |
| B. thuringiensis BT013A | SEQ ID NO: 104 | Lipase | 81.5% |

Several targeting sequences linked to lipase result in higher expression levels and activity of enzyme on the surface of spores. In particular, SEQ ID NOs. 96, 98, and 100, each containing a shorter targeting sequence, resulted in enhanced fusion expression on the surface of the BEMD spores. All the fusion proteins containing targeting sequences tested resulted in surface display of lipase.

Example 35. Use of Various Exosporium Sequences to Express Lipase on the Surface of *Bacillus thuringiensis* and Demonstration of Fusion Protein Localization to the Exosporium Surface A wide variety of exosporium proteins can be used to display enzymes, proteins, and peptides on the surface of *Bacillus cereus* family members. Several different exosporium proteins were compared by making fusion proteins containing the exosporium proteins linked to *Bacillus subtilis* lipase as described in Example 34. Fusion constructs were synthesized using the promoter native to the exosporium protein indicated in Table 40 below, cloned into the replicating plasmid pMK4, and introduced into *Bacillus thuringiensis* BT013A. Spores displaying the various exosporium protein-*Bacillus subtilis* 168 lipase fusions were made by growing the transformed bacteria in brain heart infusion broth with selective pressure from 10 µg/ml chloramphenicol, plating onto nutrient agar plates, and incubating at 30° C. for 3 days. After 3 days, the spores were washed off the plates, purified by centrifugation, and resuspended in PBS at $1\times10^8$ CFU/ml.

$1\times10^5$ spores for each fusion construct were resuspended in 400 µl dH$_2$O. The reactions were warmed with the reaction components to the desired reaction temperature (40° C.). 200 µl of working buffer was added (9:1 Solution A: Solution B). Solution A was 50 mM Tris pH 10 and 13.6 mM deoxycholic acid and Solution B was 3 mg/ml p-nitrophenyl palmitate in isopropanol. The reaction was incubated at 40° C. for 10 minutes and placed on ice, centrifuged to remove spores and absorbance at 420 nm was recorded. Results are shown in Table 40 below. Activity was normalized to SEQ ID NO: 109 linked to lipase.

TABLE 40

| Strain | Exosporium protein | Enzyme | Relative activity |
|---|---|---|---|
| B. thuringiensis BT013A | SEQ ID NO: 109 | Lipase | 100% |
| B. thuringiensis BT013A | SEQ ID NO: 110 | Lipase | 134.5% |
| B. thuringiensis BT013A | SEQ ID NO: 113 | Lipase | 17.8% |
| B. thuringiensis BT013A | SEQ ID NO: 117 | Lipase | 19.8% |
| B. thuringiensis BT013A | SEQ ID NO: 118 | Lipase | 8.2% |

Use of the exosporium proteins of SEQ ID NOs. 109 and 110 resulted in the highest enzyme activity on the spore. All the fusion proteins containing exosporium proteins resulted in surface display of active *Bacillus subtilis* 168 lipase, albeit at different levels.

Additional exosporium proteins were demonstrated to result in targeting of fusion proteins to the exosporium using the fluorescent reporter mCherry. Fusion constructs were created that contained the exosporium proteins of SEQ ID NOs. 111, 120, and 110 linked to the mCherry reporter. Spores were grown for 1.5 days, collected, and resuspended as described above. 7 μl of fluorescent spores were put under a Nikon E1000 microscope and imaged during late sporulation. Circular localization in a ring is indicative of outer spore layer localization, and the appearance matches that of an exosporium protein. Fluorescent microscopy results are shown in FIG. 2. Panels A, B, and C of FIG. 2 are fluorescent microscopy images of spores expressing fusion proteins comprising the exosporium proteins of SEQ ID NOs. 111, 120, and 110, respectively, and the mCherry reporter. All three fusions demonstrated high levels of fluorescence and exosporium localization, demonstrating their potential utility for the expression of foreign proteins on the surface of the exosporium.

Example 36. Use of Various Targeting Sequences and Exosporium Proteins to Express Phosphatase in *Bacillus subtilis* Spores and Effects of the Phosphatase-Expressing Spores in Soybeans BEMD spores expressing *Bacillus subtilis* EE148 Phosphatase A4 (PhoA4) were created by gene synthesis of the genes coding for various targeting sequences and exosporium proteins under the control of their native promoters linked to PhoA4. The synthesized genes were cloned into pMK4 and introduced into *Bacillus thuringiensis* BT013A. Spores displaying the various exosporium protein-*Bacillus subtilis* EE148 PhoA4 fusions were made by growing the transformed bacteria in brain heart infusion broth with selective pressure from 10 μg/ml chloramphenicol, plating onto nutrient agar plates, and incubating at 30° C. for three days. After three days, the spores were washed off the plates, purified by centrifugation, and resuspended in PBS at 1×10$^8$ CFU/ml.

Soybeans were planted 2.54 cm deep in 10 cm deep pots filled with standard loam topsoil. BEMD spores expressing PhoA4 were diluted to a concentration of 1×10$^4$/ml in 50 ml of water and applied to each plant at planting. A water-only control was also included. Polyphosphate was added to pots in liquid at a rate of 0.5 mg/pot. Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, and measurements were normalized to control water-only plants.

Results are shown in Table 41. Soy grown in the presence of BEMD spores expressing fusion proteins containing PhoA4 linked to various targeting sequences and exosporium proteins with different fusion partners with PhoA4 all exhibited enhanced growth, but the extent of the effect varied depending on the targeting sequence or exosporium protein used.

TABLE 41

| *Bacillus* species | Targeting sequence or exosporium protein linked to PhoA4 | Height at 2 weeks, Normalized |
|---|---|---|
| H2O (No bacteria) | N/A | 100% |
| *Bacillus thuringiensis* Strain BT013A | Amino acids 1-35 of SEQ ID NO: 1 | 100% |
| *Bacillus thuringiensis* Strain BT013A | Amino acids 1-28 of SEQ ID NO: 3 | 117.4% |
| *Bacillus thuringiensis* Strain BT013A | Amino acids 1-33 of SEQ ID NO: 21 | 107.3% |
| *Bacillus thuringiensis* Strain BT013A | SEQ ID NO: 96 | 123.3% |
| *Bacillus thuringiensis* Strain BT013A | SEQ ID NO: 98 | 124.1% |
| *Bacillus thuringiensis* Strain BT013A | SEQ ID NO: 109 | 131.7% |
| *Bacillus thuringiensis* Strain BT013A | SEQ ID NO: 110 | 104.8% |

Example 37. Co-Application of BEMD Spores and Seed Treatments, Liquid Fertilizers, and Other Additives BEMD spores expressing fusion proteins were tested for compatibility with various seed treatments. The BEMD spores expressed fusion proteins comprising the targeting sequence of amino acids 1-35 SEQ ID NO: 1 linked to a phosphatase (PhoA4) from *Bacillus subtilis* EE148 or the POLARIS peptide. The synthesized genes were cloned into pMK4 and introduced into *Bacillus thuringiensis* BT013A. Spores displaying the various exosporium protein-*Bacillus subtilis* EE148 PhoA4 or POLARIS fusions were made by growing the transformed bacteria in brain heart infusion broth with selective pressure from 10 μg/ml chloramphenicol, plating onto nutrient agar plates, and incubating at 30° C. for three days. After three days, the spores were washed off the plates, purified by centrifugation, and resuspended in PBS at 1×10$^8$ CFU/ml.

Plants were grown under ideal light using T5 lamps, 54 watts, and exposed to 13 hours of light a day under controlled temperature conditions between 15.5-25.5° C. Plants were watered to saturation every three days over the two week trial. At the end of two weeks, the height of each plant was measured, and measurements were normalized to control water only plants. Results are shown in Table 42 below. Drench=applied to soil at 50 ml per pot. Polymer=ACCELERON seed coating polymer only. BEMD spores were added at 1×10$^4$ cells/50 ml for drench applications. BEMD spores were added at 1.3×10$^4$/cells/seed for seed coating applications. 10-34-0 and 6-24-6 are standard commercial starter fertilizer compositions. 10-34-0 is liquid ammonium phosphate. 6-24-6 is low salt liquid phosphate fertilizer with an ortho/poly formulation. Colorant=Becker Underwood red seed coating coloring agent. MACHO, APRON, and CRUISER are commercial fungicides used on seeds. MACHO contains the active ingredient imidacloprid, APRON contains the active ingredient mefenoxam, and CRUISER contains a mixture of the active ingredients thiamethoxam, mefenoxam, and fludioxonil. The spores were found to be compatible with many seed applications and retained their ability to stimulate plant growth in corn.

TABLE 42

| BEMD treatment | Chemical | Corn height at 2 weeks, normalized |
|---|---|---|
| None | None (Water Drench) | 100% |
| None | Polymer Only | 101.3% |
| BEMD PhoA4 | N/A (Drench) | 111.3% |
| BEMD POLARIS | N/A (Drench) | 106.7% |
| BEMD PhoA4 | Polymer | 109.3% |
| BEMD POLARIS | Polymer | 107.3% |
| BEMD PhoA4 | Polymer + Colorant | 102.3% |
| BEMD PhoA4 | Polymer + MACHO | 107.9% |
| BEMD PhoA4 | Polymer + APRON | 112.3% |
| BEMD PhoA4 | Polymer + CRUISER | 116.8% |
| BEMD PhoA4 | Polymer + Colorant + MACHO + APRON + CRUISER | 113.7% |
| None | 10-34-0 Starter (Drench) | 108.5% |
| BEMD PhoA4 | 10-34-0 Starter Fertilizer (Drench) | 114.7% |
| None | 6-24-6 Starter Fertilizer (Drench) | 102.6% |
| BEMD PhoA4 | 6-24-6 Starter Fertilizer (Drench) | 112.9% |

BEMD spores were found to be compatible with all seed coating amendments tested. There was a slight decrease in activity when BEMD PhA4 spores were combined with colorant and polymer alone, but the spores regained full activity with colorant in combination with other fungicides. BEMD spores also worked well with liquid fertilizers. Starter fertilizers contributed to plant growth most likely through direct nutrient supplementation. BEMD spores worked with both starter fertilizers, suggesting that phosphatase activity can still lead to increased plant growth in the presence of excess nutrients. Combinations of BEMD spores with fungicides exhibited greater increases in plant growth than BEMD spores alone, likely due to protection given to young corn plants during early growth.

Example 38. The Use of the BEMD Spores as a Foliar Addition for Reducing Stress Inhibition of Growth on Corn The BEMD spore display system can be used to deliver enzymes that can alleviate some stress from growing plants in the field or greenhouse. To accomplish this, enzymes were selected that selectively act upon reactive oxygen species in soil. Reactive oxygen species are a key marker of stress in plants.

BEMD spores expressing fusion proteins comprising the targeting sequence of amino acids 1-35 of SEQ ID NO: 1 linked to chitosanase, superoxide dismutase, catalase, or β1,3 glucanase from *Bacillus thuringiensis* BT013A were generated. The synthesized genes were cloned into pMK4 and introduced into *Bacillus thuringiensis* BT013A. Spores displaying the various protein fusions were made by growing the transformed bacteria in brain heart infusion broth with selective pressure from 10 μg/ml chloramphenicol, plating onto nutrient agar plates, and incubating at 30° C. for three days. After three days, the spores were washed off the plates, purified by centrifugation, and resuspended in PBS at $1\times10^8$ CFU/ml.

Three week old corn plants at the V5 stage were grown under ideal light using T5 lamps, 54 watts, and exposed to 13 hours of light a day under controlled temperature conditions between 15.5-25.5° C. Plants were watered to saturation every three days over the course of the trial. As the plants reach V5, BEMD spores or positive control chemicals were sprayed on the leaves at either $1\times10^5$ BEMD spores/ml or at the recommended rates for the chemicals. A total of 1 ml of spray was applied to each plant individually. Plant heights were taken just prior to the application of the foliar sprays. The corn plants were then stressed by warming to 32.2° C. and decreasing watering to once per week. Plants were kept under stressed conditions for two weeks. At the end of the two weeks, plant heights were again measured, and visual appearance recorded. Under these stressed conditions, plant growth was minimal in control treatments. The ability to continue to grow under stressed conditions was measured by an increase in plant height over the two week span as compared to the water-only control. Results are shown in Table 43 below.

TABLE 43

| Treatment | Rate | Change in plant Height over 2 week stress |
|---|---|---|
| None | None | 0% |
| *Bacillus thuringiensis* BT013A spores | 1 ml/plant | −1.6% |
| BEMD Chitosanase | 1 ml/plant | 0.3% |
| BEMD Chitosanase and Chitosan | 1 ml/plant and 5 mM | 4.7% |
| BEMD Superoxide Dismutase | 1 ml/plant | 8.3% |
| BEMD B1,3 Glucanase | 1 ml/plant | 4.9% |
| Salicylic Acid | 1 ml/plant | 5.8% |
| Benzothiadiazole (BTH) | 1 ml/plant | 7.3% |
| BEMD Catalase | 1 ml/plant | −0.5% |

Several destressing enzymes were applied to corn using the BEMD system, as shown in in Table 43 above. Control spores had no significant effect (decrease in plant height of −1.6%. The BEMD chitosanase enzyme had a positive effect when combined with its substrate, chitosan. The two best performing enzymes were BEMD β-1,3-glucanase and BEMD superoxide dismutase. BEMD β-1,3-glucanase has a primarily antifungal activity, but can also have direct effects on plants. Salicylic acid and BTH were positive controls for the foliar assay, and positive responses were seen for both. This foliar delivery method can be used for delivering destressing enzymes to the plants at various times of the season.

Example 39. Expression Levels of Fusion Proteins Using Various Sigma-K Containing Promoters As shown in Example 23 above, replacing native promoter of a targeting sequence, exosporium protein, or exosporium protein fragment can greatly affect the level of fusion protein expressed on the exosporium of a *Bacillus cereus* family spore. For example, replacing the native BclA promoter with the BclB promoter greatly reduces the level of fusion protein on the surface of *Bacillus cereus* family member spores. Alternatively, replacement of native BclB promoter with the BclA promoter increases fusion protein levels on the exosporium dramatically.

Relative promoter expression levels for various exosporium proteins under the control of their native sporulation promoters were obtained from microarray data from Bergman et al., 2008. The relative expression levels were determined during late sporulation timing (300 minutes after the start of the experiment), when sigma K promoters are most active. Sigma K promoters are key promoters for expression of exosporium localized genes and associated proteins.

Relative expression is the increase in a gene's expression level when compared to the average of all other genes of the chromosome at all given times. Table 44 below shows the relative expression levels of a variety of sigma K driven genes in *Bacillus cereus* family members.

TABLE 44

| Protein (Promoter SEQ ID NO.) | Relative Expression (Fold increase in mRNA) |
|---|---|
| CotO (SEQ ID NO: 226) | 79.21 |
| Rhamnose (SEQ ID NO: 225) | 75.69 |
| BclC (SEQ ID NO: 179) | 14.44 |
| Sigma K (SEQ ID NO: 227) | 64 |
| BclA adjacent US Glycosyl transferase promoter 1 (SEQ ID NO: 229) | 72.25 |
| BclA adjacent DS Glycosyl transferase promoter 2 (SEQ ID NO: 230) | 73.96 |
| BclA (SEQ ID NO: 215) | 77.44 |
| ExsY (SEQ ID NO: 220) | 32.49 |
| YjcA (SEQ ID NO: 222) | 64 |
| YjcB (SEQ ID NO: 223) | 70.56 |
| BxpB/ExsFA (SEQ ID NO: 224) | 30.25 |
| InhA (SEQ ID NO: 228) | 34.25 |

Example 40. Preparation and Testing of BEMD Spores Expressing a Fusion Protein Comprising a Nitric Oxide Synthase, and Use of Such Spores for Stimulating Germination of Plant Seeds BEMD spores expressing a fusion protein containing amino acids 20-35 of BclA, a 6-alanine linker, and the nitric oxide synthase enzyme from *Bacillus subtilis* 168 were generated. The nitric oxide synthase (NOS) enzyme from *Bacillus subtilis* 168 was gene synthesized in fusion to the BclA promoter, ribosomal binding site (RBS), start codon and amino acids 20-35 of BclA. A six-alanine linker region was included to separate the BclA targeting sequence from the NOS enzymes. The amino acids sequences of these fusion proteins, including the methionine encoded by the BclA start codon, amino acids 20-35 of BclA, the six-amino acid linker, and the NOS enzyme, are provided above in Table 9. These clones were subcloned in the shuttle vector pHP13 via digestion with XhoI and ligation into the SalI site of pHP13. Correct constructs were sequenced and verified, transformed into *E. coli* cells. The resultant plasmids were transformed into *Bacillus thuringiensis* BT013A and *Bacillus mycoides* EE155.

The recombinant *Bacillus thuringiensis* BT013A and *Bacillus mycoides* EE155 transformed with the plasmids encoding the NOS fusion proteins were then induced to sporulate by swabbing the bacteria onto nutrient agar plates and incubating the plates at 30° C. for 72 hours. After 72 hours, the bacterial spores were collected from the plate by swabbing into sterile phosphate buffered saline (PBS), and were purified by density centrifugation three times.

The spores were then applied to commercial corn and soy hybrid seeds at rates of 1×10$^5$ spores/seed. The soybean hybrid variety was BECK 335NR, which contains the cyst nematode protection gene, the ROUNDUP READY glyphosate resistance gene, and the K-gene for *Phytophthora* resistance. The corn hybrid variety was BECK 5540RR, which contains the ROUNDUP READY glyphosate resistance gene. The seeds were then lightly dusted with L-arginine. A control set of seeds was dusted with L-arginine, but with no spores. Seeds were then placed between two paper towels, which were then wetted with 25 ml of H$_2$O. The paper towels were then rolled, placed into a small sandwich bag, and sealed tightly. These bags were then placed in a 30° C. incubator and allowed to germinate for 24, or 48 hours. The number of seeds germinated at each timepoint was measured, and the results compared to untreated and control seeds. The results of these experiments are shown in Tables 45 and 46 below.

TABLE 45

Increase in germination rate in hybrid soybean seeds treated with spores of recombinant *Bacillus cereus* family members expressing a fusion protein containing nitric oxide synthase.

| Treatment | Germination Day 1 (%) | Germination Day 2 (%) |
|---|---|---|
| Naked soybean seed | 15.0% | 92.3% |
| Soybean seed plus L-Arginine | 20.5% | 94.9% |
| Soybean seed plus *B. thuringiensis* BT013A expressing *B. subtilis* NOS fusion protein | 28.9% | 97.5% |
| Soybean seed with L-arginine and *B. mycoides* EE155 expressing *B. subtilis* NOS | 30.0% | 97.5% |

TABLE 46

Increase in germination rate in hybrid corn seeds treated with spores of recombinant *Bacillus cereus* family members expressing a fusion protein containing nitric oxide synthase.

| Treatment | Germination Day 1 (%) | Germination Day 2 (%) |
|---|---|---|
| Naked corn seed | 0.0% | 77.5% |
| Corn seed plus L-Arginine | 4.1% | 80.5% |
| Corn seed plus *B. thuringiensis* BT013A expressing *B. subtilis* NOS fusion protein | 6.5% | 82.5% |
| Corn seed with L-arginine and *B. mycoides* EE155 expressing *B. subtilis* NOS | 4.3% | 95.0% |

As can be seen from Tables 45 and 46, treatment of seeds with L-arginine and a recombinant *Bacillus cereus* family member expressing a fusion protein comprising a nitric oxide synthase enzyme led to an increase in the number of germinated seeds, in both soybeans and corn.

Example 41. Preparation and Testing of BEMD Spores Expressing a Fusion Protein Comprising Nucleic Acid Binding Proteins BEMD spores expressing a fusion protein containing amino acids 20-35 of BclA, an eight-alanine linker, and the non-specific DNA binding protein SASPα from *Bacillus subtilis* 168 or the non-specific DNA binding protein SASPγ from *Bacillus subtilis* 168. DNA encoding SASPα and SASPγ was gene synthesized in frame with the BclA promoter, RBS, start codon BclA and amino acids 20-35 of BclA. An eight alanine linker region was included between the BclA targeting sequence and the RNA/DNA binding proteins. The linker allows for greater flexibility and protein folding of the fusion proteins. The amino acid sequences for these fusion proteins, including the methionine encoded by the BclA start codon, amino acids 20-35 of BclA, the eight-amino acid linker, and the SASPα or SASPγ protein are provided above in Table 11. The synthesized genes were digested with XhoI, and ligated into the SalI site of pHP13 to generate the plasmids pHP13-BclA20-35-SASPα and pHP13-BclA20-25-SASPγ. pHP13 is a well characterized 5.5 kbp shuttle vector plasmid having chloramphenicol and erythromycin resistance cassettes. It was constructed by the ligation of plasmids pE194, pC194, and pUC9.

Correct clones were subjected to DNA sequencing and transformed into the SCS110 strain of *E. coli*. The plasmid DNA was then purified, and transformed into the *Bacillus thuringiensis* BT013A. These bacteria were then induced to sporulate by swabbing onto nutrient agar plates for 72 hours at 30° C. The spores were collected and purified as described above in the immediately preceding example.

To assess the ability of the recombinant spores to bind nucleic acids, the recombinant *Bacillus cereus* family members transformed with the plasmids encoding the SASPα and SASPγ fusion proteins were then incubated in PBS with random DNA primers that contained a fluorescein tag on the 5' ends. A control using non-recombinant spores was also included in the experiment. The spores were incubated for ten minutes with 50 mM tagged DNA, and then washed by centrifugation for one minute at 10,000 rpm. The supernatant was removed, and the spores were resuspended in 1 ml of PBS. The spores were again pelleted and the supernatant removed after centrifugation, and then subjected to analysis. The fluorescein-labeled DNA treated spores were examined under an E600 Nikon fluorescent microscope and DNA binding was determined by the change in the total fluorescence overall as compared to the control spores that did not contain the DNA-binding fusion proteins. The results this assays are shown in Table 47 below.

TABLE 47

DNA binding to recombinant *Bacillus cereus* family member spores expressing a fusion protein comprising a DNA binding protein

| Treatment | DNA Binding (Normalized) |
| --- | --- |
| *B. thuringiensis* BT013A spores (non-recombinant) | 100% |
| *B. thuringiensis* BT013A spores expressing BclA-SASPα fusion protein | 341.2% |
| *B. thuringiensis* BT013A spores expressing BclA-SASPγ fusion protein | 250.1% |

Figure 3:
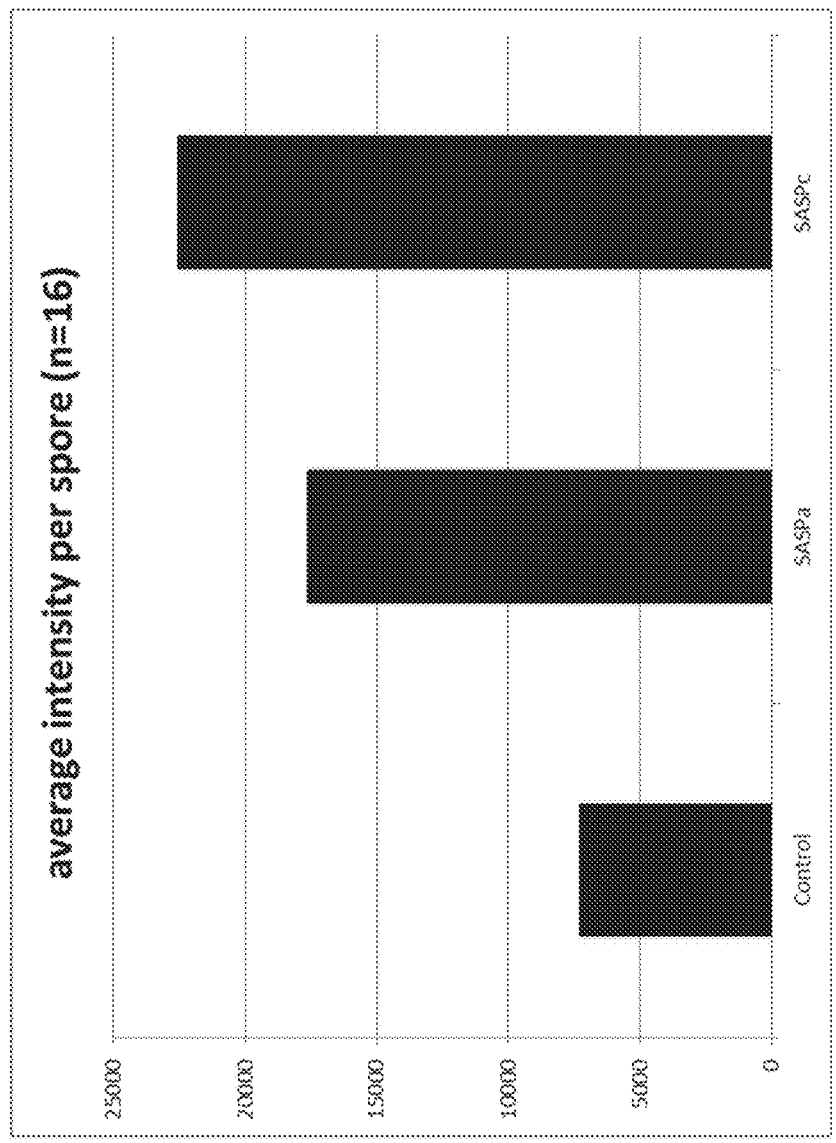
FIG. 3 provides data showing to recombinant *Bacillus thuringiensis* BT013A spores expressing a fusion protein comprising a DNA binding protein.

In addition, FIG. 3 shows DNA binding to spores as measured by fluorescein-labeled DNA binding. In FIG. 3, "control" refers to non-recombinant *B. thuringiensis* BT013A spores (non-recombinant), "SASPα" refers to *B. thuringiensis* BT013A spores expressing BclA-SASPα fusion protein, and SASPc refers to *B. thuringiensis* BT013A spores expressing BclA-SASPγ fusion protein.

As can be seen from the data shown in Table 47 and FIG. 3, the spores expressing the SASPα or SASPγ fusion proteins bound a significantly greater amount of DNA than the non-recombinant spores, demonstrating a strong affinity of these spores for DNA.

Example 42. Preparation and Testing of BEMD Spores Expressing a Fusion Protein Comprising a Nuclease In addition to the non-specific DNA and RNA binding proteins discussed above in the immediately preceding example, nucleases can also be used to both bind to and cleave nucleic acid molecules. BEMD spores expressing a fusion protein containing amino acids 20-35 of BclA and an endonuclease enzyme were generated and assayed for their ability to bind to and cleave DNA.

The *Bacillus subtilis* endonuclease 1 was PCR amplified and fused in frame to the BclA promoter, RBS, start codon and amino acids 20-35 of BclA. This construct was then cloned into the pHP13 plasmid to create the plasmid pHP13-BclA20-35-endonuclease. This construct was sequenced and transformed into and propagated in *E. coli*. The plasmid DNA was then isolated from the *E. coli* and introduced into *Bacillus thuringiensis* BT013A. Spores were created and purified as described in Example 40 above.

Endonuclease activity was assayed by incubating recombinant spores expressing the endonuclease fusion protein and non-recombinant control spores in PBS at a concentration of $1\times10^8$ spores/ml in PBS with 300 ng of salmon sperm DNA and 1 µg/ml DAPI (4',6-diamidino-2-phenylindole) DNA stain. The reaction was allowed to proceed continue for 10 minutes at 37° C. After 10 minutes, the supernatant was assayed for cleaved DNA using a fluorometer. As DNA is cleaved, the DAPI stain is released from the individual freed nucleotides, and thus cleavage can be determined by loss of DAPI staining over time. The results of this assay are shown in Table 48 below.

TABLE 48

Nuclease Activity and DNA binding by BEMD spores expressing an endonuclease fusion protein

| Treatment | Construct | Loss of DNA signal (supernatant) | Spore-bound DNA (fluorescence on spores) |
| --- | --- | --- | --- |
| *Bacillus thuringiensis* BT013A Spores | — | 5% | 5.3% |
| *Bacillus thuringiensis* BT013A Spores | BclA-endonuclease | 65% | 21.9% |

The data provided above in Table 48 show that the endonuclease fusion protein was expressed on the exosporium of the *Bacillus thuringiensis* BT013A spores, and was able to cleave the salmon sperm DNA as evidenced by the loss of DAPI signal in the supernatant. Surprisingly, a portion of the endonuclease bound the DNA tightly without cleaving it, retaining the DAPI fluorescence signal on the spores, even after washing the spores to remove excess DNA. This demonstrates that not all the DNA was processed, and that nucleases expressed on the outside of the spore can bind DNA tightly. To increase this effect, a nuclease having an inactivated active site could be used in the fusion protein, which would lead to less cleavage of the DNA and even more binding DNA on the spores.

Example 43. Agricultural Use of Spores Expressing Fusion Proteins Containing Nucleic Acid Binding Proteins or Peptides The recombinant *Bacillus cereus* family or recombinant spore-forming bacteria members expressing fusion proteins comprising nucleic acid binding proteins or peptides can be used in agriculture to deliver nucleic acids to a plant growth medium (e.g., soil) and/or to plants. For example, the recombinant *Bacillus cereus* family members or recombinant spore-forming bacteria can be delivered to plants via seed treatment, in furrow/soil drench treatment, or foliar treatment. Furthermore, the fusion proteins comprising nucleic acid binding proteins or peptides can be expressed in any of the endophytic *Bacillus cereus* family members or any of the other endophytic *Bacillus* species described herein, enabling delivery of nucleic acids bound to the nucleic acid binding proteins internally to the plant, where they would be more effective in reaching their target cells. For example, the fusion proteins comprising nucleic acid binding proteins can be expressed in the endophytic strain *Bacillus cereus* family member EE349. Expression of another fusion protein (comprising endoglucanase as the protein of interest) in this strain is described in Example 51 hereinbelow, demonstrating that the fusion proteins expressed in this endophytic strain are delivered internally to plants. Thus, expression of the fusion proteins comprising SASPα, SASPγ, Hfq, or a nuclease having an inactivated active site in endophytic *Bacillus cereus* family member strains such as *Bacillus cereus* family member EE349 can provide a means to deliver RNA and DNA (e.g., RNAi or rDNA) internally to a plant. Other non-specific binding nucleic acid binding proteins or peptides could also be used in the fusion proteins for this purpose.

Example 44. Preparation of BEMD Spores that Express a Fusion Protein and Also Overexpress a Protein that Modulates Expression of Fusion Proteins Overexpression of various exosporium proteins (referred to herein as "modulator proteins") in a recombinant *Bacillus cereus* family member expressing any of the fusion proteins described herein can modulate (increase or decrease) the expression level of the fusion protein. These modulator proteins include ExsY, ExsFA/BxpB, CotY, CotO, ExsFB, InhA1, InhA2, ExsJ, ExsH, YjcA, YjcB, BclC, AcpC, InhA3, alanine racemase 1, alanine racemase 2, BclA, BclB, BxpB, BclE, BetA/BAS3290, CotE, ExsA, ExsK, ExsB, YabG, Tgl, superoxide dismutase 1 (SODA1), and superoxide dismutase 2 (SODA2).

The ability to control the expression level of the fusion protein allows for control of the amount of the protein or peptide of interest of the fusion protein that is displayed on the outside of the spore of the recombinant *Bacillus cereus* family member. For example, when the protein or peptide of interest of the fusion protein comprises a plant growth stimulating protein or peptide (e.g., an enzyme that degrades or modifies a bacterial, fungal, or plant nutrient source), the recombinant *Bacillus cereus* family member expressing the fusion protein produces a spore that when applied to a seed, plant, or plant growth medium, has a beneficial effect on the plant due to the action of the plant growth stimulating protein or peptide. Modulation of the expression level of the fusion protein results in modulation of the level of the peptide or protein of interest that is displayed on the outside of the recombinant *Bacillus cereus* family member spore. In some cases, increasing the level of fusion protein expression would be beneficial (e.g., where there is a desire to increase the expression of an enzyme and thereby increase the amount of enzyme per spore that can be delivered to a plant). In other cases, decreasing the level of fusion protein expression would be beneficial (e.g., where there is a desire to decrease the expression of a protein and thereby decrease the amount of protein per spore that is delivered to a plant, for example, where high levels of the protein would have detrimental effects on the plant).

To generate plasmids for expression of fusion proteins in *Bacillus cereus* family members, PCR fragments were generated that contained the BclA promoter (SEQ ID NO: 85), start codon, and amino acids 20-3 5 of BclA fused in frame to either *Bacillus subtilis* 168 endoglucanase or the β-galactosidase gene from *E. coli* DH5α. These PCR fragments were digested with XhoI and ligated into the SalI site of the pSUPER plasmid to generate the plasmids pSUPER-BclA 20-35-Endoglucanase and pSUPER-BclA 20-35-βgal, respectively. The pSUPER plasmid was generated through fusion of the pUC57 plasmid (containing an ampicillin resistance cassette) with the pBC16-1 plasmid from *Bacillus* (containing a tetracycline resistance). This 5.5 kbp plasmid can replicate in both *E. coli* and *Bacillus* spp.

The pSUPER-BclA 20-35-Endoglucanase and pSUPER-BclA 20-35-βgal plasmids were transformed into and propagated in dam methylase negative *E. coli* strains. The sequences of the pSUPER-BclA 20-35-Endoglucanase and pSUPER-BclA 20-35-βgal plasmids were verified by DNA sequencing.

The pSUPER-BclA 20-35-Endoglucanase and pSUPER-BclA 20-35-βgal plasmids were transformed into the host strains *Bacillus thuringiensis* BT013A (for pSUPER-BclA 20-35-Endo) or *Bacillus mycoides* BT155 (pSUPER-BclA 20-35-βgal). These transformed strains expressed either the β-galactosidase enzyme or the endoglucanase enzyme on the outside of the spore.

To generate plasmids for overexpression of modulator proteins, PCR fragments containing the native promoter regions for and genes encoding ExsFA/BxpB, CotO, ExsFB, YjcB, BclC, AcpC, BclA, BclB, BxpB, and CotE were generated, digested with SalI, and ligated into the pHP13 plasmid. The nucleotide sequences for the native promoter regions are provided above in Table 3. The pHP13 plasmid is a multicopy plasmid and therefore results in high expression levels of the encoded modulator proteins when the plasmids are transformed into a *Bacillus cereus* family member host cell. The pHP13 plasmids containing the promoter regions and genes encoding ExsFA/BxpB, CotO, ExsFB, YjcB, BclC, AcpC, BclA, BclB, BxpB, BclE, BetA/BAS3290, and CotE are referred to herein as pHP13-ExsFA/BxpB, pHP13-CotO, pHP13-ExsFB, pHP13-YjcB, pHP13-BclC, pHP13-AcpC, pHP13-BclA, pHP13-BclB, pHP13-BxpB, and pHP13-CotE, respectively.

The pHP13 plasmids containing the promoter regions and genes encoding the modulator proteins were transformed into and propagated in *E. coli* strains. The sequences of these plasmids were verified by DNA sequencing.

The pHP13 plasmids encoding the modulator proteins were transformed into *Bacillus thuringiensis* BT013A containing pSUPER-BclA 20-35-Endoglucanase or *Bacillus mycoides* BT155 containing pSUPER-BclA 20-35-βgal. The resultant recombinant bacteria were plated onto nutrient agar plates containing 10 µg/ml chloramphenicol to select for the pHP13 plasmids and 10 µg/ml tetracycline to select for the pSUPER plasmids. Bacteria containing both plasmids were then grown in brain heart infusion broth overnight with both tetracycline and chloramphenicol. The overnight cultures were then swabbed onto nutrient agar, and bacteria were allowed to sporulate at 30° C. for 72 hours. After 72 hours, the bacterial spores were collected from the plate by swabbing into sterile PBS, and were purified by density centrifugation three times. The pure spores were then diluted to $1 \times 10^8$ CFU/ml, and assayed for enzyme activity using on a population of $1 \times 10^8$ colony forming units (CFU).

Example 45. Enhanced or Diminished Expression of Fusion Proteins on the BEMD System by Overexpression of a Protein that Modulates Expression of the Fusion Construct The recombinant *Bacillus mycoides* EE155 spores generated as described above in the immediately preceding example were assayed for β-galactosidase activity, and the recombinant *Bacillus thuringiensis* BT013A spores generated as described above in the immediate preceding example were assayed for endoglucanase activity.

β-galactosidase activity was assayed by measuring hydrolysis of the chromogenic substrate ortho-Nitrophenyl-β-galactoside (ONPG). A commercial source of β-galactosidase was used to prepare standards (0.2 μg, 0.4 μg, and 0.8 μg from a 100 μg/mL stock). 250 al of spore preparation was pelleted and the spores were resuspended in 50 μL of enzyme dilution buffer (10 mM TRIS, pH 7.6, 0.2 M $NaCl_2$, 5% glycerol). 600 al of prewarmed 37° C. substrate mixture (10 mM KCl, 1 mM $MgSO_4.7H_2O$, 100 mM $NaH_2PO_4$, pH 7.5) containing 1.14 mg/mL ONPG was added to each sample and standard. Each reaction was incubated at room temperature for 2 minutes. 250 μl of 1M sodium carbonate was added to stop the reaction. The solution was centrifuged for 5 min at 14,000×g to remove the spores from the absorbance reading. The absorbance was determined at 420 nm using an IMPLEN nanospectrophotometer model P330. Samples were performed in triplicate with a blank for each reaction. The results of this assay are shown below in Table 49.

TABLE 49

Effects of overexpression of exosporium proteins on the expression levels of BclA 20-35-βgal.

| Plasmid encoding fusion protein | Plasmid encoding modulator protein | Enzyme Activity (Normalized) |
|---|---|---|
| — | — | 0% |
| pSUPER-BclA 20-35-βgal | — | 100% |
| pSUPER-BclA 20-35-βgal | pHP13-CotO | 112.8% |
| pSUPER-BclA 20-35-βgal | pHP13-CotE | 135.4% |
| pSUPER-BclA 20-35-βgal | pHP13-YjcB | 45.4% |
| pSUPER-BclA 20-35-βgal | pHP13-BclA | 144.7% |
| pSUPER-BclA 20-35-βgal | pHP13-BclB | 132.6% |
| pSUPER-BclA 20-35-βgal | pHP13-AcpC | 76.1% |
| pSUPER-BclA 20-35-βgal | pHP13-BxpB | 103% |

As can be seen from results shown in Table 49, overexpression of CotO, CotE, BclA, BclB, and BxpB increased the expression of the fusion protein containing β-galactosidase, resulting in increased enzyme activity on the spores. By contrast, overexpression of YjcB or AcpC decreased the expression of the fusion protein containing β-galactosidase, resulting in decreased enzyme activity on the spores.

The assay for endoglucanase activity was performed by determining cellulase activity using a carboxymethylcellulose (CMC) substrate and a dinitrosalicylic acid (DNS reagent). A commercial source of cellulase enzyme was used to prepare standards in 50 mM citrate buffer, pH 4.8. 1% CMC (carboxymethylcellulose sodium salt) was prepared in 50 mM citrate buffer, pH 4.8 to serve as the substrate for the reaction. 250 μl of spore preparation was pelleted and the spores were resuspended in 150 μL of 50 mM citrate buffer, pH 4.8. The reaction was carried out with a reagent composed of 1% DNS, 1% NaOH, 0.05% $Na_2SO_4$, 0.2% phenol, and 18.2% Rochelle salts. 150 μl of the sample was mixed with 250 μl of the 1% CMC substrate and incubated in a water bath at 50° C. for 15 minutes. 300 μl of DNS reagent was added and the samples boiled at 100° C. for 10 minutes and then cooled on ice. The solution was centrifuged for 5 minutes at 14,000×g to remove the spores from the absorbance reading. The absorbance was determined at 540 nm using an IMPLEN nanospectrophotometer model P330. Samples were performed in triplicate with a blank for each reaction. The results from this assay are shown in Table 50 below.

TABLE 50

Effects of overexpression of exosporium proteins on the expression levels of BclA 20-35-Endoglucanase.

| Plasmid encoding fusion protein | Plasmid encoding modulator protein | Enzyme Activity (Normalized) |
|---|---|---|
| — | — | 0% |
| pSUPER-BclA 20-35-endoglucanase | — | 100% |
| pSUPER-BclA 20-35-endoglucanase | pHP13-CotO | 215.7% |
| pSUPER-BclA 20-35-endoglucanase | pHP13-CotE | 125.5% |
| pSUPER-BclA 20-35-endoglucanase | pHP13-YjcB | 89.3% |
| pSUPER-BclA 20-35-endoglucanase | pHP13-BclB | 193.0% |
| pSUPER-BclA 20-35-endoglucanase | pHP13-AcpC | 33.7% |
| pSUPER-BclA 20-35-endoglucanase | pHP13-BxpB | 202.3% |
| pSUPER-BclA 20-35-endoglucanase | pHP13-BclC | 3.2% |

As shown in Table 50, overexpression of CotO, CotE, BclB, and BxpB increased expression of the fusion protein containing endoglucanase, resulting in increased enzyme activity on the spores. Overexpression of YjcB, AcpC, or BclC, on the other hand, decreased expression of the fusion protein, resulting in decreased enzyme activity on the spores.

In sum, overexpression of CotO, CotE, BclB, or BxpB increased expression of both fusion proteins, resulting in increased activity of both β-galactosidase and endogloconase on spores expressing the BclA 20-35-βgal or BclA 20-35-endoglucanase fusion proteins, respectively. Overexpression of YjcB or AcpC on the other hand, decreased expression of both fusion proteins, resulting in decreased activity of β-galactosidase and endogloconase on spores expressing the BclA 20-35-βgal or BclA 20-35-endoglucanase fusion proteins, respectively. Overexpression of BclC and BclA20-35 tagged eGFP also decreased expression of the BclA 20-35-endoglucanase fusion protein, while overexpression of BclA increased expression of the BclA 20-35-βgal fusion protein.

Example 46. Effects of BEMD Spores Expressing a Fusion Protein and Overexpressing a Modulator Protein on Corn Growth Application of recombinant *Bacillus thuringiensis* BT103A and *Bacillus mycoides* BT155 spores expressing a fusion protein comprising *Bacillus subtilis* 168 endoglucanase to corn results in increased seedling vigor and growth response over the course of two weeks. Alternations in the expression level of the fusion protein comprising endoglucanase induced by overexpression of a modulator protein in such spores as described above in the immediately preceding example results in corresponding alterations in the effects of the BEMD spores on corn growth.

To demonstrate this, pSUPER-BclA 20-35-Endoglucanase and the pHP13-CotO or pHP13-BclB were coexpressed in *Bacillus thuringiensis* BT013A. Spores were created on nutrient agar as described above in Example 40. The spores were diluted to a concentration of $1\times10^4$ spores/50 ml water, and the 50 ml of water was added to commercial hybrid corn seed in potting soil at planting. The corn hybrid variety was BECK 5540RR, which contains the ROUNDUP READY glyphosate resistance gene. The corn seeds were coated with a fungicide and a biological inoculant.

Plants were grown under artificial light for 14 hours a day and plant growth over a ten day period was determined. Plants were watered every three days over the course of the experiment. After ten days, the plants were measured for height and normalized against the height of untreated corn plants. The results of these experiments are shown in Table 51 below.

TABLE 51

Effects of BEMD spores expressing a fusion protein comprising an endogloconase and overexpressing a modulator protein on hybrid corn growth

| Plasmid encoding fusion protein | Plasmid encoding modulator protein | Expression Strain | Corn Growth (Normalized to pSUPER-BclA 20-35 Endoglucanase alone control) |
|---|---|---|---|
| pSUPER-BclA 20-35-Endoglucanase | None | Bacillus thuringiensis BT013A | 100% |
| pSUPER-BclA 20-35-Endoglucanase | pHP13-CotO | Bacillus thuringiensis BT013A | 103.8% |
| pSUPER-BclA 20-35-Endoglucanase | pHP13-BclB | Bacillus thuringiensis BT013A | 107.6% |

As shown in Table 51, overexpression of the exosporium proteins CotO and BclB increased the effects of the BclA 20-35-endoglucanase fusion protein on corn seedling growth and vigor at 10 days. These effects correlate with the expression levels of the fusion protein in BEMD spores expressing BclA 20-35-endoglucanase and pHP13-CotO or pHP13-BclB, indicating that the effects on seedling growth and vigor are attributable to the alteration of fusion protein expression levels by the modulator proteins Example 47. Genetic Inactivation of *Bacillus cereus* Family Members and Use of Such Inactivated *Bacillus cereus* Family Members for Expression of Fusion Proteins As described above, overexpression of germination spore protease (GPR) in its active form in the forespore of a *Bacillus cereus* family member during sporulation results in proteolytic cleavage of proteins in the forespore and inactivation of the spore. Similarly, overexpression of a non-specific endonuclease in the forespore during sporulation destroys the DNA in the spore, leading to an inactivated spore particle in a percentage of the spore population.

A plasmid encoding a non-specific endonuclease under the control of a sigma G promoter was generated. The non-specific endonuclease 1 from *Bacillus subtilis* 168 and a sigma G promoter (SEQ ID NO: 235) were gene synthesized and ligated into the pHP13 plasmid using the SalI site to generate the plasmid pHP13-SigG-nuclease. Correct clones were sequenced and transformed into and propagated in *E. coli* cells. Plasmid DNA was isolated from the *E. coli* cells and transformed into *Bacillus thuringiensis* BT013A. Correct clones were verified by PCR. The amino acid sequence for *Bacillus subtilis* 168 endonuclease 1 is provided above in Table 4.

*Bacillus thuringiensis* BT013A cells expressing the sigma G endonuclease were created and purified on nutrient agar plates as described above in Example 40. Spores were quantified visually using a hemocytometer, diluted, and dilution plated onto nutrient agar plates. The ratio of live spores to killed spores was calculated by determining the change from visual counting to plate counts. Control spores (untreated) were included in each assay. Additionally, 1×10⁸ spores were UV irradiated for 10 minutes using a handheld UV lamp, and the assay repeated. The visual count and plate count were again compared to assess spore killing. The results from these assays are shown in Table 52 below.

TABLE 52

Viability of *Bacillus cereus* family member spores expressing a non-specific nuclease under the control of a sigma G promoter

| Treatment | Live Ratio | UV Live Ratio |
|---|---|---|
| *Bacillus thuringiensis* BT013A | 100% | 61.3% |
| *Bacillus thuringiensis* BT013A expressing SigG-endonuclease | 70.4% | 24.5% |

As can be seen from Table 52, expression of endonuclease 1 under the control of a sigma G promoter decreased cell viability by about 30% in spores that were not exposed to UV irradiation and by about 75% in spores that were exposed to UV irradiation.

Co-expression of both a germination spore protease and a nonspecific endonuclease under the control of sigma G promoters would be expected to further decrease spore viability.

Example 48. Preparation of Exosporium Fragments from Recombinant *Bacillus cereus* Family Members Comprising a Knockout of the CotE Gene The plasmid pUCpE was constructed that contained the pUC19 backbone, which is able to replicate in *E. coli*, as well as the origin of replication erythromycin resistance cassette from pE194. This construct is able to replicate in both *E. coli* and *Bacillus* spp. A 1 kb DNA region that corresponding to the upstream region of the CotE gene and a 1 kb region corresponding to the downstream region of the gene CotE were PCR amplified from *Bacillus anthracis* ΔSterne. The two 1 kb regions were then spliced together using splicing by overlapping extension via 15 bp homologous overhangs that corresponded to the opposing PCR amplicons. This 2 kb fragment was digested with XhoI (in external primers) and ligated into the SalI site of pUCpE. This plasmid construct was verified by digestion and DNA sequencing. A Gram-positive omega-kanamycin resistance gene was digested with BamHI and placed between the two 1-kb regions. The final construct was again PCR verified and sequenced, and the final plasmid was introduced into *Bacillus anthracis* ΔSterne. Correct clones were screened by looking for both erythromycin resistance and kanamycin resistance.

Clones were passaged under high temperature (40° C.) in brain heart infusion broth in the presence of kanamycin (25 μg/ml) and were routinely struck for isolation onto LB agar plates containing kanamycin and grown at 30° C. Individual colonies were toothpicked onto LB agar plates containing erythromycin 5 μg/ml and grown at 30° C. Clones that maintained kanamycin resistance but lost erythromycin resistance (signifying loss of the plasmid but recombination and removal of the CotE gene) were grown in brain heart infusion broth plus kanamycin, and chromosomal DNA was isolated using a Qiagen Chromosomal DNA isolation kit. Proper deletion of the CotE gene was determined by PCR amplification of the CotE gene region and loss of CotE, and gain of the kanamycin resistance cassette.

A construct was generated (pHP13-AcpC-eGFP) that encoded the exosporium protein ApcC (acid phosphatase) fused in frame to the fluorescent reporter protein eGFP (enhanced green fluorescent protein). The pHP13-ApcC-eGFP construct included the native ApcC promoter, ribosomal binding site, and coding sequence for ApcC (from *B. anthracis* ΔSterne), fused in frame to eGFP (from pGFPuv). This construct was generated by PCR amplification of the individual AcpC and eGFP genes with corresponding primers that contained a 15 bp overlapping region corresponding to the alternate amplicons. The two PCR amplicons were then purified, and combined into a second PCR reaction using external primers that contained XhoI sites. The two amplicons prime each other with their compatible ends, and create a fusion PCR amplicons, that were purified and digested with XhoI for 1 hour at 37° C. The spliced PCR product was cloned into the SalI site of pHP13, and correct clones were sequence verified and transformed into SCS110 *E. coli*. The plasmid DNA was subsequently isolated from the *E. coli* and introduced into *B. anthracis* ΔSterne CotE:: Kan generated as described above, which was grown in brain heart infusion broth containing 10 µg/ml chloramphenicol overnight at 30° C. One milliliter of this culture was inoculated into nutrient broth (50 ml) in a baffled flask and grown at 30° C. for 3 days. Spores were collected via centrifugation at 10,000×g for 5 minutes, and the supernatant (containing the broken exosporium fragments) was filtered through a 100,000 Da membrane filter to obtain purified exosporium fragments containing the fusion proteins.

Figure 4:
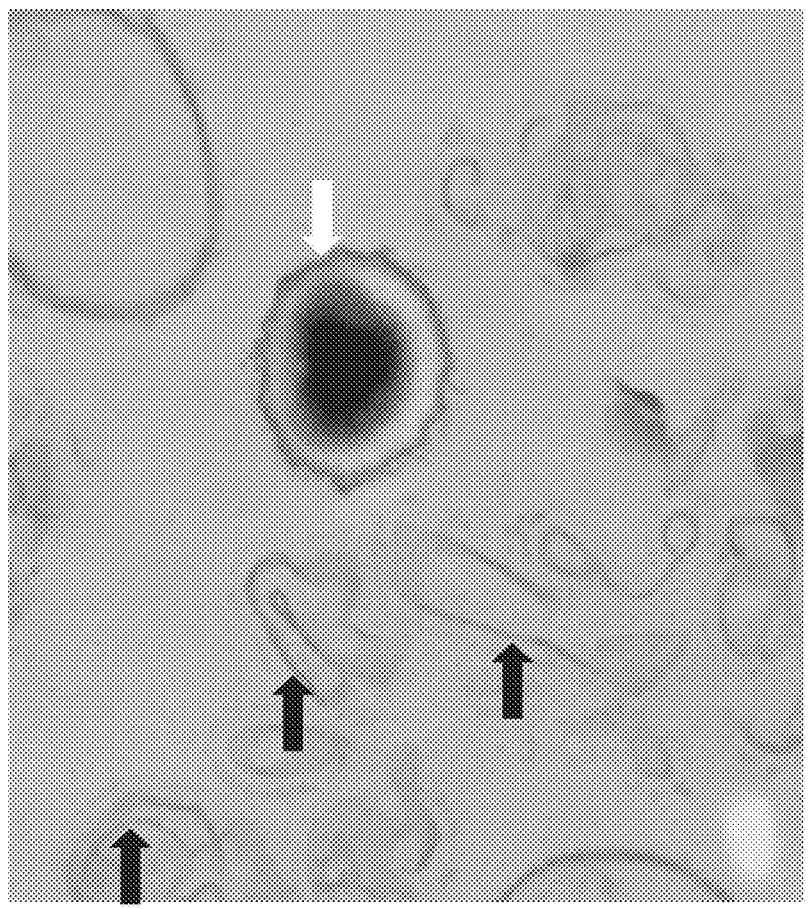
FIG. 4 is a transmission electron micrograph showing exosporium fragments and a *Bacillus cereus* family member spore from which the exosporium has been lost, generated using a recombinant *Bacillus cereus* family member having a knock-out mutation of its CotE gene.

A transmission electron micrograph showing the CotE knockout spores is provided in FIG. 4. The closed arrows indicate fragments of exosporium that have been separated from the spores, and the open arrow indicates a spore from which the exosporium has been removed.

Figure 5:
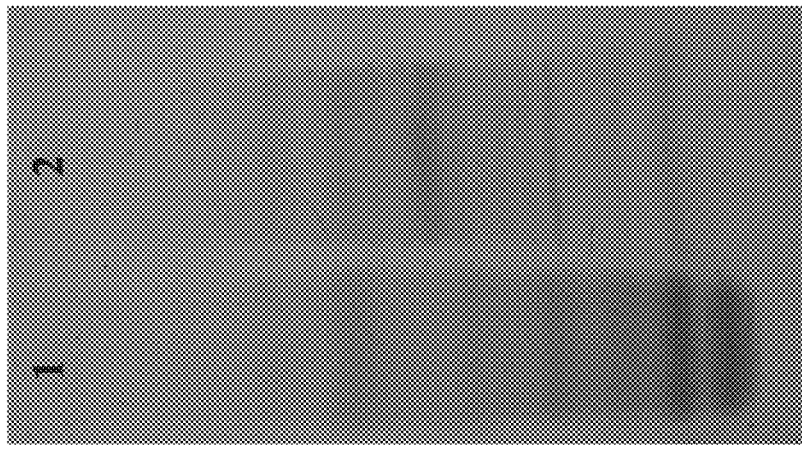
FIG. 5 is a photograph of an SDS-PAGE gel showing a protein marker standard (lane 1) and proteins from exosporium fragments generated using a recombinant *Bacillus cereus* family member having a knock-out mutation of its CotE gene (lane 2).

The purification of the exosporium fragments was performed as follows: CotE::kan spores were grown in brain heart infusion broth overnight at 30° C. and swabbed onto nutrient agar plates and grown at 30° C. for 3 days. After 3 days, the spores were collected by swabbing the plates with cotton swabs wetted with PBS and resuspended into 1 ml of PBS in a microcentrifuge tube. The spores were separated from the culture by centrifugation, and supernatant containing the exosporium fragments filtered through a 0.22 µM filter to remove any residual spores. The filtrate was then filtered through a 100 kDa filter to collect exosporium fragments but allow free proteins to pass through the filter. The 100 kDa filter was washed, and the collected exosporium fragments boiled in SDS buffer for 5 minutes and separated by SDS-PAGE electrophoresis. FIG. 5 provides a photograph of an SDS-PAGE gel showing the purified exosporium fragments (lane 2) and a protein marker standard (lane 1). The exosporium fragments shown in lane 2 represent the individual proteins that constitute the exosporium fragments. Only a subset of bands that would normally be seen in a whole spore SDS-PAGE preparation are apparent.

Figure 6:
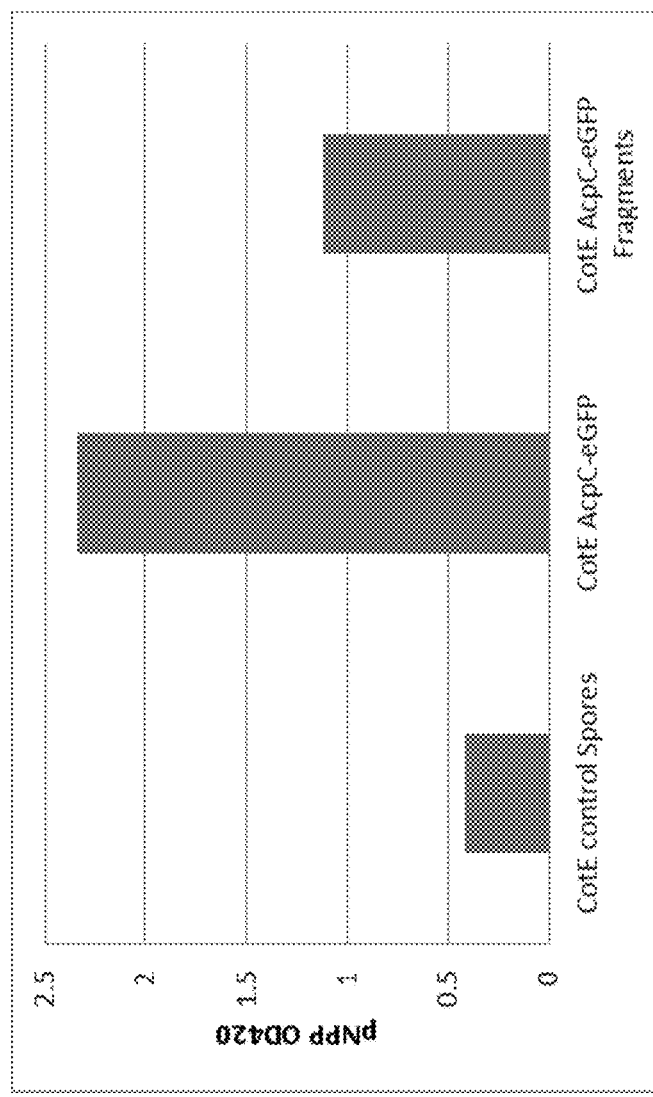
FIG. 6 provides data illustrating enzyme activity of an acid phosphatase in exosporium fragments derived from a *Bacillus cereus* family member having a knock-out mutation of its CotE gene.

Ten microliters of the exosporium fragment preparation containing the AcpC-eGFP fusion protein was tested for activity in a phosphatase assay against pNPP (p-nitrophenyl polyphosphate). Acid phosphatase activity was detected by spectrophotometry based on release of p-nitrophenol from phosphate through phosphatase activity. Briefly, 1 ml of 10 mM pNPP in phosphate buffer at pH 6.0 was incubated with exosporium fragments in a 1 ml microcentrifuge tube and allowed to incubate at 37° C. for 10 minutes. After 10 minutes, the tube was centrifuged for 1 minute to remove excess spores, and the supernatant read on a spectrophotometer at 420 nm for free p-nitrophenol. It was found that the purified exosporium fragments were able to effectively release the phosphate groups from pNPP, demonstrating that the ApcC was present in the exosporium fragments. The results of this assay are shown in FIG. 6. In FIG. 6, "CotE control spores" refers to CotE knock-out spores alone (not expressing the AcpC-eGFP fusion protein), "CotE AcpeGFP" refers to the CotE knock-out spores expressing the AcpC-eGFP fusion protein, and "CotE AcpC-eGFP fragments" refers to the exosporium fragments obtained as described above from the CotE knock-out spores expressing the AcpC-eGFP fusion protein.

These results demonstrate that mutations that disrupt the exosporium, such as a knock-out mutation in the CotE gene, can be used to generate exosporium fragments that are substantially free of spores, and demonstrates that these exosporium fragments contain fusion proteins that are targeted to the exosporium.

Example 49. Expression of Fusion Proteins in Recombinant *Bacillus cereus* Family Members that are Capable of Degrading Herbicides, and Use of Such Recombinant *Bacillus cereus* Family Members for Stimulation of Plant Growth Recombinant *Bacillus cereus* family members expressing fusion proteins can have potent effects on plant health and growth, as illustrated, for example, in Examples 1-4, 7, 9, 11, 33, 36, 37, and 38 above. The fusion proteins comprising a targeting sequence, an exosporium protein, or an exosporium protein fragment described herein can be used in a number of different species and strains within the *Bacillus cereus* family, which includes *Bacillus anthracis*, *Bacillus cereus*, *Bacillus thuringiensis*, *Bacillus mycoides*, *Bacillus pseudomycoides*, *Bacillus samanii*, *Bacillus gaemokensis*, *Bacillus weihenstephensis*, and *Bacillus toyoiensis*. Many members of the *Bacillus cereus* family are potent degraders of organic and inorganic material in the environment, and some *Bacillus cereus* family members have the ability to degrade herbicides. Expression of the fusion proteins in such strains would be advantageous since this would provide herbicide degrading activity, thereby alleviating the stress on plants that can be caused by the use of herbicides, in addition to the ability to stimulate plant growth or confer other benefits to plant health, depending on the peptide or protein of interest selected for inclusion in the fusion protein.

*Bacillus cereus* family member EE349 was isolated, identified, and characterized as described above in Example 25, and was found to have the ability to stimulate plant growth. This strain has further been found to have the ability to degrade multiple herbicides, including sulfonylureas and aryl triazines.

To demonstrate the ability of *Bacillus cereus* family member EE349 to degrade herbicides, $1 \times 10^5$ *Bacillus cereus* family member EE349 spores were coated onto lentils planted into soil containing various concentrations of sulfentrazone. The seeds were allowed to grow at 24° C. for 3 weeks on a 13 hour day/night cycle, with watering every 3 days. After 3 weeks, the plants were measured for root growth. A control set of seeds without *Bacillus cereus* family member EE349 was planted under identical conditions.

Figure 7:
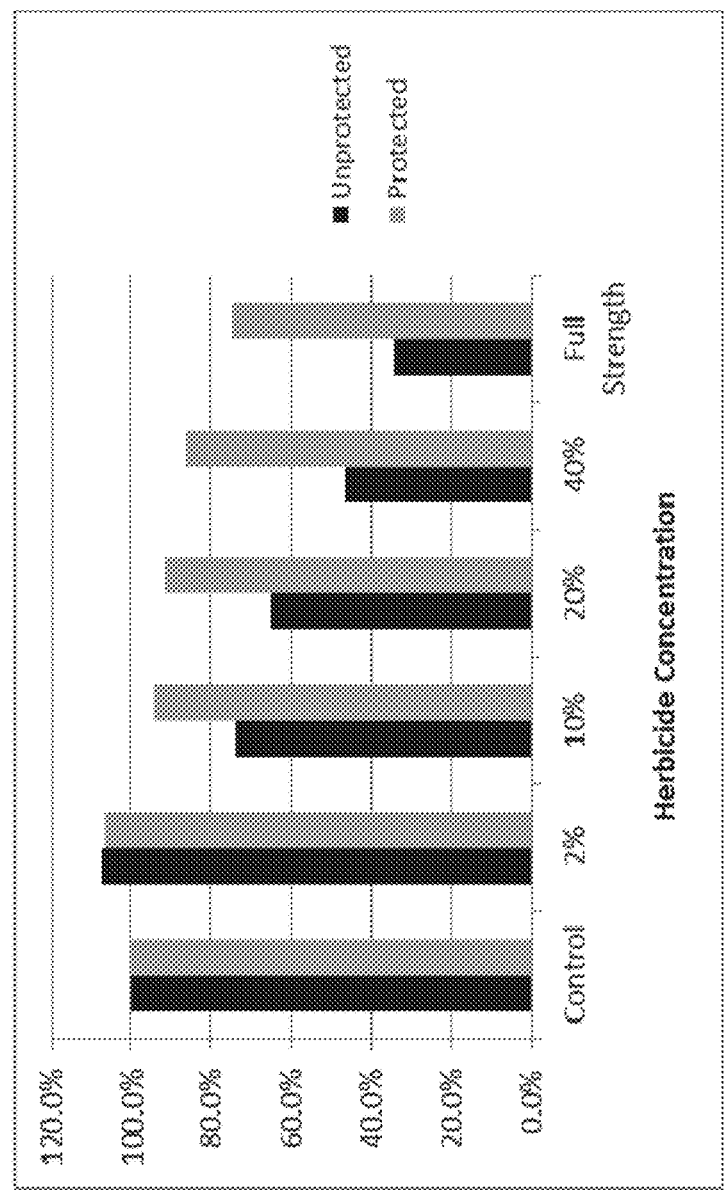
FIG. 7 provides data illustrating that *Bacillus cereus* family member EE349 reduces the inhibitory effects of herbicide on root length in lentils.

The results of this experiment can be seen in FIG. 7. In FIG. 7, "protected" refers to seeds treated with *Bacillus cereus* family member EE349, and "unprotected" refers to untreated seeds. The y-axis shows the root length normalized against a water-only control. FIG. 7 shows that as the concentration of the herbicide was increased, the inhibition of root growth also increased. However, application of *Bacillus cereus* family member EE349 to seeds alleviated the majority of this inhibition, even at full strength of the herbicide in soil. Thus, as can be seen from FIG. 7, *Bacillus cereus* family member EE349 can act as a safener.

Moreover, the ability of *Bacillus cereus* family member EE349 to express fusion proteins is demonstrated in Example 51 below. Thus, *Bacillus cereus* family member EE349 can be used as a dual-purpose safener and host for expression of the fusion proteins comprising a targeting sequence, an exosporium protein, or an exosporium protein fragment that targets the fusion protein to the exosporium.

Example 50. Preparation of Recombinant *Bacillus cereus* Family Members that Overexpress Exosporium Enzymes and Effects of Such Recombinant *Bacillus cereus* Family Members on Plants The exosporiums of *Bacillus cereus* family members naturally contain various natural enzymes that can have beneficial effects on plants. For example, the exosporiums of *Bacillus cereus* family members contain enzymes involved in nutrient solubilization (e.g., acid phosphatases such as AcpC), inosine uridine hydrolases, proteases (e.g., metalloproteases such as InhA1, InhA2, and InhA3), enzymes that catalyze the degradation of free radicals (e.g., superoxide dismutases such as SODA1 and SODA2), arginases, and alanine racemases. Overexpression of such enzymes in *Bacillus cereus* family members can provide recombinant *Bacillus cereus* family members that will have beneficial effects when applied to seeds, plants, a plant growth media, or an area surrounding a plant or a plant seed.

The metalloproteases InhA2 and InhA3, acid phosphatase (AcpC), and superoxide dismutase 1 and 2 were PCR amplified with their native promoters with primers that contained XhoI sites (amino acid sequences for InhA2, InhA3, AcpC, SODA1 and SODA 2 are provided above in Tables 1 and 2, and nucleotide sequences for the native promoters for these proteins are provided above in Table 3). The PCR products were digested with XhoI, and cloned into the *E. coli/Bacillus* shuttle vector pHP13 via its SalI site. Correct clones were verified by PCR and DNA sequencing. The plasmids were introduced into *Bacillus thuringiensis* BT013A and *Bacillus mycoides* EE155. Correct clones were screened by plating onto LB agar plates containing chloramphenicol. Overnight cultures of correct clones were grown in brain heart infusion broth containing chloramphenicol, and 1 ml of this overnight culture was inoculated into 50 ml of nutrient broth and cultured for 3 days at 30° C. Sporulation was verified via light microscopy. Spores were then subjected to enzymatic assays.

Figure 8:
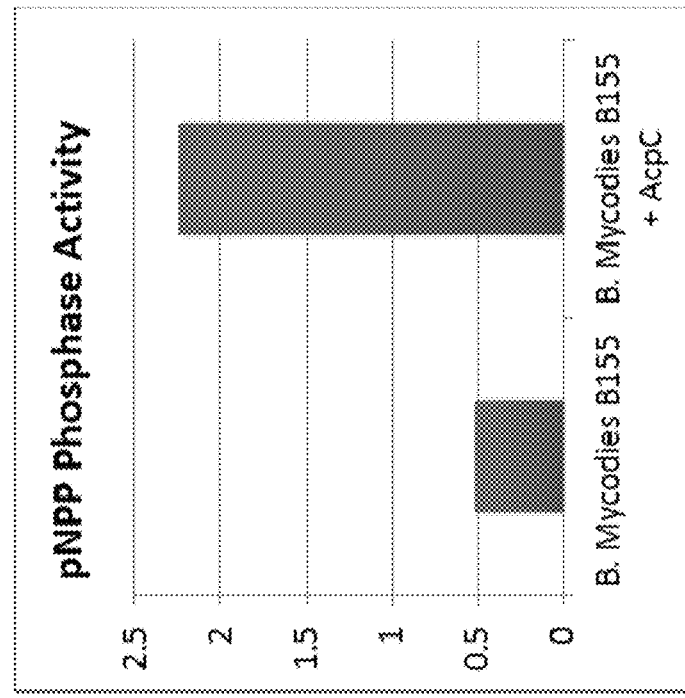
FIG. 8 provides data illustrating increased phosphatase activity in a *Bacillus cereus* family member modified to overexpress acid phosphatase (AcpC).
Figure 9:
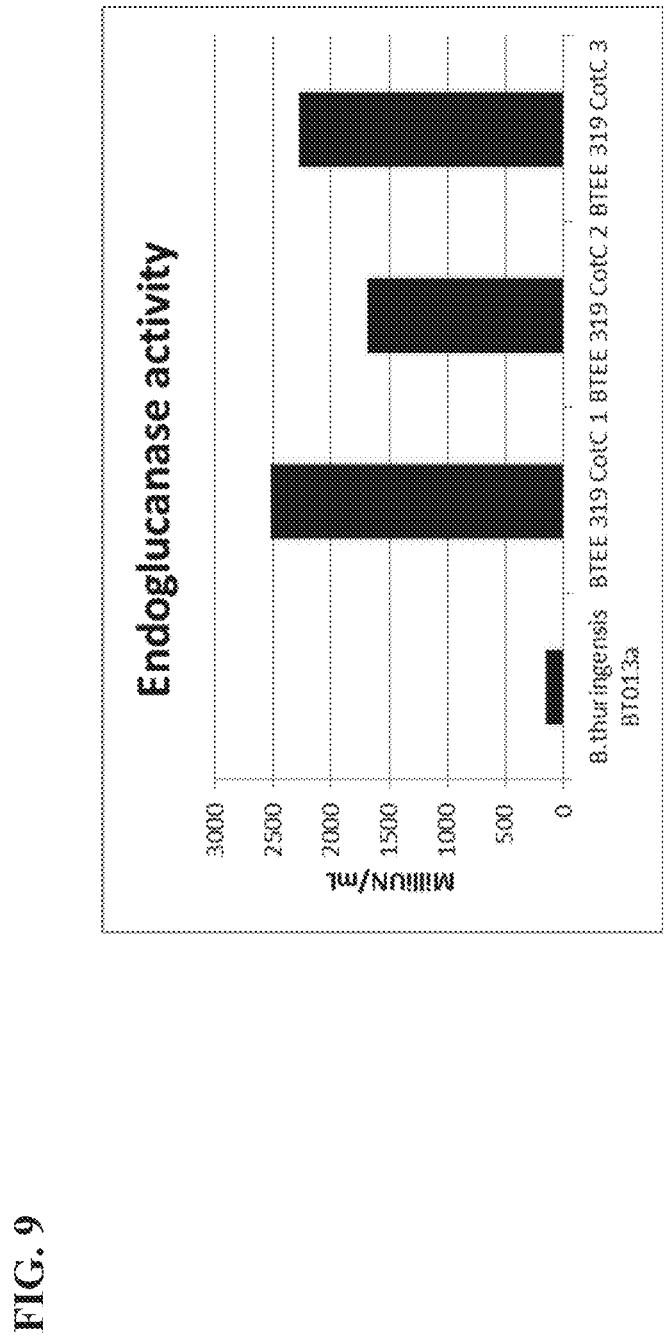
FIG. 9 provides data showing the endoglucanase activity of recombinant *Bacillus thuringiensis* spores expressing a CotC-endoglucanase fusion protein.

*Bacillus mycoides* EE155 spores overexpressing AcpC (i.e., spores containing the pHP13-AcpC (acid phosphatase) plasmid) were assayed for phosphatase activity. One milliliter of the sporulation culture pelleted and the pellet was resuspended in 1 ml of PBS, and tested for activity in a phosphatase assay against pNPP (p-nitrophenyl polyphosphate) as described above in Example 48. The AcpC overexpressing spores had a much higher phosphatase activity, as illustrated in FIG. 8. In FIG. 8, the y-axis shows units of phosphatase activity, indicated by the release of p-nitrophenol.

The increased acid phosphatase activity observed for the *Bacillus mycoides* EE155 spores modified to overexpress AcpC can solubilize nutrients in the environment upon the addition of such spores to a plant growth medium or application of such spores to a plant seed, a plant, or an area surrounding a plant or a plant seed. Since phosphate is a very important nutrient for plant growth and development, this can increase plant growth and provide beneficial effects on plant health.

Similarly, superoxide dismutase is a very powerful antioxidant protein. Overexpression of a superoxide dismutase in a *Bacillus cereus* family member would provide spores having the ability to degrade free radicals, which exert stress on plants. Removal of the free radicals would alleviate some of this stress and lead to increased plant vigor under stressful conditions. *Bacillus thuringiensis* BT013A spores overexpressing SODA1 and SODA2 (i.e., spores transformed with the pHP13-SODA1 and pHP13-SODA2 plasmids, respectively) can be subjected to enzymatic analysis. One milliliter of the sporulation culture can be pelleted and the pellet and resuspended in 1 ml of $dH_2O$ containing xanthine. Xanthine oxidase can then be added to the reaction mixture, as well as cytochrome C. Inhibition of the degradation of cytochrome C in this assay indicates activity of the superoxide dismutase.

*Bacillus mycoides* EE155 spores overexpressing a zinc metalloprotease (i.e., spores transformed with the pHP13-InhA2 plasmid) were subjected to enzymatic analysis. One milliliter of the sporulation culture was pelleted and the pellet was resuspended in 1 ml of PBS. The spores were then reacted with 0.5% azocasein, a protease substrate, for 5 minutes. These reaction mixtures were precipitated with TCA (trichloroacetic acid) to remove undigested casein, and the absorbance of the remaining free azo dye was read at ABS595. The spores overexpressing InhA2 generated 211% more protease activity as compared to non-recombinant *Bacillus mycoides* EE155 spores.

Examples 3 and 7 above illustrate that expression of a protease on the exosporium of a *Bacillus cereus* family member can provide beneficial effects on plants. The *Bacillus thuringiensis* BT013A spores InhA1, InhA2, or InhA3 would have similar effects upon introduction into a plant growth medium, or application to plant seeds, plants, or an area surrounding a plant or a plant seed.

Example 51. Expression of Fusion Proteins in an Endophytic *Bacillus cereus* Family Strain

*Bacillus cereus* family member EE349 was found to have the ability to grow endophytically and to be capable as serving as a host strain for the BEMD system. To demonstrate the ability of *Bacillus cereus* family member EE349 to grow endophytically and to serve as a host strain for the BEMD system, *Bacillus cereus* family member EE349 was transformed with the pSUPER-BclA 20-35-endoglucanase plasmid (described above in Example 44). Spores were made and purified as described above in Example 40.

These spores were diluted to a concentration of $1 \times 10^5$ spores/50 ml water, and the 50 ml of water was then added to commercial hybrid corn seed in potting soil at planting. The corn seeds were coated with a fungicide and a biological inoculant. The corn hybrid variety was BECK 5475RR, which contains the ROUNDUP READY glyphosate resistance gene and AQUAMAX drought resistance gene. Plants were grown under artificial light for 14 hours a day and plant growth over a ten day period was determined. Plants were watered every three days over the course of the experiment. After ten days, the plants were measured for height and normalized against the height of untreated corn plants. The results of these experiments are shown in Table 53.

TABLE 53

Effects of an endophytic *Bacillus cereus* family member expressing the BclA 20-35-endoglucanase fusion protein on corn seedling growth

| Plasmid | Expression Strain | Corn Growth (Normalized) |
| --- | --- | --- |
| None (Control) | None | 100% |
| None | *Bacillus cereus* family member EE349 | 104.1% |
| pSUPER-BclA 20-35-endoglucanase | *Bacillus cereus* family member EE349 | 111.5% |

As can be seen from the data shown in Table 53, expression of the pSUPER-BclA 20-35-endoglucanase in the endophytic strain *Bacillus cereus* family member EE349 resulted in increased corn growth as compared to untreated plants, or plants treated with *Bacillus cereus* family member EE349 alone.

*Bacillus cereus* family member 349 expressing the BclA 20-35-endoglucanase was then isolated from the inside of the corn plants. The ten day old plants were extracted from the soil and washed to remove excess debris. The plants were then inverted, exposed to 5% bleach for ten minutes, washed in water, exposed to hydrogen peroxide (10%) for ten minutes, washed again in water, and the stalks split with a sterile razor blade. The split halves of the stalks were placed face down onto nutrient agar plates for two hours. After two hours, the stalks were removed, and the agar plates incubated at 30° C. for 48 hours. After 48 hours, the plates were examined for colony morphology, and *Bacillus cereus* family member colonies found internal to the plant were toothpicked onto nutrient agar and nutrient agar plus tetracycline plates (to select for bacteria containing the pSUPER-20-35 BclA-endoglucanase plasmid). The resultant increase in *Bacillus cereus* family member 349 colony numbers is indicated shown in Table 54. These results demonstrate the ability of the BEMD system to be introduced into the target plant by expression in an endophytic strain of the *Bacillus cereus* family.

TABLE 54

Endophytic assay on *Bacillus cereus* family member EE349

| Treatment | Endophytic Bacteria (Total) | *Bacillus cereus* family bacteria (all strains) | Tetracycline resistant *Bacillus cereus* family members |
| --- | --- | --- | --- |
| H$_2$O (Control) | 156 | 31 | 0 |
| *Bacillus cereus* family member EE349 transformed with pSUPER-20-35 BclA-endoglucanase | 221 | 64 | 21 |

Tetracycline resistant *Bacillus* clones were grown overnight at 30° C. in brain heart infusion broth plus tetracycline, and spun down at 10,000×g for 5 minutes. The supernatant was removed, and the pellet frozen overnight at −20 C. Chromosomal DNA was then extracted from each clone, and the presence of the pSUPER-20-35 BclA-endoglucanase plasmid determined by transformation of the chromosomal DNA (containing the plasmid) into DH5α *E. coli* cells and plating on LB plus ampicillin plates. Correct clones were subjected to DNA sequence analysis, which verified that *Bacillus cereus* family member 349 was internal to the plant (endophytic) and contained the plasmid.

Many endophytic bacteria were found in the corn seedlings, with a number of different strains and species within the *Bacillus cereus* family found inside both the control and the EE349 treated plants. The tetracycline resistant *Bacillus cereus* family members (indicating the presence of the pSUPER-20-35 BclA-endoglucanase plasmid) were only found in the treated corn seedlings, and all had the same colony morphology of the original expression host, *Bacillus cereus* family members EE349. The presence of the pSUPER 20-35 BclA-endoglucanase plasmid was verified by PCR amplification using unique primers.

Example 52. Isolation, Identification, and Characterization of Endophytic *Bacillus cereus* Family Bacterial Strains In addition to the endophytic strain *Bacillus cereus* family member 349 discussed above in the immediately preceding example, several other *Bacillus cereus* family members that have the ability to grow endophytically were also identified: *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus mycoides* EE-B00363, *Bacillus pseudomycoides* EE-B00366, and *Bacillus cereus* family member EE-B00377.

To obtain these additional *Bacillus cereus* family members, commercial hybrid corn seed was planted in potting soil and allowed to grow. The corn seeds were coated with a fungicide and a biological inoculant. Plants were grown under artificial light for 14 hours a day and plant growth over a 14 day period was determined. Plants were watered every three days over the course of the experiment. After 14 days, the plants were extracted from the soil and washed to remove excess debris. The plants were then inverted, exposed to 5% bleach for ten minutes, washed in water, exposed to hydrogen peroxide (10%) for ten minutes, washed again in water, and the stalks split with a sterile razor blade. The split halves of the stalks were placed face down onto nutrient agar plates for two hours. After two hours, the stalks were removed, and the agar plates incubated at 30° C. for 48 hours. After 48 hours, the plates were examined for colony morphology, and *Bacillus cereus* family member colonies found internal to the plant were toothpicked onto nutrient agar. These were then were grown overnight at 30° C. in brain heart infusion broth, and spun down at 10,000×g for 5 minutes. The supernatant was removed, and the pellet frozen overnight at −20° C. Chromosomal DNA was then extracted from each clone, and the identity of each colony verified by PCR using 16S rRNA primers and amplicons were sent for DNA sequencing and identification. The 16S rRNA sequences for these strains are provided above in Table 13.

Example 53. Isolation, Identification, and Characterization of Additional Endophytic Bacterial Strains (Non-*Bacillus cereus* Family Members The endophytic bacterial strains *Bacillus megaterium* EE385, *Bacillus* sp. EE387, *Bacillus circulans* EE388, Bacillus subtilis EE405, Lysinibacillus fusiformis EE442, Lysinibacillus spp. EE443, and Bacillus pumilus EE-B00143 were isolated from corn seedlings. Two week old corn seedlings were first sterilized. The plants were extracted them from the soil and washed them to remove excess debris. The plants were then inverted, exposed to 5% bleach for ten minutes, washed in water, exposed to hydrogen peroxide (10%) for ten minutes, and washed again in water. The stalks were then split with a sterile razor blade. The split halves of the stalks were placed face down onto nutrient agar plates for two hours. After two hours, the plant stems were removed from the plates, and the plates were then incubated at 30° C. for 48 hours. Bacilli colonies that were endophytic were selected for further analysis. These strains were grown up in brain heart infusion broth overnight at 30° C., and the cultures subjected to extraction of DNA using a Qiagen Chromosomal DNA Kit. The DNA was PCR amplified to obtain the 16S rRNA gene, which was sent for DNA sequencing. The resultant sequences BLAST searched using the NCBI databases to establish the identity of the Bacilli species. The 16S rRNA sequences are provided above in Table 14.

Example 54. Expression of Fusion Proteins Comprising a Spore Coat Protein in Endophytic Bacillus Bacterial Strains The endophytic bacterial strains *Bacillus thuringiensis* EE319, *Bacillus firmus* A30, and *Bacillus lichenformis* A4 were transformed to contain plasmids encoding various spore coat proteins fused to endoglucanase. The plasmids pHP13-CotC-endoglucanase and pHP13-CgeA-endoglucanase were created. Each of these plasmids encoded the spore coat protein (CotC or CgeA) fused in frame with to a polyalanine linker containing eight alanine residues and endoglucanase. The polyalanine linker and endoglucanase were fused to the carboxy terminus of the spore coat proteins.

To create the plasmids encoding the fusion proteins, the endoglucanase gene from *Bacillus subtilis* 168 was PCR amplified. The genes encoding the spore coat proteins CotC and CgeA were also PCR amplified from the chromosomal DNA of *Bacillus subtilis* 168 (CotC) or *Bacillus amyloliquefaciens* (CgeA). Correct amplicons were then subject to splicing by overlapping extension PCR to generate the fusion protein DNA fragment through annealing of homologous 15 bp overhangs. External primers were each engineered to contain XhoI sites. The amplicons were cleaned up with a Promega PCR clean up kit, and the DNA digested with XhoI and ligated into the SalI site of pHP13. The plasmid DNAs were then sequenced, transformed into *E. coli* cells, and the DNA introduced into the various endophytic *Bacillus* strains.

Spores of each of the recombinant *Bacillus* species expressing the fusion proteins were generated by swabbing overnight cultures onto nutrient agar plates, which were then incubated at 30° C. for 72 hours. After 72 hours, bacterial spores were collected from the plates by swabbing into sterile PBS. Spores were purified by density centrifugation three times, diluted to $1\times10^8$ CFU/ml, and assayed for endogloconase activity as described above in Example 45. The results of this assay are shown in Table 55 below and in FIG. 9.

TABLE 55

Endogloconase activity in *Bacillus* spores expressing fusion proteins CotC-endoglucanase or CgeA-endoglucanase

| Plasmid | Expression Strain | Enzyme Reading/ Activity |
|---|---|---|
| Spore Control | *Bacillus firmus* A30 | .201 |
| Spore Control | *Bacillus thuringiensis* BT013A | .206 |
| pHP13-CgeA-endoglucanase | *Bacillus firmus* A30 | .818 |
| pHP13-CotC-endoglucanase | *Bacillus thuringiensis* EE319 | 1.738 |
| pHP13-CotC-endoglucanase | *Bacillus licheniformis* A4 | 0.414 |

In FIG. 9, CotC1, CotC2, and CotC3 are three separate experimental sporulation cultures of *Bacillus thuringiensis* EE319 with pHP13-CotC-Endo.

Example 55. Effects of *Bacillus* Spores Expressing Fusion Proteins CotC-Endoglucanase, CotB-Endoglucanase, or CgeA-Endoglucanase on Growth of Corn and Soy Seeds Spores of the recombinant *Bacillus* species expressing the fusion proteins comprising a spore coat protein and endoglucanase (e.g., the CotC-endoglucanase, CotB-endoglucanase, or CgeA-endoglucanase fusion proteins described above in the immediately preceding example) can be tested for their effects on the growth of plants (e.g., corn and soy) as follows. Spores can be generated as described above in the immediately preceding example, washed, diluted to $1\times10^8$ CFU/ml in water, and applied to plant seeds (e.g., corn and soy seeds) at a rate of $1\times10^{5-7}$ spores/seed. The spores can then be applied either as a seed treatment or as a soil drench. The plants can be planted 1" deep in 4" pots, and grown at 18.3° C. with a 13 hour light/dark cycle. After two weeks, plant height and root length can be determined.

Example 56. Delivery of Probiotic Bacteria to Animals by Feeding Plants Comprising Such Bacteria to the Animal Probiotic bacteria can be delivered to animals (e.g., livestock, fish, or other animals) by applying the probiotic bacteria to a plant seed, to a plant growth medium (e.g., by in furrow application to soil), to a plant (e.g., by foliar application) or to an area surrounding a plant or a plant seed, and subsequently feeding such plants or plants grown from the plant seeds to the animal. Bacteria can be applied to plant leaves or stems while plants are growing, and will colonize the phylloplane (leaf and stem surface). The plants can be subjected to processing into animal feed prior to feeding to the animal.

The use of endophytic strains of bacteria in such methods allows the bacteria to survive and persist in plant tissue, such that they will be ingested in significant numbers by the animal upon ingestion of plant matter from the plant. For example, the strains *Bacillus cereus* family member EE349, *Bacillus cereus* family member EE439, *Bacillus thuringiensis* EE417, *Bacillus cereus* EE444, *Bacillus megaterium* EE385, *Bacillus* sp. EE387, *Bacillus circulans* EE388, *Bacillus subtilis* EE405, *Lysinibacillus fusiformis* EE442, *Lysinibacillus* spp. EE443, and *Bacillus pumilus* EE-B00143 are thought to be probiotic and are endophytic and can be used in these methods.

Any of these strains or other probiotic and endophytic strains can be grown and spores generated as described above in Example 40. The spores can then be applied to a plant growth medium, a plant seed, a plant, or an area surrounding a plant or a plant seed. Plants grown in the plant growth medium, plants grown from the plant seeds, plants to which the bacteria were applied, or plants or plant seeds grown in an area to which the bacteria were applied can grow and subsequently be fed to an animal. Endophytic bacteria can colonize the internal tissue of the plant, and replicate to great numbers inside the plant. The bacteria will sporulate upon the use of traditional harvesting methods, allowing for prolonged storage of plant matter (e.g., as hay or silage) that can later be fed to a target animal.

Only a small amount of bacteria needs to be used in these methods, since the endophytic bacteria will naturally colonize and proliferate on and in the plants.

Example 57. Delivery of Beneficial Enzymes to Animals by Feeding to the Animals Plants Comprising a Recombinant *Bacillus cereus* Family Member or Other Recombinant Bacteria Expressing a Fusion Protein Comprising the Beneficial Enzyme The recombinant *Bacillus cereus* family members expressing a fusion protein comprising a protein or peptide of interest and a targeting sequence, exosporium protein, or exosporium protein fragment that targets the fusion protein to the exosporium that are described herein can also be used to deliver beneficial enzymes to animals. The recombinant *Bacillus cereus* family members can be fed directly to the animals (e.g., by mixing a recombinant *Bacillus cereus* family member into animal feed that is subsequently fed to the animal). Alternatively, the methods described above in the immediately preceding example for delivering bacteria to animals can be used in connection with recombinant *Bacillus cereus* family member expressing a fusion protein that comprises a protein or peptide that has beneficial effects in an animal (e.g., an enzyme that aids digestion of plant matter).

Enzymes present in feed for livestock, fish, and other animals can impact the nutrient uptake, yield, and health of the animal that ingests the enzymes. Enzymes that are beneficial for animal health include, for example, xylanases, phytases, phosphatases, proteases, cellulases, endoglucanases, glucanases, amylases, lipases, phospholipases, glycosylases, galactanases, α-galactosidases, amylases, pectinases, biotinases, and polygalacturonases, among others. The BEMD system can be used to express such enzymes on the surface of the exosporium. Recombinant *Bacillus cereus* family members expressing a fusion protein comprising one of these enzymes can be applied to a plant growth medium, a plant seed, a plant, or an area surrounding a plant or a plant seed. Similarly, the recombinant bacteria that express a fusion protein comprising one of these enzymes and a spore coat protein that targets the fusion protein to a surface of a spore of the bacterium can be used in these methods. The recombinant bacteria can be applied to a plant growth medium, a plant seed, a plant, or an area surrounding a plant or a plant seed. Plants grown in the plant growth medium, plants grown from the plant seeds, plants to which the bacteria were applied, or plants or plant seeds grown in an area to which the bacteria were applied can be grown and subsequently fed to an animal, and the beneficial enzyme thereby delivered to the animal. The bacteria will sporulate upon the use of traditional harvesting methods, allowing for prolonged storage of plant matter (e.g., as hay or silage) that can later be fed to a target animal.

Endophytic strains of *Bacillus cereus* family members can be used as hosts for expression of the fusion proteins comprising a protein or peptide of interest (e.g., an enzyme having beneficial effects in animals) and a targeting sequence, exosporium protein, or exosporium protein fragment that targets the fusion protein to the exosporium. For example, the endophytic strains *Bacillus cereus* family member EE349, *Bacillus cereus* family member EE439, *Bacillus thuringiensis* EE417, *Bacillus cereus* EE444, and *Bacillus thuringiensis* EE319 described herein can be used as hosts.

Additional *Bacillus cereus* family members can be selected to be applied to the aerial portions of the plant, as these bacteria do not have to be endophytic to colonize the phylloplane. For example, *Bacillus mycoides* BT155, *Bacillus mycoides* EE118, *Bacillus mycoides* EE141, *Bacillus mycoides* BT46-3, *Bacillus cereus* family member EE218, *Bacillus thuringiensis* BT013A, *Bacillus thuringiensis* EE-B00184, *Bacillus mycoides* EE-B00363, *Bacillus pseudomycoides* EE-B00366, or *Bacillus cereus* family member EE-B00377 can be used for this purpose.

Similarly, endophytic strains of recombinant bacteria can be used as hosts for the expression of fusion proteins comprising a protein or peptide of interest and a spore coat protein that targets the fusion protein to a surface of a spore of the bacterium. For example, the endophytic strains *Bacillus megaterium* EE385, *Bacillus* sp. EE387, *Bacillus circulans* EE388, *Bacillus subtilis* EE405, *Lysinibacillus fusiformis* EE442, *Lysinibacillus* spp. EE443, or *Bacillus pumilus* EE-B00143 can be used as hosts.

The use of endophytic strains of bacteria in these methods allows the bacteria to survive and persist in plant tissue, such that both the bacteria and the fusion proteins expressed by the bacteria will be ingested in significant numbers by the animal upon ingestion of plant matter from the plant. Thus, through a simple addition of the recombinant *Bacillus cereus* family member or other recombinant bacteria at planting, beneficial enzymes can be spread throughout the plant tissue and delivered to animals upon ingestion of plant matter.

Example 58: Use of Various Targeting Sequences to Express Endoglucanase on the Surface of *Bacillus cereus* Family Member Spores, and Use of Such Spores for Promoting Plant Growth The pSUPER plasmid was modified by cloning of a PCR generated fragment through homologous recombination that fused the BclA promoter, start codon, and amino acids 20-35 of BclA (amino acids 20-35 of SEQ ID NO: 1) in frame with *Bacillus subtilis* 168 endoglucanase (pSUPER-BclA 20-35-Endo) as described above in Example 44. This plasmid was then subjected to inverse PCR to amplify the entire plasmid backbone, but leaving out the sequence corresponding to amino acids 20-35 of BclA. This inverse PCR product was combined with a PCR product that amplified the equivalent region from each of SEQ ID NOs. 5, 15, 25, 81, 85, 87, or amino acids 20-33 of SEQ ID NO: 1. Thus, constructs were created that contained each of the following targeting sequences fused in frame with *Bacillus subtilis* 168 endoglucanase: (1) amino acids 20-35 of SEQ ID NO: 1; (2) amino acids 23-38 of SEQ ID NO: 5; (3) amino acids 28-43 of SEQ ID NO: 15; (4) amino acids 9-24 of SEQ ID NO: 25; (5) amino acids 23-38 of SEQ ID NO: 81; (6) amino acids 13-28 of SEQ ID NO: 85; (7) amino acids 13-28 of SEQ ID NO: 87; and (8) amino acids 20-33 of SEQ ID NO: 1. Each construct contained the wildtype BclA promoter and a methionine at the start codon, followed by the targeting sequence fused in frame to the *Bacillus subtilis* endoglucanase gene. Each of these constructs was transformed into *E. coli* and plated to obtain single colonies on Luria plates plus ampicillin (100 µg/ml). Plasmids from each single colony were grown up in overnight cultures in Luria broth plus ampicillin, and purified using a WIZARD SV miniprep kit, and sequences were verified by Sanger sequencing. DNA was also quantified via spectrophotometry, and the DNA was introduced into *Bacillus thuringiensis* BT013A. In addition, the pSUPER-BclA-20-35 Endo construct was introduced into *Bacillus thuringiensis* BT013A which had the native BclA protein removed from its genome through homologous recombination (BclA knockout, "BclA KO"). Correct colonies were screened by plating on nutrient broth plate containing antibiotic (tetracycline at 10 µg/ml). Each positive colony was grown up in brain heart infusion broth at 30° C. overnight at 300 rpm, with antibiotic, and genomic DNA was purified and re-sequenced to verify genetic purity. Verified colonies were grown overnight in brain heart infusion broth with 10 µg/ml tetracycline, and induced to sporulate through sporulation in a yeast extract-based media.

Each of the production runs in the yeast extract-based media were collected at 48 hours post production of spores, and subjected to enzyme comparison of the resultant spores using the methodology described above in Example 45. The absorbance was determined at 540 nm using an IMPLEN nanophotometer model P330. There were three samples and a blank for each reaction. The results from the enzyme readings are shown in Table 56.

For corn, 1 µl of each of the whole broth for each of the constructs was placed onto each seed. For summer squash, 2 µl of whole broth for each construct was placed onto each seed. To accomplish this, 50 seeds were placed in a 50 ml conical bottom polypropylene tube and vortexed lightly using a vortex mixer. To this swirling of seeds, 50 µl (for corn) or 100 µl (for squash) of broth containing the recombinant spores was slowly pipetted into the tube, and the vortexing action coated the seeds with an even coating of the whole cell broth from each construct. These seeds were then planted at 1" deep into native soil using a 39.6 cm$^3$ (15.6 in$^3$) planting pot, with two seeds per pot. The pots were then watered to saturation, and the plants allowed to germinate. The plants were grown in a controlled growth room, set to 70° F. during the day, and 60° F. during the evening, with a light period of 14 hours/day, under artificial light conditions, for 14 days. After 14 days, the plants were measured for height, and results were normalized to a control group that received only water as treatment on the seeds.

TABLE 56

Enzyme levels and plant growth phenotypes.

| Targeting Sequence | Endo Enzyme Levels (mU/ml) | Sequence Identity to AA 20-35 of BclA | Sequence Identity to AA 25-35 of BclA | Corn Growth Phenotype | Squash Growth Phenotype | Average Plant Phenotype Change |
|---|---|---|---|---|---|---|
| Control (H$_2$O) | 0 mU/ml | N/A | N/A | 100% | 100% | 100% |
| AA 20-35 of BclA (SEQ ID NO: 1) | 38.2 | 100% | 100% | 112% | 94.7% | 103.4% |
| AA 23-38 of SEQ ID NO: 5 | 33.5 | 50.0% | 72.7% | 106.7% | 102.3% | 104.5% |
| AA 28-43 of SEQ ID NO: 15 | 16.7 | 68.8% | 81.8% | 115.7% | 103.4% | 109.6% |
| AA 9-24 of SEQ ID NO: 25 | 25.7 | 56.3% | 63.6% | 118.4% | 107.1% | 112.8% |
| AA 23-38 of SEQ ID NO: 81 | 21.5 | 50.0% | 72.7% | 106.7% | 98.3% | 102.5% |
| AA 13-28 of SEQ ID NO: 85 | 38.3 | 43.8% | 54.5% | 99.7% | 100.5% | 100.1% |
| AA 13-28 of SEQ ID NO: 87 | 14.4 | 43.8% | 54.5% | 102.6% | 104.1% | 103.4% |
| AA 20-33 of SEQ ID NO: 1 | 30.5 | N/A | 100% | 104.6% | 100.7% | 102.7% |
| AA 20-35 of SEQ ID NO: 1 in BT013A BclA KO | 100.8 | 100% | 100% | ND | ND | ND |

AA = amino acids
ND = not determined

The above data show that each of these constructs was able to stimulate plant growth and show that the use of different targeting sequences allows for control of the expression level of the enzyme on the outside of the spore.

Use of amino acids 20-35 of SEQ ID NO: 1 or AA 13-28 of SEQ ID NO: 85 as the targeting sequence resulted in the highest levels of enzyme production. This is surprising considering the low degree of identity between these targeting sequences (43.8% identity over the entire length of the targeting sequence). Use of amino acids 28-43 of SEQ ID NO: 15 or amino acids 9-24 of SEQ ID NO: 25 resulted in the largest plant response across the two plant types. Expression of the fusion protein containing amino acids 20-25 of SEQ ID NO: 1 as the targeting sequence in the BT013A BclA KO host led to very large (263.8%) increase in the amount of enzyme activity on the surface of the spores as compared to expression of the same fusion protein in the wild-type strain.

Example 59: Use of Various Targeting Sequences and Exosporium Proteins to Express Phospholipase, Lipase, and Endoglucanase on the Surface of *Bacillus cereus* Family Member Spores, and Use of Such Spores for Promoting Plant Growth The pSUPER plasmid was modified by cloning of a PCR generated fragment (XhoI digestion and ligation) that fused the BclA promoter, start codon, and amino acids 20-35 of BclA (amino acids 20-35 of SEQ ID NO: 1) followed by a six alanine linker sequence in frame with either *Bacillus thuringiensis* phosphatidylcholine-specific phospholipase C gene (PC-PLC) (pSUPER-BclA 20-35-PL) or *Bacillus subtilis* lipase LipA (pSUPER-BclA-20-35-Lipase), or *Bacillus subtilis* endoglucanase eglS (pSUPER-BclA-20-35-Endo) as described above in Example 44. These plasmids were then subjected to inverse PCR to amplify the entire plasmid backbone, but leaving out the sequence corresponding to the amino acids 20-35 of BclA. This inverse PCR product was combined with a PCR product that amplified the equivalent region from each of SEQ ID NOs. 5 (i.e., amino acids 23-38 of SEQ ID NO: 5), 15 (i.e., amino acids 28-43 of SEQ ID NO: 15), and 25 (i.e., amino acids 9-24 of SEQ ID NO: 25; the full-length exosporium proteins of SEQ ID NOs. 120, 111, 121, 108, and 114; or amino acids 20-33, 20-31, 21-33, 23-33, or 23-31 of SEQ ID NO: 1. Each of these constructs contained the wild-type BclA promoter, a methionine at the start codon, followed by the targeting sequence or exosporium protein fused in frame to the *Bacillus cereus* phosphatidylcholine-specific phospholipase C, *Bacillus subtilis* 168 Lipase LipA, or *Bacillus subtilis* 168 eglS endoglucanase gene. Each of these constructs was screened for correct transformants as described in Example 58 above.

Each of the production runs in the yeast extract-based media were collected at 48 hours post production of spores, and subjected to enzyme comparison of the resultant spores. Determination of enzyme data for endoglucanase was performed as described above in Example 58. For the phospholipase C enzyme assay, 1 ml of recombinant spores was pelleted at 10,000×g for 3 minutes, and supernatant removed and discarded. The spore pellet was then resuspended in 500 µl reaction buffer (0.25 mM Tris-HCL, 60% glycerol, 20 mM o-nitrophenyl phosphorylcholine, pH 7.2). A negative control for enzyme assays contained BT013A spores with no enzyme expression. Each sample was incubated at 37° C. for 18 hours, centrifuged again to remove the spores, diluted 1:1 in water, and the Abs540 read using a spectrophotometer. This was compared to a standard curve against commercially purchased phospholipase and lipase controls to establish the U/ml of activity. The results from the enzyme readings are shown in Tables 57 and Table 58.

TABLE 57

Endoglucanase Enzyme Levels

|  | Endoglucanase Levels (mU/ml) |
|---|---|
| Targeting Sequence, Experiment #1 | |
| Control (H₂O) | 0 mU/ml |
| AA 20-35 SEQ ID NO: 1 | 38.2 |
| SEQ ID NO: 120 | 25.7 |
| SEQ ID NO: 111 | 29.7 |
| SEQ ID NO: 121 | 24.4 |
| SEQ ID NO: 108 | 24.0 |
| SEQ ID NO: 114 | 11.0 |
| AA 20-33 of SEQ ID NO: 1 | 30.5 |
| Targeting Sequence, Experiment #2 | |
| AA 20-31 of SEQ ID NO: 1 | 48.22 |
| AA 21-33 of SEQ ID NO: 1 | 60.86 |
| AA 23-33 of SEQ ID NO: 1 | 19.93 |
| AA 23-31 of SEQ ID NO: 1 | 45.31 |
| AA 20-35 of SEQ ID NO: 1 | 54.1 |

AA = Amino acids

Many of the targeting sequences and exosporium proteins were able to display a large amount of active enzymes on the surface of the spores, including SEQ ID NOs. 108, 111, 114, 120, and 121. Amino acids 20-31, 21-33, and 23-31 of SEQ ID NO: 1 provided similar enzyme expression levels to amino acids 20-35 of SEQ ID NO: 1, indicating that smaller fragments are adequate for the display of enzymes on the surface of the spores. Only amino acids 23-33 of SEQ ID NO: 1 exhibited a diminished enzyme display level on the spores.

TABLE 58

Phospholipase Enzyme levels

| Targeting Sequence | PC-PLC Enzyme Levels | Lipase Enzyme Levels |
|---|---|---|
| Control (H₂O) | 0.0 | 0.0 |
| AA 20-35 SEQ ID NO: 1 | .787 | .436 |
| AA 23-38 of SEQ ID NO: 5 | .688 | .602 |
| AA 28-43 of SEQ ID NO: 15 | .372 | .228 |
| AA 9-24 of SEQ ID NO: 25 | .247 | .359 |
| SEQ ID NO: 114 | .446 | .798 |
| SEQ ID NO: 120 | 3.612 | .753 |
| SEQ ID NO: 111 | .738 | .329 |

AA = Amino acids

Similar to the results shown above in Table 57, the highest levels of phospholipase or lipase on the spore surface were observed when amino acids 20-35 of SEQ ID NO: 1, amino acids 23-38 of SEQ ID NO: 5, or the exosporium protein sequence of SEQ ID NO: 120 were used.

The effects of these spores expressing several of these constructs on nodulation in soybeans are shown below in Table 59.

TABLE 59

Phospholipase Plant Responses

| Targeting Sequence | Nodulation per Plant (Soybean) |
|---|---|
| Control (H₂O) | 9.8 |
| Strain Control (*Bacillus thuringiensis* BT013A) | 8.2 |
| *Bacillus thuringiensis* BT013A expressing a fusion protein of AA 20-35 of SEQ ID NO: 1 and phospholipase | 14.0 |

Soybeans plants were coated as above, but the assay was run out to 3 weeks' time. Plants were carefully removed, dirt washed gently off of the roots, and nodules counted for each plant. As shown in Table 59, addition of spores displaying phospholipase onto the seeds of soybean allows for an accelerated number of nodules on the plants, which is a positive indication for both early growth as well as eventual increases in yield in soybeans.

Example 60: Binding of MIR319 RNA and Random RNA 1 to *Bacillus cereus* Spores Expressing a Fusion Protein Containing a Nucleic Acid Binding Protein, and Use of Such Spores to Deliver RNA to Plants DNA and RNA can be bound to *Bacillus cereus* family member spores that express fusion proteins containing a targeting sequence and a nucleic acid binding protein or peptide on their exosporium, as described in the above Examples and in the Description. The spores act as a delivery mechanism, delivering the target nucleic acid (e.g., a miRNA) to the target plant. To demonstrate this ability of the recombinant *Bacillus cereus* family member spores, a common miRNA, MIR319 was delivered to soybeans using spores expressing a fusion protein containing amino acids 20-35 of SEQ ID NO: 1 fused in frame to the known DNA binding gene SspC. MIR319 has different effects on plant phenotype in different plants, and even within different parts of the same plant. For example, in some species, treatment of leaves with MIR319 leads to curling of leaves, whereas in other species, application of MIR319 leads to stress resistance. MIR319 is ubiquitous across plant genomes, is a global regulator of pathways, and its delivery into various plants leads to various phenotypes.

TABLE 60

RNAs used in this study

| RNA | 3' Sequence | 5' Sequence |
|---|---|---|
| MIR319 | UUGGACUGAAGGGUGCUCCC (SEQ ID NO: 306) | GAGCUCUCUUCAGUCCACUC (SEQ ID NO: 307) or AGAGCGUCCUUCAGUCCACUC (SEQ ID NO: 308) |
| Random RNA #1 | GAGCCCATGGTTGAATGAGT (SEQ ID NO: 309) | ACTCATTCAACCATGGGCTC (SEQ ID NO: 310) |

Synthetic MIR319 microRNA from *Glycine max* (soybean) was designed to match the MIR319 sequence available in miRBase (miRBase.org, central repository for microRNA sequences). Two partially complementary single stranded sequences were synthesized by Integrated DNA Technologies (IDT, Iowa) to represent the 3' and 5' mature gene products known to exist in vivo (two different versions of the 5' sequence were used). Likewise, two single stranded RNAs were synthesized with random sequences not matching anything in the soy genome as a control. The double stranded (ds) gene products were made by combining the two single stranded (ss) products at 95° C. for 10 min and then cooling slowly at room temperature to allow for annealing. *Bacillus thuringiensis* expressing a fusion protein containing the BclA promoter, a methionine residue as the start codon, and amino acids 20-35 of SEQ ID NO: 1 fused in frame to the known DNA binding gene SspC (an α/β type SASP, Small Acid-soluble Spore Protein C of *Bacillus thuringiensis* BT013A) was engineered by standard cloning procedures as described above in Example 58. This construct (SspC-BclA) was created in *E. coli*, transformed into *Bacillus thuringiensis* BT013A and clones verified by DNA sequencing. *B. thuringiensis* spores expressing SspC-BclA were obtained by an overnight growth of transformed bacteria in brain heart infusion broth (BHI) for 2 days in a yeast extract-based media until a density of 2×10$^8$ spores per milliliter (ml) was achieved with less than 1% vegetative cells. DNA was extracted from an aliquot of the parent BHI culture and sent for sequencing to confirm incorporation of the SspC-BclA plasmid. To prepare spores for seed treatments, 1 ml of spore culture in the yeast extract-based media was pelleted by centrifugation and resuspended in 100 μl of water. This concentrated suspension was counted and spores were used at 6×10$^8$ spores/ml. For each soy seed, 1 μl of spores was combined with 10 μl of RNA at 10 μM and incubated at 30° C. for 2 hours (scaled up for multiple seeds). After this incubation spores were pelleted (carrying bound RNA) and unbound excess RNA in the supernatant was discarded and the pellet was resuspended in 10 μl of water. Samples were applied to the seeds as follows: 39.6 cm$^3$ (15.6 in$^3$) of Timberline brand commercial top soil was prepared in each pot and a 1 inch indentation was made where 2 ml of water was applied and a single seed was set on top. The 10 μl spore+bound RNA sample was applied by micropipetting directly on to the top of the seed. Seeds were allowed to sit for 30 min and then the adjacent soil was pushed to loosely cover the seed. The seeds were allowed to germinate for 4 days in an artificial light plant growth room with a 13/11 hour light/day cycle, and at 21° C. day/15° C. night temperature range. On day 14 soy plants were uprooted, photographed and measured. Heights were normalized to water control treated plants (See Table 61).

Figure 10:
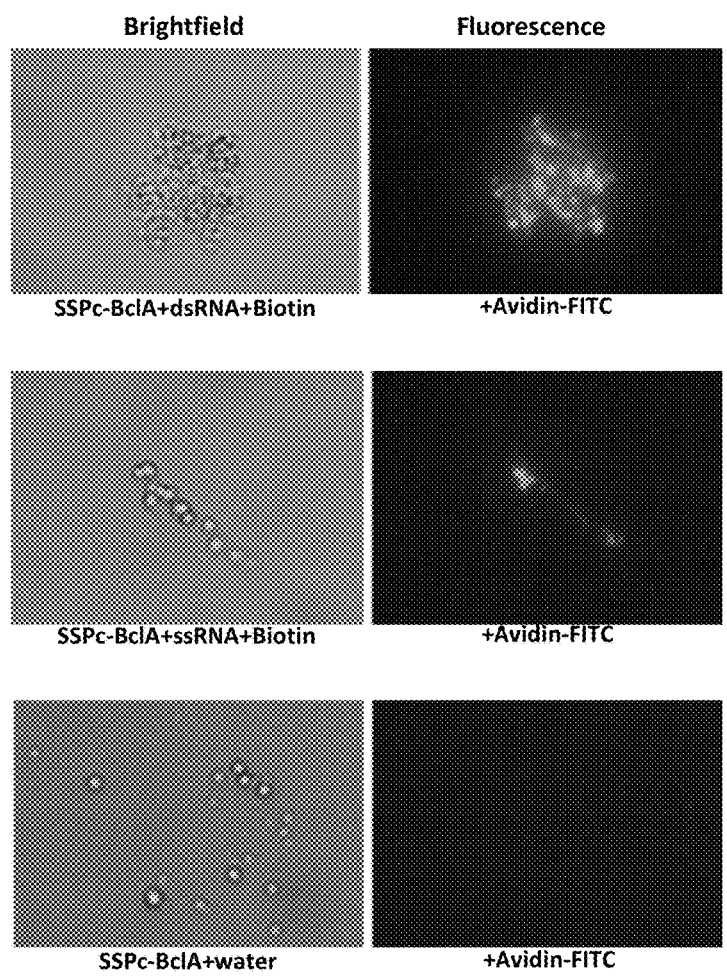
FIG. 10 provides bright-field and fluorescence microscopy images showing detection of RNA on the surface of recombinant *B. thuringiensis* spores expressing a fusion protein comprising amino acids 20-35 of SEQ ID NO: 1 and SspC bound to either single-stranded RNA (ssRNA) or double-stranded RNA (dsRNA).

Example 41 above describes the ability of the SspC-BclA recombinant *Bacillus cereus* family member spores to bind to and hold DNA. To assess RNA binding ability of the SspC-BclA expressing spores, biotin labeled random RNA sequences were synthesized by IDT and incubated with the spores exactly as was done for the treatments described above (1 μl of spores at 6×10$^8$ spores/ml+10 μl of 10 μM RNA for 2 hours at 30° C., pelleted and resuspended in 10 μl of water). Avidin conjugated to Fluorescein (FITC) (Life Technologies) was added to the 10 μl spore+RNA sample at 20 μg/ml final concentration and incubated for 1 hour at room temperature in the dark. Avidin is known to bind biotin and FITC is a fluorescent tracer. Spores were pelleted once again to remove excess unbound avidin-FITC and resuspended in 4% paraformaldehyde made in PBS and stored at 4° C. overnight in the dark. Spores were inspected for fluorescence and photographed (See Table 62). In addition, as shown in FIG. 10, the Sspc-BclA tagged spores were able to bind and retain both ssRNA and dsRNA, as shown by the FITC-avidin labeling of spores in the presence of the ssRNA or dsRNA bound with biotin. To generate the results shown in FIG. 10, spores were incubated with either double or single stranded RNA (of a random sequence) tagged with biotin and detected with avidin conjugated to fluorescein (FITC). No fluorescence was detected on spores incubated with water only. Brightfield and corresponding fluorescent images were taken with 40× objective and 10× ocular lenses.

Figure 11:
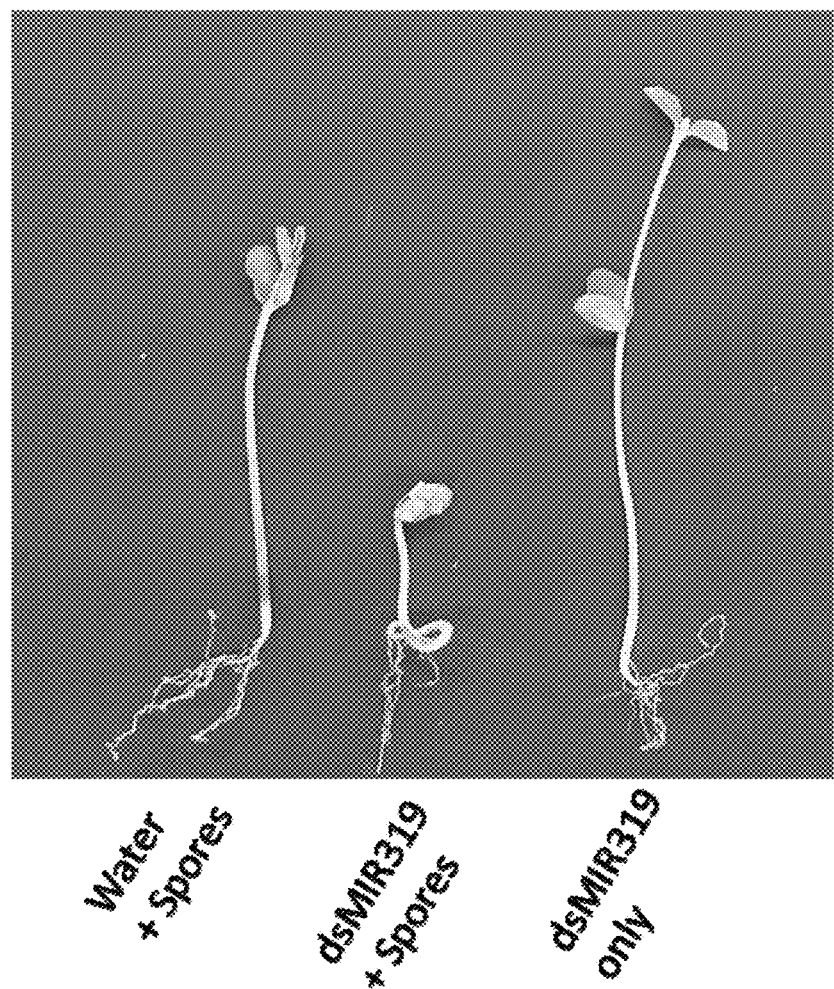
FIG. 11 provides a photograph showing the effects of the microRNA MIR319 on soy height and root development, following delivery to soybean plants using recombinant *B. thuringiensis* spores expressing a fusion protein comprising amino acids 20-35 of SEQ ID NO: 1 and SspC bound to MIR319.

As can be seen in Table 61 below, the major effect of MIR319 as a seed treatment on soybeans is on root growth and overall height. Curly roots were defined as having at least two 180° turns. Heights were measured along the main stalk. When soybean plants were uprooted and assayed for the presence of "curly roots", a phenotype observed by our group specific to soybeans, no evidence of curly roots was found in the water control, the BT013A strain control, the double stranded (dsRNA) RNA alone control, or the spores alone (carrier control). The only evidence of curly roots is noted when both the SspC-BclA spores (the carrier) was delivered to the seed with the dsRNA (60% curly roots) (also see FIG. 10). FIG. 11 also shows the phenotypic changes in the soybean plants when exposed to SspC-BclA spores combined with ds MIR319 RNA. When the spores are used to deliver the RNA, the impact of the RNA is amplified, leading to an increased stunting and curly root phenotype in FIG. 11. To generate the results shown in FIG. 11, soy seeds were treated with double stranded (ds) MIR319 with or without prior binding to *B. thuringiensis* spores expressing SspC-BclA. Application of dsMIR319 resulted in slightly taller plants on average; however, application of dsMIR319 bound to spores resulted in "curly" roots defined as having at least two 180° turns and overall less height. The median sample from each experimental condition is shown. Images were taken using a digital camera with plants together in a single image.

As an RNA control, a random set of ssRNA (single-stranded) and dsRNA was applied to soybeans. In these experiments, the random ssRNA had no effect when applied alone, while the dsRNA had a stunting effect on the height of the plants when delivered to the seeds. In both cases, when the spores (carrier) were used in conjunction with either the random ssRNA or the dsRNA version, the stunting phenotype was increased significantly (33% and 27.8% stunted, respectively). This stunting is not evident in the spore (carrier control) alone samples. These data, when taken together, demonstrate the ability of the spores to amplify and specifically deliver ssRNA and dsRNA to plants by application to the seed, and demonstrate the ability of two different RNAs (Random #1 and MIR319) to affect phenotype when delivered via *Bacillus cereus* spores expressing a fusion protein containing a DNA/RNA binding protein.

TABLE 61

Root and Height effect of MIR319 on soybean development

| Seed Treatment (5 replicates each) | % Curly Roots | Height (Normalized to Control) |
|---|---|---|
| Water (Control) | 0 | 100% |
| Water + Spores (Control) | 0 | 105.21% |
| Random ssRNA #1 no spores | 0 | 102.62% |
| Random ssRNA #1 + spores | 0 | 69.62% |
| dsMIR319 no spores | 0 | 125.30% |
| dsMIR319 + spores | 60% | 67.10% |
| Random dsRNA #1 no spores | 0 | 82.40% |
| Random dsRNA #1 + spores | 0 | 54.61% |

TABLE 62

Fluorescence detection on SspC-BclA expression spores with bound biotin labeled RNA

| Spore Treatment | Fluoresence Detected on Spores |
|---|---|
| Spores + Water (control for background spore fluorescence) | Not detected |
| Spores + Water + Avidin-Fitc (control for background spore + FITC fluorescence) | Not Detected |
| Spores + biotin labeled ssRNA + Avidin-FITC | Detected |
| Spores + biotin labeled dsRNA + Avidin-FITC | Detected |

As can be seen in Table 62, no fluorescence was detected on the spores without the presence of RNA. Both single stranded (ss) and double stranded (ds) RNA was detected on the spores.

Example 61: Delivery of Nucleic Acids to *Caenorhabditis elegans* Nematodes by Ingestion of Recombinant *Bacillus thuringiensis* Spores Expressing a Fusion Protein Delivery of RNA and DNA to nematodes has a great deal of applications in both plant science, animal health, and in basic research. Nematodes cause a great deal of damage and yield loss to commercial and non-commercial growing operations for key crops, and parasitic nematodes cause high morbidity in humans and other animals in many impoverished areas of the world. Delivery of RNA and DNA has the potential to alleviate and treat many nematode problems, and delivery of RNA and DNA constructs has been demonstrated to be useful in impacting target nematodes. This example illustrates the utility of the RNA/DNA delivery mechanism described above in Example 60 in delivering spores to nematodes.

Wild type *C. elegans* nematodes were purchased from Carolina Biological (North Carolina) and maintained at 23° C. on NGM-Lite agar plates coated with OP50 *E. coli* for food. Two different *Bacillus thuringiensis* BT013A strains were engineered by standard cloning procedures to express amino acids 20-35 of SEQ ID NO: 1 fused in frame to green fluorescent protein (GFP) or mCherry to trace the presence of spores in the gut. These green or red fluorescently tagged spores were obtained by an overnight growth in BHI (brain heart infusion) medium, followed by three days in a yeast extract-based media until a density of approximately $2 \times 10^8$ spores per milliliter (ml) was achieved with less than 1% vegetative cells. To prepare spores for feeding to nematodes, 1 ml of spore culture in media was pelleted by centrifugation and resuspended in 100 µl of water to remove excess media. This concentrated suspension was counted and diluted to $1 \times 10^8$ spores/ml. To feed spores to the worms, 1 µl of the spore suspension containing both the red and green fluorescently tagged spores was added to a 60 mm NGM-lite agar plate with 10 µl of PBS (phosphate buffered saline) to aid in spreading. No other food source was made available. Twenty wild type nematodes of various ages were transferred to the plates immediately. Living nematodes were checked 5 hours later for ingestion of spores using standard fluorescence microscopy.

Figure 12:
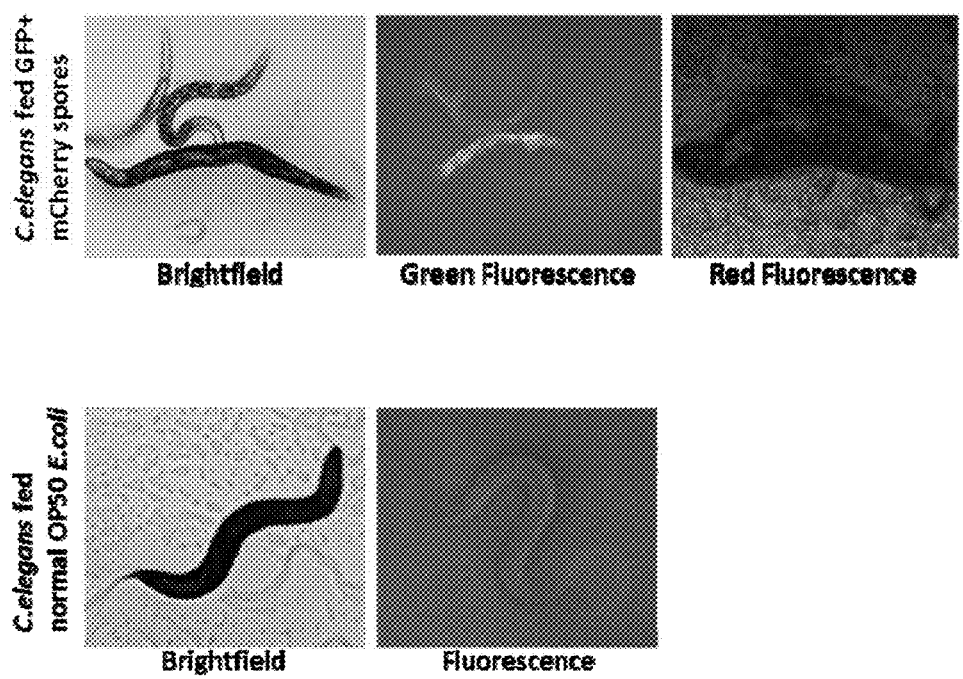
FIG. 12 provides bright-field and fluorescence microscopy images showing detection of GFP and mCherry in the gut of nematodes fed normal OP50 *E. coli* bacterial food (two right-hand panels) or nematodes fed *B. thuringiensis* spores expressing a fusion protein comprising amino acids 20-35 of SEQ ID NO: 1 and either GFP or mCherry (three left-hand panels).

As can be seen in FIG. 12 and Table 63, the centralized gut of the nematodes fluoresced when fed recombinant *Bacillus cereus* family member spores expressing the fusion protein containing the targeting sequence and GFP, whereas the gut did not fluoresce when fed OP50 *E. coli* (standard food). Images were taken of live nematodes with 4× objective and 10× ocular lenses. This demonstrates the ability of these spores to be both ingested and delivery of a "cargo" of target proteins, exemplified by the green fluorescence protein. Other Exosporium proteins and targeting proteins can also be used interchangeably with a targeting sequence to deliver RNA and DNA to a nematode or other target organism. Other recombinant *Bacillus cereus* family member spores can also be used due to the high degree of conserved nature of the exosporium and its creation on the surface of the spore.

TABLE 63

C. elegans fluorescence detected in the gut

| Food Source | Green Fluorescence Detected in gut |
|---|---|
| OP50 E. coli (control) | No |
| GFP expressing B. thuringiensis BT013A | Yes (High) |

Example 62: Construction, Purification, and Uses of Exosporium Fragments

Knock Out (KO) Mutants:

To make exsY and cotE knockout (KO) mutant strains of Bacillus thuringiensis BT013A, the plasmid pKOKI shuttle and integration vector was constructed that contained the pUC57 backbone, which is able to replicate in E. coli, as well as the origin of replication erythromycin resistance cassette from pE194. This construct is able to replicate in both E. coli and Bacillus spp. A 1 kb DNA region that corresponded to the upstream region of the cotE gene and a 1 kb region that corresponded to the downstream region of the gene cotE were PCR amplified from Bacillus thuringiensis BT013A. A second construct was made that contained the 1 kb DNA region that corresponded to the upstream region of the exsY gene and a 1 kb region that corresponded to the downstream region of the gene exsY, both of which were PCR amplified from Bacillus thuringiensis BT013A. For each construct, the two 1 kb regions were then spliced together using homologous recombination with overlapping regions with the pKOKI plasmid. This plasmid construct was verified by digestion and DNA sequencing. Clones were screened by looking for erythromycin resistance.

Clones were passaged under high temperature (40° C.) in brain heart infusion broth. Individual colonies were toothpicked onto LB agar plates containing erythromycin 5 µg/ml, grown at 30° C., and screened for the presence of the pKOKI plasmid as a free plasmid by colony PCR. Colonies that had an integration event were continued through passaging to screen for single colonies that lost erythromycin resistance (signifying loss of the plasmid but recombination and removal of the exsY or cotE gene). Verified deletions were confirmed by PCR amplification and sequencing of the target region of the chromosome. The pSUPER-BclA 20-35 Endo plasmid (described above in Example 58) was transformed into each of the exsY and cotE KO mutants. As described above in Example 48, the cotE KO mutant was also transformed with the pSUPER BclA 20-35 eGFP plasmid (made as described above in Example 44, but with endoglucanase swapped for eGFP by homologous recombination).

Dominant Negative Mutants:

To create a dominant negative mutant, we PCR amplified the N-terminal half and the C-terminal half of CotO (Seq ID NO: 126), containing the amino acids 1-81 and 81-199 respectively, and cloned these fragments into the pHP13 vector using homologous recombination (the pHP13 vector is described above in Example 1). Correct clones were verified by Sanger sequencing. Each of the two CotO dominant negative mutants was introduced into Bacillus thuringiensis BT013A that contained the pSUPER-BclA 20-35 Endo construct, which produces endoglucanase on the surface of the spore as illustrated above in Example 58.

Exosporium Fragment Creation:

For each of the two KO mutants, and both of the dominant negative mutants, an overnight culture was grown in BHI media at 30° C., 300 rpm, in baffled flasks with antibiotic selection. One milliliter of this overnight culture was inoculated into a yeast extract-based media (50 ml) in a baffled flask and grown at 30° C. for 3 days. An aliquot of spores was removed, 1% Tween was added, and the spores were agitated by vortexing for one minute. The spores were collected via centrifugation at 10,000×g for 5 minutes, and supernatant containing the exosporium fragments was filtered through a 0.22 µM filter to remove any residual spores. The supernatant (containing the broken exosporium fragments) was filtered through a 100,000 Da membrane filter to obtain purified exosporium fragments containing the fusion proteins. Smaller MW proteins were removed by passaging through the 100 kDa filter. No spores were found in the filtrate or retentate of the supernatant.

Figure 15:
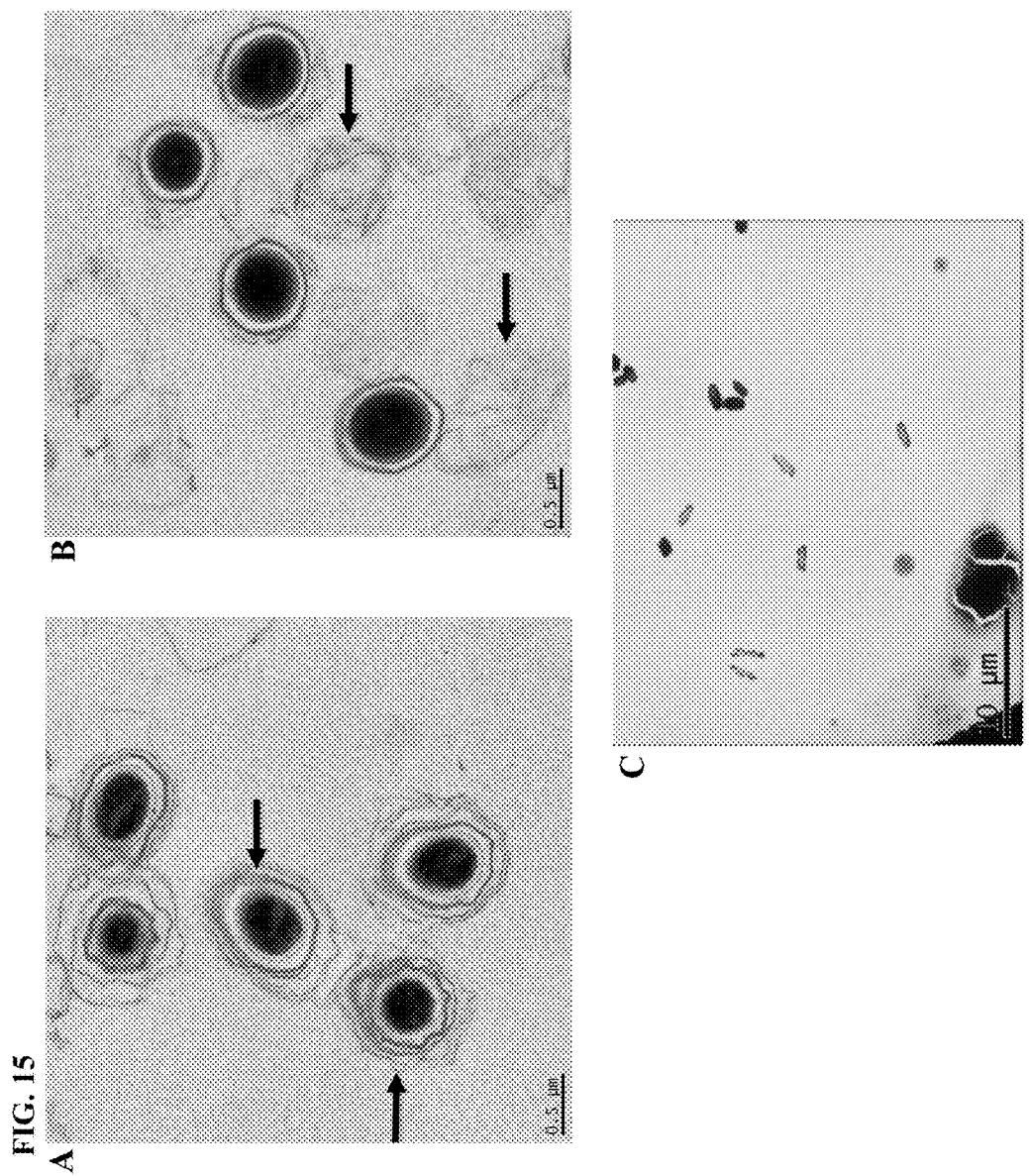
FIG. 15 provides a transmission electron micrographs showing: (A) intact spores of *Bacillus thuringiensis* BT013A surrounded by attached exosporium; (B) spores of a CotE knockout strain of *Bacillus thuringiensis* BT013A, with detached exosporium; and (C) a purified exosporium fragment preparation of exosporium fragments derived from a CotE knockout strain of *Bacillus thuringiensis* BT013A.

Transmission electron micrographs are provided in FIG. 15 showing intact spores of Bacillus thuringiensis BT013A (panel A) surrounded by attached exosporium, and spores of the Bacillus thuringiensis BT013A CotE knock-out mutant (panel B), from which the exosporium has detached. Arrows in panel A of FIG. 15 indicate the exosporium of intact spores, while arrows in panel B of FIG. 15 indicate exosporium that has detached from the spores. Panel C of FIG. 15 shows a transmission electron micrograph of a purified exosporium fragment preparation of derived from the Bacillus thuringiensis BT013A CotE knock-out (prepared as described above by vortexing, centrifugation, and filtration of the supernatant), visualized by negative staining. Images were taken on a JEOL JEM 1400 transmission electron microscope. No visible exosporium fragments were observed when control spores (Bacillus thuringiensis BT013A without the CotE knockout, expressing the BclA 20-35 Endo fusion protein, data not shown) were subjected to same vortexing, centrifugation, filtration procedures described above.

Presence of BclA 20-35 Endoglucanase in Exosporium Fragments Collection from the CotE and ExsY Knockout and CotO Dominant Negative Mutants:

Exosporium fragments were created and purified as described above that contained the pSUPER BclA 20-35-Endo plasmid that creates an exosporium that contains the endoglucanase enzymes on the surface of the spores. Exosporium fragments containing this construct were created from the cotE knockout mutant spores, exsY knockout mutant spores, CotO N-terminal dominant mutant spores, or CotO C-terminal dominant mutant spores. In each of these experiments, the amount of activity for the endoglucanase on the exosporium fragments was quantified as a percentage of the total enzyme levels. These results were compared against a wildtype construct that did not contain any mutants, but did contain the pSUPER BclA 20-35-Endo plasmid.

Effects of Exosporium Fragments on Plant Growth:

These exosporium fragments were then delivered as a seed treatment onto soybean seeds (as described in Example 59 above). A wild-type control (B. thuringiensis BT013A expressing the BclA 20-35 Endo construct) was also coated onto soybeans seeds. For each experiment, 1 µl of exosporium fragments from each construct, or a 1:2, a 1:4, or a 1:8 dilution of the fragments was applied to each seed.

TABLE 64

Exosporium Fragment Enzyme Activity and Plant Growth Response

| Mutation | Construct | Endoglucanase Activity, Exosporium Fragments (mU/ml) | Soy Plant Growth Response, 1:2 dilution | Soy Plant Growth Response, 1:4 dilution | Soy Plant Growth Response, 1:8 dilution | Presence of Spores? |
|---|---|---|---|---|---|---|
| Wild-type BT013A | BclA 20-35 Endo | 10.3 | 93.1% | 92.2% | 83.4% | No |
| cotE KO | BclA 20-35 Endo | 269.0 | 121.4% | 110.7% | 90.7% | No |
| exsY KO | BclA 20-35 Endo | 238.0 | 107.7% | 89.1% | 90.7% | No |
| CotO NTD dominant | BclA 20-35 Endo | 22.4 | 99.6% | N/A | N/A | No |
| CotO CTD dominant | BclA 20-35 Endo | 27.5 | 95.8% | N/A | N/A | No |

These results demonstrate that mutations that disrupt the exosporium, such as a knock-out mutation in the cotE or exsY gene, or a dominant negative mutation in the CotO protein, can be used to generate exosporium fragments that are substantially free of spores, and demonstrates that these exosporium fragments contain fusion proteins that are targeted to the exosporium. These fragments can be utilized to promote plant growth and in other applications. There was a small amount of background endoglucanase activity in the exosporium fragment preparation from the BT013 strain having no mutations and expressing the BclA 20-25 Endo construct (BT013A BclA 20-35 Endo). This was unexpected and may represent a low level of unstable exosporium that is being released from spores and captured during the exosporium fragment collection process. CotE and ExsY KO strains contain the highest amount of enzyme in the exosporium fragment fraction. The CotO dominant negative mutants that express a fusion protein also have an elevated level of enzyme in the exosporium fragment fraction as well.

The exosporium fragments from the CotE and ExsY mutants (not expressing BclA 20-35 Endo) applied directly to plants had a negative effect on growth and were removed from this experiment. When the exosporium fragments from BT013A BclA 20-35 Endo were applied to soybeans, there was a negative growth phenotype. When exosporium fragments from the CotE or ExsY mutants expressing the BclA 20-35 Endo fusion protein were added to soybeans, a substantial increase in growth rate occurred (+28.3% and +14.8% over BT013A BclA 20-35 Endo fragments). The CotE mutant exosporium fragments were still active at the 1:4 dilution, but the ExsY exosporium fragments were no longer giving a growth benefit to the soybeans at this dilution. The CotO dominant negative mutants expressing the BclA 20-35 Endo fusion protein gave a small increase in soybean growth compared to the fragments from BT013A BclA 20-35 Endo, giving +6.5% and +2.7% growth, respectively.

Example 63: Additional Demonstration of the Utility of Endophytic *Bacillus cereus* Family Members and Other Recombinant *Bacillus* Species to Deliver Peptides, Proteins, and Enzymes Endophytically to the Plant

*Bacillus thuringiensis* EE417, *Bacillus thuringiensis* EE-B00184, *Bacillus cereus* EE439, and *Bacillus* sp. EE387 were found to have the ability to grow endophytically and to be capable as serving as a host strain for the BEMD system (See Examples 52 and 53). To demonstrate the ability of these Bacilli to grow endophytically and to serve as a host strain for the BEMD system, each of these strains was transformed with the pMK4-BclA 20-35-eGFP plasmid (described above in Example 62). Spores were made and purified as described above in Example 40.

These spores were diluted to a concentration of $1\times10^8$/ml, and 1 µl of whole cell broth was then added to commercial hybrid corn seed in potting soil at planting. The corn seeds were coated with a fungicide and a biological inoculant. The corn hybrid variety was BECK 6175YE, which contains the ROUNDUP READY glyphosate resistance gene and AQUAMAX drought resistance gene. Plants were grown under artificial light for 14 hours a day and plant growth over a ten day period was determined. Plants were watered every three days over the course of the experiment.

Figure 13:
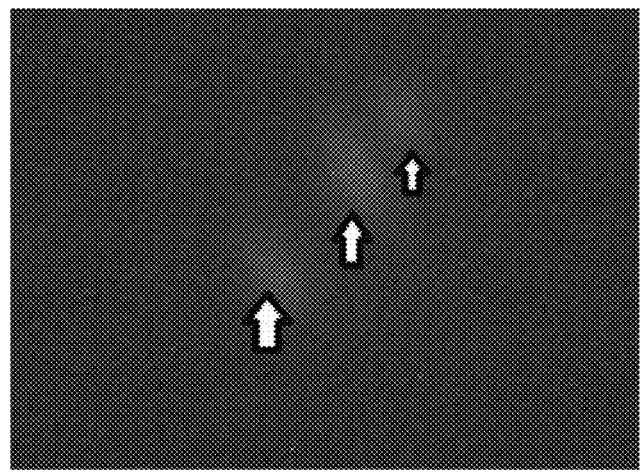
FIG. 13 provides a fluorescence microscopy image showing detection of endophytic bacteria isolated from inside of corn plants treated with *Bacillus thuringiensis* EE-B00184 expressing a fusion protein comprising amino acids 20-35 of SEQ ID NO: 1 and GFP. Arrows denote single spores.
Figure 14:
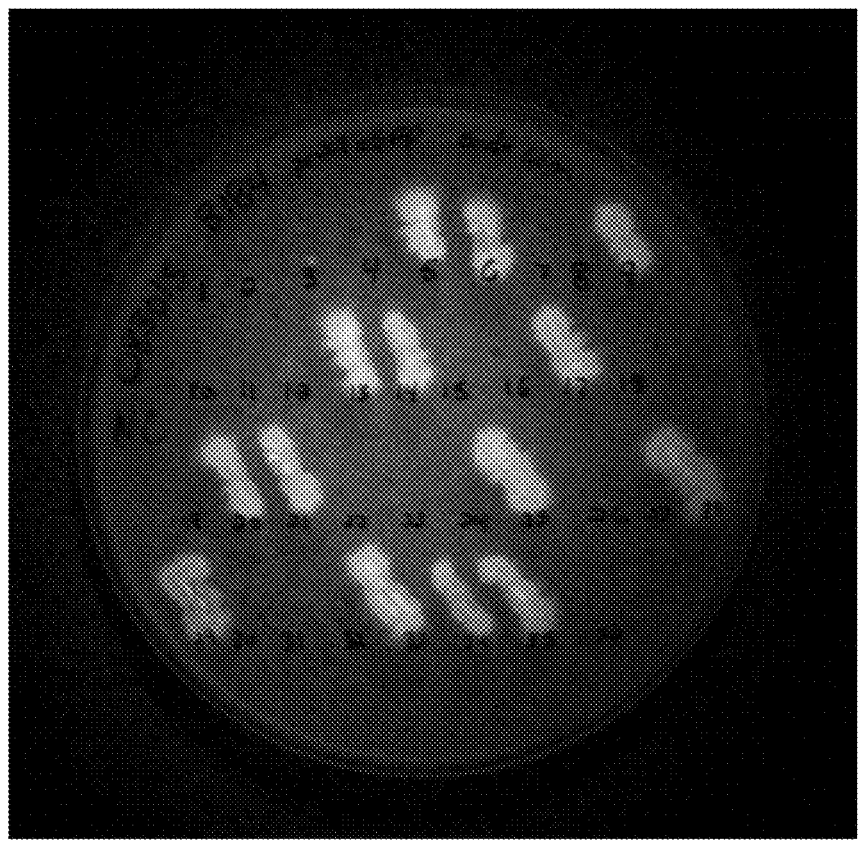
FIG. 14 provides a photograph showing fluorescence of bacterial colonies containing recombinant *Bacillus cereus* family members expressing a fusion protein comprising amino acids 20-35 of SEQ ID NO: 1 and GFP, isolated from inside of corn plants grown from seeds coated with the recombinant bacteria.

*Bacillus thuringiensis* EE417, *Bacillus thuringiensis* EE-B00184, *Bacillus cereus* EE439, and *Bacillus* sp. EE387, expressing the BclA 20-35-eGFP were then isolated from the inside of the corn plants. The ten day old plants were extracted from the soil and washed to remove excess debris. The plants were then inverted, washed in water, exposed to 5% bleach for ten minutes, washed in water, exposed to 70% ethanol for ten minutes, washed again in water, and the stalks split with a sterile razor blade. The split halves of the stalks were placed face down onto nutrient agar plates for two hours at 30° C. After two hours, the stalks were removed, and the agar plates incubated at 30° C. for 48 hours. After 48 hours, the plates were examined for colony morphology, and *Bacillus* colonies found internal to the plant were toothpicked onto nutrient agar and nutrient agar plus chloramphenicol plates (to select for bacteria containing the pMK4-20-35 BclA-eGFP plasmid). Results are shown in Table 65. These results demonstrate the ability of the BEMD system to be introduced into the target plant by expression in an endophytic strain of the *Bacillus cereus* family. FIG. 13 also demonstrates the ability of *Bacillus thuringiensis* EE-B00184 to express eGFP on the spores, as evidenced by fluorescent microscopy. In FIG. 13, arrows denote single spores. FIG. 14 demonstrates the ability of the isolated bacterial colonies from plants to fluoresce green, demonstrating that they do in fact deliver the protein of interest (herein eGFP) inside the plants. FIG. 14 shows fluorescence of colonies of endophytic bacteria isolated from inside corn plants on plates, illuminated with a GFP filtered lamp.

TABLE 65

Endophytic delivery of "cargo" proteins

| Strain | Endo-phytic | "Cargo" | % Bacillus colonies + for plasmid | % Bacillus colonies + for eGFP |
|---|---|---|---|---|
| Bacillus thuringiensis EE417 | Yes | BclA 20-35 eGFP | 29.8% | 29.8% |
| Bacillus thuringiensis EE-B00184 | Yes | BclA 20-35 eGFP | 38.9% | 38.9% |
| Bacillus sp. EE387 | Yes | BclA 20-35 eGFP | 50% | 50% |
| Bacillus cereus EE439 | Yes | BclA 20-35 eGFP | 23.9% | 23.9% |

To further demonstrate the ability of these endophytic strains to express proteins on the surface of the spores, the following constructs were introduced into Bacillus sp. EE387: pHP13 plasmid with endoglucanase fused to either: BclA 20-35, CotB, CotG, CotC, CgeA, InhA, InhA2, InhA1, CotY, or AcpC (amino acids 20-25 of SEQ ID NO: 1 or SEQ ID NOs. 252, 256, 253, 254, 108, 121, 114, 111, and 120, respectively). The pSUPER BclA-20-35 Endo construct described above in Example 58 was also introduced into Bacillus thuringiensis EE-B00184, another endophytic strain. Transformed cells were screen by PCR and Sanger sequencing. Spores for each of these constructs was made by growing up an overnight culture in BHI plus selection (chloramphenicol), and 500 µl of each culture was swabbed onto nutrient broth agar plates and allowed to incubate at 30° C. for 3 days. After 3 days, the spores were swabbed off into PBS, diluted to a concentration of $1\times10^8$/ml, spun down to recover the spores, and enzyme measurement of the spores was performed as described above in Example 58. The enzyme concentration was calculated as mU/ml for each construct. The ability of Bacillus sp. EE387 to express fusion proteins on its spore surface is indicated by the levels of enzyme. Bacillus sp. EE387 was able to express all of the spore fusion proteins on its surface, but AcpC (SEQ ID NO: 120) was a superior fusion protein for this strain. This finding was surprising since Bacillus sp. EE387 is not a Bacillus cereus family member strain and does not have an exosporium, yet exhibited surface expression of fusion proteins containing exosporium proteins or targeting sequences derived from exosporium proteins (e.g., CotY, AcpC, and amino acids 20-35 of SEQ ID NO: 1).

TABLE 66

Endophytic strains Bacillus sp. EE387 (EE387) and Bacillus thuringiensis EE-B00184 (EE-B00184) expressing fusion proteins

| Exosporium Protein or Targeting Sequence Fusion Partner | Host Endophytic Strain | Endoglucanase activity (mU/ml) |
|---|---|---|
| CotB (SEQ ID NO: 252) | EE387 | 4.0 |
| CotG (SEQ ID NO: 256) | EE387 | 4.2 |
| CotC (SEQ ID NO: 253) | EE387 | 4.4 |
| CgeA (SEQ ID NO: 254) | EE387 | 4.1 |
| AA 20-35 of SEQ ID NO: 1 | EE387 | 16.3 |
| InhA (SEQ ID NO: 108) | EE387 | 7.5 |
| InhA2 (SEQ ID NO: 121) | EE387 | 6.0 |
| CotY (SEQ ID NO: 111) | EE387 | 4.9 |
| AcpC (SEQ ID NO: 120) | EE387 | 36.0 |
| InhA (SEQ ID NO: 114) | EE387 | 4.5 |
| AA 20-35 of SEQ ID NO: 1 | EE-B00184 | 95.8 |

These endophytic strains can also be administered to the plant through addition into the plant growth medium, including soil, irrigation, and granular formulations. Endophytic strains can also enter the target plant through the aerial portions of the plants. These create a unique and effective delivery mechanism for delivering proteins and peptides of interest into the plant, or in the case of DNA and RNA binding proteins, delivering RNA and DNA into the plant.

These data, in Bacillus sp. EE387 also demonstrate demonstrates that amino acids 20-35 of BclA (SEQ ID NO: 1), and SEQ ID NOs. 108, 121, and 120 all have noticeably positive data in Bacillus strains outside of the Bacillus cereus family. Bacillus thuringiensis EE-B00184 is also an exceptional host expression system. These levels are both noticeable and positive, indicating a conserved mechanism for attachment may be present in other Bacillus species for these proteins.

Spore Surface Expression of Bacillus thuringiensis EE-B00184.

Bacillus thuringiensis EE-B00184 was transformed with pSUPER BclA 20-35 eGFP, and allowed to sporulate as described above. Spores were pelleted, washed, and subjected to fluorescence microscopy to demonstrate the spore surface laden with eGFP proteins in FIG. 13.

Example 64: Expression of Fusion Proteins in Herbicide- and Pesticide-Degrading Bacillus Cereus Family Member Strains Examples 49 and 51 above demonstrate the ability of the herbicide-degrading strain Bacillus cereus family member EE349 in both degrading herbicides and serving as a host strain for expression of a fusion protein attached the exosporium of its spores. To further demonstrate the ability of herbicide-degrading strains to produce enzyme laden exosporium on their spores, we introduced the pHP13 CotC-Endo (SEQ ID NO: 253), pSUPER AcpC-Endo (SEQ ID NO: 120), pSUPER InhA2-Endo (SEQ ID NO: 121) and pSUPER 23-38 SEQ ID NO:5-Endo) into Bacillus cereus family member EE-B00377. A description of pHP13 CotC-Endo can be found in Example 54, a description of pSUPER AcpC-Endo and pSUPER InhA2-Endo can be found in Example 59, and a description of pSUPER 23-38 SEQ ID NO:5-Endo can be found in Example 58. Bacillus cereus family member EE-B00377 was identified as a potent degrader of pyrethrin, dicamba, and 2,4-D. Herbicide and pesticide degradation was verified by both growth on the herbicide or pesticide as a nutrient source, as well as by reduction of dicamba and 2,4-D in the presence of the herbicide or pesticide-degrading strain. Plasmids were made and cells transformed identically to Example 48 above. Each construct was verified by Sanger sequencing. Spores were created by using the sporulation media and conditions outlined in Example 48. Enzyme activity was also performed as in Example 58 above.

TABLE 67

Enzyme expression levels of fusion proteins in pesticide degrading strain Bacillus cereus family member EE-B00377.

| Expression Construct | Endoglucanase activity (mU/ml) |
|---|---|
| CotC-Endo (SEQ ID NO: 253) | 46.9 |
| AcpC-Endo (SEQ ID NO: 120) | 4.3 |
| pSUPER 23-38 SEQ ID NO: 5-Endo | 108 |

As can be seen in Table 67, Bacillus cereus family member EE-B00377 is able to produce endoglucanase and display the endoglucanase on its exosporium using several different exosporium proteins or targeting sequences. Of the constructs tested, amino acids 23-38 of SEQ ID NO: 5 or SEQ ID NO: 253 gave the highest enzymes levels in this strain.

This example demonstrates the ability of the spore displayed system to be expressed in herbicide- and pesticide-degrading strains. This system can be used to express other target proteins on the surface of the spores, including those that act on herbicides or pesticides themselves, such as herbicide-degradation enzymes, pesticide-degradation enzymes, metabolic enzymes, reductases, oxidases, and other useful enzymes for the breakdown of pesticides alone or in the presence of plants.

Example 65: Use of Free Nitric Oxide Synthase (NOS) and Spore-Bound NOS to Enhance Plant Germination Example 40 demonstrates the ability of nitric oxide synthatase (NOS) from *Bacillus subtilis* 168 to stimulate germination when attached to the exosporium of *Bacillus cereus* family members, and delivering that NOS—spore protein fusion to seeds or in the vicinity of seeds. In this example, free NOS from *Bacillus thuringiensis* BT013A (SEQ ID NO: 261) and free eNOS (epithelial NOS from bovine neutrophils, Sigma-Aldrich, Cat No N1533) can also help induce germination, or increased outgrowth of seeds exposed to NOS. The pHP13 BclA-BT NOS, pHP13 BclA-BS NOS, and pHP13 BclA-SODA (superoxide dismutase) plasmids were made in identical fashion to pHP13 BclA-BS NOS that described in Example 40 and were transformed into *Bacillus thuringiensis* BT013A. pHP13 BclA-BT NOS contains the BclA promoter, start codon, BclA amino acids 20-3 5, a 6 alanine linker, and the *Bacillus thuringiensis* BT013A NOS gene (see Table 9, SEQ ID NO: 263). pHP13 BclA-BS NOS contains the BclA promoter, start codon, BclA amino acids 20-3 5, a 6 alanine linker, and the *Bacillus subtilis* 168 NOS gene (see Table 9, SEQ ID NO: 264). pHP13 BclA-SODA contains the BclA promoter, BclA amino acids 20-35, a 6 alanine linker, and the *Bacillus cereus* superoxide dismutase 1 (SODA1) gene (SEQ ID NO: 155).

Table 68 shows the results of a soil germination assay. In this assay, commercial variety BECK'S 294NR (ROUNDUP READY) was coated with either 1 μl water (control) or 1 μl of water spiked with 34.2 mU of Bovine Neutrophil eNOS. 50 seeds of each were then planted and grown as described in Example 58, but with 4 seeds per pot. After 7 days, the plants were measured for height. As can be seen in Table 68, the presence of the eNOS allowed for increased outgrowth of the seeds, leading to a 30.7% increase in shoot height of the treated soybeans.

TABLE 68

Influence of free eNOS on plant height in soybeans.

| Treatment | Height Normalized to Control |
|---|---|
| $H_2O$, 1 μl/seed | 100.0% |
| $H_2O$ with 34.2 mU eNOS/seed | 130.7% |

In addition to the soil germination test described above, standard germination assays were performed as described in Example 40. For soybeans, we choose 2 year old soybean seed with a lower germination rate, and coated 1 μl on each of 50 seeds with the treatments. Treatments were $H_2O$ control (water), L-arginine, *Bacillus thuringiensis* BT013A (strain control), *Bacillus thuringiensis* BT013A with pHP13 BclA-BT NOS, and *Bacillus thuringiensis* BT013A with pHP13 BclA BS NOS. The results for soybeans are shown in Table 69 below.

TABLE 69

Influence of spore-displayed NOS on germination rate in soybeans.

| Treatment | Germination Rate |
|---|---|
| $H_2O$, 1 μl/seed | 38% |
| $H_2O$ Control with L-Arginine | 58% |
| *Bacillus thuringiensis* BT013A (strain control) | 52% |
| *Bacillus thuringiensis* BT013A with BS NOS | 82% |
| *Bacillus thuringiensis* BT013A with BT NOS | 54% |

Standard germination assays were also performed as described above for commercial hybrids of sorghum. Each sorghum seed was coated with 0.5 μl on each of 50 seeds with the treatments. Treatments were $H_2O$ control (water), L-arginine, *Bacillus thuringiensis* BT013A (strain control), *Bacillus thuringiensis* BT013A with pHP13 BclA-BS NOS, *Bacillus thuringiensis* BT013A with pHP13 BclA-BT NOS. After 4 days, the seeds were measured for shoot height and root length to examine increased outgrowth of the seeds, and all data were normalized to the water control. The results are shown in Table 70 below. The addition of either BT NOS or BS NOS led to a greatly increased root length and shoot growth, with the difference most evident in the BS NOS treatment.

TABLE 70

Spore bound NOS and increased *sorghum* outgrowth

| Treatment | Root Growth (Normalized) | Shoot Growth (Normalized) |
|---|---|---|
| $H_2O$, 1 μl/seed | 100.0% | 100.0% |
| $H_2O$ Control with L-Arginine | 109% | 89% |
| *Bacillus thuringiensis* BT013A (strain control) | 75% | 145% |
| *Bacillus thuringiensis* BT013A with BS NOS | 163% | 293% |
| *Bacillus thuringiensis* BT013A with BT NOS | 141% | 190% |

The sorghum experiment above was repeated, but with slightly different treatments. Treatments were $H_2O$ control (water), *Bacillus thuringiensis* BT013A (strain control), *Bacillus thuringiensis* BT013A with pHP13 BclA-SODA, or free bovine eNOS. After 4 days, the seeds were measured for shoot height and root length to look at increased outgrowth of the seeds, and all data normalized to the water control. The results are shown in Table 71 below. The addition of either BT SODA or free NOS (eNOS) leads to a greatly increased root length and shoot growth.

TABLE 71

Spore bound SODA and free NOS and increased *sorghum* outgrowth

| Treatment | Root Growth (Normalized) | Shoot Growth (Normalized) |
|---|---|---|
| $H_2O$, 0.5 μl/seed | 100.0% | 100.0% |
| *Bacillus thuringiensis* BT013A (strain control) | 79% | 117% |
| *Bacillus thuringiensis* BT013A with pHP13 BclA-SODA 1 | 125% | 228% |
| Free eNOS, 34.2 mU/seed | 123% | 311% |

Taken together, these results demonstrate that overexpression of nitric oxide synthatases from multiple sources can be added to seeds and increase their germination rate and outgrowth of seeds, in both soil and traditional germination methods. This effect can is also found when adding free NOS to seeds. The addition of superoxide dismutase with the spores also leads to an increase in the outgrowth of seeds. L-arginine assisted in the germination rate increases when utilized alone, or assisted in a lesser extent when mixed with NOS enzymes.

The NOS genes are prevalent in a variety of microorganisms, and these microorganisms can be genetically modified to enhance their ability to express NOS on the seed, or in the vicinity of the seed in plant growth media. Expression of NOS on a spore leads provides a superior delivery system, as vegetative microorganisms are more fragile and do not survive on the seed for long periods of time. Expression on spores using the targeting sequences, exosporium proteins, exosporium protein fragments, and spore coat proteins described herein would all be viable ways of delivery the NOS to seeds.

Example 66: Modulation of Enzyme Expression and Plant Growth

As demonstrated in Examples 44, 45, and 46, overexpression of a modulator protein in a recombinant *Bacillus cereus* family member that co-expresses a fusion protein can lead to increased and decreased levels of that fusion protein being incorporated into the exosporium. Fusion proteins and constructs were made and spores made as described above in Examples 44 and 45. Growth assays were performed as described above in Example 46.

As can be seen in Table 72, expression of the pSUPER BclA 20-35 Endo fusion proteins on the surface of the *Bacillus thuringiensis* BT013A spores using amino acids 20-35 of SEQ ID NO: 1 as the targeting sequence led to increased growth in corn, soy, and squash. This effect can be increased when a second exosporium protein is overexpressed. Each of the CotO, BxpB, and YjcB overexpression strains had a pronounced effect on corn, soy, and/or squash growth, with increases most prominent in corn.

TABLE 72

Spore bound SODA and free NOS and increased *sorghum* outgrowth

| Treatment | Corn Growth | Soy Growth | Squash Growth |
| --- | --- | --- | --- |
| H₂O, 1.0 µl/seed | 100.0% | 100.0% | 100.0% |
| *Bacillus thuringiensis* BT013A with pSUPER BclA 20-35 Endo (Base) | 103.8% | 108.8% | 105.8% |
| Base with pHP13 BclA-CotO | 109.6% | 106.4% | 105.2% |
| Base with pHP13 BclA-BxpB | 106.8% | 117.2% | 113.9% |
| Base with pHP13 BclA-YjcB | 110.4% | 122.4% | 106.7% |

Overexpression of other modulator proteins can also modulate fusion protein expression levels as well as plant growth effects, including those described herein and in Examples 44 and 45 above. Each of these can be used to alter or tailor the enzyme levels to desired effective levels.

Example 67: Overexpression of Exosporium Proteins and Effects of on Plants

Overexpression of naturally occurring spore and exosporium proteins can impact the effect that plant growth promoting, endophytic, and other *Bacillus cereus* family members have on plants. Expression of various exosporium proteins as part of a fusion protein or as free enzyme can have beneficial effects on plants, as illustrated above for phosphatases (Examples 11 and 36), nitric oxide synthatase (Example 65), and proteases such as InhA (Examples 3, 6, 7, 13). Other exosporium and spore proteins, such as alanine racemase and inosine uridine preferring hydrolases, can prevent or delay germination of spores, and their overexpression will make spore less prone to quick germination, an unwanted side effect in the use of many types of spores. Lastly, spores that overexpress certain exosporium proteins can alter the overall assembly of the exosporium, leading to alterations in the binding of spores to plants. An example of this can be seen in Table 73 below.

Spores were created as described for *Bacillus thuringiensis* BT013A in Example 58. Growth assays were performed by placement of 1 µl of whole cell broth from each construct per corn seed, or 2 µl per squash seed. Treatment of seeds, planting, and data recording was performed as in Example 58.

*Bacillus mycoides* strain EE155, a plant growth promoting strain of the *Bacillus cereus* family, was transformed with overexpression plasmids as described in Example 44. Overexpression of exosporium proteins in this strain directly led to an increase in the binding of the spores to the plant, and leads to higher plant growth promotion. Specifically, overexpression of BclB, BclA, CotO, CotE led to enhanced plant growth promotion. Other exosporium proteins can be overexpressed that can lead to alterations in the structure of the exosporium, including ExsY, ExsFA/BxpB, CotY, CotO, ExsFB, InhA1, InhA2, ExsJ, ExsH, YjcA, YjcB, BclC, AcpC, InhA3, alanine racemase 1, alanine racemase 2, BclA, BclB, BxpA, BclE, BetA/BAS3290, CotE, ExsA, ExsK, ExsB, YabG, Tgl, superoxide dismutase 1 (SODA1), and superoxide dismutase 2 (SODA2). Overexpression or mutation of any of these genes will lead to alterations of exosporium structure, and lead to potentiating the plant growth benefits associated with members of the *Bacillus cereus* family.

TABLE 73

Overexpression of exosporium proteins in *Bacillus mycoides* EE155

| Bacteria | Overexpression protein on plasmid pHP13 | Squash Growth (Normalized to control) | Corn Growth (Normalized to control) |
| --- | --- | --- | --- |
| *Bacillus mycoides* B155 | N/A (Control) | 100% | 100% |
| *Bacillus mycoides* B155 | BclB | 116.3% | 101.4% |
| *Bacillus mycoides* B155 | BclA | 106.8% | 108.5% |
| *Bacillus mycoides* B155 | CotE | 134.5% | 106.3% |
| *Bacillus mycoides* B155 | CotO | 118.6% | 111.7% |

Example 68: Plant Tissues Binding Through Use of Exosporium Displayed Binding Proteins Spores that are useful for the display of exogenous and endogenous proteins can be utilized as fusion partners to enhance spore binding to surfaces, including plant tissue. To demonstrate this attribute, *Bacillus thuringiensis* BT013A spores were transformed with plasmids pSUPER BclA 20-35 TasA, pSUPER BclA 20-35 Expansin, pSUPER BclA 20-35 Endo, and pSUPER BclA 20-35 Control. TasA and expansin are plant binding proteins. The control plasmid contained the BclA promoter, a start codon and amino acids 20-35 of SEQ ID NO: 1, but did not include a fusion partner. These constructs were prepared as in identical fashion to the others described in above in Example 58.

To perform the tissue binding assay, 2 week old corn plants and 3 week old soybean plants were grown as described in Example 58, but without any seed treatment. The primary leaf and first trifoliate of the plants was then swabbed with 1 ml of spores containing each of the above constructs. The leaves were allowed to dry, clipped from the plants and placed into a 50 ml conical tube with 10 ml of water, and vortexed heavily. The spores that were released from the leaf into the water were counted on a hemacytometer, and the counts compared to those expected if no spores bound to the leaves. This experiment was repeated in ten times, and a second experiment was performed which involved plating of the water onto antibiotic plates (tetracycline plus nutrient agar) overnight at 30° C. The final counts are shown in Table 74.

TABLE 74

Plant tissue binding is increased with binding protein expression on spores

| Treatment (Construct) | Crop | Overall Binding % | Change in Binding from control | Binding % (plate assay) | Change in Binding from control |
|---|---|---|---|---|---|
| Control (BclA 20-35 Control) | Corn | 42.9% | N/A | 0% | N/A |
| BclA 20-35 Endoglucansae | Corn | 75.9% | +33% | 15.6% | +15.6% |
| BclA 20-35 Expansin | Corn | 38.4% | −4.5% | 41.1% | +41.1% |
| BclA 20-35 TasA | Corn | 54.9% | +12% | 100% | +100% |
| Control (BclA 20-35 Control) | Soy | 58.3% | N/A | 65.2% | N/A |
| BclA 20-35 Endoglucansae | Soy | 93.7% | +35.4% | 61% | −4.2% |
| BclA 20-35 Expansin | Soy | 87.9% | +29.6% | 99.1% | +33.9 |
| BclA 20-35 TasA | Soy | 75.7% | +20.8% | 91.7% | +26.5% |

As can be seen from Table 74, the control BT013A spores have a high affinity for the BT013A spores for soybeans, with 58.3% and 65.2% of the spores bound for the controls. Despite this, expression of endoglucanase, expansin, or TasA on the surface of the spores led to an increase in binding of spores to the soy leaves, with many spore preparations approaching 100% bound to the leaves. In corn, there was much less binding for the control spores, especially in the plate assay. The results from the plate assay are the most striking, with an increase in each of the expression constructs, with TasA at 100% of spores bound in that assay.

These binding proteins can also be utilized in any of the recombinant spore forming microorganisms, utilizing any of the expression systems or fusion partners described herein. This system would also be useful in conjunction with the exosporium strips, to create a protein delivery system that is both cell free and binds tightly to leaves.

Example 69: Use of Recombinant Spore-Forming Bacteria Expressing Fusion Proteins Containing Cot/Cge Proteins and an Enzyme for Promoting Plant Growth Coat proteins form protein layers that are found on all *Bacillus* species spores described to date, as well as related genera Virginibacillus, *Lysinibacillus*, Clostridia, and *Paenibacillus*. Fusion of proteins or peptides of interest to the coat proteins allows expression of foreign proteins on the surface of the spore, and delivery of these proteins or peptides of interest to plants. To demonstrate the ability of the coat proteins to deliver enzymes to plants, a series of constructs were created. The pHP13 plasmid from the *Bacillus* Genetic Stock Culture collection was used to clone each of the constructs described below into the multiple cloning site using homologous recombination utilizing their native promoter elements.

CotB, CotG, and CotC from *Bacillus subtilis* M01099 or CgeA from *Bacillus amyloliquefaciens* was fused in frame with the endoglucanase eglS gene from *Bacillus subtilis* 168, the lipA lipase gene from *Bacillus subtilis* 168, or the pc-plc gene from *Bacillus thuringiensis* BT013A. These constructs were cloned into pHP13 via homologous recombination, verified by Sanger sequencing, and transformed into *Bacillus subtilis* EE405, *Bacillus subtilis* A09, *Bacillus cereus* family member EE439, *Bacillus* sp. EE398, or *Bacillus thuringiensis* EE-B00184. Each transformant was also screened for correct clones by Sanger sequencing. After confirmation of the clones, each clone was grown up in brain heart infusion broth (BHI) plus tetracycline (10 μg/ml) overnight at 30° C., and 100 μl of the overnight culture was swabbed onto nutrient agar plates plus tetracycline. These plates were incubated at 30° C. for 3 days, and spores were collected by swabbing with a water-wettened cotton swab and resuspended in water.

Spores for endoglucanase assays were then diluted to $1\times10^8$ CFU/ml in water, and assayed for enzyme activity by utilizing the chromophore 4 chloro 2 nitrophenyl cellotetrose (4C2NC, 3 mM in water). For this method, 50 μl of spores was placed into a 96 well plate, and 50 μl of a 300 nM 4C2NC solution added to each plate. The plate was then incubated at 30° C. and absorbance at 410 nm read after 0.5 hours. In all cases, the respective strain control absorbance was subtracted out of the total absorbance of each clone to negate any background activity.

Spores for lipases assays were diluted to $1\times10^8$ CFU/ml in water, and assayed for enzyme activity in a second method utilizing the chromophore 4-nitrophenyl palmitate (4NP, 3 mM in water). For this method, 50 μl of spores was placed into a 96 well plate, and 50 μl of a 300 nM 4NP solution added to each plate. The plate was then incubated at 30° C. and absorbance at 410 nm read after 0.5 hours. In all cases, the respective strain control absorbance was subtracted out of the total absorbance of each clone to negate any background activity.

Spores for phospholipase assays were diluted to $1\times10^8$ CFU/ml in water, and assayed for enzyme activity as described above for phospholipase in Example 58. In all cases, the respective strain control absorbance was subtracted out of the total absorbance of each clone to negate any background activity.

Plant growth responses and treatments were applied and collected as described for squash in Example 58 above. All heights were normalized against a strain control with no enzyme displayed on the spores.

TABLE 75

Coat protein fusions and their enzyme expression levels.

| Treatment (Construct) | Fusion partner for endo | Endoglucanase Enzyme Activity, (Absorbance minus control) | Lipase Enzyme Activity, (Absorbance minus control) | Phospholipase Enzyme Activity, (Absorbance minus control) | Plant growth response above strain control, Squash |
|---|---|---|---|---|---|
| Bacillus subtilis A09 Strain Control | N/A | 0.0 | 0.0 | 0.0 | 100% |
| A09 | CotB | 0.01 | 0.03 | .198 | 101.5% |
| A09 | CotG | ND | .117 | .196 | 101.0% |
| A09 | CotC | 0.09 | .069 | .154 | 99.4% |
| A09 | CgeA | 0.13 | 0 | .218 | ND |
| Bacillus subtilis EE405 Strain Control | N/A | 0.0 | 0.0 | 0.0 | 100% |
| EE405 | CgeA | 1.84 | ND | ND | 104.7% |
| B. thuringiensis EE184 strain control | N/A | 0.0 | 0.0 | 0.0 | 100% |
| EE184 | CotB | 2.42 | .262 | 1.37 | 95.5% |
| EE184 | CotG | 2.41 | 0 | .330 | 105% |
| EE184 | CotC | 2.00 | 0.08 | .373 | 119.4% |
| EE184 | CgeA | 2.70 | .520 | 0 |

```
            20                  25                  30

Ile Pro Pro Phe Thr Leu Pro Thr Gly Pro Thr Gly Pro Phe Thr Thr
            35                  40                  45

Gly Pro Thr Gly Pro Thr Gly Pro Thr Gly Pro Thr Gly Pro Thr Gly
        50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
            115                 120                 125

Gly Pro Thr Gly Pro Thr Gly Pro Thr Gly Pro Thr Gly Asp Thr Gly
            130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
            195                 200                 205

Ile Ser Leu Asp Leu Gly Ile Asn Asp Pro Val Pro Phe Asn Thr Val
            210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
                245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
            275                 280                 285

Pro Phe Thr Ile Val Ile Gln Ala Ile Thr Gln Ile Thr Thr Thr Pro
            290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
            325                 330

<210> SEQ ID NO 3
<211> LENGTH: 33
<212> TYPE: PRT
<213> ORGANISM: Bacillus anthracis

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly

<210> SEQ ID NO 4
<211> LENGTH: 209
<212> TYPE: PRT
```

<213> ORGANISM: Bacillus anthracis

<400> SEQUENCE: 4

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Leu Gly Ile Leu Pro Val Phe
65                  70                  75                  80

Gly Thr Ile Thr Thr Asp Val Gly Ile Gly Phe Ser Val Ile Val Asn
                85                  90                  95

Thr Asn Ile Asn Phe Thr Leu Pro Gly Pro Val Ser Gly Thr Thr Leu
            100                 105                 110

Asn Pro Val Asp Asn Ser Ile Ile Ile Asn Thr Thr Gly Val Tyr Ser
        115                 120                 125

Val Ser Phe Ser Ile Val Phe Val Ile Gln Ala Ile Ser Ser Ser Ile
    130                 135                 140

Leu Asn Leu Thr Ile Asn Asp Ser Ile Gln Phe Ala Ile Glu Ser Arg
145                 150                 155                 160

Ile Gly Gly Gly Pro Gly Val Arg Ala Thr Ser Ala Arg Thr Asp Leu
                165                 170                 175

Leu Ser Leu Asn Gln Gly Asp Val Leu Arg Val Arg Ile Arg Glu Ala
            180                 185                 190

Thr Gly Asp Ile Ile Tyr Ser Asn Ala Ser Leu Val Val Ser Lys Val
        195                 200                 205

Asp

<210> SEQ ID NO 5
<211> LENGTH: 44
<212> TYPE: PRT
<213> ORGANISM: Bacillus anthracis

<400> SEQUENCE: 5

Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
        35                  40

<210> SEQ ID NO 6
<211> LENGTH: 647
<212> TYPE: PRT
<213> ORGANISM: Bacillus anthracis

<400> SEQUENCE: 6

Val Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45

```
Ala Thr Gly Asn Thr Gly Pro Thr Gly Glu Thr Gly Ala Thr Gly Ser
 50                  55                  60

Ala Gly Ile Thr Gly Ser Thr Gly Pro Thr Gly Asn Thr Gly Gly Thr
 65                  70                  75                  80

Gly Ser Thr Gly Pro Thr Gly Asn Thr Gly Ala Thr Gly Ser Thr Gly
                 85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
            115                 120                 125

Gly Ser Thr Gly Val Thr Gly Ser Thr Gly Ala Thr Gly Ser Thr Gly
            130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175

Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
            195                 200                 205

Thr Gly Val Thr Gly Ser Thr Gly Pro Thr Gly Ser Thr Gly Val Thr
            210                 215                 220

Gly Ser Thr Gly Pro Thr Gly Ser Thr Gly Val Thr Gly Ser Thr Gly
225                 230                 235                 240

Val Thr Gly Asn Met Gly Pro Thr Gly Ser Thr Gly Val Thr Gly Asn
                245                 250                 255

Thr Gly Ser Thr Gly Thr Thr Gly Ala Thr Gly Glu Thr Gly Pro Met
            260                 265                 270

Gly Ser Thr Gly Ala Thr Gly Thr Thr Gly Pro Thr Gly Glu Thr Gly
            275                 280                 285

Glu Thr Gly Glu Thr Gly Gly Thr Gly Ser Thr Gly Pro Thr Gly Asn
            290                 295                 300

Thr Gly Ala Thr Gly Ser Thr Gly Val Thr Gly Ser Thr Gly Val Thr
305                 310                 315                 320

Gly Ser Thr Gly Val Thr Gly Glu Thr Gly Pro Thr Gly Ser Thr Gly
            325                 330                 335

Ala Thr Gly Asn Thr Gly Pro Thr Gly Glu Thr Gly Gly Thr Gly Ser
            340                 345                 350

Thr Gly Ala Thr Gly Ser Thr Gly Val Thr Gly Asn Thr Gly Pro Thr
            355                 360                 365

Gly Ser Thr Gly Val Thr Gly Asn Thr Gly Ala Thr Gly Glu Thr Gly
            370                 375                 380

Pro Thr Gly Asn Thr Gly Ala Thr Gly Asn Thr Gly Pro Thr Gly Glu
385                 390                 395                 400

Thr Gly Val Thr Gly Ser Thr Gly Pro Thr Gly Glu Thr Gly Val Thr
            405                 410                 415

Gly Ser Thr Gly Pro Thr Gly Asn Thr Gly Ala Thr Gly Glu Thr Gly
            420                 425                 430

Ala Thr Gly Ser Thr Gly Val Thr Gly Asn Thr Gly Ser Thr Gly Glu
            435                 440                 445

Thr Gly Pro Thr Gly Ser Thr Gly Pro Thr Gly Ser Thr Gly Ala Thr
450                 455                 460

Gly Val Thr Gly Asn Thr Gly Pro Thr Gly Ser Thr Gly Ala Thr Gly
```

```
            465                 470                 475                 480
Ala Thr Gly Ser Thr Gly Pro Thr Gly Ser Thr Gly Thr Thr Gly Asn
                    485                 490                 495

Thr Gly Val Thr Gly Asp Thr Gly Pro Thr Gly Ala Thr Gly Val Ser
            500                 505                 510

Thr Thr Ala Thr Tyr Ala Phe Ala Asn Asn Thr Ser Gly Ser Val Ile
            515                 520                 525

Ser Val Leu Leu Gly Gly Thr Asn Ile Pro Leu Pro Asn Asn Gln Asn
530                 535                 540

Ile Gly Pro Gly Ile Thr Val Ser Gly Gly Asn Thr Val Phe Thr Val
545                 550                 555                 560

Ala Asn Ala Gly Asn Tyr Tyr Ile Ala Tyr Thr Ile Asn Leu Thr Ala
                565                 570                 575

Gly Leu Leu Val Ser Ser Arg Ile Thr Val Asn Gly Ser Pro Leu Ala
                580                 585                 590

Gly Thr Ile Asn Ser Pro Thr Val Ala Thr Gly Ser Phe Ser Ala Thr
                595                 600                 605

Ile Ile Ala Ser Leu Pro Ala Gly Ala Ala Val Ser Leu Gln Leu Phe
                610                 615                 620

Gly Val Val Ala Leu Ala Thr Leu Ser Thr Ala Thr Pro Gly Ala Thr
625                 630                 635                 640

Leu Thr Ile Ile Arg Leu Ser
                645

<210> SEQ ID NO 7
<211> LENGTH: 34
<212> TYPE: PRT
<213> ORGANISM: Bacillus anthracis

<400> SEQUENCE: 7

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
                20                  25                  30

Thr Gly

<210> SEQ ID NO 8
<211> LENGTH: 366
<212> TYPE: PRT
<213> ORGANISM: Bacillus anthracis

<400> SEQUENCE: 8

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
                20                  25                  30

Thr Gly Ile Thr Gly Ala Thr Gly Ala Thr Gly Ile Thr Gly Ala Thr
                35                  40                  45

Gly Pro Thr Gly Thr Thr Gly Ala Thr Gly Ala Thr Gly Ile Thr Gly
            50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
                100                 105                 110
```

```
Pro Ala Gly Ile Thr Gly Val Thr Gly Pro Thr Gly Ile Thr Gly Ala
            115                 120                 125

Thr Gly Pro Thr Gly Thr Thr Gly Val Thr Gly Pro Thr Gly Asp Thr
        130                 135                 140

Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
            165                 170                 175

Thr Gly Leu Ala Gly Ala Thr Gly Pro Thr Gly Ala Thr Gly Leu Thr
        180                 185                 190

Gly Ala Thr Gly Ala Thr Gly Ala Thr Gly Gly Ala Ile Ile Pro
            195                 200                 205

Phe Ala Ser Gly Thr Thr Pro Ala Leu Leu Val Asn Ala Val Leu Ala
            210                 215                 220

Asn Thr Gly Thr Leu Leu Gly Phe Gly Phe Ser Gln Pro Gly Ile Ala
225                 230                 235                 240

Pro Gly Val Gly Gly Thr Leu Thr Ile Leu Pro Gly Val Val Gly Asp
            245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
            290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
            325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
            355                 360                 365

<210> SEQ ID NO 9
<211> LENGTH: 30
<212> TYPE: PRT
<213> ORGANISM: Bacillus anthracis

<400> SEQUENCE: 9

Met Asp Glu Phe Leu Ser Ser Ala Leu Asn Pro Gly Ser Val Gly
1               5                   10                  15

Pro Thr Leu Pro Pro Met Gln Pro Phe Gln Phe Arg Thr Gly
            20                  25                  30

<210> SEQ ID NO 10
<211> LENGTH: 77
<212> TYPE: PRT
<213> ORGANISM: Bacillus anthracis

<400> SEQUENCE: 10

Met Asp Glu Phe Leu Ser Ser Ala Leu Asn Pro Gly Ser Val Gly
1               5                   10                  15

Pro Thr Leu Pro Pro Met Gln Pro Phe Gln Phe Arg Thr Gly Pro Thr
            20                  25                  30

Gly Ser Thr Gly Ala Lys Gly Ala Ile Gly Asn Thr Glu Pro Tyr Trp
        35                  40                  45
```

```
His Thr Gly Pro Pro Gly Ile Val Leu Leu Thr Tyr Asp Phe Lys Ser
    50                  55                  60

Leu Ile Ile Ser Phe Ala Phe Arg Ile Leu Pro Ile Ser
65                  70                  75

<210> SEQ ID NO 11
<211> LENGTH: 39
<212> TYPE: PRT
<213> ORGANISM: Bacillus weihenstephensis

<400> SEQUENCE: 11

Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
                20                  25                  30

Pro Phe Thr Leu Pro Thr Gly
            35

<210> SEQ ID NO 12
<211> LENGTH: 299
<212> TYPE: PRT
<213> ORGANISM: Bacillus weihenstephensis

<400> SEQUENCE: 12

Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
                20                  25                  30

Pro Phe Thr Leu Pro Thr Gly Pro Thr Gly Val Thr Gly Pro Thr Gly
            35                  40                  45

Val

```
Asp Phe Ser Val Glu Gln Thr Gly Leu Gly Ile Val Leu Gly Thr Leu
            260                 265                 270

Pro Ile Asn Pro Thr Thr Thr Val Arg Phe Ala Ile Ser Thr Cys Lys
        275                 280                 285

Ile Thr Ala Val Asn Ile Thr Pro Ile Thr Met
    290                 295

<210> SEQ ID NO 13
<211> LENGTH: 39
<212> TYPE: PRT
<213> ORGANISM: Bacillus weihenstephensis
<400> SEQUENCE: 13

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly
        35

<210> SEQ ID NO 14
<211> LENGTH: 289
<212> TYPE: PRT
<213> ORGANISM: Bacillus weihenstephensis
<400> SEQUENCE: 14

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly Pro Thr Gly Pro Thr Gly Pro Thr Gly
        35                  40                  45

Pro Thr Gly Pro Thr Gly Pro Thr Gly Pro Thr Gly Pro Thr Gly Pro
    50                  55                  60

Thr Gly Pro Thr Gly Pro Thr Gly Pro Thr Gly Pro Thr Gly Leu Thr
65                  70                  75                  80

Gly Pro Thr Gly Pro Thr Gly Leu Thr Gly Pro Thr Gly Leu Thr Gly
                85                  90                  95

Pro Thr Gly Pro Thr Gly Leu Thr Gly Gln Thr Gly Ser Thr Gly Pro
            100                 105                 110

Thr Gly Ala Thr Glu Gly Cys Leu Cys Asp Cys Cys Val Phe Pro Met
        115                 120                 125

Gln Glu Val Leu Arg Gln Leu Val Gly Gln Thr Val Ile Leu Ala Thr
    130                 135                 140

Ile Ala Asp Ala Pro Asn Val Ala Pro Arg Phe Phe Leu Phe Asn Ile
145                 150                 155                 160

Thr Ser Val Asn Asp Phe Leu Val Thr Val Thr Asp Pro Val Ser Asn
                165                 170                 175

Thr Thr Phe Val Val Asn Ile Ser Asp Val Ile Gly Val Gly Phe Ser
            180                 185                 190

Leu Thr Val Pro Pro Leu Thr Leu Leu Pro Pro Ala Asp Leu Gly Cys
        195                 200                 205

Glu Cys Asp Cys Arg Glu Arg Pro Ile Arg Glu Leu Leu Asp Thr Leu
    210                 215                 220

Ile Gly Ser Thr Val Asn Leu Leu Val Ser Asn Gly Ser Ile Ala Thr
225                 230                 235                 240
```

```
Gly Phe Asn Val Glu Gln Thr Ala Leu Gly Ile Val Gly Thr Leu
                245                 250                 255

Pro Ile Pro Ile Asn Pro Pro Pro Thr Leu Phe Arg Phe Ala Ile
            260                 265                 270

Ser Thr Cys Lys Ile Thr Ala Val Asp Ile Thr Pro Thr Pro Thr Ala
        275                 280                 285

Thr

<210> SEQ ID NO 15
<211> LENGTH: 49
<212> TYPE: PRT
<213> ORGANISM: Bacillus cereus

<400> SEQUENCE: 15

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly

<210> SEQ ID NO 16
<211> LENGTH: 189
<212> TYPE: PRT
<213> ORGANISM: Bacillus cereus

<400> SEQUENCE: 16

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly Ile Thr Gly Pro Thr Phe Asn Ile Asn Phe Arg Ala Glu Lys Asn
    50                  55                  60

Val Ala Gln Ser Phe Thr Pro Pro Ala Asp Ile Gln Val Ser Tyr Gly
65                  70                  75                  80

Asn Ile Ile Phe Asn Asn Gly Gly Gly Tyr Ser Ser Val Thr Asn Thr
                85                  90                  95

Phe Thr Ala Pro Ile Asn Gly Ile Tyr Leu Phe Ser Ala Ser Ile Gly
            100                 105                 110

Phe Asn Pro Thr Leu Gly Thr Thr Ser Thr Leu Arg Ile Thr Ile Arg
        115                 120                 125

Lys Asn Leu Val Ser Val Ala Ser Gln Thr Gly Thr Ile Thr Thr Gly
    130                 135                 140

Gly Thr Pro Gln Leu Glu Ile Thr Ile Ile Asp Leu Leu Ala Ser
145                 150                 155                 160

Gln Thr Ile Asp Ile Gln Phe Ser Ala Ala Glu Ser Gly Thr Leu Thr
                165                 170                 175

Val Gly Ser Ser Asn Phe Phe Ser Gly Ala Leu Leu Pro
            180                 185

<210> SEQ ID NO 17
<211> LENGTH: 33
<212> TYPE: PRT
```

<213> ORGANISM: Bacillus cereus

<400> SEQUENCE: 17

Met Asn Glu Glu Tyr Ser Ile Leu His Gly Pro Ala Leu Glu Pro Asn
1 5 10 15

Leu Ile Gly Pro Thr Leu Pro Ser Ile Pro Pro Phe Thr Phe Pro Thr
20 25 30

Gly

<210> SEQ ID NO 18
<211> LENGTH: 84
<212> TYPE: PRT
<213> ORGANISM: Bacillus cereus

<400> SEQUENCE: 18

Met Asn Glu Glu Tyr Ser Ile Leu His Gly Pro Ala Leu Glu Pro Asn
1 5 10 15

Leu Ile Gly Pro Thr Leu Pro Ser Ile Pro Pro Phe Thr Phe Pro Thr
20 25 30

Gly Pro Thr Gly Ile Thr Gly Pro Thr Gly Ala Thr Gly Phe Thr Gly
35 40 45

Ile Gly Ile Thr Gly Pro Thr Gly Val Thr Gly Pro Thr Gly Ile Gly
50 55 60

Ile Thr Gly Pro Thr Gly Ala Thr Gly Pro Thr Gly Ile Gly Ile Thr
65 70 75 80

Gly Pro Thr Gly

<210> SEQ ID NO 19
<211> LENGTH: 39
<212> TYPE: PRT
<213> ORGANISM: Bacillus cereus

<400> SEQUENCE: 19

Met Lys Asn Arg Asp Asn Asn Arg Lys Gln Asn Ser Leu Ser Ser Asn
1 5 10 15

Phe Arg Ile Pro Pro Glu Leu Ile Gly Pro Thr Phe Pro Pro Val Pro
20 25 30

Thr Gly Phe Thr Gly Ile Gly
35

<210> SEQ ID NO 20
<211> LENGTH: 1056
<212> TYPE: PRT
<213> ORGANISM: Bacillus cereus

<400> SEQUENCE: 20

Met Lys Asn Arg Asp Asn Asn Arg Lys Gln Asn Ser Leu Ser Ser Asn
1 5 10 15

Phe Arg Ile Pro Pro Glu Leu Ile Gly Pro Thr Phe Pro Pro Val Pro
20 25 30

Thr Gly Phe Thr Gly Ile Gly Ile Thr Gly Pro Thr Gly Pro Gln Gly
35 40 45

Pro Thr Gly Pro Gln Gly Pro Arg Gly Leu Gln Gly Pro Met Gly Glu
50 55 60

Met Gly Pro Thr Gly Pro Gln Gly Val Gln Gly Ile Gln Gly Ser Val
65 70 75 80

Gly Pro Ile Gly Ala Thr Gly Pro Glu Gly Gln Gln Gly Pro Gln Gly
85 90 95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
            115                 120                 125

Gly Ile Gln Gly Ile Gln Gly Leu Gln Gly Pro Ile Gly Ala Thr Gly
            130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
            165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
            195                 200                 205

Gly Pro Ser Gly Gly Pro Pro Gly Pro Thr Gly Pro Thr Gly Ala Thr
            210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
            245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
            275                 280                 285

Gly Ile Gln Gly Ile Pro Gly Pro Thr Gly Val Thr Gly Glu Gln Gly
            290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
            325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
            355                 360                 365

Met Gly Asp Ile Gly Pro Thr Gly Pro Glu Gly Pro Glu Gly Leu Gln
            370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
            405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gly Ala Thr Gly Ile Gln Gly
            435                 440                 445

Ile Gln Gly Glu Ile Gly Ala Thr Gly Pro Glu Gly Pro Gln Gly Val
            450                 455                 460

Gln Gly Ala Gln Gly Ala Ile Gly Pro Thr Gly Met Gly Pro Gln
465                 470                 475                 480

Gly Val Gln Gly Val Gln Gly Ile Gly Ala Thr Gly Ala Gln Gly
            485                 490                 495

Val Gln Gly Pro Gln Gly Ile Gln Gly Ile Gln Gly Pro Thr Gly Ala
            500                 505                 510

-continued

```
Thr Gly Asp Met Gly Ala Thr Gly Ala Thr Gly Glu Gly Thr Thr Gly
            515                 520                 525

Pro Thr Gly Val Thr Gly Pro Thr Gly Val Thr Gly Pro Ser Gly Gly
            530                 535                 540

Pro Ala Gly Pro Thr Gly Pro Thr Gly Pro Ser Gly Pro Ala Gly Val
545                 550                 555                 560

Thr Gly Pro Ser Gly Pro Pro Gly Pro Thr Gly Ala Thr Gly Ala
            565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
            595                 600                 605

Pro Gln Gly Ile Gln Gly Val Gln Gly Glu Ile Gly Pro Thr Gly Pro
            610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
            645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
            675                 680                 685

Gly Pro Gln Gly Asp Ile Gly Leu Thr Gly Ser Gln Gly Pro Thr Gly
            690                 695                 700

Ile Gln Gly Ile Gln Gly Glu Ile Gly Pro Thr Gly Pro Glu Gly Pro
705                 710                 715                 720

Glu Gly Leu Gln Gly Pro Gln Gly Ile Gln Gly Ile Gln Gly Pro Val
            725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
            755                 760                 765

Gln Gly Val Gln Gly Ile Thr Gly Ala Thr Gly Ala Gln Gly Ala Thr
770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
            805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
            835                 840                 845

Pro Thr Gly Ala Thr Gly Glu Thr Gly Ala Thr Gly Ala Thr Gly Glu
            850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
            885                 890                 895

Pro Ala Gly Val Thr Gly Pro Ser Gly Gly Pro Pro Gly Pro Thr Gly
            900                 905                 910

Ala Thr Gly Ala Thr Gly Val Thr Gly Asp Thr Gly Ala Thr Gly Ser
            915                 920                 925

Thr Gly Val Thr Gly Ala Thr Gly Ala Thr Gly Ala Thr Gly Val Thr
```

930 935 940

Gly Leu Gln Gly Pro Gln Gly Ile Gln Gly Val Gln Gly Glu Ile Gly
945 950 955 960

Pro Thr Gly Pro Gln Gly Ile Gln Gly Pro Gln Gly Ile Gln Gly Val
965 970 975

Thr Gly Ala Thr Gly Ala Gln Gly Pro Gln Gly Ile Gln Gly Pro Gln
980 985 990

Gly Asp Ile Gly Pro Thr Gly Ser Gln Gly Ile Gln Gly Pro Gln Gly
995 1000 1005

Pro Gln Gly Ile Gln Gly Ala Thr Gly Ala Thr Gly Ala Gln Gly
1010 1015 1020

Pro Gln Gly Ile Gln Gly Pro Gln Gly Glu Ile Gly Pro Thr Gly
1025 1030 1035

Pro Gln Gly Pro Gln Gly Ile Gln Gly Pro Gln Gly Ile Gln Gly
1040 1045 1050

Pro Thr Gly
1055

<210> SEQ ID NO 21
<211> LENGTH: 39
<212> TYPE: PRT
<213> ORGANISM: Bacillus weihenstephensis

<400> SEQUENCE: 21

Met Ser Asp Lys His Gln Met Lys Lys Ile Ser Glu Val Leu Gln Ala
1 5 10 15

His Ala Leu Asp Pro Asn Leu Ile Gly Pro Pro Leu Pro Pro Ile Thr
20 25 30

Pro Phe Thr Phe Pro Thr Gly
35

<210> SEQ ID NO 22
<211> LENGTH: 365
<212> TYPE: PRT
<213> ORGANISM: Bacillus weihenstephensis

<400> SEQUENCE: 22

Met Ser Asp Lys His Gln Met Lys Lys Ile Ser Glu Val Leu Gln Ala
1 5 10 15

His Ala Leu Asp Pro Asn Leu Ile Gly Pro Pro Leu Pro Pro Ile Thr
20 25 30

Pro Phe Thr Phe Pro Thr Gly Ser Thr Gly Pro Thr Gly Ser Thr Gly
35 40 45

Ser Thr Gly Pro Thr Gly Ser Thr Gly Asn Thr Gly Pro Thr Gly Pro
50 55 60

Thr Gly Pro Pro Val Gly Thr Asn Leu Asp Thr Ile Tyr Val Thr Asn
65 70 75 80

Asp Ile Ser Asn Asn Val Ser Ala Ile Asp Gly Asn Thr Asn Thr Val
85 90 95

Leu Thr Thr Ile Pro Val Gly Thr Asn Pro Val Gly Val Gly Val Asn
100 105 110

Ser Ser Thr Asn Leu Ile Tyr Val Val Asn Asn Gly Ser Asp Asn Ile
115 120 125

Ser Val Ile Asn Gly Ser Thr Asn Thr Val Val Ala Thr Ile Pro Val
130 135 140

Gly Thr Gln Pro Phe Gly Val Gly Val Asn Pro Ser Thr Asn Leu Ile

```
145                 150                 155                 160

Tyr Val Ala Asn Arg Thr Ser Asn Asn Val Ser Val Ile Lys Gly Gly
                165                 170                 175

Thr Asn Thr Val Leu Thr Thr Ile Pro Val Gly Thr Asn Pro Val Gly
            180                 185                 190

Val Gly Val Asn Ser Ser Thr Asn Leu Ile Tyr Val Thr Asn Glu Ile
        195                 200                 205

Pro Asn Ser Val Ser Val Ile Lys Gly Gly Thr Asn Thr Val Val Ala
    210                 215                 220

Thr Ile Pro Val Gly Leu Phe Pro Phe Gly Val Gly Val Asn Ser Leu
225                 230                 235                 240

Thr Asn Leu Ile Tyr Val Val Asn Asn Ser Pro His Asn Val Ser Val
                245                 250                 255

Ile Asp Gly Asn Thr Asn Thr Val Leu Thr Thr Ile Ser Val Gly Thr
            260                 265                 270

Ser Pro Val Gly Val Gly Val Asn Leu Ser Thr Asn Leu Ile Tyr Val
        275                 280                 285

Ala Asn Glu Val Pro Asn Asn Ile Ser Val Ile Asn Gly Asn Thr Asn
    290                 295                 300

Thr Val Leu Thr Thr Ile Pro Val Gly Thr Thr Pro Phe Glu Val Gly
305                 310                 315                 320

Val Asn Ser Ser Thr Asn Leu Ile Tyr Val Ser Asn Leu Asn Ser Asn
                325                 330                 335

Asn Val Ser Val Ile Asn Gly Ser Ala Asn Thr Val Ile Ala Thr Val
            340                 345                 350

Pro Val Gly Ser Val Pro Arg Gly Ile Gly Val Lys Pro
        355                 360                 365

<210> SEQ ID NO 23
<211> LENGTH: 30
<212> TYPE: PRT
<213> ORGANISM: Bacillus weihenstephensis

<400> SEQUENCE: 23

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly
            20                  25                  30

<210> SEQ ID NO 24
<211> LENGTH: 160
<212> TYPE: PRT
<213> ORGANISM: Bacillus weihenstephensis

<400> SEQUENCE: 24

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly Pro Thr
            20                  25                  30

Gly Ser Thr Gly Ser Thr Gly Pro Thr Gly Ser Thr Gly Ser Thr Gly
        35                  40                  45

Pro Thr Gly Phe Asn Leu Pro Ala Gly Pro Ala Ser Ile Thr Leu Thr
    50                  55                  60

Ser Asn Glu Thr Thr Ala Cys Val Ser Thr Gln Gly Asn Asn Thr Leu
65                  70                  75                  80

Phe Phe Ser Gly Gln Val Leu Val Asn Gly Ser Pro Thr Pro Gly Val
```

```
                    85                  90                  95
Val Val Ser Phe Ser Phe Ser Asn Pro Ser Leu Ala Phe Met Val Pro
            100                 105                 110

Leu Ala Val Ile Thr Asn Ala Ser Gly Asn Phe Thr Ala Val Phe Leu
            115                 120                 125

Ala Ala Asn Gly Pro Gly Thr Val Thr Val Thr Ala Ser Leu Leu Asp
        130                 135                 140

Ser Pro Gly Thr Met Ala Ser Val Thr Ile Thr Ile Val Asn Cys Pro
145                 150                 155                 160

<210> SEQ ID NO 25
<211> LENGTH: 30
<212> TYPE: PRT
<213> ORGANISM: Bacillus weihenstephensis

<400> SEQUENCE: 25

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly
            20                  25                  30

<210> SEQ ID NO 26
<211> LENGTH: 69
<212> TYPE: PRT
<213> ORGANISM: Bacillus weihenstephensis

<400> SEQUENCE: 26

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly Pro Thr
            20                  25                  30

Gly Ser Thr Gly Thr Thr Gly Pro Thr Gly Ser Ile Gly Pro Thr Gly
        35

Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Ala Gly Gln Met
65                  70                  75                  80

Gly Ala Thr Gly Pro Glu Gly Gln Gly Pro Gln Gly Leu Arg Gly
                85                  90                  95

Pro Gln Gly Glu Thr Gly Ala Thr Gly Pro Gln Gly Val Gln Gly Leu
                100                 105                 110

Gln Gly Pro Ile Gly Pro Thr Gly Ala Thr Gly Ala Gln Gly Ile Gln
            115                 120                 125

Gly Ile Gln Gly Leu Gln Gly Pro Ile Gly Ala Thr Gly Pro Glu Gly
        130                 135                 140

Pro Gln Gly Ile Gln Gly Val Gln Gly Val Pro Gly Ala Thr Gly Ser
145                 150                 155                 160

Gln Gly Ile Gln Gly Ala Gln Gly Ile Gln Gly Pro Gln Gly Pro Ser
            165                 170                 175

Gly Asn Thr Gly Ala Thr Gly Val Thr Gly Gln Gly Ile Ser Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Ala Thr Gly Ala Thr Gly Pro Gly Gly Gly Pro
    210                 215                 220

Ser Gly Ser Thr Gly Ala Thr Gly Ala Thr Gly Asn Thr Gly Val Thr
225                 230                 235                 240

Gly Ser Ala Gly Val Thr Gly Asn Thr Gly Ser Thr Gly Ser Thr Gly
                245                 250                 255

Glu Thr Gly Ala Gln Gly Leu Gln Gly Ile Gln Gly Val Gln Gly Pro
        260                 265                 270

Ile Gly Pro Thr Gly Pro Glu Gly Pro Gln Ile Gln Gly Ile Pro
        275                 280                 285

Gly Pro Thr Gly Val Thr Gly Glu Gln Gly Ile Gln Gly Val Gln Gly
    290                 295                 300

Ile Gln Gly Ile Thr Gly Ala Thr Gly Asp Gln Gly Pro Gln Gly Ile
305                 310                 315                 320

Gln Gly Ala Ile Gly Pro Gln Gly Ile Thr Gly Ala Thr Gly Asp Gln
            325                 330                 335

Gly Pro Gln Gly Ile Gln Gly Val Pro Gly Pro Thr Gly Asp Thr Gly
            340                 345                 350

Ser Gln Gly Val Gln Gly Ile Gln Gly Pro Met Gly Asp Ile Gly Pro
        355                 360                 365

Thr Gly Pro Glu Gly Pro Glu Gly Leu Gln Gly Pro Gln Gly Ile Gln
    370                 375                 380

Gly Val Pro Gly Pro Ala Gly Ala Thr Gly Pro Glu Gly Pro Gln Gly
385                 390                 395                 400

Ile Gln Gly Ile Gln Gly Pro Ile Gly Val Thr Gly Pro Glu Gly Pro
                405                 410                 415

Gln Gly Ile Gln Gly Ile Gln Gly Ile Gln Gly Ile Thr Gly Ala Thr
            420                 425                 430

Gly Ala Gln Gly Ala Thr Gly Val Gln Gly Val Gln Gly Asn Ile Gly

```
                435                 440                 445
Ala Thr Gly Pro Glu Gly Pro Gln Gly Val Gln Gly Thr Gln Gly Asp
    450                 455                 460
Ile Gly Pro Thr Gly Pro Met Gly Pro Gln Gly Val Gln Gly Ile Gln
465                 470                 475                 480
Gly Ile Gln Gly Pro Thr Gly Ala Gln Gly Val Gln Gly Pro Gln Gly
                485                 490                 495
Ile Gln Gly Ile Gln Gly Pro Thr Gly Val Thr Gly Asp Thr Gly Thr
            500                 505                 510
Thr Gly Ala Thr Gly Glu Gly Thr Thr Gly Ala Thr Gly Val Thr Gly
            515                 520                 525
Pro Ser Gly Val Thr Gly Pro Ser Gly Gly Pro Ala Gly Pro Thr Gly
            530                 535                 540
Pro Thr Gly Pro Ser Gly Pro Thr Gly Leu Thr Gly Pro Ser Gly Gly
545                 550                 555                 560
Pro Pro Gly Pro Thr Gly Ala Thr Gly Val Thr Gly Val Gly Asp
                565                 570                 575
Thr Gly Ala Thr Gly Ser Thr Gly Val Thr Gly Ala Thr Gly Val Thr
            580                 585                 590
Gly Ala Thr Gly Ala Thr Gly Leu Gln Gly Pro Gln Gly Ile Gln Gly
            595                 600                 605
Val Gln Gly Asp Ile Gly Pro Thr Gly Pro Gln Gly Val Gln Gly Pro
610                 615                 620
Gln Gly Ile Gln Gly Ile Thr Gly Ala Thr Gly Asp Gln Gly Pro Gln
625                 630                 635                 640
Gly Ile Gln Gly Pro Gln Gly Ile Gln Gly Pro Thr Gly Pro Gln Gly
                645                 650                 655
Ile Gln Gly Gly Gln Gly Pro Gln Gly Ile Gln Gly Ala Thr Gly Ala
            660                 665                 670
Thr Gly Ala Gln Gly Pro Gln Gly Ile Gln Gly Ile Gln Gly Val Gln
            675                 680                 685
Gly Pro Thr Gly Pro Gln Gly Pro Thr Gly Ile Gln Gly Val Gln Gly
            690                 695                 700
Glu Ile Gly Pro Thr Gly Pro Gln Gly Val Gln Gly Leu Gln Gly Pro
705                 710                 715                 720
Gln Gly Pro Thr Gly Asp Thr Gly Pro Thr Gly Pro Gln Gly Pro Gln
                725                 730                 735
Gly Ile Gln Gly Pro Thr Gly Ala Thr Gly Ala Thr Gly Ser Gln Gly
                740                 745                 750
Ile Gln Gly Pro Thr Gly Ala Thr Gly Ala Thr Gly Ser Gln Gly Ile
            755                 760                 765
Gln Gly Pro Thr Gly Ala Thr Gly Ala Thr Gly Thr Gly Ala Thr
            770                 775                 780
Gly Ala Thr Gly Ala Thr Gly Ala Thr Gly Val Thr Gly Val Ser Thr
785                 790                 795                 800
Thr Ala Thr Tyr Ser Phe Ala Asn Asn Thr Gly Ser Ala Ile Ser
                805                 810                 815
Val Leu Leu Gly Gly Thr Asn Ile Pro Leu Pro Asn Asn Gln Asn Ile
            820                 825                 830
Gly Pro Gly Ile Thr Val Ser Gly Gly Asn Thr Val Phe Thr Val Thr
            835                 840                 845
Asn Ala Gly Asn Tyr Tyr Ile Ala Tyr Thr Ile Asn Ile Thr Ala Ala
            850                 855                 860
```

```
Leu Leu Val Ser Ser Arg Ile Thr Val Asn Gly Ser Pro Leu Ala Gly
865                 870                 875                 880

Thr Ile Asn Ser Pro Ala Val Ala Thr Gly Ser Phe Asn Ala Thr Ile
            885                 890                 895

Ile Ser Asn Leu Ala Ala Gly Ser Ala Ile Ser Leu Gln Leu Phe Gly
            900                 905                 910

Leu Leu Ala Val Ala Thr Leu Ser Thr Thr Thr Pro Gly Ala Thr Leu
        915                 920                 925

Thr Ile Ile Arg Leu Ser
        930

<210> SEQ ID NO 29
<211> LENGTH: 39
<212> TYPE: PRT
<213> ORGANISM: Bacillus mycoides

<400> SEQUENCE: 29

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35

<210> SEQ ID NO 30
<211> LENGTH: 287
<212> TYPE: PRT
<213> ORGANISM: Bacillus mycoides

<400> SEQUENCE: 30

Val Phe Asp

```
Asp Val Gly Cys Glu Cys Glu Cys Arg Glu Arg Pro Ile Arg Gln Leu
        210                 215                 220
Leu Asp Ala Phe Ile Gly Ser Thr Val Ser Leu Leu Ala Ser Asn Gly
225                 230                 235                 240
Ser Ile Ala Ala Asp Phe Ser Val Glu Gln Thr Gly Leu Gly Ile Val
                245                 250                 255
Leu Gly Thr Leu Pro Ile Asn Pro Thr Thr Thr Val Arg Phe Ala Ile
            260                 265                 270
Ser Thr Cys Lys Ile Thr Ala Val Asn Ile Thr Pro Ile Thr Met
        275                 280                 285
```

<210> SEQ ID NO 31
<211> LENGTH: 30
<212> TYPE: PRT
<213> ORGANISM: Bacillus mycoides

<400> SEQUENCE: 31

```
Met Asp Glu Phe Leu Tyr Phe Ala Ala Leu Asn Pro Gly Ser Ile Gly
1               5                   10                  15
Pro Thr Leu Pro Pro Val Gln Pro Phe Gln Phe Pro Thr Gly
            20                  25                  30
```

<210> SEQ ID NO 32
<211> LENGTH: 190
<212> TYPE: PRT
<213> ORGANISM: Bacillus mycoides

<400> SEQUENCE: 32

```
Met Asp Glu Phe Leu Tyr Phe Ala Ala Leu Asn Pro Gly Ser Ile Gly
1               5                   10                  15
Pro Thr Leu Pro Pro Val Gln Pro Phe Gln Phe Pro Thr Gly Pro Thr
            20                  25                  30
Gly Ser Thr Gly Ala Thr Gly Ser Thr Gly Ser Thr Gly Ser Thr Gly
        35                  40                  45
Pro Thr Gly Ser Thr Gly Ser Thr Gly Ser Thr Gly Ser Thr Gly Pro
    50                  55                  60
Thr Gly Pro Thr Gly Pro Thr Gly Ser Thr Gly Pro Thr Gly Pro Thr
65                  70                  75                  80
Gly Phe Asn Leu Pro Ala Gly Pro Ala Ser Ile Thr Leu Thr Ser Asn
                85                  90                  95
Glu Thr Thr Ala Cys Val Ser Thr Gln Gly Asn Asn Thr Leu Phe Phe
            100                 105                 110
Ser Gly Gln Val Leu Val Asn Gly Ser Pro Thr Pro Gly Val Val Val
        115                 120                 125
Ser Phe Ser Phe Ser Asn Pro Ser Leu Ala Phe Met Val Pro Leu Ala
    130                 135                 140
Val Ile Thr Asn Ala Ser Gly Asn Phe Thr Ala Val Phe Leu Ala Ala
145                 150                 155                 160
Asn Gly Pro Gly Thr Val Thr Val Thr Ala Ser Leu Leu Asp Ser Pro
                165                 170                 175
Gly Thr Met Ala Ser Val Thr Ile Thr Ile Val Asn Cys Pro
            180                 185                 190
```

<210> SEQ ID NO 33
<211> LENGTH: 21
<212> TYPE: PRT
<213> ORGANISM: Bacillus mycoides

```
<400> SEQUENCE: 33

Met Asp Ser Lys Asn Ile Gly Pro Thr Phe Pro Pro Leu Pro Ser Ile
1               5                   10                  15

Asn Phe Pro Thr Gly
            20

<210> SEQ ID NO 34
<211> LENGTH: 335
<212> TYPE: PRT
<213> ORGANISM: Bacillus mycoides

<400> SEQUENCE: 34

Met Asp Ser Lys Asn Ile Gly Pro Thr Phe Pro Pro Leu Pro Ser Ile
1               5                   10                  15

Asn Phe Pro Thr Gly Val Thr Gly Glu Thr Gly Ala Thr Gly Glu Thr
            20                  25                  30

Gly Ala Thr Gly Ala Thr Gly Glu Thr Gly Ala Thr Gly Glu Thr Gly
        35                  40                  45

Glu Thr Gly Ala Thr Gly Ala Thr Gly Ala Thr Gly Ala Thr Gly Glu
    50                  55                  60

Thr Gly Ala Thr Gly Ala Thr Gly Ala Thr Gly Ala Ala Gly Ala Thr
65                  70                  75                  80

Gly Glu Thr Gly Ala Thr Gly Glu Thr Gly Ala Thr Gly Glu Thr Gly
                85                  90                  95

Ala Thr Gly Glu Thr Gly Ala Thr Gly Val Thr Gly Glu Thr Gly Ala
            100                 105                 110

Thr Gly Glu Thr Gly Ala Ala Gly Glu Thr Gly Ile Thr Gly Val Thr
        115                 120                 125

Gly Pro Thr Gly Glu Thr Gly Ala Thr Gly Glu Thr Gly Ala Thr Gly
    130                 135                 140

Ala Thr Gly Ile Thr Gly Ala Thr Gly Ile Thr Gly Val Ala Gly Ala
145                 150                 155                 160

Thr Gly Glu Thr Gly Ala Ala Gly Glu Thr Gly Pro Thr Gly Ala Thr
                165                 170                 175

Gly Ala Ile Gly Ala Ile Gly Ala Thr Gly Ala Thr Gly Ile Thr Gly
            180                 185                 190

Val Thr Gly Ala Thr Gly Glu Thr Gly Ala Ala Gly Ala Thr Gly Ile
        195                 200                 205

Thr Gly Val Thr Gly Ala Thr Gly Glu Thr Gly Ala Ala Gly Ala Thr
    210                 215                 220

Gly Ile Thr Gly Ala Thr Gly Ile Thr Gly Val Ala Gly Ala Thr Gly
225                 230                 235                 240

Ile Thr Gly Pro Thr Gly Ile Pro Gly Thr Ile Pro Thr Thr Asn Leu
                245                 250                 255

Leu Tyr Phe Thr Phe Ser Asp Gly Glu Lys Leu Ile Tyr Thr Asn Ala
            260                 265                 270

Asp Gly Ile Ala Gln Tyr Gly Thr Thr Gln Ile Leu Ser Pro Ser Glu
        275                 280                 285

Val Ser Tyr Ile Asn Leu Phe Ile Asn Gly Ile Leu Gln Pro Gln Pro
    290                 295                 300

Phe Tyr Glu Val Thr Ala Gly Gln Leu Thr Leu Leu Asp Asp Glu Pro
305                 310                 315                 320

Pro Ser Gln Gly Ser Ser Ile Ile Leu Gln Phe Ile Ile Ile Asn
                325                 330                 335
```

<210> SEQ ID NO 35
<211> LENGTH: 22
<212> TYPE: PRT
<213> ORGANISM: Bacillus thuringiensis

<400> SEQUENCE: 35

Met Ile Gly Pro Glu Asn Ile Gly Pro Thr Phe Pro Ile Leu Pro Pro
1               5                   10                  15

Ile Tyr Ile Pro Thr Gly
            20

<210> SEQ ID NO 36
<211> LENGTH: 234
<212> TYPE: PRT
<213> ORGANISM: Bacillus thuringiensis

<400> SEQUENCE: 36

Met Ile Gly Pro Glu Asn Ile Gly Pro Thr Phe Pro Ile Leu Pro Pro
1               5                   10                  15

Ile Tyr Ile Pro Thr Gly Glu Thr Gly Pro Thr Gly Ile Thr Gly Ala
            20                  25                  30

Thr Gly Glu Thr Gly Pro Thr Gly Ile Thr Gly Pro Thr Gly Ile Thr
        35                  40                  45

Gly Ala Thr Gly Glu Thr Gly Ser Thr Gly Ile Thr Gly Ala Thr Gly
    50                  55                  60

Glu Thr Gly Ser Thr Gly Ile Thr Gly Pro Ile Gly Ile Thr Gly Ala
65                  70                  75                  80

Thr Gly Glu Thr Gly Pro Ile Gly Ile Thr Gly Ala Thr Gly Glu Thr
                85                  90                  95

Gly Pro Thr Gly Ile Thr Gly Ser Thr Gly Ile Thr Gly Leu Thr Gly
            100                 105                 110

Val Thr Gly Leu Thr Gly Glu Thr Gly Pro Ile Gly Ile Thr Gly Pro
        115                 120                 125

Thr Gly Ile Thr Gly Pro Thr Gly Val Thr Gly Ala Thr Gly Pro Thr
    130                 135                 140

Gly Gly Ile Gly Pro Ile Thr Thr Asn Leu Leu Tyr Tyr Thr Phe
145                 150                 155                 160

Ala Asp Gly Glu Lys Leu Ile Tyr Thr Asp Thr Asp Gly Ile Pro Gln
                165                 170                 175

Tyr Gly Thr Thr Asn Ile Leu Ser Pro Ser Glu Val Ser Tyr Ile Asn
            180                 185                 190

Leu Phe Val Asn Gly Ile Leu Gln Pro Gln Pro Leu Tyr Glu Val Ser
        195                 200                 205

Thr Gly Lys Leu Thr Leu Leu Asp Thr Gln Pro Pro Ser Gln Gly Ser
    210                 215                 220

Ser Ile Ile Leu Gln Phe Ile Ile Ile Asn
225                 230

<210> SEQ ID NO 37
<211> LENGTH: 23
<212> TYPE: DNA
<213> ORGANISM: Artificial sequence
<220> FEATURE:
<223> OTHER INFORMATION: Primer

<400> SEQUENCE: 37
ggatccatgg ctgaacacaa tcc                                          23

<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38
ggatccttaa ttcgtattct ggcc                                              24

<210> SEQ ID NO 39
<211> LENGTH: 21
<212> TYPE: DNA
<213> ORGANISM: Artificial sequence
<220> FEATURE:
<223> OTHER INFORMATION: Primer

<400> SEQUENCE: 39
ggatccatga aacggtcaat c                                                 21

<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40
ggatccttac taatttggtt ctgt                                              24

<210> SEQ ID NO 41
<211> LENGTH: 21
<212> TYPE: DNA
<213> ORGANISM: Artificial sequence
<220> FEATURE:
<223> OTHER INFORMATION: Primer

<400> SEQUENCE: 41
ggatccatgc taccaaaagc c                                                 21

<210> SEQ ID NO 42
<211> LENGTH: 24
<212> TYPE: DNA
<213> ORGANISM: Artificial sequence
<220> FEATURE:
<223> OTHER INFORMATION: Primer

<400> SEQUENCE: 42
ggatccttag tccgcaggcg tagc                                              24

<210> SEQ ID NO 43
<211> LENGTH: 35
<212> TYPE: PRT
<213> ORGANISM: Bacillus cereus

<400> SEQUENCE: 43

Met Ser Asn Asn Asn Ile Pro Ser Pro Phe Phe Phe Asn Asn Phe Asn
1               5                   10                  15

Pro Glu Leu Ile Gly Pro Thr Phe Pro Pro Ile Pro Pro Leu Thr Leu
            20                  25                  30

Pro Thr Gly
        35

```
<210> SEQ ID NO 44
<211> LENGTH: 222
<212> TYPE: PRT
<213> ORGANISM: Bacillus cereus

<400> SEQUENCE: 44
```

Met Ser Asn Asn Asn Ile Pro Ser Pro Phe Phe Asn Asn Phe Asn
1               5                   10                  15

Pro Glu Leu Ile Gly Pro Thr Phe Pro Ile Pro Pro Leu Thr Leu
                20                  25                  30

Pro Thr Gly Pro Thr Gly Ser Thr Gly Ala Thr Gly Ala Thr Gly Pro
            35                  40                  45

Thr Gly Ala Thr Gly Pro Thr Gly Ala Thr Gly Pro Thr Gly Ala Thr
        50                  55                  60

Gly Ala Thr Gly Ser Thr Gly Ala Thr Gly Pro Thr Gly Ala Thr Gly
65                  70                  75                  80

Thr Phe Ser Ser Ala Asn Ala Ser Ile Val Thr Pro Ala Pro Gln Thr
                85                  90                  95

Val Asn Asn Leu Ala Pro Ile Gln Phe Thr Ala Pro Val Leu Ile Ser
                100                 105                 110

Lys Asn Val Thr Phe Asn Gly Ile Asp Thr Phe Thr Ile Gln Ile Pro
                115                 120                 125

Gly Asn Tyr Phe Phe Ile Gly Ala Val Met Thr Ser Asn Asn Gln Ala
130                 135                 140

Gly Pro Val Ala Val Gly Val Gly Phe Asn Gly Ile Pro Val Pro Ser
145                 150                 155                 160

Leu Asp Gly Ala Asn Tyr Gly Thr Pro Thr Gly Gln Glu Val Val Cys
                165                 170                 175

Phe Gly Phe Ser Gly Gln Ile Pro Ala Gly Thr Thr Ile Asn Leu Tyr
                180                 185                 190

Asn Ile Ser Asp Lys Thr Ile Ser Ile Gly Gly Ala Thr Ala Ala Gly
                195                 200                 205

Ser Ser Ile Val Ala Ala Arg Leu Ser Phe Phe Arg Ile Ser
210                 215                 220

```
<210> SEQ ID NO 45
<211> LENGTH: 41
<212> TYPE: PRT
<213> ORGANISM: Bacillus cereus

<400> SEQUENCE: 45
```

Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
                20                  25                  30

Ile Pro Ser Phe Thr Leu Pro Thr Gly
                35                  40

```
<210> SEQ ID NO 46
<211> LENGTH: 293
<212> TYPE: PRT
<213> ORGANISM: Bacillus cereus

<400> SEQUENCE: 46
```

Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
                20                  25                  30

-continued

```
Ile Pro Ser Phe Thr Leu Pro Thr Gly Ser Thr Gly Pro Thr Gly Pro
            35                  40                  45

Thr Gly Asp Thr Gly Pro Thr Gly Pro Thr Ala Thr Ile Cys Ile Arg
 50                  55                  60

Thr Asp Pro Asp Asn Gly Cys Ser Val Ala Glu Gly Ser Gly Thr Val
 65                  70                  75                  80

Ala Ser Gly Phe Ala Ser His Ala Glu Ala Cys Asn Thr Gln Ala Ile
                85                  90                  95

Gly Asp Cys Ser His Ala Glu Gly Gln Phe Ala Thr Ala Ser Gly Thr
            100                 105                 110

Ala Ser His Ala Glu Gly Phe Gln Thr Thr Ala Ser Gly Phe Ala Ser
            115                 120                 125

His Thr Glu Gly Ser Gly Thr Thr Ala Asp Ala Asn Phe Ser His Thr
            130                 135                 140

Glu Gly Ile Asn Thr Ile Val Asp Val Leu His Pro Gly Ser His Ile
145                 150                 155                 160

Met Gly Lys Asn Gly Thr Thr Arg Ser Ser Phe Ser Trp His Leu Ala
                165                 170                 175

Asn Gly Leu Ala Val Gly Pro Ser Leu Asn Ser Ala Val Ile Glu Gly
            180                 185                 190

Val Thr Gly Asn Leu Tyr Leu Asp Gly Val Val Ile Ser Pro Asn Ala
            195                 200                 205

Ala Asp Tyr Ala Glu Met Phe Glu Thr Ile Asp Gly Asn Leu Ile Asp
            210                 215                 220

Val Gly Tyr Phe Val Thr Leu Tyr Gly Glu Lys Ile Arg Lys Ala Asn
225                 230                 235                 240

Ala Asn Asp Asp Tyr Ile Leu Gly Val Val Ser Ala Thr Pro Ala Met
                245                 250                 255

Ile Ala Asp Ala Ser Asp Leu Arg Trp His Asn Leu Phe Val Arg Asp
            260                 265                 270

Glu Trp Gly Arg Thr Gln Tyr His Glu Val Val Pro Glu Lys Lys
            275                 280                 285

Met Ala Met Glu Glu
    290

<210> SEQ ID NO 47
<211> LENGTH: 49
<212> TYPE: PRT
<213> ORGANISM: Bacillus cereus

<400> SEQUENCE: 47

Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
                20                  25                  30

Leu Val Gly Pro Thr Phe Pro Pro Ile Pro Ser Phe Thr Leu Pro Thr
            35                  40                  45

Gly

<210> SEQ ID NO 48
<211> LENGTH: 83
<212> TYPE: PRT
<213> ORGANISM: Bacillus cereus

<400> SEQUENCE: 48
```

-continued

```
Met Thr Arg Lys Asp Lys Phe Asn Arg Ser Arg Ile Ser Arg Asp
1               5                   10                  15

Arg Phe Asn Ser Pro Lys Ile Lys Ser Glu Ile Leu Ile Ser Pro Asp
            20                  25                  30

Leu Val Gly Pro Thr Phe Pro Pro Ile Pro Ser Phe Thr Leu Pro Thr
            35                  40                  45

Gly Val Thr Gly Pro Thr Gly Asn Thr Gly Pro Thr Gly Ile Thr Gly
50                  55                  60

Pro Thr Gly Asp Thr Gly Pro Thr Gly Asp Thr Gly Pro Thr Gly Ile
65                  70                  75                  80

Thr Gly Pro
```

<210> SEQ ID NO 49
<211> LENGTH: 38
<212> TYPE: PRT
<213> ORGANISM: Bacillus cereus

<400> SEQUENCE: 49

```
Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly
            35
```

<210> SEQ ID NO 50
<211> LENGTH: 163
<212> TYPE: PRT
<213> ORGANISM: Bacillus cereus

<400> SEQUENCE: 50

```
Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly Ile Thr Gly Pro Thr Gly Asn Thr Gly Pro
            35                  40                  45

Thr Gly Asp Thr Gly Pro Thr Gly Pro Thr Phe Asn Ile Asn Phe Arg
50                  55                  60

Ala Glu Lys Asn Gly Ala Gln Ser Phe Thr Pro Pro Ala Asp Ile Gln
65                  70                  75                  80

Val Ser Tyr Gly Asn Ile Ile Phe Asn Asn Gly Gly Gly Tyr Ser Ser
            85                  90                  95

Val Thr Asn Thr Phe Thr Ala Pro Ile Asn Gly Ile Tyr Leu Phe Ser
            100                 105                 110

Ala Asn Ile Gly Phe Asn Pro Thr Leu Gly Thr Thr Ser Thr Leu Arg
            115                 120                 125

Ile Thr Ile Arg Lys Asn Leu Val Ser Val Ala Ser Gln Thr Ile Asp
            130                 135                 140

Ile Gln Phe Ser Ala Ala Glu Ser Gly Thr Leu Thr Val Gly Ser Ser
145                 150                 155                 160

Asn Phe Phe
```

<210> SEQ ID NO 51
<211> LENGTH: 39
<212> TYPE: PRT
<213> ORGANISM: Bacillus cereus

<400> SEQUENCE: 51

Met Lys Glu Arg Asp Asn Lys Gly Lys Gln His Ser Leu Asn Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
            35

<210> SEQ ID NO 52
<211> LENGTH: 323
<212> TYPE: PRT
<213> ORGANISM: Bacillus cereus

<400> SEQUENCE: 52

Met Lys Glu Arg Asp Asn Lys Gly Lys Gln His Ser Leu Asn Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
            35                  40                  45

Pro Thr Gly Pro Gln Gly Pro Arg Gly Phe Gln Gly Pro Met Gly Glu
50                  55                  60

Met Gly Pro Thr Gly Pro Gln Gly Val Gln Gly Ile Gln Gly Pro Ala
65                  70                  75                  80

Gly Gln Met Gly Ala Thr Gly Pro Glu Gly Gln Gln Gly Pro Glu Gly
                85                  90                  95

Leu Arg Gly Pro Val Gly Ala Thr Gly Ala Thr Gly Leu Gln Gly Val
            100                 105                 110

Gln Gly Ile Gln Gly Pro Ile Gly Ser Thr Gly Ala Thr Gly Ala Gln
            115                 120                 125

Gly Ile Gln Gly Ile Gln Gly Leu Gln Gly Pro Ile Gly Ala Thr Gly
        130                 135                 140

Pro Glu Gly Pro Gln Gly Ile Gln Gly Val Gln Gly Leu Pro Gly Ala
145                 150                 155                 160

Thr Gly Pro Gln Gly Val Gln Gly Val Gln Gly Val Ile Gly Pro Gln
                165                 170                 175

Gly Pro Ser Gly Ser Thr Gly Thr Gly Ala Thr Gly Gln Gly Val
            180                 185                 190

Thr Gly Pro Thr Gly Ile Thr Gly Ser Thr Gly Val Thr Gly Pro Ser
            195                 200                 205

Gly Gly Pro Pro Gly Pro Thr Gly Pro Thr Gly Ala Thr Gly Pro Gly
        210                 215                 220

Gly Gly Pro Ser Gly Ser Thr Gly Val Thr Gly Ser Thr Gly Asn Thr
225                 230                 235                 240

Gly Ala Thr Gly Ser Pro Gly Val Thr Gly Ala Thr Gly Pro Thr Gly
                245                 250                 255

Ser Thr Gly Ala Thr Gly Ile Gln Gly Ser Gln Gly Ile Gln Gly Ile
            260                 265                 270

Gln Gly Ile Gln Gly Pro Leu Gly Pro Thr Gly Pro Glu Gly Pro Gln
            275                 280                 285

Gly Ile Gln Gly Ile Pro Gly Pro Thr Gly Ile Thr Gly Glu Gln Gly
        290                 295                 300

Ile Gln Gly Val Gln Gly Ile Gln Gly Ile Thr Gly Ala Thr Gly Asp
305                 310                 315                 320

```
Gln Gly Thr

<210> SEQ ID NO 53
<211> LENGTH: 39
<212> TYPE: PRT
<213> ORGANISM: Bacillus cereus

<400> SEQUENCE: 53

Met Arg Glu Arg Asp Asn Lys Arg Gln Gln His Ser Leu Asn Pro Asn
1               5                   10                  15

Phe Arg Ile Ser Pro Glu Leu Ile Gly Pro Thr Phe Pro Pro Val Pro
            20                  25                  30

Thr Gly Phe Thr Gly Ile Gly
        35

<210> SEQ ID NO 54
<211> LENGTH: 436
<212> TYPE: PRT
<213> ORGANISM: Bacillus cereus

<400> SEQUENCE: 54

Met Arg Glu Arg Asp Asn Lys Arg Gln Gln His Ser Leu Asn Pro Asn
1               5                   10                  15

Phe Arg Ile Ser Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Phe Gln Gly Pro Met Gly Glu
50                  55                  60

Met Gly Pro Thr Gly Pro Gln Gly Val Gln Gly Ile Gln Gly Pro Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Val Gln Gly Ile Gln Gly Leu Gln Gly Pro Ile Gly Ala Thr Gly
130                 135                 140

Pro Glu Gly Pro Gln Gly Ile Gln Gly Val Gln Gly Leu Pro Gly Ala
145                 150                 155                 160

Thr Gly Ser Gln Gly Ile Gln Gly Val Gln Gly Ile Gln Gly Pro Gln
                165                 170                 175

Gly Pro Ser Gly Asn Thr Gly Ala Thr Gly Ala Thr Gly Gln Gly Ile
            180                 185                 190

Thr Gly Pro Thr Gly Ile Thr Gly Pro Thr Gly Ile Thr Gly Pro Ser
        195                 200                 205

Gly Gly Pro Pro Gly Pro Thr Gly Pro Thr Gly Thr Ala Thr Gly Pro Gly
210                 215                 220

Gly Gly Pro Ser Gly Ser Thr Gly Ala Thr Gly Ala Thr Gly Asn Thr
225                 230                 235                 240

Gly Ala Thr Gly Asn Thr Gly Ile Thr Gly Ala Thr Gly Ser Thr Gly
                245                 250                 255

Pro Thr Gly Ser Thr Gly Ala Gln Gly Leu Gln Gly Ile Gln Gly Ile
            260                 265                 270
```

```
Gln Gly Pro Ile Gly Pro Thr Gly Pro Glu Gly Pro Gln Gly Ile Gln
            275                 280                 285

Gly Ile Pro Gly Pro Thr Gly Val Thr Gly Glu Gln Gly Ile Gln Gly
        290                 295                 300

Val Gln Gly Ile Gln Gly Ile Thr Gly Ala Thr Gly Asp Gln Gly Pro
305                 310                 315                 320

Gln Gly Ile Gln Gly Val Ile Gly Ala Gln Gly Val Thr Gly Ala Thr
            325                 330                 335

Gly Asp Gln Gly Pro Gln Gly Ile Gln Gly Val Pro Gly Pro Ser Gly
            340                 345                 350

Ala Thr Gly Pro Gln Gly Val Gln Gly Ile Gln Gly Pro Met Gly Asp
        355                 360                 365

Ile Gly Pro Thr Gly Pro Glu Gly Pro Glu Gly Leu Gln Gly Pro Gln
        370                 375                 380

Gly Ile Gln Gly Val Pro Gly Pro Val Gly Ala Thr Gly Pro Glu Gly
385                 390                 395                 400

Pro Gln Gly Ile Gln Gly Ile Gln Gly Val Gln Gly Ala Thr Gly Pro
            405                 410                 415

Gln Gly Pro Gln Gly Ile Gln Gly Ile Gln Gly Val Gln Gly Ile Thr
            420                 425                 430

Gly Ala Thr Gly
        435

<210> SEQ ID NO 55
<211> LENGTH: 36
<212> TYPE: PRT
<213> ORGANISM: Bacillus thuringiensis

<400> SEQUENCE: 55

Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly
        35

<210> SEQ ID NO 56
<211> LENGTH: 470
<212> TYPE: PRT
<213> ORGANISM: Bacillus thuringiensis

<400> SEQUENCE: 56

Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
        50                  55                  60

Thr Gly Pro Gln Gly Val Gln Gly Ile Gln Gly Pro Val Gly Pro Ile
65                  70                  75                  80

Gly Ala Thr Gly Pro Glu Gly Gln Gly Ala Gln Gly Leu Arg Gly
            85                  90                  95

Pro Gln Gly Glu Thr Gly Ala Thr Gly Pro Gln Gly Val Gln Gly Leu
            100                 105                 110
```

Gln Gly Pro Ile Gly Pro Thr Gly Ala Thr Gly Ala Gln Gly Ile Gln
            115                 120                 125

Gly Ile Gln Gly Leu Gln Gly Pro Ile Gly Ala Thr Gly Pro Glu Gly
        130                 135                 140

Pro Gln Gly Ile Gln Gly Val Gln Gly Leu Pro Gly Ala Thr Gly Pro
145                 150                 155                 160

Gln Gly Ile Gln Gly Ala Gln Gly Ile Gln Gly Thr Gln Gly Pro Ser
            165                 170                 175

Gly Asn Thr Gly Ala Thr Gly Ala Gly Gln Gly Leu Thr Gly Pro
            180                 185                 190

Thr Gly Ile Thr Gly Pro Thr Gly Ile Thr Gly Pro Ser Gly Gly Pro
            195                 200                 205

Pro Gly Pro Thr Gly Pro Thr Gly Ala Thr Gly Pro Gly Gly Pro
            210                 215                 220

Ser Gly Ser Thr Gly Ala Thr Gly Ala Thr Gly Asp Thr Gly Ala Thr
225                 230                 235                 240

Gly Ser Thr Gly Val Thr Gly Ala Thr Gly Ala Gln Gly Pro Gln Gly
            245                 250                 255

Val Gln Gly Ile Gln Gly Pro Thr Gly Ala Thr Gly Ala Thr Gly Ala
            260                 265                 270

Thr Gly Pro Gln Gly Ile Gln Gly Pro Gln Gly Ile Gln Gly Pro Thr
            275                 280                 285

Gly Ala Thr Gly Ala Thr Gly Ser Gln Gly Pro Thr Gly Asn Thr Gly
            290                 295                 300

Pro Thr Gly Ser Gln Gly Ile Gln Gly Pro Thr Gly Pro Thr Gly Ala
305                 310                 315                 320

Gly Ala Thr Gly Ala Thr Gly Ala Thr Gly Ala Thr Gly Val Ser Thr
            325                 330                 335

Thr Ala Thr Tyr Ala Phe Ala Asn Asn Thr Ser Gly Ser Ile Ile Ser
            340                 345                 350

Val Leu Leu Gly Gly Thr Asn Ile Pro Leu Pro Asn Asn Gln Asn Ile
            355                 360                 365

Gly Pro Gly Ile Thr Val Ser Gly Gly Asn Thr Val Phe Thr Val Ala
            370                 375                 380

Asn Ala Gly Asn Tyr Tyr Ile Ala Tyr Thr Ile Asn Leu Thr Ala Gly
385                 390                 395                 400

Leu Leu Val Ser Ser Arg Ile Thr Val Asn Gly Ser Pro Leu Ala Gly
            405                 410                 415

Thr Ile Asn Ser Pro Ala Val Ala Ala Gly Ser Phe Ser Ala Thr Ile
            420                 425                 430

Ile Ala Asn Leu Pro Ala Gly Ala Ala Val Ser Leu Gln Leu Phe Gly
            435                 440                 445

Val Ile Ala Leu Ala Thr Leu Ser Thr Ala Thr Pro Gly Ala Thr Leu
450                 455                 460

Thr Ile Ile Arg Leu Ser
465                 470

<210> SEQ ID NO 57
<211> LENGTH: 136
<212> TYPE: PRT
<213> ORGANISM: Bacillus mycoides

<400> SEQUENCE: 57

Met Lys Phe Ser Lys Lys Ser Thr Val Asp Ser Ser Ile Val Gly Lys
1               5                   10                  15

```
Arg Val Val Ser Lys Val Asn Ile Leu Arg Phe Tyr Asp Ala Arg Ser
            20                  25                  30

Cys Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly
    130                 135

<210> SEQ ID NO 58
<211> LENGTH: 384
<212> TYPE: PRT
<213> ORGANISM: Bacillus mycoides

<400> SEQUENCE: 58

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Cys Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly Pro Thr Gly Gly Thr Gly Pro Thr
    130                 135                 140

Gly Val Thr Gly Pro Thr Gly Val Thr Gly Pro Thr Gly Val Thr Gly
145                 150                 155                 160

Pro Thr Gly Val Thr Gly Pro Thr Gly Val Thr Gly Pro Thr Gly Val
                165                 170                 175

Thr Gly Pro Thr Gly Val Thr Gly Pro Thr Gly Val Thr Gly Pro Thr
            180                 185                 190

Gly Val Thr Gly Pro Thr Gly Val Thr Gly Pro Thr Gly Val Thr Gly
        195                 200                 205

Pro Thr Gly Val Thr Gly Pro Thr Gly Gly Thr Glu Gly Cys Leu Cys
    210                 215                 220

Asp Cys Cys Val Leu Pro Met Gln Ser Val Leu Gln Gln Leu Ile Gly
225                 230                 235                 240

Glu Thr Val Ile Leu Gly Thr Ile Ala Asp Thr Pro Asn Thr Pro Pro
```

```
                        245                 250                 255
Leu Phe Leu Phe Thr Ile Thr Ser Val Asn Asp Phe Leu Val Thr
                260                 265                 270

Val Thr Asp Gly Thr Thr Thr Phe Val Val Asn Ile Ser Asp Val Thr
            275                 280                 285

Gly Val Gly Phe Leu Pro Pro Gly Pro Pro Ile Thr Leu Leu Pro Pro
        290                 295                 300

Thr Asp Val Gly Cys Glu Cys Glu Cys Arg Glu Arg Pro Ile Arg Gln
305                 310                 315                 320

Leu Leu Asp Ala Phe Ile Gly Ser Thr Val Ser Leu Leu Ala Ser Asn
                325                 330                 335

Gly Ser Ile Ala Ala Asp Phe Ser Val Glu Gln Thr Gly Leu Gly Ile
            340                 345                 350

Val Leu Gly Thr Leu Pro Ile Asn Pro Thr Thr Val Arg Phe Ala
        355                 360                 365

Ile Ser Thr Cys Lys Ile Thr Ala Val Asn Ile Thr Pro Ile Thr Met
370                 375                 380
```

<210> SEQ ID NO 59
<211> LENGTH: 36
<212> TYPE: PRT
<213> ORGANISM: Bacillus cereus

<400> SEQUENCE: 59

```
Met Lys Glu Arg Asp Lys Gln Asn Ser Leu Asn Ser Asn Phe Arg Ile
1               5                   10                  15

Ser Pro Asn Leu Ile Gly Pro Thr Phe Pro Pro Val Pro Thr Gly Phe
                20                  25                  30

Thr Gly Ile Gly
            35
```

<210> SEQ ID NO 60
<211> LENGTH: 1321
<212> TYPE: PRT
<213> ORGANISM: Bacillus cereus

<400> SEQUENCE: 60

```
Met Lys Glu Arg Asp Lys Gln Asn Ser Leu Asn Ser Asn Phe Arg Ile
1               5                   10                  15

Ser Pro Asn Leu Ile Gly Pro Thr Phe Pro Pro Val Pro Thr Gly Phe
                20                  25                  30

Thr Gly Ile Gly Ile Thr Gly Pro Thr Gly Pro Gln Gly Pro Thr Gly
            35                  40                  45

Pro Gln Gly Pro Arg Gly Leu Gln Gly Pro Met Gly Glu Met Gly Pro
        50                  55                  60

Thr Gly Pro Gln Gly Val Gln Gly Ile Gln Gly Pro Val Gly Ser Ile
65                  70                  75                  80

Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ala Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Leu Pro Gly Ala Thr Gly Pro
```

-continued

```
              145                 150                 155                 160
          Gln Gly Ile Gln Gly Ala Gln Gly Met Gln Gly Leu Gln Gly Pro Ser
                          165                 170                 175
          Gly Asn Thr Gly Ala Thr Gly Ala Thr Gly Gln Gly Ile Thr Gly Pro
                          180                 185                 190
          Thr Gly Val Thr Gly Pro Thr Gly Ile Thr Gly Pro Ser Gly Gly Pro
                          195                 200                 205
          Pro Gly Pro Thr Gly Pro Thr Gly Ala Thr Gly Pro Gly Gly Pro
              210                 215                 220
          Ser Gly Ser Thr Gly Ala Thr Gly Ala Thr Gly Asn Thr Gly Ala Thr
              225                 230                 235                 240
          Gly Ser Thr Gly Val Thr Gly Ser Thr Gly Val Thr Gly Ala Thr Gly
                          245                 250                 255
          Ser Thr Gly Pro Thr Gly Ser Thr Gly Ala Gln Gly Leu Gln Gly Ile
                          260                 265                 270
          Gln Gly Ile Gln Gly Pro Ile Gly Pro Thr Gly Glu Gly Pro Gln
                          275                 280                 285
          Gly Ile Gln Gly Ile Pro Gly Pro Thr Gly Val Thr Gly Glu Gln Gly
                          290                 295                 300
          Ile Gln Gly Val Gln Gly Ile Gln Gly Ala Thr Gly Ala Thr Gly Asp
              305                 310                 315                 320
          Gln Gly Pro Gln Gly Ile Gln Gly Ala Ile Gly Pro Gln Gly Ala Thr
                          325                 330                 335
          Gly Ala Thr Gly Asp Gln Gly Pro Gln Gly Ile Gln Gly Val Pro Gly
                          340                 345                 350
          Pro Ser Gly Ala Thr Gly Pro Gln Gly Val Gln Gly Leu Gln Gly Pro
                          355                 360                 365
          Met Gly Asp Ile Gly Pro Thr Gly Pro Glu Gly Pro Glu Gly Leu Gln
                          370                 375                 380
          Gly Pro Gln Gly Ile Gln Gly Val Pro Gly Pro Val Gly Ala Thr Gly
              385                 390                 395                 400
          Pro Glu Gly Pro Gln Gly Ile Gln Gly Ile Gln Gly Pro Val Gly Ala
                          405                 410                 415
          Thr Gly Pro Gln Gly Pro Gln Gly Ile Gln Gly Ile Gln Gly Val Gln
                          420                 425                 430
          Gly Ile Thr Gly Ala Thr Gly Val Gln Gly Ala Thr Gly Ile Gln Gly
                          435                 440                 445
          Ile Gln Gly Glu Ile Gly Ala Thr Gly Pro Glu Gly Pro Gln Gly Val
              450                 455                 460
          Gln Gly Ala Gln Gly Ile Gly Pro Thr Gly Pro Met Gly Pro Gln
              465                 470                 475                 480
          Gly Val Gln Gly Val Gly Ile Gln Gly Ala Thr Gly Ala Gln Gly
                          485                 490                 495
          Val Gln Gly Pro Gln Gly Ile Gln Gly Ile Gln Gly Ile Gln Gly Ile
                          500                 505                 510
          Gln Gly Pro Thr Gly Ala Thr Gly Asp Thr Gly Ala Thr Gly Ala Thr
                          515                 520                 525
          Gly Glu Gly Thr Thr Gly Pro Thr Gly Val Thr Gly Pro Thr Gly Pro
                          530                 535                 540
          Ser Gly Gly Pro Ala Gly Pro Thr Gly Pro Thr Gly Pro Ser Gly Pro
              545                 550                 555                 560
          Ala Gly Val Thr Gly Pro Ser Gly Gly Pro Pro Gly Pro Thr Gly Ala
                          565                 570                 575
```

```
Thr Gly Ala Thr Gly Val Thr Gly Asp Thr Gly Ala Thr Gly Ser Thr
            580                 585                 590

Gly Val Thr Gly Ala Thr Gly Glu Thr Gly Ala Thr Gly Val Thr Gly
        595                 600                 605

Leu Gln Gly Pro Gln Gly Ile Gln Gly Val Gln Gly Glu Ile Gly Pro
610                 615                 620

Thr Gly Pro Gln Gly Val Gln Gly Pro Gln Gly Ile Gln Gly Val Thr
625                 630                 635                 640

Gly Ala Thr Gly Asp Gln Gly Pro Gln Gly Val Gln Gly Pro Gln Gly
                645                 650                 655

Asp Ile Gly Pro Thr Gly Pro Gln Gly Ile Gln Gly Pro Gln Gly Ser
            660                 665                 670

Gln Gly Ile Gln Gly Ala Thr Gly Thr Gly Ala Gln Gly Pro Gln
        675                 680                 685

Gly Ile Gln Gly Pro Gln Gly Asp Val Gly Pro Thr Gly Pro Gln Gly
    690                 695                 700

Pro Thr Gly Ile Gln Gly Ile Gln Gly Glu Ile Gly Pro Thr Gly Pro
705                 710                 715                 720

Glu Gly Pro Glu Gly Leu Gln Gly Pro Gln Gly Ile Gln Gly Val Gln
                725                 730                 735

Gly Pro Val Gly Ala Thr Gly Pro Glu Gly Pro Gln Gly Ile Gln Gly
            740                 745                 750

Ile Gln Gly Val Gln Gly Ala Thr Gly Ser Gln Gly Pro Gln Gly Ile
        755                 760                 765

Gln Gly Ile Gln Gly Val Gln Gly Ile Thr Gly Ala Thr Gly Ala Gln
770                 775                 780

Gly Ala Thr Gly Ile Gln Gly Ile Gln Gly Glu Ile Gly Ala Thr Gly
785                 790                 795                 800

Pro Glu Gly Pro Gln Gly Val Gln Gly Val Gln Gly Glu Ile Gly Pro
                805                 810                 815

Thr Gly Pro Met Gly Pro Gln Gly Val Gln Gly Val Gln Gly Ile Gln
            820                 825                 830

Gly Ala Thr Gly Ala Gln Gly Val Gln Gly Pro Gln Gly Ile Gln Gly
        835                 840                 845

Ile Gln Gly Pro Thr Gly Ala Thr Gly Glu Thr Gly Ala Thr Gly Ala
850                 855                 860

Thr Gly Glu Gly Thr Thr Gly Pro Thr Gly Val Thr Gly Pro Thr Gly
865                 870                 875                 880

Val Thr Gly Pro Ser Gly Pro Ala Gly Pro Thr Gly Pro Thr Gly
                885                 890                 895

Pro Ser Gly Pro Ala Gly Val Thr Gly Pro Ser Gly Pro Pro Gly
            900                 905                 910

Pro Thr Gly Ala Thr Gly Ala Thr Gly Ala Thr Gly Val Thr Gly Asp
        915                 920                 925

Thr Gly Ala Thr Gly Ser Thr Gly Val Thr Gly Ala Thr Gly Glu Thr
930                 935                 940

Gly Ala Thr Gly Val Thr Gly Leu Gln Gly Pro Gln Gly Ile Gln Gly
945                 950                 955                 960

Val Gln Gly Glu Ile Gly Pro Thr Gly Pro Gln Gly Ile Gln Gly Pro
                965                 970                 975

Gln Gly Ile Gln Gly Val Thr Gly Ala Thr Gly Ala Gln Gly Pro Gln
            980                 985                 990
```

-continued

Gly Ile Gln Gly Pro Gln Gly Asp Ile Gly Pro Thr Gly Pro Gln Gly
            995                 1000                1005

Ile Gln Gly Pro Gln Gly Pro Gln Gly Ile Gln Gly Ala Thr Gly
        1010                1015                1020

Ala Thr Gly Ala Gln Gly Pro Gln Gly Ile Gln Gly Pro Gln Gly
        1025                1030                1035

Glu Ile Gly Pro Thr Gly Pro Gln Gly Pro Gln Gly Ile Gln Gly
        1040                1045                1050

Pro Gln Gly Ile Gln Gly Pro Thr Gly Ala Thr Gly Ala Thr Gly
        1055                1060                1065

Ala Thr Gly Leu Gln Gly Ile Gln Gly Pro Gln Gly Ile Gln Gly
        1070                1075                1080

Pro Gln Gly Ile Gln Gly Pro Thr Gly Ala Thr Gly Ala Thr Gly
        1085                1090                1095

Ala Thr Gly Leu Gln Gly Ile Gln Gly Pro Gln Gly Ile Gln Gly
        1100                1105                1110

Pro Gln Gly Ile Gln Gly Pro Thr Gly Ala Thr Gly Ala Thr Gly
        1115                1120                1125

Ala Thr Gly Leu Gln Gly Ile Gln Gly Pro Gln Gly Ile Gln Gly
        1130                1135                1140

Pro Gln Gly Ile Gln Gly Pro Thr Gly Ala Thr Gly Ala Thr Gly
        1145                1150                1155

Ala Thr Gly Ser Gln Gly Pro Thr Gly Asp Thr Gly Pro Thr Gly
        1160                1165                1170

Ala Gly Ala Thr Gly Ala Thr Gly Ala Thr Gly Val Ser Thr Thr
        1175                1180                1185

Ala Thr Tyr Ala Phe Ala Asn Asn Thr Ser Gly Thr Ala Ile Ser
        1190                1195                1200

Val Leu Leu Gly Gly Thr Asn Ile Pro Leu Pro Asn Asn Gln Asn
        1205                1210                1215

Ile Gly Pro Gly Ile Thr Val Ser Gly Gly Asn Thr Val Phe Thr
        1220                1225                1230

Val Ala Ser Ala Gly Asn Tyr Tyr Ile Ala Tyr Thr Ile Asn Leu
        1235                1240                1245

Thr Ala Gly Leu Leu Val Ser Ser Arg Ile Thr Val Asn Gly Ser
        1250                1255                1260

Pro Leu Ala Gly Thr Ile Asn Ala Pro Thr Val Ala Thr Gly Ser
        1265                1270                1275

Phe Ser Ala Thr Ile Ile Ala Asn Leu Pro Ala Gly Ala Ala Ile
        1280                1285                1290

Ser Leu Gln Leu Phe Gly Leu Val Ala Ile Ala Thr Leu Ser Thr
        1295                1300                1305

Thr Thr Pro Gly Ala Thr Leu Thr Ile Ile Arg Leu Ser
        1310                1315

<210> SEQ ID NO 61
<211> LENGTH: 39
<212> TYPE: PRT
<213> ORGANISM: Bacillus cereus

<400> SEQUENCE: 61

Met Met Glu Asn Lys Lys Gly Ser Lys His Asn Glu Phe Leu Ser Ala
1               5                   10                  15

Lys Ala Phe Asn Pro Asn Leu Val Gly Pro Thr Leu Pro Pro Val Pro
            20                  25                  30

```
Ser Phe Thr Leu Pro Thr Gly
        35

<210> SEQ ID NO 62
<211> LENGTH: 309
<212> TYPE: PRT
<213> ORGANISM: Bacillus cereus

<400> SEQUENCE: 62

Met Met Glu Asn Lys Lys Gly Ser Lys His Asn Glu Phe Leu Ser Ala
1               5                   10                  15

Lys Ala Phe Asn Pro Asn Leu Val Gly Pro Thr Leu Pro Pro Val Pro
            20                  25                  30

Ser Phe Thr Leu Pro Thr Gly Pro Thr Gly Ala Thr Gly Ala Thr Gly
        35                  40                  45

Val Thr Gly Ala Thr Gly Ala Thr Gly Ala Thr Gly Ala Thr Gly Val
    50                  55                  60

Thr Gly Ala Thr Gly Ala Thr Gly Val Thr Gly Ala Thr Gly Ala Thr
65                  70                  75                  80

Gly Val Thr Gly Ala Thr Gly Ala Thr Gly Ala Thr Gly Ala Thr Gly
                85                  90                  95

Val Thr Gly Ala Thr Gly Ala Thr Gly Val Thr Gly Ala Thr Gly Ala
            100                 105                 110

Thr Gly Val Thr Gly Ala Thr Gly Ala Thr Gly Val Thr Gly Val Thr
        115                 120                 125

Gly Ala Thr Gly Ala Thr Gly Ala Thr Gly Val Thr Gly Pro Thr Gly
    130                 135                 140

Ala Thr Gly Ala Thr Gly Ala Thr Gly Val Thr Gly Pro Thr Gly Ala
145                 150                 155                 160

Thr Gly Ala Thr Gly Ala Thr Gly Gly Leu Ala Val Ala Ser Ala Ser
                165                 170                 175

Ala Met Thr Ser Thr Ala Gln Thr Val Asp Asn Leu Val Ala Val Gln
            180                 185                 190

Phe Thr Ala Pro Val Leu Glu Leu Asp Ser Val Ile Phe Asn Gly Thr
        195                 200                 205

Asp Thr Phe Thr Val Leu Val Pro Gly Asn Tyr Tyr Cys Ile Gly Ser
    210                 215                 220

Leu Met Pro Ala Glu Thr Gln Thr Gly Pro Phe Ala Val Gly Ile Gly
225                 230                 235                 240

Leu Asn Gly Ile Pro Val Pro Ala Leu Asp Gly Ala Asn Tyr Ala Gln
                245                 250                 255

Ser Ala Gly Gln Glu Val Val Gly Phe Gly Leu Thr Gly Gln Ile Pro
            260                 265                 270

Ala Gly Thr Thr Ile Ser Leu Phe Asn Leu Ser Gly His Thr Ile Ser
        275                 280                 285

Ile Gly Gly Thr Ile Ser Gly Ala Thr Ser Val Ala Ala Arg Leu Leu
    290                 295                 300

Leu Phe Arg Ile Ser
305

<210> SEQ ID NO 63
<211> LENGTH: 41
<212> TYPE: PRT
<213> ORGANISM: Bacillus weihenstephanensis

<400> SEQUENCE: 63
```

Met Ser Asn Asn Tyr Ser Asp Gly Leu Asn Pro Asp Glu Phe Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40

<210> SEQ ID NO 64
<211> LENGTH: 292
<212> TYPE: PRT
<213> ORGANISM: Bacillus weihenstephanensis

<400> SEQUENCE: 64

Met Ser Asn Asn Tyr Ser Asp Gly Leu Asn Pro Asp Glu Phe Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Val Pro Thr Gly Pro Thr Gly Pro Thr
    50                  55                  60

Gly Pro Thr Gly Pro Thr Gly Pro Thr Gly Asp Thr Gly Thr Thr Gly
65                  70                  75                  80

Ala Thr Gly Asp Thr Gly Ala Thr Gly Asp Thr Gly Ala Thr Gly Pro
                85                  90                  95

Thr Gly Pro Thr Gly Asp Thr Gly Ala Thr Gly Pro Thr Gly Pro Thr
            100                 105                 110

Gly Asp Thr Gly Ala Thr Gly Pro Thr Gly Pro Thr Gly Asp Thr Gly
        115                 120                 125

Ala Thr Gly Pro Thr Gly Pro Thr Gly Asp Thr Gly Ala Thr Gly Ala
    130                 135                 140

Thr Gly Pro Thr Gly Pro Thr Gly Pro Thr Gly Pro Ser Gly Leu Gly
145                 150                 155                 160

Leu Pro Ala Gly Leu Tyr Ala Phe Asn Ser Ala Thr Ile Ser Leu Ala
                165                 170                 175

Leu Gly Ile Asn Asp Pro Val Pro Phe Asn Thr Val Gly Ser Gln Phe
            180                 185                 190

Gly Thr Ala Ile Ser Gln Leu Asp Ala Asp Thr Phe Ile Ile Ser Glu
        195                 200                 205

Thr Gly Phe Tyr Lys Ile Thr Val Ile Ala Tyr Thr Ala Ala Val Ser
    210                 215                 220

Ile Leu Gly Ser Leu Ala Ile Gln Val Asn Gly Val Asn Ile Pro Gly
225                 230                 235                 240

Ala Gly Thr Ser Leu Ile Ser Leu Gly Ala Pro Leu Val Ile Gln Ala
                245                 250                 255

Ile Thr Gln Ile Thr Ile Thr Pro Ser Met Val Glu Ala Val Val Thr
            260                 265                 270

Gly Leu Gly Leu Ser Leu Ala Leu Gly Thr Ser Ala Ser Ile Ile Ile
        275                 280                 285

Glu Lys Ile Ala
    290

<210> SEQ ID NO 65
<211> LENGTH: 30
<212> TYPE: PRT

<213> ORGANISM: Bacillus thuringiensis

<400> SEQUENCE: 65

Met Asp Glu Phe Leu Ser Ser Ala Ala Ile Asn Pro As

<210> SEQ ID NO 68
<211> LENGTH: 295
<212> TYPE: PRT
<213> ORGANISM: Bacillus cereus

<400> SEQUENCE: 68

Met Phe Asp Lys Asn Lys Ile Leu Gln Ala Asn Ala Phe Asn Ser Asn
1               5                   10                  15

Leu Ile Gly Pro Thr Leu Pro Ile Pro Pro Phe Thr Leu Pro Thr
            20                  25                  30

Gly Pro Thr Gly Gly Thr Gly Pro Thr Gly Val Thr Gly Pro Thr Gly
            35                  40                  45

Val Thr Gly Pro Ile Gly Val Thr Gly Pro

Leu Pro Pro Thr Pro Pro Phe Thr Leu Pro Thr Gly
         35                  40

<210> SEQ ID NO 70
<211> LENGTH: 639
<212> TYPE: PRT
<213> ORGANISM: Bacillus cereus

<400> SEQUENCE: 70

Met Ser Asp Glu Asn Glu Lys Lys Tyr Ser Asn Glu Leu Ala Gln Ala
1               5                   10                  15

Asp Phe Ile Ser Ala Ala Ala Phe Asp Pro Ser Leu Val Gly Pro Thr
            20                  25                  30

Leu Pro P

Pro Thr Gly Ile Thr Gly Pro Thr Gly Ala Thr Gly Thr Thr Gly Ser
        370                 375                 380

Thr Gly Pro Thr Gly Val Thr Gly Pro Thr Gly Val Thr Gly Pro Thr
385                 390                 395                 400

Gly Val Thr Gly Pro Thr Gly Ala Thr Gly Pro Thr Gly Ala Thr Gly
                405                 410                 415

Ser Thr Gly Val Thr Gly Pro Thr Gly Ile Thr Gly Pro Thr Gly Ala
            420                 425                 430

Thr Gly Thr Thr Gly Ser Thr Gly Pro Thr Gly Val Thr Gly Pro Thr
        435                 440                 445

Gly Val Thr Gly Pro Thr Gly Ala Thr Gly Pro Thr Gly Val Thr Gly
    450                 455                 460

Pro Thr Gly Ala Thr Gly Pro Thr Gly Ala Thr Gly Ala Thr Ala Thr
465                 470                 475                 480

Thr Ser Thr Lys Ala Ile Leu Phe Gly Gly Thr Asn Ala Gly Phe Gln
                485                 490                 495

Arg Ile Ala Gly Ser Pro Gly Ala Asp Ser Gln Thr Leu Pro Tyr Val
            500                 505                 510

Thr Ala Gly Ala Gly Ser Val Val Ala Phe Ser Ala Ser Ile Asn Val
        515                 520                 525

Asn Asn Leu Gly Thr Gly Val Tyr Leu Leu Arg Val Cys Asp Asn Val
530                 535                 540

Pro Thr Asn Leu Ala Ser Pro Gly Ala Gly Gln Ile Val Ser Thr Ile
545                 550                 555                 560

Thr Leu Thr Leu Thr Ala Asn Ile Thr Gly Thr Ile Val Phe Ser Ile
                565                 570                 575

Lys Pro Thr Asp Ile Gly Ala Gln Pro Val Lys Val Phe Asn Pro Asn
            580                 585                 590

Pro Val Val Ala Pro Ala Thr Val Thr Trp Thr Ser Thr Ile Pro Gly
        595                 600                 605

Asn Pro Val Ala Arg Thr Asp Ala Ile Ser Leu Phe Ile Thr Pro Gly
    610                 615                 620

Ile Thr Gln Ser Ala Val Tyr Ser Val Phe Ile Ser Thr Ala Val
625                 630                 635

<210> SEQ ID NO 71
<211> LENGTH: 38
<212> TYPE: PRT
<213> ORGANISM: Bacillus cereus

<400> SEQUENCE: 71

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Ile Pro Ser
            20                  25                  30

Phe Thr Leu Pro Thr Gly
        35

<210> SEQ ID NO 72
<211> LENGTH: 163
<212> TYPE: PRT
<213> ORGANISM: Bacillus cereus

<400> SEQUENCE: 72

Met Ser Arg Lys Asp Arg Phe Asn Ser Pro Lys Ile Lys Ser Glu Ile
1               5                   10                  15

```
Ser Ile Ser Pro Asp Leu Val Gly Pro Thr Phe Pro Ile Pro Ser
         20                  25                  30

Phe Thr Leu Pro Thr Gly Ile Thr Gly Pro Thr Gly Asn Thr Gly Ala
         35                  40                  45

Thr Gly Asp Thr Gly Pro Thr Gly Pro Thr Phe Asn Ile Asn Phe Arg
 50                  55                  60

Ala Glu Lys Asn Gly Ala Gln Ser Phe Thr Pro Ala Asp Ile Gln
 65                  70                  75                  80

Val Ser Tyr Gly Asn Ile Ile Phe Asn Asn Gly Gly Tyr Ser Ser
                 85                  90                  95

Val Thr Asn Thr Phe Thr Ala Pro Ile Asn Gly Ile Tyr Leu Phe Ser
             100                 105                 110

Ala Asn Ile Gly Phe Asn Pro Thr Leu Gly Thr Thr Ser Thr Leu Arg
             115                 120                 125

Ile Thr Ile Arg Lys Asn Leu Val Ser Val Ala Ser Gln Thr Ile Asp
 130                 135                 140

Ile Gln Phe Ser Ala Ala Glu Ser Gly Thr Leu Thr Val Gly Ser Ser
 145                 150                 155                 160

Asn Phe Phe

<210> SEQ ID NO 73
<211> LENGTH: 30
<212> TYPE: PRT
<213> ORGANISM: Bacillus cereus

<400> SEQUENCE: 73

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Ser Thr Gly
         20                  25                  30

<210> SEQ ID NO 74
<211> LENGTH: 77
<212> TYPE: PRT
<213> ORGANISM: Bacillus cereus

<400> SEQUENCE: 74

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Ser Thr Gly Pro Thr
         20                  25                  30

Gly Ser Thr Gly Ala Thr Gly Ala Thr Gly Asn Thr Glu Pro Tyr Trp
         35                  40                  45

His Thr Gly Pro Pro Gly Ile Val Leu Leu Thr Tyr Asp Phe Lys Ser
 50                  55                  60

Leu Ile Ile Ser Phe Ala Phe Gln Ile Leu Pro Ile Ser
 65                  70                  75

<210> SEQ ID NO 75
<211> LENGTH: 48
<212> TYPE: PRT
<213> ORGANISM: Bacillus weihenstephanensis

<400> SEQUENCE: 75

Met Phe Leu Gly Gly Gly Tyr Met Glu Arg Lys Asn Lys Trp Tyr Gly
1               5                   10                  15

Leu Asn Ser Asn Val Asn Leu Ser Ala Ser Ser Phe Asp Pro Asn Leu
```

```
                    20                  25                  30

Val Gly Pro Thr Leu Pro Pro Ile Ser Pro Ile Ser Val Pro Thr Gly
            35                  40                  45

<210> SEQ ID NO 76
<211> LENGTH: 247
<212> TYPE: PRT
<213> ORGANISM: Bacillus weihenstephanensis

<400> SEQUENCE: 76

Met Phe Leu Gly Gly Gly Tyr Met Glu Arg Lys Asn Lys Trp Tyr Gly
1               5                   10                  15

Leu Asn Ser Asn Val Asn Leu Ser Ala Ser Ser Phe Asp Pro Asn Leu
            20                  25                  30

Val Gly Pro Thr Leu Pro Pro Ile Ser Pro Ile Ser Val Pro Thr Gly
            35                  40                  45

Pro Thr Gly Glu Thr Gly Ile Thr Gly Pro Thr Gly Pro Thr Gly Pro
        50                  55                  60

Thr Gly Pro Thr Gly Val Thr Gly Ile Thr Gly Pro Thr Gly Pro Thr
65                  70                  75                  80

Gly Ala Thr Gly Ile Thr Gly Pro Thr Gly Pro Thr Gly Glu Thr Gly
                85                  90                  95

Ile Thr Gly Pro Thr Gly Pro Gly Pro Thr Val Ser Leu Lys Phe Leu
            100                 105                 110

Tyr Val Ala Asn Phe Asn Glu Asn Thr Val Glu Ile Tyr Asp Ile Phe
        115                 120                 125

Asn Pro Ile Phe Pro Val Arg Ile Gly Glu Phe Asn Gly Gly Asn Leu
    130                 135                 140

Ala Asn Pro Ala Gly Leu Ala Ile Thr Gly Thr Thr Leu Tyr Val Thr
145                 150                 155                 160

Asn Asn Gly Asp Asn Thr Val Glu Ile Tyr Asp Ile Leu Asn Pro Ile
                165                 170                 175

Ala Pro Val His Val Gly Glu Phe Asn Gly Gly Asn Leu Ser Glu Pro
            180                 185                 190

Asp Gly Leu Ala Ile Thr Gly Thr Thr Leu Tyr Val Ala Asn Phe Asn
        195                 200                 205

Asp Asn Thr Val Glu Ile Tyr Asp Ile Leu Asn Pro Ile Ala Pro Val
    210                 215                 220

Arg Val Gly Glu Phe Asn Ala Gly Asn Leu Ser Ser Pro Ala Gly Leu
225                 230                 235                 240

Ile Ile Phe Ser Leu Phe Gly
                245

<210> SEQ ID NO 77
<211> LENGTH: 30
<212> TYPE: PRT
<213> ORGANISM: Bacillus cereus

<400> SEQUENCE: 77

Met Asp Glu Leu Leu Ser Ser Thr Leu Ile Asn Pro Asp Leu Leu Gly
1               5                   10                  15

Pro Thr Leu Pro Ala Ile Pro Pro Phe Thr Leu Pro Thr Gly
            20                  25                  30

<210> SEQ ID NO 78
<211> LENGTH: 536
<212> TYPE: PRT
```

<213> ORGANISM: Bacillus cereus

<400> SEQUENCE: 78

```
Met Asp Glu Leu Leu Ser Ser Thr Leu Ile As

```
Ile Asn Ser Gln Ala Thr Thr Asp Thr Gln Val Asn Leu Val Gly Gly
                405                 410                 415

Gly Ile Asn Gly Asn Val Ile Ile Asn Val Leu Pro Gly His Ile Pro
            420                 425                 430

Ile Asp Pro Leu Asn Leu Thr Ser Phe Ala Ile Thr Glu Asn Ile Phe
        435                 440                 445

Asn Pro Ser Pro Asn Ser Gly Asn Leu Phe Val Asn Gly Ala Asn Asn
    450                 455                 460

Val Ile Thr Arg Val Arg Ala Thr Val Asp Ser Leu Pro Ile Arg Ser
465                 470                 475                 480

Arg Ile Asn Leu Ile Gly Thr Ser Thr Ser Leu Ile Arg Val Asp Asp
                485                 490                 495

Ala Phe Asp Leu Ala Tyr Thr Pro Ile Asn Pro Ala Asn Trp Ala Pro
            500                 505                 510

Leu Pro Pro Thr Thr Val Gln Glu Ala Leu Asp Arg Ile Ala Ala Leu
        515                 520                 525

Met Ala Ile Thr Ile Gly Thr Pro
    530                 535

<210> SEQ ID NO 79
<211> LENGTH: 39
<212> TYPE: PRT
<213> ORGANISM: Bacillus cereus

<400> SEQUENCE: 79

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35

<210> SEQ ID NO 80
<211> LENGTH: 1309
<212> TYPE: PRT
<213> ORGANISM: Bacillus cereus

<400> SEQUENCE: 80

```
Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
            165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Gly Pro Thr Gly Pro Thr Gly Ala Thr
        210                 215                 220

Gly Pro Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Glu Gly Ser Gln
        275                 280                 285

Gly Ile Gln Gly Ile Pro Gly Pro Thr Gly Val Thr Gly Glu Gln Gly
290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
            325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
            355                 360                 365

Met Gly Asp Ile Gly Pro Thr Gly Pro Glu Gly Pro Glu Gly Leu Gln
            370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
            405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
            435                 440                 445

Ile Gln Gly Glu Ile Gly Ala Thr Gly Pro Glu Gly Pro Gln Gly Val
    450                 455                 460

Gln Gly Ala Gly Gly Ala Ile Gly Pro Thr Gly Pro Met Gly Pro Gln
465                 470                 475                 480

Gly Val Gln Gly Val Gln Gly Ile Gly Ala Thr Gly Ala Gln Gly
            485                 490                 495

Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
            515                 520                 525

Pro Thr Gly Val Thr Gly Pro Thr Gly Val Thr Gly Pro Ser Gly Gly
            530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
```

-continued

```
                565                 570                 575
Thr Gly Val Thr Gly Asp Thr Gly Ala Thr Gly Ser Thr Gly Val Thr
                580                 585                 590
Gly Ala Thr Gly Glu Thr Gly Ala Thr Gly Val Thr Gly Leu Gln Gly
                595                 600                 605
Pro Gln Gly Ile Gln Gly Val Gln Gly Glu Ile Gly Pro Thr Gly Pro
                610                 615                 620
Gln Gly Val Gln Gly Pro Gln Gly Ile Gln Gly Val Thr Gly Ala Thr
625                 630                 635                 640
Gly Asp Gln Gly Pro Gln Gly Ile Gln Gly Pro Gln Gly Asp Ile Gly
                645                 650                 655
Pro Thr Gly Pro Gln Gly Ile Gln Gly Pro Gln Gly Ser Gln Gly Ile
                660                 665                 670
Gln Gly Ala Thr Gly Gly Thr Gly Ala Gln Gly Pro Gln Gly Ile Gln
                675                 680                 685
Gly Pro Gln Gly Asp Ile Gly Pro Thr Gly Ser Gln Gly Pro Thr Gly
                690                 695                 700
Ile Gln Gly Ile Gln Gly Glu Ile Gly Pro Thr Gly Pro Arg Arg Pro
705                 710                 715                 720
Glu Gly Cys Arg Gly Arg Lys Arg Ile Gln Gly Val Gln Gly Pro Val
                725                 730                 735
Gly Ala Thr Gly Pro Glu Gly Pro Gln Gly Ile Gln Gly Ile Gln Gly
                740                 745                 750
Val Gln Gly Ala Thr Gly Pro Gln Gly Pro Gln Gly Ile Gln Gly Ile
                755                 760                 765
Gln Gly Val Gln Gly Ile Thr Gly Ala Thr Gly Ala Gln Gly Ala Thr
                770                 775                 780
Gly Ile Gln Gly Ile Gln Gly Glu Ile Gly Ala Thr Gly Pro Glu Gly
785                 790                 795                 800
Pro Gln Gly Val Gln Gly Ile Gln Gly Ala Ile Gly Pro Thr Gly Pro
                805                 810                 815
Met Gly Ala Gln Gly Val Gln Gly Ile Gln Gly Ile Gln Gly Ala Thr
                820                 825                 830
Gly Ala Gln Gly Val Gln Gly Pro Gln Gly Ile Gln Gly Val Gln Gly
                835                 840                 845
Pro Thr Gly Ala Thr Gly Asp Thr Gly Ala Thr Gly Ala Thr Gly Glu
                850                 855                 860
Gly Thr Thr Gly Pro Thr Gly Val Thr Gly Pro Thr Gly Val Thr Gly
865                 870                 875                 880
Pro Ser Gly Gly Pro Ala Gly Pro Thr Gly Pro Thr Gly Pro Ser Gly
                885                 890                 895
Pro Ala Gly Val Thr Gly Pro Ser Gly Gly Pro Pro Gly Pro Thr Gly
                900                 905                 910
Ala Thr Gly Ala Thr Gly Val Thr Gly Asp Thr Gly Ala Thr Gly Ser
                915                 920                 925
Thr Gly Val Thr Gly Ala Thr Gly Ala Thr Gly Val Thr Gly Leu Gln
                930                 935                 940
Gly Pro Gln Gly Ile Gln Gly Val Gln Gly Glu Ile Gly Pro Thr Gly
945                 950                 955                 960
Pro Gln Gly Ile Gln Gly Pro Gln Gly Ile Gln Gly Val Thr Gly Ala
                965                 970                 975
Thr Gly Ala Gln Gly Pro Gln Gly Ile Gln Gly Pro Gln Gly Asp Ile
                980                 985                 990
```

```
Gly Pro Thr Gly Ser Gln Gly Ile Gln Gly Pro Gln Gly Pro Gln Gly
            995                 1000                1005

Ile Gln Gly Ala Thr Gly Ala Thr Gly Ala Gln Gly Pro Gln Gly
        1010                1015                1020

Ile Gln Gly Pro Gln Gly Glu Ile Gly Pro Thr Gly Pro Gln Gly
        1025                1030                1035

Pro Gln Gly Ile Gln Gly Pro Gln Gly Ile Gln Gly Pro Thr Gly
        1040                1045                1050

Ala Thr Gly Ala Thr Gly Ala Thr Gly Pro Gln Gly Ile Gln Gly
        1055                1060                1065

Pro Gln Gly Ile Gln Gly Pro Gln Gly Ile Gln Gly Pro Thr Gly
        1070                1075                1080

Val Thr Gly Ala Thr Gly Ala Thr Gly Pro Gln Gly Ile Gln Gly
        1085                1090                1095

Pro Gln Gly Ile Gln Gly Pro Gln Gly Ile Gln Gly Pro Thr Gly
        1100                1105                1110

Ala Thr Gly Ala Thr Gly Ala Thr Gly Pro Gln Gly Ile Gln Gly
        1115                1120                1125

Pro Gln Gly Ile Gln Gly Pro Gln Gly Ile Gln Gly Pro Thr Gly
        1130                1135                1140

Ala Thr Gly Ala Thr Gly Ser Gln Gly Pro Thr Gly Asp Thr Gly
        1145                1150                1155

Pro Thr Gly Ala Gly Ala Thr Gly Ala Thr Gly Ala Thr Gly Val
        1160                1165                1170

Ser Thr Thr Ala Thr Tyr Ala Phe Ala Asn Asn Thr Ser Gly Thr
        1175                1180                1185

Ala Ile Ser Val Leu Leu Gly Gly Thr Asn Val Pro Leu Pro Asn
        1190                1195                1200

Asn Gln Asn Ile Gly Pro Gly Ile Thr Val Ser Gly Gly Asn Thr
        1205                1210                1215

Val Phe Thr Val Ala Asn Ala Gly Asn Tyr Tyr Ile Ala Tyr Thr
        1220                1225                1230

Ile Asn Leu Thr Ala Gly Leu Leu Val Ser Ser Arg Ile Thr Val
        1235                1240                1245

Asn Gly Ser Pro Leu Ala Gly Thr Ile Asn Ala Pro Thr Val Ala
        1250                1255                1260

Thr Gly Ser Phe Ser Ala Thr Ile Ile Ala Asn Leu Pro Ala Gly
        1265                1270                1275

Ala Ala Val Ser Leu Gln Leu Phe Gly Val Val Ala Val Ala Thr
        1280                1285                1290

Leu Ser Thr Ala Thr Pro Gly Ala Thr Leu Thr Ile Ile Arg Leu
        1295                1300                1305

Ser

<210> SEQ ID NO 81
<211> LENGTH: 44
<212> TYPE: PRT
<213> ORGANISM: Bacillus cereus

<400> SEQUENCE: 81

Met Val Lys Val Val Glu Gly Asn Ser Gly Lys Ser Lys Ile Lys Ser
1               5                   10                  15

Ser Leu Asn Ser Asn Phe Lys Leu Ser Ser Gly Leu Val Gly Pro Thr
            20                  25                  30
```

```
Phe Pro Pro Val Pro Thr Gly Met Thr Gly Ile Thr
        35                  40
```

<210> SEQ ID NO 82
<211> LENGTH: 815
<212> TYPE: PRT
<213> ORGANISM: Bacillus cereus

<400> SEQUENCE: 82

```
Met Val Lys Val Val Glu Gly Asn Ser Gly Lys Ser Lys Ile Lys Ser
1               5                   10                  15

Ser Leu Asn Ser Asn Phe Lys Leu Ser Ser Gly Leu Val Gly Pro Thr
            20

-continued

```
            355                 360                 365
Gly Asn Thr Gly Ala Thr Gly Asn Thr Gly Ala Thr Gly
            370                 375                 380
Ala Thr Gly Ala Thr Gly Ser Thr Gly Pro Thr Gly Asn Thr Gly Ala
385                 390                 395                 400
Thr Gly Asn Thr Gly Pro Thr Gly Val Thr Gly Ser Thr Gly Pro Thr
                405                 410                 415
Gly Ser Thr Gly Glu Thr Gly Glu Thr Gly Pro Thr Gly Glu Thr Gly
                420                 425                 430
Val Thr Gly Ser Thr Gly Pro Thr Gly Pro Thr Gly Ala Thr Gly Asn
                435                 440                 445
Thr Gly Pro Thr Gly Glu Thr Gly Ala Thr Gly Ser Thr Gly Glu Thr
                450                 455                 460
Gly Glu Thr Gly Pro Thr Gly Glu Thr Gly Val Thr Gly Ser Thr Gly
465                 470                 475                 480
Pro Thr Gly Asn Thr Gly Ala Thr Gly Asn Thr Gly Pro Thr Gly Glu
                485                 490                 495
Thr Gly Val Thr Gly Ser Thr Gly Pro Thr Gly Asn Thr Gly Ala Thr
                500                 505                 510
Gly Asn Thr Gly Pro Thr Gly Glu Thr Gly Glu Thr Gly Val Thr Gly
                515                 520                 525
Ser Thr Gly Val Thr Gly Asn Thr Gly Ala Thr Gly Ser Thr Gly Ala
                530                 535                 540
Thr Gly Asn Thr Gly Pro Thr Gly Glu Thr Gly Ala Thr Gly Pro Thr
545                 550                 555                 560
Gly Ala Thr Gly Val Thr Gly Ser Thr Gly Pro Thr Gly Asn Thr Gly
                565                 570                 575
Pro Thr Gly Glu Thr Gly Ser Thr Gly Ser Thr Gly Ala Thr Gly Ser
                580                 585                 590
Thr Gly Val Thr Gly Asn Thr Gly Ala Thr Gly Glu Thr Gly Pro Thr
                595                 600                 605
Gly Ser Thr Gly Ala Thr Gly Asn Thr Gly Ala Thr Gly Glu Thr Gly
                610                 615                 620
Pro Thr Gly Ala Thr Gly Val Thr Gly Pro Thr Gly Ser Thr Gly Val
625                 630                 635                 640
Thr Gly Ser Thr Gly Pro Thr Gly Ser Thr Gly Ala Thr Gly Ala Thr
                645                 650                 655
Gly Ser Thr Gly Pro Thr Gly Ser Thr Gly Thr Thr Gly Asp Thr Gly
                660                 665                 670
Pro Thr Gly Ala Thr Gly Val Ser Thr Thr Ala Thr Tyr Ala Phe Ala
                675                 680                 685
Asn Asn Thr Ser Gly Ser Val Ile Ser Val Leu Leu Gly Gly Thr Asn
                690                 695                 700
Ile Pro Leu Pro Asn Asn Gln Asn Ile Gly Pro Gly Ile Thr Val Ser
705                 710                 715                 720
Gly Gly Asn Thr Val Phe Thr Val Ala Asn Ala Gly Asn Tyr Tyr Ile
                725                 730                 735
Ala Tyr Thr Ile Asn Leu Thr Ala Gly Leu Leu Val Ser Ser Arg Ile
                740                 745                 750
Thr Val Asn Gly Ser Pro Leu Ala Gly Thr Ile Asn Ser Pro Thr Val
                755                 760                 765
Ala Thr Gly Ser Phe Asn Ala Thr Ile Ile Ala Ser Leu Pro Ala Gly
                770                 775                 780
```

```
Ala Ala Val Ser Leu Gln Leu Phe Gly Val Val Ala Leu Ala Thr Leu
785                 790                 795                 800

Ser Thr Ala Thr Pro Gly Ala Thr Leu Thr Ile Ile Arg Leu Ser
                805                 810                 815

<210> SEQ ID NO 83
<211> LENGTH: 40
<212> TYPE: PRT
<213> ORGANISM: Bacillus anthracis

<400> SEQUENCE: 83

Met Glu Gly Asn Gly Gly Lys Ser Lys Ile Lys Ser Pro Leu Asn Ser
1               5                   10                  15

Asn Phe Lys Ile Leu Ser Asp Leu Val Gly Pro Thr Phe Pro Pro Val
            20                  25                  30

Pro Thr Gly Met Thr Gly Ile Thr
            35                  40

<210> SEQ ID NO 84
<211> LENGTH: 469
<212> TYPE: PRT
<213> ORGANISM: Bacillus anthracis

<400> SEQUENCE: 84

Met Glu Gly Asn Gly Gly Lys Ser Lys Ile Lys Ser Pro Leu Asn Ser
1               5                   10                  15

Asn Phe Lys Ile Leu Ser Asp Leu Val Gly Pro Thr Phe Pro Pro Val
            20                  25                  30

Pro Thr Gly Met Thr Gly Ile Thr Gly Ser Thr Gly Ala Thr Gly Asn
            35                  40                  45

Thr Gly Pro Thr Gly Glu Thr Gly Ala Thr Gly Ser Ala Gly Ile Thr
        50                  55                  60

Gly Ser Thr Gly Pro Thr Gly Asn Thr Gly Thr Gly Ser Thr Gly
65                  70                  75                  80

Ser Thr Gly Asn Thr Gly Ala Thr Gly Ser Thr Gly Val Thr Gly Ser
                85                  90                  95

Thr Gly Val Thr Gly Ser Thr Gly Val Thr Gly Ser Thr Gly Val Thr
            100                 105                 110

Gly Ser Thr Gly Pro Thr Gly Glu Thr Gly Thr Gly Ser Thr Gly
            115                 120                 125

Val Thr Gly Ser Thr Gly Ala Thr Gly Ser Thr Gly Val Thr Gly Ser
        130                 135                 140

Thr Gly Val Thr Gly Glu Thr Gly Pro Thr Gly Ser Thr Gly Ala Thr
145                 150                 155                 160

Gly Asn Thr Gly Pro Thr Gly Glu Thr Gly Thr Gly Ser Thr Gly
                165                 170                 175

Ala Thr Gly Ser Thr Gly Val Thr Gly Asn Thr Gly Pro Thr Gly Ser
            180                 185                 190

Thr Gly Val Thr Gly Asn Thr Gly Ala Thr Gly Glu Thr Gly Pro Thr
        195                 200                 205

Gly Asn Thr Gly Ala Thr Gly Asn Thr Gly Pro Thr Gly Glu Thr Gly
        210                 215                 220

Val Thr Gly Ser Thr Gly Pro Thr Gly Glu Thr Gly Val Thr Gly Ser
225                 230                 235                 240

Thr Gly Pro Thr Gly Asn Thr Gly Ala Thr Gly Glu Thr Gly Ala Thr
                245                 250                 255
```

```
Gly Ser Thr Gly Val Thr Gly Asn Thr Gly Ser Thr Gly Glu Thr Gly
            260                 265                 270

Pro Thr Gly Ser Thr Gly Pro Thr Gly Ser Thr Gly Ala Thr Gly Val
                275                 280                 285

Thr Gly Asn Thr Gly Pro Thr Gly Ser Thr Gly Ala Thr Gly Ala Thr
            290                 295                 300

Gly Ser Thr Gly Pro Thr Gly Ser Thr Gly Thr Gly Asn Thr Gly
305                 310                 315                 320

Val Thr Gly Asp Thr Gly Pro Thr Gly Ala Thr Gly Val Ser Thr Thr
                325                 330                 335

Ala Thr Tyr Ala Phe Ala Asn Asn Thr Ser Gly Ser Val Ile Ser Val
                340                 345                 350

Leu Leu Gly Gly Thr Asn Ile Pro Leu Pro Asn Asn Gln Asn Ile Gly
                355                 360                 365

Pro Gly Ile Thr Val Ser Gly Gly Asn Thr Val Phe Thr Val Ala Asn
            370                 375                 380

Ala Gly Asn Tyr Tyr Ile Ala Tyr Thr Ile Asn Leu Thr Ala Gly Leu
385                 390                 395                 400

Leu Val Ser Ser Arg Ile Thr Val Asn Gly Ser Pro Leu Ala Gly Thr
                405                 410                 415

Ile Asn Ser Pro Thr Val Ala Thr Gly Ser Phe Ser Ala Thr Ile Ile
            420                 425                 430

Ala Ser Leu Pro Ala Gly Ala Ala Val Ser Leu Gln Leu Phe Gly Val
                435                 440                 445

Val Ala Leu Ala Thr Leu Ser Thr Ala Thr Pro Gly Ala Thr Leu Thr
                450                 455                 460

Ile Ile Arg Leu Ser
465

<210> SEQ ID NO 85
<211> LENGTH: 34
<212> TYPE: PRT
<213> ORGANISM: Bacillus thuringiensis

<400> SEQUENCE: 85

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly

<210> SEQ ID NO 86
<211> LENGTH: 285
<212> TYPE: PRT
<213> ORGANISM: Bacillus thuringiensis

<400> SEQUENCE: 86

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
                35                  40                  45

Gly Pro Thr Gly Thr Thr Gly Ala Thr Gly Ala Thr Gly Ile Thr Gly
            50                  55                  60
```

```
Val Thr Gly Ala Thr Gly Ile Thr Gly Val Thr Gly Ala Thr Gly Ile
 65                  70                  75                  80

Thr Gly Ala Thr Gly Pro Thr Gly Ile Thr Gly Ala Thr Gly Pro Ala
                 85                  90                  95

Gly Ile Thr Gly Ala Thr Gly Pro Ala Gly Ile Thr Gly Ala Thr Gly
            100                 105                 110

Pro Ala Gly Ile Thr Gly Ala Thr Gly Pro Thr Gly Ile Thr Gly Ala
            115                 120                 125

Thr Gly Pro Thr Gly Ile Thr Gly Ala Thr Gly Pro Thr Gly Ile Thr
        130                 135                 140

Gly Ala Thr Gly Pro Ala Gly Ile Thr Gly Ala Thr Gly Pro Thr Gly
145                 150                 155                 160

Thr Thr Gly Val Thr Gly Ala Thr Gly Ile Thr Gly Val Thr Gly Ala
                165                 170                 175

Thr Gly Ile Thr Gly Ala Thr Gly Pro Thr Gly Thr Thr Gly Val Thr
            180                 185                 190

Gly Pro Thr Gly Val Ile Gly Pro Ile Thr Thr Thr Asn Leu Leu Phe
        195                 200                 205

Tyr Thr Phe Ala Asp Gly Glu Lys Leu Ile Tyr Thr Asp Ser Asp Gly
    210                 215                 220

Leu Ala Gln Tyr Gly Thr Thr His Ile Leu Ser Pro Asp Glu Val Ser
225                 230                 235                 240

Tyr Ile Asn Leu Phe Ile Asn Gly Ile Leu Gln Pro Gln Pro Leu Tyr
                245                 250                 255

Gln Val Ser Thr Gly Gln Leu Thr Leu Leu Asp Asn Gln Pro Pro Ser
            260                 265                 270

Gln Gly Ser Ser Ile Ile Leu Gln Phe Ile Ile Ile Asn
        275                 280                 285

<210> SEQ ID NO 87
<211> LENGTH: 34
<212> TYPE: PRT
<213> ORGANISM: Bacillus cereus

<400> SEQUENCE: 87

Met Asn Ser Asn Glu Lys Leu Ser Leu Asn Lys Gly Met Val Arg Pro
 1               5                  10                  15

Glu Asn Ile Gly Pro Thr Phe Pro Val Leu Pro Pro Ile Tyr Ile Pro
            20                  25                  30

Thr Gly

<210> SEQ ID NO 88
<211> LENGTH: 258
<212> TYPE: PRT
<213> ORGANISM: Bacillus cereus

<400> SEQUENCE: 88

Met Asn Ser Asn Glu Lys Leu Ser Leu Asn Lys Gly Met Val Arg Pro
 1               5                  10                  15

Glu Asn Ile Gly Pro Thr Phe Pro Val Leu Pro Pro Ile Tyr Ile Pro
            20                  25                  30

Thr Gly Ala Thr Gly Ala Thr Gly Ala Thr Gly Ala Thr Gly Ala Thr
             35                  40                  45

Gly Ala Thr Gly Ala Thr Gly Ala Thr Gly Ala Thr Gly Ala Thr Gly
         50                  55                  60

Ala Thr Gly Ala Thr Gly Ala Thr Gly Ala Thr Gly Val Thr Gly Ala
```

65 70 75 80

Thr Gly Ala Thr Gly Ala Thr Gly Val Thr Gly Ala Thr Gly Ala Thr
85 90 95

Gly Val Thr Gly Ala Thr Gly Val Thr Gly Ala Thr Gly Ala Thr Gly
100 105 110

Val Thr Gly Ala Thr Gly Val Thr Gly Ala Thr Gly Ala Thr Gly Ala
115 120 125

Thr Gly Val Thr Gly Ala Thr Gly Ala Thr Gly Ala Thr Gly Ala Thr
130 135 140

Gly Val Thr Gly Ala Thr Gly Val Thr Gly Val Thr Gly Val Thr Gly
145 150 155 160

Ala Thr Gly Ala Thr Gly Pro Thr Gly Val Ile Gly Pro Ile Thr Thr
165 170 175

Thr Asn Leu Leu Phe Tyr Thr Phe Ser Asp Gly Glu Lys Leu Ile Tyr
180 185 190

Thr Asp Ser Asp Gly Leu Ala Gln Tyr Gly Thr Thr His Ile Leu Ser
195 200 205

Pro Asp Glu Val Ser Tyr Ile Asn Leu Phe Ile Asn Gly Ile Leu Gln
210 215 220

Pro Gln Pro Leu Tyr Gln Val Ser Thr Gly Gln Leu Thr Leu Leu Asp
225 230 235 240

Asn Gln Pro Pro Ser Gln Gly Ser Ser Ile Ile Leu Gln Phe Ile Ile
245 250 255

Ile Asn

<210> SEQ ID NO 89
<211> LENGTH: 34
<212> TYPE: PRT
<213> ORGANISM: Bacillus cereus

<400> SEQUENCE: 89

Met Lys Arg Asn Asp Asn Leu Ser Leu Asn Lys Gly Met Ile Gly Pro
1 5 10 15

Glu Asn Ile Gly Pro Thr Phe Pro Ile Leu Pro Pro Ile Tyr Ile Pro
20 25 30

Thr Gly

<210> SEQ ID NO 90
<211> LENGTH: 279
<212> TYPE: PRT
<213> ORGANISM: Bacillus cereus

<400> SEQUENCE: 90

Met Lys Arg Asn Asp Asn Leu Ser Leu Asn Lys Gly Met Ile Gly Pro
1 5 10 15

Glu Asn Ile Gly Pro Thr Phe Pro Ile Leu Pro Pro Ile Tyr Ile Pro
20 25 30

Thr Gly Ala Thr Gly Pro Thr Gly Ile Thr Gly Pro Thr Gly Glu Thr
35 40 45

Gly Pro Thr Gly Ile Thr Gly Pro Thr Gly Val Thr Gly Pro Thr Gly
50 55 60

Ile Thr Gly Pro Thr Gly Ala Thr Gly Pro Thr Gly Ile Thr Gly Pro
65 70 75 80

Thr Gly Ala Thr Gly Pro Thr Gly Ile Thr Gly Pro Thr Gly Ala Thr
85 90 95

```
Gly Pro Thr Gly Glu Thr Gly Pro Thr Gly Ile Thr Gly Pro Thr Gly
            100                 105                 110

Ala Thr Gly Pro Thr Gly Ile Thr Gly Pro Thr Gly Ala Thr Gly Pro
        115                 120                 125

Thr Gly Glu Thr Gly Pro Thr Gly Glu Thr Gly Pro Thr Gly Val Thr
    130                 135                 140

Gly Pro Thr Gly Ile Thr Gly Pro Thr Gly Ala Thr Gly Pro Thr Gly
145                 150                 155                 160

Ile Thr Gly Pro Thr Gly Ala Thr Gly Pro Thr Gly Glu Thr Gly Pro
                165                 170                 175

Thr Gly Ile Thr Gly Pro Thr Gly Ala Thr Gly Pro Thr Gly Gly Ile
            180                 185                 190

Gly Pro Ile Thr Thr Thr Asn Leu Leu Tyr Tyr Thr Phe Ala Asp Gly
        195                 200                 205

Glu Lys Leu Ile Tyr Thr Asp Ala Asp Gly Ile Pro Gln Tyr Gly Thr
    210                 215                 220

Thr Asn Ile Leu Ser Pro Ser Glu Val Ser Tyr Ile Asn Leu Phe Val
225                 230                 235                 240

Asn Gly Ile Leu Gln Pro Gln Pro Leu Tyr Glu Val Ser Thr Gly Lys
                245                 250                 255

Leu Thr Leu Leu Asp Thr Gln Pro Pro Ser Gln Gly Ser Ser Ile Ile
            260                 265                 270

Leu Gln Phe Ile Ile Ile Asn
            275

<210> SEQ ID NO 91
<211> LENGTH: 99
<212> TYPE: PRT
<213> ORGANISM: Bacillus cereus

<400> SEQUENCE: 91

Met Asp Ser Phe Val Asp Val Gly Glu Ile Phe Thr Ile Phe Arg Lys
1               5                   10                  15

Leu Asn Met Glu Gly Ser Leu Gln Phe Lys Val His Asn Ser Met Gly
            20                  25                  30

Lys Thr Tyr Tyr Ile Thr Ile Asn Glu Val Tyr Val Tyr Val Thr

```
                    35                  40                  45
Leu Leu Gln Tyr Ser Thr Leu Ile Gly Gly Ser Tyr Val Phe Asp Lys
 50                  55                  60

Asn Glu Ile Gln Lys Ile Asn Gly Ile Leu Gln Ala Asn Ala Leu Asn
 65                  70                  75                  80

Pro Asn Leu Ile Gly Pro Thr Leu Pro Pro Ile Pro Pro Phe Thr Leu
                     85                  90                  95

Pro Thr Gly Pro Thr Gly Val Thr Gly Pro Thr Gly Gly Thr Gly Pro
                    100                 105                 110

Thr Gly Val Thr Gly Pro Thr Gly Val Thr Gly Pro Thr Gly Val Thr
                    115                 120                 125

Gly Val Thr Gly Pro Thr Gly Val Thr Gly Pro Thr Gly Val Thr Gly
                    130                 135                 140

Pro
145

<210> SEQ ID NO 93
<211> LENGTH: 136
<212> TYPE: PRT
<213> ORGANISM: Bacillus weihenstephanensis

<400> SEQUENCE: 93

Met Lys Phe Ser Lys Lys Ser Thr Val Asp Ser Ser Ile Val Gly Lys
  1               5                  10                  15

Arg Val Val Ser Lys Val Asn Ile Leu Arg Phe Tyr Asp Ala Arg Ser
                 20                  25                  30

Trp Gln Asp Lys Asp Val Asp Gly Phe Val Asp Val Gly Glu Leu Phe
             35                  40                  45

Thr Ile Phe Arg Lys Leu Asn Met Glu Gly Ser Val Gln Phe Lys Ala
 50                  55                  60

His Asn Ser Ile Gly Lys Thr Tyr Tyr Ile Thr Ile Asn Glu Val Tyr
 65                  70                  75                  80

Val Phe Val Thr Val Leu Leu Gln Tyr Ser Thr Leu Ile Gly Gly Ser
                 85                  90                  95

Tyr Val Phe Asp Lys Asn Glu Ile Gln Lys Ile Asn Gly Ile Leu Gln
                100                 105                 110

Ala Asn Ala Leu Asn Pro Asn Leu Ile Gly Pro Thr Leu Pro Pro Ile
            115                 120                 125

Pro Pro Phe Thr Leu Pro Thr Gly
            130                 135

<210> SEQ ID NO 94
<211> LENGTH: 142
<212> TYPE: PRT
<213> ORGANISM: Bacillus weihenstephanensis

<400> SEQUENCE: 94

Met Lys Phe Ser Lys Lys Ser Thr Val Asp Ser Ser Ile Val Gly Lys
  1               5                  10                  15

Arg Val Val Ser Lys Val Asn Ile Leu Arg Phe Tyr Asp Ala Arg Ser
                 20                  25                  30

Trp Gln Asp Lys Asp Val Asp Gly Phe Val Asp Val Gly Glu Leu Phe
             35                  40                  45

Thr Ile Phe Arg Lys Leu Asn Met Glu Gly Ser Val Gln Phe Lys Ala
 50                  55                  60

His Asn Ser Ile Gly Lys Thr Tyr Tyr Ile Thr Ile Asn Glu Val Tyr
```

```
            65                  70                  75                  80
Val Phe Val Thr Val Leu Leu Gln Tyr Ser Thr Leu Ile Gly Gly Ser
                85                  90                  95
Tyr Val Phe Asp Lys Asn Glu Ile Gln Lys Ile Asn Gly Ile Leu Gln
                100                 105                 110
Ala Asn Ala Leu Asn Pro Asn Leu Ile Gly Pro Thr Leu Pro Pro Ile
                115                 120                 125
Pro Pro Phe Thr Leu Pro Thr Gly Pro Thr Gly Thr Gly
        130                 135                 140

<210> SEQ ID NO 95
<211> LENGTH: 196
<212> TYPE: PRT
<213> ORGANISM: Bacillus anthracis

<400> SEQUENCE: 95

Met Ser Asn Asn Tyr Ser Asn Gly Leu Asn Pro Asp Glu Ser Leu
1               5                   10                  15
Ser Ala Ser Ala Phe Asp Pro Asn Leu Val Gly Pro Thr Leu Pro Pro
                20                  25                  30
Ile Pro Pro Phe Thr Leu Pro Thr Gly Pro Thr Gly Pro Phe Thr Thr
                35                  40                  45
Gly Pro Thr Gly Pro Thr Gly Pro Thr Gly Pro Thr Gly Pro Thr Gly
            50                  55                  60
Pro Thr Gly Pro Thr Gly Pro Thr Gly Asp Thr Gly Thr Thr Gly Pro
65                  70                  75                  80
Thr Gly Pro Thr Gly Pro Thr Gly Pro Thr Gly Pro Thr Gly Pro Thr
                85                  90                  95
Gly Pro Thr Gly Pro Thr Gly Pro Thr Gly Phe Thr Pro Thr Gly Pro
                100                 105                 110
Thr Gly Pro Thr Gly Pro Thr Gly Asp Thr Gly Thr Thr Gly Pro Thr
                115                 120                 125
Gly Pro Thr Gly Pro Thr Gly Pro Thr Gly Pro Thr Gly Asp Thr Gly
            130                 135                 140
Thr Thr Gly Pro Thr Gly Pro Thr Gly Pro Thr Gly Pro Thr Gly Pro
145                 150                 155                 160
Thr Gly Pro Thr Gly Pro Thr Phe Thr Gly Pro Thr Gly Pro Thr Gly
                165                 170                 175
Pro Thr Gly Ala Thr Gly Leu Thr Gly Pro Thr Gly Pro Thr Gly Pro
                180                 185                 190
Ser Gly Leu Gly
        195

<210> SEQ ID NO 96
<211> LENGTH: 17
<212> TYPE: PRT
<213> ORGANISM: Bacillus anthracis

<400> SEQUENCE: 96

Met Ala Phe Asp Pro Asn Leu Val Gly Pro Thr Leu Pro Pro Ile Pro
1               5                   10                  15
Pro

<210> SEQ ID NO 97
<211> LENGTH: 17
<212> TYPE: PRT
<213> ORGANISM: Bacillus anthracis
```

```
<400> SEQUENCE: 97

Met Ala Leu Glu Pro Asn Leu Ile Gly Pro Thr Leu Pro Pro Ile Pro
1               5                   10                  15

Pro

<210> SEQ ID NO 98
<211> LENGTH: 17
<212> TYPE: PRT
<213> ORGANISM: Bacillus weihenstephanensis

<400> SEQUENCE: 98

Met Ala Leu Asn Pro Asn Leu Ile Gly Pro Thr Leu Pro Pro Ile Pro
1               5                   10                  15

Pro

<210> SEQ ID NO 99
<211> LENGTH: 17
<212> TYPE: PRT
<213> ORGANISM: Bacillus weihenstephanensis

<400> SEQUENCE: 99

Met Ala Leu Asp Pro Asn Ile Ile Gly Pro Thr Leu Pro Pro Ile Pro
1               5                   10                  15

Pro

<210> SEQ ID NO 100
<211> LENGTH: 17
<212> TYPE: PRT
<213> ORGANISM: Bacillus cereus

<400> SEQUENCE: 100

Met Ala Leu Glu Pro Asn Leu Ile Gly Pro Thr Leu Pro Ser Ile Pro
1               5                   10                  15

Pro

<210> SEQ ID NO 101
<211> LENGTH: 17
<212> TYPE: PRT
<213> ORGANISM: Bacillus weihenstephanensis

<400> SEQUENCE: 101

Met Ala Leu Asp Pro Asn Leu Ile Gly Pro Pro Leu Pro Pro Ile Thr
1               5                   10                  15

Pro

<210> SEQ ID NO 102
<211> LENGTH: 17
<212> TYPE: PRT
<213> ORGANISM: Bacillus weihenstephanensis

<400> SEQUENCE: 102

Met Ala Leu Asn Pro Gly Ser Ile Gly Pro Thr Leu Pro Pro Val Pro
1               5                   10                  15

Pro

<210> SEQ ID NO 103
<211> LENGTH: 17
<212> TYPE: PRT
<213> ORGANISM: Bacillus weihenstephanensis
```

-continued

<400> SEQUENCE: 103

Met Ala Leu Asn Pro Cys Ser Ile Gly Pro Thr Leu Pro Pro Met Gln
1               5                   10                  15

Pro

<210> SEQ ID NO 104
<211> LENGTH: 17
<212> TYPE: PRT
<213> ORGANISM: Bacillus mycoides

<400> SEQUENCE: 104

Met Ala Leu Asn Pro Gly Ser Ile Gly Pro Thr Leu Pro Pro Val Gln
1               5                   10                  15

Pro

<210> SEQ ID NO 105
<211> LENGTH: 17
<212> TYPE: PRT
<213> ORGANISM: Bacillus anthracis

<400> SEQUENCE: 105

Met Ala Leu Asn Pro Gly Ser Val Gly Pro Thr Leu Pro Pro Met Gln
1               5                   10                  15

Pro

<210> SEQ ID NO 106
<211> LENGTH: 17
<212> TYPE: PRT
<213> ORGANISM: Bacillus cereus

<400> SEQUENCE: 106

Met Ala Leu Asp Pro Asn Leu Ile Gly Pro Thr Phe Pro Pro Ile Pro
1               5                   10                  15

Ser

<210> SEQ ID NO 107
<211> LENGTH: 18
<212> TYPE: PRT
<213> ORGANISM: Bacillus thuringiensis

<400> SEQUENCE: 107

Met Ala Ala Ile Asn Pro Asn Leu Val Gly Pro Thr Leu Pro Pro Val
1               5                   10                  15

Pro Pro

<210> SEQ ID NO 108
<211> LENGTH: 799
<212> TYPE: PRT
<213> ORGANISM: Bacillus mycoides

<400> SEQUENCE: 108

Met Lys Arg Lys Thr Pro Phe Lys Val Phe Ser Ser Leu Ala Ile Thr
1               5                   10                  15

Thr Met Leu Gly Cys Thr Phe Ala Leu Gly Thr Ser Val Ala Tyr Ala
            20                  25                  30

Glu Thr Thr Ser Gln Ser Lys Gly Ser Ile Ser Thr Thr Pro Ile Asp
        35                  40                  45

Asn Asn Leu Ile Gln Glu Glu Arg Leu Ala Glu Ala Leu Lys Glu Arg
    50                  55                  60

```
Gly Thr Ile Asp Gln Ser Ala Ser Lys Glu Glu Thr Gln Lys Ala Val
 65                  70                  75                  80

Glu Gln Tyr Ile Glu Lys Lys Gly Asp Gln Pro Asn Lys Glu Ile
                 85                  90                  95

Leu Pro Asp Asp Pro Ala Lys Glu Ala Ser Asp Phe Val Lys Lys Val
                100                 105                 110

Lys Glu Lys Lys Met Glu Glu Lys Glu Lys Val Lys Lys Ser Val Glu
            115                 120                 125

Asn Ala Ser Ser Glu Gln Thr Pro Ser Gln Asn Lys Lys Gln Leu Asn
            130                 135                 140

Gly Lys Val Pro Thr Ser Pro Ala Lys Gln Ala Pro Tyr Asn Gly Ala
145                 150                 155                 160

Val Arg Thr Asp Lys Val Leu Val Leu Leu Val Glu Phe Ser Asp Tyr
                165                 170                 175

Lys His Asn Asn Ile Glu Gln Ser Pro Gly Tyr Met Tyr Ala Asn Asp
                180                 185                 190

Phe Ser Arg Glu His Tyr Gln Lys Met Leu Phe Gly Asn Glu Pro Phe
            195                 200                 205

Thr Leu Phe Asp Gly Ser Lys Val Lys Thr Phe Lys Gln Tyr Tyr Glu
210                 215                 220

Glu Gln Ser Gly Gly Ser Tyr Thr Thr Asp Gly Tyr Val Thr Glu Trp
225                 230                 235                 240

Leu Thr Val Pro Gly Lys Ala Ala Asp Tyr Gly Ala Asp Gly Lys Thr
                245                 250                 255

Gly His Asp Asn Lys Gly Pro Lys Gly Ala Arg Asp Leu Val Lys Glu
            260                 265                 270

Ala Leu Lys Ala Ala Glu Lys Gly Leu Asp Leu Ser Gln Phe Asp
            275                 280                 285

Gln Phe Asp Arg Tyr Asp Thr Asn Gly Asp Gly Asn Gln Asn Glu Pro
            290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg
                325                 330                 335

Ser Lys Leu Ala Gln Asp Pro Val Ala Ile Glu Gly Thr Lys Ser Lys
            340                 345                 350

Val Ser Tyr Trp Asp Gly Lys Val Ala Ala His Asp Tyr Thr Ile Glu
            355                 360                 365

Pro Glu Asp Gly Ala Val Gly Val Phe Ala His Glu Phe Gly His Asp
            370                 375                 380

Leu Gly Leu Pro Asp Glu Tyr Asp Thr Asn Tyr Thr Gly Ala Gly Ser
385                 390                 395                 400

Pro Val Glu Ala Trp Ser Leu Met Ser Gly Ser Trp Thr Gly Arg
                405                 410                 415

Ile Ala Gly Thr Glu Pro Thr Ser Phe Ser Pro Gln Asn Lys Asp Phe
                420                 425                 430

Leu Gln Lys Asn Met Asp Gly Asn Trp Ala Lys Ile Val Glu Val Asp
            435                 440                 445

Tyr Asp Lys Ile Lys Arg Gly Val Gly Phe Pro Thr Tyr Ile Asp Gln
            450                 455                 460

Ser Val Thr Lys Ser Asn Arg Pro Gly Leu Val Arg Val Asn Leu Pro
465                 470                 475                 480

Glu Lys Ser Val Glu Thr Ile Lys Thr Gly Phe Gly Lys His Ala Tyr
```

```
                485                 490                 495
Tyr Ser Thr Arg Gly Asp Asp Met His Thr Thr Leu Glu Thr Pro Leu
            500                 505                 510

Phe Asp Leu Thr Lys Ala Ala Asn Ala Lys Phe Asp Tyr Lys Ala Asn
            515                 520                 525

Tyr Glu Leu Glu Ala Glu Cys Asp Phe Ile Glu Val His Ala Val Thr
530                 535                 540

Glu Asp Gly Thr Lys Thr Leu Ile Asp Lys Leu Gly Asp Lys Val Val
545                 550                 555                 560

Lys Gly Asp Gln Asp Thr Thr Glu Gly Lys Trp Ile Asp Lys Ser Tyr
                565                 570                 575

Asp Leu Ser Gln Phe Lys Gly Lys Val Lys Leu Gln Phe Asp Tyr
            580                 585                 590

Ile Thr Asp Pro Ala Leu Thr Tyr Lys Gly Phe Ala Met Asp Asn Val
            595                 600                 605

Asn Val Thr Val Asp Gly Lys Val Phe Ser Asp Ala Glu Gly
610                 615                 620

Gln Ala Lys Met Lys Leu Asn Gly Phe Val Val Ser Asp Gly Thr Glu
625                 630                 635                 640

Lys Lys Pro His Tyr Tyr Leu Glu Trp Arg Asn Tyr Ala Gly Ser
                645                 650                 655

Asp Glu Gly Leu Lys Val Gly Arg Gly Pro Val Tyr Asn Thr Gly Leu
            660                 665                 670

Val Val Trp Tyr Ala Asp Asp Ser Phe Lys Asp Asn Trp Val Gly Arg
            675                 680                 685

His Pro Gly Glu Gly Phe Leu Gly Val Val Asp Ser His Pro Glu Ala
690                 695                 700

Val Val Gly Asn Leu Asn Gly Lys Pro Val Tyr Gly Asn Thr Gly Leu
705                 710                 715                 720

Gln Ile Ala Asp Ala Ala Phe Ser Leu Asp Gln Thr Pro Ala Trp Asn
            725                 730                 735

Val Asn Ser Phe Thr Arg Gly Gln Phe Asn Tyr Pro Gly Leu Pro Gly
            740                 745                 750

Val Ala Thr Phe Asp Asp Ser Lys Val Tyr Ser Asn Thr Gln Ile Pro
            755                 760                 765

Asp Ala Gly Arg Lys Val Pro Gln Leu Gly Leu Lys Phe Gln Val Val
            770                 775                 780

Gly Gln Ala Asp Asp Lys Ser Ala Gly Ala Ile Trp Ile Arg Arg
785                 790                 795

<210> SEQ ID NO 109
<211> LENGTH: 152
<212> TYPE: PRT
<213> ORGANISM: Bacillus anthracis

<400> SEQUENCE: 109

Met Ser Cys Asn Glu Asn Lys His His Gly Ser Ser His Cys Val Val
1               5                   10                  15

Asp Val Val Lys Phe Ile Asn Glu Leu Gln Asp Cys Ser Thr Thr Thr
            20                  25                  30

Cys Gly Ser Gly Cys Glu Ile Pro Phe Leu Gly Ala His Asn Thr Ala
        35                  40                  45

Ser Val Ala Asn Thr Arg Pro Phe Ile Leu Tyr Thr Lys Ala Gly Ala
    50                  55                  60
```

```
Pro Phe Glu Ala Phe Ala Pro Ser Ala Asn Leu Thr Ser Cys Arg Ser
 65                  70                  75                  80

Pro Ile Phe Arg Val Glu Ser Val Asp Asp Ser Cys Ala Val Leu
                 85                  90                  95

Arg Val Leu Ser Val Val Leu Gly Asp Ser Ser Pro Val Pro Pro Thr
                100                 105                 110

Asp Asp Pro Ile Cys Thr Phe Leu Ala Val Pro Asn Ala Arg Leu Val
                115                 120                 125

Ser Thr Ser Thr Cys Ile Thr Val Asp Leu Ser Cys Phe Cys Ala Ile
                130                 135                 140

Gln Cys Leu Arg Asp Val Thr Ile
145                 150
```

<210> SEQ ID NO 110
<211> LENGTH: 167
<212> TYPE: PRT
<213> ORGANISM: Bacillus anthracis

<400> SEQUENCE: 110

```
Met Phe Ser Ser Asp Cys Glu Phe Thr Lys Ile Asp Cys Glu Ala Lys
 1               5                  10                  15

Pro Ala Ser Thr Leu Pro Ala Phe Gly Phe Ala Phe Asn Ala Ser Ala
                 20                  25                  30

Pro Gln Phe Ala Ser Leu Phe Thr Pro Leu Leu Leu Pro Ser Val Ser
             35                  40                  45

Pro Asn Pro Asn Ile Thr Val Pro Val Ile Asn Asp Thr Val Ser Val
 50                  55                  60

Gly Asp Gly Ile Arg Ile Leu Arg Ala Gly Ile Tyr Gln Ile Ser Tyr
 65                  70                  75                  80

Thr Leu Thr Ile Ser Leu Asp Asn Ser Pro Val Ala Pro Glu Ala Gly
                 85                  90                  95

Arg Phe Phe Leu Ser Leu Gly Thr Pro Ala Asn Ile Ile Pro Gly Ser
                100                 105                 110

Gly Thr Ala Val Arg Ser Asn Val Ile Gly Thr Gly Glu Val Asp Val
                115                 120                 125

Ser Ser Gly Val Ile Leu Ile Asn Leu Asn Pro Gly Asp Leu Ile Arg
                130                 135                 140

Ile Val Pro Val Glu Leu Ile Gly Thr Val Asp Ile Arg Ala Ala Ala
145                 150                 155                 160

Leu Thr Val Ala Gln Ile Ser
                165
```

<210> SEQ ID NO 111
<211> LENGTH: 156
<212> TYPE: PRT
<213> ORGANISM: Bacillus anthracis

<400> SEQUENCE: 111

```
Met Ser Cys Asn Cys Asn Glu Asp His His His Asp Cys Asp Phe
 1               5                  10                  15

Asn Cys Val Ser Asn Val Val Arg Phe Ile His Glu Leu Gln Glu Cys
                 20                  25                  30

Ala Thr Thr Thr Cys Gly Ser Gly Cys Glu Val Pro Phe Leu Gly Ala
             35                  40                  45

His Asn Ser Ala Ser Val Ala Asn Thr Arg Pro Phe Ile Leu Tyr Thr
 50                  55                  60
```

```
Lys Ala Gly Ala Pro Phe Glu Ala Phe Ala Pro Ser Ala Asn Leu Thr
 65                  70                  75                  80

Ser Cys Arg Ser Pro Ile Phe Arg Val Glu Ser Ile Asp Asp Asp Asp
                 85                  90                  95

Cys Ala Val Leu Arg Val Leu Ser Val Val Leu Gly Asp Thr Ser Pro
                100                 105                 110

Val Pro Pro Thr Asp Asp Pro Ile Cys Thr Phe Leu Ala Val Pro Asn
                115                 120                 125

Ala Arg Leu Ile Ser Thr Asn Thr Cys Leu Thr Val Asp Leu Ser Cys
        130                 135                 140

Phe Cys Ala Ile Gln Cys Leu Arg Asp Val Thr Ile
145                 150                 155
```

<210> SEQ ID NO 112
<211> LENGTH: 182
<212> TYPE: PRT
<213> ORGANISM: Bacillus anthracis

<400> SEQUENCE: 112

```
Met Glu Val Gly Gly Thr Ser Val Lys Asn Lys Asn Lys Ser Ser Thr
  1               5                  10                  15

Val Gly Lys Pro Leu Leu Tyr Ile Ala Gln Val Ser Leu Glu Leu Ala
                 20                  25                  30

Ala Pro Lys Thr Lys Arg Ile Ile Leu Thr Asn Phe Glu Asn Glu Asp
                 35                  40                  45

Arg Lys Glu Glu Ser Asn Arg Asn Glu Asn Val Val Ser Ser Ala Val
         50                  55                  60

Glu Glu Val Ile Glu Gln Glu Gln Gln Gln Gln Gln Gln Gln Gln Glu
 65                  70                  75                  80

Gln Glu Glu Gln Val Glu Lys Thr Glu Glu Glu Glu Gln Val Gln
                 85                  90                  95

Glu Gln Gln Glu Pro Val Arg Thr Val Pro Tyr Asn Lys Ser Phe Lys
                100                 105                 110

Asp Met Asn Asn Glu Glu Lys Ile His Phe Leu Leu Asn Arg Pro His
                115                 120                 125

Tyr Ile Pro Lys Val Arg Cys Arg Ile Lys Thr Ala Thr Ile Ser Tyr
        130                 135                 140

Val Gly Ser Ile Ile Ser Tyr Arg Asn Gly Ile Val Ala Ile Met Pro
145                 150                 155                 160

Pro Asn Ser Met Arg Asp Ile Arg Leu Ser Ile Glu Glu Ile Lys Ser
                165                 170                 175

Ile Asp Met Ala Gly Phe
                180
```

<210> SEQ ID NO 113
<211> LENGTH: 174
<212> TYPE: PRT
<213> ORGANISM: Bacillus anthracis

<400> SEQUENCE: 113

```
Met Lys Glu Arg Ser Glu Asn Met Arg Ser Ser Arg Lys Leu Thr
  1               5                  10                  15

Asn Phe Asn Cys Arg Ala Gln Ala Pro Ser Thr Leu Pro Ala Leu Gly
                 20                  25                  30

Phe Ala Phe Asn Ala Thr Ser Pro Gln Phe Ala Thr Leu Phe Thr Pro
                 35                  40                  45
```

Leu Leu Leu Pro Ser Thr Gly Pro Asn Pro Asn Ile Thr Val Pro Val
 50                  55                  60

Ile Asn Asp Thr Ile Ser Thr Gly Thr Gly Ile Arg Ile Gln Val Ala
 65                  70                  75                  80

Gly Ile Tyr Gln Ile Ser Tyr Thr Leu Thr Ile Ser Leu Asp Asn Val
                 85                  90                  95

Pro Val Thr Pro Glu Ala Ala Arg Phe Phe Leu Thr Leu Asn Ser Ser
            100                 105                 110

Thr Asn Ile Ile Ala Gly Ser Gly Thr Ala Val Arg Ser Asn Ile Ile
            115                 120                 125

Gly Thr Gly Glu Val Asp Val Ser Ser Gly Val Ile Leu Ile Asn Leu
130                 135                 140

Asn Pro Gly Asp Leu Ile Gln Ile Val Pro Val Glu Val Ile Gly Thr
145                 150                 155                 160

Val Asp Ile Arg Ser Ala Ala Leu Thr Val Ala Gln Ile Arg
                165                 170

<210> SEQ ID NO 114
<211> LENGTH: 796
<212> TYPE: PRT
<213> ORGANISM: Bacillus thuringiensis

<400> SEQUENCE: 114

Met Ser Lys Lys Pro Phe Lys Val Leu Ser Ile Ala Leu Thr Ala
 1               5                  10                  15

Val Leu Gly Leu Ser Phe Gly Ala Gly Thr Gln Ser Ala Tyr Ala Glu
                 20                  25                  30

Thr Pro Val Asn Lys Thr Ala Thr Ser Pro Val Asp Asp His Leu Ile
             35                  40                  45

Pro Glu Glu Arg Leu Ala Asp Ala Leu Lys Lys Arg Gly Val Ile Asp
         50                  55                  60

Ser Lys Ala Ser Glu Thr Glu Thr Lys Lys Ala Val Glu Lys Tyr Val
 65                  70                  75                  80

Glu Asn Lys Lys Gly Glu Asn Pro Gly Lys Glu Ala Ala Asn Gly Asp
                 85                  90                  95

Gln Leu Thr Lys Asp Ala Ser Asp Phe Leu Lys Lys Val Lys Asp Ala
            100                 105                 110

Lys Ala Asp Thr Lys Glu Lys Leu Asn Gln Pro Ala Thr Gly Thr Pro
            115                 120                 125

Ala Ala Thr Gly Pro Val Lys Gly Gly Leu Asn Gly Lys Val Pro Thr
130                 135                 140

Ser Pro Ala Lys Gln Lys Asp Tyr Asn Gly Glu Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Asn Asp Phe Asn Lys Glu His
            180                 185                 190

Tyr Glu Lys Met Leu Phe Gly Asn Glu Pro Phe Thr Leu Asp Asp Gly
        195                 200                 205

Ser Lys Ile Glu Thr Phe Lys Gln Tyr Glu Glu Gln Ser Gly Gly
            210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Pro Gly Gly Gly His Asp Asn
                245                 250                 255

```
Lys Gly Pro Lys Gly Pro Arg Asp Leu Val Lys Asp Ala Leu Lys Ala
            260                 265                 270

Ala Val Asp Ser Gly Ile Asp Leu Ser Glu Phe Asp Gln Phe Asp Gln
            275                 280                 285

Tyr Asp Val Asn Gly Asp Gly Asn Lys Asn Gln Pro Asp Gly Leu Ile
            290                 295                 300

Asp His Leu Met Ile Ile His Ala Gly Val Gly Gln Glu Ala Gly Gly
305                 310                 315                 320

Gly Lys Leu Gly Asp Asp Ala Ile Trp Ser His Arg Trp Thr Val Gly
                325                 330                 335

Pro Lys Pro Phe Pro Ile Glu Gly Thr Gln Ala Lys Val Pro Tyr Trp
                340                 345                 350

Gly Gly Lys Met Ala Ala Phe Asp Tyr Thr Ile Glu Pro Glu Asp Gly
                355                 360                 365

Ala Val Gly Val Phe Ala His Glu Tyr Gly His Asp Leu Gly Leu Pro
            370                 375                 380

Asp Glu Tyr Asp Thr Gln Tyr Ser Gly Gln Gly Pro Ile Glu Ala
385                 390                 395                 400

Trp Ser Ile Met Ser Gly Gly Ser Trp Ala Gly Lys Ile Ala Gly Thr
                405                 410                 415

Thr Pro Thr Ser Phe Ser Pro Gln Asn Lys Glu Phe Phe Gln Lys Thr
                420                 425                 430

Ile Gly Gly Asn Trp Ala Asn Ile Val Glu Val Asp Tyr Glu Lys Leu
            435                 440                 445

Asn Lys Gly Ile Gly Leu Ala Thr Tyr Leu Asp Gln Ser Val Thr Lys
450                 455                 460

Ser Ala Arg Pro Gly Met Ile Arg Val Asn Leu Pro Asp Lys Asp Val
465                 470                 475                 480

Lys Thr Ile Glu Pro Ala Phe Gly Lys Gln Tyr Tyr Ser Thr Lys
                485                 490                 495

Gly Asp Asp Leu His Thr Lys Met Glu Thr Pro Leu Phe Asp Leu Thr
                500                 505                 510

Asn Ala Thr Ser Ala Lys Phe Asp Phe Lys Ser Leu Tyr Glu Ile Glu
            515                 520                 525

Ala Gly Tyr Asp Phe Leu Glu Val His Ala Val Thr Glu Asp Gly Lys
530                 535                 540

Gln Thr Leu Ile Glu Arg Leu Gly Glu Lys Ala Asn Ser Gly Asn Ala
545                 550                 555                 560

Asp Ser Thr Asn Gly Lys Trp Ile Asp Lys Ser Tyr Asp Leu Ser Gln
                565                 570                 575

Phe Lys Gly Lys Lys Val Lys Leu Thr Phe Asp Tyr Ile Thr Asp Gly
            580                 585                 590

Gly Leu Ala Leu Asn Gly Phe Ala Leu Asp Asn Ala Ser Leu Thr Val
            595                 600                 605

Asp Gly Lys Val Val Phe Ser Asp Asp Ala Glu Gly Thr Pro Gln Leu
            610                 615                 620

Lys Leu Asp Gly Phe Val Val Ser Asn Gly Thr Glu Lys Lys His
625                 630                 635                 640

Asn Tyr Tyr Val Glu Trp Arg Asn Tyr Ala Gly Ala Asp Asn Ala Leu
                645                 650                 655

Lys Phe Ala Arg Gly Pro Val Phe Asn Thr Gly Met Val Val Trp Tyr
                660                 665                 670
```

```
Ala Asp Ser Ala Tyr Thr Asp Asn Trp Val Gly Val His Pro Gly His
        675                 680                 685

Gly Phe Leu Gly Val Val Asp Ser His Pro Glu Ala Ile Val Gly Thr
    690                 695                 700

Leu Asn Gly Lys Pro Thr Val Lys Ser Ser Thr Arg Phe Gln Ile Ala
705                 710                 715                 720

Asp Ala Ala Phe Ser Phe Asp Lys Thr Pro Ala Trp Lys Val Val Ser
                725                 730                 735

Pro Thr Arg Gly Thr Phe Thr Tyr Asp Gly Leu Ala Gly Val Pro Lys
            740                 745                 750

Phe Asp Asp Ser Lys Thr Tyr Ile Asn Gln Gln Ile Pro Asp Ala Gly
        755                 760                 765

Arg Ile Leu Pro Lys Leu Gly Leu Lys Phe Glu Val Val Gly Gln Ala
    770                 775                 780

Asp Asp Asn Ser Ala Gly Ala Val Arg Leu Tyr Arg
785                 790                 795

<210> SEQ ID NO 115
<211> LENGTH: 430
<212> TYPE: PRT
<213> ORGANISM: Bacillus cereus

<400> SEQUENCE: 115

Met Lys His Asn Asp Cys Phe Asp His Asn Asn Cys Asn Pro Ile Val
1               5                   10                  15

Phe Ser Ala Asp Cys Cys Lys Asn Pro Gln Ser Val Pro Ile Thr Arg
            20                  25                  30

Glu Gln Leu Ser Gln Leu Ile Thr Leu Leu Asn Ser Leu Val Ser Ala
        35                  40                  45

Ile Ser Ala Phe Phe Ala Asn Pro Ser Asn Ala Asn Arg Leu Val Leu
    50                  55                  60

Leu Asp Leu Phe Asn Gln Phe Leu Ile Phe Leu Asn Ser Leu Leu Pro
65                  70                  75                  80

Ser Pro Glu Val Asn Phe Leu Lys Gln Leu Thr Gln Ser Ile Ile Val
                85                  90                  95

Leu Leu Gln Ser Pro Ala Pro Asn Leu Gly Gln Leu Ser Thr Leu Leu
            100                 105                 110

Gln Gln Phe Tyr Ser Ala Leu Ala Gln Phe Phe Phe Ala Leu Asp Leu
        115                 120                 125

Ile Pro Ile Ser Cys Asn Ser Asn Val Asp Ser Ala Thr Leu Gln Leu
    130                 135                 140

Leu Phe Asn Leu Leu Ile Gln Leu Ile Asn Ala Thr Pro Gly Ala Thr
145                 150                 155                 160

Gly Pro Thr Gly Pro Thr Gly Pro Thr Gly Pro Thr Gly Pro Ala Gly
                165                 170                 175

Thr Gly Ala Gly Pro Thr Gly Ala Thr Gly Ala Thr Gly Ala Thr Gly
            180                 185                 190

Pro Thr Gly Ala Thr Gly Pro Ala Gly Thr Gly Gly Ala Thr Gly Ala
        195                 200                 205

Thr Gly Ala Thr Gly Val Thr Gly Ala Thr Gly Ala Thr Gly Ala Thr
    210                 215                 220

Gly Pro Thr Gly Pro Thr Gly Ala Thr Gly Pro Thr Gly Ala Thr Gly
225                 230                 235                 240

Ala Thr Gly Ala Thr Gly Pro Thr Gly Ala Thr Gly Pro Thr Gly Ala
                245                 250                 255
```

```
Thr Gly Leu Thr Gly Ala Thr Gly Ala Ala Gly Gly Gly Ala Ile Ile
            260                 265                 270

Pro Phe Ala Ser Gly Thr Thr Pro Ser Ala Leu Val Asn Ala Leu Val
        275                 280                 285

Ala Asn Thr Gly Thr Leu Leu Gly Phe Gly Phe Ser Gln Pro Gly Val
    290                 295                 300

Ala Leu Thr Gly Gly Thr Ser Ile Thr Leu Ala Leu Gly Val Gly Asp
305                 310                 315                 320

Tyr Ala Phe Val Ala Pro Arg Ala Gly Thr Ile Thr Ser Leu Ala Gly
                325                 330                 335

Phe Phe Ser Ala Thr Ala Ala Leu Ala Pro Ile Ser Pro Val Gln Val
            340                 345                 350

Gln Ile Gln Ile Leu Thr Ala Pro Ala Ala Ser Asn Thr Phe Thr Val
        355                 360                 365

Gln Gly Ala Pro Leu Leu Leu Thr Pro Ala Phe Ala Ala Ile Ala Ile
    370                 375                 380

Gly Ser Thr Ala Ser Gly Ile Ile Ala Glu Ala Ile Pro Val Ala Ala
385                 390                 395                 400

Gly Asp Lys Ile Leu Leu Tyr Val Ser Leu Thr Ala Ala Ser Pro Ile
                405                 410                 415

Ala Ala Val Ala Gly Phe Val Ser Ala Gly Ile Asn Ile Val
            420                 425                 430

<210> SEQ ID NO 116
<211> LENGTH: 437
<212> TYPE: PRT
<213> ORGANISM: Bacillus cereus

<400> SEQUENCE: 116

Met Lys His Asn Asp Cys Phe Gly His Asn Asn Cys Asn Asn Pro Ile
1               5                   10                  15

Val Phe Thr Pro Asp Cys Cys Asn Asn Pro Gln Thr Val Pro Ile Thr
            20                  25                  30

Ser Glu Gln Leu Gly Arg Leu Ile Thr Leu Leu Asn Ser Leu Ile Ala
        35                  40                  45

Ala Ile Ala Ala Phe Phe Ala Asn Pro Ser Asp Ala Asn Arg Leu Ala
    50                  55                  60

Leu Leu Asn Leu Phe Thr Gln Leu Leu Asn Leu Leu Asn Glu Leu Ala
65                  70                  75                  80

Pro Ser Pro Glu Gly Asn Phe Leu Lys Gln Leu Ile Gln Ser Ile Ile
                85                  90                  95

Asn Leu Leu Gln Ser Pro Asn Pro Asn Leu Gly Gln Leu Leu Ser Leu
            100                 105                 110

Leu Gln Gln Phe Tyr Ser Ala Leu Ala Pro Phe Phe Phe Ser Leu Ile
        115                 120                 125

Leu Asp Pro Ala Ser Leu Gln Leu Leu Leu Asn Leu Leu Ala Gln Leu
    130                 135                 140

Ile Gly Val Thr Pro Gly Gly Gly Ala Thr Gly Pro Thr Gly Pro Thr
145                 150                 155                 160

Gly Pro Gly Gly Gly Ala Thr Gly Pro Thr Gly Pro Thr Gly Pro Gly
                165                 170                 175

Gly Gly Ala Thr Gly Pro Thr Gly Ala Thr Gly Pro Thr Gly Asp Thr
            180                 185                 190

Gly Leu Ala Gly Ala Thr Gly Ala Thr Gly Pro Thr Gly Asp Thr Gly
```

```
                195                 200                 205
Val Ala Gly Pro Ala Gly Pro Thr Gly Pro Thr Gly Asp Thr Gly Leu
210                 215                 220

Ala Gly Ala Thr Gly Pro Thr Gly Pro Thr Gly Asp Thr Gly Leu Ala
225                 230                 235                 240

Gly Ala Thr Gly Pro Thr Gly Ala Thr Gly Leu Ala Gly Ala Thr Gly
                245                 250                 255

Pro Thr Gly Ala Thr Gly Leu Thr Gly Ala Thr Gly Ala Thr Gly Ala
                260                 265                 270

Ala Gly Gly Ala Ile Ile Pro Phe Ala Ser Gly Thr Thr Pro Ala
                275                 280                 285

Ala Leu Val Asn Ala Leu Ile Ala Asn Thr Gly Thr Leu Leu Gly Phe
290                 295                 300

Gly Phe Ser Gln Pro Gly Ile Gly Leu Ala Gly Gly Thr Ser Ile Thr
305                 310                 315                 320

Leu Ala Leu Gly Val Gly Asp Tyr Ala Phe Val Ala Pro Arg Asp Gly
                325                 330                 335

Val Ile Thr Ser Leu Ala Gly Phe Phe Ser Ala Thr Ala Ala Leu Ser
                340                 345                 350

Pro Leu Ser Pro Val Gln Val Gln Ile Gln Ile Leu Thr Ala Pro Ala
                355                 360                 365

Ala Ser Asn Thr Phe Thr Val Gln Gly Ala Pro Leu Leu Leu Thr Pro
                370                 375                 380

Ala Phe Ala Ala Ile Ala Ile Gly Ser Thr Ala Ser Gly Ile Ile Pro
385                 390                 395                 400

Glu Ala Ile Pro Val Val Ala Gly Asp Lys Ile Leu Leu Tyr Val Ser
                405                 410                 415

Leu Thr Ala Ala Ser Pro Ile Ala Ala Val Ala Gly Phe Val Ser Ala
                420                 425                 430

Gly Ile Asn Ile Val
                435

<210> SEQ ID NO 117
<211> LENGTH: 119
<212> TYPE: PRT
<213> ORGANISM: Bacillus anthracis

<400> SEQUENCE: 117

Met Leu Phe Thr Ser Trp Leu Leu Phe Phe Ile Phe Ala Leu Ala Ala
1               5                   10                  15

Phe Arg Leu Thr Arg Leu Ile Val Tyr Asp Lys Ile Thr Gly Phe Leu
                20                  25                  30

Arg Arg Pro Phe Ile Asp Glu Leu Glu Ile Thr Glu Pro Asp Gly Ser
                35                  40                  45

Val Ser Thr Phe Thr Lys Val Lys Gly Lys Gly Leu Arg Lys Trp Ile
50                  55                  60

Gly Glu Leu Leu Ser Cys Tyr Trp Cys Thr Gly Val Trp Val Ser Ala
65                  70                  75                  80

Phe Leu Leu Val Leu Tyr Asn Trp Ile Pro Ile Val Ala Glu Pro Leu
                85                  90                  95

Leu Ala Leu Leu Ala Ile Ala Gly Ala Ala Ile Ile Glu Thr Ile
                100                 105                 110

Thr Gly Tyr Phe Met Gly Glu
                115
```

```
<210> SEQ ID NO 118
<211> LENGTH: 61
<212> TYPE: PRT
<213> ORGANISM: Bacillus anthracis

<400> SEQUENCE: 118

Met Phe Ala Val Ser Asn Asn Pro Arg Gln Asn Ser Tyr Asp Leu Gln
1               5                   10                  15

Gln Trp Tyr His Met Gln Gln His Gln Ala Gln Gln Gln Ala Tyr
            20                  25                  30

Gln Glu Gln Leu Gln Gln Gln Gly Phe Val Lys Lys Lys Gly Cys Asn
        35                  40                  45

Cys Gly Lys Lys Lys Ser Thr Ile Lys His Tyr Glu Glu
        50                  55                  60

<210> SEQ ID NO 119
<211> LENGTH: 481
<212> TYPE: PRT
<213> ORGANISM: Bacillus anthracis

<400> SEQUENCE: 119

Met Ser Arg Tyr Asp Asp Ser Gln Asn Lys Phe Ser Lys Pro Cys Phe
1               5                   10                  15

Pro Ser Ser Ala Gly Arg Ile Pro Asn Thr Pro Ser Ile Pro Val Thr
            20                  25                  30

Lys Ala Gln Leu Arg Thr Phe Arg Ala Ile Ile Ile Asp Leu Thr Lys
        35                  40                  45

Ile Ile Pro Lys Leu Phe Ala Asn Pro Ser Pro Gln Asn Ile Glu Asp
    50                  55                  60

Leu Ile Asp Thr Leu Asn Leu Leu Ser Lys Phe Ile Cys Ser Leu Asp
65                  70                  75                  80

Ala Ala Ser Ser Leu Lys Ala Gln Gly Leu Ala Ile Ile Lys Asn Leu
                85                  90                  95

Ile Thr Ile Leu Lys Asn Pro Thr Phe Val Ala Ser Ala Val Phe Ile
            100                 105                 110

Glu Leu Gln Asn Leu Ile Asn Tyr Leu Leu Ser Ile Thr Lys Leu Phe
        115                 120                 125

Arg Ile Asp Pro Cys Thr Leu Gln Glu Leu Leu Lys Leu Ile Ala Ala
    130                 135                 140

Leu Gln Thr Ala Leu Val Asn Ser Ala Ser Phe Ile Gln Gly Pro Thr
145                 150                 155                 160

Gly Pro Thr Gly Pro Thr Gly Pro Thr Pro Ala Gly Ala Thr Gly
                165                 170                 175

Ala Thr Gly Pro Gln Gly Val Gln Gly Pro Ala Gly Ala Thr Gly Ala
            180                 185                 190

Thr Gly Pro Gln Gly Val Gln Gly Pro Ala Gly Ala Thr Gly Ala Thr
        195                 200                 205

Gly Pro Gln Gly Ala Gln Gly Pro Ala Gly Ala Thr Gly Ala Thr Gly
    210                 215                 220

Pro Gln Gly Ala Gln Gly Pro Ala Gly Ala Thr Gly Ala Thr Gly Pro
225                 230                 235                 240

Gln Gly Ile Gln Gly Pro Ala Gly Ala Thr Gly Ala Thr Gly Pro Gln
                245                 250                 255

Gly Val Gln Gly Pro Thr Gly Ala Thr Gly Ile Gly Val Thr Gly Pro
            260                 265                 270
```

```
Thr Gly Pro Ser Gly Gly Pro Ala Gly Ala Thr Gly Pro Gln Gly Pro
            275                 280                 285

Gln Gly Asn Thr Gly Ala Thr Gly Pro Gln Gly Ile Gln Gly Pro Ala
        290                 295                 300

Gly Ala Thr Gly Ala Thr Gly Pro Gln Gly Ala Gln Gly Pro Ala Gly
305                 310                 315                 320

Ala Thr Gly Ala Thr Gly Pro Gln Gly Val Gln Gly Pro Thr Gly Ala
                325                 330                 335

Thr Gly Ile Gly Val Thr Gly Pro Thr Gly Pro Ser Gly Pro Ser Phe
            340                 345                 350

Pro Val Ala Thr Ile Val Val Thr Asn Asn Ile Gln Gln Thr Val Leu
            355                 360                 365

Gln Phe Asn Asn Phe Ile Phe Asn Thr Ala Ile Asn Val Asn Asn Ile
        370                 375                 380

Ile Phe Asn Gly Thr Asp Thr Val Thr Val Ile Asn Ala Gly Ile Tyr
385                 390                 395                 400

Val Ile Ser Val Ser Ile Ser Thr Thr Ala Pro Gly Cys Ala Pro Leu
                405                 410                 415

Gly Val Gly Ile Ser Ile Asn Gly Ala Val Ala Thr Asp Asn Phe Ser
            420                 425                 430

Ser Asn Leu Ile Gly Asp Ser Leu Ser Phe Thr Thr Ile Glu Thr Leu
        435                 440                 445

Thr Ala Gly Ala Asn Ile Ser Val Gln Ser Thr Leu Asn Glu Ile Thr
450                 455                 460

Ile Pro Ala Thr Gly Asn Thr Asn Ile Arg Leu Thr Val Phe Arg Ile
465                 470                 475                 480

Ala

<210> SEQ ID NO 120
<211> LENGTH: 275
<212> TYPE: PRT
<213> ORGANISM: Bacillus thuringiensis

<400> SEQUENCE: 120

Met Lys Met Lys Arg Gly Ile Thr Thr Leu Leu Ser Val Ala Val Leu
1               5                   10                  15

Ser Thr Ser Leu Val Ala Cys Ser Gly Ile Thr Glu Lys Thr Val Ala
            20                  25                  30

Lys Glu Glu Lys Val Lys Leu Thr Asp Gln Gln Leu Met Ala Asp Leu
        35                  40                  45

Trp Tyr Gln Thr Ala Gly Glu Met Lys Ala Leu Tyr Tyr Gln Gly Tyr
    50                  55                  60

Asn Ile Gly Gln Leu Lys Leu Asp Ala Val Leu Ala Lys Gly Thr Glu
65                  70                  75                  80

Lys Lys Pro Ala Ile Val Leu Asp Leu Asp Glu Thr Val Leu Asp Asn
                85                  90                  95

Ser Pro His Gln Ala Met Ser Val Lys Thr Gly Lys Gly Tyr Pro Tyr
            100                 105                 110

Lys Trp Asp Asp Trp Ile Asn Lys Ala Glu Ala Glu Ala Leu Pro Gly
        115                 120                 125

Ala Ile Asp Phe Leu Lys Tyr Thr Glu Ser Lys Gly Val Asp Ile Tyr
    130                 135                 140

Tyr Ile Ser Asn Arg Lys Thr Asn Gln Leu Asp Ala Thr Ile Lys Asn
145                 150                 155                 160
```

```
Leu Glu Arg Val Gly Ala Pro Gln Ala Thr Lys Glu His Ile Leu Leu
            165                 170                 175

Gln Asp Pro Lys Glu Lys Gly Lys Glu Lys Arg Arg Glu Leu Val Ser
        180                 185                 190

Gln Thr His Asp Ile Val Leu Phe Phe Gly Asp Asn Leu Ser Asp Phe
        195                 200                 205

Thr Gly Phe Asp Gly Lys Ser Val Lys Asp Arg Asn Gln Ala Val Ala
        210                 215                 220

Asp Ser Lys Ala Gln Phe Gly Glu Lys Phe Ile Ile Phe Pro Asn Pro
225                 230                 235                 240

Met Tyr Gly Asp Trp Glu Gly Ala Leu Tyr Asp Tyr Asp Phe Lys Lys
                245                 250                 255

Ser Asp Ala Glu Lys Asp Lys Ile Arg Arg Asp Asn Leu Lys Ser Phe
            260                 265                 270

Asp Thr Lys
        275

<210> SEQ ID NO 121
<211> LENGTH: 795
<212> TYPE: PRT
<213> ORGANISM: Bacillus thuringiensis

<400> SEQUENCE: 121

Met Lys Lys Lys Lys Leu Lys Pro Leu Ala Val Leu Thr Thr Ala
1               5                   10                  15

Ala Val Leu Ser Ser Thr Phe Ala Phe Gly Gly His Ala Ala Tyr Ala
            20                  25                  30

Glu Thr Pro Thr Ser Ser Leu Pro Ile Asp Glu His Leu Ile Pro Glu
        35                  40                  45

Glu Arg Leu Ala Glu Ala Leu Lys Gln Arg Gly Val Ile Asp Gln Ser
    50                  55                  60

Ala Ser Gln Ala Glu Thr Ser Lys Ala Val Glu Lys Tyr Val Glu Lys
65                  70                  75                  80

Lys Lys Gly Glu Asn Pro Gly Lys Glu Ile Leu Thr Gly Asp Ser Leu
                85                  90                  95

Thr Gln Glu Ala Ser Asp Phe Met Lys Lys Val Lys Asp Ala Lys Met
            100                 105                 110

Arg Glu Asn Glu Gln Ala Gln Gln Pro Glu Val Gly Pro Val Ala Gly
        115                 120                 125

Gln Gly Ala Ala Leu Asn Pro Gly Lys Leu Asn Gly Lys Val Pro Thr
    130                 135                 140

Thr Ser Ala Lys Gln Glu Glu Tyr Asn Gly Ala Val Arg Lys Asp Lys
145                 150                 155                 160

Val Leu Val Leu Leu Val Glu Phe Ser Asp Phe Lys His Asn Asn Ile
                165                 170                 175

Asp Gln Glu Pro Gly Tyr Met Tyr Ser Lys Asp Phe Asn Arg Glu His
            180                 185                 190

Tyr Gln Lys Met Leu Phe Gly Asp Glu Pro Phe Thr Leu Phe Asp Gly
        195                 200                 205

Ser Lys Ile Asn Thr Phe Lys Gln Tyr Glu Glu Gln Ser Gly Gly
    210                 215                 220

Ser Tyr Thr Val Asp Gly Thr Val Thr Glu Trp Leu Thr Val Pro Gly
225                 230                 235                 240

Lys Ala Ser Asp Tyr Gly Ala Asp Ala Gly Thr Gly His Asp Asn Lys
                245                 250                 255
```

-continued

Gly Pro Leu Gly Pro Lys Asp Leu Val Lys Glu Ala Leu Ala Ala
            260                 265                 270

Val Ala Lys Gly Ile Asn Leu Ala Asp Phe Asp Gln Tyr Asp Gln Tyr
        275                 280                 285

Asp Gln Asn Gly Asn Gly Asn Lys Asn Glu Pro Asp Gly Ile Ile Asp
290                 295                 300

His Leu Met Val Val His Ala Gly Val Gly Gln Glu Ala Gly Gly
305                 310                 315                 320

Lys Leu Lys Asp Asp Ala Ile Trp Ser His Arg Ser Lys Leu Gly Ser
                325                 330                 335

Lys Pro Tyr Ala Ile Asp Gly Thr Lys Ser Ser Val Ser Asn Trp Gly
            340                 345                 350

Gly Lys Met Ala Ala Tyr Asp Tyr Thr Ile Glu Pro Glu Asp Gly Ala
        355                 360                 365

Val Gly Val Phe Ala His Glu Tyr Gly His Asp Leu Gly Leu Pro Asp
    370                 375                 380

Glu Tyr Asp Thr Lys Tyr Ser Gly Gln Gly Glu Pro Val Glu Ser Trp
385                 390                 395                 400

Ser Ile Met Ser Gly Gly Ser Trp Ala Gly Lys Ile Ala Gly Thr Glu
                405                 410                 415

Pro Thr Ser Phe Ser Pro Gln Asn Lys Glu Phe Phe Gln Lys Asn Met
            420                 425                 430

Lys Gly Asn Trp Ala Asn Ile Leu Glu Val Asp Tyr Asp Lys Leu Ser
        435                 440                 445

Lys Gly Ile Gly Val Ala Thr Tyr Val Asp Gln Ser Thr Thr Lys Ser
    450                 455                 460

Lys Arg Pro Gly Ile Val Arg Val Asn Leu Pro Asp Lys Asp Ile Lys
465                 470                 475                 480

Asn Ile Glu Ser Ala Phe Gly Lys Lys Phe Tyr Tyr Ser Thr Lys Gly
                485                 490                 495

Asn Asp Ile His Thr Thr Leu Glu Thr Pro Val Phe Asp Leu Thr Asn
            500                 505                 510

Ala Lys Asp Ala Lys Phe Asp Tyr Lys Ala Phe Tyr Glu Leu Glu Ala
        515                 520                 525

Lys Tyr Asp Phe Leu Asp Val Tyr Ala Ile Ala Glu Asp Gly Thr Lys
    530                 535                 540

Thr Arg Ile Asp Arg Met Gly Glu Lys Asp Ile Lys Gly Gly Ala Asp
545                 550                 555                 560

Thr Thr Asp Gly Lys Trp Val Asp Lys Ser Tyr Asp Leu Ser Gln Phe
                565                 570                 575

Lys Gly Lys Lys Val Lys Leu Gln Phe Glu Tyr Leu Thr Asp Ile Ala
            580                 585                 590

Val Ala Tyr Lys Gly Phe Ala Leu Asp Asn Ala Ala Leu Thr Val Asp
        595                 600                 605

Gly Lys Val Val Phe Ser Asp Asp Ala Glu Gly Gln Pro Ala Met Thr
    610                 615                 620

Leu Lys Gly Phe Thr Val Ser Asn Gly Phe Glu Gln Lys Lys His Asn
625                 630                 635                 640

Tyr Tyr Val Glu Trp Arg Asn Tyr Ala Gly Ser Asp Thr Ala Leu Gln
                645                 650                 655

Tyr Ala Arg Gly Pro Val Phe Asn Thr Gly Met Val Val Trp Tyr Ala
            660                 665                 670

```
Asp Gln Ser Phe Thr Asp Asn Trp Val Gly Val His Pro Gly Glu Gly
            675                 680                 685
Phe Leu Gly Val Val Asp Ser His Pro Glu Ala Ile Val Gly Thr Leu
690                 695                 700
Asn Gly Gln Pro Thr Val Lys Ser Ser Thr Arg Tyr Gln Ile Ala Asp
705                 710                 715                 720
Ala Ala Phe Ser Phe Asp Gln Thr Pro Ala Trp Lys Val Asn Ser Pro
            725                 730                 735
Thr Arg Gly Ile Phe Asp Tyr Lys Gly Leu Pro Gly Val Ala Lys Phe
            740                 745                 750
Asp Asp Ser Lys Gln Tyr Ile Asn Ser Val Ile Pro Asp Ala Gly Arg
            755                 760                 765
Lys Leu Pro Lys Leu Gly Leu Lys Phe Glu Val Val Gly Gln Ala Glu
770                 775                 780
Asp Lys Ser Ala Gly Ala Val Trp Leu His Arg
785                 790                 795

<210> SEQ ID NO 122
<211> LENGTH: 798
<212> TYPE: PRT
<213> ORGANISM: Bacillus mycoides

<400> SEQUENCE: 122

Lys Arg Lys Thr Pro Phe Lys Val Phe Ser Ser Leu Ala Ile Thr Thr
1               5                   10                  15
Met Leu Gly Cys Thr Phe Ala Leu Gly Thr Ser Val Ala Tyr Ala Glu
            20                  25                  30
Thr Thr Ser Gln Ser Lys Gly Ser Ile Ser Thr Thr Pro Ile Asp Asn
            35                  40                  45
Asn Leu Ile Gln Glu Glu Arg Leu Ala Glu Ala Leu Lys Glu Arg Gly
50                  55                  60
Thr Ile Asp Gln Ser Ala Ser Lys Glu Thr Gln Lys Ala Val Glu
65                  70                  75                  80
Gln Tyr Ile Glu Lys Lys Gly Asp Gln Pro Asn Lys Glu Ile Leu
            85                  90                  95
Pro Asp Asp Pro Ala Lys Glu Ala Ser Asp Phe Val Lys Lys Val Lys
            100                 105                 110
Glu Lys Lys Met Glu Lys Glu Lys Val Lys Ser Val Glu Asn
            115                 120                 125
Ala Ser Ser Glu Gln Thr Pro Ser Gln Asn Lys Lys Gln Leu Asn Gly
130                 135                 140
Lys Val Pro Thr Ser Pro Ala Lys Gln Ala Pro Tyr Asn Gly Ala Val
145                 150                 155                 160
Arg Thr Asp Lys Val Leu Val Leu Leu Val Glu Phe Ser Asp Tyr Lys
            165                 170                 175
His Asn Asn Ile Glu Gln Ser Pro Gly Tyr Met Tyr Ala Asn Asp Phe
            180                 185                 190
Ser Arg Glu His Tyr Gln Lys Met Leu Phe Gly Asn Glu Pro Phe Thr
            195                 200                 205
Leu Phe Asp Gly Ser Lys Val Lys Thr Phe Lys Gln Tyr Tyr Glu Glu
            210                 215                 220
Gln Ser Gly Gly Ser Tyr Thr Thr Asp Gly Tyr Val Thr Glu Trp Leu
225                 230                 235                 240
Thr Val Pro Gly Lys Ala Ala Asp Tyr Gly Ala Asp Gly Lys Thr Gly
            245                 250                 255
```

-continued

```
His Asp Asn Lys Gly Pro Lys Gly Ala Arg Asp Leu Val Lys Glu Ala
            260                 265                 270
Leu Lys Ala Ala Glu Lys Gly Leu Asp Leu Ser Gln Phe Asp Gln
        275                 280                 285
Phe Asp Arg Tyr Asp Thr Asn Gly Asp Gly Asn Gln Asn Glu Pro Asp
290                 295                 300
Gly Val Ile Asp His Leu Met Val Ile His Ala Gly Val Gly Gln Glu
305                 310                 315                 320
Ala Gly Gly Gly Lys Leu Gly Asp Asp Ala Ile Trp Ser His Arg Ser
                325                 330                 335
Lys Leu Ala Gln Asp Pro Val Ala Ile Glu Gly Thr Lys Ser Lys Val
            340                 345                 350
Ser Tyr Trp Asp Gly Lys Val Ala Ala His Asp Tyr Thr Ile Glu Pro
        355                 360                 365
Glu Asp Gly Ala Val Gly Val Phe Ala His Glu Phe Gly His Asp Leu
370                 375                 380
Gly Leu Pro Asp Glu Tyr Asp Thr Asn Tyr Thr Gly Ala Gly Ser Pro
385                 390                 395                 400
Val Glu Ala Trp Ser Leu Met Ser Gly Ser Trp Thr Gly Arg Ile
                405                 410                 415
Ala Gly Thr Glu Pro Thr Ser Phe Ser Pro Gln Asn Lys Asp Phe Leu
            420                 425                 430
Gln Lys Asn Met Asp Gly Asn Trp Ala Lys Ile Val Glu Val Asp Tyr
        435                 440                 445
Asp Lys Ile Lys Arg Gly Val Gly Phe Pro Thr Tyr Ile Asp Gln Ser
        450                 455                 460
Val Thr Lys Ser Asn Arg Pro Gly Leu Val Arg Val Asn Leu Pro Glu
465                 470                 475                 480
Lys Ser Val Glu Thr Ile Lys Thr Gly Phe Gly Lys His Ala Tyr Tyr
                485                 490                 495
Ser Thr Arg Gly Asp Asp Met His Thr Thr Leu Glu Thr Pro Leu Phe
            500                 505                 510
Asp Leu Thr Lys Ala Ala Asn Ala Lys Phe Asp Tyr Lys Ala Asn Tyr
        515                 520                 525
Glu Leu Glu Ala Glu Cys Asp Phe Ile Glu Val His Ala Val Thr Glu
530                 535                 540
Asp Gly Thr Lys Thr Leu Ile Asp Lys Leu Gly Asp Lys Val Val Lys
545                 550                 555                 560
Gly Asp Gln Asp Thr Thr Glu Gly Lys Trp Ile Asp Lys Ser Tyr Asp
                565                 570                 575
Leu Ser Gln Phe Lys Gly Lys Val Lys Leu Gln Phe Asp Tyr Ile
            580                 585                 590
Thr Asp Pro Ala Leu Thr Tyr Lys Gly Phe Ala Met Asp Asn Val Asn
        595                 600                 605
Val Thr Val Asp Gly Lys Val Val Phe Ser Asp Ala Glu Gly Gln
        610                 615                 620
Ala Lys Met Lys Leu Asn Gly Phe Val Val Ser Asp Gly Thr Glu Lys
625                 630                 635                 640
Lys Pro His Tyr Tyr Tyr Leu Glu Trp Arg Asn Tyr Ala Gly Ser Asp
                645                 650                 655
Glu Gly Leu Lys Val Gly Arg Gly Pro Val Tyr Asn Thr Gly Leu Val
            660                 665                 670
```

```
Val Trp Tyr Ala Asp Asp Ser Phe Lys Asp Asn Trp Val Gly Arg His
            675                 680                 685

Pro Gly Glu Gly Phe Leu Gly Val Val Asp Ser His Pro Glu Ala Val
        690                 695                 700

Val Gly Asn Leu Asn Gly Lys Pro Val Tyr Gly Asn Thr Gly Leu Gln
705                 710                 715                 720

Ile Ala Asp Ala Ala Phe Ser Leu Asp Gln Thr Pro Ala Trp Asn Val
                725                 730                 735

Asn Ser Phe Thr Arg Gly Gln Phe Asn Tyr Pro Gly Leu Pro Gly Val
            740                 745                 750

Ala Thr Phe Asp Asp Ser Lys Val Tyr Ser Asn Thr Gln Ile Pro Asp
        755                 760                 765

Ala Gly Arg Lys Val Pro Gln Leu Gly Leu Lys Phe Gln Val Val Gly
770                 775                 780

Gln Ala Asp Asp Lys Ser Ala Gly Ala Ile Trp Ile Arg Arg
785                 790                 795

<210> SEQ ID NO 123
<211> LENGTH: 155
<212> TYPE: PRT
<213> ORGANISM: Bacillus thuringiensis

<400> SEQUENCE: 123

Met Thr Leu Met Ser Cys Asn Glu Asn Lys His His Gly Ser Ser His
1               5                   10                  15

Cys Val Val Asp Val Val Lys Phe Ile Asn Glu Leu Gln Asp Cys Ser
            20                  25                  30

Thr Thr Thr Cys Gly Ser Gly Cys Glu Ile Pro Phe Leu Gly Ala His
        35                  40                  45

Asn Thr Ala Ser Val Ala Asn Thr Arg Pro Phe Ile Leu Tyr Thr Lys
    50                  55                  60

Ala Gly Ala Pro Phe Glu Ala Phe Ala Pro Ser Ala Asn Leu Thr Ser
65                  70                  75                  80

Cys Arg Ser Pro Ile Phe Arg Val Glu Ser Val Asp Asp Ser Cys
                85                  90                  95

Ala Val Leu Arg Val Leu Ser Val Val Leu Gly Asp Ser Ser Pro Val
            100                 105                 110

Pro Pro Thr Asp Asp Pro Ile Cys Thr Phe Leu Ala Val Pro Asn Ala
        115                 120                 125

Arg Leu Val Ser Thr Ser Thr Cys Ile Thr Val Asp Leu Ser Cys Phe
    130                 135                 140

Cys Ala Ile Gln Cys Leu Arg Asp Val Thr Ile
145                 150                 155

<210> SEQ ID NO 124
<211> LENGTH: 167
<212> TYPE: PRT
<213> ORGANISM: Bacillus thuringiensis

<400> SEQUENCE: 124

Met Phe Ser Ser Asp Cys Glu Phe Thr Lys Ile Asp Cys Glu Ala Lys
1               5                   10                  15

Pro Ala Ser Thr Leu Pro Ala Phe Gly Phe Ala Phe Asn Ala Ser Ala
            20                  25                  30

Pro Gln Phe Ala Ser Leu Phe Thr Pro Leu Leu Leu Pro Ser Val Ser
        35                  40                  45
```

```
Pro Asn Pro Asn Ile Thr Val Pro Val Ile Asn Asp Thr Val Ser Val
    50                  55                  60

Gly Asp Gly Ile Arg Ile Leu Arg Ala Gly Ile Tyr Gln Ile Ser Tyr
65                  70                  75                  80

Thr Leu Thr Ile Ser Leu Asp Asn Ser Pro Val Ala Pro Glu Ala Gly
                85                  90                  95

Arg Phe Phe Leu Ser Leu Gly Thr Pro Ala Asn Ile Ile Pro Gly Ser
            100                 105                 110

Gly Thr Ala Val Arg Ser Asn Val Ile Gly Thr Gly Glu Val Asp Val
        115                 120                 125

Ser Ser Gly Val Ile Leu Ile Asn Leu Asn Pro Gly Asp Leu Ile Arg
130                 135                 140

Ile Val Pro Val Glu Leu Ile Gly Thr Val Asp Ile Arg Ala Ala Ala
145                 150                 155                 160

Leu Thr Val Ala Gln Ile Ser
                165

<210> SEQ ID NO 125
<211> LENGTH: 156
<212> TYPE: PRT
<213> ORGANISM: Bacillus cereus

<400> SEQUENCE: 125

Met Ser Cys Asn Cys Asn Glu Asp His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
130                 135                 140

Phe Cys Ala Ile Gln Cys Leu Arg Asp Val Thr Ile
145                 150                 155

<210> SEQ ID NO 126
<211> LENGTH: 182
<212> TYPE: PRT
<213> ORGANISM: Bacillus anthracis

<400> SEQUENCE: 126

Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45
```

```
Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125

Tyr Ile Pro Lys Val Arg Cys Arg Ile Lys Thr Ala Thr Ile Ser Tyr
    130                 135                 140

Val Gly Ser Ile Ile Ser Tyr Arg Asn Gly Ile Val Ala Ile Met Pro
145                 150                 155                 160

Pro Asn Ser Met Arg Asp Ile Arg Leu Ser Ile Glu Glu Ile Lys Ser
                165                 170                 175

Ile Asp Met Ala Gly Phe
            180
```

<210> SEQ ID NO 127
<211> LENGTH: 174
<212> TYPE: PRT
<213> ORGANISM: Bacillus cereus

<400> SEQUENCE: 127

```
Met Lys Glu Arg Ser Glu Asn Met Arg Ser Ser Ser Arg Lys Leu Thr
1               5                   10                  15

Asn Phe Asn Cys Arg Ala Gln Ala Pro Ser Thr Leu Pro Ala Leu Gly
            20                  25                  30

Phe Ala Phe Asn Ala Thr Ser Pro Gln Phe Ala Thr Leu Phe Thr Pro
        35                  40                  45

Leu Leu Leu Pro Ser Thr Gly Pro Asn Pro Asn Ile Thr Val Pro Val
    50                  55                  60

Ile Asn Asp Thr Ile Ser Thr Gly Thr Gly Ile Arg Ile Gln Val Ala
65                  70                  75                  80

Gly Ile Tyr Gln Ile Ser Tyr Thr Leu Thr Ile Ser Leu Asp Asn Val
                85                  90                  95

Pro Val Thr Pro Glu Ala Ala Arg Phe Phe Leu Thr Leu Asn Ser Ser
            100                 105                 110

Thr Asn Ile Ile Ala Gly Ser Gly Thr Ala Val Arg Ser Asn Ile Ile
        115                 120                 125

Gly Thr Gly Glu Val Asp Val Ser Ser Gly Val Ile Leu Ile Asn Leu
    130                 135                 140

Asn Pro Gly Asp Leu Ile Gln Ile Val Pro Val Glu Val Ile Gly Thr
145                 150                 155                 160

Val Asp Ile Arg Ser Ala Ala Leu Thr Val Ala Gln Ile Arg
                165                 170
```

<210> SEQ ID NO 128
<211> LENGTH: 167
<212> TYPE: PRT
<213> ORGANISM: Bacillus cereus

<400> SEQUENCE: 128

```
Met Arg Ser Ser Ser Arg Lys Leu Thr Asn Phe Asn Cys Arg Ala Gln
1               5                   10                  15
```

```
Ala Pro Ser Thr Leu Pro Ala Leu Gly Phe Ala Phe Asn Ala Thr Ser
            20                  25                  30

Pro Gln Phe Ala Thr Leu Phe Thr Pro Leu Leu Leu Pro Ser Thr Gly
        35                  40                  45

Pro Asn Pro Asn Ile Thr Val Pro Val Ile Asn Asp Thr Ile Ser Thr
    50                  55                  60

Gly Thr Gly Ile Arg Ile Gln Val Ala Gly Ile Tyr Gln Ile Ser Tyr
65                  70                  75                  80

Thr Leu Thr Ile Ser Leu Asp Asn Val Pro Val Thr Pro Glu Ala Ala
                85                  90                  95

Arg Phe Phe Leu Thr Leu Asn Ser Ser Thr Asn Ile Ile Ala Gly Ser
            100                 105                 110

Gly Thr Ala Val Arg Ser Asn Ile Ile Gly Thr Gly Glu Val Asp Val
        115                 120                 125

Ser Ser Gly Val Ile Leu Ile Asn Leu Asn Pro Gly Asp Leu Ile Gln
    130                 135                 140

Ile Val Pro Val Glu Val Ile Gly Thr Val Asp Ile Arg Ser Ala Ala
145                 150                 155                 160

Leu Thr Val Ala Gln Ile Arg
                165

<210> SEQ ID NO 129
<211> LENGTH: 796
<212> TYPE: PRT
<213> ORGANISM: Bacillus cereus

<400> SEQUENCE: 129

Met Ser Lys Lys Pro Phe Lys Val Leu Ser Ser Ile Ala Leu Thr Ala
1               5                   10                  15

Val Leu Gly Leu Ser Phe Gly Ala Gly Thr Gln Ser Ala Tyr Ala Glu
            20                  25                  30

Thr Pro Val Asn Lys Thr Ala Thr Ser Pro Val Asp Asp His Leu Ile
        35                  40                  45

Pro Glu Glu Arg Leu Ala Asp Ala Leu Lys Lys Arg Gly Val Ile Asp
    50                  55                  60

Ser Lys Ala Ser Glu Thr Glu Thr Lys Lys Ala Val Glu Lys Tyr Val
65                  70                  75                  80

Glu Asn Lys Lys Gly Glu Asn Pro Gly Lys Glu Ala Ala Asn Gly Asp
                85                  90                  95

Gln Leu Thr Lys Asp Ala Ser Asp Phe Leu Lys Lys Val Lys Asp Ala
            100                 105                 110

Lys Ala Asp Thr Lys Glu Lys Leu Asn Gln Pro Ala Thr Gly Thr Pro
        115                 120                 125

Ala Ala Thr Gly Pro Val Lys Gly Gly Leu Asn Gly Lys Val Pro Thr
    130                 135                 140

Ser Pro Ala Lys Gln Lys Asp Tyr Asn Gly Glu Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Asn Asp Phe Asn Lys Glu His
            180                 185                 190

Tyr Glu Lys Met Leu Phe Gly Asn Glu Pro Phe Thr Leu Asp Asp Gly
        195                 200                 205

Ser Lys Ile Glu Thr Phe Lys Gln Tyr Tyr Glu Glu Gln Ser Gly Gly
    210                 215                 220
```

```
Ser Tyr Thr Val Asp Gly Thr Val Thr Lys Trp Leu Thr Val Pro Gly
225                 230                 235                 240

Lys Ala Ala Asp Tyr Gly Ala Asp Ala Pro Gly Gly His Asp Asn
            245                 250                 255

Lys Gly Pro Lys Gly Pro Arg Asp Leu Val Lys Asp Ala Leu Lys Ala
        260                 265                 270

Ala Val Asp Ser Gly Ile Asp Leu Ser Glu Phe Asp Gln Phe Asp Gln
            275                 280                 285

Tyr Asp Val Asn Gly Asp Gly Asn Lys Asn Gln Pro Asp Gly Leu Ile
        290                 295                 300

Asp His Leu Met Ile Ile His Ala Gly Val Gly Gln Glu Ala Gly Gly
305                 310                 315                 320

Gly Lys Leu Gly Asp Asp Ala Ile Trp Ser His Arg Trp Thr Val Gly
            325                 330                 335

Pro Lys Pro Phe Pro Ile Glu Gly Thr Gln Ala Lys Val Pro Tyr Trp
            340                 345                 350

Gly Gly Lys Met Ala Ala Phe Asp Tyr Thr Ile Glu Pro Glu Asp Gly
        355                 360                 365

Ala Val Gly Val Phe Ala His Glu Tyr Gly His Asp Leu Gly Leu Pro
        370                 375                 380

Asp Glu Tyr Asp Thr Gln Tyr Ser Gly Gln Gly Glu Pro Ile Glu Ala
385                 390                 395                 400

Trp Ser Ile Met Ser Gly Ser Trp Ala Gly Lys Ile Ala Gly Thr
            405                 410                 415

Thr Pro Thr Ser Phe Ser Pro Gln Asn Lys Glu Phe Phe Gln Lys Thr
            420                 425                 430

Ile Gly Gly Asn Trp Ala Asn Ile Val Glu Val Asp Tyr Glu Lys Leu
        435                 440                 445

Asn Lys Gly Ile Gly Leu Ala Thr Tyr Leu Asp Gln Ser Val Thr Lys
        450                 455                 460

Ser Ala Arg Pro Gly Met Ile Arg Val Asn Leu Pro Asp Lys Asp Val
465                 470                 475                 480

Lys Thr Ile Glu Pro Ala Phe Gly Lys Gln Tyr Tyr Tyr Ser Thr Lys
            485                 490                 495

Gly Asp Asp Leu His Thr Lys Met Glu Thr Pro Leu Phe Asp Leu Thr
            500                 505                 510

Asn Ala Thr Ser Ala Lys Phe Asp Phe Lys Ser Leu Tyr Glu Ile Glu
        515                 520                 525

Ala Gly Tyr Asp Phe Leu Glu Val His Ala Val Thr Glu Asp Gly Lys
        530                 535                 540

Gln Thr Leu Ile Glu Arg Leu Gly Glu Lys Ala Asn Ser Gly Asn Ala
545                 550                 555                 560

Asp Ser Thr Asn Gly Lys Trp Ile Asp Lys Ser Tyr Asp Leu Ser Gln
            565                 570                 575

Phe Lys Gly Lys Lys Val Lys Leu Thr Phe Asp Tyr Ile Thr Asp Gly
            580                 585                 590

Gly Leu Ala Leu Asn Gly Phe Ala Leu Asp Asn Ala Ser Leu Thr Val
        595                 600                 605

Asp Gly Lys Val Val Phe Ser Asp Asp Ala Glu Gly Thr Pro Gln Leu
        610                 615                 620

Lys Leu Asp Gly Phe Val Val Ser Asn Gly Thr Glu Lys Lys His
625                 630                 635                 640
```

Asn Tyr Tyr Val Glu Trp Arg Asn Tyr Ala Gly Asp Asn Ala Leu
                645                 650                 655

Lys Phe Ala Arg Gly Pro Val Phe Asn Thr Gly Met Val Val Trp Tyr
            660                 665                 670

Ala Asp Ser Ala Tyr Thr Asp Asn Trp Val Gly Val His Pro Gly His
        675                 680                 685

Gly Phe Leu Gly Val Val Asp Ser His Pro Glu Ala Ile Val Gly Thr
    690                 695                 700

Leu Asn Gly Lys Pro Thr Val Lys Ser Ser Thr Arg Phe Gln Ile Ala
705                 710                 715                 720

Asp Ala Ala Phe Ser Phe Asp Lys Thr Pro Ala Trp Lys Val Val Ser
                725                 730                 735

Pro Thr Arg Gly Thr Phe Thr Tyr Asp Gly Leu Ala Gly Val Pro Lys
            740                 745                 750

Phe Asp Asp Ser Lys Thr Tyr Ile Asn Gln Gln Ile Pro Asp Ala Gly
        755                 760                 765

Arg Ile Leu Pro Lys Leu Gly Leu Lys Phe Glu Val Val Gly Gln Ala
    770                 775                 780

Asp Asp Asn Ser Ala Gly Ala Val Arg Leu Tyr Arg
785                 790                 795

<210> SEQ ID NO 130
<211> LENGTH: 799
<212> TYPE: PRT
<213> ORGANISM: Bacillus mycoides

<400> SEQUENCE: 130

Met Lys Arg Lys Thr Pro Phe Lys Val Phe Ser Ser Leu Ala Ile Thr
1               5                   10                  15

Thr Met Leu Gly Cys Thr Phe Ala Leu Gly Thr Ser Val Ala Tyr Ala
            20                  25                  30

Glu Thr Thr Ser Gln Ser Lys Gly Ser Ile Ser Thr Thr Pro Ile Asp
        35                  40                  45

Asn Asn Leu Ile Gln Glu Glu Arg Leu Ala Glu Ala Leu Lys Glu Arg
    50                  55                  60

Gly Thr Ile Asp Gln Ser Ala Ser Lys Glu Glu Thr Gln Lys Ala Val
65                  70                  75                  80

Glu Gln Tyr Ile Glu Lys Lys Lys Gly Asp Gln Pro Asn Lys Glu Ile
                85                  90                  95

Leu Pro Asp Asp Pro Ala Lys Glu Ala Ser Asp Phe Val Lys Lys Val
            100                 105                 110

Lys Glu Lys Lys Met Glu Glu Lys Glu Lys Val Lys Lys Ser Val Glu
        115                 120                 125

Asn Ala Ser Ser Glu Gln Thr Pro Ser Gln Asn Lys Lys Gln Leu Asn
    130                 135                 140

Gly Lys Val Pro Thr Ser Pro Ala Lys Gln Ala Pro Tyr Asn Gly Ala
145                 150                 155                 160

Val Arg Thr Asp Lys Val Leu Val Leu Leu Val Glu Phe Ser Asp Tyr
                165                 170                 175

Lys His Asn Asn Ile Glu Gln Ser Pro Gly Tyr Met Tyr Ala Asn Asp
            180                 185                 190

Phe Ser Arg Glu His Tyr Gln Lys Met Leu Phe Gly Asn Glu Pro Phe
        195                 200                 205

Thr Leu Phe Asp Gly Ser Lys Val Lys Thr Phe Lys Gln Tyr Tyr Glu
    210                 215                 220

-continued

Glu Gln Ser Gly Gly Ser Tyr Thr Thr Asp Gly Tyr Val Thr Glu Trp
225                 230                 235                 240

Leu Thr Val Pro Gly Lys Ala Ala Asp Tyr Gly Ala Asp Gly Lys Thr
            245                 250                 255

Gly His Asp Asn Lys Gly Pro Lys Gly Ala Arg Asp Leu Val Lys Glu
        260                 265                 270

Ala Leu Lys Ala Ala Ala Glu Lys Gly Leu Asp Leu Ser Gln Phe Asp
    275                 280                 285

Gln Phe Asp Arg Tyr Asp Thr Asn Gly Asp Gly Asn Gln Asn Glu Pro
290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg
            325                 330                 335

Ser Lys Leu Ala Gln Asp Pro Val Ala Ile Glu Gly Thr Lys Ser Lys
        340                 345                 350

Val Ser Tyr Trp Asp Gly Lys Val Ala Ala His Asp Tyr Thr Ile Glu
    355                 360                 365

Pro Glu Asp Gly Ala Val Gly Val Phe Ala His Glu Phe Gly His Asp
370                 375                 380

Leu Gly Leu Pro Asp Glu Tyr Asp Thr Asn Tyr Thr Gly Ala Gly Ser
385                 390                 395                 400

Pro Val Glu Ala Trp Ser Leu Met Ser Gly Ser Trp Thr Gly Arg
            405                 410                 415

Ile Ala Gly Thr Glu Pro Thr Ser Phe Ser Pro Gln Asn Lys Asp Phe
            420                 425                 430

Leu Gln Lys Asn Met Asp Gly Asn Trp Ala Lys Ile Val Glu Val Asp
        435                 440                 445

Tyr Asp Lys Ile Lys Arg Gly Val Gly Phe Pro Thr Tyr Ile Asp Gln
    450                 455                 460

Ser Val Thr Lys Ser Asn Arg Pro Gly Leu Val Arg Val Asn Leu Pro
465                 470                 475                 480

Glu Lys Ser Val Glu Thr Ile Lys Thr Gly Phe Gly Lys His Ala Tyr
            485                 490                 495

Tyr Ser Thr Arg Gly Asp Asp Met His Thr Thr Leu Glu Thr Pro Leu
        500                 505                 510

Phe Asp Leu Thr Lys Ala Ala Asn Ala Lys Phe Asp Tyr Lys Ala Asn
    515                 520                 525

Tyr Glu Leu Glu Ala Glu Cys Asp Phe Ile Glu Val His Ala Val Thr
530                 535                 540

Glu Asp Gly Thr Lys Thr Leu Ile Asp Lys Leu Gly Asp Lys Val Val
545                 550                 555                 560

Lys Gly Asp Gln Asp Thr Thr Glu Gly Lys Trp Ile Asp Lys Ser Tyr
            565                 570                 575

Asp Leu Ser Gln Phe Lys Gly Lys Val Lys Leu Gln Phe Asp Tyr
        580                 585                 590

Ile Thr Asp Pro Ala Leu Thr Tyr Lys Gly Phe Ala Met Asp Asn Val
    595                 600                 605

Asn Val Thr Val Asp Gly Lys Val Val Phe Ser Asp Ala Glu Gly
610                 615                 620

Gln Ala Lys Met Lys Leu Asn Gly Phe Val Val Ser Asp Gly Thr Glu
625                 630                 635                 640

-continued

```
Lys Lys Pro His Tyr Tyr Tyr Leu Glu Trp Arg Asn Tyr Ala Gly Ser
                645                 650                 655

Asp Glu Gly Leu Lys Val Gly Arg Gly Pro Val Tyr Asn Thr Gly Leu
            660                 665                 670

Val Val Trp Tyr Ala Asp Asp Ser Phe Lys Asp Asn Trp Val Gly Arg
        675                 680                 685

His Pro Gly Glu Gly Phe Leu Gly Val Val Asp Ser His Pro Glu Ala
    690                 695                 700

Val Val Gly Asn Leu Asn Gly Lys Pro Val Tyr Gly Asn Thr Gly Leu
705                 710                 715                 720

Gln Ile Ala Asp Ala Ala Phe Ser Leu Asp Gln Thr Pro Ala Trp Asn
                725                 730                 735

Val Asn Ser Phe Thr Arg Gly Gln Phe Asn Tyr Pro Gly Leu Pro Gly
            740                 745                 750

Val Ala Thr Phe Asp Asp Ser Lys Val Tyr Ser Asn Thr Gln Ile Pro
        755                 760                 765

Asp Ala Gly Arg Lys Val Pro Gln Leu Gly Leu Lys Phe Gln Val Val
    770                 775                 780

Gly Gln Ala Asp Asp Lys Ser Ala Gly Ala Ile Trp Ile Arg Arg
785                 790                 795

<210> SEQ ID NO 131
<211> LENGTH: 430
<212> TYPE: PRT
<213> ORGANISM: Bacillus cereus

<400> SEQUENCE: 131

Met Lys His Asn Asp Cys Phe Asp His Asn Asn Cys Asn Pro Ile Val
1               5                   10                  15

Phe Ser Ala Asp Cys Cys Lys Asn Pro Gln Ser Val Pro Ile Thr Arg
            20                  25                  30

Glu Gln Leu Ser Gln Leu Ile Thr Leu Leu Asn Ser Leu Val Ser Ala
        35                  40                  45

Ile Ser Ala Phe Phe Ala Asn Pro Ser Asn Ala Asn Arg Leu Val Leu
    50                  55                  60

Leu Asp Leu Phe Asn Gln Phe Leu Ile Phe Leu Asn Ser Leu Leu Pro
65                  70                  75                  80

Ser Pro Glu Val Asn Phe Leu Lys Gln Leu Thr Gln Ser Ile Ile Val
                85                  90                  95

Leu Leu Gln Ser Pro Ala Pro Asn Leu Gly Gln Leu Ser Thr Leu Leu
            100                 105                 110

Gln Gln Phe Tyr Ser Ala Leu Ala Gln Phe Phe Phe Ala Leu Asp Leu
        115                 120                 125

Ile Pro Ile Ser Cys Asn Ser Asn Val Asp Ser Ala Thr Leu Gln Leu
    130                 135                 140

Leu Phe Asn Leu Leu Ile Gln Leu Ile Asn Ala Thr Pro Gly Ala Thr
145                 150                 155                 160

Gly Pro Thr Gly Pro Thr Gly Pro Thr Gly Pro Thr Gly Pro Ala Gly
                165                 170                 175

Thr Gly Ala Gly Pro Thr Gly Ala Thr Gly Ala Thr Gly Ala Thr Gly
            180                 185                 190

Pro Thr Gly Ala Thr Gly Pro Ala Gly Thr Gly Gly Ala Thr Gly Ala
        195                 200                 205

Thr Gly Ala Thr Gly Val Thr Gly Ala Thr Gly Ala Thr Gly Ala Thr
    210                 215                 220
```

```
Gly Pro Thr Gly Pro Thr Gly Ala Thr Gly Pro Thr Gly Ala Thr Gly
225                 230                 235                 240

Ala Thr Gly Ala Thr Gly Pro Thr Gly Ala Thr Gly Pro Thr Gly Ala
                245                 250                 255

Thr Gly Leu Thr Gly Ala Thr Gly Ala Ala Gly Gly Gly Ala Ile Ile
            260                 265                 270

Pro Phe Ala Ser Gly Thr Thr Pro Ser Ala Leu Val Asn Ala Leu Val
        275                 280                 285

Ala Asn Thr Gly Thr Leu Leu Gly Phe Gly Phe Ser Gln Pro Gly Val
    290                 295                 300

Ala Leu Thr Gly Gly Thr Ser Ile Thr Leu Ala Leu Gly Val Gly Asp
305                 310                 315                 320

Tyr Ala Phe Val Ala Pro Arg Ala Gly Thr Ile Thr Ser Leu Ala Gly
                325                 330                 335

Phe Phe Ser Ala Thr Ala Ala Leu Ala Pro Ile Ser Pro Val Gln Val
            340                 345                 350

Gln Ile Gln Ile Leu Thr Ala Pro Ala Ala Ser Asn Thr Phe Thr Val
        355                 360                 365

Gln Gly Ala Pro Leu Leu Leu Thr Pro Ala Phe Ala Ala Ile Ala Ile
    370                 375                 380

Gly Ser Thr Ala Ser Gly Ile Ile Ala Glu Ala Ile Pro Val Ala Ala
385                 390                 395                 400

Gly Asp Lys Ile Leu Leu Tyr Val Ser Leu Thr Ala Ala Ser Pro Ile
                405                 410                 415

Ala Ala Val Ala Gly Phe Val Ser Ala Gly Ile Asn Ile Val
            420                 425                 430

<210> SEQ ID NO 132
<211> LENGTH: 437
<212> TYPE: PRT
<213> ORGANISM: Bacillus cereus

<400> SEQUENCE: 132

Met Lys His Asn Asp Cys Phe Gly His Asn Asn Cys Asn Asn Pro Ile
1               5                   10                  15

Val Phe Thr Pro Asp Cys Cys Asn Asn Pro Gln Thr Val Pro Ile Thr
            20                  25                  30

Ser Glu Gln Leu Gly Arg Leu Ile Thr Leu Leu Asn Ser Leu Ile Ala
        35                  40                  45

Ala Ile Ala Ala Phe Phe Ala Asn Pro Ser Asp Ala Asn Arg Leu Ala
    50                  55                  60

Leu Leu Asn Leu Phe Thr Gln Leu Leu Asn Leu Leu Asn Glu Leu Ala
65                  70                  75                  80

Pro Ser Pro Glu Gly Asn Phe Leu Lys Gln Leu Ile Gln Ser Ile Ile
                85                  90                  95

Asn Leu Leu Gln Ser Pro Asn Pro Asn Leu Gly Gln Leu Leu Ser Leu
            100                 105                 110

Leu Gln Gln Phe Tyr Ser Ala Leu Ala Pro Phe Phe Phe Ser Leu Ile
        115                 120                 125

Leu Asp Pro Ala Ser Leu Gln Leu Leu Leu Asn Leu Leu Ala Gln Leu
    130                 135                 140

Ile Gly Val Thr Pro Gly Gly Gly Ala Thr Gly Pro Thr Gly Pro Thr
145                 150                 155                 160

Gly Pro Gly Gly Gly Ala Thr Gly Pro Thr Gly Pro Thr Gly Pro Gly
```

-continued

```
                165                 170                 175

Gly Gly Ala Thr Gly Pro Thr Gly Ala Thr Gly Pro Thr Gly Asp Thr
            180                 185                 190

Gly Leu Ala Gly Ala Thr Gly Ala Thr Gly Pro Thr Gly Asp Thr Gly
        195                 200                 205

Val Ala Gly Pro Ala Gly Pro Thr Gly Pro Thr Gly Asp Thr Gly Leu
    210                 215                 220

Ala Gly Ala Thr Gly Pro Thr Gly Pro Thr Gly Asp Thr Gly Leu Ala
225                 230                 235                 240

Gly Ala Thr Gly Pro Thr Gly Ala Thr Gly Leu Ala Gly Ala Thr Gly
                245                 250                 255

Pro Thr Gly Ala Thr Gly Leu Thr Gly Ala Thr Gly Ala Thr Gly Ala
            260                 265                 270

Ala Gly Gly Gly Ala Ile Ile Pro Phe Ala Ser Gly Thr Thr Pro Ala
        275                 280                 285

Ala Leu Val Asn Ala Leu Ile Ala Asn Thr Gly Thr Leu Leu Gly Phe
    290                 295                 300

Gly Phe Ser Gln Pro Gly Ile Gly Leu Ala Gly Gly Thr Ser Ile Thr
305                 310                 315                 320

Leu Ala Leu Gly Val Gly Asp Tyr Ala Phe Val Ala Pro Arg Asp Gly
                325                 330                 335

Val Ile Thr Ser Leu Ala Gly Phe Phe Ser Ala Thr Ala Ala Leu Ser
            340                 345                 350

Pro Leu Ser Pro Val Gln Val Gln Ile Gln Ile Leu Thr Ala Pro Ala
        355                 360                 365

Ala Ser Asn Thr Phe Thr Val Gln Gly Ala Pro Leu Leu Leu Thr Pro
    370                 375                 380

Ala Phe Ala Ala Ile Ala Ile Gly Ser Thr Ala Ser Gly Ile Ile Pro
385                 390                 395                 400

Glu Ala Ile Pro Val Val Ala Gly Asp Lys Ile Leu Leu Tyr Val Ser
                405                 410                 415

Leu Thr Ala Ala Ser Pro Ile Ala Ala Val Ala Gly Phe Val Ser Ala
            420                 425                 430

Gly Ile Asn Ile Val
        435

<210> SEQ ID NO 133
<211> LENGTH: 119
<212> TYPE: PRT
<213> ORGANISM: Bacillus cereus

<400> SEQUENCE: 133

Met Leu Phe Thr Ser Trp Leu Leu Phe Phe Ile Phe Ala Leu Ala Ala
1               5                   10                  15

Phe Arg Leu Thr Arg Leu Ile Val Tyr Asp Lys Ile Thr Gly Phe Leu
            20                  25                  30

Arg Arg Pro Phe Ile Asp Glu Leu Glu Ile Thr Glu Pro Asp Gly Ser
        35                  40                  45

Val Ser Thr Phe Thr Lys Val Lys Gly Lys Gly Leu Arg Lys Trp Ile
    50                  55                  60

Gly Glu Leu Leu Ser Cys Tyr Trp Cys Thr Gly Val Trp Val Ser Ala
65                  70                  75                  80

Phe Leu Leu Val Leu Tyr Asn Trp Ile Pro Ile Val Ala Glu Pro Leu
                85                  90                  95
```

```
Leu Ala Leu Leu Ala Ile Ala Gly Ala Ala Ile Ile Glu Thr Ile
            100                 105                 110
Thr Gly Tyr Phe Met Gly Glu
            115
```

<210> SEQ ID NO 134
<211> LENGTH: 61
<212> TYPE: PRT
<213> ORGANISM: Bacillus cereus

<400> SEQUENCE: 134

```
Met Phe Ala Val Ser Asn Asn Pro Arg Gln Asn Ser Tyr Asp Leu Gln
1               5                   10                  15
Gln Trp Tyr His Met Gln Gln Gln His Gln Ala Gln Gln Gln Ala Tyr
                20                  25                  30
Gln Glu Gln Leu Gln Gln Gln Gly Phe Val Lys Lys Lys Gly Cys Asn
            35                  40                  45
Cys Gly Lys Lys Lys Ser Thr Ile Lys His Tyr Glu Glu
        50                  55                  60
```

<210> SEQ ID NO 135
<211> LENGTH: 66
<212> TYPE: PRT
<213> ORGANISM: Bacillus cereus

<400> SEQUENCE: 135

```
Leu Thr Val Glu Glu Met Phe Ala Val Ser Asn Asn Pro Arg Gln Asn
1               5                   10                  15
Ser Tyr Asp Leu Gln Gln Trp Tyr His Met Gln Gln His Gln Ala
                20                  25                  30
Gln Gln Gln Ala Tyr Gln Glu Gln Leu Gln Gln Gln Gly Phe Val Lys
            35                  40                  45
Lys Lys Gly Cys Asn Cys Gly Lys Lys Lys Ser Thr Ile Lys His Tyr
        50                  55                  60
Glu Glu
65
```

<210> SEQ ID NO 136
<211> LENGTH: 481
<212> TYPE: PRT
<213> ORGANISM: Bacillus anthracis

<400> SEQUENCE: 136

```
Met Ser Arg Tyr Asp Asp Ser Gln Asn Lys Phe Ser Lys Pro Cys Phe
1               5                   10                  15
Pro Ser Ser Ala Gly Arg Ile Pro Asn Thr Pro Ser Ile Pro Val Thr
                20                  25                  30
Lys Ala Gln Leu Arg Thr Phe Arg Ala Ile Ile Ile Asp Leu Thr Lys
            35                  40                  45
Ile Ile Pro Lys Leu Phe Ala Asn Pro Ser Pro Gln Asn Ile Glu Asp
        50                  55                  60
Leu Ile Asp Thr Leu Asn Leu Leu Ser Lys Phe Ile Cys Ser Leu Asp
65                  70                  75                  80
Ala Ala Ser Ser Leu Lys Ala Gln Gly Leu Ala Ile Ile Lys Asn Leu
                85                  90                  95
Ile Thr Ile Leu Lys Asn Pro Thr Phe Val Ala Ser Ala Val Phe Ile
            100                 105                 110
Glu Leu Gln Asn Leu Ile Asn Tyr Leu Leu Ser Ile Thr Lys Leu Phe
```

```
                    115                 120                 125
Arg Ile Asp Pro Cys Thr Leu Gln Glu Leu Leu Lys Leu Ile Ala Ala
            130                 135                 140

Leu Gln Thr Ala Leu Val Asn Ser Ala Ser Phe Ile Gln Gly Pro Thr
145                 150                 155                 160

Gly Pro Thr Gly Pro Thr Gly Pro Thr Pro Ala Gly Ala Thr Gly
                165                 170                 175

Ala Thr Gly Pro Gln Gly Val Gln Gly Pro Ala Gly Ala Thr Gly Ala
            180                 185                 190

Thr Gly Pro Gln Gly Val Gln Gly Pro Ala Gly Ala Thr Gly Ala Thr
            195                 200                 205

Gly Pro Gln Gly Ala Gln Gly Pro Ala Gly Ala Thr Gly Ala Thr Gly
            210                 215                 220

Pro Gln Gly Ala Gln Gly Pro Ala Gly Ala Thr Gly Ala Thr Gly Pro
225                 230                 235                 240

Gln Gly Ile Gln Gly Pro Ala Gly Ala Thr Gly Ala Thr Gly Pro Gln
            245                 250                 255

Gly Val Gln Gly Pro Thr Gly Ala Thr Gly Ile Gly Val Thr Gly Pro
            260                 265                 270

Thr Gly Pro Ser Gly Gly Pro Ala Gly Ala Thr Gly Pro Gln Gly Pro
            275                 280                 285

Gln Gly Asn Thr Gly Ala Thr Gly Pro Gln Gly Ile Gln Gly Pro Ala
            290                 295                 300

Gly Ala Thr Gly Ala Thr Gly Pro Gln Gly Ala Gln Gly Pro Ala Gly
305                 310                 315                 320

Ala Thr Gly Ala Thr Gly Pro Gln Gly Val Gln Gly Pro Thr Gly Ala
                325                 330                 335

Thr Gly Ile Gly Val Thr Gly Pro Thr Gly Pro Ser Gly Pro Ser Phe
            340                 345                 350

Pro Val Ala Thr Ile Val Val Thr Asn Asn Ile Gln Gln Thr Val Leu
            355                 360                 365

Gln Phe Asn Asn Phe Ile Phe Asn Thr Ala Ile Asn Val Asn Asn Ile
            370                 375                 380

Ile Phe Asn Gly Thr Asp Thr Val Thr Val Ile Asn Ala Gly Ile Tyr
385                 390                 395                 400

Val Ile Ser Val Ser Ile Ser Thr Thr Ala Pro Gly Cys Ala Pro Leu
                405                 410                 415

Gly Val Gly Ile Ser Ile Asn Gly Ala Val Ala Thr Asp Asn Phe Ser
            420                 425                 430

Ser Asn Leu Ile Gly Asp Ser Leu Ser Phe Thr Thr Ile Glu Thr Leu
            435                 440                 445

Thr Ala Gly Ala Asn Ile Ser Val Gln Ser Thr Leu Asn Glu Ile Thr
            450                 455                 460

Ile Pro Ala Thr Gly Asn Thr Asn Ile Arg Leu Thr Val Phe Arg Ile
465                 470                 475                 480

Ala
```

<210> SEQ ID NO 137
<211> LENGTH: 275
<212> TYPE: PRT
<213> ORGANISM: Bacillus cereus

<400> SEQUENCE: 137

Met Lys Met Lys Arg Gly Ile Thr Thr Leu Leu Ser Val Ala Val Leu

```
1               5                   10                  15

Ser Thr Ser Leu Val Ala Cys Ser Gly Thr Thr Glu Lys Thr Val Ala
            20                  25                  30

Lys Glu Glu Lys Val Lys Leu Thr Asp Gln Gln Leu Met Ala Asp Leu
        35                  40                  45

Trp Tyr Gln Thr Ala Gly Glu Met Lys Ala Leu Tyr Tyr Gln Gly Tyr
    50                  55                  60

Asn Ile Gly Gln Leu Lys Leu Asp Ala Val Leu Ala Lys Gly Thr Glu
65                  70                  75                  80

Lys Lys Pro Ala Ile Val Leu Asp Leu Asp Glu Thr Val Leu Asp Asn
                85                  90                  95

Ser Pro His Gln Ala Met Ser Val Lys Thr Gly Lys Gly Tyr Pro Tyr
            100                 105                 110

Lys Trp Asp Asp Trp Ile Asn Lys Ala Glu Ala Glu Ala Leu Pro Gly
        115                 120                 125

Ala Ile Asp Phe Leu Lys Tyr Thr Glu Ser Lys Gly Val Asp Ile Tyr
    130                 135                 140

Tyr Ile Ser Asn Arg Lys Thr Asn Gln Leu Asp Ala Thr Ile Lys Asn
145                 150                 155                 160

Leu Glu Arg Val Gly Ala Pro Gln Ala Thr Lys Glu His Ile Leu Leu
                165                 170                 175

Gln Asp Pro Lys Glu Lys Gly Lys Glu Lys Arg Arg Glu Leu Val Ser
            180                 185                 190

Gln Thr His Asp Ile Val Leu Phe Phe Gly Asp Asn Leu Ser Asp Phe
        195                 200                 205

Thr Gly Phe Asp Gly Lys Ser Val Lys Asp Arg Asn Gln Ala Val Ala
    210                 215                 220

Asp Ser Lys Ala Gln Phe Gly Glu Lys Phe Ile Ile Phe Pro Asn Pro
225                 230                 235                 240

Met Tyr Gly Asp Trp Glu Gly Ala Leu Tyr Asp Tyr Asp Phe Lys Lys
                245                 250                 255

Ser Asp Ala Glu Lys Asp Lys Ile Arg His Asp Asn Leu Lys Ser Phe
            260                 265                 270

Asp Thr Lys
        275

<210> SEQ ID NO 138
<211> LENGTH: 795
<212> TYPE: PRT
<213> ORGANISM: Bacillus cereus

<400> SEQUENCE: 138

Met Lys Lys Lys Lys Lys Leu Lys Pro Leu Ala Val Leu Thr Thr Ala
1               5                   10                  15

Ala Val Leu Ser Ser Thr Phe Ala Phe Gly Gly His Ala Ala Tyr Ala
            20                  25                  30

Glu Thr Pro Thr Ser Ser Leu Pro Ile Asp Glu His Leu Ile Pro Glu
        35                  40                  45

Glu Arg Leu Ala Glu Ala Leu Lys Gln Arg Gly Val Ile Asp Gln Ser
    50                  55                  60

Ala Ser Gln Ala Glu Thr Ser Lys Ala Val Glu Lys Tyr Val Glu Lys
65                  70                  75                  80

Lys Lys Gly Glu Asn Pro Gly Lys Glu Ile Leu Thr Gly Asp Ser Leu
                85                  90                  95
```

```
Thr Gln Glu Ala Ser Asp Phe Met Lys Lys Val Lys Asp Ala Lys Met
            100                 105                 110

Arg Glu Asn Glu Gln Ala Gln Gln Pro Glu Val Gly Pro Val Ala Gly
            115                 120                 125

Gln Gly Ala Ala Leu Asn Pro Gly Lys Leu Asn Gly Lys Val Pro Thr
            130                 135                 140

Thr Ser Ala Lys Gln Glu Glu Tyr Asn Gly Ala Val Arg Lys Asp Lys
145                 150                 155                 160

Val Leu Val Leu Leu Val Glu Phe Ser Asp Phe Lys His Asn Asn Ile
                    165                 170                 175

Asp Gln Glu Pro Gly Tyr Met Tyr Ser Lys Asp Phe Asn Arg Glu His
            180                 185                 190

Tyr Gln Lys Met Leu Phe Gly Asp Glu Pro Phe Thr Leu Phe Asp Gly
            195                 200                 205

Ser Lys Ile Asn Thr Phe Lys Gln Tyr Tyr Glu Glu Gln Ser Gly Gly
            210                 215                 220

Ser Tyr Thr Val Asp Gly Thr Val Thr Glu Trp Leu Thr Val Pro Gly
225                 230                 235                 240

Lys Ala Ser Asp Tyr Gly Ala Asp Ala Gly Thr Gly His Asp Asn Lys
                    245                 250                 255

Gly Pro Leu Gly Pro Lys Asp Leu Val Lys Glu Ala Leu Lys Ala Ala
            260                 265                 270

Val Ala Lys Gly Ile Asn Leu Ala Asp Phe Asp Gln Tyr Asp Gln Tyr
            275                 280                 285

Asp Gln Asn Gly Asn Gly Asn Lys Asn Glu Pro Asp Gly Ile Ile Asp
            290                 295                 300

His Leu Met Val Val His Ala Gly Val Gly Gln Glu Ala Gly Gly Gly
305                 310                 315                 320

Lys Leu Lys Asp Asp Ala Ile Trp Ser His Arg Ser Lys Leu Gly Ser
                    325                 330                 335

Lys Pro Tyr Ala Ile Asp Gly Thr Lys Ser Ser Val Ser Asn Trp Gly
            340                 345                 350

Gly Lys Met Ala Ala Tyr Asp Tyr Thr Ile Glu Pro Glu Asp Gly Ala
            355                 360                 365

Val Gly Val Phe Ala His Glu Tyr Gly His Asp Leu Gly Leu Pro Asp
            370                 375                 380

Glu Tyr Asp Thr Lys Tyr Ser Gly Gln Gly Glu Pro Val Glu Ser Trp
385                 390                 395                 400

Ser Ile Met Ser Gly Gly Ser Trp Ala Gly Lys Ile Ala Gly Thr Glu
                    405                 410                 415

Pro Thr Ser Phe Ser Pro Gln Asn Lys Glu Phe Phe Gln Lys Asn Met
            420                 425                 430

Lys Gly Asn Trp Ala Asn Ile Leu Glu Val Asp Tyr Asp Lys Leu Ser
            435                 440                 445

Lys Gly Ile Gly Val Ala Thr Tyr Val Asp Gln Ser Thr Thr Lys Ser
            450                 455                 460

Lys Arg Pro Gly Ile Val Arg Val Asn Leu Pro Asp Lys Asp Ile Lys
465                 470                 475                 480

Asn Ile Glu Ser Ala Phe Gly Lys Lys Phe Tyr Tyr Ser Thr Lys Gly
                    485                 490                 495

Asn Asp Ile His Thr Thr Leu Glu Thr Pro Val Phe Asp Leu Thr Asn
            500                 505                 510

Ala Lys Asp Ala Lys Phe Asp Tyr Lys Ala Phe Tyr Glu Leu Glu Ala
```

```
        515                 520                 525

Lys Tyr Asp Phe Leu Asp Val Tyr Ala Ile Ala Glu Asp Gly Thr Lys
    530                 535                 540
Thr Arg Ile Asp Arg Met Gly Glu Lys Asp Ile Lys Gly Gly Ala Asp
545                 550                 555                 560
Thr Thr Asp Gly Lys Trp Val Asp Lys Ser Tyr Asp Leu Ser Gln Phe
                565                 570                 575
Lys Gly Lys Lys Val Lys Leu Gln Phe Glu Tyr Leu Thr Asp Ile Ala
            580                 585                 590
Val Ala Tyr Lys Gly Phe Ala Leu Asp Asn Ala Ala Leu Thr Val Asp
        595                 600                 605
Gly Lys Val Val Phe Ser Asp Asp Ala Glu Gly Gln Pro Ala Met Thr
    610                 615                 620
Leu Lys Gly Phe Thr Val Ser Asn Gly Phe Glu Gln Lys Lys His Asn
625                 630                 635                 640
Tyr Tyr Val Glu Trp Arg Asn Tyr Ala Gly Ser Asp Thr Ala Leu Gln
                645                 650                 655
Tyr Ala Arg Gly Pro Val Phe Asn Thr Gly Met Val Val Trp Tyr Ala
            660                 665                 670
Asp Gln Ser Phe Thr Asp Asn Trp Val Gly Val His Pro Gly Glu Gly
        675                 680                 685
Phe Leu Gly Val Val Asp Ser His Pro Glu Ala Ile Val Gly Thr Leu
    690                 695                 700
Asn Gly Gln Pro Thr Val Lys Ser Ser Thr Arg Tyr Gln Ile Ala Asp
705                 710                 715                 720
Ala Ala Phe Ser Phe Asp Gln Thr Pro Ala Trp Lys Val Asn Ser Pro
                725                 730                 735
Thr Arg Gly Ile Phe Asp Tyr Lys Gly Leu Pro Gly Val Ala Lys Phe
            740                 745                 750
Asp Asp Ser Lys Gln Tyr Ile Asn Ser Val Ile Pro Asp Ala Gly Arg
        755                 760                 765
Lys Leu Pro Lys Leu Gly Leu Lys Phe Glu Val Val Gly Gln Ala Glu
    770                 775                 780
Asp Lys Ser Ala Gly Ala Val Trp Leu His Arg
785                 790                 795

<210> SEQ ID NO 139
<211> LENGTH: 389
<212> TYPE: PRT
<213> ORGANISM: Bacillus cereus

<400> SEQUENCE: 139

Met Glu Glu Ala Pro Phe Tyr Arg Asp Thr Trp Val Glu Val Asp Leu
1               5                   10                  15

Asp Ala Ile Tyr Asn Asn Val Thr His Ile Lys Glu Phe Ile Pro Ser
            20                  25                  30

Asp Val Glu Ile Phe Ala Val Val Lys Gly Asn Ala Tyr Gly His Asp
        35                  40                  45

Tyr Val Pro Val Ala Lys Ile Ala Leu Glu Ala Gly Ala Thr Arg Leu
    50                  55                  60

Ala Val Ala Phe Leu Asp Glu Ala Leu Val Leu Arg Arg Ala Gly Ile
65                  70                  75                  80

Thr Ala Pro Ile Leu Val Leu Gly Pro Ser Pro Pro Arg Asp Ile Asn
                85                  90                  95
```

```
Val Ala Ala Glu Asn Asp Val Ala Leu Thr Val Phe Gln Lys Glu Trp
            100                 105                 110

Val Asp Glu Ala Ile Lys Leu Trp Asp Gly Ser Ser Thr Met Lys Tyr
        115                 120                 125

His Ile Asn Phe Asp Ser Gly Met Gly Arg Ile Gly Ile Arg Glu Arg
    130                 135                 140

Lys Glu Leu Lys Gly Phe Leu Lys Ser Leu Glu Gly Ala Pro Phe Leu
145                 150                 155                 160

Glu Leu Glu Gly Val Tyr Thr His Phe Ala Thr Ala Asp Glu Val Glu
                165                 170                 175

Thr Ser Tyr Phe Asp Lys Gln Tyr Asn Thr Phe Leu Glu Gln Leu Ser
            180                 185                 190

Trp Leu Lys Glu Phe Gly Val Asp Pro Lys Phe Val His Thr Ala Asn
        195                 200                 205

Ser Ala Ala Thr Leu Arg Phe Gln Gly Ile Thr Phe Asn Ala Val Arg
    210                 215                 220

Ile Gly Ile Ala Met Tyr Gly Leu Ser Pro Ser Val Glu Ile Arg Pro
225                 230                 235                 240

Phe Leu Pro Phe Lys Leu Glu Pro Ala Leu Ser Leu His Thr Lys Val
                245                 250                 255

Ala His Ile Lys Gln Val Ile Lys Gly Asp Gly Ile Ser Tyr Asn Val
            260                 265                 270

Thr Tyr Arg Thr Lys Thr Glu Glu Trp Ile Ala Thr Val Ala Ile Gly
        275                 280                 285

Tyr Ala Asp Gly Trp Leu Arg Arg Leu Gln Gly Phe Glu Val Leu Val
    290                 295                 300

Asn Gly Lys Arg Val Pro Ile Val Gly Arg Val Thr Met Asp Gln Phe
305                 310                 315                 320

Met Ile His Leu Pro Cys Glu Val Pro Leu Gly Thr Lys Val Thr Leu
                325                 330                 335

Ile Gly Arg Gln Gly Asp Glu Tyr Ile Ser Ala Thr Glu Val Ala Glu
            340                 345                 350

Tyr Ser Gly Thr Ile Asn Tyr Glu Ile Ile Thr Thr Ile Ser Phe Arg
        355                 360                 365

Val Pro Arg Ile Phe Ile Arg Asn Gly Lys Val Val Glu Val Ile Asn
    370                 375                 380

Tyr Leu Asn Asp Ile
385

<210> SEQ ID NO 140
<211> LENGTH: 391
<212> TYPE: PRT
<213> ORGANISM: Bacillus cereus

<400> SEQUENCE: 140

Met Ser Leu Lys Tyr Gly Arg Asp Thr Ile Val Glu Val Asp Leu Asn
1               5                   10                  15

Ala Val Lys His Asn Val Lys Glu Phe Lys Lys Arg Val Asn Asp Glu
            20                  25                  30

Asn Ile Ala Met Met Ala Ala Val Lys Ala Asn Gly Tyr Gly His Gly
        35                  40                  45

Ala Val Glu Val Ala Lys Ala Ala Ile Glu Ala Gly Ile Asn Gln Leu
    50                  55                  60

Ala Ile Ala Phe Val Asp Glu Ala Ile Glu Leu Arg Glu Ala Gly Ile
65                  70                  75                  80
```

Asn Val Pro Ile Leu Ile Leu Gly Tyr Thr Ser Val Ala Ala Glu
                85                  90                  95

Glu Ala Ile Gln Tyr Asp Val Met Met Thr Val Tyr Arg Ser Glu Asp
            100                 105                 110

Leu Gln Gly Ile Asn Glu Ile Ala Asn Arg Leu Gln Lys Lys Ala Gln
            115                 120                 125

Ile Gln Val Lys Ile Asp Thr Gly Met Ser Arg Ile Gly Leu Gln Glu
130                 135                 140

Glu Glu Val Lys Pro Phe Leu Glu Glu Leu Lys Arg Met Glu Tyr Val
145                 150                 155                 160

Glu Val Val Gly Met Phe Thr His Tyr Ser Thr Ala Asp Glu Ile Asp
                165                 170                 175

Lys Ser Tyr Thr Asn Met Gln Thr Ser Leu Phe Glu Lys Ala Val Asn
                180                 185                 190

Thr Ala Lys Glu Leu Gly Ile His Ile Pro Tyr Ile His Ser Ser Asn
            195                 200                 205

Ser Ala Gly Ser Met Glu Leu Ser Asn Thr Phe Gln Asn Met Val Arg
210                 215                 220

Val Gly Ile Gly Ile Tyr Gly Met Tyr Pro Ser Lys Glu Val Asn His
225                 230                 235                 240

Ser Val Val Ser Leu Gln Pro Ala Leu Ser Leu Lys Ser Lys Val Ala
                245                 250                 255

His Ile Lys His Ala Lys Lys Asn Arg Gly Val Ser Tyr Gly Asn Thr
                260                 265                 270

Tyr Val Thr Thr Gly Glu Glu Trp Ile Ala Thr Val Pro Ile Gly Tyr
            275                 280                 285

Ala Asp Gly Tyr Asn Arg Gln Leu Ser Asn Lys Gly His Ala Leu Ile
290                 295                 300

Asn Gly Val Arg Val Pro Val Ile Gly Arg Val Cys Met Asp Gln Leu
305                 310                 315                 320

Met Leu Asp Val Ser Lys Ala Met Pro Val Gln Val Gly Asp Glu Val
                325                 330                 335

Val Phe Tyr Gly Lys Gln Gly Glu Glu Asn Ile Ala Val Glu Glu Ile
            340                 345                 350

Ala Asp Met Leu Gly Thr Ile Asn Tyr Glu Val Thr Cys Met Leu Asp
            355                 360                 365

Arg Arg Ile Pro Arg Val Tyr Lys Glu Asn Asn Glu Thr Thr Ala Val
370                 375                 380

Val Asn Ile Leu Arg Lys Asn
385                 390

<210> SEQ ID NO 141
<211> LENGTH: 332
<212> TYPE: PRT
<213> ORGANISM: Bacillus anthracis

<400> SEQUENCE: 141

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
            35                  40                  45

Gly Pro Thr Gly Pro Thr Gly Pro Thr Gly Pro Thr Gly Pro Thr Gly

Pro Thr Gly Pro Thr Gly Pro Thr Gly Asp Thr Gly Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
            115                 120                 125

Gly Pro Thr Gly Pro Thr Gly Pro Thr Gly Pro Thr Gly Asp Thr Gly
            130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
            165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
            195                 200                 205

Ile Ser Leu Asp Leu Gly Ile Asn Asp Pro Val Pro Phe Asn Thr Val
210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
            245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
            275                 280                 285

Pro Phe Thr Ile Val Ile Gln Ala Ile Thr Gln Ile Thr Thr Thr Pro
            290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
            325                 330

<210> SEQ ID NO 142
<211> LENGTH: 400
<212> TYPE: PRT
<213> ORGANISM: Bacillus anthracis

<400> SEQUENCE: 142

Met Ser Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
                20                  25                  30

Ile Pro Pro Phe Thr Leu Pro Thr Gly Pro Thr Gly Pro Thr Gly Pro
            35                  40                  45

Thr Gly Pro Thr Gly Pro Thr Gly Pro Thr Gly Pro Thr Gly Pro Thr
            50                  55                  60

Gly Pro Thr Gly Pro Thr Gly Pro Thr Gly Pro Thr Gly Pro Thr Gly
65                  70                  75                  80

Asp Thr Gly Thr Thr Gly Pro Thr Gly Pro Thr Gly Pro Thr Gly Pro
            85                  90                  95

```
Thr Gly Pro Thr Gly Asp Thr Gly Thr Gly Pro Thr Gly Pro Thr
                100                 105                 110

Gly Pro Thr Gly Pro Thr Gly Pro Thr Gly Pro Thr Gly Pro Thr Gly
            115                 120                 125

Pro Thr Gly Pro Thr Gly Pro Thr Gly Asp Thr Gly Thr Thr Gly Pro
        130                 135                 140

Thr Gly Pro Thr Gly Pro Thr Gly Pro Thr Gly Pro Thr Gly Asp Thr
145                 150                 155                 160

Gly Thr Thr Gly Pro Thr Gly Pro Thr Gly Pro Thr Gly Pro Thr Gly
                165                 170                 175

Pro Thr Gly Pro Thr Gly Pro Thr Gly Pro Thr Gly Pro Thr Gly Pro
            180                 185                 190

Thr Gly Pro Thr Gly Pro Thr Gly Pro Thr Gly Asp Thr Gly Thr Thr
                195                 200                 205

Gly Pro Thr Gly Pro Thr Gly Pro Thr Gly Pro Thr Gly Pro Thr Gly
            210                 215                 220

Asp Thr Gly Thr Thr Gly Pro Thr Gly Pro Thr Gly Pro Thr Gly Pro
225                 230                 235                 240

Thr Gly Pro Thr Gly Pro Thr Gly Pro Thr Gly Ala Thr Gly Leu Thr
                245                 250                 255

Gly Pro Thr Gly Pro Thr Gly Pro Ser Gly Leu Gly Leu Pro Ala Gly
            260                 265                 270

Leu Tyr Ala Phe Asn Ser Gly Ile Ser Leu Asp Leu Gly Ile Asn
                275                 280                 285

Asp Pro Val Pro Phe Asn Thr Val Gly Ser Gln Phe Gly Thr Ala Ile
290                 295                 300

Ser Gln Leu Asp Ala Asp Thr Phe Val Ile Ser Glu Thr Gly Phe Tyr
305                 310                 315                 320

Lys Ile Thr Val Ile Ala Asn Thr Ala Thr Ala Ser Val Leu Gly Gly
                325                 330                 335

Leu Thr Ile Gln Val Asn Gly Val Pro Val Pro Gly Thr Gly Ser Ser
                340                 345                 350

Leu Ile Ser Leu Gly Ala Pro Ile Val Ile Gln Ala Ile Thr Gln Ile
                355                 360                 365

Thr Thr Thr Pro Ser Leu Val Glu Val Ile Val Thr Gly Leu Gly Leu
                370                 375                 380

Ser Leu Ala Leu Gly Thr Ser Ala Ser Ile Ile Ile Glu Lys Val Ala
385                 390                 395                 400

<210> SEQ ID NO 143
<211> LENGTH: 366
<212> TYPE: PRT
<213> ORGANISM: Bacillus anthracis

<400> SEQUENCE: 143

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
                20                  25                  30

Thr Gly Ile Thr Gly Ala Thr Gly Ala Thr Gly Ile Thr Gly Ala Thr
            35                  40                  45

Gly Pro Thr Gly Thr Thr Gly Ala Thr Gly Ala Thr Gly Ile Thr Gly
        50                  55                  60

Val Thr Gly Ala Thr Gly Ile Thr Gly Val Thr Gly Ala Thr Gly Ile
65                  70                  75                  80
```

```
Thr Gly Val Thr Gly Ala Thr Gly Ile Thr Gly Val Thr Gly Pro Thr
                 85                  90                  95
Gly Ile Thr Gly Ala Thr Gly Pro Thr Gly Ile Thr Gly Ala Thr Gly
            100                 105                 110
Pro Ala Gly Ile Thr Gly Val Thr Gly Pro Thr Gly Ile Thr Gly Ala
            115                 120                 125
Thr Gly Pro Thr Gly Thr Gly Val Thr Gly Pro Thr Gly Asp Thr
        130                 135                 140
Gly Leu Ala Gly Ala Thr Gly Pro Thr Gly Ala Thr Gly Leu Ala Gly
145                 150                 155                 160
Ala Thr Gly Pro Thr Gly Asp Thr Gly Ala Thr Gly Pro Thr Gly Ala
                165                 170                 175
Thr Gly Leu Ala Gly Ala Thr Gly Pro Thr Gly Ala Thr Gly Leu Thr
            180                 185                 190
Gly Ala Thr Gly Ala Thr Gly Ala Thr Gly Gly Ala Ile Ile Pro
            195                 200                 205
Phe Ala Ser Gly Thr Thr Pro Ala Leu Leu Val Asn Ala Val Leu Ala
            210                 215                 220
Asn Thr Gly Thr Leu Leu Gly Phe Gly Phe Ser Gln Pro Gly Ile Ala
225                 230                 235                 240
Pro Gly Val Gly Gly Thr Leu Thr Ile Leu Pro Gly Val Val Gly Asp
                245                 250                 255
Tyr Ala Phe Val Ala Pro Arg Asp Gly Ile Ile Thr Ser Leu Ala Gly
                260                 265                 270
Phe Phe Ser Ala Thr Ala Ala Leu Ala Pro Leu Thr Pro Val Gln Ile
            275                 280                 285
Gln Met Gln Ile Phe Ile Ala Pro Ala Ala Ser Asn Thr Phe Thr Pro
        290                 295                 300
Val Ala Pro Pro Leu Leu Leu Thr Pro Ala Leu Pro Ala Ile Ala Ile
305                 310                 315                 320
Gly Thr Thr Ala Thr Gly Ile Gln Ala Tyr Asn Val Pro Val Val Ala
                325                 330                 335
Gly Asp Lys Ile Leu Val Tyr Val Ser Leu Thr Gly Ala Ser Pro Ile
                340                 345                 350
Ala Ala Val Ala Gly Phe Val Ser Ala Gly Leu Asn Ile Val
            355                 360                 365

<210> SEQ ID NO 144
<211> LENGTH: 347
<212> TYPE: PRT
<213> ORGANISM: Bacillus anthracis

<400> SEQUENCE: 144

Met Gln Asn Asp Lys Leu Trp Leu Asp Lys Gly Ile Ile Gly Pro Glu
1               5                   10                  15
Asn Ile Gly Pro Thr Phe Pro Val Leu Pro Pro Ile His Ile Pro Thr
                20                  25                  30
Gly Ile Thr Gly Ala Thr Gly Ala Thr Gly Ile Thr Gly Ala Thr Gly
            35                  40                  45
Pro Thr Gly Thr Thr Gly Ala Thr Gly Ala Thr Gly Ile Thr Gly Val
        50                  55                  60
Thr Gly Ala Thr Gly Ile Thr Gly Val Thr Gly Ala Thr Gly Ile Thr
65                  70                  75                  80
Gly Val Thr Gly Ala Thr Gly Ile Thr Gly Val Thr Gly Ala Thr Gly
```

```
                85                  90                  95
Ile Thr Gly Val Thr Gly Pro Thr Gly Ile Thr Gly Ala Thr Gly Pro
            100                 105                 110

Thr Gly Thr Thr Gly Val Thr Gly Pro Thr Gly Asp Thr Gly Leu Ala
            115                 120                 125

Gly Ala Thr Gly Pro Thr Gly Ala Thr Gly Leu Ala Gly Ala Thr Gly
            130                 135                 140

Pro Thr Gly Asp Thr Gly Ala Thr Gly Pro Thr Gly Ala Thr Gly Leu
145                 150                 155                 160

Ala Gly Ala Thr Gly Pro Thr Gly Ala Thr Gly Leu Thr Gly Ala Thr
                165                 170                 175

Gly Ala Thr Gly Ala Thr Gly Gly Ala Ile Ile Pro Phe Ala Ser
                180                 185                 190

Gly Thr Thr Pro Ala Leu Leu Val Asn Ala Val Leu Ala Asn Thr Gly
                195                 200                 205

Thr Leu Leu Gly Phe Gly Phe Ser Gln Pro Gly Ile Ala Pro Gly Val
            210                 215                 220

Gly Gly Thr Leu Thr Ile Leu Pro Gly Val Val Gly Asp Tyr Ala Phe
225                 230                 235                 240

Val Ala Pro Arg Asp Gly Ile Ile Thr Ser Leu Ala Gly Phe Phe Ser
                245                 250                 255

Ala Thr Ala Ala Leu Ala Pro Leu Thr Pro Val Gln Ile Gln Met Gln
                260                 265                 270

Ile Phe Ile Ala Pro Ala Ala Ser Asn Thr Phe Thr Pro Val Ala Pro
            275                 280                 285

Pro Leu Leu Leu Thr Pro Ala Leu Pro Ala Ile Ala Ile Gly Thr Thr
290                 295                 300

Ala Thr Gly Ile Gln Ala Tyr Asn Val Pro Val Val Ala Gly Asp Lys
305                 310                 315                 320

Ile Leu Val Tyr Val Ser Leu Thr Gly Ala Ser Pro Ile Ala Ala Val
                325                 330                 335

Ala Gly Phe Val Ser Ala Gly Leu Asn Ile Val
            340                 345

<210> SEQ ID NO 145
<211> LENGTH: 248
<212> TYPE: PRT
<213> ORGANISM: Bacillus anthracis

<400> SEQUENCE: 145

Met Phe Tyr Asn Asn Gln Pro Pro Tyr Pro Gln Gln Pro Phe Tyr Pro
1               5                   10                  15

Gln Gln Gln Glu Gln Tyr Glu Glu Gln Glu Leu Gln Gln Gln Glu Gln
                20                  25                  30

Gln Tyr Glu Gln Asn Pro Tyr Ala Thr Pro Gln Asn Gln Glu Leu Gln
            35                  40                  45

Tyr Pro Gln Asn Pro Tyr Thr Ala Pro Gln Thr Gln Glu Gln Gln Phe
    50                  55                  60

Gln Gln Asn Ser Tyr Asp Thr Arg Pro Ser Tyr Glu Tyr Pro Gln Asn
65                  70                  75                  80

Pro Tyr Ala Ala Pro Gln Asn Gln Glu Leu Gln Tyr Pro Gln Asn Pro
                85                  90                  95

Tyr Val Thr Pro Gln Thr Gln Glu Gln Gln Phe Gln Gln Asn Pro Tyr
            100                 105                 110
```

```
Pro Thr Gln Pro Gln Thr Gln Tyr Gln Gln Met Tyr Gln Pro
            115                 120                 125

Asn Tyr Asp Ala Arg Val Ser Pro Pro Lys Pro Pro Thr Phe Asp Ile
        130                 135                 140

Thr Gln Pro Gln Ile Leu Pro Pro Gly Pro Thr Leu Asp Ile Thr Gln
145                 150                 155                 160

Pro Gln Ile Leu Pro Pro Gly Pro Ile Thr Glu Pro Thr Gln Gln Gln
                165                 170                 175

Ile Gln Gln Val Val Gly Thr Gln Phe Leu Pro Leu Lys Lys Pro Val
            180                 185                 190

Leu Asp Phe Val Lys Pro Trp Val Asp Tyr Gly Leu Asn Glu Ala Lys
            195                 200                 205

His Thr Ser His Lys His Ala Leu Thr Glu Val Ala Ala Ile Met Phe
        210                 215                 220

Leu Val Gly Lys Gly Phe Asn Pro Thr Ile Ala His Tyr Ile Val Glu
225                 230                 235                 240

Ser Trp Glu Lys Asn Glu Gln Phe
                245

<210> SEQ ID NO 146
<211> LENGTH: 647
<212> TYPE: PRT
<213> ORGANISM: Bacillus anthracis

<400> SEQUENCE: 146

Val Val Lys Val Val Glu Gly Asn Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45

Ala Thr Gly Asn Thr Gly Pro Thr Gly Glu Thr Gly Ala Thr Gly Ser
    50                  55                  60

Ala Gly Ile Thr Gly Ser Thr Gly Pro Thr Gly Asn Thr Gly Gly Thr
65                  70                  75                  80

Gly Ser Thr Gly Pro Thr Gly Asn Thr Gly Ala Thr Gly Ser Thr Gly
                85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
            115                 120                 125

Gly Ser Thr Gly Val Thr Gly Ser Thr Gly Ala Thr Gly Ser Thr Gly
        130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175

Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
        195                 200                 205

Thr Gly Val Thr Gly Ser Thr Gly Pro Thr Gly Ser Thr Gly Val Thr
    210                 215                 220

Gly Ser Thr Gly Pro Thr Gly Ser Thr Gly Val Thr Gly Ser Thr Gly
225                 230                 235                 240
```

```
Val Thr Gly Asn Met Gly Pro Thr Gly Ser Thr Gly Val Thr Gly Asn
                245                 250                 255
Thr Gly Ser Thr Gly Thr Thr Gly Ala Thr Gly Glu Thr Gly Pro Met
            260                 265                 270
Gly Ser Thr Gly Ala Thr Gly Thr Thr Gly Pro Thr Gly Glu Thr Gly
            275                 280                 285
Glu Thr Gly Glu Thr Gly Gly Thr Gly Ser Thr Gly Pro Thr Gly Asn
        290                 295                 300
Thr Gly Ala Thr Gly Ser Thr Gly Val Thr Gly Ser Thr Gly Val Thr
305                 310                 315                 320
Gly Ser Thr Gly Val Thr Gly Glu Thr Gly Pro Thr Gly Ser Thr Gly
                325                 330                 335
Ala Thr Gly Asn Thr Gly Pro Thr Gly Glu Thr Gly Gly Thr Gly Ser
            340                 345                 350
Thr Gly Ala Thr Gly Ser Thr Gly Val Thr Gly Asn Thr Gly Pro Thr
            355                 360                 365
Gly Ser Thr Gly Val Thr Gly Asn Thr Gly Ala Thr Gly Glu Thr Gly
        370                 375                 380
Pro Thr Gly Asn Thr Gly Ala Thr Gly Asn Thr Gly Pro Thr Gly Glu
385                 390                 395                 400
Thr Gly Val Thr Gly Ser Thr Gly Pro Thr Gly Glu Thr Gly Val Thr
                405                 410                 415
Gly Ser Thr Gly Pro Thr Gly Asn Thr Gly Ala Thr Gly Glu Thr Gly
            420                 425                 430
Ala Thr Gly Ser Thr Gly Val Thr Gly Asn Thr Gly Ser Thr Gly Glu
            435                 440                 445
Thr Gly Pro Thr Gly Ser Thr Gly Pro Thr Gly Ser Thr Gly Ala Thr
        450                 455                 460
Gly Val Thr Gly Asn Thr Gly Pro Thr Gly Ser Thr Gly Ala Thr Gly
465                 470                 475                 480
Ala Thr Gly Ser Thr Gly Pro Thr Gly Ser Thr Gly Thr Thr Gly Asn
                485                 490                 495
Thr Gly Val Thr Gly Asp Thr Gly Pro Thr Gly Ala Thr Gly Val Ser
            500                 505                 510
Thr Thr Ala Thr Tyr Ala Phe Ala Asn Asn Thr Ser Gly Ser Val Ile
            515                 520                 525
Ser Val Leu Leu Gly Gly Thr Asn Ile Pro Leu Pro Asn Asn Gln Asn
        530                 535                 540
Ile Gly Pro Gly Ile Thr Val Ser Gly Gly Asn Thr Val Phe Thr Val
545                 550                 555                 560
Ala Asn Ala Gly Asn Tyr Tyr Ile Ala Tyr Thr Ile Asn Leu Thr Ala
                565                 570                 575
Gly Leu Leu Val Ser Ser Arg Ile Thr Val Asn Gly Ser Pro Leu Ala
            580                 585                 590
Gly Thr Ile Asn Ser Pro Thr Val Ala Thr Gly Ser Phe Ser Ala Thr
            595                 600                 605
Ile Ile Ala Ser Leu Pro Ala Gly Ala Ala Val Ser Leu Gln Leu Phe
        610                 615                 620
Gly Val Val Ala Leu Ala Thr Leu Ser Thr Ala Thr Pro Gly Ala Thr
625                 630                 635                 640
Leu Thr Ile Ile Arg Leu Ser
                645
```

<210> SEQ ID NO 147
<211> LENGTH: 647
<212> TYPE: PRT
<213> ORGANISM: Bacillus anthracis

<400> SEQUENCE: 147

Val Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45

Ala Thr Gly Asn Thr Gly Pro Thr Gly Glu Thr Gly Ala Thr Gly Ser
    50                  55                  60

Ala Gly Ile Thr Gly Ser Thr Gly Pro Thr Gly Asn Thr Gly Gly Thr
65                  70                  75                  80

Gly Ser Thr Gly Pro Thr Gly Asn Thr Gly Ala Thr Gly Ser Thr Gly
                85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
        115                 120                 125

Gly Ser Thr Gly Val Thr Gly Ser Thr Gly Ala Thr Gly Ser Thr Gly
    130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175

Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
        195                 200                 205

Thr Gly Val Thr Gly Ser Thr Gly Pro Thr Gly Ser Thr Gly Val Thr
    210                 215                 220

Gly Ser Thr Gly Pro Thr Gly Ser Thr Gly Val Thr Gly Ser Thr Gly
225                 230                 235                 240

Val Thr Gly Asn Met Gly Pro Thr Gly Ser Thr Gly Val Thr Gly Asn
                245                 250                 255

Thr Gly Ser Thr Gly Thr Thr Gly Ala Thr Gly Glu Thr Gly Pro Met
            260                 265                 270

Gly Ser Thr Gly Ala Thr Gly Thr Thr Gly Pro Thr Gly Glu Thr Gly
        275                 280                 285

Glu Thr Gly Glu Thr Gly Thr Thr Gly Ser Thr Gly Pro Thr Gly Asn
    290                 295                 300

Thr Gly Ala Thr Gly Ser Thr Gly Val Thr Gly Ser Thr Gly Val Thr
305                 310                 315                 320

Gly Ser Thr Gly Val Thr Gly Glu Thr Gly Pro Thr Gly Ser Thr Gly
                325                 330                 335

Ala Thr Gly Asn Thr Gly Pro Thr Gly Glu Thr Gly Gly Thr Gly Ser
            340                 345                 350

Thr Gly Ala Thr Gly Ser Thr Gly Val Thr Gly Asn Thr Gly Pro Thr
        355                 360                 365

Gly Ser Thr Gly Val Thr Gly Asn Thr Gly Ala Thr Gly Glu Thr Gly
    370                 375                 380

-continued

```
Pro Thr Gly Asn Thr Gly Ala Thr Gly Asn Thr Gly Pro Thr Gly Glu
385                 390                 395                 400

Thr Gly Val Thr Gly Ser Thr Gly Pro Thr Gly Glu Thr Gly Val Thr
            405                 410                 415

Gly Ser Thr Gly Pro Thr Gly Asn Thr Gly Ala Thr Gly Glu Thr Gly
            420                 425                 430

Ala Thr Gly Ser Thr Gly Val Thr Gly Asn Thr Gly Ser Thr Gly Glu
            435                 440                 445

Thr Gly Pro Thr Gly Ser Thr Gly Pro Thr Gly Ser Thr Gly Ala Thr
            450                 455                 460

Gly Val Thr Gly Asn Thr Gly Pro Thr Gly Ser Thr Gly Ala Thr Gly
465                 470                 475                 480

Ala Thr Gly Ser Thr Gly Pro Thr Gly Ser Thr Gly Thr Thr Gly Asn
            485                 490                 495

Thr Gly Val Thr Gly Asp Thr Gly Pro Thr Gly Ala Thr Gly Val Ser
            500                 505                 510

Thr Thr Ala Thr Tyr Ala Phe Ala Asn Asn Thr Ser Gly Ser Val Ile
            515                 520                 525

Ser Val Leu Leu Gly Gly Thr Asn Ile Pro Leu Pro Asn Asn Gln Asn
530                 535                 540

Ile Gly Pro Gly Ile Thr Val Ser Gly Gly Asn Thr Val Phe Thr Val
545                 550                 555                 560

Ala Asn Ala Gly Asn Tyr Tyr Ile Ala Tyr Thr Ile Asn Leu Thr Ala
            565                 570                 575

Gly Leu Leu Val Ser Ser Arg Ile Thr Val Asn Gly Ser Pro Leu Ala
            580                 585                 590

Gly Thr Ile Asn Ser Pro Thr Val Ala Thr Gly Ser Phe Ser Ala Thr
            595                 600                 605

Ile Ile Ala Ser Leu Pro Ala Gly Ala Ala Val Ser Leu Gln Leu Phe
610                 615                 620

Gly Val Val Ala Leu Ala Thr Leu Ser Thr Ala Thr Pro Gly Ala Thr
625                 630                 635                 640

Leu Thr Ile Ile Arg Leu Ser
            645

<210> SEQ ID NO 148
<211> LENGTH: 209
<212> TYPE: PRT
<213> ORGANISM: Bacillus anthracis

<400> SEQUENCE: 148

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly Pro Thr Gly Ile Thr Gly Pro Thr Gly Ala Thr Gly Phe Thr Gly
            35                  40                  45

Ile Gly Ile Thr Gly Pro Thr Gly Val Thr Gly Pro Thr Gly Ile Gly
50                  55                  60

Ile Thr Gly Pro Thr Gly Ala Thr Gly Leu Gly Ile Leu Pro Val Phe
65                  70                  75                  80

Gly Thr Ile Thr Thr Asp Val Gly Ile Gly Phe Ser Val Ile Val Asn
            85                  90                  95

Thr Asn Ile Asn Phe Thr Leu Pro Gly Pro Val Ser Gly Thr Thr Leu
```

```
            100                 105                 110

Asn Pro Val Asp Asn Ser Ile Ile Ile Asn Thr Thr Gly Val Tyr Ser
        115                 120                 125

Val Ser Phe Ser Ile Val Phe Val Ile Gln Ala Ile Ser Ser Ser Ile
    130                 135                 140

Leu Asn Leu Thr Ile Asn Asp Ser Ile Gln Phe Ala Ile Glu Ser Arg
145                 150                 155                 160

Ile Gly Gly Gly Pro Gly Val Arg Ala Thr Ser Ala Arg Thr Asp Leu
                165                 170                 175

Leu Ser Leu Asn Gln Gly Asp Val Leu Arg Val Arg Ile Arg Glu Ala
            180                 185                 190

Thr Gly Asp Ile Ile Tyr Ser Asn Ala Ser Leu Val Val Ser Lys Val
        195                 200                 205

Asp

<210> SEQ ID NO 149
<211> LENGTH: 180
<212> TYPE: PRT
<213> ORGANISM: Bacillus cereus

<400> SEQUENCE: 149

Met Ser Glu Phe Arg Glu Ile Ile Thr Lys Ala Val Val Gly Lys Gly
1               5                   10                  15

Arg Lys Tyr Thr Lys Ser Thr His Thr Cys Glu Ser Asn Asn Glu Pro
            20                  25                  30

Thr Ser Ile Leu Gly Cys Trp Val Ile Asn His Ser Tyr Glu Ala Arg
        35                  40                  45

Lys Asn Gly Lys His Val Glu Ile Glu Gly Phe Tyr Asp Val Asn Thr
    50                  55                  60

Trp Tyr Ser Phe Asp Gly Asn Thr Lys Thr Glu Val Val Thr Glu Arg
65                  70                  75                  80

Val Asn Tyr Thr Asp Glu Val Ser Ile Gly Tyr Arg Asp Lys Asn Phe
                85                  90                  95

Ser Gly Asp Asp Leu Glu Ile Ile Ala Arg Val Ile Gln Pro Pro Asn
            100                 105                 110

Cys Leu Glu Ala Leu Val Ser Pro Asn Gly Asn Lys Ile Val Val Thr
        115                 120                 125

Val Glu Arg Glu Phe Val Thr Glu Val Val Gly Glu Thr Lys Ile Cys
    130                 135                 140

Val Ser Val Asn Pro Glu Gly Cys Val Glu Ser Asp Glu Asp Phe Gln
145                 150                 155                 160

Ile Asp Asp Asp Glu Phe Glu Glu Leu Asp Pro Asn Phe Ile Val Asp
                165                 170                 175

Ala Glu Glu Glu
            180

<210> SEQ ID NO 150
<211> LENGTH: 643
<212> TYPE: PRT
<213> ORGANISM: Bacillus cereus

<400> SEQUENCE: 150

Met Lys Ile His Ile Val Gln Lys Gly Asp Thr Leu Trp Lys Ile Ala
1               5                   10                  15

Lys Lys Tyr Gly Val Asp Phe Asp Thr Leu Lys Lys Thr Asn Thr Gln
            20                  25                  30
```

```
Leu Ser Asn Pro Asp Leu Ile Met Pro Gly Met Lys Ile Lys Val Pro
    35                  40                  45

Ser Lys Ser Val His Met Lys Gln Gln Ala Gly Ala Gly Ser Ala Pro
50                  55                  60

Pro Lys Gln Tyr Val Lys Glu Val Gln Lys Glu Phe Ala Ala Thr
65                  70                  75                  80

Pro Thr Pro Leu Gly Ile Glu Asp Glu Glu Val Thr Tyr Gln Ser
                85                  90                  95

Ala Pro Ile Thr Gln Gln Pro Ala Met Gln Gln Thr Gln Lys Glu Val
            100                 105                 110

Gln Ile Lys Pro Gln Lys Glu Met Gln Val Lys Pro Gln Lys Glu Val
            115                 120                 125

Gln Val Lys Pro Gln Lys Glu Met Gln Val Lys Pro Gln Lys Glu Val
            130                 135                 140

Gln Lys Glu Gln Pro Ile Gln Lys Glu Lys Pro Val Glu Lys Pro Ser
145                 150                 155                 160

Val Ile Gln Lys Pro Pro Val Ile Glu Lys Gln Lys Pro Ala Glu Lys
                165                 170                 175

Glu Asn Thr Lys Phe Ser Val Asn Val Leu Pro Gln Pro Pro Gln Pro
            180                 185                 190

Pro Ile Lys Pro Lys Lys Glu Tyr Lys Ile Ser Asp Val Ile Lys Lys
            195                 200                 205

Gly Ser Glu Leu Ile Ala Pro Gln Ile Ser Lys Met Lys Pro Asn Asn
    210                 215                 220

Ile Ile Ser Pro Gln Thr Lys Lys Asn Asn Ile Ile Ser Pro Gln Val
225                 230                 235                 240

Lys Lys Glu Asn Val Gly Asn Ile Val Ser Pro Gln Val Lys Lys Glu
                245                 250                 255

Asn Val Gly Asn Ile Val Ser Pro Gln Val Lys Lys Glu Asn Val Gly
            260                 265                 270

Asn Ile Val Ser Pro Gln Val Lys Lys Glu Asn Val Gly Asn Ile Val
            275                 280                 285

Ser Pro Gln Val Lys Lys Glu Asn Val Gly Asn Ile Val Ser Pro Gln
    290                 295                 300

Val Lys Lys Glu Asn Val Gly Asn Ile Val Ser Pro Gln Val Lys Lys
305                 310                 315                 320

Glu Asn Val Gly Asn Ile Val Ser Pro Asn Val Ser Lys Glu Asn Val
                325                 330                 335

Val Ile Pro Gln Val Ile Pro Asn Ile Gln Met Pro Asn Ile Met
            340                 345                 350

Pro Ile Met Asp Asn Asn Gln Pro Pro Asn Ile Met Pro Ile Met Asp
            355                 360                 365

Asn Asn Gln Pro Pro Asn Ile Met Pro Ile Met Asp Asn Asn Gln Met
    370                 375                 380

Pro Asn Met Met Pro Ile Met Asp Asn Asn Gln Met Pro Asn Met Met
385                 390                 395                 400

Pro Ile Met Asp Asn Asn Gln Met Pro Asn Met Met Pro Ile Met Asp
                405                 410                 415

Asn Asn Gln Met Pro Asn Met Met Pro Ile Met Asp Asn Asn Gln Met
            420                 425                 430

Pro Asn Met Met Pro Ile Met Asp Asn Asn Gln Met Pro Asn Met Met
            435                 440                 445
```

Pro Ile Met Asp Asn Asn Gln Met Pro Asn Met Met Pro Ile Met Asp
    450                 455                 460

Asn Asn Gln Met Pro Asn Ile Met Pro Ile Met Asp Asn Asn Gln Met
465                 470                 475                 480

Pro Asn Met Met Pro Ile Met Asp Asn Asn Gln Met Pro Asn Ile Met
                485                 490                 495

Pro Ile Met Asp Asn Asn Gln Met Pro Asn Met Met Pro Ile Met Asp
            500                 505                 510

Asn Asn Gln Pro Pro Asn Met Met Pro Tyr Gln Met Pro Tyr Gln Gln
        515                 520                 525

Pro Met Met Pro Pro Asn Pro Tyr Tyr Gln Gln Pro Asn Pro Tyr Gln
530                 535                 540

Met Pro Tyr Gln Gln Gly Ala Pro Phe Gly Pro Gln His Thr Ser Met
545                 550                 555                 560

Pro Asn Gln Asn Met Met Pro Met Asp Asn Asn Met Pro Pro Leu Val
                565                 570                 575

Gln Gly Glu Glu Asp Cys Gly Cys Gly Gly Glu Ser Arg Leu Tyr Ser
                580                 585                 590

Pro Gln Pro Gly Gly Pro Gln Tyr Ala Asn Pro Leu Tyr Tyr Gln Pro
            595                 600                 605

Thr Gln Ser Ala Tyr Ala Pro Gln Pro Gly Thr Met Tyr Tyr Gln Pro
        610                 615                 620

Asp Pro Pro Asn Val Phe Gly Glu Pro Val Ser Glu Glu Asp Glu
625                 630                 635                 640

Glu Glu Val

<210> SEQ ID NO 151
<211> LENGTH: 646
<212> TYPE: PRT
<213> ORGANISM: Bacillus cereus

<400> SEQUENCE: 151

Met Lys Gln Ala Val Trp Phe Pro Thr Glu Glu Tyr Lys Glu Lys Thr
1               5                   10                  15

Arg Leu Tyr Gly Trp Met Lys Ser Leu Gly Tyr Glu Asp Tyr Glu Thr
            20                  25                  30

Phe Tyr Asn Lys Ser Ile Glu Glu Thr Ala Trp Phe Trp Gly Glu Ala
        35                  40                  45

Glu Lys Val Val Gly Tyr Gln Trp Met Lys Pro Tyr Thr Glu Val Leu
    50                  55                  60

Asp Leu Gln Asn Gly Thr Pro Phe Ala Gln Trp Tyr Asn Gly Gly Thr
65                  70                  75                  80

Cys Asn Val Val Glu Ser Val Leu Ser Arg Trp Leu Ala Asp Asp Glu
                85                  90                  95

Thr Arg Thr Gln Pro Ala Leu Gln Tyr Glu Gly Glu Asn Gly Thr Ser
            100                 105                 110

Lys Ser Phe Thr Tyr Glu Glu Leu Asp Ser Trp Val Ser Arg Ala Ala
        115                 120                 125

Asn Gly Leu Lys His Ala Gly Ile Glu Lys Gly Asp Arg Val Thr Ile
    130                 135                 140

Tyr Met Pro Met Ile Pro Glu Thr Val Val Ala Met Leu Ala Val Met
145                 150                 155                 160

Lys Ile Gly Ala Ile Ile Ser Pro Ile Phe Ser Gly Phe Ala Ser Asp
                165                 170                 175

```
Ala Val Met Thr Arg Val Gln Ala Ala Gly Ser Lys Met Ile Ile Thr
            180                 185                 190
Ala Asp Gly Phe Ser Arg Arg Gly Lys Ile Val Ser Leu Lys Asp Glu
        195                 200                 205
Val Asp Lys Ala Cys Glu His Cys Pro Thr Val Glu Lys Val Val Ile
        210                 215                 220
Val Arg His Ala Gly Asn Asp Phe Thr Pro His Asn Tyr Asp Phe Ser
225                 230                 235                 240
Trp Ser Thr Leu Glu Lys Glu Lys Pro Phe Val His Ala Glu Glu Met
                245                 250                 255
His Ser Asp Asp Pro Leu Met Leu Ile Tyr Thr Ser Gly Thr Thr Gly
            260                 265                 270
Lys Pro Lys Gly Thr Val His Thr His Ala Gly Phe Pro Leu Lys Ala
        275                 280                 285
Ala Phe Asp Ala Gly Phe Gly Met Asn Ile Lys Gln Gly Asp Arg Val
        290                 295                 300
Leu Trp Val Thr Asp Met Gly Trp Met Met Gly Pro Phe Leu Leu Phe
305                 310                 315                 320
Gly Ser Leu Ile Asn Gly Ala Thr Met Val Met Tyr Glu Gly Val Pro
                325                 330                 335
Asp Phe Pro Lys Ala Asp Arg Leu Trp Glu Thr Val Asp Lys Tyr Glu
            340                 345                 350
Ile Thr His Leu Gly Ile Ser Pro Thr Leu Ile Arg Ala Leu Met Ala
        355                 360                 365
Lys Gly Asp Glu Tyr Val Asn Lys His Ser Leu Lys Ser Leu Glu Val
        370                 375                 380
Phe Ala Ser Thr Gly Glu Pro Trp Asn Pro Asp Pro Trp Met Trp Leu
385                 390                 395                 400
Phe Glu Thr Val Gly Lys Ser Asn Val Pro Ile Cys Asn Tyr Ser Gly
                405                 410                 415
Gly Thr Glu Ile Ser Gly Gly Ile Phe Gly Asn Val Leu Ile Lys Pro
            420                 425                 430
Ile Ala Pro Ile Ser Phe Asn Ala Ser Leu Pro Gly Met Ala Ala Val
        435                 440                 445
Val Leu Asp Asp Gln Gly Asn Pro Ile Arg Asp Glu Val Gly Glu Leu
        450                 455                 460
Cys Leu Glu Lys Pro Trp Val Gly Met Thr Lys Ser Phe Trp Glu Asp
465                 470                 475                 480
Asp Glu Arg Tyr Val Asn Thr Tyr Trp Ser Arg Phe Glu Asn Lys Trp
                485                 490                 495
Val His Gly Asp Trp Val Val Tyr Asp Gly Glu Gln Tyr Ile Ile Thr
            500                 505                 510
Gly Arg Ser Asp Asp Thr Leu Asn Ile Ala Gly Lys Arg Ile Gly Pro
        515                 520                 525
Ala Glu Tyr Glu Ser Ile Leu Val Lys His Asn Asp Val Ile Glu Ala
        530                 535                 540
Ala Ala Ile Gly Val Pro Asp Asp Val Lys Gly Glu Val Cys His Cys
545                 550                 555                 560
Phe Val Val Leu Arg Asp Asn Val Thr Phe Thr Gly Glu Leu Lys Lys
                565                 570                 575
Glu Leu Met Ser Leu Val Asn Ser His Ile Gly Lys Ala Leu Cys Pro
            580                 585                 590
Lys Asp Ile His Val Val Glu Asp Leu Pro Lys Thr Arg Asn Ser Lys
```

```
        595                 600                 605

Val Met Arg Arg Val Ile Lys Ala Ala Tyr Leu Gly Lys Glu Leu Gly
    610                 615                 620

Asp Leu Ser Ser Leu Val Asn Pro Glu Val Val Pro Phe Ile Gln Gly
625                 630                 635                 640

Leu Gln Ser Ser Lys Leu
                645

<210> SEQ ID NO 152
<211> LENGTH: 220
<212> TYPE: PRT
<213> ORGANISM: Bacillus cereus

<400> SEQUENCE: 152

Met Lys Lys Glu Lys Ala Val Val Val Phe Ser Gly Gly Gln Asp Ser
1               5                   10                  15

Thr Thr Cys Leu Phe Trp Ala Ile Glu Gln Phe Ala Glu Val Glu Ala
            20                  25                  30

Val Thr Phe Asn Tyr Asn Gln Arg His Lys Leu Glu Ile Asp Cys Ala
        35                  40                  45

Val Glu Ile Ala Lys Glu Leu Gly Ile Lys His Thr Val Leu Asp Met
    50                  55                  60

Ser Leu Leu Asn Gln Leu Ala Pro Asn Ala Leu Thr Arg Thr Asp Met
65                  70                  75                  80

Glu Ile Thr His Glu Glu Gly Glu Leu Pro Ser Thr Phe Val Asp Gly
                85                  90                  95

Arg Asn Leu Leu Phe Leu Ser Phe Ala Ala Val Leu Ala Lys Gln Val
            100                 105                 110

Gly Ala Arg His Ile Val Thr Gly Val Cys Glu Thr Asp Phe Ser Gly
        115                 120                 125

Tyr Pro Asp Cys Arg Asp Val Phe Val Lys Ser Leu Asn Val Thr Leu
    130                 135                 140

Asn Leu Ser Met Asp Tyr Pro Phe Val Ile His Thr Pro Leu Met Trp
145                 150                 155                 160

Ile Asp Lys Ala Glu Thr Trp Lys Leu Ser Asp Glu Leu Gly Ala Phe
                165                 170                 175

Glu Phe Val Arg Glu Lys Thr Leu Thr Cys Tyr Asn Gly Ile Ile Gly
            180                 185                 190

Asp Gly Cys Gly Glu Cys Pro Ala Cys Gln Leu Arg Lys Ala Gly Leu
        195                 200                 205

Asp Thr Tyr Leu Gln Glu Arg Glu Gly Ala Ser Asn
    210                 215                 220

<210> SEQ ID NO 153
<211> LENGTH: 287
<212> TYPE: PRT
<213> ORGANISM: Bacillus cereus

<400> SEQUENCE: 153

Met Ala Leu His Val Gly Glu Leu Val Glu Arg Tyr Ser His Asn Arg
1               5                   10                  15

Asp Ile Leu Phe Arg Ile Ile Glu Ile Lys Gly Glu Ile Ala Ile Leu
            20                  25                  30

Phe Gly Glu Glu Ile Arg Leu Val Ala Asp Ala Pro Leu Glu Asp Leu
        35                  40                  45

Ile Ser Ile Asp Gln Arg Glu His Lys Lys Arg Ala Lys Arg Glu Lys
```

```
    50                  55                  60

Glu Thr Met Glu Arg Thr Tyr Arg Leu Phe Gln Gln Asp Tyr Val Leu
65                  70                  75                  80

Met Lys Gln Arg His Glu His Thr Ser Thr Gly Gly Tyr Thr Ser Glu
                85                  90                  95

Val Asn Tyr Phe Gln Met Pro Gly Arg Val Leu His Ile Asp Gly Asp
            100                 105                 110

Pro Leu Tyr Leu Arg Lys Cys Leu Asp Leu Tyr Asn Lys Ile Gly Val
        115                 120                 125

Pro Val Gln Gly Ile His Cys Lys Glu Thr Glu Met His Glu Lys Val
    130                 135                 140

Val Asp Leu Ile Asp His Phe Arg Pro Asp Ile Leu Val Ile Thr Gly
145                 150                 155                 160

His Asp Ala Tyr Thr Lys Ser Lys Gly Val Lys Gly Asp Leu Ala Ala
                165                 170                 175

Tyr Arg His Ser Arg His Phe Val Gln Ala Val Arg Glu Val Arg Lys
            180                 185                 190

Lys Tyr Pro Ser Leu Asp Gln Leu Val Ile Phe Ala Gly Ala Cys Gln
        195                 200                 205

Ser His Phe Glu Ala Leu Ile Arg Ala Gly Ala Asn Phe Ala Ser Ser
    210                 215                 220

Pro Ser Arg Ile Asn Ile His Ala Leu Asp Pro Val Tyr Val Val Gly
225                 230                 235                 240

Lys Ile Ser Phe Thr Ser Phe Met Glu Arg Val Asn Val Trp Asp Val
                245                 250                 255

Val Arg Asn Thr Ile Thr Gly Glu Lys Gly Leu Gly Gly Ile Glu Thr
            260                 265                 270

Arg Gly Ile Leu Arg Thr Gly Leu Pro Phe Gln His Tyr Glu Glu
        275                 280                 285

<210> SEQ ID NO 154
<211> LENGTH: 276
<212> TYPE: PRT
<213> ORGANISM: Bacillus cereus

<400> SEQUENCE: 154

Met Ile Val Ile Gly Arg Ser Ile Val His Pro Tyr Ile Thr Asn Glu
1               5                   10                  15

Tyr Glu Pro Phe Ala Ala Glu Lys Gln Gln Ile Leu Ser Ile Met Ala
            20                  25                  30

Gly Asn Gln Glu Ile Tyr Ser Phe Arg Thr Ser Asp Glu Leu Ser Phe
        35                  40                  45

Asp Leu Asn Leu Arg Val Asn Ile Ile Thr Ser Ala Leu Glu Leu Phe
    50                  55                  60

Gln Ser Gly Phe Gln Phe Arg Thr Phe Gln Gln Ser Phe Cys Asn Pro
65                  70                  75                  80

Gln Tyr Trp Lys Arg Thr Ser Leu Gly Gly Phe Glu Leu Leu Pro Asn
                85                  90                  95

Ile Pro Pro Ser Ile Ala Ile Gln Asp Ile Phe Lys Asn Gly Lys Leu
            100                 105                 110

Tyr Gly Thr Glu Cys Ala Thr Ala Met Ile Ile Ile Phe Tyr Lys Ala
        115                 120                 125

Leu Leu Ser Leu Tyr Glu Lys Glu Thr Phe Asn Arg Leu Phe Ala Asn
    130                 135                 140
```

```
Leu Leu Leu Tyr Thr Trp Asp Tyr Asp Gln Asp Leu Lys Leu Ile Thr
145                 150                 155                 160

Lys Thr Gly Gly Asp Leu Val Pro Gly Asp Leu Val Tyr Phe Lys Asn
            165                 170                 175

Pro Gln Val Asn Pro Ala Thr Ile Glu Trp Gln Gly Glu Asn Thr Ile
            180                 185                 190

Tyr Leu Gly Asn Phe Phe Tyr Gly His Gly Val Gly Val Lys Thr
            195                 200                 205

Lys Glu Glu Ile Ile Tyr Ala Leu Asn Glu Arg Arg Val Pro Tyr Ala
    210                 215                 220

Phe Ile Ser Ala Phe Leu Thr Asp Thr Ile Thr Arg Ile Asp Ser Arg
225                 230                 235                 240

Leu Met Ser Tyr His Ala Ser Pro Ser Thr Pro Gln Thr Ser Ile Gly
            245                 250                 255

Phe Ile Pro Ile Arg Asp Asp Ala Ile Val Ala Thr Val Gly Asn Thr
            260                 265                 270

Thr Thr Val Tyr
        275

<210> SEQ ID NO 155
<211> LENGTH: 203
<212> TYPE: PRT
<213> ORGANISM: Bacillus cereus

<400> SEQUENCE: 155

Met Ala Lys His Glu Leu Pro Asn Leu Pro Tyr Ala Tyr Asp Ala Leu
1               5                   10                  15

Glu Pro His Phe Asp Lys Glu Thr Met Asn Ile His His Thr Lys His
            20                  25                  30

His Asn Thr Tyr Ile Thr Asn Leu Asn Ala Ala Leu Glu Gly His Ala
        35                  40                  45

Glu Leu Ala Asp Lys Ser Val Glu Glu Leu Val Ala Asn Leu Asn Glu
    50                  55                  60

Val Pro Glu Ala Ile Arg Thr Ala Val Arg Asn Asn Gly Gly His
65                  70                  75                  80

Ala Asn His Thr Phe Phe Trp Thr Ile Leu Ser Pro Asn Gly Gly Gly
                85                  90                  95

Gln Pro Val Gly Glu Leu Ala Thr Ala Ile Glu Ala Lys Phe Gly Ser
            100                 105                 110

Phe Asp Ala Phe Lys Glu Glu Phe Ala Lys Ala Gly Ala Thr Arg Phe
        115                 120                 125

Gly Ser Gly Trp Ala Trp Leu Val Asn Asn Gly Glu Leu Glu Val
    130                 135                 140

Thr Ser Thr Pro Asn Gln Asp Ser Pro Leu Thr Glu Gly Lys Thr Pro
145                 150                 155                 160

Val Val Gly Leu Asp Val Trp Glu His Ala Tyr Tyr Leu Asn Tyr Gln
            165                 170                 175

Asn Arg Arg Pro Asp Tyr Ile Gly Ala Phe Trp Asn Val Val Asp Trp
            180                 185                 190

Asn Ala Ala Glu Lys Arg Tyr Gln Glu Ala Lys
        195                 200

<210> SEQ ID NO 156
<211> LENGTH: 179
<212> TYPE: PRT
<213> ORGANISM: Bacillus thuringiensis
```

<400> SEQUENCE: 156

```
Met Lys Lys Arg Leu Phe Phe Ser Cys Cys Leu Leu Phe Leu Met Ala
1               5                   10                  15

Gly Cys Asp Gln Gly Lys Pro Lys Glu Ile Asp Val Lys Leu His Asn
            20                  25                  30

Ala Ser Gly Asp Glu Val Gly Thr Ala Lys Val Thr Gln Gln Thr Ser
        35                  40                  45

Gly Val Lys Ile Thr Ile Lys Gly Glu Gly Phe Ala Pro Gly Pro His
    50                  55                  60

Gly Leu His Val His Glu Ile Gly Glu Cys Lys Ala Pro Arg Phe Glu
65                  70                  75                  80

Ser Ala Gly Asn His Phe Asn Pro Asp Asp Lys Lys His Gly Leu Leu
                85                  90                  95

Asn Pro Lys Gly Ala Glu Asn Gly Asp Leu Pro Asn Val Ile Ala Asp
            100                 105                 110

Gly Ser Gly Lys Ile Lys Ala Glu Ile Asp Ala Pro His Ile Thr Leu
        115                 120                 125

Glu Glu Gly Lys Thr Thr Ile His Arg Lys Asp Gly Ala Ser Ile Ile
    130                 135                 140

Ile Thr Glu Asn Ala Asp Asp Gly Met Thr Gln Pro Thr Gly Lys Ser
145                 150                 155                 160

Gly Asp Arg Ile Ala Cys Gly Val Ile Val Lys Lys Ala Ser Asp Met
                165                 170                 175

Lys Lys Lys
```

<210> SEQ ID NO 157
<211> LENGTH: 299
<212> TYPE: DNA
<213> ORGANISM: Bacillus cereus

<400> SEQUENCE: 157

```
tttcttaatc ctttacccctt tacttttgta aaagttgata cacttccatc cggctctgta    60
atttctaatt catcaataaa tggtcttcgc aaaaagcctg taattttatc ataaacaatt   120
aaacgagtga gcctaaaagc agctaacgcg aaaataaaaa ataaaagcca gcttgtaaac   180
agcataattc caccttccct tatcctcttt cgcctattta aaaaaggtc ttgagattgt    240
gaccaaatct cctcaactcc aatatcttat taatgtaaat acaacaaga agataagga     299
```

<210> SEQ ID NO 158
<211> LENGTH: 58
<212> TYPE: DNA
<213> ORGANISM: Bacillus cereus

<400> SEQUENCE: 158

```
accaaatctc ctcaactcca atatcttatt aatgtaaata caaacaagaa gataagga      58
```

<210> SEQ ID NO 159
<211> LENGTH: 300
<212> TYPE: DNA
<213> ORGANISM: Bacillus anthracis

<400> SEQUENCE: 159

```
accacctacc gacgatccaa tctgtacatt cctagctgta ccaaatgcaa gattaatatc    60
gactaacact tgtcttactg ttgatttaag ttgcttctgt gcgattcaat gcttgcgtga   120
tgttacgatt taaaactaaa taatgagcta agcatggatt gggtggcaga attatctgcc   180
```

```
acccaatcca tgcttaacga gtattattat gtaaatttct taaaattggg aacttgtcta    240
gaacatagaa cctgtccttt tcattaactg aaagtagaaa cagataaagg agtgaaaaac    300
```

<210> SEQ ID NO 160
<211> LENGTH: 58
<212> TYPE: DNA
<213> ORGANISM: Bacillus anthracis

<400> SEQUENCE: 160

```
acatagaacc tgtccttttc attaactgaa agtagaaaca gataaaggag tgaaaaac     58
```

<210> SEQ ID NO 161
<211> LENGTH: 300
<212> TYPE: DNA
<213> ORGANISM: Bacillus anthracis

<400> SEQUENCE: 161

```
tagaagaaga acgccgacta ctttatgtcg caattacacg ggcgaaagaa gaactttaca    60
tttcctctcc gcaattttt agaggaaaaa aattagatat atctcgtttt ttatacactg    120
tgcgaaaaga tttacctgaa aagacatcca ctaaataagg atgtctttt ttatattgta    180 ttatgtacat ccctactata taaattccct gcttttatcg taagaattaa cgtaatatca    240
accatatccc gttcatattg tagtagtgta tgtcagaact cacgagaagg agtgaacata    300
```

<210> SEQ ID NO 162
<211> LENGTH: 63
<212> TYPE: DNA
<213> ORGANISM: Bacillus anthracis

<400> SEQUENCE: 162

```
tcaaccatat cccgttcata ttgtagtagt gtatgtcaga actcacgaga aggagtgaac    60
ata                                                                 63
```

<210> SEQ ID NO 163
<211> LENGTH: 300
<212> TYPE: DNA
<213> ORGANISM: Bacillus cereus

<400> SEQUENCE: 163

```
taactcaatc ttaagagaaa ttgaggagcg cgcaccactt cgtcgtacaa caacgcaaga    60
agaagttggg gatacagcag tattcttatt cagtgattta gcacgcggcg taacaggaga    120
aaacattcac gttgattcag ggtatcatat cttaggataa atataatatt aattttaaag    180
gacaatctct acatgttgag attgtccttt ttatttgttc ttagaaagaa cgattttaa    240 cgaaagttct taccacgtta tgaatataag tataatagta cacgatttat tcagctacgt    300
```

<210> SEQ ID NO 164
<211> LENGTH: 172
<212> TYPE: DNA
<213> ORGANISM: Bacillus cereus

<400> SEQUENCE: 164

```
acgttgattc agggtatcat atcttaggat aaatataata ttaattttaa aggacaatct    60
ctacatgttg agattgtcct ttttatttgt tcttagaaag aacgattttt aacgaaagtt    120
cttaccacgt tatgaatata agtataatag tacacgattt attcagctac gt           172
```

<210> SEQ ID NO 165

<211> LENGTH: 291
<212> TYPE: DNA
<213> ORGANISM: Bacillus cereus

<400> SEQUENCE: 165
cataaaaatc tacttttctt gtcaaagagt atgcttatat gcgtgctctt tttatttggt 60
tttctttcat ttctaaataa cattttcaac tctattcata ctattctttc aactttaggt 120
tacaaactat ttctgtaagc gtagtgtttc ttttgtacta taggcagtta gttttatcca 180
taacagtaca cctctgcact attcactata aattttcata tattatattg tgcttgtcca 240
aaacatgtgg ttattactca cgcgatctaa atgaaagaaa ggagtgaaaa t 291

<210> SEQ ID NO 166
<211> LENGTH: 94
<212> TYPE: DNA
<213> ORGANISM: Bacillus cereus

<400> SEQUENCE: 166
actattcact ataaattttc atatattata ttgtgcttgt ccaaaacatg tggttattac 60
tcacgcgatc taaatgaaag aaaggagtga aaat 94

<210> SEQ ID NO 167
<211> LENGTH: 300
<212> TYPE: DNA
<213> ORGANISM: Bacillus thuringiensis

<400> SEQUENCE: 167
aatacatgat aatgaaatcc gattttgtgt tttatatagt gaattatcaa atattgtgta 60
gatgaaacaa agataaaatc cccattaaac tccctctatg gaaattataa attgttcgat 120
aaaaactttc aatattttca gaaaacattg ttgaattgtg atatattcgt atgctaacta 180
tgaaattttt acaaatatat taaaaacatt acataatatg actaaatatt gaaaaaatat 240
tgaattttta ataaaattta atttgtaata catattattt attaggggag gaaataaggg 300

<210> SEQ ID NO 168
<211> LENGTH: 48
<212> TYPE: DNA
<213> ORGANISM: Bacillus thuringiensis

<400> SEQUENCE: 168
aaaatttaat ttgtaataca tattatttat taggggagga aataaggg 48

<210> SEQ ID NO 169
<211> LENGTH: 300
<212> TYPE: DNA
<213> ORGANISM: Bacillus mycoides

<400> SEQUENCE: 169
aattgtgcat attgtctttt aaattttcta tctaagttat ttaatatata ataaataact 60
cttttttgtg agttttttttg atacgaggta aataatcagt acagggtctg accagaggac 120
tggagggcat gattctataa gggaatattt actattccat gattatagaa ctatgtcttt 180
tttattgtat atagaagggg ggataggtct atattataga acttatatat attgtgcatt 240
ccatattatc aattatctaa attttaagtc ttgttacaat taataaggga ggaaatagta 300

<210> SEQ ID NO 170
<211> LENGTH: 80
<212> TYPE: DNA
<213> ORGANISM: Bacillus mycoides

```
<400> SEQUENCE: 170
acttatatat attgtgcatt ccatattatc aattatctaa attttaagtc ttgttacaat    60
taataaggga ggaaatagta                                                80

<210> SEQ ID NO 171
<211> LENGTH: 141
<212> TYPE: DNA
<213> ORGANISM: Bacillus thuringiensis

<400> SEQUENCE: 171
aatgacgttt tcaagtttga ttatcattca tgtttcctat tttaagagaa acatataact    60
caactacttt tttcaatggc atcttttata gtacttagaa taggaaaaca ctcaactata   120
agaaaagtaa ggaggaaata a                                             141

<210> SEQ ID NO 172
<211> LENGTH: 79
<212> TYPE: DNA
<213> ORGANISM: Bacillus thuringiensis

<400> SEQUENCE: 172 actactttt tcaatggcat cttttatagt acttagaata ggaaaacact caactataag     60
aaaagtaagg aggaaataa                                                 79

<210> SEQ ID NO 173
<211> LENGTH: 300
<212> TYPE: DNA
<213> ORGANISM: Bacillus cereus

<400> SEQUENCE: 173
atatgctaat gcttagtttt tatactcaag ttaaaatgtg cttttggacc taagagataa    60
acgtggaaaa ataaaataaa ctcttaagtt taggtgttta atctaagcag tcaattatta   120
aaaacatata attaatatgt gagtcatgaa cataattaaa taatgttttc aagtttaatt   180
atcgttcatg tttcctattt taagcagaac aaataactca attactttt tcgattggat    240 ctttttaac tcttataata ggaaaacact caactataaa aataagtaag gaggaaataa    300

<210> SEQ ID NO 174
<211> LENGTH: 167
<212> TYPE: DNA
<213> ORGANISM: Bacillus cereus

<400> SEQUENCE: 174
aatatgtgag tcatgaacat aattaaataa tgttttcaag tttaattatc gttcatgttt    60
cctattttaa gcagaacaaa taactcaatt acttttttcg attggatctt ttttaactct   120
tataatagga aaacactcaa ctataaaaat aagtaaggag gaaataa                 167

<210> SEQ ID NO 175
<211> LENGTH: 300
<212> TYPE: DNA
<213> ORGANISM: Bacillus thuringiensis

<400> SEQUENCE: 175
tataaaataa aagggcgtgt atttgctact gatgcagtat tgtgtgcgcc taaaaatgga    60
atttcacaac cagatccaca tgttgttgta gaacaatctt gtaattcatt gatgaatttt   120
acaacgtcaa ctacacaatg agaagagcca tggtgtttat tttcgttaca actcattaat   180
```

```
gtcactcctt atcttcttgt ttgtatttac attaataaga tattggagtt gaggagattt    240
ggtcacaatc tcaagacctt ttttttaaat aggcgaaaga ggataaggga aggtggaatt    300

<210> SEQ ID NO 176
<211> LENGTH: 106
<212> TYPE: DNA
<213> ORGANISM: Bacillus thuringiensis

<400> SEQUENCE: 176
tcttgtttgt atttacatta ataagatatt ggagttgagg agatttggtc acaatctcaa     60
gacctttttt ttaaataggc gaaagaggat aagggaaggt ggaatt                   106

<210> SEQ ID NO 177
<211> LENGTH: 300
<212> TYPE: DNA
<213> ORGANISM: Bacillus thuringiensis

<400> SEQUENCE: 177
atcaactttt acaaaagtaa agggtaaagg attaagaaag tggattggcg aattattaag     60
ctgttattgg tgtacaggtg tatgggttag tgcttttttta ttagttttat ataattggat   120
tccgatcgtt gcagagccgt tacttgcatt attagctatt gcaggagcag cagcaatcat    180
tgaaacgatt acaggatatt ttatgggaga ataatatatt tcataatac gagaaaaagc    240 ggagtttaaa agaatgaggg aacggaaata aagagttgtt catatagtaa atagacagaa    300

<210> SEQ ID NO 178
<211> LENGTH: 39
<212> TYPE: DNA
<213> ORGANISM: Bacillus thuringiensis

<400> SEQUENCE: 178
acggaaataa agagttgttc atatagtaaa tagacagaa                            39

<210> SEQ ID NO 179
<211> LENGTH: 300
<212> TYPE: DNA
<213> ORGANISM: Bacillus anthracis

<400> SEQUENCE: 179
tgaagtatct agagctaatt tacgcaaagg aatctcagga caacactttc gcaacaccta     60
tattttaaat ttaataaaaa aagagactcc ggagtcagaa attataaagc tagctgggtt    120
caaatcaaaa atttcactaa aacgatatta tcaatacgca gaaaatggaa aaaacgcctt    180
atcataaggc gttttttcca ttttttcttc aaacaaacga ttttactatg accatttaac    240
taattttgtc atctactatg atgagtttca ttcacattct cattagaaag gagagattta    300

<210> SEQ ID NO 180
<211> LENGTH: 70
<212> TYPE: DNA
<213> ORGANISM: Bacillus anthracis

<400> SEQUENCE: 180
accatttaac taattttgtc atctactatg atgagtttca ttcacattct cattagaaag     60
gagagattta                                                            70

<210> SEQ ID NO 181
<211> LENGTH: 300
<212> TYPE: DNA
<213> ORGANISM: Bacillus cereus
```

<400> SEQUENCE: 181

```
gactatgttt attcaggata aaatatagca ctacactctc tcctcttatt atgtagcatc    60
tctctaatcc atcatttgtt tcatttagtt aaaattgtaa ataaaatcac atgatttgtc   120
aattataatt gtcatttcga caattaaact tgtcaaaata attctcatca ttttttctca   180
tctttctaat ataggacata ctactatata tacaaaagac aatatgcaaa tgttcataca   240
aaaaatatta ttttcgata tataatatta actgattttc taacatcaag gagggtacat   300
```

<210> SEQ ID NO 182
<211> LENGTH: 84
<212> TYPE: DNA
<213> ORGANISM: Bacillus cereus

<400> SEQUENCE: 182

```
agacaatatg caaatgttca tacaaaaaat attatttttc gatatataat attaactgat    60
tttctaacat caaggagggt acat                                          84
```

<210> SEQ ID NO 183
<211> LENGTH: 300
<212> TYPE: DNA
<213> ORGANISM: Bacillus thuringiensis

<400> SEQUENCE: 183

```
atagtgagta atatggtaat ccatagatta aatagtatag aaaatattta attcttattt    60
ttattaaaaa agcatgaatc ccagatttac tgggttttga ttgtaactaa gaacatataa   120
aagttcactg ttatttatag gagagtctgt ttgttttat atcttatgta tttcaccctg   180
cataaaaaaa tatttctcaa cattttattt gttgaaaaat attgaatatt cgtattataa   240
cgaatattat gttgttatcg gcaaaaaacg ataatttgca gacactgggg aggaaataca   300
```

<210> SEQ ID NO 184
<211> LENGTH: 139
<212> TYPE: DNA
<213> ORGANISM: Bacillus thuringiensis

<400> SEQUENCE: 184

```
tcttatgtat ttcaccctgc ataaaaaaat atttctcaac attttatttg ttgaaaaata    60
ttgaatattc gtattataac gaatattatg ttgttatcgg caaaaaacga taatttgcag   120
acactgggga ggaaataca                                               139
```

<210> SEQ ID NO 185
<211> LENGTH: 300
<212> TYPE: DNA
<213> ORGANISM: Bacillus cereus

<400> SEQUENCE: 185

```
cttcgtcagc aataagtgtg agcggagaat tggttgatct tggctttaca attggagcat    60
tgacgaaaga ctctttaacg tggtcgcata acggagtaga atatatgctc gtgtctaaag   120
gtttagagcc gaaggagcta ttaatggttg ctcgttcagt tacagagaag caagtgaagt   180
aaacttctta gacgtggtga tatatgtgca ccacgtctt tcttagtttg aagggtggat   240
ttcataaaag aagcatataa aagaataagc ttcgcatatc gtgtataagg aagtgtattt   300
```

<210> SEQ ID NO 186
<211> LENGTH: 44
<212> TYPE: DNA

<213> ORGANISM: Bacillus cereus

<400> SEQUENCE: 186

| ataaaagaat aagcttcgca tatcgtgtat aaggaagtgt attt | 44 |

<210> SEQ ID NO 187
<211> LENGTH: 300
<212> TYPE: DNA
<213> ORGANISM: Bacillus thuringiensis

<400> SEQUENCE: 187

| catttcaaat aatgaacgct tcgattgaat cggagctatt ttcaaatcaa tttcagtata | 60 |
| ttgatccagc atttgaatag aagtatcaac agcaacttta agttgatgca atgcagattg | 120 |
| tacaaacatt gtaattctcc tcttctccgt atataatagt ttcttgaggg tattatatca | 180 |
| tgctcaaaat tccgaaaatt ctagtagttt gactagcata ttgaaaagta ttatattgta | 240 |
| aaaggtcata tgaaacgtga aatagaatgg aatgcaatta ttgagttagg agttagacca | 300 |

<210> SEQ ID NO 188
<211> LENGTH: 70
<212> TYPE: DNA
<213> ORGANISM: Bacillus thuringiensis

<400> SEQUENCE: 188

| ttatattgta aaaggtcata tgaaacgtga aatagaatgg aatgcaatta ttgagttagg | 60 |
| agttagacca | 70 |

<210> SEQ ID NO 189
<211> LENGTH: 300
<212> TYPE: DNA
<213> ORGANISM: Bacillus cereus

<400> SEQUENCE: 189

| atcgatggaa cctgtatcaa ccactataat ttcatccaca atttttttcaa ctgagtctaa | 60 |
| acaacgggct attgtcttct cctcatctcg aacaatcata cataaactaa ttgtaattcc | 120 |
| ttgcttgttc aacataatca ccctcttcca aatcaatcat atgttataca tatactaaac | 180 |
| tttccatttt tttaaattgt tcaagtagtt taagatttct tttcaataat tcaaatgtcc | 240 |
| gtgtcatttt ctttcggttt tgcatctact atataatgaa cgctttatgg aggtgaattt | 300 |

<210> SEQ ID NO 190
<211> LENGTH: 150
<212> TYPE: DNA
<213> ORGANISM: Bacillus cereus

<400> SEQUENCE: 190

| aatcaatcat atgttataca tatactaaac tttccatttt tttaaattgt tcaagtagtt | 60 |
| taagatttct tttcaataat tcaaatgtcc gtgtcatttt ctttcggttt tgcatctact | 120 |
| atataatgaa cgctttatgg aggtgaattt | 150 |

<210> SEQ ID NO 191
<211> LENGTH: 300
<212> TYPE: DNA
<213> ORGANISM: Bacillus thuringiensis

<400> SEQUENCE: 191

| gacctgtaag tctgtaggga agaataattt caagagccag tgataataga ttttttgtt | 60 |
| ttttcattct tatcttgaat ataaatcacc tcatctttta attagaacgt aaccaattta | 120 |

```
gtattttgaa atagagctat cattttataa tatgaatact actagttata gaaacggcaa      180
aaagtttaat atatgtaaaa atcatttgga tatgaaaaaa gtagccatag atttttttcga    240 aatgataaat gttttatttt gttaattagg aaacaaaaat gtggaatgag ggggatttaa    300
```

<210> SEQ ID NO 192
<211> LENGTH: 91
<212> TYPE: DNA
<213> ORGANISM: Bacillus thuringiensis

<400> SEQUENCE: 192

```
atatgaaaaa agtagccata gatttttttcg aaatgataaa tgttttatttt tgttaattag    60 gaaacaaaaa tgtggaatga gggggattta a                                    91
```

<210> SEQ ID NO 193
<211> LENGTH: 300
<212> TYPE: DNA
<213> ORGANISM: Bacillus anthracis

<400> SEQUENCE: 193

```
ttttcatctg ctacatcgtg aagtaatgct gccatttcaa ttataaaacg atttcctcct      60
tcttgctcgg ataaagaaat cgccagttta tgtacacgct caatatgata ccaatcatgc    120
ccactggcat cttttttctaa aatatgtttt acaaaagtaa ttgttttttc tatcttttct    180
tgttttgtca ttttatcttc acccagttac ttattgtaac acgcccgcat ttttcatca     240 catattttct tgtccgccca tacactaggt ggtaggcatc atcatgaagg aggaatagat    300
```

<210> SEQ ID NO 194
<211> LENGTH: 61
<212> TYPE: DNA
<213> ORGANISM: Bacillus anthracis

<400> SEQUENCE: 194

```
acatattttc ttgtccgccc atacactagg tggtaggcat catcatgaag gaggaataga    60
t                                                                     61
```

<210> SEQ ID NO 195
<211> LENGTH: 300
<212> TYPE: DNA
<213> ORGANISM: Bacillus anthracis

<400> SEQUENCE: 195

```
ggtgacgaca acatatacaa gaggcactcc tgctggtact gtaacaggaa caaatatggg      60
gcaaagtgta aatacatcgg gtatagcaca agctgtcccg aatacagata atatggattc    120
aacggcggga ctcccttaag aaattagggg agtcttatt tggaaaaaga gcttatgtta     180
cataaaaaca ggagtaattg ttttaaaagt agtattggtg acgttgttag aaaatacaat    240
ttaagtagaa ggtgcgtttt tatatgaaat atattttata gctgtacttt acctttcaag    300
```

<210> SEQ ID NO 196
<211> LENGTH: 213
<212> TYPE: DNA
<213> ORGANISM: Bacillus anthracis

<400> SEQUENCE: 196

```
acaagctgtc ccgaatacag ataatatgga ttcaacggcg ggactcccctt aagaaattag     60 gggagtcttt atttggaaaa agagcttatg ttacataaaa acaggagtaa ttgttttaaa    120
```

```
agtagtattg gtgacgttgt tagaaaatac aatttaagta gaaggtgcgt ttttatatga    180
aatatatttt atagctgtac tttacctttc aag                                 213

<210> SEQ ID NO 197
<211> LENGTH: 300
<212> TYPE: DNA
<213> ORGANISM: Bacillus anthracis

<400> SEQUENCE: 197
atttatttca ttcaattttt cctatttagt acctaccgca ctcacaaaaa gcacctctca     60
ttaatttata ttatagtcat tgaaatctaa tttaatgaaa tcatcatact atatgtttta    120
taagaagtaa aggtaccata cttaattaat acatatctat acacttcaat atcacagcat    180
gcagttgaat tatatccaac tttcatttca aattaaataa gtgcctccgc tattgtgaat    240
gtcatttact ctccctacta catttaataa ttatgacaag caatcatagg aggttactac    300

<210> SEQ ID NO 198
<211> LENGTH: 180
<212> TYPE: DNA
<213> ORGANISM: Bacillus anthracis

<400> SEQUENCE: 198
taagaagtaa aggtaccata cttaattaat acatatctat acacttcaat atcacagcat     60
gcagttgaat tatatccaac tttcatttca aattaaataa gtgcctccgc tattgtgaat    120
gtcatttact ctccctacta catttaataa ttatgacaag caatcatagg aggttactac    180

<210> SEQ ID NO 199
<211> LENGTH: 300
<212> TYPE: DNA
<213> ORGANISM: Bacillus cereus

<400> SEQUENCE: 199
agttgtacaa gaatttaaat cttcacaaac atatgtaaat gacttactac agctagttgc     60
aagtacgatt tctaacaacg taacagatga atattaatt tcaactaatg gcgatgtatt    120
gaagggtgaa acgggcgcag cggtagaaag taaaaaagga aattgtggtt gttaaagaga    180
tgtcgaaatg acatctcttt ttttagtgga ttaaacgtaa gttcttctca aaaaaagaat    240
gacacattcc gctattgtca cgcatatgat taagtgaata gtgattgagg agggttacga    300

<210> SEQ ID NO 200
<211> LENGTH: 57
<212> TYPE: DNA
<213> ORGANISM: Bacillus cereus

<400> SEQUENCE: 200
acattccgct attgtcacgc atatgattaa gtgaatagtg attgaggagg gttacga        57

<210> SEQ ID NO 201
<211> LENGTH: 300
<212> TYPE: DNA
<213> ORGANISM: Bacillus cereus

<400> SEQUENCE: 201
aacgttatta gcgtagacaa acaagtaacg gcagaagcag ttcttgcatt aaatcgtatg     60
ttagagcgtg tgtaaagcaa cggtattccc gttgcttttt ttcatacata taatcataac    120
gagaacgaaa tgggcataca ttgttttgaa gaaatcattg tggttcttta tgcttattcc    180
acttcgaatg atattgaaaa tcgaagaagt gataaaagta aaagaagtt aatgttattt     240
```
agaaagagtt acttcatgag atttgttact tatagataag ttatacagga gggggaaaat    300

<210> SEQ ID NO 202
<211> LENGTH: 47
<212> TYPE: DNA
<213> ORGANISM: Bacillus cereus

<400> SEQUENCE: 202
tcatgagatt tgttacttat agataagtta tacaggaggg ggaaaat                  47

<210> SEQ ID NO 203
<211> LENGTH: 300
<212> TYPE: DNA
<213> ORGANISM: Bacillus thuringiensis

<400> SEQUENCE: 203
aagccgcggt caatgctgta tatgcaaata agattgcagc tttacctgaa gaagagcgtg    60
atagcttcat tgctgaaaaa cgagaagagt ataagaaaga tattgatatt taccatttag   120
catcagagat ggtcattgat ggtattgttc atccaaacaa tttaagagaa gagttaaaag   180
gacgattcga atgtatatg agtaaatatc aagtatttac ggatcgtaaa catcctgttt    240
atccagttta aaagccctat ttagggcttt cttgctcaaa aagttaagga ggggaaaaca   300

<210> SEQ ID NO 204
<211> LENGTH: 92
<212> TYPE: DNA
<213> ORGANISM: Bacillus thuringiensis

<400> SEQUENCE: 204
tcaagtattt acggatcgta aacatcctgt ttatccagtt taaaagccct atttagggct    60
ttcttgctca aaaagttaag gaggggaaaa ca                                  92

<210> SEQ ID NO 205
<211> LENGTH: 300
<212> TYPE: DNA
<213> ORGANISM: Bacillus cereus

<400> SEQUENCE: 205
aggatttcag tgggacgcct cctctcttct tacattaaat taatcatact ataaaatgaa    60
agaaatgaaa tgaaaaatag cggaaaaatc agaaattttt tctggtagta tacaatatgt   120
tacaataagc tttgtcaatg aaagaaggaa ttccgtgcaa tgcacgggag aggttcgcga   180
actccctcta taaaaaacta tggaaacaac aatatcttta ggtattgttt tgttttttta   240
ttgtgacagt tcaagaacgt tctttcttct tattcgtagt agagaaggag aatgagtgaa   300

<210> SEQ ID NO 206
<211> LENGTH: 104
<212> TYPE: DNA
<213> ORGANISM: Bacillus cereus

<400> SEQUENCE: 206
actatggaaa caacaatatc tttaggtatt gttttgtttt tttattgtga cagttcaaga    60
acgttctttc ttcttattcg tagtagagaa ggagaatgag tgaa                    104

<210> SEQ ID NO 207
<211> LENGTH: 300
<212> TYPE: DNA
<213> ORGANISM: Bacillus cereus

<400> SEQUENCE: 207

```
ttttgcacaa cgccgtaaaa ctttaatgaa taatttatca aataatttaa atggtttccc    60
gaaagataaa gagctgttgg atcgaattt aacagaagta ggaattgatc caaaacgaag   120
aggcgaaacg ctatctatcg aagagtttgc gacattaagt aatgcattag ttcttcataa   180
gttatcataa gaatacaaaa gggacagttc aatttgaact gtccctttg tcacctttct    240
cctcctaaat tcatactta aaaacaggta agatggccta acgagtttgg aggtaggaga   300
```

<210> SEQ ID NO 208
<211> LENGTH: 63
<212> TYPE: DNA
<213> ORGANISM: Bacillus cereus

<400> SEQUENCE: 208

```
tctcctccta aattcatact ttaaaaacag gtaagatggc taacgagtt tggaggtagg    60
aga                                                                 63
```

<210> SEQ ID NO 209
<211> LENGTH: 300
<212> TYPE: DNA
<213> ORGANISM: Bacillus thuringiensis

<400> SEQUENCE: 209

```
ggaaacagaa gtcatcccat tgaaaatgc agcaggtcgt attatagctg atttcgttat     60
ggtttatccg ccagggattc caatctttac tccgggggaa attattacac aagacaactt   120
agtatatatt cgtaaaaact agaagcagg tttacctgta caaggtcctg aagatatgac   180
attacaaaca ttacgcgtga tcaaagagta caagcctatc agttgatagg cttttttttca   240
cccttttcc cttttctcat acgatattat gtaatgtaac gtataggtgg ggatactact   300
```

<210> SEQ ID NO 210
<211> LENGTH: 61
<212> TYPE: DNA
<213> ORGANISM: Bacillus thuringiensis

<400> SEQUENCE: 210

```
acccttttc ccttttctca tacgatatta tgtaatgtaa cgtataggtg gggatactac    60
t                                                                   61
```

<210> SEQ ID NO 211
<211> LENGTH: 300
<212> TYPE: DNA
<213> ORGANISM: Bacillus cereus

<400> SEQUENCE: 211

```
attgtggacc cttagctcag ctggttagag cagacggctc ataaccgtcc ggtcgtaggt     60
tcgagtccta cagggtccat atccatttca catgtttatt atgtcggcag gaagcttcct   120
tgtagaaggg agcttttttt atgaaatata tgagcatttt aattgaaatg aagtgggaat   180
tttgctactt taatgatagc aagacaatgt gatttatttg tttgcaccct atggcaatta   240
gggtagaatg aagttgtatg tcacttaagt ggcaatacat aaactgggag gaatataaca   300
```

<210> SEQ ID NO 212
<211> LENGTH: 38
<212> TYPE: DNA
<213> ORGANISM: Bacillus cereus

<400> SEQUENCE: 212

```
acttaagtgg caatacataa actgggagga atataaca                                    38
```

<210> SEQ ID NO 213
<211> LENGTH: 300
<212> TYPE: DNA
<213> ORGANISM: Bacillus cereus

<400> SEQUENCE: 213

```
aatataacag aaaattctga tgttttttca aatcctataa taaggagtgt tccgtatgat            60
gcctttatat tttccggaag ataaaacaga atatattatt ccagggattg tttgtgttct           120
atttatcatc ggtgcgattg ctacgtggcg tatgttcatt cgtgtatcaa aacgagaagc           180
agagcgatta cagaaagttg aagaaaagct gttagctgaa agaaacagt aactcatttt            240
tgtatgtttc cctctatgct cggacaatct aagggcagaa tgtattttgg agggaatgaa           300
```

<210> SEQ ID NO 214
<211> LENGTH: 228
<212> TYPE: DNA
<213> ORGANISM: Bacillus cereus

<400> SEQUENCE: 214

```
tccggaagat aaaacagaat atattattcc aggattgtt tgtgttctat ttatcatcgg             60
tgcgattgct acgtggcgta tgttcattcg tgtatcaaaa cgagaagcag agcgattaca           120
gaaagttgaa gaaaagctgt tagctgaaaa gaaacagtaa ctcattttg tatgtttccc            180
tctatgctcg gacaatctaa gggcagaatg tattttggag ggaatgaa                        228
```

<210> SEQ ID NO 215
<211> LENGTH: 166
<212> TYPE: DNA
<213> ORGANISM: Bacillus anthracis

<400> SEQUENCE: 215

```
taatcaccct cttccaaatc aatcatatgt tatacatata ctaaactttc cattttttta            60
aattgttcaa gtagtttaag atttcttttc aataattcaa atgtccgtgt cattttcttt           120
cggttttgca tctactatat aatgaacgct ttatggaggt gaattt                          166
```

<210> SEQ ID NO 216
<211> LENGTH: 173
<212> TYPE: DNA
<213> ORGANISM: Bacillus anthracis

<400> SEQUENCE: 216

```
aattacataa caagaactac attagggagc aagcagtcta gcgaaagcta actgcttttt            60
tattaaataa ctattttatt aaatttcata tatacaatcg cttgtccatt tcatttggct           120
ctacccacgc atttactatt agtaatatga atttttcaga ggtggatttt att                  173
```

<210> SEQ ID NO 217
<211> LENGTH: 121
<212> TYPE: DNA
<213> ORGANISM: Bacillus weihenstephanensis

<400> SEQUENCE: 217

```
ctatgattta agatacacaa tagcaaaaga gaaacatatt atataacgat aaatgaaact            60
tatgtatatg tatggtaact gtatatatta ctacaataca gtatactcat aggaggtagg           120
t                                                                          121
```

<210> SEQ ID NO 218
<211> LENGTH: 373
<212> TYPE: DNA
<213> ORGANISM: Bacillus weihenstephanensis

<400> SEQUENCE: 218

| | | |
|---|---|---|
| ggtaggtaga tttgaaatat gatgaagaaa aggaataact aaaaggagtc gatatccgac | 60 |
| tccttttagt tataaataat gtggaattag agtataatttt tatataggta tattgtatta | 120 |
| gatgaacgct ttatccttta attgtgatta atgatggatt gtaagagaag gggcttacag | 180 |
| tcctttttt atggtgttct ataagccttt ttaaaagggg taccacccca cacccaaaaa | 240 |
| caggggggt tataactaca tattggatgt tttgtaacgt acaagaatcg gtattaatta | 300 |
| ccctgtaaat aagttatgtg tatataaggt aactttatat attctcctac aataaaataa | 360 |
| aggaggtaat aaa | 373 |

<210> SEQ ID NO 219
<211> LENGTH: 225
<212> TYPE: DNA
<213> ORGANISM: Bacillus thuringiensis

<400> SEQUENCE: 219

| | | |
|---|---|---|
| aacccttaat gcattggtta aacattgtaa agtctaaagc atggataatg ggcgagaagt | 60 |
| aagtagattg ttaacaccct gggtcaaaaa ttgatattta gtaaaattag ttgcactttg | 120 |
| tgcattttt cataagatga gtcatatgtt ttaaattgta gtaatgaaaa acagtattat | 180 |
| atcataatga attggtatct taataaaaga gatggaggta actta | 225 |

<210> SEQ ID NO 220
<211> LENGTH: 115
<212> TYPE: DNA
<213> ORGANISM: Bacillus thuringiensis

<400> SEQUENCE: 220

| | | |
|---|---|---|
| taattccacc ttcccttatc ctctttcgcc tatttaaaaa aaggtcttga gattgtgacc | 60 |
| aaatctcctc aactccaata tcttattaat gtaaatacaa acaagaagat aagga | 115 |

<210> SEQ ID NO 221
<211> LENGTH: 144
<212> TYPE: DNA
<213> ORGANISM: Bacillus thuringiensis

<400> SEQUENCE: 221

| | | |
|---|---|---|
| aggatgtctt tttttatatt gtattatgta catccctact atataaattc cctgcttta | 60 |
| tcgtaagaat taacgtaata tcaaccatat cccgttcata ttgtagtagt gtatgtcaga | 120 |
| actcacgaga aggagtgaac ataa | 144 |

<210> SEQ ID NO 222
<211> LENGTH: 125
<212> TYPE: DNA
<213> ORGANISM: Bacillus thuringiensis

<400> SEQUENCE: 222

| | | |
|---|---|---|
| ttaatgtcac tccttatctt cttgtttgta tttacattaa taagatattg gagttgagga | 60 |
| gatttggtca caatctcaag acctttttt taaataggcg aaagaggata agggaaggtg | 120 |
| gaatt | 125 |

```
<210> SEQ ID NO 223
<211> LENGTH: 87
<212> TYPE: DNA
<213> ORGANISM: Bacillus thuringiensis

<400> SEQUENCE: 223
atatattttc ataatacgag aaaaagcgga gtttaaaaga atgagggaac ggaaataaag    60
agttgttcat atagtaaata gacagaa                                        87

<210> SEQ ID NO 224
<211> LENGTH: 168
<212> TYPE: DNA
<213> ORGANISM: Bacillus thuringiensis

<400> SEQUENCE: 224
aaactaaata atgagctaag catggattgg gtggcagaat tatctgccac ccaatccatg    60
cttaacgagt attattatgt aaatttctta aaattgggaa cttgtctaga acatagaacc   120
tgtccttttc attaactgaa agtagaaaca gataaaggag tgaaaaac                168

<210> SEQ ID NO 225
<211> LENGTH: 111
<212> TYPE: DNA
<213> ORGANISM: Bacillus thuringiensis

<400> SEQUENCE: 225
attcactaca acggggatga gtttgatgcg gatacatatg agaagtaccg gaaagtgttt    60
gtagaacatt acaaagatat attatctcca tcataaagga gagatgcaaa g            111

<210> SEQ ID NO 226
<211> LENGTH: 273
<212> TYPE: DNA
<213> ORGANISM: Bacillus anthracis

<400> SEQUENCE: 226
cgcgcaccac ttcgtcgtac aacaacgcaa gaagaagttg gggatacagc agtattctta    60
ttcagtgatt tagcacgcgg cgtaacagga gaaaacattc acgttgattc agggtatcat   120
atcttaggat aaatataata ttaattttaa aggacaatct ctacatgttg agattgtcct   180 tttatttgt tcttagaaag aacgattttt aacgaaagtt cttaccacgt tatgaatata    240 agtataaatag tacacgattt attcagctac gta                               273

<210> SEQ ID NO 227
<211> LENGTH: 240
<212> TYPE: DNA
<213> ORGANISM: Bacillus anthracis

<400> SEQUENCE: 227
tatatcatat gtaaaattag ttcttattcc cacatatcat atagaatcgc catattatac    60
atgcagaaaa ctaagtatgg tattattctt aaattgttta gcaccttcta atattacaga   120
tagaatccgt cattttcaac agtgaacatg gatttcttct gaacacaact cttttctttt   180
ccttatttcc aaaagaaaa gcagcccatt ttaaaatacg gctgcttgta atgtacatta    240

<210> SEQ ID NO 228
<211> LENGTH: 267
<212> TYPE: DNA
<213> ORGANISM: Bacillus thuringiensis

<400> SEQUENCE: 228
```

```
tatcacataa ctctttattt ttaatatttc gacataaagt gaaactttaa tcagtggggg    60
ctttgttcat cccccactg attattaatt gaaccaaggg ataaaaagat agagggtctg   120
accagaaaac tggagggcat gattctataa caaaaagctt aatgtttata gaattatgtc   180
tttttatata gggagggtag taaacagaga tttggacaaa aatgcaccga tttatctgaa   240
ttttaagttt tataaagggg agaaatg                                      267

<210> SEQ ID NO 229
<211> LENGTH: 124
<212> TYPE: DNA
<213> ORGANISM: Bacillus thuringiensis

<400> SEQUENCE: 229 atttttact tagcagtaaa actgatatca gttttactgc ttttcattt ttaaattcaa    60 tcattaaatc ttccttttct acatagtcat aatgttgtat gacattccgt aggaggcact   120
tata                                                               124

<210> SEQ ID NO 230
<211> LENGTH: 170
<212> TYPE: DNA
<213> ORGANISM: Bacillus thuringiensis

<400> SEQUENCE: 230
acataaattc acctccataa agcgttcatt atatagtaga tgcaaaaccg aaagaaaatg    60
acacggacat ttgaattatt gaaagaaat cttaaactac ttgaacaatt taaaaaaatg   120
gaaagtttag tatatgtata acatatgatt gatttggaag agggtgatta              170

<210> SEQ ID NO 231
<211> LENGTH: 212
<212> TYPE: DNA
<213> ORGANISM: Bacillus thuringiensis

<400> SEQUENCE: 231 ttctatttc caacataaca tgctacgatt aaatggtttt ttgcaaatgc cttcttggga    60
agaaggatta gagcgttttt ttatagaaac caaaagtcat taacaatttt aagttaatga   120 ctttttgtt tgccttaag aggttttatg ttactataat tatagtatca ggtactaata   180
acaagtataa gtatttctgg gaggatat ca                                   212

<210> SEQ ID NO 232
<211> LENGTH: 353
<212> TYPE: PRT
<213> ORGANISM: Bacillus subtilis

<400> SEQUENCE: 232

Met Leu Ala Val Glu Ala His Gln Met Leu Gln Glu Arg Gln Gln Glu
  1               5                  10                  15

Lys Lys Ser Ile Asn Gly Val Ile Val Lys Glu Arg Glu Glu Glu Gly
             20                  25                  30

Val Thr Ile Thr Lys Val Ile Ile Asp Glu Ser Ala Ser Glu Ser Met
         35                  40                  45

Gly Lys Lys Pro Gly Asn Tyr Leu Thr Leu Glu Val Gln Gly Ile Arg
     50                  55                  60

Gln Gln Asp Thr Glu Leu Gln Gln Lys Val Glu Arg Ile Phe Ala Lys
 65                  70                  75                  80

Glu Phe Ser Tyr Leu Leu Glu Glu Ile Gly Ile Asp Lys Glu Ala Ser
                 85                  90                  95
```

```
Cys Leu Ile Val Gly Leu Gly Asn Trp Asn Val Thr Pro Asp Ala Leu
                100                 105                 110

Gly Pro Ile Val Glu Asn Val Leu Val Thr Arg His Leu Phe Lys
            115                 120                 125

Leu Gln Pro Glu Ser Val Glu Glu Gly Phe Arg Pro Val Ser Ala Ile
130                 135                 140

Arg Pro Gly Val Met Gly Ile Thr Gly Ile Glu Thr Ser Asp Val Ile
145                 150                 155                 160

Tyr Gly Ile Ile Glu Lys Thr Lys Pro Asp Phe Val Ile Ala Ile Asp
                165                 170                 175

Ala Leu Ala Ala Arg Ser Ile Glu Arg Val Asn Ser Thr Ile Gln Ile
            180                 185                 190

Ser Asp Thr Gly Ile His Pro Gly Ser Gly Val Gly Asn Lys Arg Lys
            195                 200                 205

Glu Leu Ser Lys Glu Thr Leu Gly Ile Pro Val Ile Ala Ile Gly Val
            210                 215                 220

Pro Thr Val Val Asp Ala Val Ser Ile Thr Ser Asp Thr Ile Asp Phe
225                 230                 235                 240

Ile Leu Lys His Phe Gly Arg Glu Met Lys Glu Gly Asp Lys Pro Ser
                245                 250                 255

Arg Ser Leu Leu Pro Ala Gly Phe Thr Phe Gly Glu Lys Lys Lys Leu
            260                 265                 270

Thr Glu Glu Asp Met Pro Asp Glu Lys Ser Arg Asn Met Phe Leu Gly
            275                 280                 285

Ala Val Gly Thr Leu Glu Asp Glu Glu Lys Arg Lys Leu Ile Tyr Glu
            290                 295                 300

Val Leu Ala Pro Leu Gly His Asn Leu Met Val Thr Pro Lys Glu Val
305                 310                 315                 320

Asp Thr Phe Ile Glu Asp Met Ala Asn Val Ile Ala Ser Gly Leu Asn
                325                 330                 335

Ala Ala Leu His His Gln Val Asp Gln Asp Asn Thr Gly Ala Tyr Thr
            340                 345                 350

His

<210> SEQ ID NO 233
<211> LENGTH: 368
<212> TYPE: PRT
<213> ORGANISM: Bacillus subtilis

<400> SEQUENCE: 233

Met Lys Lys Ser Glu Leu Asp Val Asn Gln Tyr Leu Ile Arg Thr Asp
1               5                   10                  15

Leu Ala Val Glu Thr Lys Glu Ala Met Ala Asn Gln Gln Ala Val Pro
            20                  25                  30

Thr Lys Glu Ile Lys Gly Phe Ile Glu Lys Glu Arg Asp His Gly Gly
        35                  40                  45

Ile Lys Ile Arg Thr Val Asp Val Thr Lys Glu Gly Ala Glu Leu Ser
    50                  55                  60

Gly Lys Lys Glu Gly Arg Tyr Leu Thr Leu Glu Ala Gln Gly Ile Arg
65                  70                  75                  80

Glu Asn Asp Ser Glu Met Gln Glu Lys Val Ser Ala Val Phe Ala Glu
                85                  90                  95

Glu Phe Ser Ala Phe Leu Glu Asn Leu Asn Ile Ser Lys Asp Ala Ser
            100                 105                 110
```

```
Cys Leu Ile Val Gly Leu Gly Asn Trp Asn Val Thr Pro Asp Ala Leu
        115                 120                 125

Gly Pro Met Ala Val Glu Asn Leu Leu Val Thr Arg His Leu Phe Lys
    130                 135                 140

Leu Gln Pro Glu Asn Val Gln Glu Gly Tyr Arg Pro Val Ser Ala Phe
145                 150                 155                 160

Ala Pro Gly Val Met Gly Ile Thr Gly Ile Glu Thr Ser Asp Ile Ile
                165                 170                 175

Lys Gly Val Ile Glu Gln Ser Lys Pro Asp Phe Val Ile Ala Ile Asp
            180                 185                 190

Ala Leu Ala Ala Arg Ala Val Glu Arg Val Asn Thr Thr Ile Gln Ile
        195                 200                 205

Ser Asp Thr Gly Ile His Pro Gly Ser Gly Val Gly Asn Lys Arg Lys
    210                 215                 220

Asp Leu Ser Lys Asp Thr Leu Gly Val Pro Val Ile Ala Ile Gly Val
225                 230                 235                 240

Pro Thr Val Val Asp Ala Val Thr Ile Ala Ser Asp Thr Val Asp Tyr
                245                 250                 255

Ile Leu Lys His Phe Gly Arg Glu Met Lys Asp Asn Arg Pro Ser Arg
            260                 265                 270

Ser Leu Val Pro Ala Gly Met Thr Phe Gly Lys Lys Lys Val Leu Thr
        275                 280                 285

Glu Asp Asp Leu Pro Asp Gln Lys Gln Arg Gln Ser Phe Leu Gly Ile
    290                 295                 300

Val Gly Thr Leu Gln Glu Asp Glu Lys Arg Gln Leu Ile His Glu Val
305                 310                 315                 320

Leu Ser Pro Leu Gly His Asn Leu Met Val Thr Pro Lys Glu Val Asp
                325                 330                 335

Ser Phe Ile Asp Asp Met Ala Asn Val Leu Ala Asn Gly Leu Asn Thr
            340                 345                 350

Ala Leu His Glu Lys Val Ser Gln Glu Asn Lys Gly Ser Tyr Asn His
        355                 360                 365

<210> SEQ ID NO 234
<211> LENGTH: 367
<212> TYPE: PRT
<213> ORGANISM: Bacillus cereus

<400> SEQUENCE: 234

Met Lys Glu Pro Leu Asp Leu Ser Lys Tyr Ser Val Arg Thr Asp Leu
1               5                   10                  15

Ala Val Glu Ala His Gln Met Leu Gln Glu Arg Gln Glu Glu Gln Lys
            20                  25                  30

Gly Ile Gln Gly Val Ile Val Lys Glu Arg Glu Glu Glu Gly Ile Thr
        35                  40                  45

Ile Thr Lys Val Thr Ile Asp Glu Ile Ala Ser Glu Ser Met Gly Lys
    50                  55                  60

Lys Pro Gly Asn Tyr Leu Thr Leu Glu Val Gln Gly Ile Arg Gln Gln
65                  70                  75                  80

Asp Thr Glu Leu Gln Gln Lys Val Glu Ser Val Phe Ala Lys Glu Phe
                85                  90                  95

Ser Tyr Phe Leu Glu Glu Val Gly Val Ser Lys Glu Ala Ser Cys Leu
            100                 105                 110

Ile Val Gly Leu Gly Asn Trp Asn Val Thr Pro Asp Ala Leu Gly Pro
```

```
               115                 120                 125
Ile Val Val Glu Asn Val Leu Val Thr Arg His Leu Phe Lys Leu Gln
130                 135                 140

Pro Glu Ser Val Glu Glu Gly Phe Arg Pro Val Ser Ala Ile Arg Pro
145                 150                 155                 160

Gly Val Met Gly Ile Thr Gly Ile Glu Thr Ser Asp Val Ile Tyr Gly
                165                 170                 175

Ile Ile Glu Lys Thr Lys Pro Asp Phe Val Ile Ala Ile Asp Ala Leu
            180                 185                 190

Ala Ala Arg Ser Ile Glu Arg Val Asn Ser Thr Ile Gln Ile Ser Asp
        195                 200                 205

Thr Gly Ile His Pro Gly Ser Gly Val Gly Asn Lys Arg Lys Glu Leu
210                 215                 220

Ser Lys Glu Thr Leu Gly Ile Pro Val Ile Ala Ile Gly Val Pro Thr
225                 230                 235                 240

Val Val Asp Ala Val Ser Ile Thr Ser Asp Thr Ile Asp Phe Ile Leu
                245                 250                 255

Lys His Phe Gly Arg Glu Leu Lys Glu Gly Asn Lys Pro Ser Arg Ser
            260                 265                 270

Leu Leu Pro Ala Gly Phe Thr Phe Gly Glu Lys Lys Leu Thr Glu
        275                 280                 285

Glu Asp Met Pro Asp Glu Lys Ser Arg Asn Met Phe Leu Gly Ala Ile
290                 295                 300

Gly Thr Leu Glu Glu Glu Lys Arg Lys Leu Ile Tyr Glu Val Leu
305                 310                 315                 320

Ser Pro Leu Gly His Asn Leu Met Val Thr Pro Lys Glu Val Asp Ala
                325                 330                 335

Phe Ile Glu Asp Met Ala Asn Val Ile Ala Ser Gly Leu Asn Ala Ala
            340                 345                 350

Leu His His Gln Ile Asp Gln Asp Asn Thr Gly Ala Tyr Thr His
        355                 360                 365

<210> SEQ ID NO 235
<211> LENGTH: 300
<212> TYPE: PRT
<213> ORGANISM: Bacillus subtilis

<400> SEQUENCE: 235

Gly Thr Ala Ala Cys Thr Ala Ala Gly Cys Thr Cys Thr Ala
1               5                   10                  15

Cys Ala Gly Thr Thr Thr Ala Ala Cys Ala Gly Cys Thr Gly Ala
                20                  25                  30

Ala Cys Gly Cys Ala Thr Gly Thr Cys Ala Gly Ala Cys Thr Thr Gly
            35                  40                  45

Ala Thr Ala Gly Ala Ala Gly Cys Gly Thr Ala Thr Gly Thr Gly
        50                  55                  60

Cys Ala Cys Gly Ala Cys Gly Cys Thr Cys Thr Cys Gly Cys Thr
65                  70                  75                  80

Ala Ala Gly Thr Thr Thr Ala Gly Cys Gly Cys Gly Thr Thr Gly
                85                  90                  95

Ala Thr Ala Gly Cys Ala Gly Ala Thr Thr Ala Ala Thr Gly Thr
            100                 105                 110

Thr Thr Gly Cys Cys Ala Thr Ala Cys Thr Thr Thr Cys Ala Cys
        115                 120                 125
```

```
Cys Thr Cys Cys Cys Thr Gly Gly Thr Gly Cys Gly Ala Thr Cys Gly
    130                 135                 140
Ala Gly Thr Gly Ala Cys Thr Cys Gly Ala Thr Ala Cys Thr Thr Ala
145                 150                 155                 160
Cys Ala Thr Ala Gly Ala Ala Cys Ala Ala Gly Thr Gly Ala Thr Ala
                165                 170                 175

Thr Thr Cys Thr Ala Thr Cys Ala Ala Ala Cys Gly Gly Ala Gly Ala
            180                 185                 190
Ala Gly Ala Gly Ala Ala Thr Thr Gly Cys Ala Ala Thr Ala Gly Cys
        195                 200                 205
Gly Ala Gly Ala Thr Cys Ala Ala Thr Gly Ala Ala Ala Thr Thr Thr
    210                 215                 220

Cys Ala Thr Gly Thr Ala Ala Ala Gly Gly Ala Ala Ala Gly Ala Ala
225                 230                 235                 240

Thr Gly Ala Cys Cys Thr Thr Ala Thr Ala Thr Ala Thr Thr Thr Thr
                245                 250                 255

Thr Gly Gly Gly Gly Ala Ala Thr Cys Thr Ala Ala Cys Thr Ala Thr
            260                 265                 270

Ala Thr Thr Thr Ala Cys Thr Ala Thr Gly Ala Ala Thr Thr Gly Cys
        275                 280                 285

Gly Gly Ala Gly Gly Ala Gly Ala Thr Ala Cys Gly
    290                 295                 300
```

<210> SEQ ID NO 236
<211> LENGTH: 100
<212> TYPE: PRT
<213> ORGANISM: Bacillus subtilis

<400> SEQUENCE: 236

```
Gly Cys Ala Ala Thr Ala Gly Cys Gly Ala Gly Ala Thr Cys Ala Ala
1               5                   10                  15

Thr Gly Ala Ala Ala Thr Thr Thr Cys Ala Thr Gly Thr Ala Ala Ala
            20                  25                  30

Gly Gly Ala Ala Ala Gly Ala Ala Thr Gly Ala Cys Cys Thr Thr Ala
        35                  40                  45

Thr Ala Thr Ala Thr Thr Thr Thr Thr Gly Gly Gly Gly Ala Ala Thr
    50                  55                  60

Cys Thr Ala Ala Cys Thr Ala Thr Ala Thr Thr Thr Ala Cys Thr Ala
65                  70                  75                  80

Thr Gly Ala Ala Thr Thr Gly Cys Gly Gly Ala Gly Gly Ala Gly Ala
                85                  90                  95

Thr Ala Cys Gly
            100
```

<210> SEQ ID NO 237
<211> LENGTH: 200
<212> TYPE: PRT
<213> ORGANISM: Bacillus subtilis

<400> SEQUENCE: 237

```
Thr Thr Thr Cys Ala Cys Cys Thr Cys Cys Thr Ala Ala Gly Ala Thr
1               5                   10                  15

Ala Cys Ala Ala Cys Cys Thr Gly Thr Ala Gly Cys Ala Cys Ala Gly
            20                  25                  30

Thr Gly Thr Cys Thr Thr Ala Ala Gly Gly Thr Thr Ala Ala Ala Thr
        35                  40                  45
```

```
Cys Thr Thr Cys Thr Thr Cys Ala Cys Ala Ala Thr Ala Gly Ala Ala
    50                  55                  60

Cys Ala Ala Ala Thr Thr Gly Thr Ala Thr Thr Cys Thr Ala Thr Cys
65                  70                  75                  80

Ala Ala Ala Cys Ala Cys Ala Cys Cys Thr Thr Ala Gly Ala Thr
                85                  90                  95

Thr Gly Cys Ala Ala Thr Ala Thr Ala Ala Thr Gly Thr Ala Ala
            100                 105                 110

Ala Gly Thr Ala Thr Thr Thr Thr Cys Ala Thr Thr Gly Ala Ala
                115                 120                 125

Gly Gly Thr Thr Cys Thr Cys Thr Thr Thr Thr Ala Gly Cys Ala
    130                 135                 140

Thr Gly Ala Thr Thr Ala Thr Thr Cys Ala Gly Cys Ala Ala Ala
145                 150                 155                 160

Thr Gly Gly Cys Ala Ala Cys Ala Ala Thr Ala Thr Ala Gly Thr
                165                 170                 175

Ala Cys Thr Thr Ala Ala Thr Gly Thr Gly Ala Ala Gly Gly Ala Gly
            180                 185                 190

Gly Cys Cys Cys Cys Thr Gly Thr
            195                 200
```

<210> SEQ ID NO 238
<211> LENGTH: 75
<212> TYPE: PRT
<213> ORGANISM: Bacillus subtilis

<400> SEQUENCE: 238

```
Gly Ala Ala Gly Gly Thr Thr Cys Thr Cys Thr Thr Thr Thr Ala
1               5                   10                  15

Gly Cys Ala Thr Gly Ala Thr Thr Ala Thr Thr Cys Ala Gly Cys
                20                  25                  30

Ala Ala Ala Thr Gly Gly Cys Ala Ala Cys Ala Ala Thr Ala Thr Ala
            35                  40                  45

Gly Gly Thr Ala Cys Thr Thr Ala Ala Thr Gly Thr Gly Ala Ala Gly
    50                  55                  60

Gly Ala Gly Gly Cys Cys Cys Cys Thr Gly Thr
65                  70                  75
```

<210> SEQ ID NO 239
<211> LENGTH: 200
<212> TYPE: PRT
<213> ORGANISM: Bacillus subtilis

<400> SEQUENCE: 239

```
Gly Cys Thr Thr Thr Gly Thr Thr Gly Ala Thr Thr Cys Gly Ala
1               5                   10                  15

Gly Cys Cys Gly Thr Ala Thr Ala Thr Thr Cys Ala Ala Gly Ala Ala
                20                  25                  30

Gly Cys Gly Gly Thr Ala Gly Ala Thr Ala Ala Cys Ala Thr Thr Gly
            35                  40                  45

Ala Gly Ala Cys Ala Ala Thr Gly Ala Cys Cys Thr Thr Thr Ala
    50                  55                  60

Thr Ala Gly Cys Gly Ala Ala Cys Ala Ala Gly Ala Ala Gly Cys Thr
65                  70                  75                  80

Ala Ala Cys Gly Ala Thr Ala Ala Ala Thr Thr Cys Gly Cys Thr Gly
                85                  90                  95
```

```
Ala Ala Cys Thr Cys Thr Thr Thr Thr Ala Ala Ala Thr Cys Ala Ala
            100                 105                 110

Thr Thr Thr Thr Cys Ala Gly Cys Thr Cys Cys Thr Gly Thr Ala Thr
        115                 120                 125

Ala Cys Ala Ala Thr Thr Ala Cys Cys Ala Ala Ala Gly Thr Thr Thr
    130                 135                 140

Thr Thr Cys Thr Gly Ala Ala Thr Gly Ala Ala Gly Cys Cys Ala Thr
145                 150                 155                 160

Gly Thr Gly Thr Thr Thr Thr Gly Ala Cys Ala Cys Ala Thr Thr Cys
                165                 170                 175

Thr Ala Thr Ala Cys Thr Cys Ala Cys Ala Ala Gly Gly Ala Gly Gly
            180                 185                 190

Thr Gly Ala Gly Ala Cys Ala Cys
        195                 200

<210> SEQ ID NO 240
<211> LENGTH: 52
<212> TYPE: PRT
<213> ORGANISM: Bacillus subtilis

<400> SEQUENCE: 240

Gly Ala Ala Thr Gly Ala Ala Gly Cys Cys Ala Thr Gly Thr Gly Thr
1               5                   10                  15

Thr Thr Thr Gly Ala Cys Ala Cys Ala Thr Thr Cys Thr Ala Thr Ala
            20                  25                  30

Cys Thr Cys Ala Cys Ala Ala Gly Gly Ala Gly Gly Thr Gly Ala Gly
        35                  40                  45

Ala Cys Ala Cys
    50

<210> SEQ ID NO 241
<211> LENGTH: 200
<212> TYPE: PRT
<213> ORGANISM: Bacillus subtilis

<400> SEQUENCE: 241

Ala Ala Ala Cys Gly Gly Cys Thr Ala Ala Gly Cys Thr Thr Thr Thr
1               5                   10                  15

Thr Thr Thr Ala Thr Thr Thr Cys Thr Cys Ala Ala Gly Ala Thr Thr
            20                  25                  30

Thr Ala Cys Cys Ala Cys Ala Cys Ala Ala Thr Thr Cys Thr Cys Cys
        35                  40                  45

Gly Cys Ala Thr Gly Ala Thr Thr Thr Thr Cys Cys Gly Gly Cys Cys
    50                  55                  60

Ala Thr Thr Thr Thr Ala Ala Cys Ala Thr Ala Ala Thr Ala Cys Gly
65                  70                  75                  80

Thr Ala Gly Thr Ala Ala Cys Ala Ala Gly Cys Cys Gly Gly Cys Ala
                85                  90                  95

Ala Ala Gly Cys Ala Thr Thr Gly Gly Gly Thr Thr Ala Cys Gly Cys
            100                 105                 110

Cys Gly Ala Gly Gly Cys Gly Gly Cys Ala Gly Thr Gly Ala Cys Ala
        115                 120                 125

Cys Cys Cys Gly Ala Gly Ala Ala Gly Gly Gly Thr Thr Cys Ala Cys
    130                 135                 140

Ala Gly Ala Thr Thr Gly Gly Thr Gly Cys Ala Ala Cys Thr Cys Cys
145                 150                 155                 160
```

```
Ala Gly Thr Thr Ala Ala Cys Cys Cys Ala Cys Cys Ala Thr Ala
                165                 170                 175

Cys Thr Ala Ala Ala Thr Ala Ala Ala Ala Gly Gly Ala Gly Ala
                180                 185                 190

Thr Thr Thr Thr Ala Cys Ala Cys
            195                 200

<210> SEQ ID NO 242
<211> LENGTH: 55
<212> TYPE: PRT
<213> ORGANISM: Bacillus subtilis

<400> SEQUENCE: 242

Gly Ala Thr Thr Gly Gly Thr Gly Cys Ala Ala Cys Thr Cys Cys Ala
1               5                   10                  15

Gly Thr Thr Ala Ala Cys Cys Cys Ala Ala Cys Cys Ala Thr Ala Cys
                20                  25                  30

Thr Ala Ala Ala Thr Ala Ala Ala Ala Ala Gly Gly Ala Gly Ala Thr
                35                  40                  45

Thr Thr Thr Ala Cys Ala Cys
            50                  55

<210> SEQ ID NO 243
<211> LENGTH: 200
<212> TYPE: PRT
<213> ORGANISM: Bacillus subtilis

<400> SEQUENCE: 243

Thr Thr Cys Gly Cys Thr Thr Cys Thr Cys Cys Cys Ala Cys Thr Thr
1               5                   10                  15

Ala Ala Thr Cys Thr Gly Ala Thr Thr Ala Cys Ala Thr Thr Cys
                20                  25                  30

Cys Ala Ala Gly Gly Ala Ala Thr Cys Cys Ala Ala Thr Gly Ala Thr
                35                  40                  45

Thr Thr Ala Thr Ala Thr Gly Gly Ala Gly Ala Thr Cys Thr Gly Ala
        50                  55                  60

Ala Ala Cys Ala Thr Ala Ala Cys Ala Ala Thr Thr Thr Thr Cys
65                  70                  75                  80

Ala Thr Thr Thr Gly Thr Cys Thr Cys Ala Cys Cys Thr
                85                  90                  95

Thr Cys Thr Thr Ala Ala Thr Gly Ala Ala Ala Ala Thr Thr Thr
            100                 105                 110

Ala Thr Thr Thr Cys Thr Thr Thr Gly Gly Cys Gly Thr Gly Thr Ala
            115                 120                 125

Thr Ala Ala Ala Thr Ala Ala Ala Thr Ala Thr Cys Thr
            130                 135                 140

Cys Thr Cys Cys Ala Thr Ala Ala Thr Ala Gly Ala Thr Cys
145                 150                 155                 160

Ala Ala Ala Cys Ala Ala Gly Cys Thr Thr Gly Thr Thr Thr Cys
                165                 170                 175

Ala Thr Thr Ala Cys Ala Cys Thr Thr Ala Gly Gly Ala Gly Ala
                180                 185                 190

Thr Gly Ala Ala Thr Ala Ala Gly
            195                 200

<210> SEQ ID NO 244
<211> LENGTH: 75
```

<212> TYPE: PRT
<213> ORGANISM: Bacillus subtilis

<400> SEQUENCE: 244

Gly Thr Ala Thr Ala Ala Ala Thr Thr Ala Ala Ala Thr Ala Ala
1               5                   10                  15

Thr Cys Thr Cys Thr Cys Cys Ala Thr Ala Ala Thr Ala Thr Gly Ala
            20                  25                  30

Thr Thr Cys Ala Ala Ala Cys Ala Ala Gly Cys Thr Thr Gly Thr Thr
        35                  40                  45

Thr Thr Cys Ala Thr Thr Ala Cys Ala Cys Thr Thr Thr Ala Gly Gly
        50                  55                  60

Ala Gly Ala Thr Gly Ala Ala Thr Ala Ala Gly
65                  70                  75

<210> SEQ ID NO 245
<211> LENGTH: 200
<212> TYPE: PRT
<213> ORGANISM: Bacillus subtilis

<400> SEQUENCE: 245

Thr Ala Cys Ala Gly Thr Cys Cys Thr Cys Thr Cys Cys Ala Thr Thr
1               5                   10                  15

Thr Thr Gly Ala Cys Ala Thr Thr Cys Cys Ala Thr Ala Thr Thr Cys
            20                  25                  30

Ala Gly Gly Cys Ala Ala Cys Cys Gly Cys Ala Cys Ala Thr Ala Ala
        35                  40                  45

Ala Ala Thr Gly Ala Cys Ala Gly Cys Ala Gly Cys Ala Thr Thr
        50                  55                  60

Cys Thr Ala Thr Ala Gly Thr Cys Thr Gly Cys Gly Cys Cys Ala Cys
65                  70                  75                  80

Cys Cys Cys Gly Gly Cys Thr Cys Ala Gly Ala Gly Gly Cys Cys Gly
                85                  90                  95

Gly Gly Gly Thr Thr Thr Thr Ala Thr Thr Thr Thr Cys Thr Cys
            100                 105                 110

Cys Ala Cys Ala Ala Cys Ala Ala Thr Thr Gly Cys Cys Ala Gly Cys
            115                 120                 125

Ala Thr Ala Ala Ala Thr Ala Ala Ala Cys Cys Cys Gly Thr Ala
            130                 135                 140

Thr Ala Thr Thr Thr Cys Ala Ala Cys Thr Ala Ala Ala Thr Ala
145                 150                 155                 160

Cys Gly Cys Gly Thr Thr Ala Ala Gly Ala Ala Thr Thr Thr Cys Thr
            165                 170                 175

Thr Thr Ala Thr Cys Gly Ala Ala Ala Ala Gly Gly Ala Gly Ala
            180                 185                 190

Thr Gly Ala Ala Ala Ala Ala Gly
        195                 200

<210> SEQ ID NO 246
<211> LENGTH: 166
<212> TYPE: PRT
<213> ORGANISM: Bacillus subtilis

<400> SEQUENCE: 246

Gly Cys Ala Ala Cys Cys Gly Cys Ala Cys Ala Thr Ala Ala Ala Ala
1               5                   10                  15

Thr Gly Ala Cys Ala Gly Cys Ala Gly Ala Cys Ala Thr Thr Cys Thr

```
            20                  25                  30
Ala Thr Ala Gly Thr Cys Thr Gly Cys Gly Cys Cys Ala Cys Cys Cys
            35                  40                  45

Cys Gly Gly Cys Thr Cys Ala Gly Ala Gly Gly Cys Cys Gly Gly Gly
            50                  55                  60

Gly Thr Thr Thr Thr Ala Thr Thr Thr Thr Cys Thr Cys Cys Ala
65                  70                  75                  80

Cys Ala Ala Cys Ala Ala Thr Thr Gly Cys Cys Ala Gly Cys Ala Thr
                85                  90                  95

Ala Ala Ala Thr Ala Ala Ala Cys Cys Cys Cys Gly Thr Ala Thr Ala
                100                 105                 110

Thr Thr Thr Cys Ala Ala Ala Cys Thr Ala Ala Thr Ala Cys Gly
            115                 120                 125

Cys Gly Thr Thr Ala Ala Gly Ala Ala Thr Thr Thr Cys Thr Thr Thr
130                 135                 140

Ala Thr Cys Gly Ala Ala Ala Ala Gly Gly Ala Gly Ala Thr Gly
145                 150                 155                 160

Ala Ala Ala Ala Ala Gly
                165
```

<210> SEQ ID NO 247
<211> LENGTH: 388
<212> TYPE: PRT
<213> ORGANISM: Bacillus anthracis

<400> SEQUENCE: 247

```
Met Glu Glu Ala Pro Phe Tyr Arg Asp Thr Trp Val Glu Val Asp Leu
1               5                   10                  15

Asp Ala Ile Tyr Asn Asn Val Thr His Ile Lys Glu Phe Ile Pro Ser
                20                  25                  30

Asp Val Glu Ile Phe Ala Val Val Lys Gly Asn Ala Tyr Gly His Asp
            35                  40                  45

Tyr Val Pro Val Ala Lys Ile Ala Leu Glu Ala Gly Ala Thr Arg Leu
        50                  55                  60

Ala Val Ala Phe Leu Asp Glu Ala Leu Val Leu Arg Arg Ala Gly Ile
65                  70                  75                  80

Thr Ala Pro Ile Leu Val Leu Gly Pro Ser Pro Arg Asp Ile Asn
                85                  90                  95

Val Ala Ala Glu Asn Asp Val Ala Leu Thr Val Phe Gln Lys Glu Trp
            100                 105                 110

Val Asp Glu Ala Ile Lys Leu Trp Asp Gly Ser Ser Thr Met Lys Tyr
        115                 120                 125

His Ile Asn Phe Asp Ser Gly Met Gly Arg Ile Gly Ile Arg Glu Arg
    130                 135                 140

Lys Glu Leu Lys Gly Phe Leu Lys Ser Leu Glu Gly Ala Pro Phe Leu
145                 150                 155                 160

Glu Leu Glu Gly Val Tyr Thr His Phe Ala Thr Ala Asp Glu Val
                165                 170                 175

Thr Ser Tyr Phe Asp Lys Gln Tyr Asn Thr Phe Leu Glu Gln Leu Ser
            180                 185                 190

Trp Leu Lys Glu Phe Gly Val Asp Pro Lys Phe Val His Thr Ala Asn
        195                 200                 205

Ser Ala Ala Thr Leu Arg Phe Gln Gly Ile Thr Phe Asn Ala Val Arg
    210                 215                 220
```

Ile Gly Ile Ala Met Tyr Gly Leu Ser Pro Ser Val Glu Ile Arg Pro
225                 230                 235                 240

Phe Leu Pro Phe Lys Leu Glu Pro Ala Leu Ser Leu His Thr Lys Val
            245                 250                 255

Ala His Ile Lys Gln Val Ile Lys Gly Asp Gly Ile Ser Tyr Asn Val
            260                 265                 270

Thr Tyr Arg Thr Lys Thr Glu Glu Trp Ile Ala Thr Val Ala Ile Gly
            275                 280                 285

Tyr Ala Asp Gly Trp Leu Arg Arg Leu Gln Gly Phe Glu Val Leu Val
            290                 295                 300

Asn Gly Lys Arg Val Pro Ile Val Gly Arg Val Thr Met Asp Gln Phe
305                 310                 315                 320

Met Ile His Leu Pro Cys Glu Val Pro Leu Gly Thr Lys Val Thr Leu
                325                 330                 335

Ile Gly Arg Gln Gly Asp Glu Tyr Ile Ser Ala Thr Glu Val Ala Glu
            340                 345                 350

Tyr Ser Gly Thr Ile Asn Tyr Glu Ile Ile Thr Thr Ile Ser Phe Arg
            355                 360                 365

Val Pro Arg Ile Phe Ile Arg Asn Gly Lys Val Val Glu Val Ile Asn
370                 375                 380

Tyr Leu Asn Asp
385

<210> SEQ ID NO 248
<211> LENGTH: 391
<212> TYPE: PRT
<213> ORGANISM: Bacillus cereus

<400> SEQUENCE: 248

```
Met Ser Leu Lys Tyr Gly Arg Asp Thr Ile Val Glu Val Asp Leu Asn
1               5                   10                  15

Ala Val Lys His Asn Val Lys Glu Phe Lys Lys Arg Val Asn Asp Glu
            20                  25                  30

Asn Ile Ala Met Met Ala Ala Val Lys Ala Asn Gly Tyr Gly His Gly
        35                  40                  45

Ala Val Glu Val Ala Lys Ala Ala Ile Glu Ala Gly Ile Asn Gln Leu
    50                  55                  60

Ala Ile Ala Phe Val Asp Glu Ala Ile Glu Leu Arg Glu Ala Gly Ile
65                  70                  75                  80

Asn Val Pro Ile Leu Ile Leu Gly Tyr Thr Ser Val Ala Ala Ala Glu
                85                  90                  95

Glu Ala Ile Gln Tyr Asp Val Met Met Thr Val Tyr Arg Ser Glu Asp
            100                 105                 110

Leu Gln Gly Ile Asn Glu Ile Ala Asn Arg Leu Gln Lys Lys Ala Gln
        115                 120                 125

Ile Gln Val Lys Ile Asp Thr Gly Met Ser Arg Ile Gly Leu Gln Glu
    130                 135                 140

Glu Glu Val Lys Pro Phe Leu Glu Glu Leu Lys Arg Met Glu Tyr Val
145                 150                 155                 160

Glu Val Val Gly Met Phe Thr His Tyr Ser Thr Ala Asp Glu Ile Asp
                165                 170                 175

Lys Ser Tyr Thr Asn Met Gln Thr Ser Leu Phe Glu Lys Ala Val Asn
            180                 185                 190

Thr Ala Lys Glu Leu Gly Ile His Ile Pro Tyr Ile His Ser Ser Asn
        195                 200                 205
```

-continued

Ser Ala Gly Ser Met Glu Leu Ser Asn Thr Phe Gln Asn Met Val Arg
            210                 215                 220

Val Gly Ile Gly Ile Tyr Gly Met Tyr Pro Ser Lys Glu Val Asn His
225                 230                 235                 240

Ser Val Val Ser Leu Gln Pro Ala Leu Ser Leu Lys Ser Lys Val Ala
            245                 250                 255

His Ile Lys His Ala Lys Lys Asn Arg Gly Val Ser Tyr Gly Asn Thr
            260                 265                 270

Tyr Val Thr Thr Gly Glu Glu Trp Ile Ala Thr Val Pro Ile Gly Tyr
            275                 280                 285

Ala Asp Gly Tyr Asn Arg Gln Leu Ser Asn Lys Gly His Ala Leu Ile
            290                 295                 300

Asn Gly Val Arg Val Pro Val Ile Gly Arg Val Cys Met Asp Gln Leu
305                 310                 315                 320

Met Leu Asp Val Ser Lys Ala Met Pro Val Gln Val Gly Asp Glu Val
            325                 330                 335

Val Phe Tyr Gly Lys Gln Gly Glu Glu Asn Ile Ala Val Glu Glu Ile
            340                 345                 350

Ala Asp Met Leu Gly Thr Ile Asn Tyr Glu Val Thr Cys Met Leu Asp
            355                 360                 365

Arg Arg Ile Pro Arg Val Tyr Lys Glu Asn Asn Glu Thr Thr Ala Val
            370                 375                 380

Val Asn Ile Leu Arg Lys Asn
385                 390

<210> SEQ ID NO 249
<211> LENGTH: 297
<212> TYPE: PRT
<213> ORGANISM: Bacillus thuringiensis

<400> SEQUENCE: 249

Met Lys Lys Glu Ile Ser Val Ile Gly Val Pro Met Asp Leu Gly Gln
1               5                   10                  15

Met Arg Arg Gly Val Asp Met Gly Pro Ser Ala Ile Arg Tyr Ala Gly
            20                  25                  30

Val Ile Glu Arg Ile Glu Ile Gly Tyr Asp Val Lys Asp Met Gly
            35                  40                  45

Asp Ile Cys Ile Glu Arg Glu Lys Glu Val Asp Val Asn Thr Ser Leu
            50                  55                  60

Arg Asn Leu Thr Gln Val Ala Thr Val Cys Asn Glu Leu Ala Ser Lys
65                  70                  75                  80

Val Asp His Ile Ile Glu Glu Gly Arg Phe Pro Leu Val Leu Gly Gly
            85                  90                  95

Asp His Ser Ile Ala Ile Gly Thr Leu Ala Gly Val Ala Lys His Tyr
            100                 105                 110

Lys Asn Leu Gly Val Ile Trp Tyr Asp Ala His Gly Asp Leu Asn Thr
            115                 120                 125

Glu Glu Thr Ser Pro Ser Gly Asn Ile His Gly Met Ser Leu Ala Ala
130                 135                 140

Ser Leu Gly Tyr Gly His Pro Thr Leu Val Asp Leu Tyr Gly Ala Tyr
145                 150                 155                 160

Pro Lys Val Lys Lys Glu Asn Val Val Ile Ile Gly Ala Arg Ala Leu
            165                 170                 175

Asp Glu Gly Glu Lys Asp Phe Ile Arg Asn Glu Gly Ile Lys Val Phe

```
            180                 185                 190
Thr Met His Glu Ile Asp Arg Met Gly Met Thr Ala Val Met Glu Glu
        195                 200                 205

Thr Ile Glu Tyr Leu Ser His Thr Asp Gly Val His Leu Ser Leu Asp
    210                 215                 220

Leu Asp Gly Leu Asp Pro His Asp Ala Pro Gly Val Gly Thr Pro Val
225                 230                 235                 240

Ile Gly Gly Leu Ser Tyr Arg Glu Ser His Leu Ala Met Glu Met Leu
                245                 250                 255

Ala Glu Ala Asp Ile Val Thr Ser Ala Glu Phe Val Glu Val Asn Thr
            260                 265                 270

Ile Leu Asp Glu Arg Asn Arg Thr Ala Thr Thr Ala Val Ala Leu Met
        275                 280                 285

Gly Ser Leu Phe Gly Glu Lys Leu Lys
    290                 295

<210> SEQ ID NO 250
<211> LENGTH: 302
<212> TYPE: PRT
<213> ORGANISM: Bacillus cereus

<400> SEQUENCE: 250

Met Ala Leu Ile Tyr Ala Asn Lys Thr Cys Lys Leu Asp Ile Leu Gly
1               5                   10                  15

Ile Val Ala Glu Tyr Gly Asn Val Ser Arg Glu Ile Val Thr Glu Asn
            20                  25                  30

Val Tyr Phe Leu Glu Arg Tyr Tyr Ala Thr Glu Val Lys Ile Ile Glu
        35                  40                  45

Gly Ala Ala Arg Pro Met Thr Ala Glu Glu Pro Leu Phe Phe Pro Glu
    50                  55                  60

Ile His Gly Glu His Gly Leu Gly Pro Ile Ile Pro Pro Asp Met Arg
65                  70                  75                  80

Ile Cys Lys Arg Glu Asn Phe Cys Glu Leu Ile Lys Leu Ile Glu Pro
                85                  90                  95

Cys Pro Glu Asp Ile Ile Ile Val Ala Thr Gly Arg Leu Thr Thr Leu
            100                 105                 110

Ala Thr Leu Phe Leu Leu Tyr Pro Asn Val Met Asp Lys Val Cys Ser
        115                 120                 125

Tyr Tyr Ile Met Gly Gly Ala Phe Leu Phe Pro Gly Asn Val Thr Pro
    130                 135                 140

Val Ser Glu Ala Asn Phe Tyr Gly Asp Pro Ile Ala Ala Asn Ile Val
145                 150                 155                 160

Met Lys Tyr Ala Lys Asn Ala His Ile Tyr Pro Leu Asn Val Thr Gln
                165                 170                 175

Glu Ala Leu Ile Thr Pro Glu Met Val Asp Ile Ile Asn Lys Glu Gly
            180                 185                 190

Thr Gly Gln Ala Lys Leu Ile Lys Pro Met Ile Asp Phe Tyr Tyr Glu
        195                 200                 205

Asn Phe Tyr Lys Lys Glu Tyr Pro Gly Ile Ala Gly Ser Pro Ile His
    210                 215                 220

Asp Leu Leu Pro Phe Ile Ser Phe Ile Asn Asp Asp Ile Phe Glu Tyr
225                 230                 235                 240

Lys Lys Ser Ala Val Trp Ile Ser Thr Thr Asn Asp Val Thr Arg Gly
                245                 250                 255
```

```
Gln Ser Val Ala Asp Phe Arg Lys Ile Ala Glu Pro Thr Arg Phe Asp
                260                 265                 270

Asp Arg Pro Ile Gln Arg Ile Ala Val Gly Phe Asn Tyr Pro Ala Phe
            275                 280                 285

Lys Glu Glu Phe Met Arg Thr Ile Leu Lys Pro Asp Cys Pro
    290                 295                 300

<210> SEQ ID NO 251
<211> LENGTH: 316
<212> TYPE: PRT
<213> ORGANISM: Bacillus thuringiensis

<400> SEQUENCE: 251

Met Pro Lys Lys Val Leu Ile Phe Cys Asp Pro Gly Ile Asp Asp Thr
1               5                   10                  15

Met Ala Leu Leu Leu Ala Phe Phe Ile Asp Glu Ile Glu Ile Ile Gly
            20                  25                  30

Ile Val Ala Asp Tyr Gly Asn Val Pro Lys Lys Met Ala Val Gln Asn
        35                  40                  45

Ala His Phe Leu Thr Asn Glu Thr Arg Asn Arg Asn Ile Lys Ile Phe
    50                  55                  60

Gly Gly Ser Glu Arg Pro Leu Thr Gly Ala Pro Ala Phe Phe Thr
65                  70                  75                  80

Glu Val His Gly Lys Gln Gly Leu Gly Pro Ile Ile Pro Asn Gly Asn
                85                  90                  95

Val Thr Asn Gly Glu Met Glu Asn Phe Phe Glu Val Ile Pro Leu Ile
            100                 105                 110

Glu Gln Tyr Lys Asp Glu Leu Ile Ile Val Ser Leu Gly Arg Leu Thr
        115                 120                 125

Ser Leu Ala Ile Leu Phe Ile Met Cys Lys Gln Leu Met Lys Gln Ile
    130                 135                 140

Lys Ser Tyr Tyr Val Met Gly Gly Ala Phe Leu His Pro Gly Asn Val
145                 150                 155                 160

Thr Pro Ile Ser Glu Ala Asn Phe Tyr Gly Asp Pro Thr Ala Ala Asn
                165                 170                 175

Ile Val Leu Gln Ser Ala Ala Asn Met Tyr Ile Tyr Pro Leu Asn Val
            180                 185                 190

Thr Gln Tyr Ser Val Ile Thr Pro Glu Met Ala Glu Tyr Ile Glu Ala
        195                 200                 205

Lys Gly Lys Ala Pro Leu Val Lys Pro Leu Phe Asp His Tyr Tyr Tyr
    210                 215                 220

Gly Tyr Tyr Lys Asn Ala Leu Pro Asp Leu Lys Gly Ser Pro Phe His
225                 230                 235                 240

Asp Thr Met Pro Ile Leu Ala Leu Leu Asp Asn Ser Met Phe Thr Tyr
                245                 250                 255

His Lys Ser Pro Ile Val Val Met Ala Glu Ser Tyr Ala Gln Gly Ala
            260                 265                 270

Ser Ile Gly Glu Phe Arg Ser Leu Gly Lys Pro Lys Pro Phe Met Asp
        275                 280                 285

Trp Pro Ser His Gln Ile Ala Ile Asp Phe Asp Tyr Asn Arg Phe Phe
    290                 295                 300

Lys His Phe Met Ser Leu Met Thr Gly Glu Gln Phe
305                 310                 315

<210> SEQ ID NO 252
```

```
<211> LENGTH: 379
<212> TYPE: PRT
<213> ORGANISM: Bacillus subtilis

<400> SEQUENCE: 252

Ser Lys Arg Arg Met Lys Tyr His Ser Asn Asn Glu Ile Ser Tyr Tyr
1               5                   10                  15

Asn Phe Leu His Ser Met Lys Asp Lys Ile Val Thr Val Tyr Arg Gly
            20                  25                  30

Gly Pro Glu Ser Lys Lys Gly Lys Leu Thr Ala Val Lys Ser Asp Tyr
        35                  40                  45

Ile Ala Leu Gln Ala Glu Lys Lys Ile Ile Tyr Tyr Gln Leu Glu His
50                  55                  60

Val Lys Ser Ile Thr Glu Asp Thr Asn Asn Ser Thr Thr Thr Ile Glu
65                  70                  75                  80

Thr Glu Glu Met Leu Asp Ala Asp Phe His Ser Leu Ile Gly His
                85                  90                  95

Leu Ile Asn Gln Ser Val Gln Phe Asn Gln Gly Gly Pro Glu Ser Lys
                100                 105                 110

Lys Gly Arg Leu Val Trp Leu Gly Asp Asp Tyr Ala Ala Leu Asn Thr
            115                 120                 125

Asn Glu Asp Gly Val Val Tyr Phe Asn Ile His His Ile Lys Ser Ile
130                 135                 140

Ser Lys His Glu Pro Asp Leu Lys Ile Glu Glu Gln Thr Pro Val Gly
145                 150                 155                 160

Val Leu Glu Ala Asp Asp Leu Ser Glu Val Phe Lys Ser Leu Thr His
                165                 170                 175

Lys Trp Val Ser Ile Asn Arg Gly Gly Pro Glu Ala Ile Glu Gly Ile
            180                 185                 190

Leu Val Asp Asn Ala Asp Gly His Tyr Thr Ile Val Lys Asn Gln Glu
        195                 200                 205

Val Leu Arg Ile Tyr Pro Phe His Ile Lys Ser Ile Ser Leu Gly Pro
210                 215                 220

Lys Gly Ser Tyr Lys Lys Glu Asp Gln Lys Asn Glu Gln Asn Gln Glu
225                 230                 235                 240

Asp Asn Asn Asp Lys Asp Ser Asn Ser Phe Ile Ser Ser Lys Ser Tyr
                245                 250                 255

Ser Ser Ser Lys Ser Lys Ser Arg Ser Leu Lys Ser Ser Asp Asp Gln
            260                 265                 270

Ser Ser Lys Ser Gly Arg Ser Ser Arg Ser Lys Ser Ser Lys Ser
        275                 280                 285

Ser Lys Arg Ser Leu Lys Ser Ser Asp Tyr Gln Ser Ser Lys Ser Gly
290                 295                 300

Arg Ser Ser Arg Ser Lys Ser Ser Lys Ser Ser Lys Arg Ser Leu
305                 310                 315                 320

Lys Ser Ser Asp Tyr Gln Ser Ser Lys Ser Ser Lys Arg Ser Pro Arg
                325                 330                 335

Ser Ser Asp Tyr Gln Ser Ser Arg Ser Pro Gly Tyr Ser Ser Ser Ile
            340                 345                 350

Lys Ser Gly Lys Gln Lys Glu Asp Tyr Ser Tyr Glu Thr Ile Val
        355                 360                 365

Arg Thr Ile Asp Tyr His Trp Lys Arg Lys Phe
370                 375
```

```
<210> SEQ ID NO 253
<211> LENGTH: 66
<212> TYPE: PRT
<213> ORGANISM: Bacillus subtilis

<400> SEQUENCE: 253

Met Gly Tyr Tyr Lys Lys Tyr Lys Glu Glu Tyr Tyr Thr Val Lys Lys
1               5                   10                  15

Thr Tyr Tyr Lys Lys Tyr Tyr Glu Tyr Asp Lys Lys Asp Tyr Asp Cys
            20                  25                  30

Asp Tyr Asp Lys Lys Tyr Asp Asp Tyr Asp Lys Lys Tyr Tyr Asp His
        35                  40                  45

Asp Lys Lys Asp Tyr Asp Tyr Val Val Glu Tyr Lys Lys His Lys Lys
50                  55                  60

His Tyr
65

<210> SEQ ID NO 254
<211> LENGTH: 132
<212> TYPE: PRT
<213> ORGANISM: Bacillus amyloliquefaciens

<400> SEQUENCE: 254

Ser Ser Glu Asn Ala Gln Leu Lys Lys Asp Leu Ile Lys Ala Val Leu
1               5                   10                  15

Ser Pro Leu Phe Pro Thr Ala Thr Glu Gly Gly Glu Asn Met Asp Ser
            20                  25                  30

Asn Leu Lys Ala Leu Leu Asp Ala Ala Ile Asp Gln Lys Val Asp Glu
        35                  40                  45

Ser Glu Thr Val Thr Ala Glu Ser Ile Leu Asp Pro Ser Leu Pro Ala
50                  55                  60

Arg Trp Ile Phe Ala Arg Ile Thr Pro Gly Thr Thr Ile Ser Ile Val
65                  70                  75                  80

Thr Asp Ser Gly Asp Met Ile Gly Pro Val Val Phe Val Ala Phe Asp
            85                  90                  95

Gln Val His Gly Ile Val Phe Val Thr Gln Glu Ser Ser Val Thr Pro
        100                 105                 110

Ala Gly Gln Ala Thr Thr Leu Ile Asp Val Asp Lys Val Glu Ser Val
    115                 120                 125

Thr Phe Phe Ser
    130

<210> SEQ ID NO 255
<211> LENGTH: 291
<212> TYPE: PRT
<213> ORGANISM: Bacillus amyloliquefaciens

<400> SEQUENCE: 255

Met Lys Arg Asn Thr Asn Arg His Arg Ser Asp Asp Asn Phe Leu His
1               5                   10                  15

Ala Met Glu Gly Lys Val Ile Thr Val Tyr Arg Gly Gly Pro Glu Ser
            20                  25                  30

Lys Thr Gly Arg Leu Ala Asp Ile Gln Ser Asp Tyr Ile Ala Leu Gln
        35                  40                  45

Val Asp Asn Lys Ile Val Tyr Tyr Gln Trp Lys His Val Lys Ser Val
50                  55                  60

Thr Glu Asn Thr Ser Glu Thr Val Ser Pro Ala Glu Ser Ala Glu Cys
65                  70                  75                  80
```

```
Glu Lys Ala Asp Asp Phe Gln Glu Leu Ile Glu Arg Met Ala Asn Arg
                85                  90                  95

Thr Val Gln Leu Asn Gln Gly Gly Pro Glu Ser Lys Lys Gly Lys Leu
            100                 105                 110

His Glu Thr Gly Asp Asp Phe Leu Val Leu Glu Thr Glu Asp Asp Gly
            115                 120                 125

Ile Val Tyr Phe Asn Ile Asp His Val Lys Ser Ile Ser Ala Glu Gln
130                 135                 140

Glu Asp Glu Asp Glu Gln Glu Asp Glu Arg Thr Glu Phe Glu Met Ala
145                 150                 155                 160

Asp Asp Phe His Gly Ile Phe Lys Arg Leu Ile His Lys Trp Val Ser
                165                 170                 175

Ile Asn Arg Gly Gly Pro Glu Ala Val Glu Gly Ile Leu Val Asp Asn
                180                 185                 190

Ser Asp Gly His Tyr Thr Leu Val Lys Asp Lys Glu Val Leu Arg Ile
                195                 200                 205

His Pro Leu His Ile Lys Ser Ile Ser Ala Gly Ala Lys Gly Ala Ala
            210                 215                 220

Lys Lys Glu Glu Asn Lys Asp Glu Asn Gln Gly Glu Lys Glu Cys Ala
225                 230                 235                 240

Glu Glu Glu Ser His Glu Glu Gln His Thr Ser Ser Glu Lys Ser Lys
                245                 250                 255

Arg Ser Ser Lys Glu Asp Arg Ser Ser Lys Arg Asp Glu Asp Glu Ser
                260                 265                 270

Tyr Ser Tyr Ala Thr Val Leu Arg Thr Ile Asp Tyr Arg Trp Lys Arg
                275                 280                 285

Gly Arg Lys
    290

<210> SEQ ID NO 256
<211> LENGTH: 195
<212> TYPE: PRT
<213> ORGANISM: Bacillus subtilis

<400> SEQUENCE: 256

Leu Gly His Tyr Ser His Ser Asp Ile Glu Glu Ala Val Lys Ser Ala
1               5                   10                  15

Lys Lys Glu Gly Leu Lys Asp Tyr Leu Tyr Gln Glu Pro His Gly Lys
                20                  25                  30

Lys Arg Ser His Lys Lys Ser His Arg Thr His Lys Lys Ser Arg Ser
            35                  40                  45

His Lys Lys Ser Tyr Cys Ser His Lys Lys Ser Arg Ser His Lys Lys
        50                  55                  60

Ser Phe Cys Ser His Lys Lys Ser Arg Ser His Lys Lys Ser Tyr Cys
65                  70                  75                  80

Ser His Lys Lys Ser Arg Ser His Lys Lys Ser Tyr Arg Ser His Lys
                85                  90                  95

Lys Ser Arg Ser Tyr Lys Lys Ser Tyr Arg Ser Tyr Lys Lys Ser Arg
                100                 105                 110

Ser Tyr Lys Lys Ser Cys Arg Ser Tyr Lys Lys Ser Arg Ser Tyr Lys
            115                 120                 125

Lys Ser Tyr Cys Ser His Lys Lys Ser Arg Ser Tyr Lys Lys Ser
        130                 135                 140

Cys Arg Thr His Lys Lys Ser Tyr Arg Ser His Lys Lys Tyr Tyr Lys
```

```
145                 150                 155                 160
Lys Pro His His His Cys Asp Asp Tyr Lys Arg His Asp Asp Tyr Asp
                165                 170                 175

Ser Lys Lys Glu Tyr Trp Lys Asp Gly Asn Cys Trp Val Val Lys Lys
                180                 185                 190

Lys Tyr Lys
        195

<210> SEQ ID NO 257
<211> LENGTH: 394
<212> TYPE: PRT
<213> ORGANISM: Bacillus megaterium

<400> SEQUENCE: 257

Met Ser Asn Tyr Tyr Gly Gln Glu Gln Gly Gln Asn Gln Asn Pro
1               5                   10                  15

Ser Gln Lys Ser Ser Gln Lys Arg Ser Arg Asn Ile Gln Met Pro Asp
                20                  25                  30

Lys Gly Tyr Ser Ser His Phe Lys Pro Leu Lys Gly Arg Val Val Thr
                35                  40                  45

Val Tyr Arg Gly Gly Pro Glu Ser Lys Thr Gly Tyr Leu Val Asp Val
        50                  55                  60

Gln Ser Asp Tyr Leu Ile Leu Ala Val Glu Ser Asn Asn Asn Asn
65                  70                  75                  80

Gly Glu Asn Asn Asn Gln Asn Asn Gln Asn Asn Gln Asn Asn Gln Asn
                85                  90                  95

Asn Asn Gln Gln Glu Tyr Thr Leu Val Tyr Tyr His Leu Ala His Val
                100                 105                 110

Lys Ser Ile Thr Glu Asp Thr Met Ser Asn Ser Ala Gln Thr Phe Thr
                115                 120                 125

Gly Ile Ser Ala Asp Leu Glu Leu Tyr Arg Gly Lys Thr Phe Ala Gly
        130                 135                 140

Thr Leu Ser Leu Met Lys Thr Lys Tyr Val Gln Val Asn Gln Gly Gly
145                 150                 155                 160

Pro Glu Lys Lys Ala Gly Gln Leu Leu Asp Val Leu Gly Ser Phe Glu
                165                 170                 175

Ser Ala Tyr Ile Val Leu Leu Thr Glu Asp Asp Gly Ile Ile Tyr Ile
                180                 185                 190

Asn Thr Asp His Val Lys Ser Val Ser Glu Tyr Gln Asn Asn Asn Gly
                195                 200                 205

Asp Gln Thr Thr Gln Ser Val Asn Glu Leu Ser Val Ser Gln Glu Pro
        210                 215                 220

Glu Tyr Met Lys Ser Lys Ser Phe Asn Asp Leu Phe Ala His Leu Ser
225                 230                 235                 240

His Lys Trp Val Ser Ile Asn Asn Gly Gly Pro Glu Ala Val Glu Gly
                245                 250                 255

Val Leu Val Gln Ser Arg Asn Gly Thr Phe Thr Leu Val Gln Asn Asn
                260                 265                 270

Gln Val Leu Arg Leu Gln Pro Arg His Val Lys Thr Ile Cys Val Gly
                275                 280                 285

Ala Lys Gly Ala Phe Lys Gln Asn Asp Asn Asn Gln Asn Asn Glu Gln
        290                 295                 300

Thr Glu Glu Asn Gly Glu Thr Glu Ala Ala Glu Ser Thr Glu Glu Arg
305                 310                 315                 320
```

```
Thr Gly Gly Arg Thr Gly Gly Arg Thr Gly Gly Arg Thr Gly Asp Arg
            325                 330                 335

Thr Gly Arg Arg Thr Gly Arg Arg Thr Gly Asp Arg Thr Gly Asp Arg
            340                 345                 350

Thr Gly Asp Arg Thr Gly Arg Arg Thr Gly Gly Arg Thr Asp Asp Arg
            355                 360                 365

Ser Arg Gly Arg Arg Thr Gly Ser Arg Ser Ala Pro Ala Glu Lys
            370                 375             380

Val Ile Lys Thr Lys Asn Tyr Arg Trp Lys
385                 390

<210> SEQ ID NO 258
<211> LENGTH: 160
<212> TYPE: PRT
<213> ORGANISM: Bacillus amyloliquefaciens

<400> SEQUENCE: 258

Met Ser Cys Gly Lys His His Gly Arg Asp Glu Asn Cys Val Cys Asp
1               5                   10                  15

Ala Val Glu Lys Ile Leu Ala Glu Gln Glu Ala Val Glu Glu Gln Cys
            20                  25                  30

Pro Thr Gly Cys Tyr Ser Asn Leu Leu Ser Pro Thr Val Thr Gly Lys
        35                  40                  45

Asp Thr Ile Pro Phe Leu Leu Phe Asp Lys Lys Gly Gly Leu Phe Ser
    50                  55                  60

Thr Phe Gly Asn Val Gly Gly Phe Ala Asp Asp Ser Gln Cys Phe Glu
65                  70                  75                  80

Ser Ile Phe Phe Arg Ala Glu Arg Val Cys Asp Cys Cys Ala Thr Leu
                85                  90                  95

Ser Ile Leu Arg Pro Val Asp Val His Gly Asp Thr Leu Ser Val Cys
            100                 105                 110

His Pro Cys Asp Pro Asp Phe Phe Gly Leu Glu Lys Thr Asp Phe Cys
        115                 120                 125

Ile Glu Val Asp Leu Ser Cys Phe Ser Ala Ile Gln Cys Leu Ser Pro
    130                 135                 140

Glu Leu Val Asp Arg Pro Ala Pro His Lys Glu Lys Lys His His Gly
145                 150                 155                 160

<210> SEQ ID NO 259
<211> LENGTH: 162
<212> TYPE: PRT
<213> ORGANISM: Bacillus licheniformis

<400> SEQUENCE: 259

Met Ser Cys Gly Lys His His Gly Arg His Glu Asn Cys Val Cys Asp
1               5                   10                  15

Ala Val Glu Gln Ile Ile Lys Glu Gln Asp Ala Val Glu Glu Thr Thr
            20                  25                  30

Ala Cys Ser Thr Ser Cys Phe Gly Asn Leu Leu Ser Pro Thr Val Ser
        35                  40                  45

Gly Lys Asp Thr Ile Pro Phe Leu Leu Tyr Asp Lys Lys Gly Gly Leu
    50                  55                  60

Phe Ser Thr Phe Gly Asn Val Gly Gly Phe Ser Asp Asp Met Gln Cys
65                  70                  75                  80

Phe Glu Ser Ile Phe Phe Arg Ala Glu Ser Leu Lys Asp Cys Cys Ala
                85                  90                  95
```

```
Thr Leu Ser Ile Leu Arg Pro Val Asp Ile Asn Gly Asp Thr Leu Ser
            100                 105                 110

Val Cys His Pro Cys Asp Pro Asp Phe Phe Gly Leu Glu Lys Thr Asp
        115                 120                 125

Phe Cys Ile Glu Val Asp Leu Thr Cys Phe Cys Ala Ile Gln Cys Leu
    130                 135                 140

Ser Pro Asp Leu Val Asp Arg Ala Ala Asp Lys Lys His Asn His His
145                 150                 155                 160

His Gly

<210> SEQ ID NO 260
<211> LENGTH: 363
<212> TYPE: PRT
<213> ORGANISM: Bacillus subtilis

<400> SEQUENCE: 260

Met Glu Glu Lys Glu Ile Leu Trp Asn Glu Ala Lys Ala Phe Ile Ala
1               5                   10                  15

Ala Cys Tyr Gln Glu Leu Gly Lys Glu Glu Val Lys Asp Arg Leu
            20                  25                  30

Ala Asp Ile Lys Ser Glu Ile Asp Leu Thr Gly Ser Tyr Val His Thr
            35                  40                  45

Lys Glu Glu Leu Glu His Gly Ala Lys Met Ala Trp Arg Asn Ser Asn
50                  55                  60

Arg Cys Ile Gly Arg Leu Phe Trp Asn Ser Leu Asn Val Ile Asp Arg
65                  70                  75                  80

Arg Asp Val Arg Thr Lys Glu Val Arg Asp Ala Leu Phe His His
            85                  90                  95

Ile Glu Thr Ala Thr Asn Asn Gly Lys Ile Arg Pro Thr Ile Thr Ile
            100                 105                 110

Phe Pro Pro Glu Glu Lys Gly Glu Lys Gln Val Glu Ile Trp Asn His
        115                 120                 125

Gln Leu Ile Arg Tyr Ala Gly Tyr Glu Ser Asp Gly Glu Arg Ile Gly
    130                 135                 140

Asp Pro Ala Ser Cys Ser Leu Thr Ala Ala Cys Glu Glu Leu Gly Trp
145                 150                 155                 160

Arg Gly Glu Arg Thr Asp Phe Asp Leu Leu Pro Leu Ile Phe Arg Met
                165                 170                 175

Lys Gly Asp Glu Gln Pro Val Trp Tyr Glu Leu Pro Arg Ser Leu Val
            180                 185                 190

Ile Glu Val Pro Ile Thr His Pro Asp Ile Glu Ala Phe Ser Asp Leu
        195                 200                 205

Glu Leu Lys Trp Tyr Gly Val Pro Ile Ile Ser Asp Met Lys Leu Glu
    210                 215                 220

Val Gly Gly Ile His Tyr Asn Ala Ala Pro Phe Asn Gly Trp Tyr Met
225                 230                 235                 240

Gly Thr Glu Ile Gly Ala Arg Asn Leu Ala Asp Glu Lys Arg Tyr Asp
                245                 250                 255

Lys Leu Lys Lys Val Ala Ser Val Ile Gly Ile Ala Ala Asp Tyr Asn
            260                 265                 270

Thr Asp Leu Trp Lys Asp Gln Ala Leu Val Glu Leu Asn Lys Ala Val
        275                 280                 285

Leu His Ser Tyr Lys Lys Gln Gly Val Ser Ile Val Asp His His Thr
    290                 295                 300
```

```
Ala Ala Ser Gln Phe Lys Arg Phe Glu Glu Gln Glu Glu Glu Ala Gly
305                 310                 315                 320

Arg Lys Leu Thr Gly Asp Trp Thr Trp Leu Ile Pro Pro Ile Ser Pro
            325                 330                 335

Ala Ala Thr His Ile Phe His Arg Ser Tyr Asp Asn Ser Ile Val Lys
        340                 345                 350

Pro Asn Tyr Phe Tyr Gln Asp Lys Pro Tyr Glu
    355                 360

<210> SEQ ID NO 261
<211> LENGTH: 355
<212> TYPE: PRT
<213> ORGANISM: Bacillus thuringiensis

<400> SEQUENCE: 261

Met Ser Lys Thr Lys Gln Leu Ile Glu Glu Ala Ser His Phe Ile Thr
1               5                   10                  15

Ile Cys Tyr Lys Glu Leu Ser Lys Glu His Phe Ile Glu Glu Arg Met
            20                  25                  30

Lys Glu Ile Gln Ala Glu Ile Glu Lys Thr Gly Thr Tyr Glu His Thr
        35                  40                  45

Phe Glu Glu Leu Val His Gly Ser Arg Met Ala Trp Arg Asn Ser Asn
50                  55                  60

Arg Cys Ile Gly Arg Leu Phe Trp Ser Lys Met His Ile Leu Asp Ala
65                  70                  75                  80

Arg Glu Val Asn Asp Glu Glu Gly Val Tyr His Ala Leu Ile His His
                85                  90                  95

Ile Lys Tyr Ala Thr Asn Asp Gly Lys Val Lys Pro Thr Ile Thr Ile
            100                 105                 110

Phe Lys Gln Tyr Gln Gly Glu Glu Asn Asn Ile Arg Ile Tyr Asn His
        115                 120                 125

Gln Leu Ile Arg Tyr Ala Gly Tyr Lys Thr Glu Met Gly Val Thr Gly
130                 135                 140

Asp Ser His Ser Thr Ala Phe Thr Asp Phe Cys Gln Glu Leu Gly Trp
145                 150                 155                 160

Gln Gly Glu Gly Thr Asn Phe Asp Val Leu Pro Leu Val Phe Ser Ile
                165                 170                 175

Asp Gly Lys Ala Pro Ile Tyr Lys Glu Ile Pro Lys Glu Glu Val Lys
            180                 185                 190

Glu Val Pro Ile Glu His Pro Glu Tyr Pro Ile Ser Ser Leu Gly Ala
        195                 200                 205

Lys Trp Tyr Gly Val Pro Met Ile Ser Asp Met Arg Leu Glu Ile Gly
210                 215                 220

Gly Ile Ser Tyr Thr Ala Ala Pro Phe Asn Gly Trp Tyr Met Gly Thr
225                 230                 235                 240

Glu Ile Gly Ala Arg Asn Leu Ala Asp His Asp Arg Tyr Asn Leu Leu
                245                 250                 255

Pro Ala Val Ala Glu Met Met Asp Leu Asp Thr Ser Arg Asn Gly Thr
            260                 265                 270

Leu Trp Lys Asp Lys Ala Leu Ile Glu Leu Asn Val Ala Val Leu His
        275                 280                 285

Ser Phe Lys Lys Gln Gly Val Ser Ile Val Asp His His Thr Ala Ala
290                 295                 300

Gln Gln Phe Gln Gln Phe Glu Lys Gln Glu Ala Ala Cys Gly Arg Val
305                 310                 315                 320
```

Val Thr Gly Asn Trp Val Trp Leu Ile Pro Pro Leu Ser Pro Ala Thr
                    325                 330                 335

Thr His Ile Tyr His Lys Pro Tyr Pro Asn Glu Ile Leu Lys Pro Asn
                340                 345                 350

Phe Phe His
        355

<210> SEQ ID NO 262
<211> LENGTH: 386
<212> TYPE: PRT
<213> ORGANISM: Bacillus subtilis

<400> SEQUENCE: 262

Met Ala Phe Asp Pro Asn Leu Val Gly Pro Thr Leu Pro Pro Ile Pro
1               5                   10                  15

Pro Ala Ala Ala Ala Ala Met Glu Glu Lys Glu Ile Leu Trp Asn
            20                  25                  30

Glu Ala Lys Ala Phe Ile Ala Ala Cys Tyr Gln Glu Leu Gly Lys Glu
            35                  40                  45

Glu Glu Val Lys Asp Arg Leu Ala Asp Ile Lys Ser Glu Ile Asp Leu
50                  55                  60

Thr Gly Ser Tyr Val His Thr Lys Glu Glu Leu Glu His Gly Ala Lys
65                  70                  75                  80

Met Ala Trp Arg Asn Ser Asn Arg Cys Ile Gly Arg Leu Phe Trp Asn
                85                  90                  95

Ser Leu Asn Val Ile Asp Arg Arg Asp Val Arg Thr Lys Glu Glu Val
            100                 105                 110

Arg Asp Ala Leu Phe His His Ile Glu Thr Ala Thr Asn Asn Gly Lys
        115                 120                 125

Ile Arg Pro Thr Ile Thr Ile Phe Pro Pro Glu Glu Lys Gly Glu Lys
130                 135                 140

Gln Val Glu Ile Trp Asn His Gln Leu Ile Arg Tyr Ala Gly Tyr Glu
145                 150                 155                 160

Ser Asp Gly Glu Arg Ile Gly Asp Pro Ala Ser Cys Ser Leu Thr Ala
                165                 170                 175

Ala Cys Glu Glu Leu Gly Trp Arg Gly Glu Arg Thr Asp Phe Asp Leu
            180                 185                 190

Leu Pro Leu Ile Phe Arg Met Lys Gly Asp Glu Gln Pro Val Trp Tyr
        195                 200                 205

Glu Leu Pro Arg Ser Leu Val Ile Glu Val Pro Ile Thr His Pro Asp
210                 215                 220

Ile Glu Ala Phe Ser Asp Leu Glu Leu Lys Trp Tyr Gly Val Pro Ile
225                 230                 235                 240

Ile Ser Asp Met Lys Leu Glu Val Gly Gly Ile His Tyr Asn Ala Ala
                245                 250                 255

Pro Phe Asn Gly Trp Tyr Met Gly Thr Glu Ile Gly Ala Arg Asn Leu
            260                 265                 270

Ala Asp Glu Lys Arg Tyr Asp Lys Leu Lys Lys Val Ala Ser Val Ile
        275                 280                 285

Gly Ile Ala Ala Asp Tyr Asn Thr Asp Leu Trp Lys Asp Gln Ala Leu
290                 295                 300

Val Glu Leu Asn Lys Ala Val Leu His Ser Tyr Lys Lys Gln Gly Val
305                 310                 315                 320

Ser Ile Val Asp His His Thr Ala Ala Ser Gln Phe Lys Arg Phe Glu

```
            325                 330                 335
Glu Gln Glu Glu Glu Ala Gly Arg Lys Leu Thr Gly Asp Trp Thr Trp
            340                 345                 350

Leu Ile Pro Pro Ile Ser Pro Ala Ala Thr His Ile Phe His Arg Ser
            355                 360                 365

Tyr Asp Asn Ser Ile Val Lys Pro Asn Tyr Phe Tyr Gln Asp Lys Pro
370                 375                 380

Tyr Glu
385

<210> SEQ ID NO 263
<211> LENGTH: 378
<212> TYPE: PRT
<213> ORGANISM: Bacillus thuringiensis

<400> SEQUENCE: 263

Met Ala Phe Asp Pro Asn Leu Val Gly Pro Thr Leu Pro Pro Ile Pro
1               5                   10                  15

Pro Ala Ala Ala Ala Ala Met Ser Lys Thr Lys Gln Leu Ile Glu
            20                  25                  30

Glu Ala Ser His Phe Ile Thr Ile Cys Tyr Lys Glu Leu Ser Lys Glu
        35                  40                  45

His Phe Ile Glu Glu Arg Met Lys Glu Ile Gln Ala Glu Ile Glu Lys
    50                  55                  60

Thr Gly Thr Tyr Glu His Thr Phe Glu Glu Leu Val His Gly Ser Arg
65                  70                  75                  80

Met Ala Trp Arg Asn Ser Asn Arg Cys Ile Gly Arg Leu Phe Trp Ser
                85                  90                  95

Lys Met His Ile Leu Asp Ala Arg Glu Val Asn Asp Glu Glu Gly Val
            100                 105                 110

Tyr His Ala Leu Ile His His Ile Lys Tyr Ala Thr Asn Asp Gly Lys
        115                 120                 125

Val Lys Pro Thr Ile Thr Ile Phe Lys Gln Tyr Gln Gly Glu Glu Asn
    130                 135                 140

Asn Ile Arg Ile Tyr Asn His Gln Leu Ile Arg Tyr Ala Gly Tyr Lys
145                 150                 155                 160

Thr Glu Met Gly Val Thr Gly Asp Ser His Ser Thr Ala Phe Thr Asp
                165                 170                 175

Phe Cys Gln Glu Leu Gly Trp Gln Gly Glu Gly Thr Asn Phe Asp Val
            180                 185                 190

Leu Pro Leu Val Phe Ser Ile Asp Gly Lys Ala Pro Ile Tyr Lys Glu
        195                 200                 205

Ile Pro Lys Glu Glu Val Lys Glu Val Pro Ile Glu His Pro Glu Tyr
    210                 215                 220

Pro Ile Ser Ser Leu Gly Ala Lys Trp Tyr Gly Val Pro Met Ile Ser
225                 230                 235                 240

Asp Met Arg Leu Glu Ile Gly Gly Ile Ser Tyr Thr Ala Ala Pro Phe
                245                 250                 255

Asn Gly Trp Tyr Met Gly Thr Glu Ile Gly Ala Arg Asn Leu Ala Asp
            260                 265                 270

His Asp Arg Tyr Asn Leu Leu Pro Ala Val Ala Glu Met Met Asp Leu
        275                 280                 285

Asp Thr Ser Arg Asn Gly Thr Leu Trp Lys Asp Lys Ala Leu Ile Glu
    290                 295                 300
```

```
Leu Asn Val Ala Val Leu His Ser Phe Lys Lys Gln Gly Val Ser Ile
305                 310                 315                 320

Val Asp His His Thr Ala Ala Gln Gln Phe Gln Gln Phe Glu Lys Gln
                325                 330                 335

Glu Ala Ala Cys Gly Arg Val Val Thr Gly Asn Trp Val Trp Leu Ile
                340                 345                 350

Pro Pro Leu Ser Pro Ala Thr Thr His Ile Tyr His Lys Pro Tyr Pro
            355                 360                 365

Asn Glu Ile Leu Lys Pro Asn Phe Phe His
        370                 375

<210> SEQ ID NO 264
<211> LENGTH: 72
<212> TYPE: PRT
<213> ORGANISM: Bacillus subtilis

<400> SEQUENCE: 264

Met Ala Gln Gln Ser Arg Ser Arg Ser Asn Asn Asn Asn Asp Leu Leu
1               5                   10                  15

Ile Pro Gln Ala Ala Ser Ala Ile Glu Gln Met Lys Leu Glu Ile Ala
            20                  25                  30

Ser Glu Phe Gly Val Gln Leu Gly Ala Glu Thr Thr Ser Arg Ala Asn
        35                  40                  45

Gly Ser Val Gly Gly Ile Thr Lys Arg Leu Val Arg Leu Ala Gln
    50                  55                  60

Gln Asn Met Gly Gly Gln Phe His
65                  70

<210> SEQ ID NO 265
<211> LENGTH: 69
<212> TYPE: PRT
<213> ORGANISM: Bacillus subtilis

<400> SEQUENCE: 265

Met Ala Asn Asn Ser Gly Asn Ser Asn Asn Leu Leu Val Pro Gly
1               5                   10                  15

Ala Ala Gln Ala Ile Asp Gln Met Lys Leu Glu Ile Ala Ser Glu Phe
            20                  25                  30

Gly Val Asn Leu Gly Ala Asp Thr Thr Ser Arg Ala Asn Gly Ser Val
        35                  40                  45

Gly Gly Glu Ile Thr Lys Arg Leu Val Ser Phe Ala Gln Gln Asn Met
    50                  55                  60

Gly Gly Gly Gln Phe
65

<210> SEQ ID NO 266
<211> LENGTH: 73
<212> TYPE: PRT
<213> ORGANISM: Bacillus thuringiensis

<400> SEQUENCE: 266

Met Lys Pro Ile Asn Ile Gln Asp Gln Phe Leu Asn Gln Ile Arg Lys
1               5                   10                  15

Glu Asn Thr Tyr Val Thr Val Phe Leu Leu Asn Gly Phe Gln Leu Arg
            20                  25                  30

Gly Gln Val Lys Gly Phe Asp Asn Phe Thr Val Leu Leu Glu Ser Glu
        35                  40                  45

Gly Lys Gln Gln Leu Ile Tyr Lys His Ala Ile Ser Thr Phe Ala Pro
```

```
                50                  55                  60
Gln Lys Asn Val Gln Leu Glu Leu Glu
 65                  70
```

<210> SEQ ID NO 267
<211> LENGTH: 97
<212> TYPE: PRT
<213> ORGANISM: Bacillus subtilis

<400> SEQUENCE: 267

```
Met Ala Phe Asp Pro Asn Leu Val Gly Pro Thr Leu Pro Pro Ile Pro
 1               5                  10                  15
Pro Ala Ala Ala Ala Ala Ala Ala Met Ala Gln Gln Ser Arg Ser
            20                  25                  30
Arg Ser Asn Asn Asn Asn Asp Leu Leu Ile Pro Gln Ala Ala Ser Ala
        35                  40                  45
Ile Glu Gln Met Lys Leu Glu Ile Ala Ser Glu Phe Gly Val Gln Leu
    50                  55                  60
Gly Ala Glu Thr Thr Ser Arg Ala Asn Gly Ser Val Gly Gly Glu Ile
 65                  70                  75                  80
Thr Lys Arg Leu Val Arg Leu Ala Gln Gln Asn Met Gly Gly Gln Phe
                85                  90                  95
His
```

<210> SEQ ID NO 268
<211> LENGTH: 94
<212> TYPE: PRT
<213> ORGANISM: Bacillus subtilis

<400> SEQUENCE: 268

```
Met Ala Phe Asp Pro Asn Leu Val Gly Pro Thr Leu Pro Pro Ile Pro
 1               5                  10                  15
Pro Ala Ala Ala Ala Ala Ala Ala Met Ala Asn Asn Ser Gly
            20                  25                  30
Asn Ser Asn Asn Leu Leu Val Pro Gly Ala Gln Ala Ile Asp Gln
        35                  40                  45
Met Lys Leu Glu Ile Ala Ser Glu Phe Gly Val Asn Leu Gly Ala Asp
    50                  55                  60
Thr Thr Ser Arg Ala Asn Gly Ser Val Gly Gly Glu Ile Thr Lys Arg
 65                  70                  75                  80
Leu Val Ser Phe Ala Gln Gln Asn Met Gly Gly Gln Phe
                85                  90
```

<210> SEQ ID NO 269
<211> LENGTH: 98
<212> TYPE: PRT
<213> ORGANISM: Bacillus thuringiensis

<400> SEQUENCE: 269

```
Met Ala Phe Asp Pro Asn Leu Val Gly Pro Thr Leu Pro Pro Ile Pro
 1               5                  10                  15
Pro Ala Ala Ala Ala Ala Ala Ala Met Lys Pro Ile Asn Ile Gln
            20                  25                  30
Asp Gln Phe Leu Asn Gln Ile Arg Lys Glu Asn Thr Tyr Val Thr Val
        35                  40                  45
Phe Leu Leu Asn Gly Phe Gln Leu Arg Gly Gln Val Lys Gly Phe Asp
    50                  55                  60
```

```
Asn Phe Thr Val Leu Leu Glu Ser Glu Gly Lys Gln Gln Leu Ile Tyr
 65                  70                  75                  80

Lys His Ala Ile Ser Thr Phe Ala Pro Gln Lys Asn Val Gln Leu Glu
                 85                  90                  95

Leu Glu

<210> SEQ ID NO 270
<211> LENGTH: 711
<212> TYPE: DNA
<213> ORGANISM: Bacillus mycoides
<220> FEATURE:
<221> NAME/KEY: misc_feature
<222> LOCATION: (20)..(21)
<223> OTHER INFORMATION: n is a, c, g, or t

<400> SEQUENCE: 270
ggagcacgcc gcgtgagtgn ngaaggcttt cgggtcgtaa aactctgttg ttagggaaga     60
acaagtgcta gttgaataag ctggcacctt gacggtacct aaccagaaag ccacggctaa   120
ctacgtgcca gcagccgcgg taatacgtag gtggcaagcg ttatccggaa ttattgggcg   180
taaagcgcgc gcaggtggtt tcttaagtct gatgtgaaag cccacggctc aaccgtggag   240
ggtcattgga aactgggaga cttgagtgca gaagaggaaa gtggaattcc atgtgtagcg   300
gtgaaatgcg tagagatatg gaggaacacc agtggcgaag cgactttctg gtctgtaac    360 tgacactgag gcgcgaaagc gtggggagca acaggatta gataccctgg tagtccacgc    420
cgtaaacgat gagtgctaag tgttagaggg tttccgccct ttagtgctga agttaacgca    480
ttaagcactc cgcctgggga gtacggccgc aaggctgaaa ctcaaaggaa ttgacggggg    540
cccgcacaag cggtggagca tgtggtttaa ttcgaagcaa cgcgaagaac cttaccaggt   600
cttgacatcc tctgaaaact ctagagatag agcttctcct tcgggagcag agtgacaggt    660
ggtgcatggt tgtcgtcagc tcgtgtcgtg agatgttggg ttaagtcccg c              711

<210> SEQ ID NO 271
<211> LENGTH: 719
<212> TYPE: DNA
<213> ORGANISM: Bacillus mycoides
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (640)..(642)
<223> OTHER INFORMATION: n is a, c, g, or t

<400> SEQUENCE: 271
aaagtctgac ggagcacgcc gcgtgagtga tgaaggcttt cgggtcgtaa aactctgttg     60
ttagggaaga acaagtgcta gttgaataag ctggcacctt gacggtacct aaccagaaag   120
ccacggctaa ctacgtgcca gcagccgcgg taatacgtag gtggcaagcg ttatccggaa   180
ttattgggcg taaagcgcgc gcaggtggtt tcttaagtct gatgtgaaag cccacggctc   240
aaccgtggag ggtcattgga aactgggaga cttgagtgca gaagaggaaa gtggaattcc   300
atgtgtagcg gtgaaatgcg tagagatatg gaggaacacc agtggcgaag cgactttct    360 ggtctgtaac tgacactgag gcgcgaaagc gtggggagca acaggatta gataccctgg    420 tagtccacgc cgtaaacgat gagtgctaag tgttagaggg tttccgccct ttagtgctga    480
agttaacgca ttaagcactc cgcctgggga gtacggccgc aaggctgaaa ctcaaaggaa    540
ttgacggggg cccgcacaag cggtggagca tgtggtttaa ttcgaagcaa cgcgaagaac    600
```

```
cttaccaggt cttgacatcc tctgaaaacn ctagagatan nncttctcct tcgggagcag    660
agtgacaggt ggtgcatggt tgtcgtcagc tcgtgtcgtg agatgttggg ttaagtccc     719
```

<210> SEQ ID NO 272
<211> LENGTH: 709
<212> TYPE: DNA
<213> ORGANISM: Bacillus mycoides

<400> SEQUENCE: 272

```
ggagcacgcc gcgtgagtga tgaaggcttt cgggtcgtaa aactctgttg ttagggaaga    60
acaagtgcta gttgaataag ctggcacctt gacggtacct aaccagaaag ccacggctaa   120
ctacgtgcca gcagccgcgg taatacgtag gtggcaagcg ttatccggaa ttattgggcg   180
taaagcgcgc gcaggtggtt tcttaagtct gatgtgaaag cccacggctc aaccgtggag   240
ggtcattgga aactgggaga cttgagtgca gaagaggaaa gtggaattcc atgtgtagcg   300
gtgaaatgcg tagagatatg gaggaacacc agtggcgaag cgactttctg gtctgtaac    360 tgacactgag gcgcgaaagc gtggggagca acaggatta gatacctgg tagtccacgc    420 cgtaaacgat gagtgctaag tgttagaggg tttccgccct ttagtgctga agttaacgca   480
ttaagcactc cgcctgggga gtacggccgc aaggctgaaa ctcaaaggaa ttgacggggg   540
cccgcacaag cggtggagca tgtggtttaa ttcgaagcaa cgcgaagaac cttaccaggt   600
cttgacatcc tctgacaacc ctagagatag gcttcccct tcggggcag agtgacaggt     660 ggtgcatggt tgtcgtcagc tcgtgtcgtg agatgttggg ttaagtccc                709
```

<210> SEQ ID NO 273
<211> LENGTH: 713
<212> TYPE: DNA
<213> ORGANISM: Bacillus cereus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t

<400> SEQUENCE: 273

```
ggancaacgc cgcgtgagtg angaaggctt tcgggtcgta aaactctgtt gttagggaag    60
aacaagtgct agttgaataa gctggcacct tgacggtacc taaccagaaa gccacggcta   120
actacgtgcc agcagccgcg gtaatacgta ggtggcaagc gttatccgga attattgggc   180
gtaaagcgcg cgcaggtggt ttcttaagtc tgatgtgaaa gcccacggct caaccgtgga   240
gggtcattgg aaactgggag acttgagtgc agaagaggaa agtggaattc catgtgtagc   300
ggtgaaatgc gtagagatat ggaggaacac cagtggcgaa ggcgactttc tggtctgtaa   360
ctgacactga ggcgcgaaag cgtggggagc aaacaggatt agataccctg gtagtccacg   420
ccgtaaacga tgagtgctaa gtgttagagg gtttccgccc tttagtgctg aagttaacgc   480
attaagcact ccgcctgggg agtacggccg caaggctgaa actcaaagga attgacgggg   540
gcccgcacaa gcggtggagc atgtggttta attcgaagca acgcgaagaa ccttaccagg   600
tcttgacatc ctctgaaaac tctagagata gagcttctcc ttcgggagca gagtgacagg   660
```
tggtgcatgg ttgtcgtcag ctcgtgtcgt gagatgntgg gttaagtccc gca 713

<210> SEQ ID NO 274
<211> LENGTH: 876
<212> TYPE: DNA
<213> ORGANISM: Bacillus thuringiensis

<400> SEQUENCE: 274
tctgacggag caacgccgcg tgagtgatga aggctttcgg gtcgtaaaac tctgttgtta 60
gggaagaaca agtgctagtt gaataagctg gcaccttgac ggtacctaac cagaaagcca 120
cggctaacta cgtgccagca gccgcggtaa tacgtaggtg gcaagcgtta tccggaatta 180
ttgggcgtaa agcgcgcgca ggtggtttct taagtctgat gtgaaagccc acggctcaac 240
cgtggagggt cattggaaac tgggagactt gagtgcagaa gaggaaagtg gaattccatg 300
tgtagcggtg aaatgcgtag agatatggag gaacaccagt ggcgaaggcg actttctggt 360
ctgtaactga cactgaggcg cgaaagcgtg gggagcaaac aggattagat accctggtag 420
tccacgccgt aaacgatgag tgctaagtgt tagagggttt ccgcccttta gtgctgaagt 480
taacgcatta agcactccgc ctggggagta cggccgcaag gctgaaactc aaaggaattg 540
acgggggccc gcacaagcgg tggagcatgt ggtttaattc gaagcaacgc gaagaacctt 600
accaggtctt gacatcctct gaaaacccta gagatagggc ttctccttcg ggagcagagt 660
gacaggtggt gcatggttgt cgtcagctcg tgtcgtgaga tgttgggtta agtcccgcaa 720
cgagcgcaac ccttgatctt agttgccatc attaagttgg gcactctaag gtgactgccg 780
gtgacaaacc ggaggaaggt ggggatgacg tcaaatcatc atgcccctta tgacctgggc 840
tacacacgtg ctacaatgga cggtacaaag agctgc 876

<210> SEQ ID NO 275
<211> LENGTH: 686
<212> TYPE: DNA
<213> ORGANISM: Bacillus cereus

<400> SEQUENCE: 275
aaggctttcg ggtcgtaaaa ctctgttgtt agggaagaac aagtgctagt tgaataagct 60
ggcaccttga cggtacctaa ccagaaagcc acggctaact acgtgccagc agccgcggta 120
atacgtaggt ggcaagcgtt atccggaatt attgggcgta aagcgcgcgc aggtggtttc 180
ttaagtctga tgtgaaagcc cacggctcaa ccgtggaggg tcattggaaa ctgggagact 240
tgagtgcaga agaggaaagt ggaattccat gtgtagcggt gaaatgcgta gagatatgga 300
ggaacaccag tggcgaaggc gactttctgg tctgtaactg acactgaggc gcgaaagcgt 360
ggggagcaaa caggattaga taccctggta gtccacgccg taaacgatga gtgctaagtg 420
ttagagggtt tccgcccttt agtgctgaag ttaacgcatt aagcactccg cctggggagt 480
acggccgcaa ggctgaaact caaaggaatt gacgggggcc cgcacaagcg gtggagcatg 540
tggtttaatt cgaagcaacg cgaagaacct taccaggtct tgacatcctc tgaaaaccct 600
agagataggg cttctccttc gggagcagag tgacaggtgg tgcatggttg tcgtcagctc 660
gtgtcgtgag atgttgggtt aagtcc 686

<210> SEQ ID NO 276
<211> LENGTH: 717
<212> TYPE: DNA
<213> ORGANISM: Bacillus mycoides
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 276

| | | | | | |
|---|---|---|---|---|---|
| gtctgangga | ncacgccgcg | tgagtgatga | aggctttcgg | gtcgtaaaac | tctgttgtta | 60 |
| gggaagaaca | agtgctagtt | gaataagctg | gcaccttgac | ggtacctaac | cagaaagcca | 120 |
| cggctaacta | cgtgccagca | gccgcggtaa | tacgtaggtg | gcaagcgtta | tccggaatta | 180 |
| ttgggcgtaa | agcgcgcgca | ggtggtttct | taagtctgat | gtgaaagccc | acggctcaac | 240 |
| cgtggagggt | cattggaaac | tgggagactt | gagtgcagaa | gaggaaagtg | gaattccatg | 300 |
| tgtagcggtg | aaatgcgtag | agatatggag | gaacaccagt | ggcgaaggcg | actttctggt | 360 |
| ctgtaactga | cactgaggcg | cgaaagcgtg | gggagcaaac | aggattagat | accctggtag | 420 |
| tccacgccgt | aaacgatgag | tgctaagtgt | tagagggttt | ccgccccttta | gtgctgaagt | 480 |
| taacgcatta | agcactccgc | ctggggagta | cggccgcaag | gctgaaactc | aaaggaattg | 540 |
| acggggccc | gcacaagcgg | tggagcatgt | ggtttaattc | gaagcaacgc | gaagaacctt | 600 |
| accaggtctt | gacatcctct | gacaacccta | gagatagggc | ttcccccttcg | ggggcagagt | 660 |
| gacaggtggt | gcatggttgt | cgtcagctcg | tgtcgtgaga | tgttgggtta | agtcccg | 717 |

<210> SEQ ID NO 277
<211> LENGTH: 720
<212> TYPE: DNA
<213> ORGANISM: Bacillus cereus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 277

| | | | | | |
|---|---|---|---|---|---|
| tntgacggan | cacgccgcgt | gagtgatgaa | ggctttcggg | tcgtaaaact | ctgttgttag | 60 |
| ggaagaacaa | gtgctagttg | aataagctgg | caccttgacg | gtacctaacc | agaaagccac | 120 |
| ggctaactac | gtgccagcag | ccgcggtaat | acgtaggtgg | caagcgttat | ccggaattat | 180 |
| tgggcgtaaa | gcgcgcgcag | gtggtttctt | aagtctgatg | tgaaagccca | cggctcaacc | 240 |
| gtggagggtc | attggaaact | gggagacttg | agtgcagaag | aggaaagtgg | aattccatgt | 300 |
| gtagcggtga | aatgcgtaga | gatatggagg | aacaccagtg | gcgaaggcga | ctttctggtc | 360 |
| tgtaactgac | actgaggcgc | gaaagcgtgg | ggagcaaaca | ggattagata | ccctggtagt | 420 |
| ccacgccgta | aacgatgagt | gctaagtgtt | agagggtttc | cgccctttag | tgctgaagtt | 480 |
| aacgcattaa | gcactccgcc | tggggagtac | ggccgcaagg | ctgaaactca | aaggaattga | 540 |
| cggggcccg | cacaagcggt | ggagcatgtg | gtttaattcg | aagcaacgcg | aagaacctta | 600 |
| ccaggtcttg | acatcctctg | aaacccctag | agatagggct | tctccttcgg | gagcagagtg | 660 |
| acaggtggtg | catggttgtc | gtcagctcgt | gtcgtgagat | gttgggttaa | gtcccgcaac | 720 |

<210> SEQ ID NO 278
<211> LENGTH: 616
<212> TYPE: DNA
<213> ORGANISM: Bacillus thuringiensis
<220> FEATURE:

```
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (123)..(124)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (192)..(194)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
```

-continued

```
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (385)..(387)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (458)..(459)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (522)..(523)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (593)..(595)
```

```
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t

<400> SEQUENCE: 278
ctttcnggnc gnaaaactct gttgttangg aanaacaant gctanttgaa taagctggcg      60
ccttgacggt acctaaccnn aaagccncgg ctaactacgt gccancagcc gcggtaatac     120
gtnngtggca agcgttatcc ggaattattg ggcgtaaagc gcgcgcaggt ggtttcttaa     180
ntctgatgtg annncccacg gctcnnccgt ggagggtcat tggaaactgg ganacttgag     240
tgcagaagag gaaagtggaa ttccatgtgt ancggtgaaa tgcgtanaga tatggangaa     300
cnccagtggc gaangcgact ttctggtctg taactgacac tgaggcgcga aagcgtgggg     360
agcaaacang attanatacc ctggnnntcc acgccgtana cnatgagtgc taagtgttan     420
agggtttccn ccctttagtg ctgaagttaa cgcattannc actccnectg gggagtacgg     480 ccgcaaggct gaaactcana ggaattgacn ggngcccnca cnngcggtgg agcatgtggt     540
ttaattcnaa gcaacncnaa naaccttacc nngtcttgac atcctctgaa aannntnnag     600
atagggcttc tccntc                                                     616

<210> SEQ ID NO 279
<211> LENGTH: 703
<212> TYPE: DNA
<213> ORGANISM: Bacillus cereus
<220> FEATURE:
<221> NAME/KEY: misc_feature
<222> LOCATION: (701)..(701)
<223> OTHER INFORMATION: n is a, c, g, or t

<400> SEQUENCE: 279
cacgccgcgt gagtgatgaa ggctttcggg tcgtaaaact ctgttgttag ggaagaacaa      60
gtgctagttg aataagctgg caccttgacg gtacctaacc agaaagccac ggctaactac     120
gtgccagcag ccgcggtaat acgtaggtgg caagcgttat ccggaattat tgggcgtaaa     180
gcgcgcgcag gtggtttctt aagtctgatg tgaaagccca cggctcaacc gtggagggtc     240
attggaaact gggagacttg agtgcagaag aggaaagtgg aattccatgt gtagcggtga     300
aatgcgtaga gatatggagg aacaccagtg gcgaaggcga ctttctggtc tgtaactgac     360
actgaggcgc gaaagcgtgg ggagcaaaca ggattagata ccctggtagt ccacgccgta     420
aacgatgagt gctaagtgtt agagggtttc cgcccttag tgctgaagtt aacgcattaa     480
gcactccgcc tggggagtac ggccgcaagg ctgaaactca aaggaattga cgggggcccg     540
cacaagcggt ggagcatgtg gtttaattcg aagcaacgcg aagaaccta ccaggtcttg     600 acatcctctg aaaaccctag atagggct tctccttcgg gagcagagtg acaggtggtg     660
catggttgtc gtcagctcgt gtcgtgagat gttgggttaa ntc                      703

<210> SEQ ID NO 280
<211> LENGTH: 717
<212> TYPE: DNA
<213> ORGANISM: Bacillus thuringiensis
<220> FEATURE:
<221> NAME/KEY: misc_feature
<222> LOCATION: (5)..(5)
<223> OTHER INFORMATION: n is a, c, g, or t
```

<220> FEATURE:
<221> NAME/KEY: misc_feature
<222> LOCATION: (8)..(9)
<223> OTHER INFORMATION: n is a, c, g, or t

<400> SEQUENCE: 280

| | | | | | |
|---|---|---|---|---|---|
| ctganggnnc | aacgccgcgt | gagtgatgaa | ggctttcggg | tcgtaaaact | ctgttgttag | 60 |
| ggaagaacaa | gtgctagttg | aataagctgg | caccttgacg | gtacctaacc | agaaagccac | 120 |
| ggctaactac | gtgccagcag | ccgcggtaat | acgtaggtgg | caagcgttat | ccggaattat | 180 |
| tgggcgtaaa | gcgcgcgcag | gtggtttctt | aagtctgatg | tgaaagccca | cggctcaacc | 240 |
| gtggagggtc | attggaaact | gggagacttg | agtgcagaag | aggaaagtgg | aattccatgt | 300 |
| gtagcggtga | aatgcgtaga | gatatggagg | aacaccagtg | gcgaaggcga | ctttctggtc | 360 |
| tgtaactgac | actgaggcgc | gaaagcgtgg | ggagcaaaca | ggattagata | ccctggtagt | 420 |
| ccacgccgta | aacgatgagt | gctaagtgtt | agagggtttc | cgcccttag | tgctgaagtt | 480 |
| aacgcattaa | gcactccgcc | tggggagtac | ggccgcaagg | ctgaaactca | aaggaattga | 540 |
| cggggcccg | cacaagcggt | ggagcatgtg | gtttaattcg | aagcaacgcg | aagaaccta | 600 |
| ccaggtcttg | acatcctctg | aaaaccctag | agatagggct | tctccttcgg | gagcagagtg | 660 |
| acaggtggtg | catggttgtc | gtcagctcgt | gtcgtgagat | gttgggttaa | gtcccgc | 717 |

<210> SEQ ID NO 281
<211> LENGTH: 712
<212> TYPE: DNA
<213> ORGANISM: Bacillus megaterium
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 281

| | | | | | |
|---|---|---|---|---|---|
| ggancacgcc | gcgtgagtga | tgaaggcttt | cgggtcgtaa | aactctgttg | ttagggaaga | 60 |
| acaagtacna | gagtaactgc | tngtaccttg | acggtaccta | accagaaagc | cacggctaac | 120 |
| tacgtgccag | cagccgcggt | aatacgtagg | tggcaagcgt | tatccggaat | tattgggcgt | 180 |
| aaagcgcgcg | caggcggttt | cttaagtctg | atgtgaaagc | ccacggctca | accgtggagg | 240 |
| gtcattggaa | actggggaac | ttgagtgcag | aagagaaaag | cggaattcca | cgtgtagcgg | 300 |
| tgaaatgcgt | agagatgtgg | aggaacacca | gtggcgaagg | cggcttttg | gtctgtaact | 360 |
| gacgctgagg | cgcgaaagcg | tggggagcaa | acaggattag | ataccctggt | agtccacgcc | 420 |
| gtaaacgatg | agtgctaagt | gttagagggt | ttccgccctt | tagtgctgca | gctaacgcat | 480 |
| taagcactcc | gcctggggag | tacggtcgca | agactgaaac | tcaaaggaat | tgacggggc | 540 |
| ccgcacaagc | ggtggagcat | gtggtttaat | tcgaagcaac | gcgaagaacc | ttaccaggtc | 600 |
| ttgacatcct | ctgacaactc | tagagataga | gcgttcccct | tcggggggaca | gagtgacagg | 660 |
| tggtgcatgg | ttgtcgtcag | ctcgtgtcgt | gagatgttgg | gttaagtccc | gc | 712 |

<210> SEQ ID NO 282
<211> LENGTH: 714
<212> TYPE: DNA

```
<213> ORGANISM: Bacillus sp.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t

<400> SEQUENCE: 282
```

| | | | | | |
|---|---|---|---|---|---|
| ggancacgcc | gcgtgnnnng | nngaaggttt | tcggatcgta | aagctctgtt | gttagggaag | 60 |
| aacaagtgca | agagtaactg | cttgcacctt | gacggtacct | aaccagaaag | ccacggctaa | 120 |
| ctacgtgcca | gcagccgcgg | taatacgtag | gtggcaagcg | ttgtccggaa | ttattgggcg | 180 |
| taaagggctc | gcaggcggtt | tcttaagtct | gatgtgaaag | cccccggctc | aaccggggag | 240 |
| ggtcattgga | aactgggaaa | cttgagtgca | gaagaggaga | gtggaattcc | acgtgtagcg | 300 |
| gtgaaatgcg | tagagatgtg | gaggaacacc | agtggcgaag | gcgactctct | ggtctgtaac | 360 |
| tgacgctgag | gagcgaaagc | gtggggagcg | aacaggatta | gatacctgg | tagtccacgc | 420 |
| cgtaaacgat | gagtgctaag | tgttagggggg | tttccgcccc | ttagtgctgc | agctaacgca | 480 |
| ttaagcactc | cgcctgggga | gtacggtcgc | aagactgaaa | ctcaaaggaa | ttgacggggg | 540 |
| cccgcacaag | cggtggagca | tgtggtttaa | ttcgaagcaa | cgcgaagaac | cttaccaggt | 600 |
| cttgacatcc | tctgacaacc | ctagagatag | ggctttccct | tcggggacag | agtgacaggt | 660 |
| ggtgcatggt | tgtcgtcagc | tcgtgtcgtg | agatgttggg | ttaagtcccg | caac | 714 |

```
<210> SEQ ID NO 283
<211> LENGTH: 718
<212> TYPE: DNA
<213> ORGANISM: Bacillus circulans
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 283
```

| | | | | | |
|---|---|---|---|---|---|
| aagtctgang | gancacgccg | cgtgagtgat | gaaggttttc | ggatcgtaaa | actctgttgt | 60 |
| tagggaagaa | caagtacaag | agtaactgct | tgtaccttga | cggtacctaa | ccagaaagcc | 120 |
| acggctaact | acgtgccagc | agccgcggta | atacgtaggt | ggcaagcgtt | gtccggaatt | 180 |
| attgggcgta | aagcgcgcgc | aggcggtcct | ttaagtctga | tgtgaaagcc | cacggctcaa | 240 |
| ccgtggaggg | tcattggaaa | ctgggggact | tgagtgcaga | agagaagagt | ggaattccac | 300 |
| gtgtagcggt | gaaatgcgta | gagatgtgga | ggaacaccag | tggcgaaggc | gactctttgg | 360 |
| tctgtaactg | acgctgaggc | gcgaaagcgt | ggggagcaaa | caggattaga | taccctggta | 420 |
| gtccacgccg | taaacgatga | gtgctaagtg | ttagagggtt | tccgccctt | agtgctgcag | 480 |
| caaacgcatt | aagcactccg | cctggggagt | acggccgcaa | ggctgaaact | caaaggaatt | 540 |
| gacggggggcc | cgcacaagcg | gtggagcatg | tggtttaatt | cgaagcaacg | cgaagaacct | 600 |
| taccaggtct | tgacatcctc | tgacactcct | agagatagga | cgttcccctt | cggggggacag | 660 |
| agtgacaggt | ggtgcatggt | tgtcgtcagc | tcgtgtcgtg | agatgttggg | ttaagtcc | 718 |

```
<210> SEQ ID NO 284
<211> LENGTH: 718
<212> TYPE: DNA
<213> ORGANISM: Bacillus subtilis
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 284
gtctgnngga ncacgccgcg tgagtgatga aggttttcgg atcgtaaagc tctgttgtta      60
gggaagaaca agtaccgttc gaatagggcg gtaccttgac ggtacctaac cagaaagcca    120
cggctaacta cgtgccagca gccgcggtaa tacgtaggtg gcaagcgttg tccggaatta    180
ttgggcgtaa agggctcgca ggcggtttct taagtctgat gtgaaagccc ccggctcaac    240
cggggagggt cattggaaac tggggaactt gagtgcagaa gaggagagtg gaattccacg    300
tgtagcggtg aaatgcgtag agatgtggag gaacaccagt ggcgaaggcg actctctggt    360
ctgtaactga cgctgaggag cgaaagcgtg gggagcgaac aggattagat accctggtag    420
tccacgccgt aaacgatgag tgctaagtgt taggggtttc cgccccttag tgctgcagc    480 taacgcatta agcactccgc ctggggagta cggtcgcaag actgaaactc aaaggaattg    540
acggggcccc gcacaagcgg tggagcatgt ggtttaattc gaagcaacgc gaagaacctt    600
accaggtctt gacatcctct gacaatccta gagataggac gtccccttcg ggggcagagt    660
gacaggtggt gcatggttgt cgtcagctcg tgtcgtgaga tgttgggtta agtcccgc      718

<210> SEQ ID NO 285
<211> LENGTH: 713
<212> TYPE: DNA
<213> ORGANISM: Lysinibacillus fusiformis
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 285
ctgatggagc acgccgcgtg agtgaagaag gatttcggtt cgtaaaactc tgttgtaagg      60
gaagaacaag tacagtagta actggctgta ccttgacggt accttattag aaagccacgg    120
ctaactacgt gccagcagcc gcggtaatac gtaggtggca agcgttgtcc ggaattattg    180
ggcgtaaagc gcgcgcaggt ggtttcttaa gtctgatgtg aaagcccacg gctcaaccgt    240
ggagggtcat tggaaactgg gagacttgag tgcagaagag gatagtggaa ttccaagtgt    300
agcggtgaaa tgcgtagaga tttggaggaa caccagtggc gaaggcgact atctggtctg    360
taactgacac tgaggcgcga aagcgtgggg agcaaacagg attagatacc ctggtagtcc    420
acgccgtaaa cgatgagtgc taagtgttag ggggtttccg ccccttagtg ctgcagctaa    480
cgcattaagc actccgcctg gggagtacgg tcgcaagact gaaactcaaa ggaattgacg    540
ggggcccgca caagcggtgg agcatgtggt ttaattcgaa gcaacgcgaa gaaccttacc    600
aggtcttgac atcccgttga ccactgtaga gatatggttt cccctt cggg ggcaacggtg    660
```

```
acaggtggtg catggttgtc gtcagctcgt gtcgtgagat gntgggttaa ntc          713
```

<210> SEQ ID NO 286
<211> LENGTH: 715
<212> TYPE: DNA
<213> ORGANISM: Lysinibcaillus sphaericus
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t

<400> SEQUENCE: 286

```
ctgatggagc ancgccgcgt gagtgaagaa ggttttcgga tcgtaaaact ctgttgtaag    60
ggaagaacaa gtacagtagt aactggctgt accttgacgg tacctttatta gaaagccacg   120
gctaactacg tgccagcagc cgcggtaata cgtaggtggc aagcgttgtc cggaattatt   180
gggcgtaaag cgcgcgcagg cggtccttta agtctgatgt gaaagcccac ggctcaaccg   240
tggagggtca ttggaaactg ggggacttga gtgcagaaga ggaaagtgga attccaagtg   300
tagcggtgaa atgcgtagag atttggagga acaccagtgg cgaaggcgac tttctggtct   360
gtaactgacg ctgaggcgcg aaagcgtggg gagcaaacag gattagatac cctggtagtc   420
cacgccgtaa acgatgagtg ctaagtgtta gggggtttcc gccccttagt gctgcagcta   480
acgcattaag cactccgcct ggggagtacg gtcgcaagac tgaaactcaa aggaattgac   540
gggggcccgc acaagcggtg gagcatgtgg tttaattcga gcaacgcga agaaccttac    600
caggtcttga catcccgttg accactgtag agatatagtt tccccttcgg ggcaacggt    660
gacaggtggt gcatggttgt cgtcagctcg tgtcgtgaga tgtngggtta antcc        715
```

<210> SEQ ID NO 287
<211> LENGTH: 717
<212> TYPE: DNA
<213> ORGANISM: Bacillus aryabhattai
<220> FEATURE:
<221> NAME/KEY: misc_feature
<222> LOCATION: (3)..(4)
<223> OTHER INFORMATION: n is a, c, g, or t

<400> SEQUENCE: 287

```
ggnncaacgc cgcgtgagtg atgaaggctt tcgggtcgta aaactctgtt gttagggaag    60
aacaagtacg agagtaactg ctcgtacctt gacggtacct aaccagaaag ccacggctaa   120
ctacgtgcca gcagccgcgg taatacgtag gtggcaagcg ttatccggaa ttattgggcg   180
taaagcgcgc gcaggcggtt cttaagtct gatgtgaaag cccacggctc aaccgtggag   240
ggtcattgga aactggggaa cttgagtgca gaagagaaaa gcggaattcc acgtgtagcg   300
gtgaaatgcg tagagatgtg gaggaacacc agtggcgaag gcggcttttt ggtctgtaac   360
tgacgctgag gcgcgaaagc gtggggagca aacaggatta gatacctgg tagtccacgc   420
cgtaaacgat gagtgctaag tgttagaggg tttccgccct tagtgctgc agctaacgca   480
ttaagcactc cgcctgggga gtacggtcgc aagactgaaa ctcaaaggaa ttgacggggg   540
cccgcacaag cggtggagca tgtggttaa ttcgaagcaa cgcgaagaac cttaccaggt   600
cttgacatcc tctgacaact ctagagatag agcgttcccc ttcggggac agagtgacag   660
```

```
gtggtgcatg gttgtcgtca gctcgtgtcg tgagatgttg ggttaagtcc cgcaacg        717
```

<210> SEQ ID NO 288
<211> LENGTH: 718
<212> TYPE: DNA
<213> ORGANISM: Bacillus aryabhattai
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 288

```
tctganggnn cacgccgcgt gagtgatgaa ggctttcggg tcgtaaaact ctgttgttag     60
ggaagaacaa gtacgagagt aactgctcgt accttgacgg tacctaacca gaaagccacg   120
gctaactacg tgccagcagc cgcggtaata cgtaggtggc aagcgttatc cggaattatt   180
gggcgtaaag cgcgcgcagg cggtttctta agtctgatgt gaaagcccac ggctcaaccg   240
tggagggtca ttggaaactg ggaacttga gtgcagaaga gaaaagcgga attccacgtg    300
tagcggtgaa atgcgtagag atgtggagga acaccagtgg cgaaggcggc ttttggtct    360
gtaactgacg ctgaggcgcg aaagcgtggg gagcaaacag gattagatac cctggtagtc   420
cacgccgtaa acgatgagtg ctaagtgtta gagggtttcc gcccttagt gctgcagcta    480
acgcattaag cactccgcct ggggagtacg gtcgcaagac tgaaactcaa aggaattgac   540
gggggcccgc acaagcggtg gagcatgtgg tttaattcga agcaacgcga agaaccttac   600
caggtcttga catcctctga caactctaga gatagagcgt tcccctccgg gggacagagt  660
gacaggtggt gcatggttgt cgtcagctcg tgtcgtgaga tgttgggtta agtcccgc    718
```

<210> SEQ ID NO 289
<211> LENGTH: 716
<212> TYPE: DNA
<213> ORGANISM: Bacillus flexus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 289

```
ggancaacgc cgcgtgagtg angaaggctt tcgggtcgta aaactctgtt gttagggaag    60
aacaagtaca agagtaactg cttgtaccct gacggtacct aaccagaaag ccacggctaa   120
ctacgtgcca gcagccgcgg taatacgtag gtggcaagcg ttatccggaa ttattgggcg   180
taaagcgcgc gcaggcggtt tcttaagtct gatgtgaaag cccacggctc aaccgtggag   240
ggtcattgga aactggggaa cttgagtgca gaagagaaaa gcggaattcc acgtgtagcg   300
gtgaaatgcg tagagatgtg gaggaacacc agtggcgaag gcggcttttt ggtctgtaac   360
tgacgctgag gcgcgaaagc gtggggagca acaggatta gataccctgg tagtccacgc    420
cgtaaacgat gagtgctaag tgttagaggg tttccgcccct ttagtgctgc agctaacgca   480
ttaagcactc cgcctgggga gtacggtcgc aagactgaaa ctcaaaggaa ttgacggggg   540
cccgcacaag cggtggagca tgtggtttaa ttcgaagcaa cgcgaagaac cttaccaggt   600
```

```
cttgacatcc tctgacaact ctagagatag agcgttcccc ttcgggggac agagtgacag    660
gtggtgcatg gttgtcgtca gctcgtgtcg tgagatgttg ggttaagtcc cgcaac        716
```

<210> SEQ ID NO 290
<211> LENGTH: 676
<212> TYPE: DNA
<213> ORGANISM: Paracoccus kondratievae
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 290

```
gccgcgtgag tgnnnaagnc cctagggttg taaagctctt tcanctggga agataatgac    60
tgtaccagca gaagaagccc cggctaactc cgtgccagca gccgcggtaa tacggagggg   120
gctagcgttg ttcggaatta ctgggcgtaa agcgcacgta ggcggaccgg aaagttgggg   180
gtgaaatccc ggggctcaac cccggaactg ccttcaaaac tatcggtctg gagttcgaga   240
gaggtgagtg gaattccgag tgtagaggtg aaattcgtag atattcggag gaacaccagt   300
ggcgaaggcg gctcactggc tcgatactga cgctgaggtg cgaaagcgtg gggagcaaac   360
aggattagat accctggtag tccacgccgt aaacgatgaa tgccagtcgt cgggcagcat   420
gctgttcggt gacacaccta acggattaag cattccgcct ggggagtacg gtcgcaagat   480
taaaactcaa aggaattgac gggggcccgc acaagcggtg gagcatgtgg tttaattcga   540
agcaacgcgc agaaccttac caacccttga catcccagga cagcccgaga gatcgggtct   600
ccacttcggt ggcctggaga caggtgctgc atggctgtcg tcagctcgtg tcgtgagatg   660
ttcggttaag tccggc                                                   676
```

<210> SEQ ID NO 291
<211> LENGTH: 728
<212> TYPE: DNA
<213> ORGANISM: Enterobacter cloacae
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t

<400> SEQUENCE: 291

```
ctgnngcagc cntgccgcgt gtatgaagaa ggncttcggg ttgtaaagta ctttcagcgg    60
ggaggaaggt gttgtggtta ataaccacag caattgacgt taccgcagaa gaagcaccg    120
```

-continued

```
gctaactccg tgccagcagc cgcggtaata cggagggtgc aagcgttaat cggaattact    180
gggcgtaaag cgcacgcagg cggtctgtca agtcggatgt gaaatccccg ggctcaacct    240
gggaactgca ttcgaaactg gcaggctaga gtcttgtaga ggggggtaga attccaggtg    300
tagcggtgaa atgcgtagag atctggagga ataccgtgg cgaaggcggc ccctggaca    360 aagactgacg ctcaggtgcg aaagcgtggg gagcaaacag gattagatac cctggtagtc    420
cacgccgtaa acgatgtcga tttggaggtt gtgcccttga ggcgtggctt ccggagctaa    480
cgcgttaaat cgaccgcctg gggagtacgg ccgcaaggtt aaaactcaaa tgaattgacg    540
ggggcccgca caagcggtgg agcatgtggt ttaattcgat gcaacgcgaa gaaccttacc    600
tggtcttgac atccacagaa ctttccagag atggattggt gccttcggga actgtgagac    660
aggtgctgca tggctgtcgt cagctcgtgt tgtgaaatgt tgggttaagt cccgcaacna    720 nncgcaac                                                             728
```

<210> SEQ ID NO 292
<211> LENGTH: 717
<212> TYPE: DNA
<213> ORGANISM: Bacillus nealsonii
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 292

```
tgnngganca acgccgcgtg agtgatgaag gttttcggat cgtaaaactc tgttgttagg     60
gaagaacaag tacgagagta actgctcgta ccttgacggt acctaaccag aaagccacgg    120
ctaactacgt gccagcagcc gcggtaatac gtaggtggca agcgttgtcc ggaattattg    180
ggcgtaaagc gcgcgcaggc ggtcctttaa gtctgatgtg aaagcccacg gctcaaccgt    240
ggagggtcat tggaaactgg gggacttgag tgcagaagag aagagtggaa ttccacgtgt    300
agcggtgaaa tgcgtagaga tgtggaggaa caccagtggc gaaggcgact ctttggtctg    360
taactgacgc tgaggcgcga aagcgtgggg agcaaacagg attagatacc ctggtagtcc    420
acgccgtaaa cgatgagtgc taagtgttag agggtttccg ccctttagtg ctgcagcaaa    480
cgcattaagc actccgcctg gggagtacgg ccgcaaggct gaaactcaaa ggaattgacg    540
ggggcccgca caagcggtgg agcatgtggt ttaattcgaa gcaacgcgaa gaaccttacc    600
aggtcttgac atctcctgac aatcctagag ataggacgtt ccccttcggg ggacaggatg    660
acaggtggtg catggttgtc gtcagctcgt gtcgtgagat gttgggttaa gtcccgc      717
```

<210> SEQ ID NO 293
<211> LENGTH: 702
<212> TYPE: DNA
<213> ORGANISM: Bacillus subtilis

<400> SEQUENCE: 293

```
cgccgcgtga gtgatgaagg ttttcggatc gtaaagctct gttgttaggg aagaacaagt     60
gccgttcaaa tagggcggca ccttgacggt acctaaccag aaagccacgg ctaactacgt    120
gccagcagcc gcggtaatac gtaggtggca agcgttgtcc ggaattattg ggcgtaaagg    180
gctcgcaggc ggtttcttaa gtctgatgtg aaagcccccg gctcaaccgg ggagggtcat    240
```

```
tggaaactgg ggaacttgag tgcagaagag gagagtggaa ttccacgtgt agcggtgaaa      300
tgcgtagaga tgtggaggaa caccagtggc gaaggcgact ctctggtctg taactgacgc      360
tgaggagcga aagcgtgggg agcgaacagg attagatacc ctggtagtcc acgccgtaaa      420
cgatgagtgc taagtgttag ggggtttccg ccccttagtg ctgcagctaa cgcattaagc      480
actccgcctg gggagtacgg tcgcaagact gaaactcaaa ggaattgacg ggggcccgca      540
caagcggtgg agcatgtggt ttaattcgaa gcaacgcgaa gaaccttacc aggtcttgac      600
atcctctgac aatcctagag ataggacgtc cccttcgggg gcagagtgac aggtggtgca      660
tggttgtcgt cagctcgtgt cgtgagatgt tgggttaagt cc                         702
```

```
<210> SEQ ID NO 294
<211> LENGTH: 680
<212> TYPE: DNA
<213> ORGANISM: Alcaligenes faecalis
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (272)..(273)
<223> OTHER INFORMATION: n is a, c, g, or t

<400> SEQUENCE: 294
```

```
cttcgggttg taaagtactt ttggcagaga agaaaaggta tctcctaata cgagatactg      60
ctgacggtat ctgcagaata agcaccggct aactacgtgc cancagccgc ggtaatacgt     120
agggtgcaag cgttaatcgg aattactggg cgtaaagcgt gtgtaggcgg ttcggaaaga     180
aagatgtgaa atcccagggc tcaaccttgg aactgcattt ttaactgccg agctagagta     240
tgtcagaggg gggtagaatt cnnntgtagc anngaaatgc gtagatatgt ggaggaatac     300
cgatggcgaa ggcagccccc tgggataata ctgacgctca gacacgaaag cgtggggagc     360
aaacaggatt agatacctcg gtagtccacg ccctaaacga tgtcaactag ctgttgggc      420 cgttaggcct tagtagcgca gctaacgcgt gaagttgacc gcctggggag tacggtcgca     480
agattaaaac tcaaaggaat tgacggggac ccgcacaagc ggtggatgat gtggattaat     540
tcgatgcaac gcgaaaaacc ttacctaccc ttgacatgtc tggaaagccg aagagatttg     600
gccgtgctcg caagagaacc ggaacacagg tgctgcatgg ctgtcgtcag ctcgtgtcgt     660
gagatgttgg gttaagtccc                                                 680
```

```
<210> SEQ ID NO 295
<211> LENGTH: 640
<212> TYPE: DNA
<213> ORGANISM: Paenibacillus massiliensis
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t
<220> FEATURE:
<221> NAME/KEY: misc_feature
```

-continued

```
<222> LOCATION: (22)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (189)..(190)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
```

-continued

```
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (364)..(365)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
```

```
-continued

<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (417)..(418)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (471)..(472)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (492)..(496)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (506)..(506)
```

```
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (516)..(517)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
```

<222> LOCATION: (633)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (637)..(640)
<223> OTHER INFORMATION: n is a, c, g, or t

<400> SEQUENCE: 295

```
cttanngnnt gannnnnctt gnnaanaaag ccccggctaa ctacntgcca ncanccgcgg    60
taatacntan ggngcaagcg ttgtccggaa ttattgggcg taaagcgcgc gcaggcggtc   120
ntttaagtct ggtgtttaag cccggggctc aaccccggat cncncgggaa actggatgac   180
ttgantgcnn aanaagagag tggaattccn ngtgtancgg tgaaatgcnt ananatgtgn   240
angaacacca ntggcnaang cnactctctg ggctgtaact gacnctgang cncgaaagcg   300
tggggagcaa acangattan ataccctggt antccacgcc ntanacnatn antgctaggt   360
gttnngggtt tcnataccct tgntgccnaa nttaacacat taancactcc gcctggnnan   420
tacngtcnca anantgaaac tcnnangaan tgacngggac ccgcacaagc nntgnantat   480
gtggtttaan tnnnnncaac ncnaanaanc ttaccnngnc ttgacatctn aatgaccngn   540
gcananatgt nccttttcctt cngnacattc nngacaggtg gtgcatggnt gtcntcnnct   600
cntgtcnngn gatgttgggt taantccccg cancnannnn                         640
```

<210> SEQ ID NO 296
<211> LENGTH: 678
<212> TYPE: DNA
<213> ORGANISM: Bacillus subtilis
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t

<400> SEQUENCE: 296

```
aagctctgtt gttagggaag aacaagtacc gttcgaatag ggcggtacct tgacggtacc    60
taaccagaaa gccacggcta actacgtgcc agcagccgcg gtaatacgta ggtggcaagc   120
gttgtccgga attattgggc gtaaagggct cgcaggcggt ttcttaagtc tgatgtgaaa   180
gcccccggct caaccgggga gggtcattgg aaactgggga acttgagtgc agaagaggag   240
agtggaattc cacgtgtagc ggtgaaatgc gtagagatgt ggaggaacac cagtggcgaa   300
ggcgactctc tggtctgtaa ctgacgctga ggagcgaaag cgtggggagc gaacaggatt   360
agataccctg gtagtccacg ccgtaaacga tgagtgctaa gtgttagggg gtttccgccc   420
cttantgctg cagctaacgc attaagcact ccgcctgggg agtacggtcg caagactgaa   480
actcaaagga attgacgggg gcccgcacaa gcggtggagc atgtggttta attcgaagca   540
acgcgaanaa ccttaccagg tcttgacatc ctctgacaat cctagagata ggacgtcccc   600
```

```
ttcgggggca gagtgacagg tggtgcatgg ttgtcgtcan ctcgtgtcgt gagatgttgg    660
nttaagtccc gcaacgag                                                  678
```

<210> SEQ ID NO 297
<211> LENGTH: 743
<212> TYPE: DNA
<213> ORGANISM: Bacillus megaterium
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (689)..(691)
<223> OTHER INFORMATION: n is a, c, g, or t
<220> FEATURE:
<221> NAME/KEY: misc_feature
<222> LOCATION: (693)..(708)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t

<400> SEQUENCE: 297

```
aagncttctcg gnncgtaaaa ctctgttgtt agggaagaac aagtacgaga gtaactgctc    60
gtaccttgac ggtacctaac cagaaagcca cggctaacta cgtgccagca gccgcggtaa   120
tacgtaggtg gcaagcgtta tccggaatta ttgggcgtaa agcgcgcgca ggcggttttct  180 taagtctgat gtgaaagccc acggctcaac cgtggagggt cattggaaac tggggaactt   240
gagtgcagaa gagaaaagcg gaattccacg tgtagcggtg aaatgcgtag agatgtggag   300
gaacaccagt ggcgaaggcg gctttttggt ctgtaactga cgctgaggcg cgaaagcgtg   360
gggagcaaac aggattagat accctggtag tccacgccgt aaacgatgag tgctaagtgt   420
tagagggttt ccgcccttta gtgctgcagc taacgcatta agcactccgc ctggggagta   480
cggtcgcaag actgaaactc aaaggaattg acggggcccc gcacaagcgg tggagcatgt   540
ggtttaattc gaagcaacgc gaagaacctt accaggtctt gacatcctct gacaactcta   600
gagatagagc gttccccttc ggggacagag tgacaggtg tgcatggtt gtcgtcagct   660 cgtgtcgtga gatgttgggt taagtcccnn ncnnnnnnn nnnnnnnntc tnagannnegn   720
```
gctgacnann ccangcaccn ngg                                          743

<210> SEQ ID NO 298
<211> LENGTH: 21
<212> TYPE: DNA
<213> ORGANISM: Artificial sequence
<220> FEATURE:
<223> OTHER INFORMATION: Primer

<400> SEQUENCE: 298
actcctacgg gaggcagcag t                                            21

<210> SEQ ID NO 299
<211> LENGTH: 16
<212> TYPE: DNA
<213> ORGANISM: Artificial Sequence
<220> FEATURE:
<223> OTHER INFORMATION: Primer

<400> SEQUENCE: 299
gggttgcgct cgttgc                                                  16

<210> SEQ ID NO 300
<211> LENGTH: 16
<212> TYPE: DNA
<213> ORGANISM: Artificial Sequence
<220> FEATURE:
<223> OTHER INFORMATION: Primer

<400> SEQUENCE: 300
gggttgcgct cgttac                                                  16

<210> SEQ ID NO 301
<211> LENGTH: 980
<212> TYPE: DNA
<213> ORGANISM: Bacillus thuringiensis
<220> FEATURE:
<221> N
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (851)..(853)
<223> OTHER INFORMATION: n is a, c, g, or t
<220> FEATURE:
<221> NAME/KEY: misc_feature
<222> LOCATION: (884)..(890)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (896)..(897)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (907)..(907)
<223> OTHER INFORMATION: n is a, c, g, or t
<220> FEATURE:
<221> NAME/KEY: misc_feature
<222> LOCATION: (911)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (923)..(925)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (937)..(939)
<223> OTHER INFORMATION: n is a, c, g, or t
<220> FEATURE:
<221> NAME/KEY: misc_feature
<222> LOCATION: (942)..(944)
<223> OTHER INFORMATION: n is a, c, g, or t
<220> FEATURE:
<221> NAME/KEY: misc_feature
<222> LOCATION: (946)..(950)
<223> OTHER INFORMATION: n is a, c, g, or t
<220> FEATURE:
<221> NAME/KEY: misc_feature
<222> LOCATION: (952)..(954)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t

<400> SEQUENCE: 301
tggacgaagt ctgacgganc acgccgcgtg agtgatgaag gctttcgggt cgtaaaactc    60
tgttgttagg gaagaacaag tgctagttga ataagctggc accttgacgg tacctaacca   120

```
gaaagccacg gctaactacg tgccagcagc cgcggtaata cgtaggtggc aagcgttatc    180
cggaattatt gggcgtaaag cgcgcgcagg tggtttctta agtctgatgt gaaagcccac    240
ggctcaaccg tggagggtca ttggaaactg ggagacttga gtgcagaaga ggaaagtgga    300
attccatgtg tagcggtgaa atgcgtagag atatggagga acaccagtgg cgaaggcgac    360
tttctggtct gtaactgaca ctgaggcgcg aaagcgtggg gagcaaacag gattagatac    420
cctggtagtc cacgccgtaa acgatgagtg ctaagtgtta gagggtttcc gcccttttagt   480 gctgaagtta acgcattaag cactccgcct ggggagtacg gccgcaaggc tgaaactcaa    540
aggaattgac gggggcccgc acaagcggtg agcatgtgg tttaattcga agcaacgcga     600
agaaccttac caggtcttga catcctctga aaaccctaga gatagggctt ctccttcggg    660
agcagagtga caggtggtgc atggttgtcg tcagctcgtg tcgtgagatg ttgggttaag    720
tcccgcaann ggccgcaacc caacanncnn cgacacgagc tgacgacaac catgnnccac    780
cagtnnctct gctctcgaag gagaagcccc annnnnaggg ttttttcgagg atgtnnngan   840 ctggtnnggg nnntcgcgtt gcttcgaatt aaaccacatg ctcnnnnnnn tgnggnnccc    900
cnagtcnatt nnttngagtc tannnctgga nccggannna annngnnnnn gnnnanttgc    960
gttaattggg gnaancccgg                                                980
```

```
<210> SEQ ID NO 302
<211> LENGTH: 732
<212> TYPE: DNA
<213> ORGANISM: Bacillus mycoides
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(727)
<223> OTHER INFORMATION: n is a, c, g, or t

<400> SEQUENCE: 302
agtctgnngg ancacgccgc gtgagtgnng aaggctttcg ggtcgtaaaa ctctgttgtt    60
agggaagaac aagtgctagt tgaataagct ggcaccttga cggtacctaa ccagaaagcc   120
acggctaact acgtgccagc agccgcggta atacgtaggt ggcaagcgtt atccggaatt   180
attgggcgta aagcgcgcgc aggtggtttc ttaagtctga tgtgaaagcc cacggctcaa   240
ccgtggaggg tcattggaaa ctgggagact tgagtgcaga agaggaaagt ggaattccat   300
gtgtagcggt gaaatgcgta gagatatgga ggaacaccag tggcgaaggc gactttctgg   360
tctgtaactg acactgaggc gcgaaagcgt ggggagcaaa caggattaga taccctggta   420
gtccacgccg taaacgatga gtgctaagtg ttagagggtt ccgcccttt agtgctgaag    480 ttaacgcatt aagcactccg cctggggagt acggccgcaa ggctgaaact caaaggaatt   540
gacgggggcc cgcacaagcg gtggagcatg tggtttaatt cgaagcaacg cgaagaacct   600
```

| | |
|---|---|
| taccaggtct tgacatcctc tgacaaccct agagataggg cttccccttc gggggcagag | 660 |
| tgacaggtgg tgcatggttg tcgtcagctc gtgtcgtgag atgttgggtt aagtcccgca | 720 |
| acnannngca ac | 732 |

<210> SEQ ID NO 303
<211> LENGTH: 714
<212> TYPE: DNA
<213> ORGANISM: Bacillus pseudomycoides
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t

<400> SEQUENCE: 303

| | |
|---|---|
| ctganggananc acgccgcgtg agtgatgaag gctttcgggt cgtaaaactc tgttgttagg | 60 |
| gaagaacaag tgctagttga ataagctggc accttgacgg tacctaacca gaaagccacg | 120 |
| gctaactacg tgccagcagc cgcggtaata cgtaggtggc aagcgttatc cggaattatt | 180 |
| gggcgtaaag cgcgcgcagg tggtttctta agtctgatgt gaaagcccac ggctcaaccg | 240 |
| tggagggtca ttggaaactg ggagacttga gtgcagaaga ggaaagtgga attccatgtg | 300 |
| tagcggtgaa atgcgtagag atatggagga acaccagtgg cgaaggcgac tttctggtct | 360 |
| gtaactgaca ctgaggcgcg aaagcgtggg gagcaaacag gattagatac cctggtagtc | 420 |
| cacgccgtaa acgatgagtg ctaagtgtta gagggtttcc gcccttagt gctgaagtta | 480 |
| acgcattaag cactccgcct ggggagtacg gccgcaaggc tgaaactcaa aggaattgac | 540 |
| gggggcccgc acaagcggtg gagcatgtgg tttaattcga agcaacgcga agaaccttac | 600 |
| caggtcttga catcctctga aaactctaga gatagagctt ctccttcggg agcagagtga | 660 |
| caggtggtgc atggttgtcg tcagctcgtg tcgtgagatg ntgggntaag tccc | 714 |

<210> SEQ ID NO 304
<211> LENGTH: 740
<212> TYPE: DNA
<213> ORGANISM: Bacillus cereus
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (733)..(734)
<223> OTHER INFORMATION: n is a, c, g, or t
<220> FEATURE:
<221> NAME/KEY: misc_feature
<222> LOCATION: (736)..(740)
<223> OTHER INFORMATION: n is a, c, g, or t

<400> SEQUENCE: 304

```
tctgnnggan caacnccgcg tgagtgatga angctttcgg gtcgtaaaac tctgttgtta      60
gggaagaaca agtgctagtt gaataagctg gcaccttgac ggtacctaac cagaaagcca     120
cggctaacta cgtgccagca gccgcggtaa tacgtaggtg gcaagcgtta tccggaatta     180
ttgggcgtaa agcgcgcgca ggtggtttct taagtctgat gtgaaagccc acggctcaac     240
cgtggagggt cattggaaac tgggagactt gagtgcagaa gaggaaagtg gaattccatg     300
tgtagcggtg aaatgcgtag agatatggag gaacaccagt ggcgaaggcg actttctggt     360
ctgtaactga cactgaggcg cgaaagcgtg gggagcaaac aggattagat accctggtag     420
tccacgccgt aaacgatgag tgctaagtgt tagagggttt ccgcccttta gtgctgaagt     480
taacgcatta agcactccgc ctggggagta cggccgcaag gctgaaactc aaaggaattg     540
acggggccc gcacaagcgg tggagcatgt ggtttaattc gaagcaacgc gaagaacctt     600
accaggtctt gacatcctct gaaaaccccta gagatagggc ttctccttcg ggagcagagt     660
gacaggtggt gcatggttgt cgtcagctcg tgtcgtgaga tgntgggtta agtcccgcaa     720
cganccgcaa ccnnannnnn                                                  740
```

<210> SEQ ID NO 305
<211> LENGTH: 850
<212> TYPE: DNA
<213> ORGANISM: Bacillus pumilus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (718)..(733)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (739)..(741)
<223> OTHER INFORMATION: n is a, c, g, or t
<220> FEATURE:
<221> NAME/KEY: misc_feature
<222> LOCATION: (743)..(744)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:

```
<221> NAME/KEY: misc_feature
<222> LOCATION: (753)..(754)
<223> OTHER INFORMATION: n is a, c, g, or t
<220> FEATURE:
<221> NAME/KEY: misc_feature
<222> LOCATION: (756)..(757)
<223> OTHER INFORMATION: n is a, c, g, or t
<220> FEATURE:
<221> NAME/KEY: misc_feature
<222> LOCATION: (767)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (779)..(784)
<223> OTHER INFORMATION: n is a, c, g, or t
<220> FEATURE:
<221> NAME/KEY: misc_feature
<222> LOCATION: (787)..(788)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (799)..(800)
<223> OTHER INFORMATION: n is a, c, g, or t
<220> FEATURE:
<221> NAME/KEY: misc_feature
<222> LOCATION: (802)..(802)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (809)..(810)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (829)..(831)
<223> OTHER INFORMATION: n is a, c, g, or t
<220> FEATURE:
<221> NAME/KEY: misc_feature
<222> LOCATION: (835)..(835)
<223> OTHER INFORMATION: n is a, c, g, or t
<220> FEATURE:
<221> NAME/KEY: misc_feature
<222> LOCATION: (838)..(841)
<223> OTHER INFORMATION: n is a, c, g, or t
<220> FEATURE:
<221> NAME/KEY: misc_feature
<222> LOCATION: (846)..(848)
<223> OTHER INFORMATION: n is a, c, g, or t
```

<400> SEQUENCE: 305

```
ctgangganc acgccgcgtg agtgatgaag gttttcggat cgtaaagctc tgttgttagg      60
gaagaacaag tgcgagagta actgctcgca ccttgacggt acctaaccag aaagccacgg     120
ctaactacgt gccagcagcc gcggtaatac gtaggtggca agcgttgtcc ggaattattg     180
ggcgtaaagg gctcgcaggc ggtttcttaa gtctgatgtg aaagccccg gctcaaccgg      240
ggagggtcat tggaaactgg gaaacttgag tgcagaagag gagagtggaa ttccacgtgt     300
agcggtgaaa tgcgtagaga tgtggaggaa caccagtggc gaaggcgact ctctggtctg     360
taactgacgc tgaggagcga aagcgtgggg agcgaacagg attagatacc ctggtagtcc     420
acgccgtaaa cgatgagtgc taagtgttag ggggtttccg ccccttagtg ctgcagctaa     480
cgcattaagc actccgcctg gggagtacgg tcgcaagact gaaactcaaa ggaattgacg     540
ggggcccgca caagcggtgg agcatgtggt ttaattcgaa gcaacgcgaa gaaccttacc     600
aggtcttgac atcctctgac aaccctagag atagggcttt ccttcgggg acagagtgac      660
aggtggtgca tggttgtcgt cagctcgtgt cgtgagatgt tgggttaagt cccgnacnnn     720
nnnnnnnnn nnncntctnn nanncgngct gannanncca tgcaccnncn gtcantctnn      780
nnnnggnnaa nncntattnn tngggtngnn cagangangt cagacnggnn nggtnctnnn     840
nttgcnnnat                                                            850
```

<210> SEQ ID NO 306
<211> LENGTH: 20
<212> TYPE: RNA
<213> ORGANISM: Glycine max

<400> SEQUENCE: 306

```
uuggacugaa gggugcuccc                                                  20
```

<210> SEQ ID NO 307
<211> LENGTH: 20
<212> TYPE: RNA
<213> ORGANISM: Glycine max

<400> SEQUENCE: 307

```
gagcucucuu caguccacuc                                                  20
```

<210> SEQ ID NO 308
<211> LENGTH: 21
<212> TYPE: RNA
<213> ORGANISM: Glycine max

<400> SEQUENCE: 308

```
agagcguccu ucaguccacu c                                                21
```

<210> SEQ ID NO 309
<211> LENGTH: 20
<212> TYPE: DNA
<213> ORGANISM: Artificial Sequence
<220> FEATURE:
<223> OTHER INFORMATION: Synthetic/artificial construct

<400> SEQUENCE: 309

```
gagcccatgg ttgaatgagt                                                  20
```

<210> SEQ ID NO 310
<211> LENGTH: 20
<212> TYPE: DNA

<213> ORGANISM: Artificial Sequence
<220> FEATURE:
<223> OTHER INFORMATION: Synthetic/artificial construct

<400> SEQUENCE: 310
actcattcaa ccatgggctc                                                                                   20

<210> SEQ ID NO 311
<211> LENGTH: 499
<212> TYPE: PRT
<213> ORGANISM: Bacillus subtilis

<400> SEQUENCE: 311

```
Met Lys Arg Ser Ile Ser Ile Phe Ile Thr Cys Leu Leu Ile Thr Leu
1               5                   10                  15

Leu Thr Met Gly Gly Met Ile Ala Ser Pro Ala Ser Ala Ala Gly Thr
            20                  25                  30

Lys Thr Pro Val Ala Lys Asn Gly Gln Leu Ser Ile Lys Gly Thr Gln
        35                  40                  45

Leu Val Asn Arg Asp Gly Lys Ala Val Gln Leu Lys Gly Ile Ser Ser
    50                  55                  60

His Gly Leu Gln Trp Tyr Gly Glu Tyr Val Asn Lys Asp Ser Leu Lys
65                  70                  75                  80

Trp Leu Arg Asp Asp Trp Gly Ile Thr Val Phe Arg Ala Ala Met Tyr
                85                  90                  95

Thr Ala Asp Gly Gly Tyr Ile Asp Asn Pro Ser Val Lys Asn Lys Val
            100                 105                 110

Lys Glu Ala Val Glu Ala Ala Lys Glu Leu Gly Ile Tyr Val Ile Ile
        115                 120                 125

Asp Trp His Ile Leu Asn Asp Gly Asn Pro Asn Gln Asn Lys Glu Lys
    130                 135                 140

Ala Lys Glu Phe Phe Lys Glu Met Ser Ser Leu Tyr Gly Asn Thr Pro
145                 150                 155                 160

Asn Val Ile Tyr Glu Ile Ala Asn Glu Pro Asn Gly Asp Val Asn Trp
                165                 170                 175

Lys Arg Asp Ile Lys Pro Tyr Ala Glu Glu Val Ile Ser Val Ile Arg
            180                 185                 190

Lys Asn Asp Pro Asp Asn Ile Ile Ile Val Gly Thr Gly Thr Trp Ser
        195                 200                 205

Gln Asp Val Asn Asp Ala Ala Asp Asp Gln Leu Lys Asp Ala Asn Val
    210                 215                 220

Met Tyr Ala Leu His Phe Tyr Ala Gly Thr His Gly Gln Phe Leu Arg
225                 230                 235                 240

Asp Lys Ala Asn Tyr Ala Leu Ser Lys Gly Ala Pro Ile Phe Val Thr
                245                 250                 255

Glu Trp Gly Thr Ser Asp Ala Ser Gly Asn Gly Gly Val Phe Leu Asp
            260                 265                 270

Gln Ser Arg Glu Trp Leu Lys Tyr Leu Asp Ser Lys Thr Ile Ser Trp
        275                 280                 285

Val Asn Trp Asn Leu Ser Asp Lys Gln Glu Ser Ser Ala Leu Lys
    290                 295                 300

Pro Gly Ala Ser Lys Thr Gly Gly Trp Arg Leu Ser Asp Leu Ser Ala
305                 310                 315                 320

Ser Gly Thr Phe Val Arg Glu Asn Ile Leu Gly Thr Lys Asp Ser Thr
                325                 330                 335
```

```
Lys Asp Ile Pro Glu Thr Pro Ser Lys Asp Lys Pro Thr Gln Glu Asn
                340                 345                 350

Gly Ile Ser Val Gln Tyr Arg Ala Gly Asp Gly Ser Met Asn Ser Asn
            355                 360                 365

Gln Ile Arg Pro Gln Leu Gln Ile Lys Asn Asn Gly Asn Thr Thr Val
        370                 375                 380

Asp Leu Lys Asp Val Thr Ala Arg Tyr Trp Tyr Lys Ala Lys Asn Lys
385                 390                 395                 400

Gly Gln Asn Phe Asp Cys Asp Tyr Ala Gln Ile Gly Cys Gly Asn Val
                405                 410                 415

Thr His Lys Phe Val Thr Leu His Lys Pro Lys Gln Gly Ala Asp Thr
                420                 425                 430

Tyr Leu Glu Leu Gly Phe Lys Asn Gly Thr Leu Ala Pro Gly Ala Ser
            435                 440                 445

Thr Gly Asn Ile Gln Leu Arg Leu His Asn Asp Asp Trp Ser Asn Tyr
        450                 455                 460

Ala Gln Ser Gly Asp Tyr Ser Phe Phe Lys Ser Asn Thr Phe Lys Thr
465                 470                 475                 480

Thr Lys Lys Ile Thr Leu Tyr Asp Gln Gly Lys Leu Ile Trp Gly Thr
                485                 490                 495

Glu Pro Asn

<210> SEQ ID NO 312
<211> LENGTH: 283
<212> TYPE: PRT
<213> ORGANISM: Bacillus thuringiensis

<400> SEQUENCE: 312

Met Lys Lys Val Leu Ala Leu Ala Ala Ile Thr Leu Val Ala
1               5                   10                  15

Pro Leu Gln Ser Val Ala Phe Ala His Glu Asn Asp Gly Gly Gln Arg
            20                  25                  30

Phe Gly Val Ile Pro Arg Trp Ser Ala Glu Asp Lys His Lys Glu Gly
        35                  40                  45

Val Asn Ser His Leu Trp Ile Val Asn Arg Ala Ile Asp Ile Met Ser
    50                  55                  60

Arg Asn Thr Thr Leu Val Lys Gln Asp Arg Val Ala Leu Leu Asn Glu
65                  70                  75                  80

Trp Arg Thr Glu Leu Glu Asn Gly Ile Tyr Ala Ala Asp Tyr Glu Asn
                85                  90                  95

Pro Tyr Tyr Asp Asn Ser Thr Phe Ala Ser His Phe Tyr Asp Pro Asp
            100                 105                 110

Asn Gly Lys Thr Tyr Ile Pro Tyr Ala Lys Gln Ala Lys Glu Thr Gly
        115                 120                 125

Ala Lys Tyr Phe Lys Leu Ala Gly Glu Ser Tyr Lys Asn Lys Asp Met
130                 135                 140

Gln Gln Ala Phe Phe Tyr Leu Gly Leu Ser Leu His Tyr Leu Gly Asp
145                 150                 155                 160

Val Asn Gln Pro Met His Ala Ala Asn Phe Thr Asn Leu Ser Tyr Pro
                165                 170                 175

Gln Gly Phe His Ser Lys Tyr Glu Asn Phe Val Asp Thr Ile Lys Asp
            180                 185                 190

Asn Tyr Lys Val Thr Asp Gly Asn Gly Tyr Trp Asn Trp Lys Gly Thr
        195                 200                 205
```

```
Asn Pro Glu Asp Trp Ile His Gly Ala Ala Val Val Ala Lys Gln Asp
    210                 215                 220
Tyr Ala Gly Ile Val Asn Asp Asn Thr Lys Asp Trp Phe Val Arg Ala
225                 230                 235                 240
Ala Val Ser Gln Glu Tyr Ala Asp Lys Trp Arg Ala Glu Val Thr Pro
                245                 250                 255
Met Thr Gly Lys Arg Leu Met Asp Ala Gln Arg Val Thr Ala Gly Tyr
                260                 265                 270
Ile Gln Leu Trp Phe Asp Thr Tyr Gly Asp Arg
                275                 280

<210> SEQ ID NO 313
<211> LENGTH: 244
<212> TYPE: PRT
<213> ORGANISM: Bacillus subtilis

<400> SEQUENCE: 313

Leu Glu Ala Gly Leu Asn Lys Asp Gln Lys Arg Arg Ala Glu Gln Leu
1               5                   10                  15
Thr Ser Ile Phe Glu Asn Gly Thr Thr Glu Ile Gln Tyr Gly Tyr Val
                20                  25                  30
Glu Arg Leu Asp Asp Gly Arg Gly Tyr Thr Cys Gly Arg Ala Gly Phe
                35                  40                  45
Thr Thr Ala Thr Gly Asp Ala Leu Glu Val Val Glu Val Tyr Thr Lys
            50                  55                  60
Ala Val Pro Asn Asn Lys Leu Lys Lys Tyr Leu Pro Glu Leu Arg Arg
65                  70                  75                  80
Leu Ala Lys Glu Glu Ser Asp Asp Thr Ser Asn Leu Lys Gly Phe Ala
                85                  90                  95
Ser Ala Trp Lys Ser Leu Ala Asn Asp Lys Glu Phe Arg Ala Ala Gln
                100                 105                 110
Asp Lys Val Asn Asp His Leu Tyr Tyr Gln Pro Ala Met Lys Arg Ser
                115                 120                 125
Asp Asn Ala Gly Leu Lys Thr Ala Leu Ala Arg Ala Val Met Tyr Asp
    130                 135                 140
Thr Val Ile Gln His Gly Asp Gly Asp Pro Asp Ser Phe Tyr Ala
145                 150                 155                 160
Leu Ile Lys Arg Thr Asn Lys Lys Ala Gly Gly Ser Pro Lys Asp Gly
                165                 170                 175
Ile Asp Glu Lys Lys Trp Leu Asn Lys Phe Leu Asp Val Arg Tyr Asp
                180                 185                 190
Asp Leu Met Asn Pro Ala Asn His Asp Thr Arg Asp Glu Trp Arg Glu
            195                 200                 205
Ser Val Ala Arg Val Asp Val Leu Arg Ser Ile Ala Lys Glu Asn Asn
    210                 215                 220
Tyr Asn Leu Asn Gly Pro Ile His Val Arg Ser Asn Glu Tyr Gly Asn
225                 230                 235                 240
Phe Val Ile Lys
```

What is claimed is:

1. A recombinant *Bacillus cereus* family member that expresses a fusion protein comprising at least one protein or peptide of interest and a targeting sequence, exosporium protein, or exosporium protein fragment that targets the fusion protein to the exosporium of the recombinant *Bacillus cereus* family member, wherein the protein or peptide of interest comprises an enzyme, a plant growth stimulating protein or peptide, a protein or peptide that protects a plant from a pathogen, a protein or peptide that enhances stress resistance in a plant, a plant binding protein or peptide, or a nucleic acid binding protein or peptide; and wherein the recombinant *Bacillus cereus* family member comprises a mutation that results in *Bacillus cereus* family member spores having an exosporium that is easier to remove from the spore as compared to the exosporium of a wild-type spore.

2. The recombinant *Bacillus cereus* family of claim 1, wherein the recombinant *Bacillus cereus* family member:
(i) comprises a mutation in a CotE gene;
(ii) comprises a mutation in an ExsY gene;
(iii) comprises a mutation in a CotY gene;
(iv) comprises a mutation in an ExsA gene; or
(v) comprises a mutation in a CotO gene.

3. The recombinant *Bacillus cereus* family member of claim 2, wherein the recombinant *Bacillus cereus* family member comprises a mutation in a CotE gene.

4. The recombinant *Bacillus cereus* family member of claim 3, wherein the mutation in the CotE gene partially or completely inhibits the ability of CotE to attach the exosporium to the spore.

5. The recombinant *Bacillus cereus* family member of claim 3, wherein the mutation in the CotE gene comprises a knock-out of the CotE gene or a dominant negative form of the CotE gene.

6. The recombinant *Bacillus cereus* family member of claim 2, wherein the recombinant *Bacillus cereus* family member comprises a mutation an ExsY gene.

7. The recombinant *Bacillus cereus* family member of claim 6, wherein the mutation in the ExsY gene partially or completely inhibits the ability of ExsY to complete the formation of the exosporium or attach the exosporium to the spore.

8. The recombinant *Bacillus cereus* family member of claim 6, wherein the mutation in the ExsY gene comprises a knock-out of the ExsY gene.

9. The recombinant *Bacillus cereus* family member of claim 2, wherein the recombinant *Bacillus cereus* family member comprises a mutation in a CotY gene, the mutation in the CotY gene comprising a knock-out of the CotY gene.

10. The recombinant *Bacillus cereus* family member of claim 2, wherein the recombinant *Bacillus cereus* family member comprises a mutation in an ExsA gene, the mutation in the ExsA gene comprising a knock-out of the ExsA gene.

11. The recombinant *Bacillus cereus* family member of claim 2, wherein the recombinant *Bacillus cereus* family member comprises a mutation in a CotO gene, the mutation in the CotO gene comprising a knock-out of the CotO gene or a dominant negative form of the CotO gene.

12. The recombinant *Bacillus cereus* family member of claim 1, wherein the targeting sequence, exosporium protein, or exosporium protein fragment comprises:
(1) a targeting sequence comprising an amino acid sequence having at least about 43% identity with amino acids 20-35 of SEQ ID NO: 1, wherein the identity with amino acids 25-35 is at least about 54%;
(2) a targeting sequence comprising amino acids 1-35 of SEQ ID NO: 1;
(3) a targeting sequence comprising amino acids 20-35 of SEQ ID NO: 1;
(4) a targeting sequence comprising SEQ ID NO: 1;
(5) an exosporium protein comprising an amino acid sequence having at least 85% identity with SEQ ID NO: 2;
(6) a targeting sequence comprising amino acids 2-35 of SEQ ID NO: 1;
(7) a targeting sequence comprising amino acids 5-35 of SEQ ID NO: 1;
(8) a targeting sequence comprising amino acids 8-35 of SEQ ID NO: 1;
(9) a targeting sequence comprising amino acids 10-35 of SEQ ID NO: 1;
(10) a targeting sequence comprising amino acids 15-35 of SEQ ID NO: 1;
(11) a targeting sequence comprising amino acids 1-27 of SEQ ID NO: 3;
(12) a targeting sequence comprising amino acids 12-27 of SEQ ID NO: 3;
(13) a targeting sequence comprising SEQ ID NO: 3;
(14) an exosporium protein comprising an amino acid sequence having at least 85% identity with SEQ ID NO: 4;
(15) a targeting sequence comprising amino acids 2-27 of SEQ ID NO: 3;
(16) a targeting sequence comprising amino acids 5-27 of SEQ ID NO: 3;
(17) a targeting sequence comprising amino acids 8-27 of SEQ ID NO: 3;
(18) a targeting sequence comprising amino acids 10-27 of SEQ ID NO: 3;
(19) a targeting sequence comprising amino acids 1-38 of SEQ ID NO: 5;
(20) a targeting sequence comprising amino acids 23-38 of SEQ ID NO: 5;
(21) a targeting sequence comprising SEQ ID NO: 5;
(22) an exosporium protein comprising an amino acid sequence having at least 85% identity with SEQ ID NO: 6;
(23) a targeting sequence comprising amino acids 2-38 of SEQ ID NO: 5;
(24) a targeting sequence comprising amino acids 5-38 of SEQ ID NO: 5;
(25) a targeting sequence comprising amino acids 8-38 of SEQ ID NO: 5;
(26) a targeting sequence comprising amino acids 10-38 of SEQ ID NO: 5;
(27) a targeting sequence comprising amino acids 15-38 of SEQ ID NO: 5;
(28) a targeting sequence comprising amino acids 20-38 of SEQ ID NO: 5;
(29) a targeting sequence comprising amino acids 1-28 of SEQ ID NO: 7;
(30) a targeting sequence comprising amino acids 13-28 of SEQ ID NO: 7;
(31) a targeting sequence comprising SEQ ID NO: 7;
(32) an exosporium protein comprising an amino acid sequence having at least 85% identity with SEQ ID NO: 8;
(33) a targeting sequence comprising amino acids 2-28 of SEQ ID NO: 7;
(34) a targeting sequence comprising amino acids 5-28 of SEQ ID NO: 7;
(35) a targeting sequence comprising amino acids 8-28 of SEQ ID NO: 7;
(36) a targeting sequence comprising amino acids 10-28 of SEQ ID NO: 7;
(37) a targeting sequence comprising amino acids 1-24 of SEQ ID NO: 9;
(38) a targeting sequence comprising amino acids 9-24 of SEQ ID NO: 9;
(39) a targeting sequence comprising SEQ ID NO: 9;
(40) an exosporium protein comprising an amino acid sequence having at least 85% identity with SEQ ID NO: 10;
(41) a targeting sequence comprising amino acids 2-24 of SEQ ID NO: 9;

(42) a targeting sequence comprising amino acids 5-24 of SEQ ID NO: 9;
(43) a targeting sequence comprising amino acids 8-24 of SEQ ID NO: 9;
(44) a targeting sequence comprising amino acids 1-33 of SEQ ID NO:11;
(45) a targeting sequence comprising amino acids 18-33 of SEQ ID NO: 11;
(46) a targeting sequence comprising SEQ ID NO: 11;
(47) an exosporium protein comprising an amino acid sequence having at least 85% identity with SEQ ID NO: 12;
(48) a targeting sequence comprising amino acids 2-33 of SEQ ID NO: 11;
(49) a targeting sequence comprising amino acids 5-33 of SEQ ID NO: 11;
(50) a targeting sequence comprising amino acids 8-33 of SEQ ID NO: 11;
(51) a targeting sequence comprising amino acids 10-33 of SEQ ID NO: 11;
(52) a targeting sequence comprising amino acids 15-33 of SEQ ID NO: 11;
(53) a targeting sequence comprising amino acids 1-33 of SEQ ID NO: 13;
(54) a targeting sequence comprising amino acids 18-33 of SEQ ID NO: 13;
(55) a targeting sequence comprising SEQ ID NO:13;
(56) an exosporium protein comprising an amino acid sequence having at least 85% identity with SEQ ID NO:14;
(57) a targeting sequence comprising amino acids 2-33 of SEQ ID NO: 13;
(58) a targeting sequence comprising amino acids 5-33 of SEQ ID NO: 13;
(59) a targeting sequence comprising amino acids 8-33 of SEQ ID NO: 13;
(60) a targeting sequence comprising amino acids 10-33 of SEQ ID NO: 13;
(61) a targeting sequence comprising amino acids 15-33 of SEQ ID NO: 13;
(62) a targeting sequence comprising amino acids 1-43 of SEQ ID NO: 15;
(63) a targeting sequence comprising amino acids 28-43 of SEQ ID NO: 15;
(64) a targeting sequence comprising SEQ ID NO:15;
(65) an exosporium protein comprising an amino acid sequence having at least 85% identity with SEQ ID NO:16;
(66) a targeting sequence comprising amino acids 2-43 of SEQ ID NO: 15;
(67) a targeting sequence comprising amino acids 5-43 of SEQ ID NO: 15;
(68) a targeting sequence comprising amino acids 8-43 of SEQ ID NO: 15;
(69) a targeting sequence comprising amino acids 10-43 of SEQ ID NO: 15;
(70) a targeting sequence comprising amino acids 15-43 of SEQ ID NO: 15;
(71) a targeting sequence comprising amino acids 20-43 of SEQ ID NO: 15;
(72) a targeting sequence comprising amino acids 25-43 of SEQ ID NO: 15;
(73) a targeting sequence comprising amino acids 1-27 of SEQ ID NO: 17;
(74) a targeting sequence comprising amino acids 12-27 of SEQ ID NO: 17;
(75) a targeting sequence comprising SEQ ID NO:17;
(76) an exosporium protein comprising an amino acid sequence having at least 85% identity with SEQ ID NO:18;
(77) a targeting sequence comprising amino acids 2-27 of SEQ ID NO: 17;
(78) a targeting sequence comprising amino acids 5-27 of SEQ ID NO: 17;
(79) a targeting sequence comprising amino acids 8-27 of SEQ ID NO: 17;
(80) a targeting sequence comprising amino acids 10-27 of SEQ ID NO: 17;
(81) a targeting sequence comprising amino acids 1-33 of SEQ ID NO: 19;
(82) a targeting sequence comprising amino acids 18-33 of SEQ ID NO: 19;
(83) a targeting sequence comprising SEQ ID NO:19;
(84) an exosporium protein comprising an amino acid sequence having at least 85% identity with SEQ ID NO:20;
(85) a targeting sequence comprising amino acids 2-33 of SEQ ID NO: 19;
(86) a targeting sequence comprising amino acids 5-33 of SEQ ID NO: 19;
(87) a targeting sequence comprising amino acids 8-33 of SEQ ID NO: 19;
(88) a targeting sequence comprising amino acids 10-33 of SEQ ID NO: 19;
(89) a targeting sequence comprising amino acids 15-33 of SEQ ID NO: 19;
(90) a targeting sequence comprising amino acids 1-33 of SEQ ID NO: 21;
(91) a targeting sequence comprising amino acids 18-33 of SEQ ID NO: 21;
(92) a targeting sequence comprising SEQ ID NO:21;
(93) an exosporium protein comprising an amino acid sequence having at least 85% identity with SEQ ID NO:22;
(94) a targeting sequence comprising amino acids 2-33 of SEQ ID NO: 21;
(95) a targeting sequence comprising amino acids 5-33 of SEQ ID NO: 21;
(96) a targeting sequence comprising amino acids 8-33 of SEQ ID NO: 21;
(97) a targeting sequence comprising amino acids 10-33 of SEQ ID NO: 21;
(98) a targeting sequence comprising amino acids 15-33 of SEQ ID NO: 21;
(99) a targeting sequence comprising amino acids 1-24 of SEQ ID NO: 23;
(100) a targeting sequence comprising amino acids 9-24 of SEQ ID NO: 23;
(101) a targeting sequence comprising SEQ ID NO:23;
(102) an exosporium protein comprising an amino acid sequence having at least 85% identity with SEQ ID NO:24;
(103) a targeting sequence comprising amino acids 2-24 of SEQ ID NO:23;
(104) a targeting sequence comprising amino acids 5-24 of SEQ ID NO: 23;
(105) a targeting sequence comprising amino acids 8-24 of SEQ ID NO: 23;
(106) a targeting sequence comprising amino acids 1-24 of SEQ ID NO: 25;
(107) a targeting sequence comprising amino acids 9-24 of SEQ ID NO: 25;
(108) a targeting sequence comprising SEQ ID NO:25;

(109) an exosporium protein comprising an amino acid sequence having at least 85% identity with SEQ ID NO:26;
(110) a targeting sequence comprising amino acids 2-24 of SEQ ID NO: 25;
(111) a targeting sequence comprising amino acids 5-24 of SEQ ID NO: 25;
(112) a targeting sequence comprising amino acids 8-24 of SEQ ID NO: 25;
(113) a targeting sequence comprising amino acids 1-30 of SEQ ID NO: 27;
(114) a targeting sequence comprising amino acids 15-30 of SEQ ID NO: 27;
(115) a targeting sequence comprising SEQ ID NO:27;
(116) an exosporium protein comprising an amino acid sequence having at least 85% identity with SEQ ID NO:28;
(117) a targeting sequence comprising amino acids 2-30 of SEQ ID NO: 27;
(118) a targeting sequence comprising amino acids 5-30 of SEQ ID NO: 27;
(119) a targeting sequence comprising amino acids 8-30 of SEQ ID NO: 27;
(120) a targeting sequence comprising amino acids 10-30 of SEQ ID NO: 27;
(121) a targeting sequence comprising amino acids 1-33 of SEQ ID NO: 29;
(122) a targeting sequence comprising amino acids 18-33 of SEQ ID NO: 29;
(123) a targeting sequence comprising SEQ ID NO:29;
(124) an exosporium protein comprising an amino acid sequence having at least 85% identity with SEQ ID NO:30;
(125) a targeting sequence comprising amino acids 2-33 of SEQ ID NO: 29;
(126) a targeting sequence comprising amino acids 5-33 of SEQ ID NO: 29;
(127) a targeting sequence comprising amino acids 8-33 of SEQ ID NO: 29;
(128) a targeting sequence comprising amino acids 10-33 of SEQ ID NO: 29;
(129) a targeting sequence comprising amino acids 15-33 of SEQ ID NO: 29;
(130) a targeting sequence comprising amino acids 1-24 of SEQ ID NO: 31;
(131) a targeting sequence comprising amino acids 9-24 of SEQ ID NO: 31;
(132) a targeting sequence comprising SEQ ID NO:31;
(133) an exosporium protein comprising an amino acid sequence having at least 85% identity with SEQ ID NO:32;
(134) a targeting sequence comprising amino acids 2-24 of SEQ ID NO: 31;
(135) a targeting sequence comprising amino acids 5-24 of SEQ ID NO: 31;
(136) a targeting sequence comprising amino acids 8-24 of SEQ ID NO: 31;
(137) a targeting sequence comprising amino acids 1-15 of SEQ ID NO: 33;
(138) a targeting sequence comprising SEQ ID NO:33;
(139) an exosporium protein comprising an amino acid sequence having at least 85% identity with SEQ ID NO:34;
(140) a targeting sequence comprising amino acids 1-16 of SEQ ID NO: 35;
(141) a targeting sequence comprising SEQ ID NO:35;
(142) an exosporium protein comprising an amino acid sequence having at least 85% identity with SEQ ID NO:36;
(143) a targeting sequence comprising amino acids 1-29 of SEQ ID NO:43;
(144) a targeting sequence comprising amino acids 14-29 of SEQ ID NO: 43;
(145) a targeting sequence comprising SEQ ID NO: 43;
(146) an exosporium protein comprising an amino acid sequence having at least 85% identity with SEQ ID NO: 44;
(147) a targeting sequence comprising amino acids 2-29 of SEQ ID NO: 43;
(148) a targeting sequence comprising amino acids 5-29 of SEQ ID NO: 43;
(149) a targeting sequence comprising amino acids 8-29 of SEQ ID NO: 43;
(150) a targeting sequence comprising amino acids 10-29 of SEQ ID NO: 43;
(151) a targeting sequence comprising amino acids 1-35 of SEQ ID NO: 45;
(152) a targeting sequence comprising amino acids 20-35 of SEQ ID NO: 45;
(153) a targeting sequence comprising SEQ ID NO: 45;
(154) an exosporium protein comprising an amino acid sequence having at least 85% identity with SEQ ID NO: 46;
(155) a targeting sequence comprising amino acids 2-35 of SEQ ID NO: 45;
(156) a targeting sequence comprising amino acids 5-35 of SEQ ID NO: 45;
(157) a targeting sequence comprising amino acids 8-35 of SEQ ID NO: 45;
(158) a targeting sequence comprising amino acids 10-35 of SEQ ID NO: 45;
(159) a targeting sequence comprising amino acids 15-35 of SEQ ID NO: 45;
(160) a targeting sequence comprising amino acids 1-43 of SEQ ID NO: 47;
(161) a targeting sequence comprising amino acids 28-43 of SEQ ID NO: 47;
(162) a targeting sequence comprising SEQ ID NO: 47;
(163) an exosporium protein comprising an amino acid sequence having at least 85% identity with SEQ ID NO: 48;
(164) a targeting sequence comprising amino acids 2-43 of SEQ ID NO: 47;
(165) a targeting sequence comprising amino acids 5-43 of SEQ ID NO: 47;
(166) a targeting sequence comprising amino acids 8-43 of SEQ ID NO: 47;
(167) a targeting sequence comprising amino acids 10-43 of SEQ ID NO: 47;
(168) a targeting sequence comprising amino acids 15-43 of SEQ ID NO: 47;
(169) a targeting sequence comprising amino acids 20-43 of SEQ ID NO: 47;
(170) a targeting sequence comprising amino acids 25-43 of SEQ ID NO: 47;
(171) a targeting sequence comprising amino acids 1-32 of SEQ ID NO: 49;
(172) a targeting sequence comprising amino acids 17-32 of SEQ ID NO: 49;
(173) a targeting sequence comprising SEQ ID NO: 49;
(174) an exosporium protein comprising an amino acid sequence having at least 85% identity with SEQ ID NO: 50;

(175) a targeting sequence comprising amino acids 2-32 of SEQ ID NO: 49;
(176) a targeting sequence comprising amino acids 5-32 of SEQ ID NO: 49;
(177) a targeting sequence comprising amino acids 8-32 of SEQ ID NO: 49;
(178) a targeting sequence comprising amino acids 10-32 of SEQ ID NO: 49;
(179) a targeting sequence comprising amino acids 15-32 of SEQ ID NO: 49;
(180) a targeting sequence comprising amino acids 1-33 of SEQ ID NO: 51;
(181) a targeting sequence comprising amino acids 18-33 of SEQ ID NO: 51;
(182) a targeting sequence comprising SEQ ID NO: 51;
(183) an exosporium protein comprising an amino acid sequence having at least 85% identity with SEQ ID NO: 52;
(184) a targeting sequence comprising amino acids 2-33 of SEQ ID NO: 51;
(185) a targeting sequence comprising amino acids 5-33 of SEQ ID NO: 51;
(186) a targeting sequence comprising amino acids 8-33 of SEQ ID NO: 51;
(187) a targeting sequence comprising amino acids 10-33 of SEQ ID NO: 51;
(188) a targeting sequence comprising amino acids 15-33 of SEQ ID NO: 51;
(189) a targeting sequence comprising amino acids 1-33 of SEQ ID NO: 53;
(190) a targeting sequence comprising amino acids 18-33 of SEQ ID NO: 53;
(191) a targeting sequence comprising SEQ ID NO: 53;
(192) an exosporium protein comprising an amino acid sequence having at least 85% identity with SEQ ID NO: 54;
(193) a targeting sequence comprising amino acids 2-33 of SEQ ID NO: 53;
(194) a targeting sequence comprising amino acids 5-33 of SEQ ID NO: 53;
(195) a targeting sequence comprising amino acids 8-33 of SEQ ID NO: 53;
(196) a targeting sequence comprising amino acids 10-33 of SEQ ID NO: 53;
(197) a targeting sequence comprising amino acids 15-33 of SEQ ID NO: 53;
(198) a targeting sequence comprising amino acids 1-30 of SEQ ID NO: 55;
(199) a targeting sequence comprising amino acids 15-30 of SEQ ID NO: 55;
(200) a targeting sequence comprising SEQ ID NO: 55;
(201) an exosporium protein comprising an amino acid sequence having at least 85% identity with SEQ ID NO: 56;
(202) a targeting sequence comprising amino acids 2-30 of SEQ ID NO: 55;
(203) a targeting sequence comprising amino acids 5-30 of SEQ ID NO: 55;
(204) a targeting sequence comprising amino acids 8-30 of SEQ ID NO: 55;
(205) a targeting sequence comprising amino acids 10-30 of SEQ ID NO: 55;
(206) a targeting sequence comprising amino acids 1-130 of SEQ ID NO: 57;
(207) a targeting sequence comprising amino acids 115-130 of SEQ ID NO: 57;
(208) a targeting sequence comprising SEQ ID NO: 57;
(209) an exosporium protein comprising an amino acid sequence having at least 85% identity with SEQ ID NO: 58;
(210) a targeting sequence comprising amino acids 2-130 of SEQ ID NO: 57;
(211) a targeting sequence comprising amino acids 5-130 of SEQ ID NO: 57;
(212) a targeting sequence comprising amino acids 10-130 of SEQ ID NO: 57;
(213) a targeting sequence comprising amino acids 20-130 of SEQ ID NO: 57;
(214) a targeting sequence comprising amino acids 30-130 of SEQ ID NO: 57;
(215) a targeting sequence comprising amino acids 40-130 of SEQ ID NO: 57;
(216) a targeting sequence comprising amino acids 50-130 of SEQ ID NO: 57;
(217) a targeting sequence comprising amino acids 60-130 of SEQ ID NO: 57;
(218) a targeting sequence comprising amino acids 70-130 of SEQ ID NO: 57;
(219) a targeting sequence comprising amino acids 80-130 of SEQ ID NO: 57;
(220) a targeting sequence comprising amino acids 90-130 of SEQ ID NO: 57;
(221) a targeting sequence comprising amino acids 100-130 of SEQ ID NO: 57;
(222) a targeting sequence comprising amino acids 110-130 of SEQ ID NO: 57;
(223) an exosporium protein fragment comprising an amino acid sequence having at least 85% identity with SEQ ID NO: 95;
(224) a targeting sequence comprising SEQ ID NO: 96;
(225) a targeting sequence comprising SEQ ID NO: 97;
(226) a targeting sequence comprising SEQ ID NO: 98;
(227) a targeting sequence comprising SEQ ID NO: 99;
(228) a targeting sequence comprising SEQ ID NO: 100;
(229) a targeting sequence comprising SEQ ID NO: 101;
(230) a targeting sequence comprising SEQ ID NO: 102;
(231) a targeting sequence comprising SEQ ID NO: 103;
(232) a targeting sequence comprising SEQ ID NO: 104;
(233) a targeting sequence comprising SEQ ID NO: 105;
(234) a targeting sequence comprising SEQ ID NO: 106;
(235) an exosporium protein comprising an amino acid sequence having at least 85% identity with SEQ ID NO: 108;
(236) an exosporium protein comprising an amino acid sequence having at least 85% identity with SEQ ID NO: 109;
(237) an exosporium protein comprising an amino acid sequence having at least 85% identity with SEQ ID NO: 110;
(238) an exosporium protein comprising an amino acid sequence having at least 85% identity with SEQ ID NO: 111;
(239) an exosporium protein comprising an amino acid sequence having at least 85% identity with SEQ ID NO: 112;
(240) an exosporium protein comprising an amino acid sequence having at least 85% identity with SEQ ID NO: 113;
(241) an exosporium protein comprising an amino acid sequence having at least 85% identity with SEQ ID NO: 114;
(242) an exosporium protein comprising an amino acid sequence having at least 85% identity with SEQ ID NO: 115;

(243) an exosporium protein comprising an amino acid sequence having at least 85% identity with SEQ ID NO: 116;
(244) an exosporium protein comprising an amino acid sequence having at least 85% identity with SEQ ID NO: 117;
(245) an exosporium protein comprising an amino acid sequence having at least 85% identity with SEQ ID NO: 118;
(246) an exosporium protein comprising an amino acid sequence having at least 85% identity with SEQ ID NO: 119;
(247) an exosporium protein comprising an amino acid sequence having at least 85% identity with SEQ ID NO: 120;
(248) an exosporium protein comprising an amino acid sequence having at least 85% identity with SEQ ID NO: 121;
(249) a targeting sequence comprising amino acids 22-31 of SEQ ID NO: 1;
(250) a targeting sequence comprising amino acids 22-33 of SEQ ID NO: 1;
(251) a targeting sequence comprising amino acids 20-31 of SEQ ID NO: 1;
(252) a targeting sequence comprising amino acids 14-23 of SEQ ID NO: 3;
(253) a targeting sequence comprising amino acids 14-25 of SEQ ID NO: 3;
(254) a targeting sequence comprising amino acids 12-23 of SEQ ID NO: 3;
(255) a targeting sequence comprising amino acids 1-30 of SEQ ID NO: 59;
(256) a targeting sequence comprising SEQ ID NO: 59;
(257) an exosporium protein comprising an amino acid sequence having at least 85% identity with SEQ ID NO: 60;
(258) a targeting sequence comprising amino acids 2-30 of SEQ ID NO: 59;
(259) a targeting sequence comprising amino acids 4-30 of SEQ ID NO: 59;
(260) a targeting sequence comprising amino acids 6-30 of SEQ ID NO: 59;
(261) a targeting sequence comprising amino acids 1-33 of SEQ ID NO: 61;
(262) a targeting sequence comprising amino acids 18-33 of SEQ ID NO: 61;
(263) a targeting sequence comprising SEQ ID NO: 61;
(264) an exosporium protein comprising an amino acid sequence having at least 85% sequence identity with SEQ ID NO: 62;
(265) a targeting sequence comprising amino acids 2-33 of SEQ ID NO: 61;
(266) a targeting sequence comprising amino acids 5-33 of SEQ ID NO: 61;
(267) a targeting sequence comprising amino acids 10-33 of SEQ ID NO: 61;
(268) a targeting sequence comprising amino acids 15-33 of SEQ ID NO: 61;
(269) a targeting sequence comprising amino acids 1-35 of SEQ ID NO: 63;
(270) a targeting sequence comprising SEQ ID NO: 63;
(271) an exosporium protein comprising an amino acid sequence having at least 85% identity with SEQ ID NO: 64;
(272) a targeting sequence comprising amino acids 2-35 of SEQ ID NO: 63;
(273) a targeting sequence comprising amino acids 5-35 of SEQ ID NO: 63;
(274) a targeting sequence comprising amino acids 8-35 of SEQ ID NO: 63;
(275) a targeting sequence comprising amino acids 10-35 of SEQ ID NO: 63;
(276) a targeting sequence comprising amino acids 15-35 of SEQ ID NO: 63;
(277) a targeting sequence comprising amino acids 1-24 of SEQ ID NO: 65;
(278) a targeting sequence comprising amino acids 9-24 of SEQ ID NO: 65;
(279) a targeting sequence comprising SEQ ID NO: 65;
(280) an exosporium protein comprising an amino acid sequence having at least 85% identity with SEQ ID NO: 66;
(281) a targeting sequence comprising SEQ ID NO: 107;
(282) a targeting sequence comprising amino acids 2-24 of SEQ ID NO: 65;
(283) a targeting sequence comprising amino acids 5-24 of SEQ ID NO: 65;
(284) a targeting sequence comprising amino acids 1-27 of SEQ ID NO: 67;
(285) a targeting sequence comprising amino acids 12-27 of SEQ ID NO: 67;
(286) a targeting sequence comprising SEQ ID NO: 67;
(287) an exosporium protein comprising an amino acid sequence having at least 85% identity with SEQ ID NO: 68;
(288) an targeting sequence comprising amino acids 2-27 of SEQ ID NO: 67;
(289) a targeting sequence comprising amino acids 5-27 of SEQ ID NO: 67;
(290) a targeting sequence comprising amino acids 10-27 of SEQ ID NO: 67;
(291) a targeting sequence comprising amino acids 1-38 of SEQ ID NO: 69;
(292) a targeting sequence comprising amino acids 23-38 of SEQ ID NO: 69;
(293) a targeting sequence comprising SEQ ID NO: 69;
(294) an exosporium protein comprising an amino acid sequence having at least 85% identity with SEQ ID NO: 70;
(295) a targeting sequence comprising amino acids 2-38 of SEQ ID NO: 69;
(296) a targeting sequence comprising amino acids 5-38 of SEQ ID NO: 69;
(297) a targeting sequence comprising amino acids 10-38 of SEQ ID NO: 69;
(298) a targeting sequence comprising amino acids 15-38 of SEQ ID NO: 69;
(299) an exosporium protein comprising SEQ ID NO: 72;
(300) a targeting sequence comprising SEQ ID NO: 73;
(301) an exosporium protein comprising an amino acid sequence having at least 95% identity with SEQ ID NO: 74;
(302) a targeting sequence comprising amino acids 1-42 of SEQ ID NO: 75;
(303) a targeting sequence comprising amino acids 27-42 of SEQ ID NO: 75;
(304) a targeting sequence comprising SEQ ID NO: 75;
(305) an exosporium protein comprising an amino acid sequence having at least 85% identity with SEQ ID NO: 76;
(306) a targeting sequence comprising amino acids 2-42 of SEQ ID NO: 75;

(307) a targeting sequence comprising amino acids 5-42 of SEQ ID NO: 75;
(308) a targeting sequence comprising amino acids 10-42 of SEQ ID NO: 75;
(309) a targeting sequence comprising amino acids 15-42 of SEQ ID NO: 75;
(310) a targeting sequence comprising amino acids 20-42 of SEQ ID NO: 75;
(311) a targeting sequence comprising amino acids 25-42 of SEQ ID NO: 75;
(312) a targeting sequence comprising amino acids 1-24 of SEQ ID NO: 77;
(313) a targeting sequence comprising amino acids 9-24 of SEQ ID NO: 77;
(314) a targeting sequence comprising SEQ ID NO: 77;
(315) an exosporium protein comprising an amino acid sequence having at least 85% identity with SEQ ID NO: 78;
(316) a targeting sequence comprising amino acids 2-24 of SEQ ID NO: 77;
(317) a targeting sequence comprising amino acids 5-24 of SEQ ID NO: 77;
(318) an exosporium protein comprising an amino acid sequence having at least 85% identity with SEQ ID NO: 80;
(319) a targeting sequence comprising amino acids 1-38 of SEQ ID NO: 81;
(320) a targeting sequence comprising amino acids 23-38 of SEQ ID NO: 81;
(321) a targeting sequence comprising SEQ ID NO: 81;
(322) an exosporium protein comprising an amino acid sequence having at least 85% identity with SEQ ID NO: 82;
(323) a targeting sequence comprising amino acids 2-38 of SEQ ID NO: 81;
(324) a targeting sequence comprising amino acids 5-38 of SEQ ID NO: 81;
(325) a targeting sequence comprising amino acids 10-38 of SEQ ID NO: 81;
(326) a targeting sequence comprising amino acids 15-38 of SEQ ID NO: 81;
(327) a targeting sequence comprising amino acids 20-38 of SEQ ID NO: 81;
(328) a targeting sequence comprising amino acids 1-34 of SEQ ID NO: 83;
(329) a targeting sequence comprising SEQ ID NO: 83;
(330) an exosporium protein comprising an amino acid sequence having at least 85% identity with SEQ ID NO: 84;
(331) an exosporium protein comprising an amino acid sequence having at least 85% identity with SEQ ID NO: 86;
(332) a targeting sequence comprising amino acids 1-28 of SEQ ID NO: 87;
(333) a targeting sequence comprising amino acids 13-28 of SEQ ID NO: 87;
(334) a targeting sequence comprising SEQ ID NO: 87;
(335) an exosporium protein comprising an amino acid sequence having at least 85% identity with SEQ ID NO: 88;
(336) a targeting sequence comprising amino acids 2-28 of SEQ ID NO: 87;
(337) a targeting sequence comprising amino acids 5-28 of SEQ ID NO: 87;
(338) a targeting sequence comprising amino acids 10-28 of SEQ ID NO: 87;
(339) a targeting sequence comprising amino acids 1-28 of SEQ ID NO: 89;
(340) a targeting sequence comprising SEQ ID NO: 89;
(341) an exosporium protein comprising an amino acid sequence having at least 85% identity with SEQ ID NO: 90;
(342) a targeting sequence comprising amino acids 2-28 of SEQ ID NO: 89;
(343) a targeting sequence comprising amino acids 5-28 of SEQ ID NO: 89;
(344) a targeting sequence comprising amino acids 10-28 of SEQ ID NO: 89;
(345) a targeting sequence comprising amino acids 1-93 of SEQ ID NO: 91;
(346) a targeting sequence comprising SEQ ID NO: 91;
(347) an exosporium protein comprising an amino acid sequence having at least 85% identity with SEQ ID NO: 92;
(348) a targeting sequence comprising amino acids 2-93 of SEQ ID NO: 91;
(349) a targeting sequence comprising amino acids 10-93 of SEQ ID NO: 91;
(350) a targeting sequence comprising amino acids 20-93 of SEQ ID NO: 91;
(351) a targeting sequence comprising amino acids 30-93 of SEQ ID NO: 91;
(352) a targeting sequence comprising amino acids 40-93 of SEQ ID NO: 91;
(353) a targeting sequence comprising amino acids 50-93 of SEQ ID NO: 91;
(354) a targeting sequence comprising amino acids 60-93 of SEQ ID NO: 91;
(355) a targeting sequence comprising amino acids 1-130 of SEQ ID NO: 93;
(356) a targeting sequence comprising SEQ ID NO: 93;
(357) an exosporium protein comprising an amino acid sequence having at least 85% identity with SEQ ID NO: 94;
(358) a targeting sequence comprising amino acids 2-130 of SEQ ID NO: 93;
(359) a targeting sequence comprising amino acids 10-130 of SEQ ID NO: 93;
(360) a targeting sequence comprising amino acids 20-130 of SEQ ID NO: 93;
(361) a targeting sequence comprising amino acids 30-130 of SEQ ID NO: 93;
(362) an exosporium protein comprising an amino acid sequence having at least 85% identity with SEQ ID NO: 122;
(363) a targeting sequence consisting of amino acids 20-33 of SEQ ID NO: 1;
(364) a targeting sequence consisting of amino acids 21-33 of SEQ ID NO: 1;
(365) a targeting sequence consisting of amino acids 23-31 of SEQ ID NO: 1;
(366) a targeting sequence consisting of amino acids 1-15 of SEQ ID NO: 96;
(367) a targeting sequence consisting of amino acids 1-13 of SEQ ID NO: 96;
(368) a targeting sequence consisting of amino acids 12-25 of SEQ ID NO: 3;
(369) a targeting sequence consisting of amino acids 13-25 of SEQ ID NO: 3;
(370) a targeting sequence consisting of amino acids 15-23 of SEQ ID NO: 3;
(371) a targeting sequence consisting of amino acids 1-15 of SEQ ID NO: 97;

(372) a targeting sequence consisting of amino acids 1-13 of SEQ ID NO: 98;
(373) a targeting sequence consisting of amino acids 23-36 of SEQ ID NO: 5;
(374) a targeting sequence consisting of amino acids 23-34 of SEQ ID NO: 5;
(375) a targeting sequence consisting of amino acids 24-36 of SEQ ID NO: 5;
(376) a targeting sequence consisting of amino acids 26-34 of SEQ ID NO: 5;
(377) a targeting sequence consisting of amino acids 13-26 of SEQ ID NO: 7;
(378) a targeting sequence consisting of amino acids 13-24 of SEQ ID NO: 7;
(379) a targeting sequence consisting of amino acids 14-26 of SEQ ID NO: 7;
(380) a targeting sequence consisting of amino acids 16-24 of SEQ ID NO: 7;
(381) a targeting sequence consisting of amino acids 9-22 of SEQ ID NO: 9;
(382) a targeting sequence consisting of amino acids 9-20 of SEQ ID NO: 9;
(383) a targeting sequence consisting of amino acids 10-22 of SEQ ID NO: 9;
(384) a targeting sequence consisting of amino acids 12-20 of SEQ ID NO: 9;
(385) a targeting sequence consisting of amino acids 1-15 of SEQ ID NO: 105;
(386) a targeting sequence consisting of amino acids 1-13 of SEQ ID NO: 105;
(387) a targeting sequence consisting of amino acids 18-31 of SEQ ID NO: 11;
(388) a targeting sequence consisting of amino acids 18-29 of SEQ ID NO: 11;
(389) a targeting sequence consisting of amino acids 19-31 of SEQ ID NO: 11;
(390) a targeting sequence consisting of amino acids 1-15 of SEQ ID NO: 98;
(391) a targeting sequence consisting of amino acids 1-13 of SEQ ID NO: 98;
(392) a targeting sequence consisting of amino acids 18-31 of SEQ ID NO: 13;
(393) a targeting sequence consisting of amino acids 18-29 of SEQ ID NO: 13;
(394) a targeting sequence consisting of amino acids 19-31 of SEQ ID NO: 13;
(395) a targeting sequence consisting of amino acids 21-29 of SEQ ID NO: 13;
(396) a targeting sequence consisting of amino acids 1-15 of SEQ ID NO: 99;
(397) a targeting sequence consisting of amino acids 1-13 of SEQ ID NO: 99;
(398) a targeting sequence consisting of amino acids 28-41 of SEQ ID NO: 15;
(399) a targeting sequence consisting of amino acids 28-39 of SEQ ID NO: 15;
(400) a targeting sequence consisting of amino acids 29-41 of SEQ ID NO: 15;
(401) a targeting sequence consisting of amino acids 31-39 of SEQ ID NO: 15;
(402) a targeting sequence consisting of amino acids 12-25 of SEQ ID NO: 17;
(403) a targeting sequence consisting of amino acids 13-25 of SEQ ID NO: 17;
(404) a targeting sequence consisting of amino acids 1-15 of SEQ ID NO: 100;
(405) a targeting sequence consisting of amino acids 18-31 of SEQ ID NO: 19;
(406) a targeting sequence consisting of amino acids 18-29 of SEQ ID NO: 19;
(407) a targeting sequence consisting of amino acids 19-31 of SEQ ID NO: 19;
(408) a targeting sequence consisting of amino acids 21-29 of SEQ ID NO: 19;
(409) a targeting sequence consisting of amino acids 18-31 of SEQ ID NO: 21;
(410) a targeting sequence consisting of amino acids 18-29 of SEQ ID NO: 21;
(411) a targeting sequence consisting of amino acids 19-31 of SEQ ID NO: 21;
(412) a targeting sequence consisting of amino acids 21-29 of SEQ ID NO: 21;
(413) a targeting sequence consisting of amino acids 1-15 of SEQ ID NO: 101;
(414) a targeting sequence consisting of amino acids 1-13 of SEQ ID NO: 101;
(415) a targeting sequence consisting of amino acids 9-22 of SEQ ID NO: 23;
(416) a targeting sequence consisting of amino acids 9-20 of SEQ ID NO: 23;
(417) a targeting sequence consisting of amino acids 10-22 of SEQ ID NO: 23;
(418) a targeting sequence consisting of amino acids 12-20 of SEQ ID NO: 23;
(419) a targeting sequence consisting of amino acids 1-15 of SEQ ID NO: 102;
(420) a targeting sequence consisting of amino acids 1-13 of SEQ ID NO: 102;
(421) a targeting sequence consisting of amino acids 9-22 of SEQ ID NO: 25;
(422) a targeting sequence consisting of amino acids 9-20 of SEQ ID NO: 25;
(423) a targeting sequence consisting of amino acids 10-22 of SEQ ID NO: 25;
(424) a targeting sequence consisting of amino acids 12-20 of SEQ ID NO: 25;
(425) a targeting sequence consisting of amino acids 1-15 of SEQ ID NO: 103;
(426) a targeting sequence consisting of amino acids 1-13 of SEQ ID NO: 103;
(427) a targeting sequence consisting of amino acids 15-28 of SEQ ID NO: 27;
(428) a targeting sequence consisting of amino acids 15-26 of SEQ ID NO: 27;
(429) a targeting sequence consisting of amino acids 16-28 of SEQ ID NO: 27;
(430) a targeting sequence consisting of amino acids 18-26 of SEQ ID NO: 27;
(431) a targeting sequence consisting of amino acids 1-15 of SEQ ID NO: 104;
(432) a targeting sequence consisting of amino acids 1-13 of SEQ ID NO: 104;
(433) a targeting sequence consisting of amino acids 1-13 of SEQ ID NO: 33;
(434) a targeting sequence consisting of amino acids 1-11 of SEQ ID NO: 33;
(435) a targeting sequence consisting of amino acids 3-11 of SEQ ID NO: 33;
(436) a targeting sequence consisting of amino acids 1-14 of SEQ ID NO: 35;
(437) a targeting sequence consisting of amino acids 1-12 of SEQ ID NO: 35;

(438) a targeting sequence consisting of amino acids 2-14 of SEQ ID NO: 35;
(439) a targeting sequence consisting of amino acids 14-27 of SEQ ID NO: 43;
(440) a targeting sequence consisting of amino acids 14-25 of SEQ ID NO: 43;
(441) a targeting sequence consisting of amino acids 15-27 of SEQ ID NO: 43;
(442) a targeting sequence consisting of amino acids 20-33 of SEQ ID NO: 45;
(443) a targeting sequence consisting of amino acids 20-31 of SEQ ID NO: 45;
(444) a targeting sequence consisting of amino acids 21-33 of SEQ ID NO: 45;
(445) a targeting sequence consisting of amino acids 1-15 of SEQ ID NO: 106;
(446) a targeting sequence consisting of amino acids 1-13 of SEQ ID NO: 106;
(447) a targeting sequence consisting of amino acids 28-41 of SEQ ID NO: 47;
(448) a targeting sequence consisting of amino acids 28-39 of SEQ ID NO: 47;
(449) a targeting sequence consisting of amino acids 18-31 of SEQ ID NO: 53;
(450) a targeting sequence consisting of amino acids 18-29 of SEQ ID NO: 53;
(451) a targeting sequence consisting of amino acids 19-31 of SEQ ID NO: 53;
(452) a targeting sequence comprising amino acids 18-31 of SEQ ID NO: 61;
(453) a targeting sequence comprising amino acids 18-29 of SEQ ID NO: 61;
(454) a targeting sequence comprising amino acids 19-31 of SEQ ID NO: 61;
(455) a targeting sequence comprising amino acids 9-22 of SEQ ID NO: 65;
(456) a targeting sequence comprising amino acids 9-20 of SEQ ID NO: 65;
(457) a targeting sequence comprising amino acids 10-22 of SEQ ID NO: 65;
(458) a targeting sequence comprising amino acids 1-15 of SEQ ID NO: 107;
(459) a targeting sequence comprising amino acids 1-13 of SEQ ID NO: 107;
(460) a targeting sequence comprising amino acids 12-25 of SEQ ID NO: 67;
(461) a targeting sequence comprising amino acids 12-23 of SEQ ID NO: 67;
(462) a targeting sequence comprising amino acids 13-25 of SEQ ID NO: 67;
(463) a targeting sequence comprising amino acids 15-23 of SEQ ID NO: 67;
(464) a targeting sequence comprising amino acids 23-36 of SEQ ID NO: 69;
(465) a targeting sequence comprising amino acids 23-34 of SEQ ID NO: 69;
(466) a targeting sequence comprising amino acids 24-36 of SEQ ID NO: 69;
(467) a targeting sequence comprising amino acids 26-34 of SEQ ID NO: 69;
(468) a targeting sequence comprising amino acids 27-40 of SEQ ID NO: 75;
(469) a targeting sequence comprising amino acids 27-38 of SEQ ID NO: 75;
(470) a targeting sequence comprising amino acids 9-22 of SEQ ID NO: 77;
(471) a targeting sequence comprising amino acids 9-20 of SEQ ID NO: 77;
(472) a targeting sequence comprising amino acids 10-22 of SEQ ID NO: 77;
(473) a targeting sequence comprising amino acids 12-20 of SEQ ID NO: 77;
(474) a targeting sequence comprising amino acids 23-36 of SEQ ID NO: 81;
(475) a targeting sequence comprising amino acids 23-34 of SEQ ID NO: 81;
(476) a targeting sequence comprising amino acids 24-36 of SEQ ID NO: 81;
(477) a targeting sequence comprising amino acids 26-34 of SEQ ID NO: 81;
(478) a targeting sequence comprising amino acids 13-26 of SEQ ID NO: 87;
(479) a targeting sequence comprising amino acids 13-24 of SEQ ID NO: 87; or
(480) a targeting sequence comprising amino acids 14-26 of SEQ ID NO: 87.

13. The recombinant *Bacillus cereus* family member of claim 12, wherein the targeting sequence comprises an amino acid sequence having at least about 50% identity with amino acids 20-35 of SEQ ID NO: 1, wherein the identity with amino acids 25-35 is at least about 63%.

14. The recombinant *Bacillus cereus* family member of claim 12, wherein the targeting sequence or exosporium protein comprises:
(a) an amino acid sequence consisting of 16 amino acids and having at least about 43% identity with amino acids 20-35 of SEQ ID NO: 1, wherein the identity with amino acids 25-35 is at least about 54%;
(b) amino acids 1-35 of SEQ ID NO: 1;
(c) amino acids 20-35 of SEQ ID NO: 1;
(d) SEQ ID NO: 1;
(e) SEQ ID NO: 96; or
(f) SEQ ID NO: 120.

15. The recombinant *Bacillus cereus* family member of claim 12, wherein the fusion protein comprises an exosporium protein or an exosporium protein fragment comprising an amino acid sequence having at least 95%, identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 76, 78, 80, 82, 84, 86, 88, 90, 92, 94, 95, 108, 109, 110, 111, 112, 113, 114, 115, 116, 117, 118, 119, 120, 121 or 122.

16. The recombinant *Bacillus cereus* family member of claim 12, wherein the targeting sequence comprises SEQ ID NO: 96.

17. The recombinant *Bacillus cereus* family member of claim 12, wherein the targeting sequence comprises an amino sequence having at least about 62% identity with amino acids 20-35 of SEQ ID NO: 1, wherein the identity with amino acids 25-35 is at least about 72%.

18. The recombinant *Bacillus cereus* family member of claim 12, wherein the targeting sequence comprises an amino acid sequence having at least about 81% identity with amino acids 20-35 of SEQ ID NO: 1, wherein the identity with amino acids 25-35 is at least about 90%.

19. The recombinant *Bacillus cereus* family member of claim 1, wherein the targeting sequence, exosporium protein, or exosporium protein fragment comprises the amino acid sequence GXT at its carboxy terminus, wherein X is any amino acid.

20. The recombinant *Bacillus cereus* family member of claim 1, wherein the targeting sequence, exosporium protein, or exosporium protein fragment further comprises a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

21. The recombinant *Bacillus cereus* family member of claim 1, wherein the fusion protein further comprises an amino acid linker between the targeting sequence, the exosporium protein, or the exosporium protein fragment and the protein or peptide of interest.

22. The recombinant *Bacillus cereus* family member of claim of claim 1, wherein the protein or peptide of interest comprises an enzyme.

23. The recombinant *Bacillus cereus* family member of claim 22, wherein the enzyme comprises an enzyme involved in the production or activation of a plant growth stimulating compound.

24. The recombinant *Bacillus cereus* family member of claim 23, wherein the plant growth stimulating compound comprises 2,3-butanediol or a plant growth hormone, the plant growth hormone comprising a cytokinin or a cytokinin derivative, ethylene, an auxin or an auxin derivative, a gibberellic acid or a gibberellic acid derivative, abscisic acid or an abscisic acid derivative, a jasmonic acid or a jasmonic acid derivative.

25. The recombinant *Bacillus cereus* family member of claim 23, wherein the enzyme involved in the production or activation of a plant growth stimulating compound comprises an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, or an enzyme involved in producing a nod factor.

26. The a recombinant *Bacillus cereus* family member of claim 25, wherein the enzyme involved in the production or activation of a plant growth stimulating compound comprises a protease or peptidase that cleaves proteins, peptides, proproteins, or preproproteins to create a bioactive peptide, the protease or peptidase comprising subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

27. The recombinant *Bacillus cereus* family member of claim 22, wherein the enzyme comprises an enzyme that degrades or modifies a bacterial, fungal, or plant nutrient source.

28. The recombinant *Bacillus cereus* family member of claim 22, wherein the enzyme comprises a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, or a chitosanase.

29. The recombinant *Bacillus cereus* family member of claim 28, wherein the enzyme comprises a cellulase, and the cellulase comprises an endocellulase, an exocellulase, or a β-glucosidase.

30. The recombinant *Bacillus cereus* family member of claim 29, wherein the cellulase comprises an endocellulase, and the endocellulase comprises an endoglucanase.

31. The recombinant *Bacillus cereus* family member of claim 29, wherein the cellulase comprises an endocellulase, and the endocellulase comprises a *Bacillus subtilis* endoglucanase, a *Bacillus thuringiensis* endoglucanase, a *Bacillus cereus* endoglucanase, or a *Bacillus clausii* endoglucanase.

32. The recombinant *Bacillus cereus* family member of claim 31, wherein the cellulase comprises a *Bacillus subtilis* endoglucanase, and the *Bacillus subtilis* endoglucanase comprises an amino acid sequence having at least 85%, identity with SEQ ID NO: 311.

33. The recombinant *Bacillus cereus* family member of claim 31, wherein the cellulase comprises a *Bacillus subtilis* endoglucanase, and the *Bacillus subtilis* endoglucanase comprises an amino acid sequence having at least 95% identity with SEQ ID NO: 311.

34. The recombinant *Bacillus cereus* family member of claim 28, wherein the enzyme comprises a lipase, and the lipase comprises a *Bacillus subtilis* lipase, a *Bacillus thuringiensis* lipase, a *Bacillus cereus* lipase, or a *Bacillus clausii* lipase.

35. The recombinant *Bacillus cereus* family member of claim 28, wherein the enzyme comprises a lignin oxidase, and the lignin oxidase comprises a lignin peroxidase, a laccase, a glyoxal oxidase, a ligninase, or a manganese peroxidase.

36. The recombinant *Bacillus cereus* family member of claim 28, wherein the enzyme comprises a protease, and the protease comprises a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

37. The recombinant *Bacillus cereus* family member of claim 28, wherein the enzyme comprises a phosphatase, and the phosphatase comprises a phosphoric monoester hydrolase, a phosphomonoesterase, a phosphoric diester hydrolase, a phosphodiesterase, a triphosphoric monoester hydrolase, a phosphoryl anhydride hydrolase, a pyrophosphatase, a phytase, a trimetaphosphatase, or a triphosphatase.

38. The recombinant *Bacillus cereus* family member of claim 28, wherein the enzyme comprises a nitrogenase, and the nitrogenase comprises a Nif family nitrogenase.

39. The recombinant *Bacillus cereus* family member of claim 1, wherein the protein or peptide of interest comprises a plant growth stimulating protein or peptide.

40. The recombinant *Bacillus cereus* family member of claim 39, wherein the plant growth stimulating protein or peptide comprises a peptide hormone or a non-hormone peptide.

41. The recombinant *Bacillus cereus* family member of claim 40, wherein the peptide hormone comprises a phytosulfokine, clavata 3 (CLV3), systemin, ZmIGF, or a SCR/SP11; or wherein the non-hormone peptide comprises a RKN 16D10, Hg-Syv46, an eNOD40 peptide, melittin, mastoparan, Mas7, RHPP, POLARIS, or kunitz trypsin inhibitor (KTI).

42. The recombinant *Bacillus cereus* family member of claim 1, wherein the protein or peptide of interest comprises a protein or peptide that protects a plant from a pathogen.

43. The recombinant *Bacillus cereus* family member of claim 42, wherein the protein or peptide that protects a plant from a pathogen comprises a plant immune system enhancer protein or peptide.

44. The recombinant *Bacillus cereus* family member of claim 43, wherein the plant immune system enhancer protein or peptide comprises a harpin, a harpin-like protein, an α-elastin, a β-elastin, a systemin, a phenylalanine ammonia-lyase, an elicitin, a defensin, a cryptogein, a flagellin protein, or a flagellin peptide.

45. The recombinant *Bacillus cereus* family member of claim 42, wherein the protein or peptide that protects a plant from a pathogen has antibacterial activity, antifungal activity, or both antibacterial and antifungal activity; or wherein the protein or peptide that protects a plant from a pathogen has insecticidal activity, helminthicidal activity, suppresses insect or worm predation, or a combination thereof.

46. The recombinant *Bacillus cereus* family member of claim 45, wherein the protein or peptide that protects a plant from a pathogen comprises a bacteriocin, a lysozyme, a lysozyme peptide, an avidin, a streptavidin, a non-ribosomal active peptide, a conalbumin, an albumin, a lactoferrin, a lactoferrin peptide, TasA, an insecticidal bacterial toxin, an endotoxin, a Cry toxin, a protease inhibitor protein or peptide, a cysteine protease, or a chitinase.

47. The recombinant *Bacillus cereus* family member of claim 46, wherein the protein or peptide that protects a plant from a pathogen comprises an insecticidal bacterial toxin and the insecticidal bacterial toxin comprises a VIP insecticidal toxin; wherein the protein or peptide that protects a plant from a pathogen comprises a protease inhibitor protein or peptide and the protease inhibitor protein or peptide comprises a trypsin inhibitor or an arrowhead protease inhibitor; or wherein the protein or peptide that protects a plant from a pathogen comprises a Cry toxin and the Cry toxin comprises a Cry toxin from *Bacillus thuringiensis*.

48. The recombinant *Bacillus cereus* family member of claim 42, wherein the protein that protects a plant from a pathogen comprises an enzyme.

49. The recombinant *Bacillus cereus* family member of claim 48, wherein the enzyme comprises a protease or a lactonase, wherein the protease or lactonase is specific for a bacterial lactone homoserine signaling molecule.

50. The recombinant *Bacillus cereus* family member of claim 48, wherein the enzyme is specific for a cellular component of a bacterium or fungus, the enzyme comprising a β-1,3-glucanase, a β-1,4-glucanase, a β-1,6-glucanase, a chitinase, a lyticase, a peptidase, a proteinase, a protease, a mutanolysin, a stapholysin, or a lysozyme.

51. The recombinant *Bacillus cereus* family member of claim 1, wherein the protein or peptide of interest comprises at least one protein or peptide that enhances stress resistance in a plant.

52. The recombinant *Bacillus cereus* family member of claim 51, wherein the protein or peptide that enhances stress resistance in a plant comprises an enzyme that degrades a stress-related compound, the stress-related compound comprising aminocyclopropane-1-carboxylic acid (ACC), a reactive oxygen species, nitric oxide, an oxylipin, a phenolic, or a combination thereof.

53. The recombinant *Bacillus cereus* family member of claim 52, wherein the enzyme that degrades a stress-related compound comprises a superoxide dismutase, an oxidase, a catalase, an aminocyclopropane-1-carboxylic acid deaminase, a peroxidase, an antioxidant enzyme, or an antioxidant peptide.

54. The recombinant *Bacillus cereus* family member of claim 51, wherein the protein or peptide that enhances stress resistance in a plant comprises a protein or peptide that protects a plant from an environmental stress, the environmental stress comprising drought, flood, heat, freezing, salt, heavy metals, low pH, high pH, or a combination thereof.

55. The recombinant *Bacillus cereus* family member of claim 1, wherein the protein or peptide of interest comprises at least one plant binding protein or peptide.

56. The recombinant *Bacillus cereus* family member of claim 55, wherein the plant binding protein or peptide comprises an adhesin, a rhicadhesin, a flagellin, an omptin, a lectin, an expansin, a biofilm structural protein, TasA, YuaB, a pilus protein, a curlus protein, an intimin, an invasin, an agglutinin, an afimbrial protein.

57. The recombinant *Bacillus cereus* family member of claim 1, wherein the protein or peptide of interest comprises a nucleic acid binding protein or peptide.

58. The recombinant *Bacillus cereus* family member of claim 57, wherein the nucleic acid binding protein or peptide comprises a nuclease having an inactivated active site.

59. The recombinant *Bacillus cereus* family member of claim 1, wherein the recombinant *Bacillus cereus* family member comprises *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis*, or a combination thereof.

60. The recombinant *Bacillus cereus* family member of claim 59, wherein the plant-growth promoting strain of bacteria comprises *Bacillus mycoides* BT155 (NRRL No. B-50921), *Bacillus mycoides* EE118 (NRRL No. B-50918), *Bacillus mycoides* EE141 (NRRL No. B-50916), *Bacillus mycoides* BT46-3 (NRRL No. B-50922), *Bacillus cereus* family member EE128 (NRRL No. B-50917), *Bacillus thuringiensis* BT013A (NRRL No. B-50924), *Bacillus cereus* family member EE349 (NRRL No. B-50928); *Bacillus cereus* family member EE-B00377 (NRRL B-67119); *Bacillus pseudomycoides* EE-B00366 (NRRL B-67120); or *Bacillus mycoides* EE-B00363 (NRRL B-67121), *Bacillus cereus* family member EE439 (NRRL B-50979); *Bacillus thuringiensis* EE417 (NRRL B-50979); *Bacillus cereus* EE444 (NRRL B-50977); *Bacillus thuringiensis* EE319 (NRRL B-50983); or *Bacillus thuringiensis* EE-B00184 (NRRL B-67122).

61. The recombinant *Bacillus cereus* family member of claim 60, wherein the recombinant *Bacillus cereus* family member comprises *Bacillus thuringiensis* BT013A (NRRL No. B-50924).

62. The recombinant *Bacillus cereus* family member of claim 60, wherein the recombinant *Bacillus cereus* family member comprises *Bacillus cereus* family member EE349 (NRRL No. B-50928).

63. The recombinant *Bacillus cereus* family member of claim 1, wherein the recombinant *Bacillus cereus* family member comprises an inactivating mutation in its BclA gene.

64. The recombinant *Bacillus cereus* family member of claim 63, wherein the inactivating mutation in the BclA gene comprises a knock-out of the BclA gene.

65. A formulation comprising exosporium fragments derived from spores of a recombinant *Bacillus cereus* family member of claim 1 and an agriculturally acceptable carrier.

66. A formulation of claim 65, wherein the exosporium fragments are derived from spores of a recombinant *Bacillus cereus* family member expressing a fusion protein comprising SEQ ID NO: 96 and a *Bacillus subtilis* endoglucanase comprising an amino acid sequence having at least 85% identity with SEQ ID NO: 311.

67. A plant seed coated with exosporium fragments derived from spores of a recombinant *Bacillus cereus* family member of claim 1.

68. A plant seed of claim 67, wherein the exosporium fragments are derived from spores of a recombinant *Bacillus cereus* family member expressing a fusion protein comprising SEQ ID NO: 96 and a *Bacillus subtilis* endoglucanase comprising an amino acid sequence having at least 85% identity with SEQ ID NO: 311.

69. A method for stimulating plant growth comprising:
   introducing exosporium fragments into a plant growth medium; or
   applying exosporium fragments to a plant, a plant seed, or an area surrounding a plant or a plant seed;
   wherein the exosporium fragments are derived from spores of a recombinant *Bacillus cereus* family member of claim 1 and comprise the fusion protein, and the fusion protein comprises a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, or a chitosanase.

70. A method of claim 69, wherein the cellulase comprises a *Bacillus subtilis* endoglucanase, and the *Bacillus subtilis* endoglucanase comprises an amino acid sequence having at least 85% identity with SEQ ID NO: 311.

71. A method for protecting a plant from a pathogen or enhancing stress resistance in a plant comprising:
   introducing exosporium fragments into a plant growth medium; or
   applying exosporium fragments to a plant, a plant seed, or an area surrounding a plant or a plant seed;
   wherein the exosporium fragments are derived from spores of a recombinant *Bacillus cereus* family member of claim 1 and comprise the fusion protein, and the fusion protein comprises a protein or peptide that protects a plant from a pathogen or a protein or peptide that enhances stress resistance in a plant.

72. A method for immobilizing exosporium fragments on a plant comprising:
   introducing exosporium fragments into a plant growth medium; or
   applying exosporium fragments to a plant, a plant seed, or an area surrounding a plant or a plant seed;
   wherein the exosporium fragments are derived from spores of a recombinant *Bacillus cereus* family member of claim 1 and comprise the fusion protein, and the fusion protein comprises a plant binding protein or peptide.

* * * * *